(12) United States Patent
Kroth et al.

(10) Patent No.: US 9,221,812 B2
(45) Date of Patent: Dec. 29, 2015

(54) COMPOUNDS FOR THE TREATMENT OF DISEASES ASSOCIATED WITH AMYLOID OR AMYLOID-LIKE PROTEINS

(75) Inventors: Heiko Kroth, Ecublens (CH); Cotinica Hamel, Bussigny-pres-Lausanne (CH); Pascal Benderitter, Orbe (CH); Wolfgang Froestl, Ecublens (CH); Nampally Sreenivasachary, Ecublens (CH); Andreas Muhs, Pully/VD (CH)

(73) Assignee: AC Immune SA, Lausanne (CH)

(*) Notice: Subject to any disclaimer, the term of this patent is extended or adjusted under 35 U.S.C. 154(b) by 505 days.

(21) Appl. No.: 13/089,019

(22) Filed: Apr. 18, 2011

(65) Prior Publication Data

US 2011/0280808 A1 Nov. 17, 2011

(30) Foreign Application Priority Data

Apr. 16, 2010 (EP) .................................... 10160223
Nov. 17, 2010 (EP) .................................... 10191616

(51) Int. Cl.

| C07D 491/00 | (2006.01) |
|---|---|
| C07D 498/00 | (2006.01) |
| C07D 513/00 | (2006.01) |
| C07D 515/00 | (2006.01) |
| C07D 471/00 | (2006.01) |
| C07D 209/82 | (2006.01) |
| C07D 209/94 | (2006.01) |
| A61K 31/44 | (2006.01) |
| A61K 31/40 | (2006.01) |
| C07D 471/04 | (2006.01) |
| C07D 209/14 | (2006.01) |
| C07D 401/14 | (2006.01) |
| C07D 495/04 | (2006.01) |

(52) U.S. Cl.
CPC ............ *C07D 471/04* (2013.01); *C07D 209/14* (2013.01); *C07D 401/14* (2013.01); *C07D 495/04* (2013.01)

(58) Field of Classification Search
None
See application file for complete search history.

(56) References Cited

U.S. PATENT DOCUMENTS

| 3,271,416 A * | 9/1966 | Shen et al. ..................... 548/494 |
| 2003/0212073 A1 | 11/2003 | Currie et al. |
| 2009/0099195 A1 | 4/2009 | Bayrakdarian et al. |

FOREIGN PATENT DOCUMENTS

| EP | 2149573 A1 | 2/2010 |
|---|---|---|
| JP | 2000105476 A | 4/2000 |
| JP | 2001506980 A | 5/2001 |
| JP | 2004501152 A | 1/2004 |
| JP | 2007501267 A | 1/2007 |
| JP | 2007099640 A | 4/2007 |
| JP | 2008-513352 A1 | 5/2008 |
| JP | 2010-511653 A1 | 4/2010 |
| WO | WO 96/13590 A2 | 5/1996 |
| WO | WO 96/29605 A2 | 9/1996 |
| WO | WO0168648 A1 | 9/2001 |
| WO | 03099821 A1 | 12/2003 |
| WO | WO 2004/058258 A1 | 7/2004 |
| WO | WO 2006/010008 A1 * | 1/2006 |
| WO | WO2006065277 A2 | 6/2006 |
| WO | WO 2007/002325 A1 * | 1/2007 |
| WO | WO 2007/002433 | 1/2007 |
| WO | WO 2007/068411 A2 | 6/2007 |
| WO | WO 2007/068412 A2 | 6/2007 |
| WO | WO 2008/011348 A2 | 1/2008 |
| WO | WO 2008/124849 A2 * | 10/2008 |
| WO | WO2009087127 A1 | 7/2009 |
| WO | 2009100406 A2 | 8/2009 |
| WO | 2009153180 A1 | 12/2009 |
| WO | 2010000364 A1 | 1/2010 |
| WO | WO 2010/080253 A1 * | 7/2010 |

OTHER PUBLICATIONS

Jong, M. et al. Somatostatin receptor-targeted radionucleotide therapy of tumors: Preclinical and clinical findings. Seminars in Nuclear Medicine. 2002, vol. 32, p. 133, left column, first paragraph.*

Beniaminovitz, A. et al. Prevention of Rejection in Cardiac Transplantation by Blockage of the Interleukin-2 Receptor with a Monoclonal Antibody. The New England Journal of Medicine. 2000, vol. 342, p. 613.*

Boyer, G. et al. Crystal structure of 5-(p-methoxyphenylamino)indane and AM1 calculations on N-arylamines derivatives, precursors of phenothiazine drugs. Journal of Chemical Crystallography. 1998, vol. 28, p. 736, scheme 1.*

Seddon, KR. Pseudopolymorph: A Polemic. Crystal Growth & Design. 2004, vol. 4, p. 1087.*

(Continued)

*Primary Examiner* — Rita Desai
*Assistant Examiner* — Ben S Michelson
(74) *Attorney, Agent, or Firm* — Ian J. Griswold; Johnson, Marcou & Isaacs, LLC

(57) ABSTRACT

The present invention relates to novel compounds that can be employed in the treatment of a group of disorders and abnormalities associated with amyloid protein, such as Alzheimer's disease, and of diseases or conditions associated with amyloid-like proteins. The compounds of the present invention can also be used in the treatment of ocular diseases associated with pathological abnormalities/changes in the tissues of the visual system. The present invention further relates to pharmaceutical compositions comprising these compounds and to the use of these compounds for the preparation of medicaments for treating or preventing diseases or conditions associated with amyloid and/or amyloid-like proteins. A method of treating or preventing diseases or conditions associated with amyloid and/or amyloid-like proteins is also disclosed.

18 Claims, 12 Drawing Sheets

(56) References Cited

OTHER PUBLICATIONS

Kirk-Othmer. Crystallization., John Wlley & Sons, 2002, vol. 8, p. 95.*
Boyer, G. et al. Crystal structure of 5-(p-methoxyphenylamino)indane and AM1 calculations on N-arylamines derivatives, precursors of phenothiazine drugs. Journal of Chemical Crystallography. 1998, vol. 28, p. 736.*
Friedman, OM. et al. Substituted Organosiloxanes as Potential Therapeutics for Treatment and Prevention of Neurodegenerative Diseases. Journal of Alzheimer's Disease. 2007, vol. 11, p. 295.*
Reinke, AA. et al. Structure-Activity Relationships of Amyloid Beta-aggregation Inhibitors Based on Curcumin: Influence of Linker Length and Flexibility. Chem. Biol. Drug Des. 2007, vol. 70, p. 206.*
Westaway, D. et al. The Expanding Universe of Prion Diseases. PLOS Pathogens. 2006, vol. 2, p. 152.*
Mason, JM. et al. Design Strategies for anti-amyloid agents. Current Opinion in Structural Biology. 2003, vol. 13, p. 1.*
Carey, FA. Organic Chemistry 6th Ed. McGraw Hill. 2006, chapter 1, p. 9.*
Patani, KV. et al. Bioisosterism: A Rational Approach in Drug Design. Chem. Rev. 1996, vol. 96, p. 3156.*
Saint-Ruf, G. et al. Synthesis, structure, and biological behavior of indolo[2,3-j]benzacridines and dihydroindolophenarsazines. Bulletin de la Societe Chimique de France. 1974, p. 521.*
Patani, KV. et al. Bioisosterism: A Rational Approach in Drug Design. Chem. Rev. 1996, vol. 96, p. 3153.*
Anderson, DH et al., "Characterization of Beta Amyloid Assemblies in Drusen: the Deposits Associated with Aging and Age-related Macular Degeneration," Experimental Eye Research, 2004, vol. 78, pp. 243-256, abstract.
Ding, J. et al., "Targeting Age-Related Macular Degeneration with Alzheimer's Disease Based Immunotherapies: Anty-Amyloid-b Anitbody Attenuates Pathologies in an Age-Related Macular Degeneration Mouse Model," Vision Research, 2008, pp. 339-345, Epub 2007.
Rzepecki, P. et al., "Prevention of Alzheimer's Disease-associated Aβ Aggregation by Rationally Designed Nonpeptidic β-Sheet Ligands," Journal of Biological Chemistry, 2004, vol. 279, No. 46, pp. 47497-47505.
Garcia, "Colombian Office Action", dated Nov. 21, 2014, for Co-Pending Colombian Patent Application No. 12-207.243, 1-18 pages.
Japanese Office Action dated Apr. 13, 2015 for counterpart Japanese Patent Application No. 2013-504296 (English translation only provided to Applicant), 1-5.
Bronner, et al., "Indolynes as Electrophilic Indole Surrogates: Fundamental Reactivity and Synthetic Applications", Organic Letters, vol. 11, No. 4., 2009, 1007-1010.
Henry, et al., "Potent Inhibitors of the Map Kinase p38", Bioorganic & Medicinal Chemistry Letters, vol. 8, 1998, 3335-3340.
Michinobu, et al., "Nitrogen-linked Aromatic Poly(2,7-carbazale)s: Partially Annulated Poly(m-aniline)s", Chemistry Letters, vol. 36, No. 5, 2007, 620-621.

* cited by examiner

COMPOUNDS FOR THE TREATMENT OF DISEASES ASSOCIATED WITH AMYLOID OR AMYLOID-LIKE PROTEINS

STATEMENT OF RELATED APPLICATIONS

This application claims priority to European application EP 10160223.3 filed Apr. 16, 2010, and European application EP 10191616.1 filed Nov. 17, 2010, the disclosures of which are incorporated by reference in their entirety.

FIELD OF THE INVENTION

The present invention relates to novel compounds that can be employed in the treatment of a group of disorders and abnormalities associated with amyloid protein, such as Alzheimer's disease, and of diseases or conditions associated with amyloid-like proteins. The present invention further relates to pharmaceutical compositions comprising these compounds and to the use of these compounds for the preparation of medicaments for the treatment of diseases or conditions associated with amyloid or amyloid-like proteins. A method of treating diseases or conditions associated with amyloid or amyloid-like proteins is also disclosed.

The compounds of the present invention can also be used in the treatment of ocular diseases associated with pathological abnormalities/changes in the tissues of the visual system, particularly associated with amyloid-beta-related pathological abnormalities/changes in the tissues of the visual system, such as neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration, for example age-related macular degeneration; the optic nerve leading to optic nerve drusen, optic neuropathy and optic neuritis; and the cornea leading to lattice dystrophy.

BACKGROUND OF THE INVENTION

Many diseases of aging are based on or associated with amyloid or amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidosis; the retina, including primary retinal degenerations and macular degeneration, in particular age-related macular degeneration; the optic nerve, including optic nerve drusen, optic neuropathy and optic neuritis; and the cornea, including lattice dystrophy.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators.

Alzheimer's disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved and responsible for the initiation of neuritic plaque formation in AD and to have, therefore, a high pathological potential. There is therefore a need for specific molecules that can target and diffuse amyloid plaque formation.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Mid-stage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after the death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Other diseases that are based on or associated with the accumulation and deposit of amyloid-like protein are mild cognitive impairment, Lewy body dementia (LBD), amyotrophic lateral sclerosis (ALS), inclusion-body myositis (IBM) and macular degeneration, in particular age-related macular degeneration (AMD).

Mild cognitive impairment (MCI) is a general term most commonly defined as a subtle but measurable memory disorder. A person with MCI experiences memory problems greater than normally expected with aging, but does not show other symptoms of dementia, such as impaired judgment or reasoning.

Lewy body dementia (LBD) is a neurodegenerative disorder that can occur in persons older than 65 years of age, which typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta (Experimental Eye Research 78 (2004) 243-256).

Prions cause neurodegenerative diseases such as scrapie in sheep, bovine spongiform encephalopathy in cattle and Creutzfeldt-Jacob disease in humans. The only known component of the particle is the scrapie isoform of the protein, PrPSc. Although prions multiply, there is no evidence that they contain nucleic acid. PrPSc is derived from the non-infectious, cellular protein PrPC by a posttranslational process during which PrPC undergoes a profound conformational change.

The scrapie protein PrPSc has a critical role in neuronal degeneration and during disease development undergoes a three stage transition as follows: PrPC (normal cellular isoform of protein)—PrPSc: infectious form (scrapie isoform of protein)—protein PrP27-30.

Such a cascade of events occurs during the development of Creutzfeldt-Jacob disease (CJD), Kuru, Gerstmann-Straussler-Scheinker Syndrome (GSS), fatal familial insomnia in man, scrapie in sheep and goats, encephalopathy in mink and bovine spongiform encephalopathy in cattle.

The cellular non-toxic protein (PrPC) is a sialoglycoprotein of molecular weight 33000 to 35000 that is expressed predominantly in neurons. In the diseases mentioned above, PrPC is converted into an altered form (PrPSc), which is distinguishable from its normal homologue by its relative resistance to protease digestion. PrPSc accumulates in the central nervous system of affected animals and individuals and its protease-resistant core aggregates extracellularly.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Glaucoma is a group of diseases of the optic nerve involving loss of retinal ganglion cells (RGCs) in a characteristic pattern of optic neuropathy. Glaucoma is often, but not always, accompanied by an increased eye pressure, which may be a result of blockage of the circulation of aqueous or its drainage.

Although raised intraocular pressure is a significant risk factor for developing glaucoma, no threshold of intraocular pressure can be defined which would be determinative for causing glaucoma.

The damage may also be caused by poor blood supply to the vital optic nerve fibers, a weakness in the structure of the nerve, and/or a problem in the health of the nerve fibers themselves.

Untreated glaucoma leads to permanent damage of the optic nerve and resultant visual field loss, which can progress to blindness.

RGCs are the nerve cells that transmit visual signals from the eye to the brain. Caspase-3 and Caspase-8, two major enzymes in the apoptotic process, are activated in the process leading to apoptosis of RGCs. Caspase-3 cleaves amyloid precursor protein (APP) to produce neurotoxic fragments, including Amyloid β. Without the protective effect of APP, Amyloid β accumulation in the retinal ganglion cell layer results in the death of RGCs and irreversible loss of vision.

The different types of glaucomas are classified as open-angle glaucomas, if the condition is chronic, or closed-angle glaucomas, if acute glaucoma occurs suddenly. Glaucoma usually affects both eyes, but the disease can progress more rapidly in one eye than in the other.

Chronic open-angle glaucoma (COAG), also known as primary open angle glaucoma (POAG), is the most common type of glaucoma. COAG is caused by microscopic blockage in the trabecular meshwork, which decreases the drainage of the aqueous outflow into the Schlemm's canal and raises the intraocular pressure (IOP). POAG usually affects both eyes and is strongly associated with age and a positive family history. Its frequency increases in elderly people as the eye drainage mechanism may gradually become clogged with aging. The increase in intraocular pressure in subjects affected by chronic open-angle glaucoma is not accompanied by any symptoms until the loss is felt on the central visual area.

Acute Angle Closure Glaucoma (AACG) or closed-angle glaucoma is a relatively rare type of glaucoma characterized by a sudden increase in intraocular pressure to 35 to 80 mmHg, leading to severe pain and irreversible loss of vision. The sudden pressure increase is caused by the closing of the filtering angle and blockage of the drainage channels. Individuals with narrow angles have an increased risk for a sudden closure of the angle. AACG usually occurs monocularly, but the risk exists in both eyes. Age, cataract and pseudoexfoliation are also risk factors since they are associated with enlargement of the lens and crowding or narrowing of the angle. A sudden glaucoma attack may be associated with severe eye pain and headache, inflamed eye, nausea, vomiting, and blurry vision.

Mixed or Combined Mechanism Glaucoma is a mixture or combination of open and closed angle glaucoma. It affects patients with acute ACG whose angle opens after laser iridotomy, but who continue to require medications for IOP control, as well as patients with POAG or pseudoexfoliative glaucoma who gradually develop narrowing of the angle.

Normal tension glaucoma (NTG), also known as low tension glaucoma (LTG), is characterized by progressive optic nerve damage and loss of peripheral vision similar to that seen in other types of glaucoma; however, the intraocular pressure is in the normal range or even below normal.

Congenital (infantile) glaucoma is a relatively rare, inherited type of open-angle glaucoma. Insufficient development of the drainage area results in increased pressure in the eye that can lead to the loss of vision from optic nerve damage and to an enlarged eye. Early diagnosis and treatment are critical to preserve vision in infants and children affected by the disease.

Secondary glaucoma may result from an ocular injury, inflammation in the iris of the eye (iritis), diabetes, cataract, or use of steroids in steroid-susceptible individuals. Secondary glaucoma may also be associated with retinal detachment or retinal vein occlusion or blockage.

Pigmentary glaucoma is characterized by the detachment of granules of pigment from the iris. The granules cause blockage of the drainage system of the eye, leading to elevated intraocular pressure and damage to the optic nerve.

Exfoliative glaucoma (pseudoexfoliation) is characterized by deposits of flaky material on the anterior capsule and in the angle of the eye. Accumulation of the flaky material blocks the drainage system and raises the eye pressure.

Diagnosis of glaucoma may be made using various tests. Tonometry determines the pressure in the eye by measuring the tone or firmness of its surface. Several types of tonometers are available for this test, the most common being the applanation tonometer. Pachymetry determines the thickness of the cornea which, in turn, measures intraocular pressure. Gonioscopy allows examination of the filtering angle and drainage area of the eye. Gonioscopy can also determine if abnormal blood vessels may be blocking the drainage of the aqueous fluid out of the eye. Ophthalmoscopy allows examination of the optic nerve and can detect nerve fiber layer drop or changes in the optic disc, or indentation (cupping) of this structure, which may be caused by increased intraocular pressure or axonal drop out. Gonioscopy is also useful in assessing damage to the nerve from poor blood flow or increased intraocular pressure. Visual field testing maps the field of vision, subjectively, which may detect signs of glaucomatous damage to the optic nerve. This is represented by specific patterns of visual field loss. Ocular coherence tomography, an objective measure of nerve fiber layer loss, is carried out by looking at the thickness of the optic nerve fiber layer (altered in glaucoma) via a differential in light transmission through damaged axonal tissue.

Optic nerve drusen are globular concretions of protein and calcium salts which are felt to represent secretions through congenitally altered vascular structures affecting the axonal nerve fiber layer. These accumulations occur in the peripapillary nerve fiber layer and are felt to damage the nerve fiber layer either directly by compression or indirectly through disruptions of the vascular supply to the nerve fiber layer. They usually become visible after the first decade of life in affected individuals. They occur most often in both eyes but may also affect one eye, and may cause mild loss of peripheral vision over many years.

Optic neuropathy is a disease characterized by damage to the optic nerve caused by demyelination, blockage of blood supply, nutritional deficiencies, or toxins. Demyelinating optic neuropathies (see optic neuritis below) are typically caused by an underlying demyelinating process such as multiple sclerosis. Blockage of the blood supply, known as ischemic optic neuropathy, can lead to death or dysfunction of optic nerve cells. Non-arteritic ischemic optic neuropathy usually occurs in middle-age people. Risk factors include high blood pressure, diabetes and atherosclerosis. Arteritic ischemic optic neuropathy usually occurs in older people following inflammation of the arteries (arteritis), particularly the temporal artery (temporal arteritis). Loss of vision may be rapid or develop gradually over 2 to 7 days and the damage may be to one or both eyes. In people with optic neuropathy caused by exposure to a toxin or to a nutritional deficiency, both eyes are usually affected.

About 40% of people with non-arteritic ischemic optic neuropathy experience spontaneous improvement over time. Non-arteritic ischemic optic neuropathy is treated by controlling blood pressure, diabetes and cholesterol levels. Arteritic ischemic optic neuropathy is treated with high doses of corticosteroids to prevent loss of vision in the second eye.

Optic neuritis is associated with mild or severe vision loss in one or both eyes and may be caused by a systemic demyelinating process (see above), viral infection, vaccination, meningitis, syphilis, multiple sclerosis and intraocular inflammation (uveitis). Eye movement may be painful and vision may deteriorate with repeat episodes. Diagnosis involves examination of the reactions of the pupils and determining whether the optic disk is swollen. Magnetic resonance imaging (MRI) may show evidence of multiple sclerosis or, rarely, a tumor pressing on the optic nerve, in which case vision improves once the tumor pressure is relieved. Most cases of optic neuritis improve over a few months without treatment. In some cases, treatment with intravenous corticosteroids may be necessary.

A cataract is an opacity that develops in the crystalline lens of the eye or in its envelope. Cataracts typically cause progressive vision loss and may cause blindness if left untreated. In the Morgagnian Cataract, the cataract cortex progressively liquefies to form a milky white fluid and may cause severe inflammation if the lens capsule ruptures and leaks. If left untreated, the cataract may also cause phacomorphic glaucoma. Cataracts may be congenital in nature or caused by genetic factors, advanced age, long-term ultraviolet exposure, exposure to radiation, diabetes, eye injury or physical trauma.

Extra-capsular (ECCE) surgery is the most effective treatment to treat cataract. In the surgery, the lens is removed, but the majority of the lens capsule is left intact. Phacoemulsification, a small incision on the side of the cornea, is typically used to break up the lens before extraction.

Ocular amyloidosis is a hereditary disorder associated with Type I Familial Amyloidotic Polyneuropathy (FAP) and characterized by abnormal conjunctival vessels, keratoconjunctivitis sicca, pupillary abnormalities and, in some cases, vitreous opacities and secondary glaucoma. Type I FAP is associated with mutations in transthyretin (TTR), a tetrameric plasma protein (prealbumin) synthesized in the liver, the retinal pigment epithelium2 and thechoroid plexus of the brain. Different mutations cause transthyretin to polymerize into a pleated structure of amyloid fibril, leading to hereditary amyloidosis. The most frequent mutation is TTR-met303, in which methionine replaces valine at position 30 in transthyretin.

Type IV FAP is associated with lattice corneal dystrophy (LCD). Lattice corneal dystrophy is an inherited, primary, usually bilateral corneal amyloidosis characterized by the presence of refractile lattice lines with a double contour in the corneal stroma. LCD type I (Biber-Haab-Dimmer) is an autosomal dominant, bilaterally symmetrical corneal disorder characterized by the presence of numerous translucent fine lattice lines with white dots and faint haze in the superficial and middle layers of the central stroma. The symptoms start during the first or second decades of life, causing a progressive loss of vision. Most patients require a corneal transplant by 40 years of age. LCD type II is associated with systemic amyloidosis (Meretoja's syndrome) and is characterized by the presence of thick lattice lines in the limbus, central cornea and stroma. Vision is not affected until later in life. LCD type III affects middle-age people and is characterized by the presence of thick lattice lines that extend from limbus to limbus. LCD type III A is characterized by the accumulation of amyloid deposits in the stroma and the presence of ribbons of amyloid between the stroma and Bowman's layer. LCD type III A differs from LCD type III because of the presence of corneal erosions, the occurrence in whites and the autosomal dominant inheritance pattern.

Down's Syndrome (DS) or trisomy 21 is the most common genetic disorder with an incidence of about 1:700 live births, and is often associated with various congenital anomalies. The disorder, which is caused by the presence of an extra chromosome 21, is associated with premature deposits of the plaque-forming protein amyloid-beta and development of Alzheimer's disease by middle age. Furthermore, many people affected by DS suffer from cataracts beginning in childhood and many suffer from congenital glaucoma. Since the gene for amyloid precursor protein, which is cleaved to form amyloid beta, is located on the long arm of chromosome 21 in humans, overexpression of this gene may lead to increased levels of amyloid precursor protein and amyloid deposition in Down's syndrome.

There is no cure for glaucoma. Medications for the treatment of glaucoma include agents that decrease production of the aqueous humor in the eye, such as beta blockers (Timoptic, Betoptic), carbonic anhydrase inhibitors (Trusopt, Azopt), and alpha agonists (Alphagan, Iopidine), and agents that redirect drainage of the aqueous humor through a different pathway at the back of the eye, such as prostaglandin (Xalatan). Laser surgeries include trabeculoplasty, a procedure that helps the aqueous humor leave the eye more efficiently. According to the Glaucoma Foundation, nearly 80% of the patients respond well enough to the procedure to delay or avoid further surgery. However, pressure increases again in the eyes of half of all patients within two years after laser surgery, according to the National Eye Institute. Incisional surgery is performed if medication and initial laser treatments are unsuccessful in reducing pressure within the eye. One type of surgery, a trabeculectomy, creates an opening in the wall of the eye so that aqueous humor can drain. However, about one-third of trabeculectomy patients develop cataracts within five years, according to the Glaucoma Foundation. If the trabeculectomy fails, additional incisional procedures include placing a drainage tube into the eye between the cornea and iris and the use of a laser or freezing treatment to destroy tissue in the eye that makes aqueous humor. Surgery may save the remaining vision in the patient, but it does not improve sight. Vision may actually be worse following surgery.

Age-related macular degeneration (AMD) is a major cause of blindness among Caucasians over age 65. Although much progress has been made recently in macular degeneration research, there are no treatments that rescue neuronal cell death that occurs during the course of the disease. There are also no definitive treatments for other ocular diseases associated with amyloid beta-related neuronal degradation, such as cortical visual deficits, optic nerve drusen, optic neuropathy, optic neuritis, ocular amyloidosis and lattice dystrophy.

Amyloid deposits typically contain three components. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulphated glycosaminoglycans (GAG), complex carbohydrates of connective tissue.

One development towards the treatment of Alzheimer's disease and prion diseases has been the design of molecules that bind the abnormal β-sheet conformation of Aβ and PrP, respectively, thereby preventing aggregation of these molecules. The β-sheet conformation of peptides is characterized in that hydrogen bonds are formed in a regular pattern between neighboring amino acid strands. This arrangement leads to a stable three dimensional structure. H-bond acceptors (C=O group) and H-bond donors (NH group) alternate in naturally occurring β-sheet peptides with the atoms to be bonded being roughly in one line. Within each amino acid strand, the distances between neighboring H-bond donors and H-bond acceptors fall within specific ranges. In particular, the distance between the H-bond donor (NH group) and the H-bond acceptor (C=O group) within one amino acid residue is from 3.5 to 4.0 Å. The distance between the H-bond acceptor (C=O group) of one amino acid residue and the H-bond donor (NH group) of the following amino acid residue participating in the inter-strand bonding is from 2.6 to 2.9 Å. In other words, the distances between neighboring H-bond donors and H-bond acceptors within one amino acid strand alternate between the following ranges:

H-bond donor (amino acid 1)–H-bond acceptor (amino acid 1)=3.5 to 4.0 Å;

H-bond acceptor (amino acid 1)–H-bond donor 2 (amino acid 2)=2.6 to 2.9 Å.

Ligands that are designed to bind β-sheets ideally have an order of H-bond donors and H-bond acceptors that is complementary to the order of H-bond donors and H-bond acceptors in the amino acid strands of the β-sheet.

WO 2007/002433 describes certain pyrrolo[2,3-B]pyridine derivatives which are stated to be suitable as protein kinase inhibitors.

It was an object of the present invention to provide compounds that can be employed in the treatment of diseases or conditions associated with amyloid or amyloid-like proteins, including amyloidosis. The compounds should be able to pass the blood-brain barrier. Furthermore, they should be pharmaceutically acceptable, in particular, they should not have mutagenic or carcinogenic properties or be metabolically unstable.

A further object of the invention is to provide improved treatment options for subjects affected by ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration, for example age-related macular degeneration; the optic nerve leading to optic nerve drusen, optic neuropathy and optic neuritis; and the cornea leading to lattice dystrophy.

The present inventors have surprisingly found that these objects can be achieved by the compounds of the general formula (I) as described hereinafter.

SUMMARY OF THE INVENTION

Accordingly, the present invention relates to a compound of general formula (I).

In a further aspect, the present invention relates to a pharmaceutical composition or a radiopharmaceutical formulation comprising a compound of general formula (I).

Yet another aspect of the present invention relates to the use of a compound of general formula (I) for the preparation of a medicament for the treatment of diseases or conditions associated with amyloid or amyloid-like proteins, including amyloidosis.

Also disclosed herein is a method of treating diseases or conditions associated with amyloid or amyloid-like proteins, comprising administering to a subject in need of such treatment an effective amount of a compound of general formula (I).

Yet another aspect of the present invention relates to the use of a compound of general formula (I) for the preparation of a medicament for treating or alleviating the effects of ocular diseases associated with pathological abnormalities/changes in the tissues of the visual system.

Also disclosed herein is a method of treating or alleviating the effects of ocular diseases associated with pathological abnormalities/changes in the tissues of the visual system comprising administering to a subject in need of such treatment an effective amount of a compound of general formula (I).

The ocular diseases associated with pathological abnormalities/changes in the tissues of the visual system are particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration, for example age-related macular degeneration; the optic nerve leading to optic nerve drusen, optic neuropathy and optic neuritis; and the cornea leading to lattice dystrophy.

In a further aspect the invention relates to a mixture (such as a pharmaceutical composition) comprising a compound according to the present invention and optionally at least one further biologically active compound and/or a pharmaceutically acceptable carrier and/or a diluent and/or an excipient. The further biologically active substance can be a known compound used in the medication of diseases and disorders which are caused by or associated with amyloid or amyloid-like proteins including amyloidosis, a group of diseases and disorders associated with amyloid or amyloid-like protein such as the Aβ protein involved in Alzheimer's disease.

The further biologically active substance or compound may exert its biological effect by the same or a similar mechanism as the compound according to the invention or by an unrelated mechanism of action or by a multiplicity of related and/or unrelated mechanisms of action.

A method of collecting data for the diagnosis of an amyloid-associated disease or condition in a sample or a patient is also disclosed which comprises:
(a) bringing a sample or a specific body part or body area suspected to contain an amyloid protein into contact with a compound according to the present invention;
(b) allowing the compound to bind to the amyloid protein;
(c) detecting the compound bound to the protein; and
(d) optionally correlating the presence or absence of compound binding with the amyloid protein with the presence or absence of amyloid protein in the sample or specific body part or area.

Another embodiment of the present invention is a method of determining the extent of amyloidogenic plaque burden in a tissue and/or a body fluid comprising:
(a) providing a sample representative of the tissue and/or body fluid under investigation;
(b) testing the sample for the presence of amyloid protein with a compound according to the present invention;
(c) determining the amount of compound bound to the amyloid protein; and
(d) calculating the plaque burden in the tissue and/or body fluid.

A further aspect relates to a method of collecting data for determining a predisposition to an amyloid-associated disease or condition in a patient comprising detecting the specific binding of a compound according to the present invention to an amyloid protein in a sample or in situ which comprises the steps of:
(a) bringing the sample or a specific body part or body area suspected to contain the amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or area; and
(e) optionally comparing the amount of the compound/protein complex to a normal control value.

Yet another aspect of the present invention is a method of collecting data for monitoring minimal residual disease in a patient following treatment with an antibody or a vaccine composition, wherein the method comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A method of collecting data for predicting responsiveness of a patient being treated with an antibody or a vaccine composition is also described which comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A further aspect of the present invention is a test kit for detection and diagnosis of an amyloid-associated disease or condition comprising a compound according to the present invention.

In another aspect of the present invention a compound according to the present invention is for use in inhibiting protein aggregation, in particular for use in inhibiting Aβ1-42 aggregation, Tau aggregation or alpha-synuclein aggregation In one aspect of the invention the use of the compound according to the present invention is disclosed for the preparation of a medicament for (a) reducing the β-amyloid plaque load, and/or (b) inhibiting the formation of β-amyloid plaques and/or (c) retarding the increase of amyloid load in the brain of a patient.

A further embodiment of the invention provides a method of (a) reducing the β-amyloid plaque load, and/or (b) inhibiting the formation of β-amyloid plaques and/or (c) retarding the increase of amyloid load in the brain of a subject comprising administering to a subject in need of such treatment an effective amount of a compound according to the present invention.

In yet another embodiment a compound according to the present invention is for use in (a) the reduction of the β-amyloid plaque load, and/or (b) the inhibition of the formation of β-amyloid plaques and/or (c) the retardation of the increase of amyloid load in the brain of a patient.

According to a further aspect the present invention relates to the use of the compound according to the present invention for the preparation of a medicament for retaining or increasing cognitive memory capacity in a subject suffering from memory impairment.

According to another aspect the present invention provides a method of retaining or increasing cognitive memory capacity in a subject suffering from memory impairment comprising administering to a subject in need of such treatment an effective amount of a compound according to the present invention.

Yet another aspect of the present invention relates to a compound according to the present invention for use in the retention or increase of cognitive memory capacity in a subject suffering from memory impairment.

Preferred embodiments of the invention are summarized in the dependent claims.

The individual compounds which are known from WO 2007/002433 are not included in the scope of the claims relating to the compounds or the pharmaceutical composition. The compounds are, for example, listed in the following:

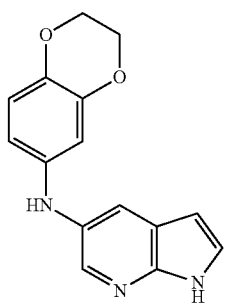

-continued

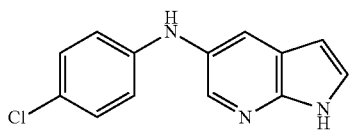

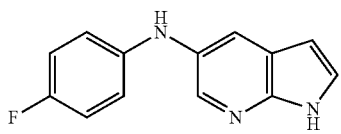

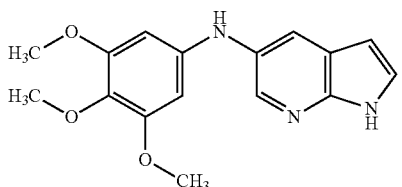

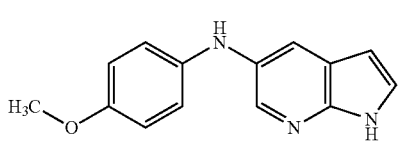

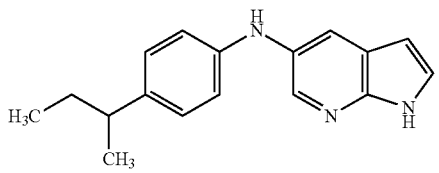

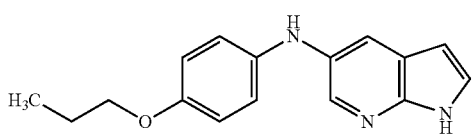

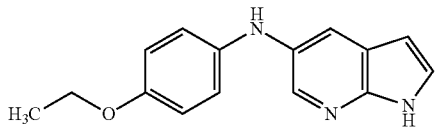

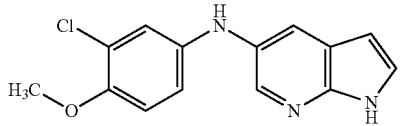

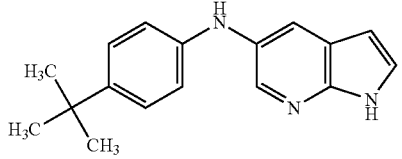

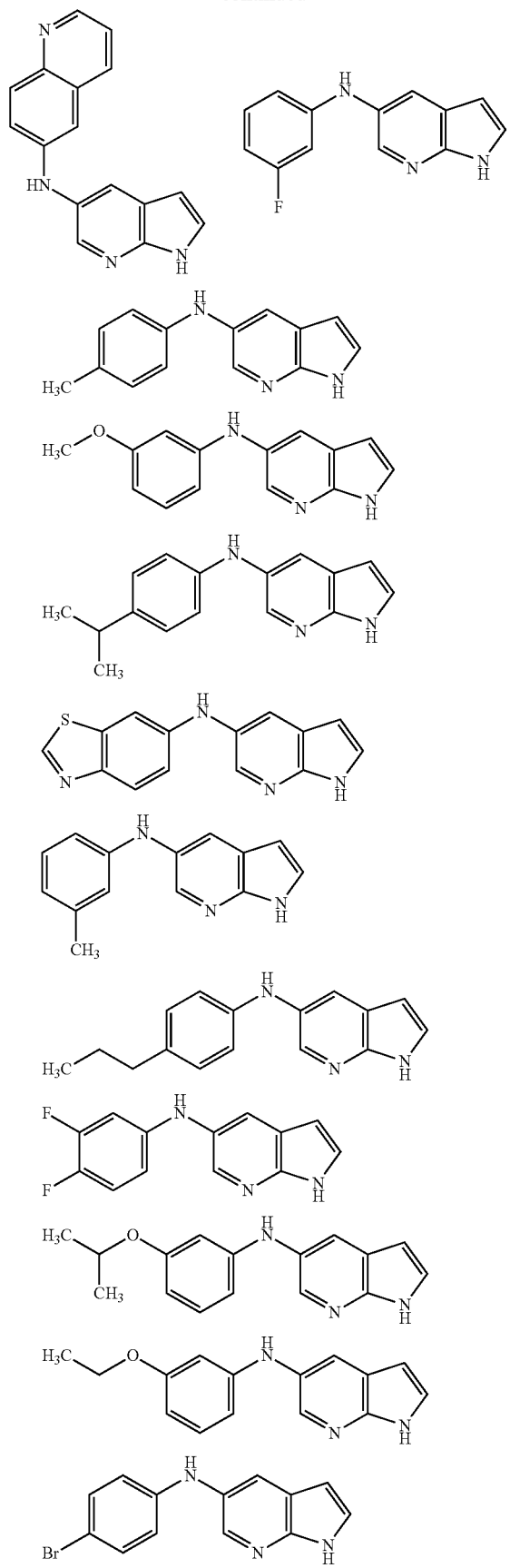
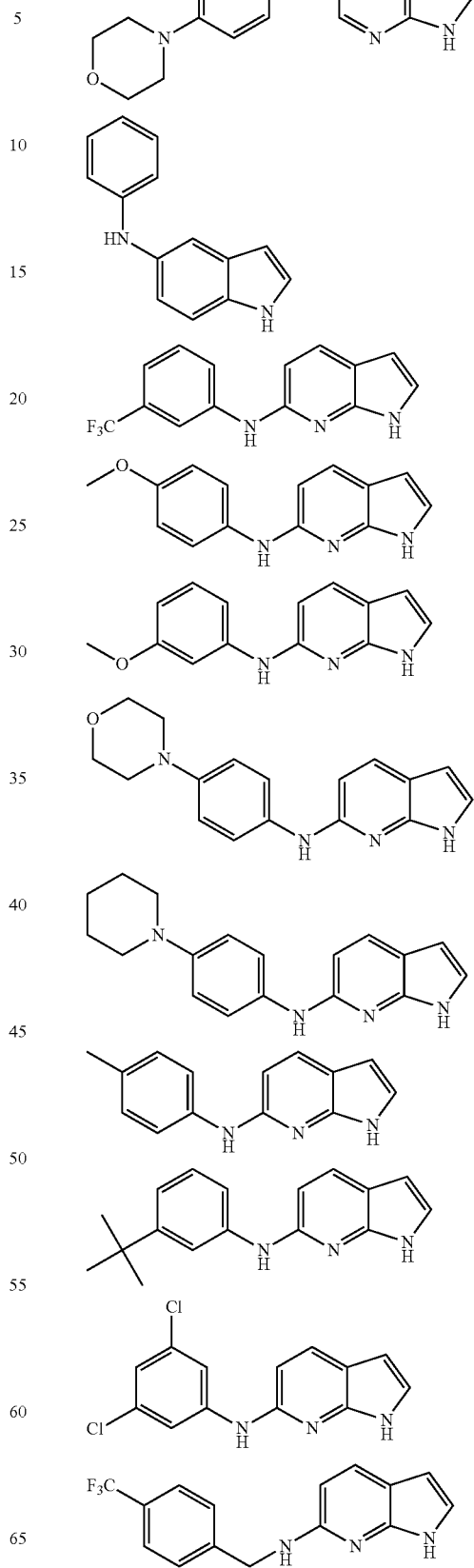

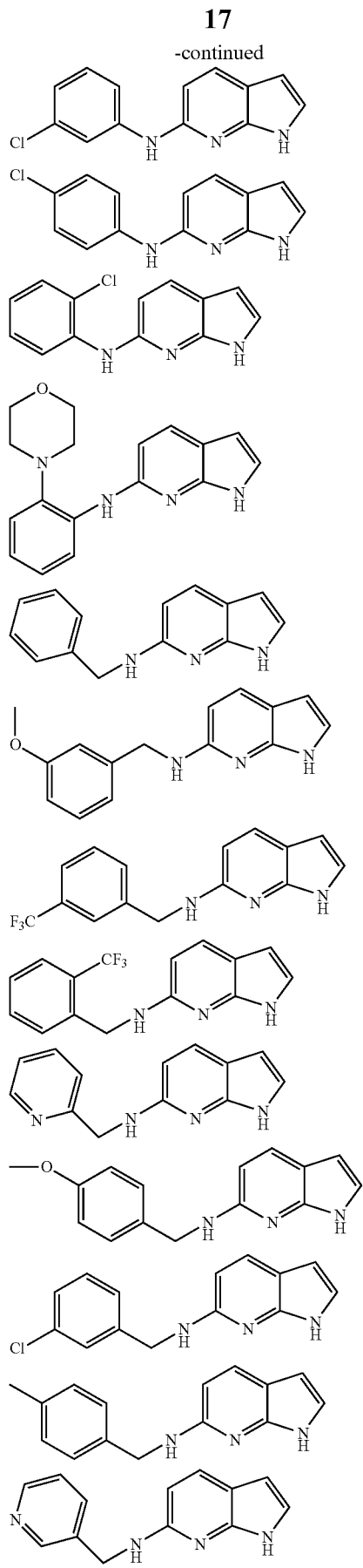
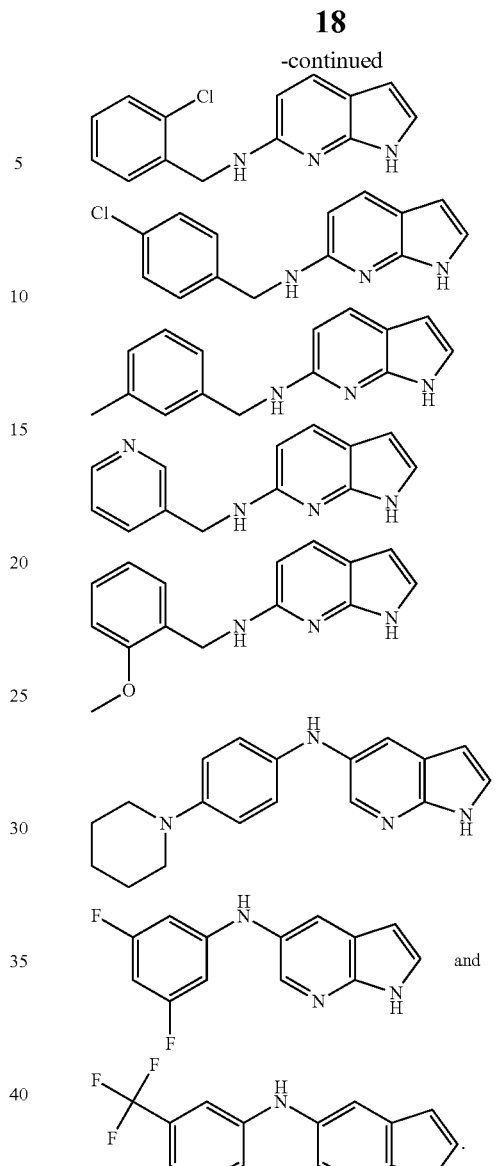

These compounds can be included in the scope of the other claims or they can be disclaimed from the scope of the other claims. The compounds can be disclaimed either alone, in combination of two or more or all of the compounds can be disclaimed from any of the other claims.

DEFINITIONS

Figure 1:
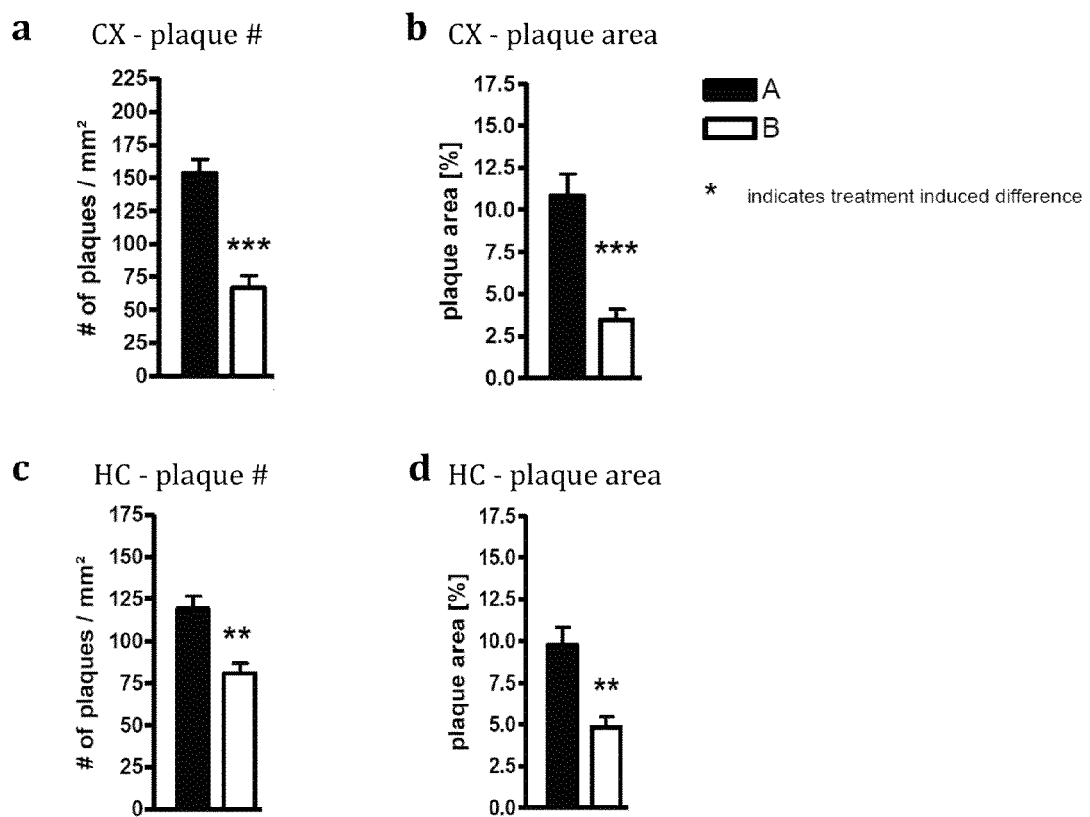
FIG. 1 shows the quantification of cortical (a and b) and hippocampal (c and d) 6E10 immunofluorescence.

Within the meaning of the present application the following definitions apply:

"Alkyl" refers to a saturated organic moiety consisting of carbon and hydrogen atoms. Examples of suitable alkyl groups have 1 to 6 carbon atoms, preferably 1 to 4 carbon atoms, and include methyl, ethyl, propyl and butyl.

"Cycloalkyl" refers to a cyclic organic moiety consisting of carbon and hydrogen atoms. Examples of suitable alkyl groups have 5 to 10 carbon atoms, preferably 5 or 6 carbon atoms, and include cyclopentyl and cyclohexyl.

"Heterocycloalkyl" refers to a cycloalkyl group as defined above in which at least one of the carbon atoms has been replaced by a heteroatom which is, e.g., selected from N, O or S, or heteroatom (e.g., N, O and/or S)-containing moiety. Examples of possible heterocycloalkyl groups include pyrrolidine, tetrahydrofuran, piperidine, etc.

"Alkenyl" refers to an organic moiety consisting of carbon and hydrogen atoms which includes at least one double bond. Examples of suitable alkenyl groups have 2 to 6 carbon atoms, preferably 2 to 4 carbon atoms, and include propenyl and butenyl.

"Alkynyl" refers to an organic moiety consisting of carbon and hydrogen atoms which includes at least one triple bond. Examples of suitable alkinyl groups have 2 to 6 carbon atoms, preferably 2 to 4 carbon atoms, and include propinyl and butinyl.

"Aryl" refers to an aromatic organic moiety consisting of carbon and hydrogen atoms which preferably has 5 to 10 carbon atoms, more preferably 5 or 6 carbon atoms. An example is a phenyl ring.

"Heteroaryl" refers to an aryl group as defined above in which at least one of the carbon atoms has been replaced by a heteroatom which is, e.g., selected from N, O or S, or heteroatom (e.g., N, O and/or S)-containing moiety. Examples of possible heteroaryl groups include pyridine, etc.

"Alkoxy" refers to the group —O-alkyl.

"Aminoalkyl" refers to the group -alkyl-$NR^1R^2$.

"Hal" or "halogen" refers to F, Cl, Br, and I. Preferred Hal are F and Cl, more preferably F.

"Arylalkyl" refers to a group aryl-alkyl-.

"Cycloalkylalkyl" refers to a group cycloalkyl-alkyl-.

"Fluoroalkyl" refers to an alkyl group in which one or more hydrogen atoms have been replaced by fluoro atoms.

"Haloalkyl" refers to an alkyl group in which one or more hydrogen atoms have been replaced by halogen atoms.

"Heteroarylalkyl" refers to a group heteroaryl-alkyl-.

"Heterocycloalkylalkyl" refers to a group heterocycloalkyl-alkyl-.

"Heteroatom-containing moieties are moieties which contain e.g., N, O and/or S. Examples of such moieties include —C(O)—, —C(O)O— and —N($R^{50}$)— in which $R^{50}$ is, for each occurrence, independently selected from the group consisting of $R^{20}$, $S(O)_rNR^{20}R^{21}$, $S(O)_rR^{20}$, $C(O)$ $OR^{20}$, $C(O)R^{20}C(=NR^a)NR^{20}R^{21}$, $C(=NR^{20})NR^{21}R^a$, $C(=NOR^{20})R^{21}$ and $C(O)NR^{20}R^{21}$. Specific examples include —C(O)—, —C(O)O— and —N($R^{50}$)— in which $R^{50}$ is, for each occurrence, independently selected from the group consisting of H or $C_{1-4}$ alkyl.

If a group is defined as being "optionally substituted" it can have one or more substituents selected from Hal, $C_{1-6}$ alkyl, $C_{1-6}$ alkoxy, —$SO_2$-alkyl, —$NH_2$, —NH($C_{1-6}$ alkyl) or —N($C_{1-6}$ alkyl)$_2$.

Compounds of the present invention having one or more optically active carbons can exist as racemates and racemic mixtures, stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all salt forms, polymorphs, hydrates and solvates.

The solvent included in the solvates is not particularly limited and can be any pharmaceutically acceptable solvent. Examples include water and $C_{1-4}$ alcohols (such as methanol or ethanol).

The patients or subjects which can be treated in the present invention are typically animals, particularly mammals, more particularly humans.

The preferred definitions given in the "Definition"-section apply to all of the embodiments described below unless stated otherwise.

DETAILED DESCRIPTION OF THE INVENTION

The present invention relates to a compound of formula (I):

$$A-L_1-B \quad (I)$$

and all stereoisomers, racemic mixtures, pharmaceutically acceptable salts, hydrates, solvates and polymorphs thereof.

A is selected from the group consisting of:

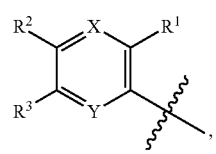

(i)

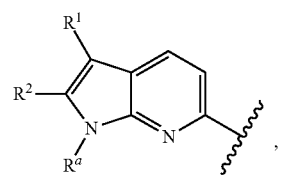

(ii)

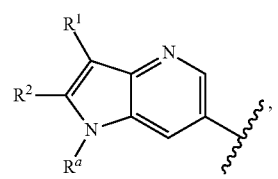

(iii)

-continued

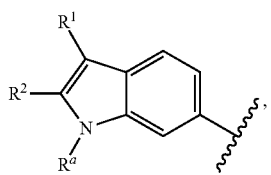
(iv)

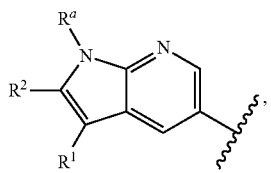
(v)

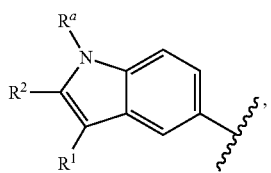
(vi)

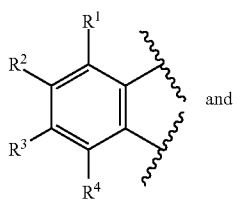
(vii)

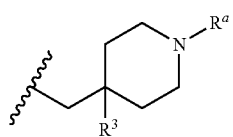
(viii)

$L_1$ is directionally selected from the group consisting of:

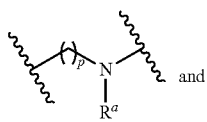
(a)

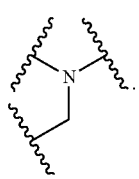
(b)

The term "directionally" means that the bond shown on the left of formula (a) and the two bonds shown on the left of formula (b) are bound to A, while the bond shown on the right of formula (a) and the bond shown on the right of formula (b) are bound to B. As is immediately evident to a skilled person, formula (b) is only to be combined with formula (vii) as the option of A. In a preferred embodiment $L_1$ is (a).

B is selected from the group consisting of:

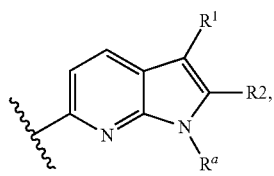
(ix)

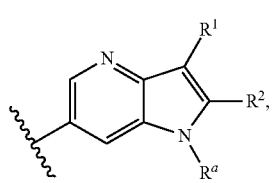
(x)

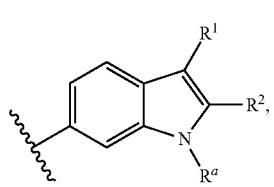
(xi)

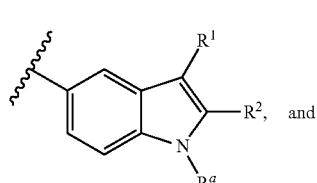
(xii)

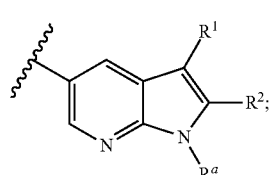
(xii)

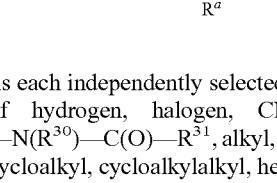
(xiii)

$R^1$ is each independently selected from the group consisting of hydrogen, halogen, CN, $CF_3$, —$CONR^{30}R^{31}$, —$N(R^{30})$—C(O)—$R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted. In a preferred embodiment $R^1$ is each independently selected from hydrogen, halogen (such as F), CN, $CF_3$, —$CONR^{30}R^{31}$, —$N(R^{30})$—C(O)—$R^{31}$, —O-alkyl, heterocycloalkyl (such as

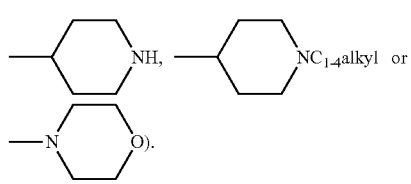
).

More preferably $R^1$ is each independently selected from hydrogen, F, CN, $CF_3$,

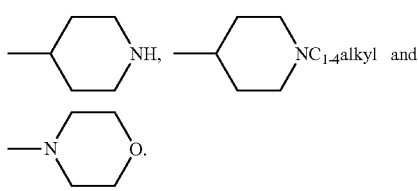

$R^2$ is each independently selected from the group consisting of hydrogen, halogen, CN, $CF_3$, —$CONR^{30}R^{31}$, —$N(R^{30})$—C(O)—$R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted. In a preferred embodiment $R^2$ is each independently selected from hydrogen, halogen (such as F), CN, $CF_3$, —$CONR^{30}R^{31}$, —$N(R^{30})$—C(O)—$R^{31}$, —O-alkyl heterocycloalkyl (such as

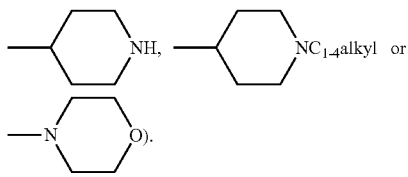

In a preferred embodiment $R^2$ is each independently selected from hydrogen, F, CN, $CF_3$, $CONR^{30}R^{31}$, —O-alkyl,

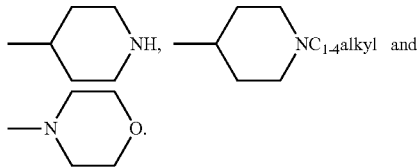

$R^3$ is each independently selected from the group consisting of hydrogen, halogen, CN, $CF_3$, —$CONR^{30}R^{31}$, —$N(R^{30})$—C(O)—$R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl and heteroarylalkyl can be optionally substituted. In a preferred embodiment $R^3$ is each independently selected from hydrogen, halogen (such as F), CN, $CF_3$, —$CONR^{30}R^{31}$, —$N(R^{30})$—C(O)—$R^{31}$, —O-alkyl, heterocycloalkyl (such as

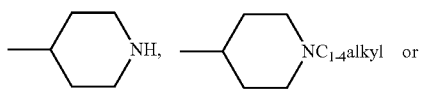

-continued

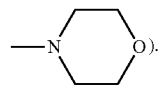

More preferably $R^3$ is each independently selected from hydrogen, F, —O-alkyl, $CF_3$,

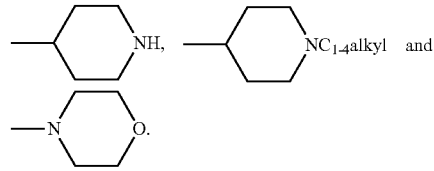

$R^4$ is each independently selected from the group consisting of hydrogen, halogen, CN, $CF_3$, —$CONR^{30}R^{31}$, —$N(R^{30})$—C(O)—$R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted. In a preferred embodiment $R^4$ is each independently selected from hydrogen, halogen (such as F), CN, $CF_3$, —$CONR^{30}R^{31}$, —$N(R^{30})$—C(O)—$R^{31}$, —O-alkyl, heterocycloalkyl (such as

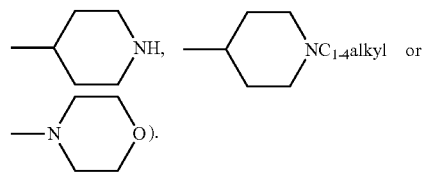

More preferably $R^4$ is hydrogen.

In a further embodiment if any of the groups $R^1/R^2/R^3/R^4$ are adjacent, they can optionally be taken together and can form a 5- to 8-membered ring containing carbon atoms and optionally one or more heteroatoms selected from O, S, or N or a heteroatom (N, O and/or S)-containing moiety wherein the 5- to 8-membered ring may be substituted by $NR^{20}R^{21}$ or —O-alkyl, wherein the alkyl can be optionally substituted, or by

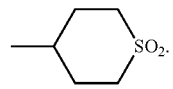

In one embodiment $R^1$ and $R^2$ when taken together can form a 5- to 8-membered ring containing carbon atoms such as a 6-membered carbocyclic ring. The ring can be saturated or include one or more double bonds (including aromatic rings). Examples of the groups which form a ring are —$(CH_2)_3$— (i.e., a saturated 5-membered ring), —$(CH_2)_4$—, —O—$(CH_2)$—O—. These rings can be optionally substituted.

Examples of the optional substituents of the 5- to 8-membered ring include —O-alkyl, —O-alkyl-Hal, —O-alkyl-O-alkyl, —NH-alkyl-O-alkyl, and -alkyl-$SO_2$alkyl.

$R^a$ is each independently selected from the group consisting of hydrogen, alkyl, haloalkyl, $S(O)_tNR^{30}R^{31}$, $S(O)_tR^{30}$, $C(O)OR^{30}$, $C(O)R^{30}$, and $C(O)NR^{30}R^{31}$. In a preferred embodiment $R^a$ is hydrogen or alkyl.

For each occurrence $R^b$ is each independently selected from the group consisting of: hydrogen, halogen, CN, $CF_3$, $CONR^{30}R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted. In a preferred embodiment $R^b$ is hydrogen, halogen (such as F), $CONR^{30}R^{31}$ or alkyl.

For each occurrence $R^{20}$ is each independently selected from the group consisting of: hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted. In a preferred embodiment $R^{20}$ is hydrogen or alkyl.

For each occurrence $R^{21}$ is each independently selected from the group consisting of: hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted. In a preferred embodiment $R^{21}$ is hydrogen or alkyl.

In one embodiment $R^{20}$ and $R^{21}$ when taken together with the nitrogen to which they are attached can form a 3- to 8-membered ring containing carbon atoms and optionally one or more further heteroatoms selected from O, S, or N or a heteroatom (N, O and/or S)-containing moiety and wherein the 3- to 8-membered ring may be optionally substituted. The ring can be saturated or include one or more double bonds (including aromatic rings). In one embodiment the ring is carbocyclic apart from the nitrogen atom to which $R^{20}$ and $R^{21}$ are attached. In a different embodiment the ring includes one further heteroatom (such as N or O) in addition to the nitrogen atom to which $R^{20}$ and $R^{21}$ are attached.

For each occurrence $R^{30}$ is each independently selected from the group consisting of: hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted. In a preferred embodiment $R^{30}$ is hydrogen or alkyl.

For each occurrence $R^{31}$ is each independently selected from the group consisting of: hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted. In a preferred embodiment $R^{31}$ is hydrogen or alkyl.

When a nitrogen atom is present in the ring formed by $R^1/R^2/R^3/R^4$ or the ring formed by $R^{20}$ and $R^{21}$, it can be in any suitable form. Possible forms include —$N(R^{50})$—, and —N=.

X is each independently selected from the group consisting of $CR^b$ and N.

Y is each independently selected from the group consisting of $CR^b$ and N.

t is 1 or 2.

p is 0, 1 or 2. In one embodiment p is 0.

In a preferred embodiment A is selected from the group consisting of:

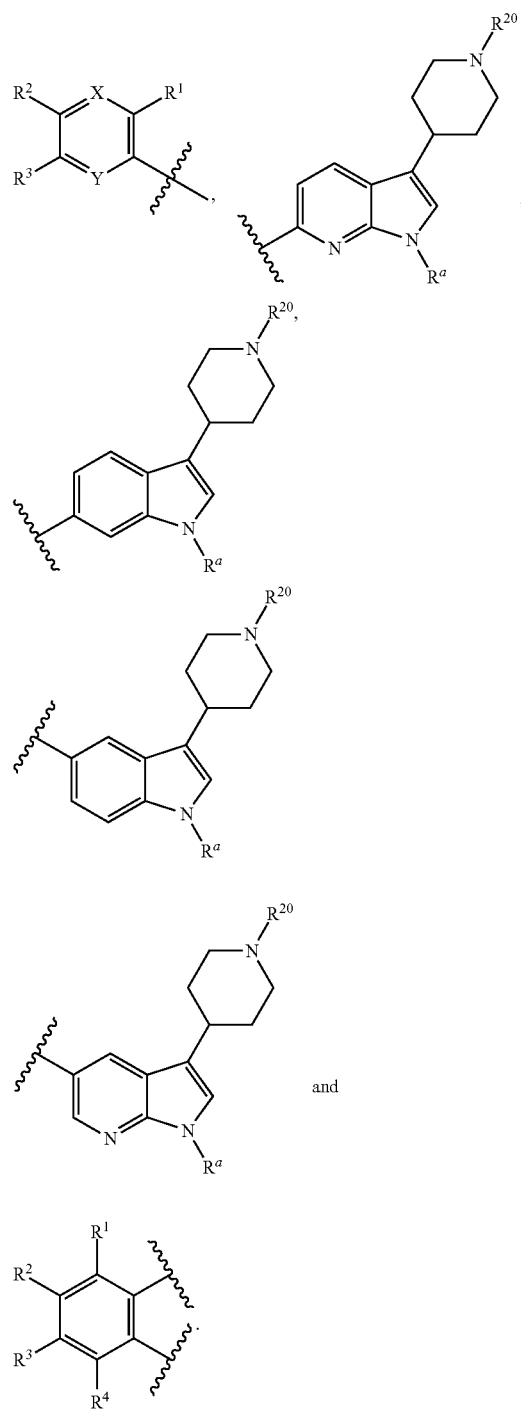

$L_1$ is

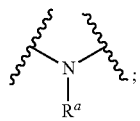

B is selected from the group consisting of:

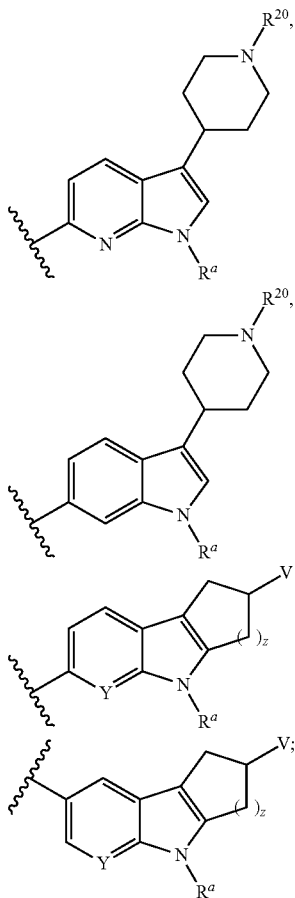

wherein:
$R^1$, $R^2$, $R^3$, $R^4$, $R^a$, $R^{20}$, X and Y have the same meanings as above;
V is absent or $NR^{20}R^{21}$ and
z is 1 or 2.

Any combination of the above mentioned definitions is also envisaged in the present specification.

In one embodiment A has the formula (i)

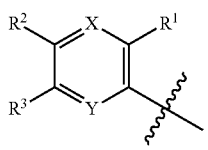

Preferred embodiments of the formula (i) include

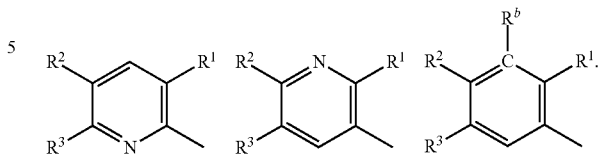

In one preferred embodiment the formula (i) is

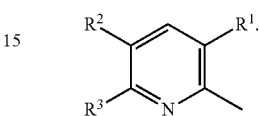

In another preferred embodiment the formula (i) is

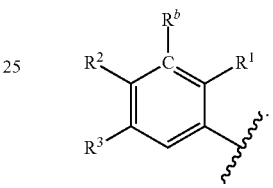

In this embodiment $R^1$, $R^2$, $R^3$ and $R^b$ are as defined above.

In one embodiment A has the formula (ii)

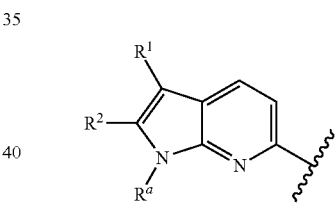

Preferred embodiments of the formula (ii) include those in which $R^a$ is hydrogen or $C_{1-4}$ alkyl. In further preferred embodiments $R^1$ and $R^2$ are hydrogen or preferably $R^1$ and $R^2$ together form —$(CH_2)_4$—. In an alternative embodiment $R^2$ and $R^a$ are hydrogen and $R^1$ is

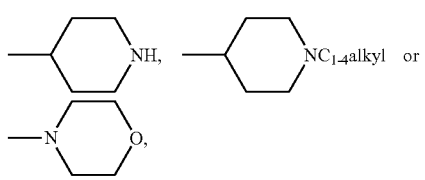

preferably $R^2$ and $R^a$ are hydrogen and $R^1$ is

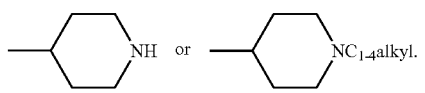

In one embodiment A has the formula (iii)

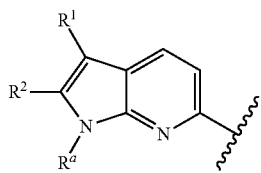

Preferred embodiments of the formula (iii) include those in which $R^a$ is hydrogen or $C_{1-4}$ alkyl. In further preferred embodiments $R^1$ and $R^2$ are hydrogen or preferably $R^2$ is hydrogen and $R^1$ is

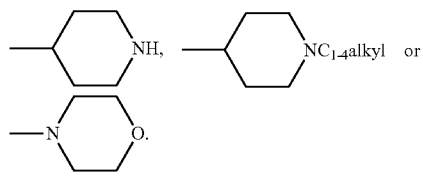

In one preferred embodiment preferably $R^2$ is hydrogen and $R^1$ is

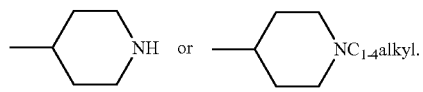

In one embodiment A has the formula (iv)

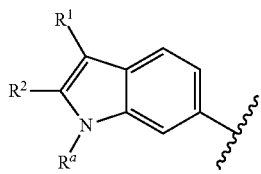

Preferred embodiments of the formula (iv) include those in which $R^a$ is hydrogen or $C_{1-4}$ alkyl. In further preferred embodiments $R^1$ and $R^2$ are hydrogen or preferably $R^2$ is hydrogen and $R^1$ is

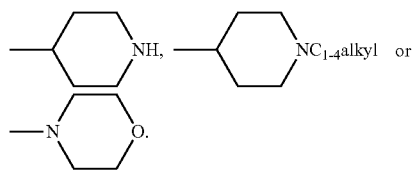

In one preferred embodiment preferably $R^2$ is hydrogen and $R^1$ is

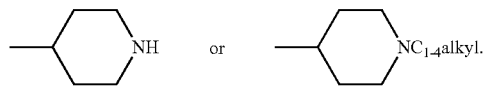

In one embodiment A has the formula (v)

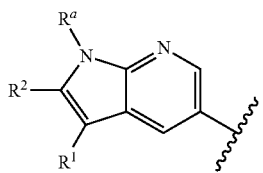

Preferred embodiments of the formula (v) include those in which $R^a$ is hydrogen or $C_{1-4}$ alkyl. In further preferred embodiments $R^1$ and $R^2$ are hydrogen or preferably $R^2$ is hydrogen and $R^1$ is

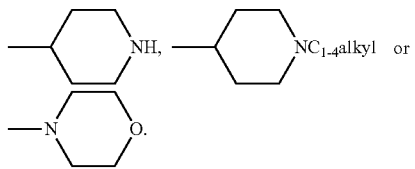

In one preferred embodiment preferably $R^2$ is hydrogen and $R^1$ is

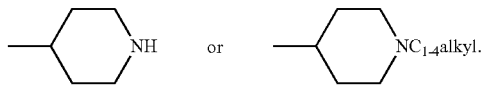

In one embodiment A has the formula (vi)

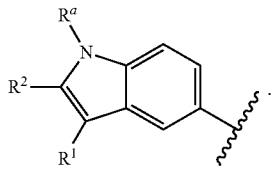

Preferred embodiments of the formula (vi) include those in which $R^a$ is hydrogen or $C_{1-4}$ alkyl. In further preferred embodiments $R^1$ and $R^2$ are hydrogen or preferably $R^2$ is hydrogen and $R^1$ is

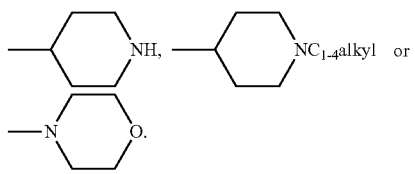

In one preferred embodiment preferably $R^2$ is hydrogen and $R^1$ is

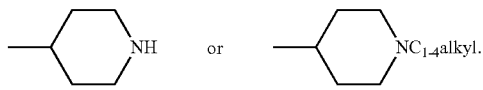

In one embodiment A has the formula (vii)

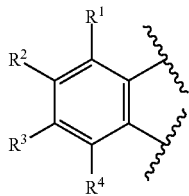

Preferred embodiments of the formula (vii) include that in which $R^1$, $R^2$, $R^3$ and $R^4$ are hydrogen. Further preferred embodiments of the formula (vii) include

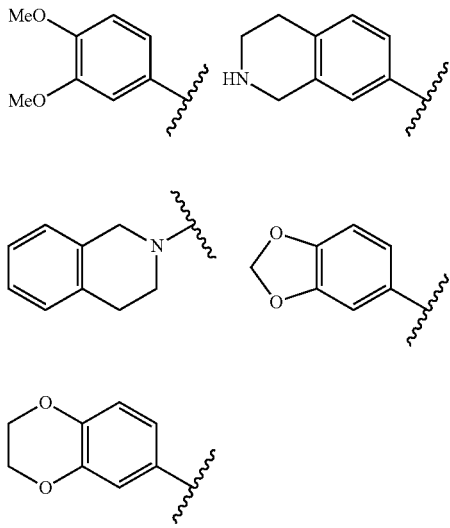

In one embodiment A has the formula (viii)

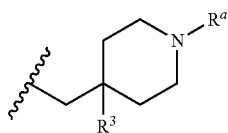

Preferred embodiments of the formula (viii) include that in which $R^3$ is F and $R^a$ is hydrogen or in which $R^3$ and $R^a$ are hydrogen.

In one embodiment $L_1$ has the formula (a)

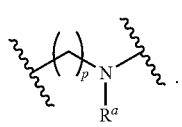

(a)

In a preferred embodiment p=0.

In one embodiment B has the formula (ix)

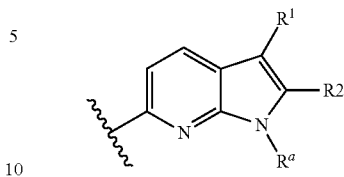

Preferred embodiments of (ix) include those in which $R^a$ is hydrogen or $C_{1-4}$ alkyl. In further preferred embodiments $R^1$ and $R^2$ are hydrogen. In further preferred embodiments $R^1$ is as defined in the general definition above (examples are CN, —COO($C_{1-4}$ alkyl),

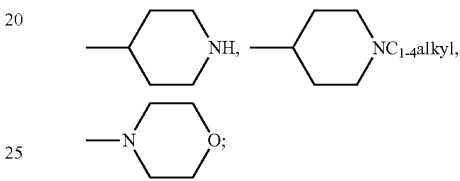

more preferably CN,

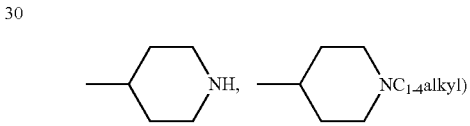

and $R^2$ is hydrogen. In further preferred embodiments $R^1$ and $R^2$ can form a ring which is optionally substituted. Examples of $R^1$ and $R^2$ which form a ring are —(CH$_2$)$_3$— and —(CH$_2$)$_4$— which can be optionally substituted.

In one embodiment B has the formula (x)

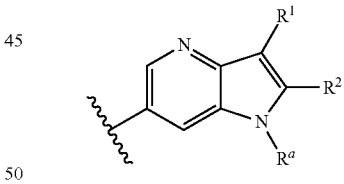

Preferred embodiments of (x) include those in which $R^a$ is hydrogen or $C_{1-4}$ alkyl. In further preferred embodiments $R^1$ and $R^2$ are hydrogen. In further preferred embodiments $R^1$ is as defined in the general definition above (examples are CN, —COO($C_{1-4}$ alkyl),

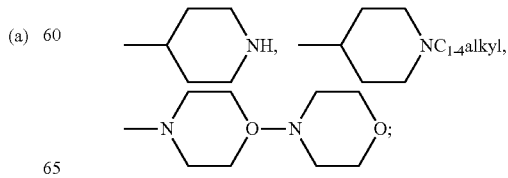

more preferably CN,

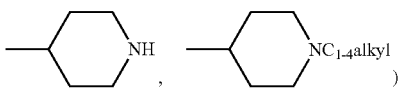

and R² is hydrogen. In further preferred embodiments R¹ and R² can form a ring which is optionally substituted. Examples of R¹ and R² which form a ring are —(CH₂)₃— and —(CH₂)₄— which can be optionally substituted.

In one embodiment B has the formula (xi)

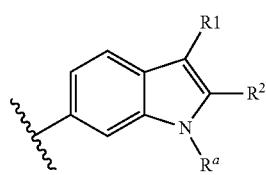

Preferred embodiments of (xi) include those in which $R^a$ is hydrogen or $C_{1-4}$ alkyl. In further preferred embodiments $R^1$ and $R^2$ are hydrogen. In further preferred embodiments $R^1$ is as defined in the general definition above (examples are CN, —COO($C_{1-4}$ alkyl),

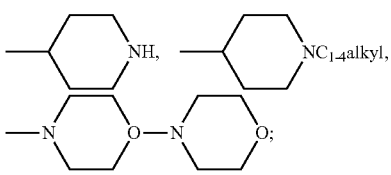

more preferably CN,

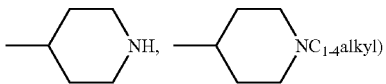

and R² is hydrogen. In further preferred embodiments R¹ and R² can form a ring which is optionally substituted. Examples of R¹ and R² which form a ring are —(CH₂)₃— and —(CH₂)₄— which can be optionally substituted.

In one embodiment B has the formula (xii)

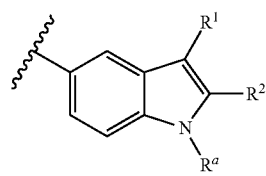

Preferred embodiments of (xii) include those in which $R^a$ is hydrogen or $C_{1-4}$ alkyl. In further preferred embodiments $R^1$ and $R^2$ are hydrogen. In further preferred embodiments $R^1$ is as defined in the general definition above (examples are CN, —COO($C_{1-4}$ alkyl),

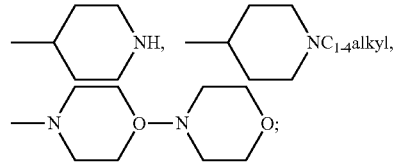

more preferably CN,

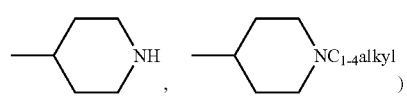

and R² is hydrogen. In further preferred embodiments R¹ and R² can form a ring which is optionally substituted. Examples of R¹ and R² which form a ring are —(CH₂)₃— and —(CH₂)₄— which can be optionally substituted.

In one embodiment B has the formula (xiii)

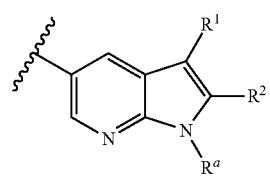

Preferred embodiments of (xiii) include those in which $R^a$ is hydrogen or $C_{1-4}$ alkyl. In further preferred embodiments $R^1$ and $R^2$ are hydrogen. In further preferred embodiments $R^1$ is as defined in the general definition above (examples are CN, —COO($C_{1-4}$ alkyl),

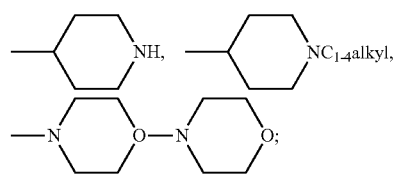

more preferably CN,

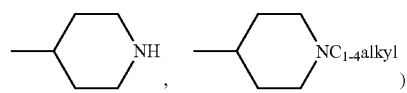

and R² is hydrogen. In further preferred embodiments R¹ and R² can form a ring which is optionally substituted. Examples of R¹ and R² which form a ring are —(CH₂)₃— and —(CH₂)₄— which can be optionally substituted.

In one embodiment the compound of the present invention preferably has the formula (I):

A-L₁-B    (I)

and all stereoisomers, racemic mixtures, pharmaceutically acceptable salts, hydrates, solvates and polymorphs thereof;

wherein A is:

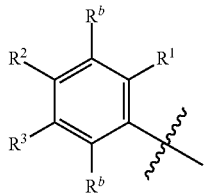

L₁ is:

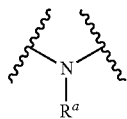

B is:

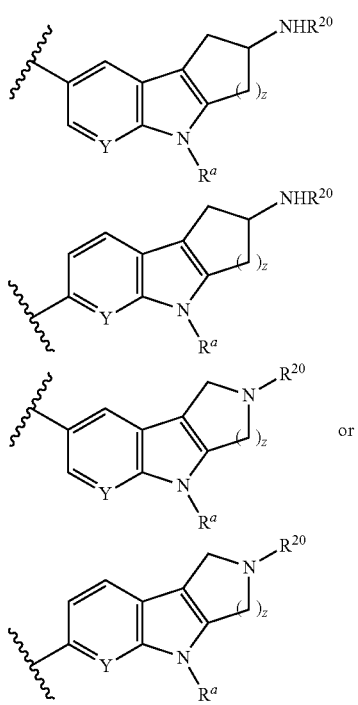

wherein
R¹ and R² are each independently selected from the group consisting of hydrogen, halogen, CN, CF$_3$, CONR$^{30}$R$^{31}$, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if R¹ and R² are adjacent, they can optionally be taken together and can form a 5- or 6-membered ring containing carbon atoms and optionally one or two heteroatoms selected from O, S, or N or the heteroatom-containing moiety NR$^{50}$;

R³ is hydrogen or halogen;
R$^a$ is hydrogen or alkyl;
for each occurrence, R$^b$ is independently selected from the group consisting of: hydrogen, halogen, CN, CF$_3$, CONR$^{30}$R$^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence, R$^{30}$, R$^{31}$, R$^{20}$ and R$^{21}$ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

R$^{50}$ is for each occurrence R$^{20}$, S(O)$_t$NR$^{20}$R$^{21}$, S(O)$_t$R$^{20}$, C(O)OR$^{20}$, C(O)R$^{20}$C(=NR$^a$)NR$^{20}$R$^{21}$, C(=NR$^{20}$)NR$^{21}$R$^a$, C(=NOR$^{20}$)R$^{21}$ or C(O)NR$^{20}$R$^{21}$;

Y is each independently CH or N
t is 1 or 2; and
z is 1 or 2.

In another embodiment the compound of the present invention preferably has the formula (I):

$$A\text{-}L_1\text{-}B \qquad (I)$$

and all stereoisomers, racemic mixtures, pharmaceutically acceptable salts, hydrates, solvates and polymorphs thereof;
wherein A is:

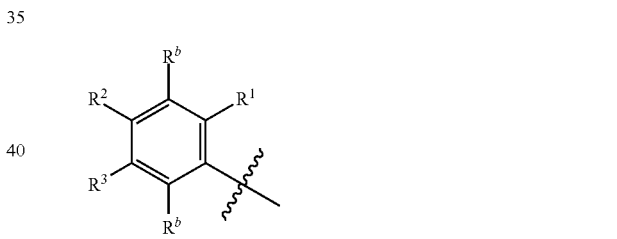

L₁ is:

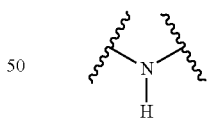

B is:

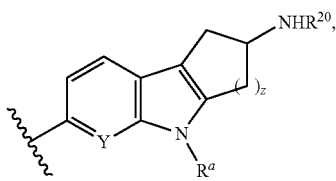

wherein
R¹ and R² are each independently selected from the group consisting of hydrogen, halogen, CN, CF$_3$, CONR$^{30}$R$^{31}$, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if $R^1$ and $R^2$ are adjacent, they can optionally be taken together and can form a 5- or 6-membered ring containing carbon atoms and optionally one or two heteroatoms selected from O, S, or N or the heteroatom-containing moiety $NR^{50}$;

$R^3$ is hydrogen or halogen;

$R^a$ is hydrogen or alkyl;

for each occurrence, $R^b$ is independently selected from the group consisting of: hydrogen, halogen, CN, $CF_3$, $CONR^{30}R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence, $R^{30}$, $R^{31}$, $R^{20}$ and $R^{21}$ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

$R^{50}$ is, for each occurrence, $R^{20}$, $S(O)_tNR^{20}R^{21}$, $S(O)_tR^{20}$, $C(O)OR^{20}$, $C(O)R^{20}C(=NR^a)NR^{20}R^{21}$, $C(=NR^{20})NR^{21}R^a$, $C(=NOR^{20})R^{21}$ or $C(O)NR^{20}R^{21}$;

Y is each independently CH or N;

t is 1 or 2; and z is 1 or 2.

In a further embodiment the compound of the present invention preferably has the formula (I):

$$A\text{-}L_1\text{-}B \qquad (I)$$

and all stereoisomers, racemic mixtures, pharmaceutically acceptable salts, hydrates, solvates and polymorphs thereof; wherein A is:

$L_1$ is:

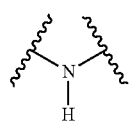

B is:

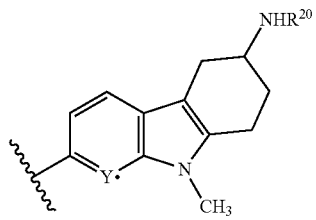

wherein $R^1$ and $R^2$ are each independently selected from the group consisting of hydrogen, halogen, CN, $CF_3$, $CONR^{30}R^{31}$, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if $R^1$ and $R^2$ are adjacent, they can optionally be taken together and can form a 5- or 6-membered ring containing carbon atoms and optionally one or two heteroatoms selected from O, S, or N or the heteroatom-containing moiety $NR^{50}$;

$R^3$ is hydrogen or halogen;

$R^a$ is hydrogen or alkyl;

for each occurrence, $R^b$ is independently selected from the group consisting of: hydrogen, halogen, CN, $CF_3$, $CONR^{30}R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence $R^{30}$, $R^{31}$, $R^{20}$ and $R^{21}$ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

$R^{50}$ is, for each occurrence, $R^{20}$, $S(O)_tNR^{20}R^{21}$, $S(O)_tR^{20}$, $C(O)OR^{20}$, $C(O)R^{20}C(=NR^a)NR^{20}R^{21}$, $C(=NR^{20})NR^{21}R^a$, $C(=NOR^{20})R^{21}$ or $C(O)NR^{20}R^{21}$;

Y is each independently CH or N; and t is 1 or 2.

Any combination of the above mentioned embodiments is also envisaged in the present specification.

Preferred compounds are summarized in Table 6.

The compounds of the present invention can be synthesized by one of the general methods shown in Schemes 1 to 20. These methods are only given for illustrative purposes and are not limiting.

General synthetic schemes for the preparation of 6-amino- or 6-bromo-7-azaindole building blocks are shown in the following.

Scheme 1

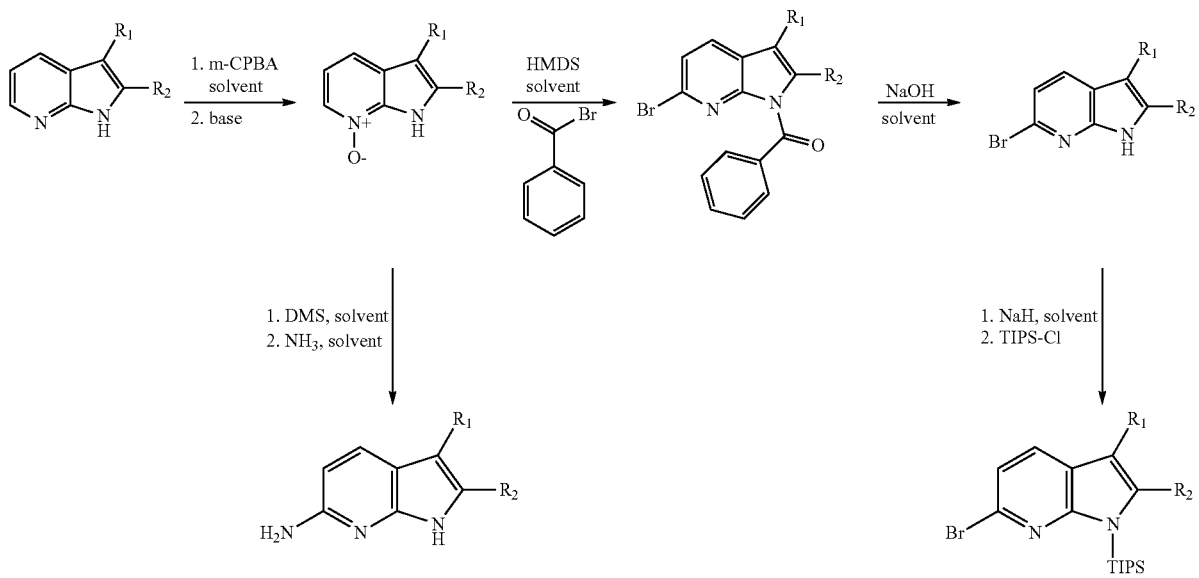

Commercially available 7-azaindole or an appropriately substituted 7-azaindole derivative were treated with meta-chloroperbenzoic acid in a suitable solvent to afford the corresponding N-oxide/meta-chlorobenzoic acid salts. Treatment of the N-oxide/salts with dimethylsulfate in a suitable solvent followed by reaction of the intermediate with ammonia in a suitable solvent afforded the desired 6-amino 7-azaindole building blocks.

Treatment of the N-oxide salts with base in a suitable solvent afforded the N-oxide after purification. Reaction of the N-oxides with hexamethyldisilazane and benzylbromide in a suitable solvent yielded the corresponding $N^1$-benzoyl protected 6-bromo 7-azaindole derivatives. Saponification of the protecting group with sodium hydroxide in a suitable solvent afforded the corresponding 6-bromo 7-azaindole derivatives after purification. Protection of the $N^1$-position with the triisopropylsilyl moiety yielded the desired $N^1$-protected 6-bromo 7-azaindole derivatives after purification.

General synthetic scheme for the preparation of 3-substituted 6-bromo 4-azaindole and 6-bromo indole building blocks with R=Boc, $CH_3$ and X=CH, N.

Scheme 2

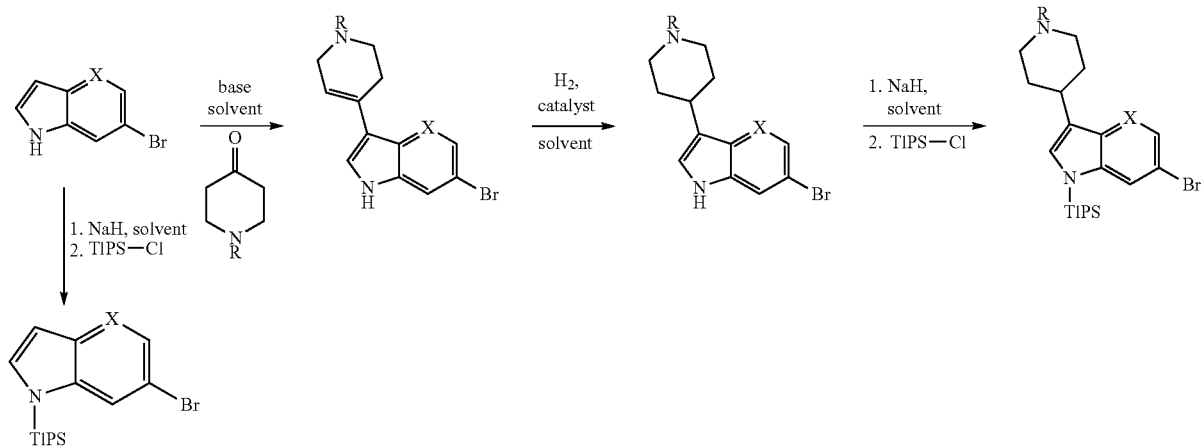

Commercially available 6-bromo 4-indole (X=CH) was treated with sodium hydride in a suitable solvent, followed by addition of triisopropylsilyl chloride to afford the $N^1$-protected derivatives after purification.

Commercially available 6-bromo 4-indole (X=CH) or 6-bromo 4-azaindole (X=N) were treated with N-Boc-piperidin-4-one or N-methyl-piperidin-4-one and an appropriate base in a suitable solvent to afford the condensation products after purification. Hydrogenation of the double bond using a suitable catalyst and solvent afforded the corresponding reduction products after purification. Protection of the $N^1$-position with the triisopropylsilyl moiety yielded the desired 3-substituted and $N^1$-protected derivatives after purification.

General synthetic scheme for the preparation of 3-substituted 5-bromo 7-azaindole and 5-bromo 7-indole building blocks with R=Boc, CH₃.

Scheme 3

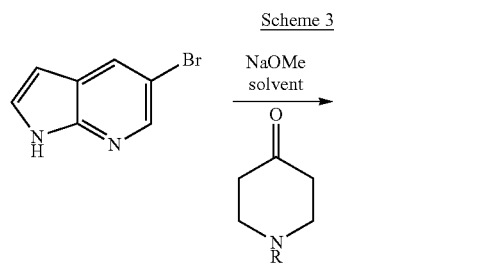

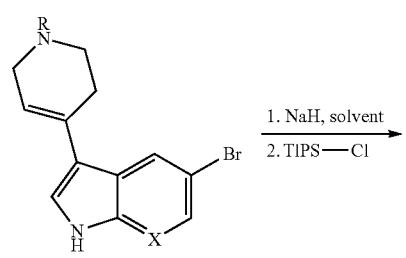

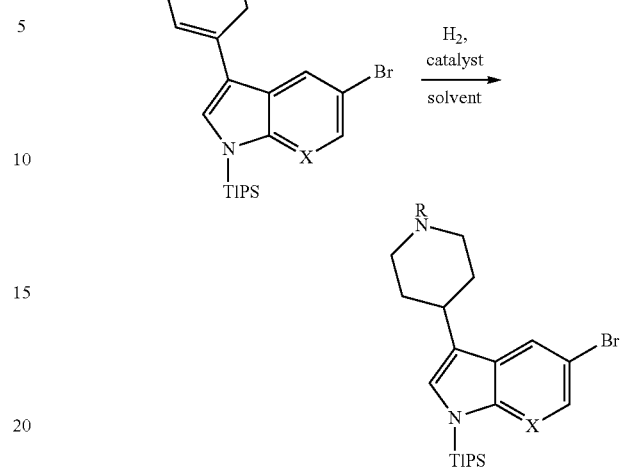

Commercially available 5-bromo indole (X═CH) or 5-bromo 7-azaindole (X═N) were treated with N-Boc-piperidin-4-one or N-methyl-piperidin-4-one and an appropriate base in a suitable solvent to afford the condensation products after purification. Protection of the $N^1$-position with the triisopropylsilyl moiety afforded the corresponding compounds. Hydrogenation of the double bond using a suitable catalyst and solvent afforded the desired $N^1$-protected derivatives after purification.

General synthetic scheme for the preparation of 3-substituted 6-amino indole building blocks of this invention with R=Boc, CH₃.

Scheme 4

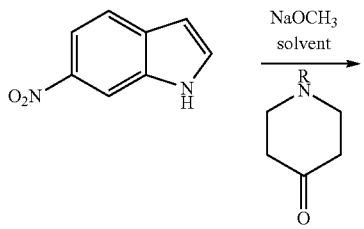

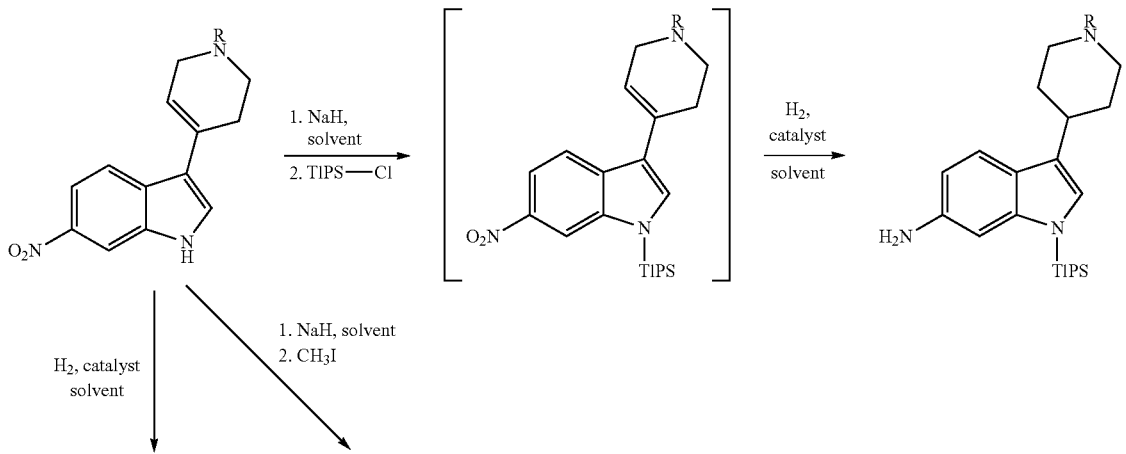

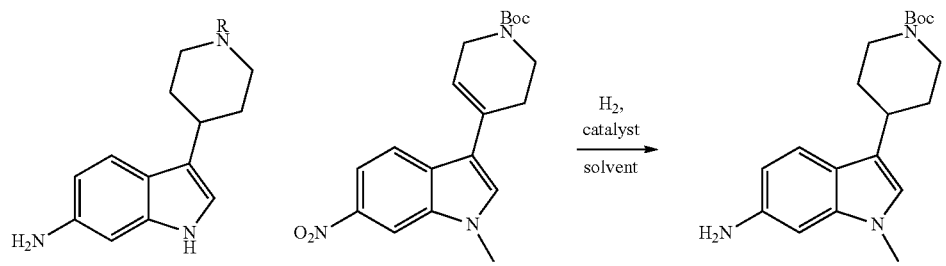

Commercially available 6-nitro indole was treated with N-Boc-piperidin-4-one or N-methyl-piperidin-4-one and an appropriate base in a suitable solvent to afford the condensation product after purification. Reduction of the nitro-group and the double bond using a suitable catalyst and solvent afforded the desired 6-amino indole derivatives after purification. Protection of the $N^1$-position of the nitro derivatives from the initial condensation with the triisopropylsilyl moiety afforded the corresponding compounds, which were used for hydrogenation without purification. Reduction of the nitro group and double bond using a suitable catalyst and solvent afforded the desired $N^1$-TIPS protected 6-amino indole derivatives after purification. Protection of the $N^1$-position of the nitro derivative from the initial condensation containing an N-Boc protected piperidine moiety with a methyl group afforded the desired compound after purification. Catalytic reduction of the nitro group and double bond using a suitable catalyst and solvent afforded the desired $N^1$-methyl protected 6-amino indole derivative after purification where the nitrogen of the piperidine moiety is protected with a Boc-moiety.

General synthetic scheme for the preparation of tricyclic 2-bromo or 2-amino tetrahydro-pyrido[2,3-b]indol building blocks when $R^1$ and $R^2$ taken together form a 5- or 6-membered ring containing carbon atoms.

Scheme 5

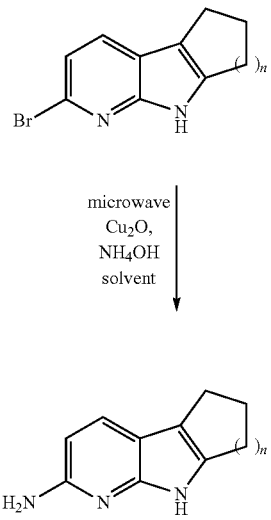

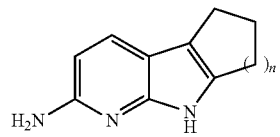

Commercially available 2,6-dibromo pyridine was treated with hydrazine hydrate in a suitable solvent to afford the mono hydrazine derivative. Condensation with an appropriate cyclic ketone in a suitable solvent afforded the desired hydrazone compounds. A thermal Fischer-indole synthesis afforded the tricyclic cyclization products after purification. A copper(I)-oxide mediated exchange of the bromo derivative with ammonia yielded the desired tricyclic 2-amino pyrido[2,3-b]indol derivatives after purification.

General synthetic scheme for the preparation of tricyclic 2-bromo tetrahydro-pyrido[2,3-b]indol (X=N, Y=Br, Z=H) or 6-bromo tetrahydro-carbazol (X=CH, Y=H, Z=Br) or 7-bromo tetrahydro-carbazol (X=CH, Y=Br, Z=H) building blocks when $R^1$ and $R^2$ taken together form a 6-membered ring containing carbon atoms and the 6-membered ring is substituted with $NCH_3Boc$.

General synthetic scheme for the preparation of protected 4-amino- and 4-hydroxycyclohexanone derivatives and unprotected 4-hydroxycyclohexanone derivatives.

Scheme 6

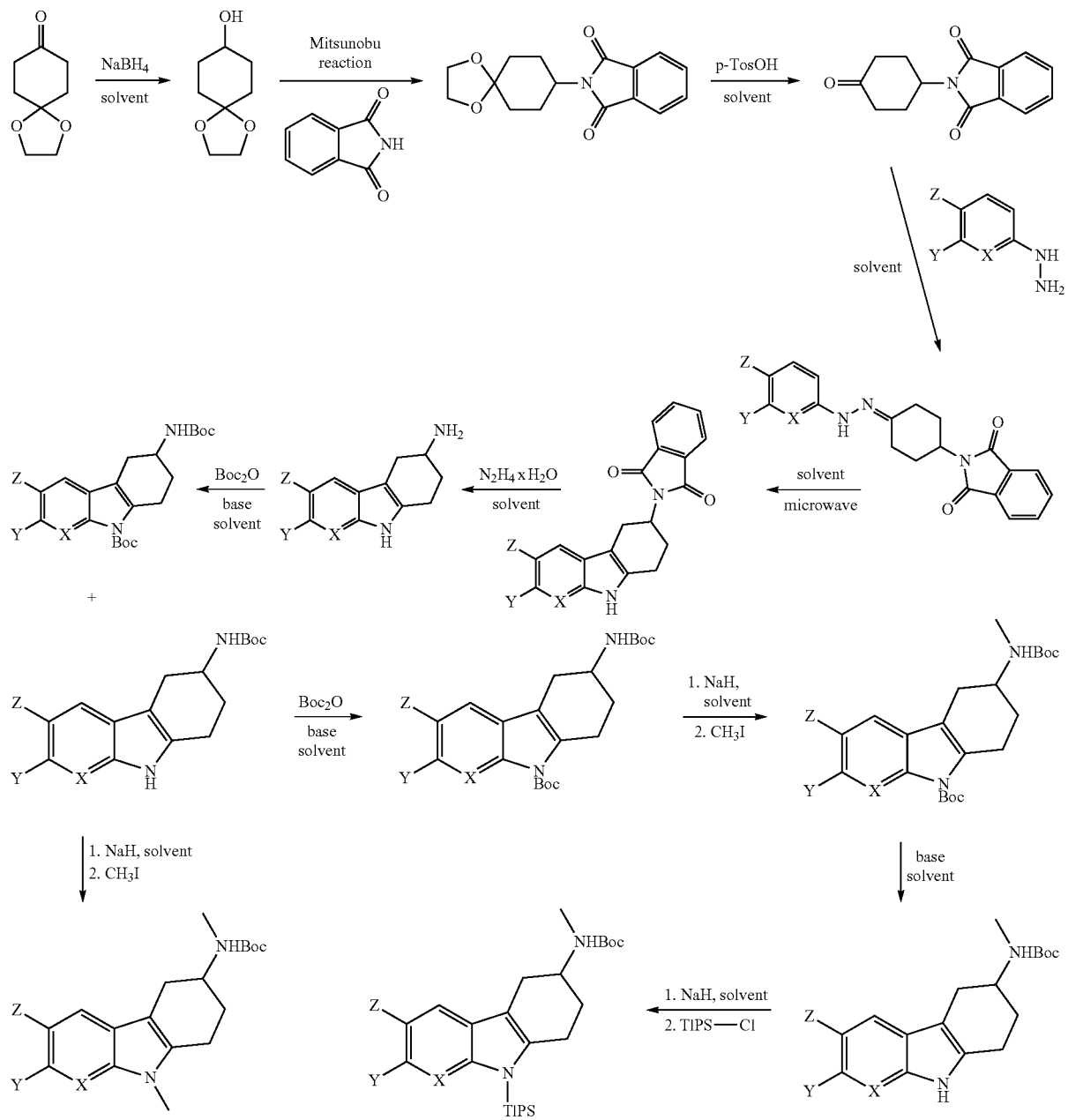

Commercially available 4-amino-cyclohexanol hydrogen chloride salt was converted to the corresponding phthalimide-protected 4-amino-cyclohexanol using a phthalimide reagent and potassium carbonate in an appropriate solvent. Oxidation of the alcohol to the ketone with pyridinium chlorochromate in an appropriate solvent afforded the phthalimide-protected 4-amino-cyclohexanone after purification. Commercially available 1,4-cyclohexanedione monoethylene acetal was treated with sodium borohydride in an appropriate solvent to afford the corresponding alcohol. Treatment of the alcohol with phthalimide employing Mitsunobu reaction conditions afforded the desired compound after purification. Cleavage of the acetals was achieved by refluxing the starting material with a trace amount of p-toluene sulfonic acid in an appropriate solvent mixture to afford the corresponding phthalimide-protected 4-amino-cyclohexanone. Treatment of the alcohol reduction product with benzoyl chloride followed by cleavage of the acetals using a trace amount of p-toluene sulfonic acid in an appropriate solvent mixture at reflux afforded the corresponding benzoyl-protected 4-hydroxy-cyclohexanone. Treatment of the alcohol reduction product using a trace amount of p-toluene sulfonic acid in an appropriate solvent mixture at reflux afforded the corresponding 4-hydroxy-cyclohexanone.

General synthetic scheme for the preparation of tricyclic 2-bromo tetrahydro-pyrido[2,3-b]indol (X=N, Y=Br, Z=H) or 3-bromo tetrahydro-pyrido[2,3-b]indol (X=N, Y=H, Z=Br) or 6-bromo tetrahydro-carbazol (X=CH, Y=H, Z=Br) or 7-bromo tetrahydro-carbazol (X=CH, Y=Br, Z=H) building blocks when R¹ and R² taken together form a 6-membered ring containing carbon atoms and the 6-membered ring is substituted with NR²⁰Boc.

of the free amine with Boc-anhydride and a suitable base in an appropriate solvent afforded the mono-Boc and bis-Boc protected derivatives after purification. Treatment of the mono-Boc derivatives with sodium hydride in a suitable solvent

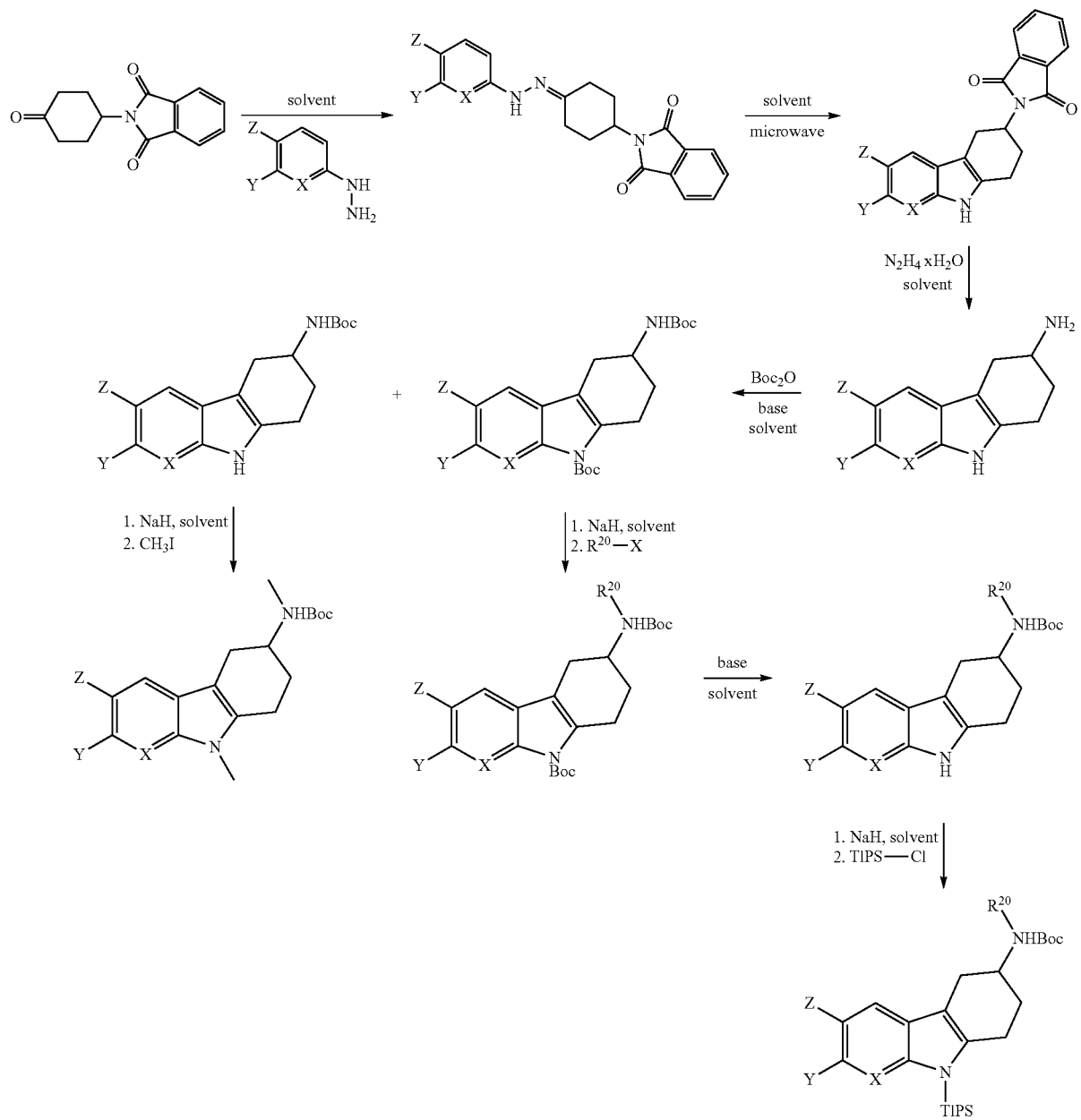

Scheme 7

Condensation of 2-bromo-6-hydrazino pyridine (X=N, Y=Br, Z=H) or 3-bromo-6-hydrazino pyridine (X=N, Y=H, Z=Br) or 4-bromo-phenylhydrazine (X=CH, Y=H, Z=Br) or 3-bromo-phenylhydrazine (X=CH, Y=Br, Z=H) with the phthalimide protected 4-amino-cyclohexanone derivative in a suitable solvent afforded the desired hydrazone condensation products. A thermal Fischer-Indole synthesis of the hydrazone afforded the tricyclic cyclization products after purification. The phthalimide protecting group was removed by treatment with hydrazine hydrate in an appropriate solvent to afford the primary amines. Treatment followed by methyl iodide afforded the desired di-methyl tricyclic derivatives after purification. The bis-Boc-protected compounds were treated with sodium hydride in a suitable solvent followed by the addition of a suitable alkylating agent to afford the mono-alkylated products after purification for X=CH. Depending on the reactivity of the alkylating agent the reaction proceeds at room temperature or requires elevated temperatures. Selective cleavage of the Boc protection group attached to the pyrrole ring for X=N was achieved by adding a suitable base in an appropriate solvent to afford the desired compounds. Protection of the NH-moiety of the pyrrole ring with a triisopropylsilyl moiety afforded the desired tricyclic derivatives for X=N after purification.

General synthetic scheme for the preparation of tricyclic 2-bromo tetrahydro-pyrido[2,3-b]indol (X=N, Y=Br, Z=H) or 3-bromo tetrahydro-pyrido[2,3-b]indol (X=N, Y=H, Z=Br) building blocks when $R^1$ and $R^2$ taken together form a 6-membered ring containing carbon atoms and the 6-membered ring is substituted with $NR^{20}Boc$.

Scheme 8

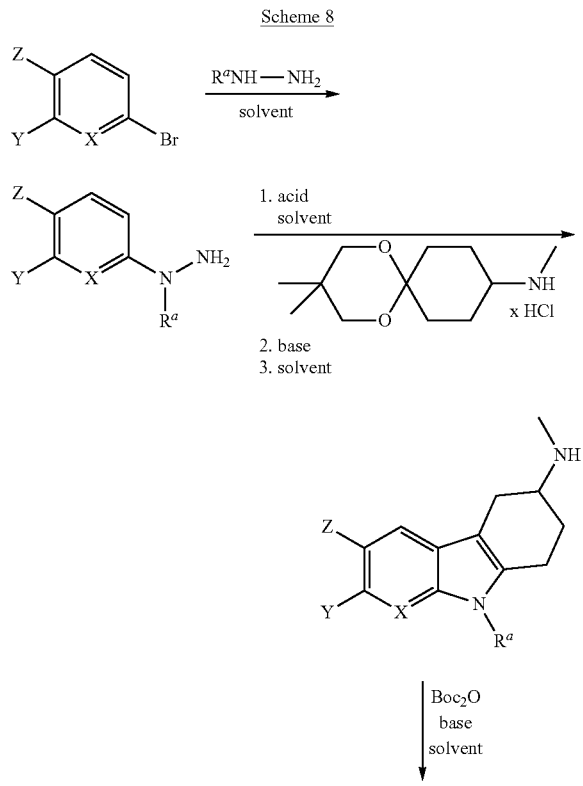

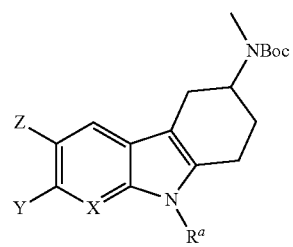

Heating of commercially available 2,6-di-bromo pyridine (X=N, Y=Br, Z=H) or 2,5-di-bromo pyridine (X=N, Y=H, Z=Br) with a suitable hydrazine derivative in an appropriate solvent affords the corresponding 2-bromo-6-hydrazino pyridine or 3-bromo-6-hydrazino pyridine derivatives after purification. Condensation of the hydrazine derivatives with commercially available 4-(methylamino) cyclohexanone 2,2-dimethyltrimethylene ketal hydrochloride in a suitable solvent under acidic conditions employed for the Fischer-Indole synthesis affords the tricyclic cyclization products. Treatment with base affords the corresponding tricyclic cyclization products as free base. Treatment of the free amine with Boc-anhydride and a suitable base in an appropriate solvent afforded the mono-Boc protected derivatives after purification.

General synthetic scheme for the preparation of tricyclic 2-bromo-6,9-dimethyl-tetrahydro-pyrido[2,3-b]indol (X=N, Y=Br, Z=H) when $R^1$ and $R^2$ taken together form a 6-membered ring containing carbon atoms and the 6-membered ring is substituted at the same position with —$CH_3$ and $NR^{20}Boc$.

Scheme 9

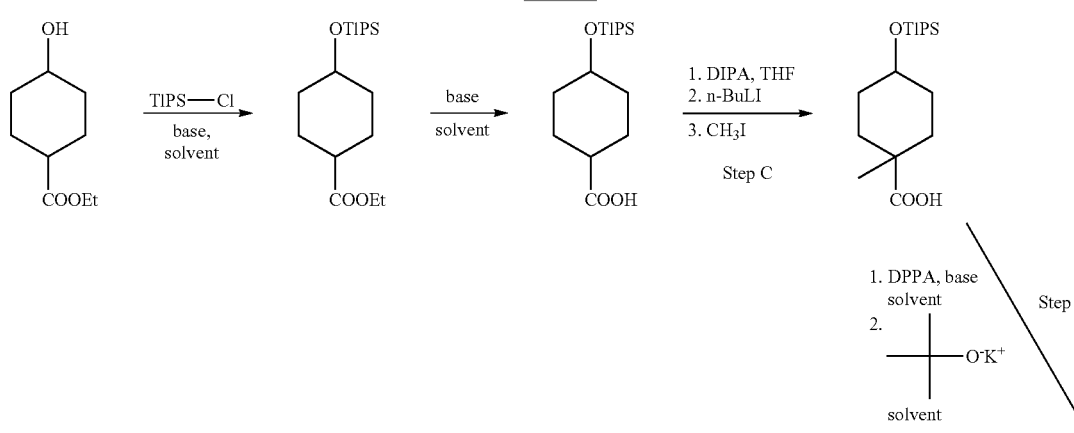

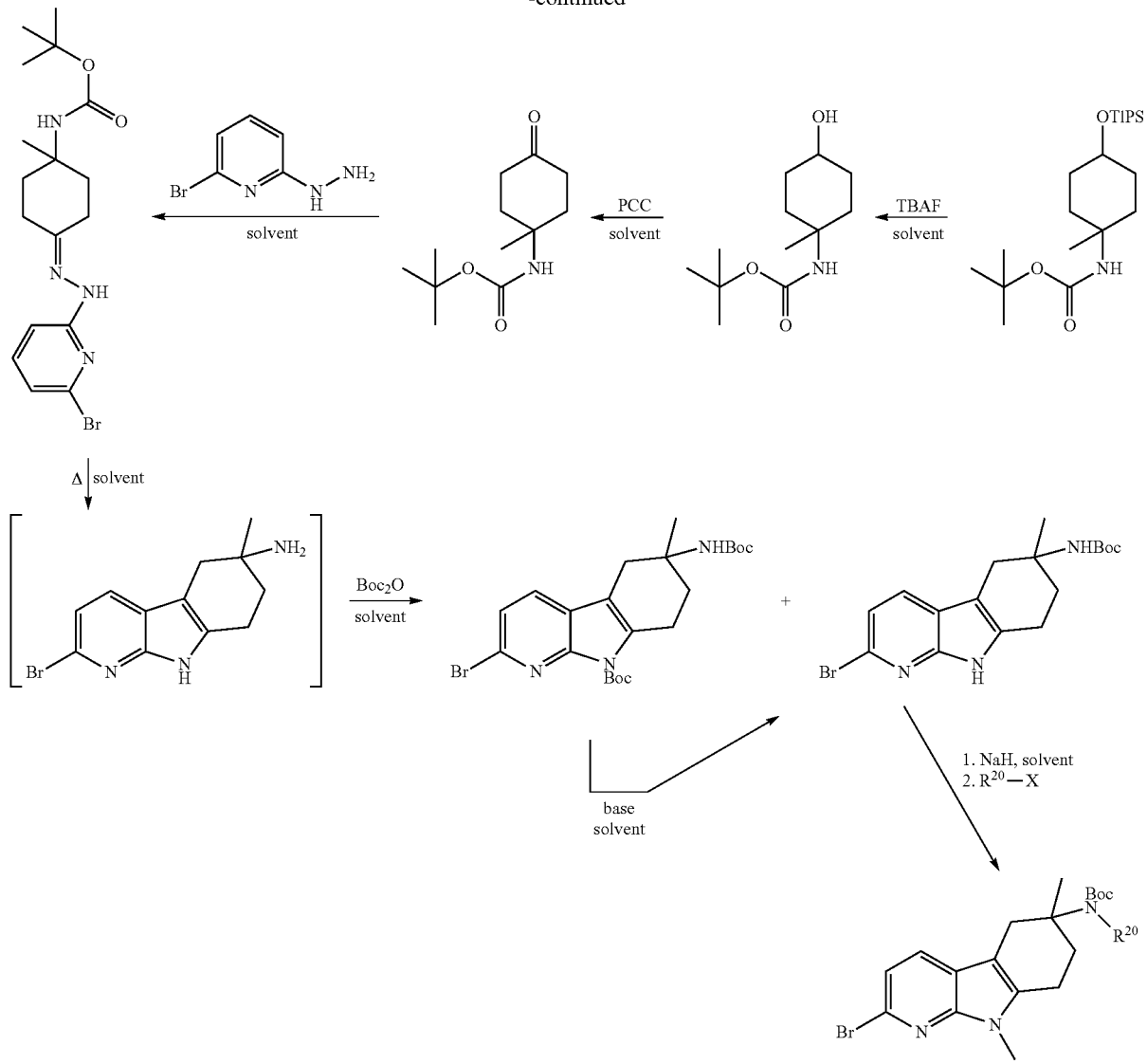

Commercially available 4-hydroxycyclohexane carboxylic acid ethyl ester is treated with triisopropylsilyl-chloride in a suitable solvent with an appropriate base to afford the silyl-protected compound. Saponification of the ester moiety with base in a suitable solvent afforded the corresponding carboxylic acid. Treatment of the carboxylic acid with an excess of lithium diisopropylamine, prepared in situ by the action of n-butyllithium on diisopropylamine, afforded the anion which was quenched by the addition of methyl iodide to afford the C-1 methylated carboxylic acid after purification. The carboxylic acid was then converted to a protected amine via a Curtius-rearrangement reaction. Treatment of the isocyanate intermediate of the Curtius rearrangement with an appropriate nucleophile, i.e. potassium tert-butylate, in a suitable solvent afforded the desired protected amine after purification. Treatment of the protected amine with tetra-butyl ammonium fluoride in a suitable solvent afforded the desired 4-hydroxyl-derivatives after purification. Oxidation of the hydroxyl moiety with pyridinium chlorochromate in a suitable solvent afforded the corresponding cyclohexanone derivative after purification. Condensation of the ketone with a suitable hydrazine derivative afforded the hydrazone compound. The hydrazone compound was then treated under the conditions of a thermal Fischer-Indol synthesis in suitable solvent to afford the cyclization product which directly treated with di-tert-butyl dicarbonate in a suitable solvent. The reaction afforded a mixture of the mono- and bis-Boc-protected products which were separated by chromatography. The bis-Boc derivative was converted to the mono-Boc derivative via treatment with base in a suitable solvent. The mono-Boc derivative was treated with sodium hydride in a suitable solvent to afford the corresponding sodium salt which was treated with an alkylating agent to afford the desired product after purification. Depending on the reactivity of the alkylating agent the reaction proceeds at room temperature or requires elevated temperatures.

General synthetic scheme for the preparation of tricyclic 2-bromo tetrahydro-pyrido[2,3-b]indol (X=N, Y=Br, Z=H) or 3-bromo tetrahydro-pyrido[2,3-b]indol (X=N, Y=H, Z=Br) or 6-bromo tetrahydro-carbazol (X=CH, Y=H, Z=Br) or 7-bromo tetrahydro-carbazol (X=CH, Y=Br, Z=H) building blocks when $R^1$ and $R^2$ taken together form a 6-membered ring containing carbon atoms and the 6-membered ring is substituted with $OR^{20}$.

Scheme 10

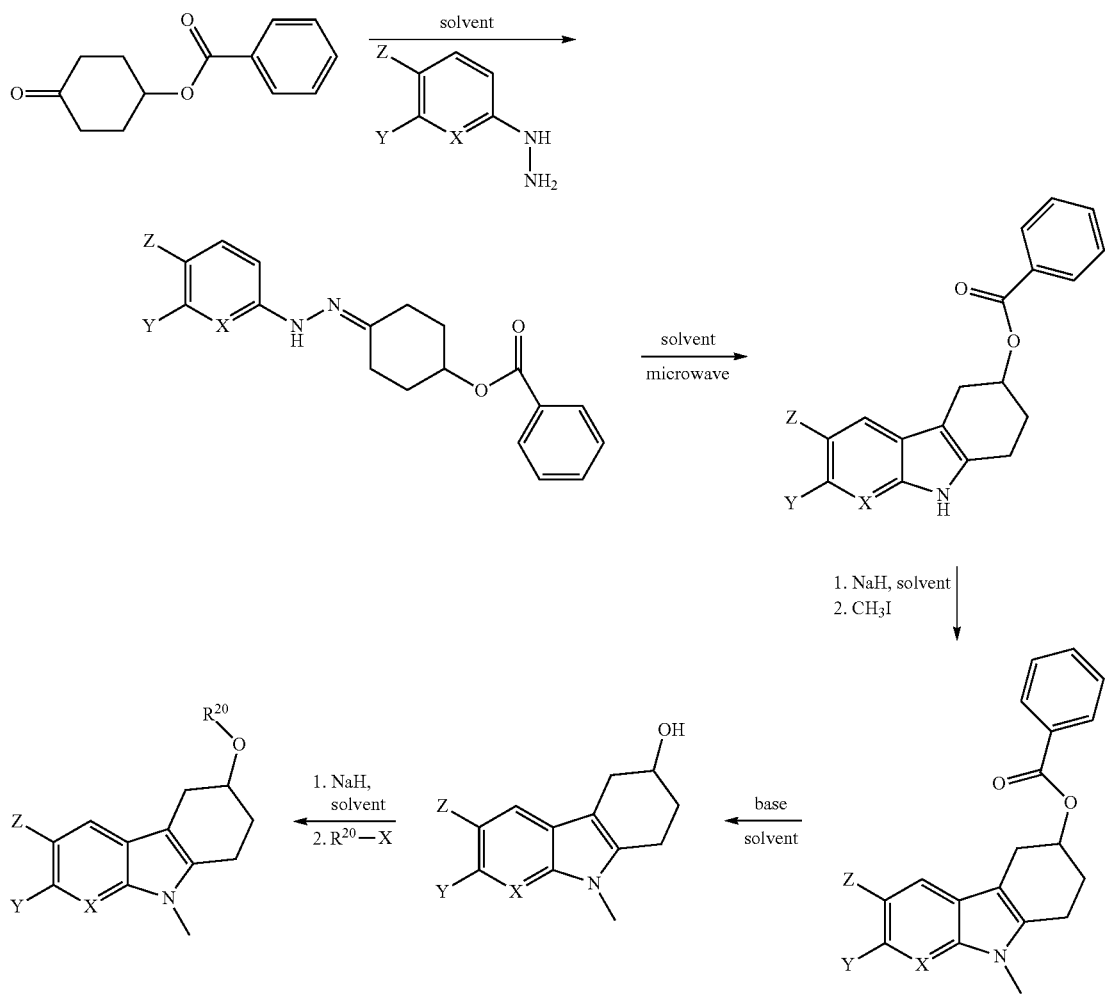

Benzoyl protected 4-hydroxycyclohexanone is treated with a suitable hydrazine-derivative in an appropriate solvent to afford the condensation product. The hydrazone-derivatives are treated under the conditions of a thermal Fischer-Indole synthesis using a microwave to afford the tricyclic cyclization products after purification. Treatment of the tricyclic products with sodium hydride in a suitable solvent followed by the addition of methyl iodide afforded the desired products after purification. Cleavage of the ester protecting group was accomplished by heating with base in a suitable solvent using a microwave to obtain the desired hydroxyl-compounds. Alkylation of the hydroxyl-group was performed with suitable alkylating agents in an appropriate solvent, after activation of the hydroxyl group into its sodium salt using sodium hydride. Depending on the reactivity of the alkylating agent the reaction proceeds at room temperature or requires elevated temperatures. The desired products were obtained after purification.

General synthetic scheme for the preparation of tricyclic 2-bromo tetrahydro-pyrido[2,3-b]indol (X=N, Y=Br, Z=H) or 3-bromo tetrahydro-pyrido[2,3-b]indol (X=N, Y=H, Z=Br) or 6-bromo tetrahydro-carbazol (X=CH, Y=H, Z=Br) or 7-bromo tetrahydro-carbazol (X=CH, Y=Br, Z=H) building blocks when $R^1$ and $R^2$ taken together form a 6-membered ring containing carbon atoms and the 6-membered ring is substituted with $OCH_3$.

Scheme 11

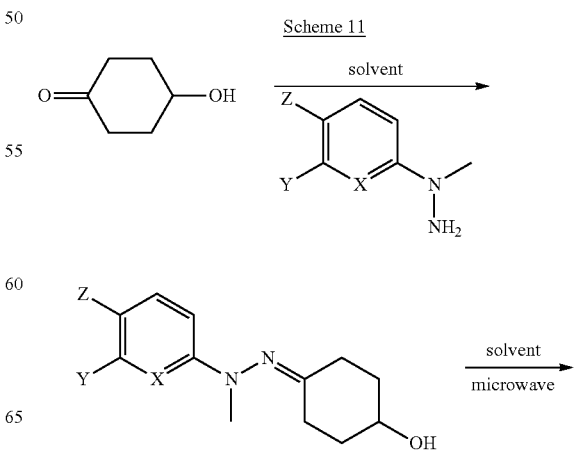

-continued

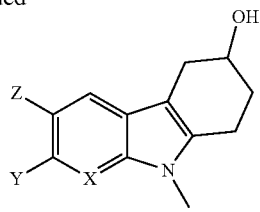

1. NaH, solvent
2. CH$_3$I

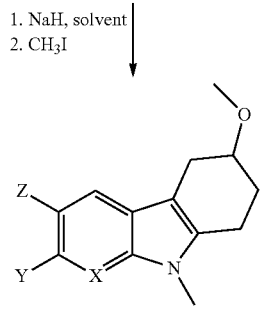

Unprotected 4-hydroxycyclohexanone is treated with a suitable methyl-hydrazine-derivative in an appropriate solvent to afford the condensation product. The methyl-hydrazone-derivatives are treated under the conditions of a thermal Fischer-Indole synthesis using a microwave to afford the tricyclic cyclization products after purification. Treatment of the tricyclic products with sodium hydride in a suitable solvent followed by the addition of methyl iodide afforded the desired products after purification.

General synthetic scheme for the preparation of compounds of this invention.

Scheme 12

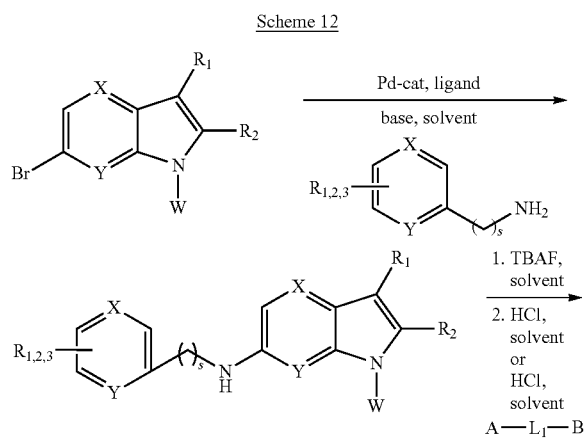

The N-protected bromo building blocks with (X═CH, Y═N, Z═N, W═CH$_3$ or TIPS) or (X═N, Y═CH, Z═CH, W═CH$_3$ or TIPS) or (X, Z═CH, Y═N, W═CH$_3$ or TIPS) or (X, Y, Z═CH, W═CH$_3$ or Boc) were reacted with suitable amines or amine building blocks with (X, Y═CH, s═0) or (X═N, Y═CH, s═0) or (X═CH, Y═N, s═0, 1, 2) utilizing Pd-coupling chemistry with an appropriate Pd-catalyst and an appropriate ligand in a suitable solvent to afford the desired amination products after purification. Deprotection of the N-TIPS protected compounds with tetra-n-butyl ammonium fluoride in a suitable solvent yielded the desired compounds after purification. Treatment of the N-unprotected compounds with hydrogen chloride in a suitable solvent afforded the final compounds. For compounds with W═CH$_3$ or Boc treatment with hydrogen Chloride in a suitable solvent afforded the final compounds.

General synthetic scheme for the preparation of compounds of this invention.

Scheme 13

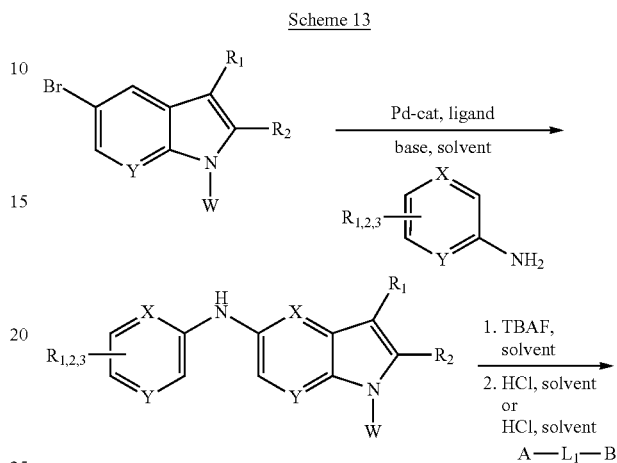

The N-protected bromo building blocks (Y═CH, W═CH$_3$, TIPS or Boc or Y═N, W═CH$_3$ or TIPS) were reacted with suitable amines or amine building blocks with (X, Z═CH) or (X═N, Z═CH) utilizing Pd-coupling chemistry with an appropriate Pd-catalyst and an appropriate ligand in a suitable solvent to afford the desired amination products after purification. Deprotection of the N-TIPS protected compounds with tetra-n-butyl ammonium fluoride in a suitable solvent yielded the desired compounds after purification. Treatment of the N-unprotected compounds with hydrogen chloride in a suitable solvent afforded the final compounds. For compounds with W═CH$_3$ or Boc treatment with hydrogen chloride in a suitable solvent afforded the final compounds.

General synthetic scheme for the preparation of compounds of this invention.

Scheme 14

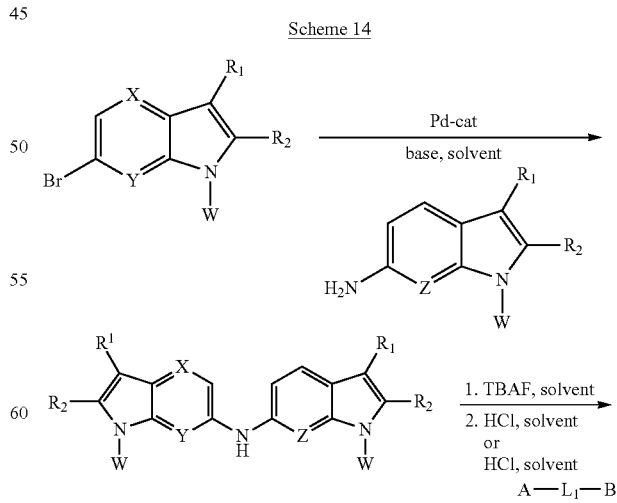

The N-protected bromo building blocks with (X═CH, Y═N, W═CH$_3$ or TIPS) or (X═N, Y═CH, W═CH$_3$ or TIPS) or (X, Y=CH, W=CH₃ or TIPS) were reacted with suitable amine building blocks with (Z=CH, W=H or CH₃ or TIPS) or (Z=N, W=H or CH₃ or TIPS) utilizing Pd-coupling chemistry with an appropriate Pd-catalyst and an appropriate ligand in a suitable solvent to afford the desired amination products after purification. Deprotection of the N-TIPS protected compounds with tetra-n-butyl ammonium fluoride in a suitable solvent yielded the desired compounds after purification. Treatment of the N-unprotected compounds with hydrogen chloride in a suitable solvent afforded the final compounds. For compounds with (W=H or CH₃) treatment with hydrogen chloride in a suitable solvent afforded the final compounds.

General synthetic scheme for the preparation of compounds of this invention.

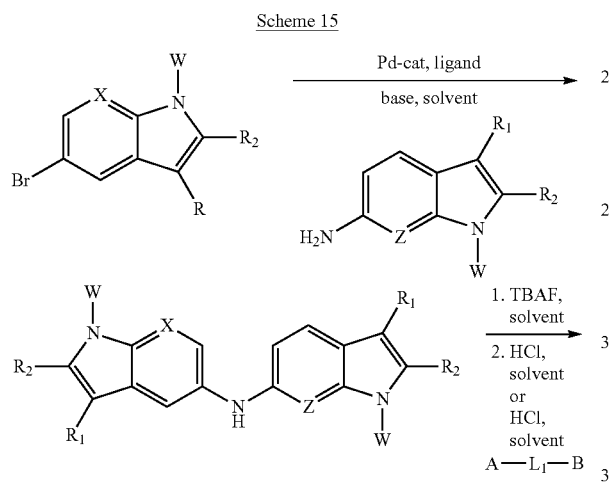

The N-protected bromo building blocks with (X=CH, W=CH₃ or TIPS) or (X=N, W=CH₃ or TIPS) were reacted with suitable amine building blocks with (Z=CH, W=H or CH₃ or TIPS) or (Z=N, W=H or CH₃ or TIPS) utilizing Pd-coupling chemistry with an appropriate Pd-catalyst and an appropriate ligand in a suitable solvent to afford the desired amination products after purification. Deprotection of the N-TIPS protected compounds with tetra-n-butyl ammonium fluoride in a suitable solvent yielded the desired compounds after purification. Treatment of the N-unprotected compounds with hydrogen chloride in a suitable solvent afforded the final compounds. For compounds with (W=H or CH₃) treatment with hydrogen chloride in a suitable solvent afforded the final compounds.

General scheme for the preparation of 2-bromo-tetrahydro-pyrido[2,3-b]indole building blocks when $R^1$ and $R^2$ taken together form a (n+4)-membered ring containing carbon atoms.

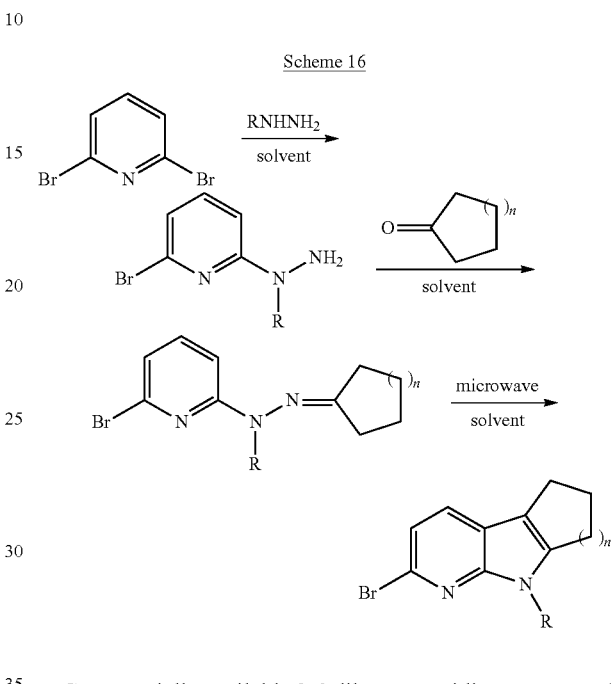

Commercially available 2,6-dibromo pyridine was treated with hydrazine derivatives (R=H, CH₃) in a suitable solvent to afford the mono hydrazine derivative. Condensation with an appropriate cyclic ketone in a suitable solvent afforded the desired hydrazone compounds. A thermal Fischer-indole synthesis afforded the tricyclic cyclization products after purification.

General synthetic scheme for the preparation of tricyclic 7-bromo tetrahydro-pyrido[4,3-b]indole (X=Br, Y=H) or 8-bromo tetrahydro-pyrido[4,3-b]indole (X=H, Y=Br) building blocks when $R^1$ and $R^2$ taken together form a (n+4)-membered ring containing carbon atoms and $NR^{20}$.

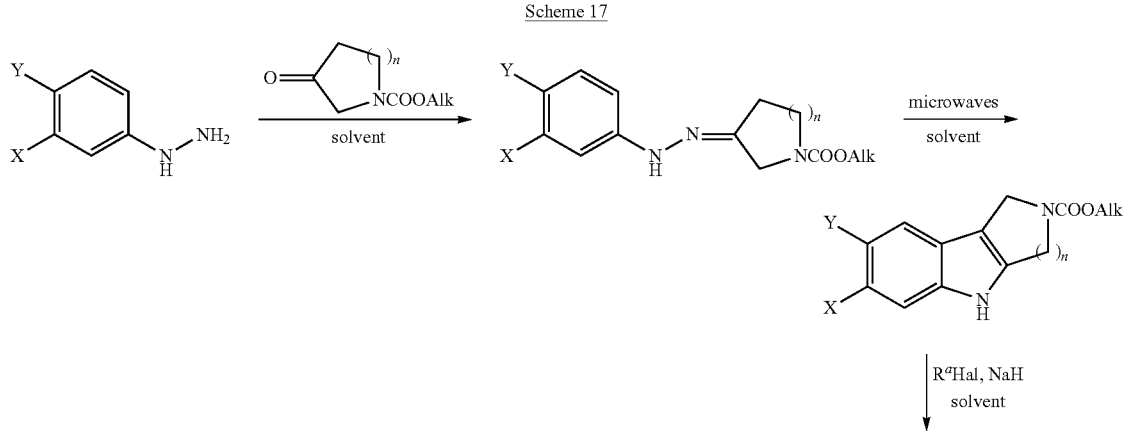

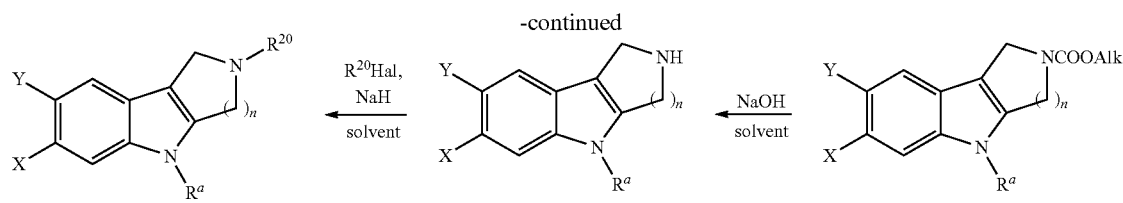

Commercially available phenylhydrazine derivatives were treated with an appropriate cyclic ketone in a suitable solvent to afford the desired hydrazone compounds. A Fischer-indole synthesis afforded the tricyclic cyclization products after purification. Treatment of the tricyclic derivatives with sodium hydride in a suitable solvent followed by an appropriate halogenated alkyl afforded the corresponding N-alkylated product. A subsequent deprotection of the carbamate derivatives was achieved by adding sodium hydroxide in an appropriate solvent under reflux conditions to afford the desired compounds. Finally the aliphatic NH derivatives were derivatized by treating them with sodium hydride followed by the addition of an appropriate halogenated alkyl in a suitable solvent to afford the desired tricyclic derivatives.

General synthetic scheme for the preparation of tricyclic 2-bromo-tetrahydro-pyrrolo[2,3-b:4,5-c']dipyridine (X=N, Y=H, Z=Br), 3-bromo-tetrahydro-pyrrolo[2,3-b:4,5-c']dipyridine (X=N, Y=Br, Z=H), 7-bromo tetrahydro-pyrido[4,3-b]indole (X=CH, Y=H, Z=Br) or 8-bromo tetrahydro-pyrido[4,3-b]indole (X=CH, Y=Br, Z=H) building blocks when $R^1$ and $R^2$ taken together form a (n+4)-membered ring containing carbon atoms and $NR^{20}$.

Scheme 18

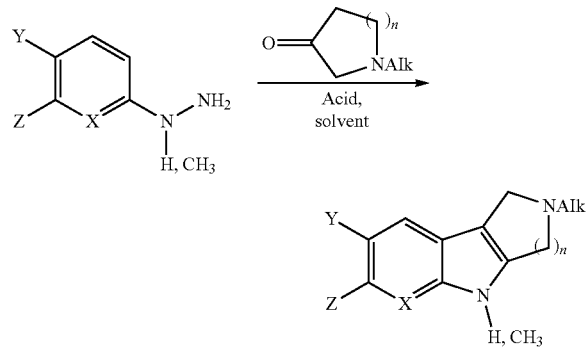

Commercially available hydrazine derivatives were treated with an appropriate cyclic ketone in the presence of a suitable acid in a suitable solvent to afford after purification the desired compounds via an acidic Fischer-indole synthesis.

General synthetic scheme for the preparation of tricyclic 2-bromo-tetrahydrothiopyrano[3',4':4,5]-pyrrolo[2,3-b]pyridine-6,6-dioxide (X=Br, Y=H) or 3-bromo-tetrahydrothiopyrano[3',4':4,5]-pyrrolo[2,3-b]pyridine-6,6-dioxide (X=H, Y=Br) building blocks when $R^1$ and $R^2$ taken together form a (n+4)-membered ring containing carbon atoms and $SO_2$.

Scheme 19

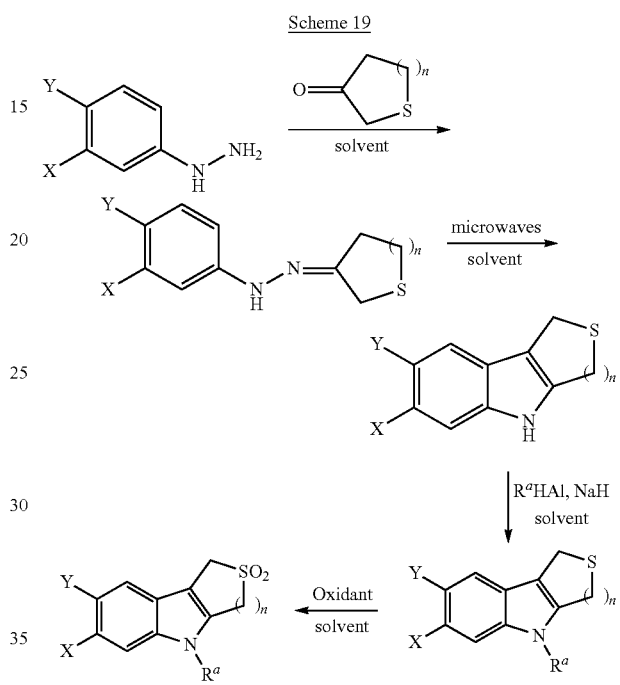

Commercially available phenylhydrazine derivatives were treated with an appropriate cyclic ketone in a suitable solvent to afford the desired hydrazone compounds. A Fischer-indole synthesis afforded the tricyclic cyclization products after purification. Treatment of the tricyclic derivatives with sodium hydride in a suitable solvent followed by an appropriate halogenated alkyl afforded the corresponding N-alkylated product. A subsequent oxidation of the sulfur derivatives using an appropriate oxidant afforded the desired sulfone compounds.

General synthetic scheme for the preparation of halogenated alkyl sulfones

Scheme 20

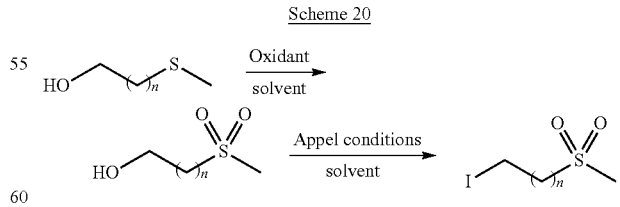

Commercially available methylthioalcohol derivatives were treated with an appropriate oxidant in a suitable solvent to afford the desired hydroxysulfone derivatives. The primary alcohols compounds were converted to the corresponding halogen derivatives using Appel conditions in a suitable solvent.

All reagents and solvents were obtained from commercial sources and used without further purification. Proton ($^1$H) spectra were recorded on a Bruker EPX 400 MHz NMR spectrometer in deuterated solvents. Mass spectra (MS) were recorded on a Finnigan MAT TSQ 7000 spectrometer. Flash purification was conducted with a Biotage Isolera One flash purification system using HP-Sil SNAP cartridges (Biotage) and the solvent gradient indicated in specific examples. Thin layer chromatography (TLC) was carried out on silica gel plates with UV detection. Preparative thin layer chromatography (Prep-TLC) was conducted with 0.5 mm or 1 mm silica gel plates (Analtech: Uniplate, $F_{254}$) and the solvents indicated in the specific examples.

While it is possible for the compounds of the present invention to be administered alone, it is preferable to formulate them into a pharmaceutical composition in accordance with standard pharmaceutical practice. Thus, the invention also provides a pharmaceutical composition which comprises a therapeutically effective amount of a compound of formula (I) in admixture with a pharmaceutically acceptable excipient.

Pharmaceutically acceptable excipients are well known in the pharmaceutical art, and are described, for example, in Remington's Pharmaceutical Sciences, 15$^{th}$ Ed., Mack Publishing Co., New Jersey (1991). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following:

mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

Diseases that can be treated with the compounds of the present invention can be associated with the formation of abnormal protein structures, in particular abnormal β-sheet structures. In the context of the present invention, an abnormal protein structure is a protein structure that arises when a protein or peptide refolds from the three-dimensional structure, which it generally adopts in healthy individuals, into a different three-dimensional structure, which is associated with a pathological condition. Likewise, an abnormal β-sheet structure in the context of the present invention is a β-sheet structure that arises when a protein or peptide refolds from the three-dimensional structure, which it generally adopts in healthy individuals, into a β-sheet structure, which is associated with a pathological condition.

In particular, in one embodiment diseases that can be treated with the compounds of the present invention are diseases or conditions associated with amyloid or amyloid-like proteins.

This group of diseases and disorders include neurological disorders such as Alzheimer's disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidosis; the retina, including primary retinal degenerations and macular degeneration, in particular age-related macular degeneration; the optic nerve, including optic nerve drusen, optic neuropathy and optic neuritis; and the cornea, including lattice dystrophy.

In a preferred embodiment the compounds of the present invention can be employed for the treatment of Alzheimer's disease, mild cognitive impairment (MCI), Lewy body dementia (LBD), amyotropic lateral sclerosis (ALS), inclusion-body myositis (IBM) and age-related macular degeneration (AMD). In a particularly preferred embodiment the compounds of the present invention can be employed for the treatment of Alzheimer's disease.

The ability of a compound to inhibit the aggregation of Aβ can, for example, be determined using fluorescence correlation spectroscopy as described in Rzepecki et al., J. Biol. Chem., 2004, 279(46), 47497-47505 or by using the thioflavin T spectrofluorescence assay.

In another embodiment the compounds of the present invention can be used for treating or alleviating the effects of ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration, for example age-related macular degeneration; the optic nerve leading to optic nerve drusen, optic neuropathy and optic neuritis; and the cornea leading to lattice dystrophy.

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. In particular, the further biologically active compound can be selected from the group consisting of a compound used in the treatment of amyloidosis, compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid or tau modifying drug and nutritive supplements, an antibody, including any functionally equivalent antibody or functional parts thereof, an Aβ antigenic peptide fragment consisting of a single or repetitive stretch of a plurality of contiguous amino acid residues from the N-terminal part of the Aβ peptide.

In a further embodiment, the mixtures according to the invention may comprise niacin or memantine together with a compound according to the present invention and, optionally, a pharmaceutically acceptable carrier and/or a diluent and/or an excipient.

In still another embodiment of the invention mixtures are provided that comprise as a further biologically active compound "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with a compound according to the invention and, optionally, a pharmaceutically acceptable carrier and/or a diluent and/or an excipient.

Other compounds that can be suitably used in mixtures in combination with the compound according to the present invention are, for example, described in WO 2004/058258 (see especially pages 16 and 17) including therapeutic drug targets (pages 36 to 39), alkanesulfonic acids and alkanolsulfuric acids (pages 39 to 51), cholinesterase inhibitors (pages 51 to 56), NMDA receptor antagonists (pages 56 to 58), estrogens (pages 58 to 59), non-steroidal anti-inflammatory drugs (pages 60 and 61), antioxidants (pages 61 and 62), peroxisome proliferators-activated receptor (PPAR) agonists (pages 63 to 67), cholesterol-lowering agents (pages 68 to 75), amyloid inhibitors (pages 75 to 77), amyloid formation inhibitors (pages 77 to 78), metal chelators (pages 78 and 79), anti-psychotics and anti-depressants (pages 80 to 82), nutritional supplements (pages 83 to 89) and compounds increasing the availability of biologically active substances in the brain (see pages 89 to 3) and prodrugs (pages 93 and 94), which document is incorporated herein by reference.

In one preferred embodiment the further biologically active compound is an antibody including any functionally equivalent antibody or functional parts thereof. The antibody can preferably be monoclonal, chimeric or humanized.

In a further aspect of the invention, a mixture is provided comprising in addition to the compound of the invention an antibody including functional parts thereof, or, more particularly, a monoclonal antibody including functional parts thereof, which recognizes and binds to amyloid β (Aβ), particularly to the native conformation of amyloid β, that is to amyloid oligomers and fibers, but not to not linearized amyloid species.

In particular, said antibodies are capable of inhibiting, in vitro and in vivo, the aggregation of amyloidogenic monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides, into high molecular polymeric amyloid fibrils or filaments. Through the inhibition of the aggregation of amyloidogenic monomeric peptides these antibodies are capable of preventing or slowing down the formation of amyloid plaques, particularly the amyloid form (1-42), which is known to become insoluble by change of secondary conformation and to be the major part of amyloid plaques in brains of diseased animals or humans.

In another aspect of the invention, the mixture comprises antibodies which, upon co-incubation with preformed high molecular polymeric amyloid fibrils or filaments formed by the aggregation of amyloid monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides, are capable of disaggregating said high molecular polymeric amyloid fibrils or filaments. Through the disaggregation of amyloidogenic polymeric fibrils or filaments these antibodies are capable of preventing or slowing down the formation of amyloid plaques which leads to an alleviation of the symptoms associated with the disease and a delay or reversal of its progression.

In still another aspect of the invention, the mixture comprises an antibody, but especially a monoclonal antibody or functional parts thereof, which antibody is bifunctional or bispecific in that it exhibits both an aggregation inhibition property as well as a disaggregation property as defined herein before, particularly paired with a high degree of conformational sensitivity.

In one embodiment, the mixture comprises an antibody which recognizes and binds to a conformational epitope, particularly a conformational epitope which is present in the N-terminal part of the amyloid β peptide, particularly embedded into the following core region of the N-terminal part of the amyloid β peptide:

| Val- | His- | His- | Gln- | Lys- | Leu- | Val- | Phe- | Phe- | Ala- | Glu- | Asp- |
|------|------|------|------|------|------|------|------|------|------|------|------|
| 12   | 13   | 14   | 15   | 16   | 17   | 18   | 19   | 20   | 21   | 22   | 23   |

Particularly an epitope localized in a region of the β-amyloid protein between amino acid residue 12 to 24, particularly between residues 14 to 23, more particularly between amino acid residues 14 and 20, comprising three distinct recognition and binding sites which residues are predominantly involved in the binding of the β-amyloid protein and located at position 16, 17, and at position 19 and 20, and at position 14, respectively.

In a specific embodiment the mixture of the present invention comprises, in addition to the compound of the invention, an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

More particularly, the invention relates to an antibody including any functionally equivalent antibody or functional parts thereof produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

The above antibodies are described in the published international application WO 2007/068412, which is incorporated herein by reference.

In a further aspect, the antibody which is comprised in the mixture according to the invention is a chimeric antibody or a fragment thereof, or a humanized antibody or a fragment thereof. These and further antibodies that can be suitably used within the mixtures according to the present invention are described, for example, in international application PCT/US2007/073504 filed Jul. 13, 2007 which is incorporated by reference.

If the antibody is a humanized antibody, it preferably exhibits a light chain and a heavy chain as depicted in SEQ ID No. 2 and SEQ ID No. 4 or exhibits a light chain variable region and a heavy chain variable region as depicted in SEQ ID No. 1 and SEQ ID No. 3. These sequences are also shown in the attached sequence listing.

In still another aspect of the invention, a mixture is provided which comprises, in addition to the compound according to the invention and as described herein before, a peptide fragment from the N-terminal part of the Aβ peptide, particularly an Aβ peptide fragment consisting of a single or repetitive stretch of between 13 and 15 contiguous amino acid residues from the N-terminal part of the Aβ peptide, but particularly an Aβ peptide fragment consisting of amino acid residues selected from the group consisting of residues 1-15, 1-14, and 1-13 from the N-terminal part of the Aβ peptide, more particularly of residue 1-15, including functionally equivalent fragments thereof, but especially a Aβ peptide fragment as mentioned herein before attached to, or incorporated or reconstituted in a carrier particle/adjuvant such as, for example, a liposome. The peptide fragment can be comprised in a vaccine composition. In particular, the peptide antigen is modified by a lipophilic or hydrophobic moiety, that facilitates insertion into the lipid bilayer of the liposome carrier/immune adjuvant, particularly by a lipophilic or hydrophobic moiety which functions as an anchor for the peptide in the liposome bilayer and has a dimension that leads to the peptide being positioned and stabilized in close proximity to the liposome surface.

In a further embodiment of the invention, the lipophilic or hydrophobic moiety is a fatty acid, a triglyceride or a phospholipid, but especially a fatty acid, a triglyceride or a phospholipid. In particular, the hydrophobic moiety is palmitic acid and the liposome preparation may in addition contain an adjuvant such as, for example, lipid A, alum, calcium phosphate, interleukin-1, and/or microcapsules of polysaccharides and proteins, but particularly a detoxified lipid A, such as monophosphoryl or diphosphoryl lipid A, or alum.

These and further compositions that can be suitably used in the mixtures of the present invention are described, for example, in the published international application WO 2007/068411.

Diagnosis of an amyloid-associated disease or condition or of a predisposition to an amyloid-associated disease or condition in a patient may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound of the invention to bind to the amyloid protein to form a compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient is suffering from or is at risk of developing an amyloid-associated disease or condition.

Monitoring minimal residual disease in a patient following treatment with a compound or a mixture according to the invention may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound to bind to the amyloid protein to form a compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient may still suffer from a minimal residual disease.

Predicting responsiveness of a patient to a treatment with a compound or composition or a mixture according to the invention may be achieved by detecting the specific binding of a compound according to the invention to the amyloid protein in a sample or in situ, which includes bringing the sample or a specific body part or body area suspected to contain the amyloid protein into contact with a compound of the invention which binds the amyloid protein, allowing the compound to bind to the amyloid protein to form a compound/protein complex, detecting the formation of the compound/protein complex and correlating the presence or absence of the compound/protein complex with the presence or absence of amyloid protein in the sample or specific body part or area, optionally comparing the amount of said compound/protein complex before and after onset of the treatment, wherein a decrease in the amount of said aggregate may indicate that said patient has a high potential of being responsive to the treatment.

In a further aspect of the present invention, the compound of formula (I) can contain a radionuclide (e.g., $^{125}$I, $^{124}$I, $^{123}$I or $^{18}$F). These compounds can be useful for in vivo diagnosis or imaging of amyloid-associated diseases, preferably of Alzheimer's disease, for example in methods such as single photon emission computed tomography (SPECT imaging) or positron emission tomography (PET).

In radiopharmaceutical applications, the compound of the present invention is preferably administered in a radiopharmaceutical formulation comprising the compound of the invention. A "radiopharmaceutical formulation" is defined in the present invention as a formulation comprising compound of the present invention (such as a compound of formula (I) or a salt thereof) in a form suitable for administration to mammals such as humans. Preferably a radiopharmaceutical formulation further comprises a physiologically acceptable excipient. Administration is preferably carried out by injection of the formulation as an aqueous solution. Such a formulation may optionally contain further ingredients such as buffers; pharmaceutically acceptable solubilisers (e.g., cyclodextrins or surfactants such as Pluronic, Tween or phospholipids); pharmaceutically acceptable stabilisers or antioxidants (such as ascorbic acid, gentisic acid or para-aminobenzoic acid). The dose of the compound of the present invention will vary depending on the exact compound to be administered, the weight of the patient, and other variables as would be apparent to a physician skilled in the art. Generally, the dose would lie in the range 0.001 µg/kg to 10 µg/kg, preferably 0.01 µg/kg to 1.0 µg/kg.

Biological samples that may be used in the diagnosis of an amyloid-associated disease or condition for diagnosing a predisposition to an amyloid-associated disease or condition or for monitoring minimal residual disease in a patient or for predicting responsiveness of a patient to a treatment with a compound or a composition or a mixture according to the invention and as described herein before are, for example, fluids such as serum, plasma, saliva, gastric secretions, mucus, cerebrospinal fluid, lymphatic fluid, and the like, or tissue or cell samples obtained from an organism such as neural, brain, cardiac or vascular tissue. For determining the presence or absence of the amyloid protein in a sample any immunoassay known to those of ordinary skill in the art (see Harlow and Lane, Antibodies: A Laboratory Manual (Cold Spring Harbor Laboratory, New York, 1988, 555 to 612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the compound or composition or mixture according to the invention and as described herein before may be administered to the organism to be diagnosed by methods known in the art such as, for example, intravenous, intranasal, intraperitoneal, intracerebral, intraarterial injection such that a specific binding between the compound according to the invention and the amyloid antigen may occur. The compound/protein complex may be detected through a label attached to the compound.

The immunoassays used in diagnostic applications or in applications for diagnosing a predisposition to an amyloid-associated disease or condition or for monitoring minimal residual disease in a patient or for predicting responsiveness of a patient to a treatment with a compound or composition or a mixture according to the invention and as described herein before, typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the compound of the invention may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein the antibody is labelled indirectly by reactivity with a second antibody that has been labelled with a detectable label. The second antibody is preferably one that binds to antibodies of the animal from which the monoclonal antibody is derived. In other words, if the monoclonal antibody is a mouse antibody, then the labelled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid antigen is determined using a pair of antibodies, each specific for amyloid antigen. One of said pairs of antibodies is referred to herein as a "detector antibody" and the other of said pair of antibodies is referred to herein as a "capture antibody". The monoclonal antibody can be used as either a capture antibody or a detector antibody. The monoclonal antibody can also be used as both capture and detector antibody, together in a single assay. One embodiment of the present invention thus uses the double antibody sandwich method for detecting amyloid antigen in a sample of biological fluid. In this method, the analyte (amyloid antigen) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The plaque burden in the tissue and/or body fluid (such as the retinal ganglion cell layer of an animal, particularly a mammal, but especially a human suffering from an ocular disease associated with pathological abnormalities/changes in the tissues of the visual system, particularly associated with amyloid-beta-related pathological abnormalities/changes in the tissues of the visual system) can be calculated by methods known in the art such as that disclosed in Ding, J. et al., "Targeting age-related macular degeneration with Alzheimer's disease based immunotherapies: Anti-amyloid-b antibody attenuates pathologies in an age-related macular degeneration mouse model", Vision Research (2007), doi:10.1016/j.visres.2007.07.025.

A compound according to the present invention can also be incorporated into a test kit for detecting an amyloid protein. The test kit typically comprises a container holding one or more compounds according to the present invention and instructions for using the compound for the purpose of binding to an amyloid protein to form a compound/protein complex and detecting the formation of the compound/protein complex such that presence or absence of the compound/protein complex correlates with the presence or absence of the amyloid protein.

The term "test kit" refers in general to any diagnostic kit known in the art. More specifically, the latter term refers to a diagnostic kit as described in Zrein et al. (1998).

The inhibition of aggregation of $A\beta_{1-42}$ by the compounds of the present invention may be measured using any suitable assay known in the art. A standard in vitro assay for measuring the inhibition of aggregation is described.

The synthesis of compounds of the invention inhibiting the aggregation of $A\beta_{1-42}$ and their biological activity assay are described in the following examples which are not intended to be limiting in any way.

EXAMPLES

All reagents and solvents were obtained from commercial sources and used without further purification. Proton ($^1$H) spectra were recorded on a 400 MHz NMR spectrometer in deuterated solvents. Mass spectra (MS) were recorded on a Finnigan MAT TSQ 7000 spectrometer. Chromatography was performed using silica gel (Fluka: Silica gel 60, 0.063-0.2 mm) and suitable solvents as indicated in specific examples. Flash purification was conducted with a Biotage Isolera One flash purification system using HP-Sil SNAP cartridges (Biotage) and the solvent gradient indicated in specific examples. Thin layer chromatography (TLC) was carried out on silica gel plates with UV detection. Preparative thin layer chromatography (Prep-TLC) was conducted with 0.5 mm or 1 mm silica gel plates (Analtech: Uniplate, $F_{254}$) and the solvents indicated in specific examples.

Preparative Example 1

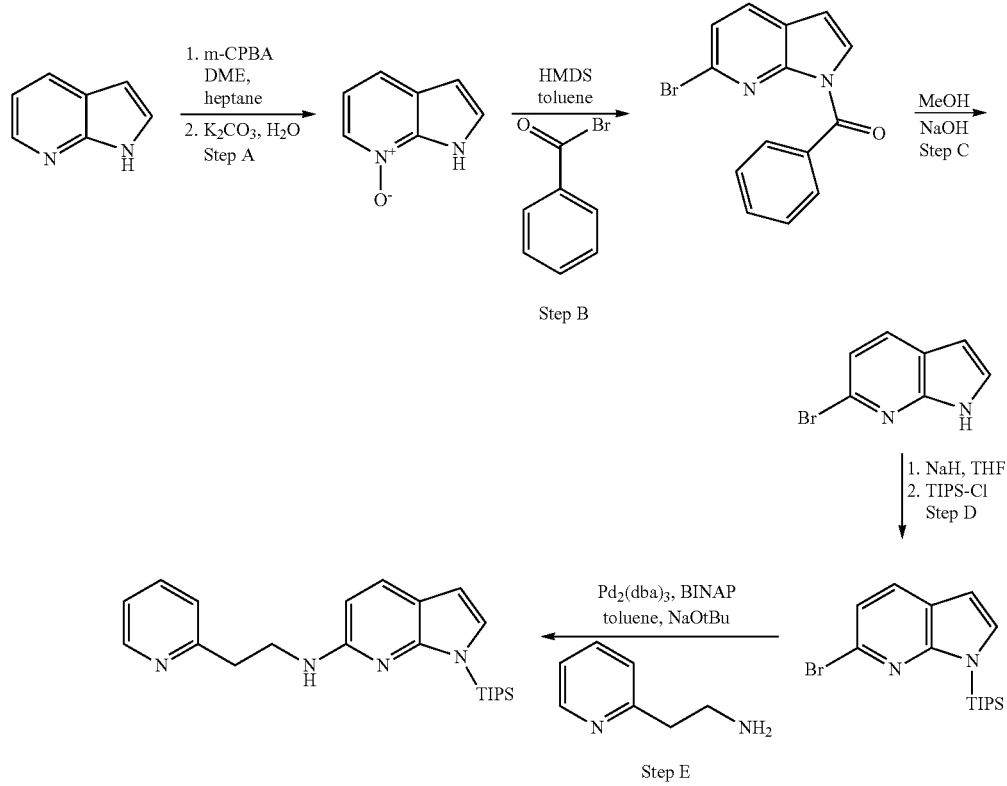

Step A

Commercially available 7-azaindole (1.98 g, 16.8 mmol) was dissolved in a mixture of 1,2-dimethoxyethane and n-heptane (30 mL, 1:2) and the mixture was placed in a cold water bath. Then m-chloroperoxybenzoic acid (5.1 g, 19.5 mmol, ~77%) was added in portions with stirring. A precipitate was formed after the addition of half of the m-chloroperoxybenzoic acid. After the addition was completed, the mixture was stirred at room temperature overnight. The precipitate was collected by filtration, washed with 1,2-dimethoxyethane/n-heptane (10 mL, 1:2) and air dried to afford the m-chloroperoxybenzoic acid salt of the title compound as a white solid (4.41 g, 91%). The salt was suspended in water (45 mL) and aqueous potassium carbonate solution was added until pH ~9. The solvents were removed and the residue was purified by chromatography on silica using dichloromethane/methanol (9/1) as a mobile phase to afford the title compound as an off-white solid (2 g, 91%).

$^1$H-NMR (400 MHz, DMSO-$d_6$): δ=6.60 (d, 1H), 7.07 (dd, 1H), 7.45 (d, 1H), 7.64 (d, 1H), 8.12 (d, 1H)

Step B

The title compound from Step A above (1 g, 7.46 mmol) was dissolved in toluene (150 mL). To this solution were added dropwise at the same time a solution of hexamethyldisilazane (1.56 mL, 7.46 mmol) in toluene (75 mL) and a solution of benzoylbromide (2.24 mL, 18.64 mmol) in toluene (75 mL). After the simultaneous addition was completed, the mixture was stirred at room temperature for 1 h. The reaction mixture was washed with saturated sodium bicarbonate (30 mL), brine (30 mL) and the organic phase was separated. The organic phase was dried over $Na_2SO_4$, filtered and the solvents were removed. The residue was purified by chromatography on silica using ethyl acetate/n-heptane (10/90) to afford the title compound as a white solid (1.48 g, 65%), which was directly used in the next step.

Step C

The title compound from Step B above (1.48 g, 4.9 mmol) was dissolved in methanol (90 mL) and a 1 M sodium hydroxide solution was added. The mixture was stirred at room temperature overnight and filtered to remove insoluble material. The filtrate was evaporated and the residue was suspended in dichloromethane (100 mL). The mixture was sonicated and then stirred at room temperature for 30 min. The mixture was filtered and the filtrate was evaporated. The residue was purified by chromatography on silica using dichloromethane/methanol (9/1) as a mobile phase to afford the title compound as a white solid (0.59 g, 60%).

$^1$H-NMR (400 MHz, $CDCl_3$): δ=6.53-6.56 (m, 1H), 7.26 (d, 1H), 7.39-7.42 (m, 1H), 7.84 (d, 1H), 10.5 (br-s, 1H)

Step D

The title compound from Step C above (0.59 g, 2.99 mmol) was dissolved in tetrahydrofurane (10 mL) and the solution was cooled to 0° C. At 0° C. sodium hydride (0.08 g, 3.3 mmol) was added in portions. After the addition was completed the mixture was stirred at room temperature for 15 min. Then triisopropylsilyl-chloride (0.4 mL, 3 mmol) was added and the mixture was heated at ~85° C. in a sand bath for 3 h. The mixture was diluted with ethyl acetate (50 mL) and brine (15 mL). The organic phase was separated, dried over $Na_2SO_4$, filtered and the solvents were removed. The residue was purified by chromatography on silica using ethyl acetate/n-heptane (10/90) to afford the title compound as a colorless oil (0.53 g, 50%).

$^1$H-NMR (400 MHz, $CDCl_3$): δ=1.10-1.12 (m, 18H), 1.73-1.82 (m, 3H), 6.51 (d, 1H), 7.17 (d, 1H), 7.23 (d, 1H), 7.70 (d, 1H)

Step E

The title compound from Preparation Step D above (0.045 g, 0.127 mmol) and commercially available 2-(2-aminoethyl)-pyridine (0.015 g, 0.127 mmol) were dissolved in toluene (2 mL) and treated with 2,2-bis-(diphenylphosphino)-1,1-naphthalene (0.016 g, 0.025 mmol) and sodium tert-butylate (0.031 g, 0.33 mmol). The reaction mixture was then degassed by bubbling argon through the reaction mixture followed by the addition of tris(dibenzylideneacetone)dipalladium chloroform complex (0.011 g, 0.0126 mmol). The reaction vessel was sealed and the mixture was heated at ~115° C. in a sand-bath for 45 minutes. The reaction mixture was diluted with ethyl acetate (20 mL), saturated sodium bicarbonate (5 mL) and brine (5 mL). The organic phase was separated, dried over $Na_2SO_4$, filtered and the solvents were removed. The residue was purified by chromatography on silica using ethyl acetate/n-heptane (20/80) to elute less polar by-products, followed by ethyl acetate/n-heptane (40/60) to afford the title compound as a pale orange oil (0.04 g, 80%).

$^1$H-NMR (400 MHz, $CDCl_3$): δ=1.10-1.12 (m, 18H), 1.81-1.88 (m, 3H), 3.10 (t, 2H), 3.78 (t, 2H), 4.45-4.67 (br-s, 1H), 6.20 (d, 1H), 6.37 (d, 1H), 6.94 (d, 1H), 7.10-7.14 (m, 2H), 7.56 (d, 1H), 7.58 (dt, 1H), 8.56 (d, 1H)

Preparative Example 2

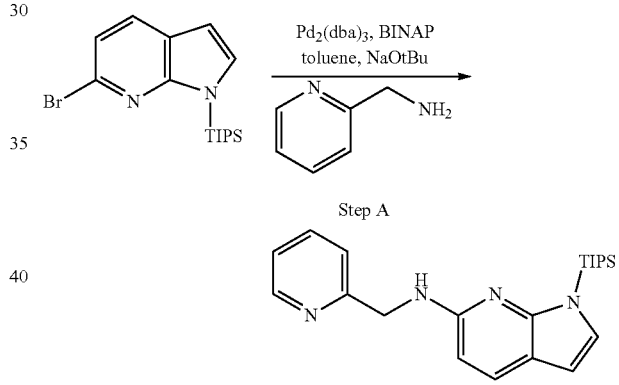

Step A

The title compound from Preparative Example 1 Step D (0.045 g, 0.127 mmol) and commercially available 2-(aminomethyl)-pyridine (0.015 g, 0.127 mmol) were dissolved in toluene (2 mL) and treated with 2,2-bis-(diphenylphosphino)-1,1-naphthalene (0.016 g, 0.025 mmol) and sodium tert-butylate (0.031 g, 0.33 mmol). The reaction mixture was then degassed by bubbling argon through the reaction mixture followed by the addition of tris(dibenzylideneacetone)dipalladium chloroform complex (0.011 g, 0.0126 mmol). The reaction vessel was sealed and the mixture was heated at ~115° C. in a sand bath for 45 minutes. The reaction mixture was diluted with ethyl acetate (20 mL), saturated sodium bicarbonate (5 mL) and brine (5 mL). The organic phase was separated, dried over $Na_2SO_4$, filtered and the solvents were removed. The residue was purified by chromatography on silica using ethyl acetate/n-heptane (20/80) to elute less polar by-products, followed by ethyl acetate/n-heptane (40/60) to afford the title compound as a pale orange oil (0.044 g, 90%).

$^1$H-NMR (400 MHz, $CDCl_3$): δ=1.10-1.12 (m, 18H), 1.62-1.76 (m, 3 H), 4.71 (s, 2H), 5.02-5.08 (br-s, 1H), 6.33-6.37

(m, 2H), 6.92 (d, 1H), 7.10-7.14 (m, 1H), 7.30 (d, 1H), 7.56 (dt, 1H), 7.61 (d, 1H), 8.53 (d, 1H)

Preparative Example 3

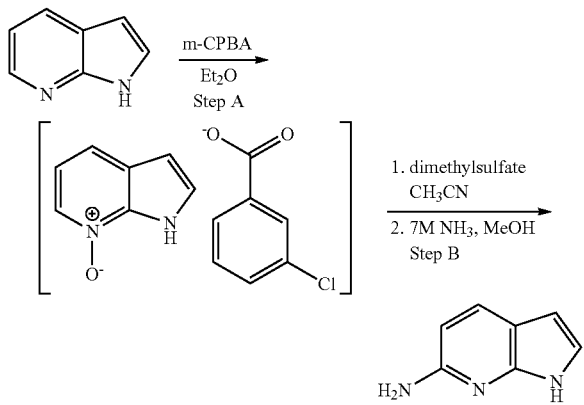

Step A

To a solution of commercially available 7-azaindole (5 g, 42.3 mmol) in diethyl ether (350 mL) was added m-chloro perbenzoic acid (11 g, 63.4 mmol) in portions at room temperature. The reaction mixture was stirred at room temperature for 5 h. The precipitated product was filtered off and washed with diethyl ether (50 mL). The solid was collected and dissolved in a mixture of water/acetone (50 mL/10 mL) with heating. The mixture was cooled to 5° C. and the crystallized product was filtered and air dried to afford the title compound (11.7 g, 96%).

$^1$H-NMR (400 MHz, CDCl$_3$): δ=6.59 (d, 1H), 7.07 (dd, 1H), 7.46 (d, 1H), 7.66 (d, 1H), 8.14 (d, 1H), 12.4 (s, 1H).

Step B

To a suspension of the title compound from Step A above (2 g, 6.92 mmol) in dry acetonitrile (15 mL) was added dimethylsulfate (0.885 g, 6.92 mmol). The reaction mixture was heated at 70° C. for 8 h. Then the clear solution was cooled to room temperature. The solution was distributed in three sealed tubes and cooled to 0° C. under an argon atmosphere. Then a 7 M solution of ammonia in methanol (5 mL) was added to each tube. The sealed tubes were heated at 50-60° C. for 48 h. The solvent was removed and the residue was dissolved in ethyl acetate (200 mL) and the organic phase was washed with dilute Na$_2$CO$_3$ solution, water, and brine. The organic phase was dried over Na$_2$SO$_4$. The solvent was evaporated and the crude product was purified by chromatography on silica using ethyl acetate to afford the title compound (0.5 g, 54%).

$^1$H-NMR (400 MHz, CDCl$_3$): δ=4.33 (m, 2H), 6.35 (dd, 1H), 6.38 (d, 1H), 6.99 (dd, 1H), 7.71 (d, 1H).

Preparative Example 4

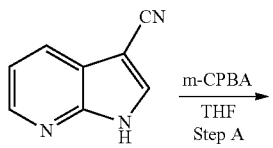

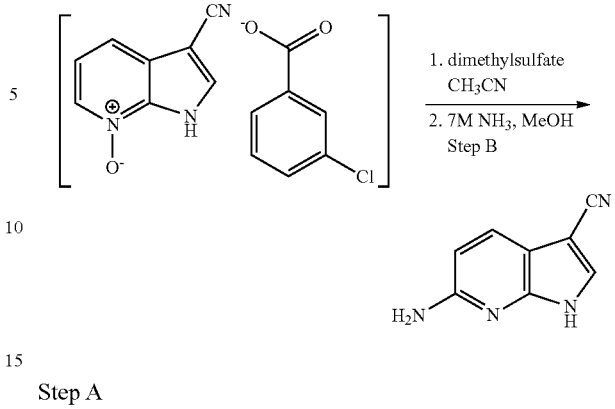

Step A

To a solution of commercially available 3-cyano-7-azaindole (2 g, 13.9 mmol) in tetrahydrofurane (150 mL) was added m-chloro perbenzoic acid. The reaction mixture was stirred at room temperature for 16 h. The precipitate was filtered off and dried to afford the title compound (1.89 g, 86%).

$^1$H-NMR (400 MHz, DMSO-d$_6$): δ=7.26 (d, 1H), 7.74 (d, 1H), 8.30 (d, 1H), 8.40 (s, 1H)

Step B

A suspension of the title compound from Step A above (1.89 g, 11.8 mmol) in dry acetonitrile (15 mL) was added dimethylsulfate (1.5 g, 11.8 mmol) and the reaction mixture was heated at 80° C. overnight. The clear solution was cooled to room temperature and transferred into three 5 mL tubes. Then a 7 M solution of ammonia in methanol (5 mL) was added to each tube. The sealed tubes were heated at 70° C. for 48 h. The reaction mixture was concentrated under reduced pressure and the residue was crystallized from ethyl acetate and n-heptane to afford the title compound (0.9 g, 48%).

$^1$H-NMR (400 MHz, CDCl$_3$): δ=3.33 (br-s, 2H), 6.00 (s, 1H), 6.42 (d, 1H), 7.64 (d, 1H), 7.83 (s, 1H)

Preparative Example 5

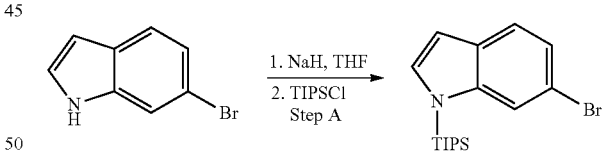

Step A

To a solution of commercially available 6-bromoindole (0.5 g, 2.55 mmol) in tetrahydrofurane (20 mL) was added sodium hydride (0.095 g, 3.22 mmol) portionwise at room temperature. The suspension was stirred at room temperature for 10 minutes and triisopropylsilyl chloride (0.489 g, 2.55 mmol) was added slowly. The reaction mixture was stirred at room temperature for 30 minutes. The reaction mixture was quenched with water and the solvent was removed under reduced pressure. The residue was dissolved in ethyl acetate (150 mL) and washed with water, brine and dried over Na$_2$SO$_4$. The solvent was removed under reduced pressure to give a residue, which was then purified by silica gel column chromatography (ethyl acetate/n-heptane 25/75) to afford the title compound (0.890 g, 99%).

$^1$H-NMR (400 MHz, CDCl$_3$): δ=1.17 (d, 18H), 1.68-1.71 (m, 3H), 6.61 (d, 1H), 7.22-7.24 (m, 2H), 7.51 (d, 1H), 7.65 (s, 1H)

Preparative Example 6

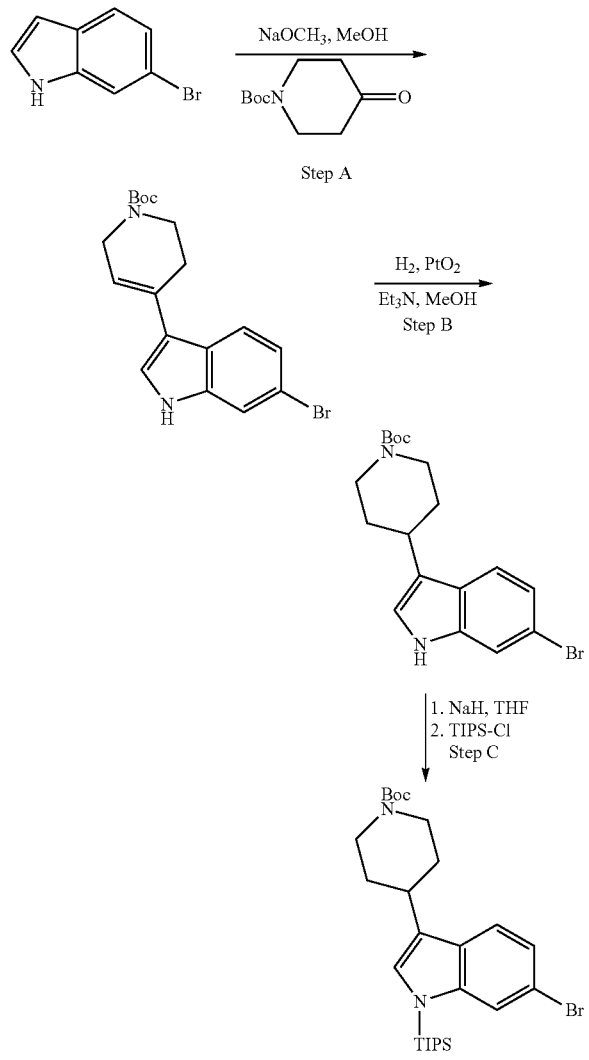

Step A

To a solution of commercially available 6-bromoindole (2.5 g, 12.7 mmol) in methanol (15 mL) was added a solution of 25% sodium methoxide in methanol (2 mL) and the reaction mixture was heated at 80° C. for 2 days. Then, the reaction mixture was concentrated to ⅓ of its volume and poured into ice water (100 mL) and extracted with ethyl acetate (3×100 mL). The organic phase was washed with water, brine and dried over Na$_2$SO$_4$. The solvent was removed under reduced pressure to give the crude product, which was then purified by column chromatography on silica (ethyl acetate/n-heptane (20/80)) to afford the title compound (3.5 g, 72%).

$^1$H-NMR (400 MHz, CDCl$_3$): δ=1.50 (s, 9H), 2.56 (m, 2H), 3.67 (t, 2H), 4.13 (d, 2H), 6.11 (s, 1H), 7.15 (d, 1H), 7.24 (d, 1H), 7.53 (d, 1H), 7.73 (d, 1H), 8.16 (s, 1H)

Step B

To a solution of the title compound from Step A (1.5 g, 3.97 mmol) in methanol (25 mL) was added triethyl amine (0.8 g, 7.94 mmol) and the mixture was degassed. Then, platinum (IV)-oxide (0.18 g, 0.79 mmol) was added to the reaction mixture, followed by evacuation and back filling with hydrogen gas. The procedure was repeated for 2-3 times and the reaction mixture was kept under a hydrogen atmosphere overnight. Then, the reaction mixture was filtered off through a celite pad. The filtrate was concentrated and dissolved in ethyl acetate (200 mL) and the organic phase was washed with water, brine and dried over Na$_2$SO$_4$. The solvent was removed under reduced pressure to give the crude product, which was then purified on a silica gel column to afford the title compound (0.95 g, 63%).

$^1$H-NMR (400 MHz, CDCl$_3$): δ=1.48 (s, 9H), 1.64 (m, 2H), 1.99-2.02 (m, 2H), 2.86-2.91 (m, 3H), 4.11-4.22 (m, 2H), 6.93 (d, 1H), 7.21 (dd, 1H), 7.48 (d, 1H), 7.51 (d, 1H), 8.09 (s, 1H)

Step C

To a solution of the title compound from Step B above (0.7 g, 1.84 mmol) in tetrahydrofurane (10 mL) was added sodium hydride (0.088 g, 3.68 mmol) and the suspension was stirred for 10 minutes. Then triisopropylsilyl chloride (0.353 g, 1.84 mmol) was added. The reaction mixture was stirred for 30 minutes. The reaction mixture was poured in ethyl acetate (200 mL) and washed with water, brine and dried over Na$_2$SO$_4$. The solvents were removed under reduced pressure to yield the crude product, which was then purified on a silica gel column using ethyl acetate/n-heptane (5/95 to 50/50) to afford the title compound (0.9 g, 91%).

$^1$H-NMR (400 MHz, CDCl$_3$): δ=1.13 (d, 18H), 1.48 (s, 9H), 1.62-1.66 (m, 5H), 1.99-2.04 (m, 2H), 2.88-2.92 (m, 3H), 4.21-4.23 (m, 2H), 6.92 (s, 1H), 7.18 (dd, 1H), 7.45 (d, 1H), 7.58 (d, 1H)

Preparative Example 7

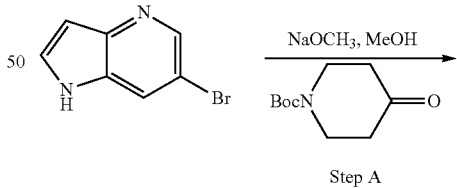

Step A

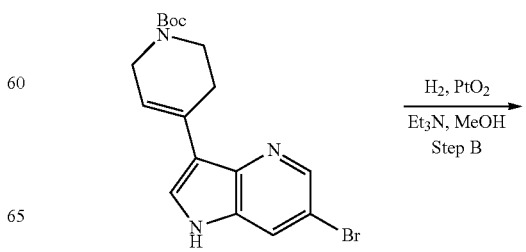

-continued

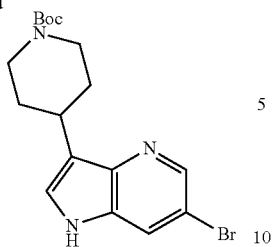

1. NaH, THF
2. TIPS-Cl
Step C

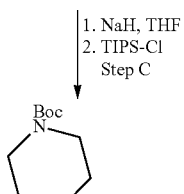

Step A

To a solution of commercially available 6-bromo-4-azaindole (3 g, 15.3 mmol) and 1-Boc-4-piperidone (3.8 g, 19 mmol) in methanol (30 mL) was added a solution of 25% sodium methoxide in methanol (4 mL, 18.5 mmol). The reaction mixture was then stirred at 80° C. for 3 h. At this time the reaction mixture was cooled to room temperature, poured into ice water (20 mL) and extracted with ethyl acetate (350 mL). The organic phase was washed with water, and brine solution. The organic phase was dried over Na$_2$SO$_4$ and the solvent was removed under reduced pressure to yield the crude product, which was then purified on silica gel column to afford the title compound (3 g, 52%).

$^1$H-NMR (400 MHz, CDCl$_3$): δ=1.60 (s, 9H), 2.55 (t, 1H), 2.66 (m, 2H), 3.81 (m, 2H), 4.27 (d, 2H), 7.22 (s, 1H), 7.44 (d, 1H), 7.91 (d, 1H), 8.63 (d, 1H), 8.97 (s, 1H)

Step B

To a solution of the title compound from Step A above (0.45 g, 1.19 mmol) in methanol (15 mL) was added triethylamine (54 mg, 0.53 mmol) and the mixture was degassed. After the addition of platinum(IV)-oxide (0.062 g, 0.185 mmol), the reaction mixture was evacuated and back filled with hydrogen gas (repeated two more times). The reaction mixture was stirred under a hydrogen atmosphere for 16 h. The reaction mixture was filtered off through celite and the filtrate was concentrated. The residue was then purified on a silica gel column using ethyl acetate/n-heptane (10/90) to afford the title compound (0.185 g, 42%).

$^1$H-NMR (400 MHz, CDCl$_3$): δ=1.50 (s, 9H), 1.69 (m, 2H), 2.15 (m, 2H), 2.97 (m, 2H), 3.23 (m, 1H), 4.22 (m, 2H), 7.18 (d, 1H), 7.82 (d, 1H), 8.26 (brs, 1H), 8.51 (d, 1H)

Step C

To a solution of the title compound from Step B above (0.110 g, 0.28 mmol) in tetrahydrofurane (5 mL) was added sodium hydride (0.014 g, 0.56 mmol). The suspension was stirred at room temperature for 10 minutes. After the addition of triisopropylsilyl chloride (0.055 g, 0.28 mmol), the reaction mixture was stirred at room temperature for 30 minutes. At this time, the reaction mixture was quenched with water, poured into ethyl acetate (150 mL), washed with water and brine solution. The organic phase was separated, dried over Na$_2$SO$_4$ and the solvent was evaporated under reduced pressure. The crude product was purified on a silica gel column to afford the title compound (0.105 g, 70%).

$^1$H-NMR (400 MHz, CDCl$_3$): δ=1.13 (d, 18H), 1.47 (s, 9H), 1.63-1.64 (m, 5H), 2.04-2.12 (m, 2H), 2.90-2.95 (m, 2H), 3.16-3.20 (m, 1H), 4.20-4.21 (m, 2H), 7.15 (s, 1H), 7.82 (d, 1H), 8.45 (d, 1H)

Preparative Example 8

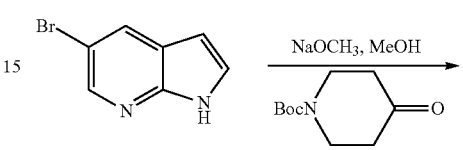

Step A

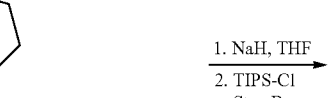

1. NaH, THF
2. TIPS-Cl
Step B

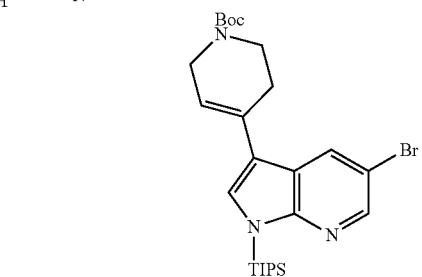

H$_2$, PtO$_2$
Et$_3$N, MeOH
Step C

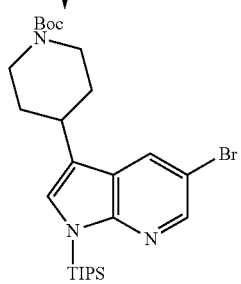

Step A

To a solution of commercially available 5-bromo-7-azaindole (3 g, 15.2 mmol) and 1-Boc-4-piperidone (4.2 g, 21.1 mmol) in methanol (25 mL) was added a solution of 25% sodium methoxide in methanol (4 mL, 18.5 mmol). Then, the reaction mixture was stirred at 80° C. for 2 days. The reaction mixture poured in ethyl acetate (350 mL) and washed with water, and brine solution. The organic phase was dried over Na$_2$SO$_4$ and the solvent was removed under reduced pressure to yield the crude product, which was then crystallized from an ethyl acetate/n-heptane mixture to afford the title compound (4.2 g, 73%).

$^1$H-NMR (400 MHz, CDCl$_3$): δ=1.52 (s, 9H), 2.55 (s, 2H), 3.70 (t, 2H), 4.16 (m, 2H), 6.11 (s, 1H), 7.32 (s, 1H), 8.32 (d, 1H), 8.38 (d, 1H), 9.40 (brs, 1H)

Step B

To a stirred solution of the title compound from Step A above (3.2 g, 8.4 mmol) in tetrahydrofurane was added sodium hydride (0.3 g, 12.6 mmol) and the suspension was stirred at room temperature for 10 minutes. Then triisopropylsilyl chloride (1.62 g, 8.4 mmol) was added slowly. The reaction mixture was stirred at room temperature for 2 h. At this time, the reaction mixture was quenched with water and concentrated under reduced pressure. The residue was dissolved in ethyl acetate (250 mL) and washed with water and brine solution. The organic phase was dried over Na$_2$SO$_4$. The removal of solvent yielded the crude product, which was purified on a silica gel column to afford the title compound (3.3 g, 75%).

$^1$H-NMR (400 MHz, CDCl$_3$): δ=1.13 (d, 18H), 1.52 (s, 9H), 1.83 (m, 2H), 2.56 (s, 2H), 3.51 (s, 2H), 3.71 (m, 2H), 4.16 (s, 2H), 7.04 (s, 1H), 7.26 (s, 1H), 8.22 (s, 1H), 8.30 (dd, 1H)

Step C

To a solution of the title compound from Step B above (1.63 g, 3.0 mmol) in methanol (20 mL) was added triethylamine (0.6 g, 6.0 mmol). The mixture was degassed and platinum(IV)-oxide (0.14 g, 0.6 mmol) was added. Then the flask was evacuated twice and back filled with hydrogen gas. The reaction mixture was stirred under a hydrogen atmosphere for 16 h. The heterogeneous reaction mixture was filtered off through celite. The filtrate was concentrated under reduced pressure to give the crude product, which was purified on a silica gel column to afford the title compound (0.240 g, 50%).

$^1$H-NMR (400 MHz, CDCl$_3$): δ=1.11 (d, 18H), 1.49 (s, 9H), 1.76-1.86 (m, 7H), 2.17-2.22 (m, 2H), 3.23 (m, 2H), 3.88-3.90 (m, 2H), 7.07 (s, 1H), 8.21 (d, 1H), 8.27 (d, 1H)

Preparative Example 9

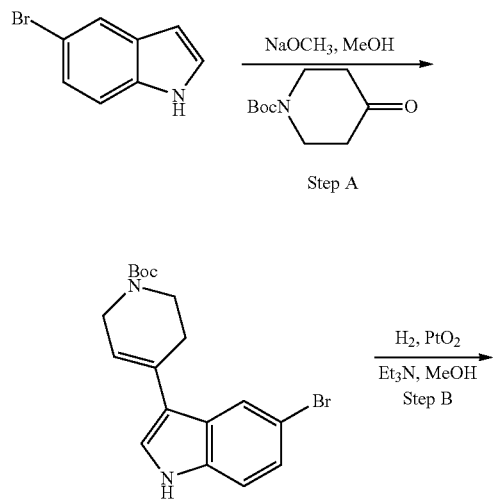

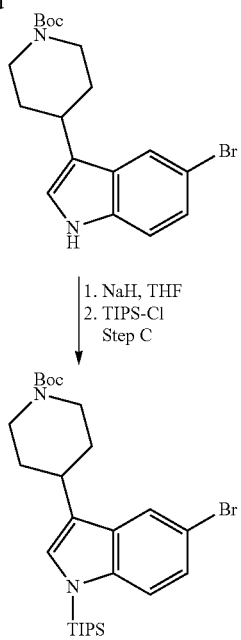

Step A

To a solution of commercially available 5-bromoindole (3.5 g, 17.9 mmol) in methanol (50 mL) was added 1-Boc-4-piperidone (5.1 g, 25.6 mmol) and a solution of 25% sodium methoxide in methanol (8 mL, 37 mmol) and the reaction mixture was heated at 80° C. for 2 days. The reaction mixture was filtered off. The solid was washed twice with ethyl acetate and dried under vacuum to give the title compound (3 g). The filtrate was diluted with ethyl acetate (250 mL) and washed with water, brine and dried over Na$_2$SO$_4$. The solvent was removed under reduced pressure to yield the crude product, which was purified on a silica gel column to afford additional title compound (2.9 g). The combined yield was 5.9 g, 86%.

$^1$H-NMR (400 MHz, CDCl$_3$): δ=1.52 (s, 9H), 2.55 (m, 2H), 3.69 (t, 2H), 4.16 (s, 2H), 6.12 (s, 1H), 7.19 (s, 1H), 7.26-7.33 (m, 2H), 8.01 (s, 1H), 8.29 (br-s, 1H)

Step B

To a degassed solution of the title compound from Step A above (1.8 g, 4.7 mmol) in ethyl acetate (50 mL) was added platinum(IV)-oxide (0.2 g, 0.88 mmol). The reaction mixture was evacuated and back filled with hydrogen gas. The procedure was repeated twice and the reaction mixture was kept under a hydrogen atmosphere at room temperature overnight. The reaction mixture was filtered off through celite, and the filtrate was concentrated. The crude product was purified on a silica gel column using ethyl acetate/n-heptane (10/90 to 50/50) to afford the title compound (0.75 g, 42%).

$^1$H-NMR (400 MHz, CDCl$_3$): δ=1.52 (s, 9H), 2.04 (m, 2H), 2.91 (m, 3H), 3.75 (m, 2H), 4.23-4.29 (m, 2H), 6.98 (s, 1H), 7.28 (m, 2H), 7.76 (s, 1H), 8.11 (s, 1H)

Step C

To a solution of the title compound from Step B above (0.6 g, 1.58 mmol) in tetrahydrofurane (20 mL) was added sodium hydride (0.056 g, 2.37 mmol), and the suspension was stirred at room temperature for 10 minutes. Then triisopropylsilyl chloride (0.34 g, 1.58 mmol) was added and the mixture was stirred for 1 h at room temperature. The reaction mixture was quenched with water and concentrated. The residue was dissolved in ethyl acetate (100 mL), washed with water and brine solution. The organic phase was dried over Na$_2$SO$_4$ and the solvent was removed under reduced pressure to yield the crude product, which was purified on a silica gel column using ethyl acetate/n-heptane (10/90) to afford the title compound (0.6 g, 70%).

$^1$H-NMR (400 MHz, CDCl$_3$): δ=1.13 (d, 18H), 1.51 (s, 9H), 1.65-1.66 (m, 5H), 2.01-2.05 (m, 2H), 2.89-2.94 (m, 3H), 4.25-4.26 (m, 2H), 6.98 (s, 1H), 7.23 (dd, 1H), 7.34 (s, 1H), 7.36 (s, 1H), 7.72 (s, 1H)

Preparative Example 10

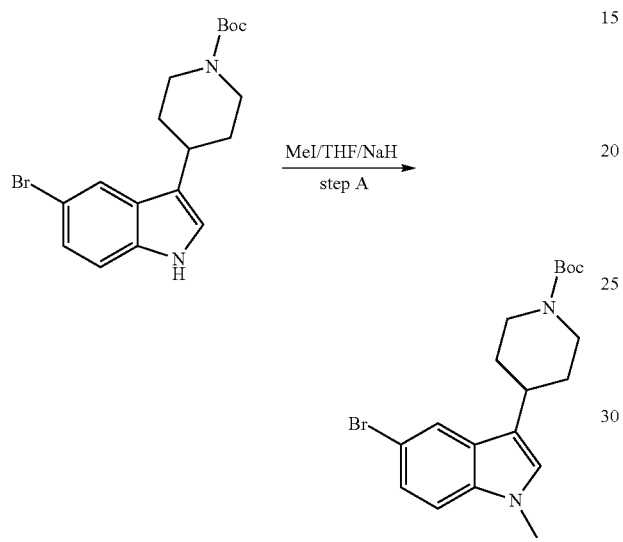

Step A

To a solution of title compound from Preparative Example 9 Step B (0.625 g, 1.64 mmol) in THF (10 ml) was added NaH (0.059 g, 2.4 mmol). The suspension was stirred for 5 minutes. Then methyliodide (0.346 g, 2.46 mmol) was added slowly. The reaction mixture was stirred at room temperature for 1 h. Then, the reaction mixture was poured into ethyl acetate (150 mL) and washed with water and brine. The organic phase was dried over Na$_2$SO$_4$. The solvent was concentrated under reduced pressure, and the crude product was purified on silica gel column (20-50%; EtOAC to heptane) to give the title compound (0.485 g, 75%).

$^1$H-NMR (400 MHz, CDCl$_3$): δ=1.51 (s, 9H), 1.61-1.65 (m, 2H), 1.99-2.02 (m, 2H), 2.87-2.95 (m, 3H), 3.74 (s, 3H), 4.24-4.25 (m, 2H), 6.82 (s, 1H), 7.16 (d, 1H), 7.32 (d, 1H), 7.74 (s, 1H)

Preparative Example 11

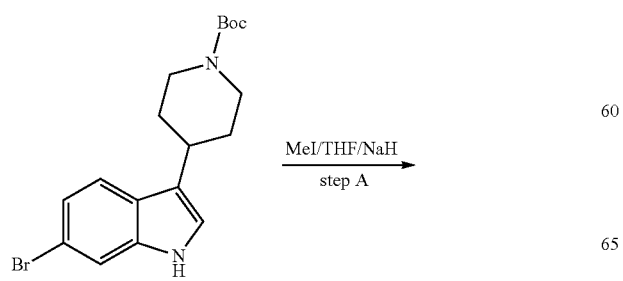

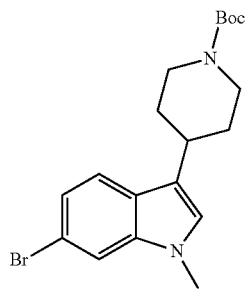

To a solution of title compound (500 mg, 0.1.31 mmol) in THF (10 ml) was added NaH (63 mg, 2.6 mmol) and the suspension was stirred for 5 min. Methyl iodide (185 mg, 0.1.31 mmol) was added and the reaction mixture was stirred for 30 min. Then, the reaction mixture was quenched with water and extracted with ethyl acetate (50 ml×3). The organic phase washed with brine and dried over Na$_2$SO$_4$ and solvent was removed under reduced pressure. The crude product was purified on silica gel column (EtOAc: heptane; 20:30) to give the title compound (485 mg, 94%).

$^1$H NMR (400 MHz, CDCl$_3$) δ 7.50-7.46 (m, 2H), 7.21 (dd, J=8.4, 1.7 Hz, 1H), 6.80 (s, 1H), 4.25 (s, 2H), 3.73 (s, 3H), 2.99-2.87 (m, 3H), 2.03-1.99 (m, 2H), 1.67-1.63 (m, 2H), 1.51 (s, 9H).

Preparative Example 12

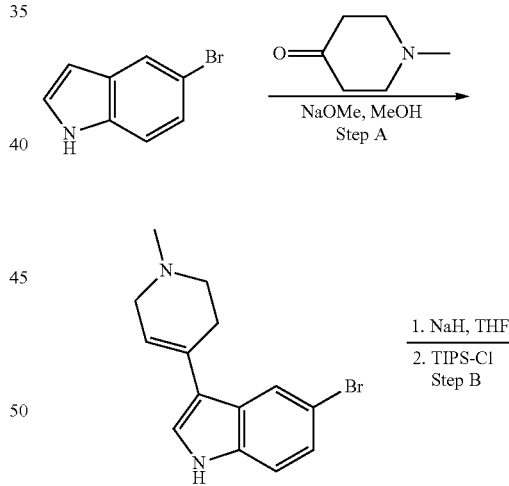

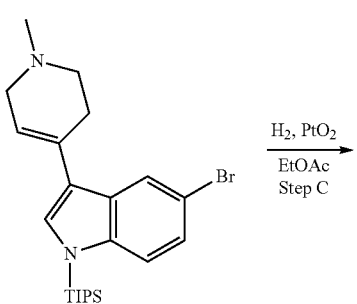

-continued

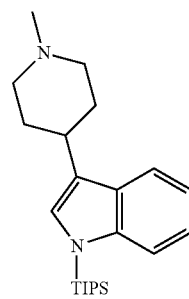

Step A

To a solution of 5-bromoindole (5 g, 25.3 mmol), and 1-methylpiperidin-4-one (4.3 g, 38.2 mmol) in methanol (50 mL) was added (28%) NaOMe in methanol (10 mL) and the reaction mixture was heated at 90° C. for 2 days. The product was precipitated, was filtered off and dried under vacuum to give the title compound (6.3 g, 85%).

$^1$H-NMR (400 MHz, CDCl$_3$): 2.28 (s, 3H), 2.55 (m, 2H), 3.04 (d, 2H), 3.34 (m, 2H), 6.07 (s, 1H), 7.21 (d, 1H), 7.35 (d, 1H), 7.45 (s, 1H), 7.92 (s, 1H)

Step B

To a solution of title compound from Step A above (0.5 g, 1.72 mmol) in THF (100 mL) was added sodium hydride (0.1 g, 4.28 mmol) portionwise and the suspension was stirred at room temperature for 10 minutes. Then triisoproyplsilyl chloride (0.33 g, 1.72 mmol) was introduced slowly and the reaction mixture was stirred at room temperature for 10 minutes. The reaction mixture was quenched with water and the solvent was removed. The residue was dissolved in ethyl acetate (150 mL). The organic phase was washed with water and brine and was dried over Na$_2$SO$_4$. The solvents were removed and the residue was purified on a silica gel column (methanol to EtOAc 10% to 20%) to give the title compound (0.498 g, 65%).

$^1$H-NMR (400 MHz, CDCl$_3$): δ=1.13 (d, 18H), 1.67-1.69 (m, 3H), 2.45 (s, 3H), 2.64 (brs, 2H), 2.72 (t, 2H), 3.19 (s, 2H), 6.12 (s, 1H), 7.18 (s, 1H), 7.23 (d, 1H), 7.34 (d, 1H), 7.98 (s, 1H)

Step C

A solution of title compound from Step B above (0.490 g, 1.09 mmol) in ethyl acetate (50 mL) was degassed and platinum(IV)-oxide was added (0.150 g, 0.67 mmol). The reaction mixture was evacuated and back filled with hydrogen gas. The procedure was repeated 2-3 times and the reaction mixture was stirred under a hydrogen atmosphere overnight. The reaction mixture was filtered through an acelite pad. The filtrate was concentrated and dissolved in ethyl acetate (200 mL). The organic phase was washed with water and brine and dried over Na$_2$SO$_4$. The solvent was removed under reduced pressure to give the crude product, which was then purified on silica gel column (MeOH to ethyl acetate 5% to 12%) to afford the title compound (0.15 g, 30%).

$^1$H-NMR (400 MHz, CDCl$_3$): δ=1.12 (d, 18H), 1.62-1.69 (m, 3H), 2.0-2.12 (m, 4H), 2.47 (t, 2H), 2.56 (s, 3H), 2.81-2.89 (m, 1H), 3.24 (d, 2H), 7.03 (s, 1H), 7.23 (d, 1H), 7.34 (d, 1H), 7.70 (s, 1H)

Preparative Example 13

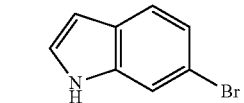
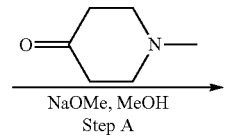
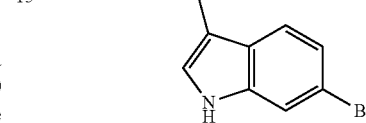
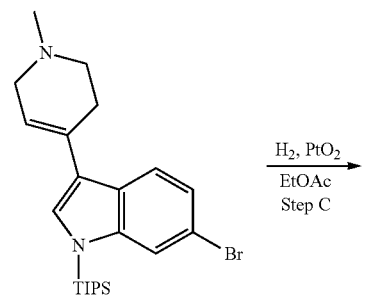
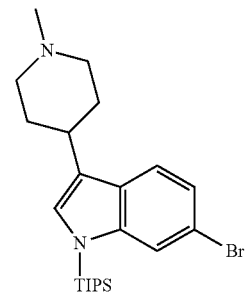

Step A

To a solution of 6-bromoindole (3 g, 15.3 mmol), and 1-methylpiperidin-4-one (3.4 g, 30.6 mmol) in methanol (50 mL) was added (28%) NaOMe in methanol (10 mL) and the reaction mixture was heated at 90° C. for 2 days. The precipitated product was filtered off and dried under vacuum to afford the title compound (4.1 g, 91%).

$^1$H-NMR (400 MHz, CDCl$_3$): δ=2.28 (s, 3H), 2.51-2.56 (m, 4H), 3.03 (s, 2H), 6.1 (s, 1H), 7.14 (d, 1H), 7.41 (s, 1H), 7.56 (s, 1H), 7.74 (d, 1H)

Step B

To a solution of title compound from Step A above (2 g, 6.8 mmol) in THF/dioxane (100 mL/10 mL) was added sodium hydride (0.25 g, 10.3 mmol) portionwise and the suspension was stirred at room temperature for 10 minutes. Then, triisopropylsilyl chloride (1.3 g, 6.8 mmol) was introduced slowly and the reaction mixture was stirred at room temperature for 10 minutes. The reaction mixture was quenched with water and the solvent was removed, and the residue was dissolved in ethyl acetate (200 mL). The organic phase was washed with water and brine and was dried over Na$_2$SO$_4$. The solvents were removed and the residue was purified on silica gel column (methanol to EtOAc 5% to 20%) to afford the title compound (2.9 g, 95%).

$^1$H-NMR (400 MHz, CDCl$_3$): δ=1.12 (d, 18H), 1.61-1.69 (m, 3H), 2.41 (s, 3H), 2.61 (brs, 2H), 2.69 (t, 2H), 3.15 (d, 2H), 6.11 (s, 1H), 7.13 (s, 1H), 7.21 (d, 1H), 7.58 (s, 1H), 7.69 (d, 1H)

Step C

A solution of the title compound from Step B above (2.8 g, 6.2 mmol) in ethyl acetate (50 mL) was degassed and platinum(IV)-oxide was added (0.18 g, 0.79 mmol). Then, the reaction mixture was evacuated and back filled with hydrogen gas. The procedure was repeated for 2-3 times and the reaction mixture was stirred under a hydrogen atmosphere overnight. Then, the reaction mixture was filtered off through a celite pad. The filtrate was concentrated and the residue was dissolved in ethyl acetate (200 mL). The organic phase was washed with water and brine and was dried over Na$_2$SO$_4$. The solvent was removed under reduced pressure to give the crude product, which was then purified on silica gel column (methanol to ethyl acetate 5% to 12%) to afford the title compound (2.3 g, 85%).

$^1$H-NMR (400 MHz, CDCl$_3$): δ=1.13 (d, 18H), 1.61-1.69 (m, 3H), 1.84-1.88 (m, 2H), 2.03-2.06 (m, 2H), 2.16 (t, 2H), 2.37 (s, 3H), 2.78 (tt, 1H), 2.99 (d, 2H), 6.97 (s, 1H), 7.19 (d, 1H), 7.47 (d, 1H), 7.59 (s, 1H)

Preparative Example 14 solution was heated under reflux for 2.5 h. The reaction solution was poured into 50 ml of ice water, extracted with ethyl acetate and the organic layer was washed with water, dried and concentrated. The resulting residue was crystallized from n-hexane/ethyl acetate to give the compound (3.4 g, 67%).

$^1$H-NMR (400 MHz, CDCl$_3$): δ=1.46 (s, 9H), 2.56 (brs, 2H), 3.68 (t, 2H), 4.13 (d, 2H), 6.13 (s, 1H), 7.12 (dd, 1H), 7.34 (s, 1H), 8.20 (dd, 1H), 8.31 (dd, 1H), 11.28 (brs, 1H).

MS (ESI); m/z=299.94 (MH$^+$)

Step B

To a solution of the title compound from Step A above (1 g, 3.34 mmol) in 65 ml of methanol were added 1 ml of acetic acid, followed by 500 mg of 10% Pd/C. The mixture was stirred under hydrogen atmosphere for 48 h. The catalyst was filtered through Celite and the solvent was removed under reduced pressure. The obtained residue was dissolved in ethyl acetate and washed with aqueous solution of NaHCO$_3$. The organic phase was evaporated to give a yellowish compound which was purified using the Biotage flash chromatography system (ethyl acetate/n-heptane: 20 to 66%) to afford a yellowish compound (0.92 g, 91%).

$^1$H-NMR (400 MHz, CDCl$_3$): δ=1.47 (s, 9H), 1.63-1.75 (m, 3H), 1.99-2.04 (m, 2H), 2.86-2.99 (m, 3H), 4.24 (brs, 2H), 7.07 (m, 2H), 7.95 (d, 1H), 8.32 (brs, 1H), 9.57 (brs, 1H).

MS (ESI); m/z=301.97 (MH$^+$)

Step C m-Chloroperbenzoic acid (0.568 g, 1.69 mmol) was added to a cold solution (0° C.) of the title compound from Step B above (0.51 g, 1.69 mmol) in 20 mL of dichloromethane. The reaction mixture was warmed to room temperature and then

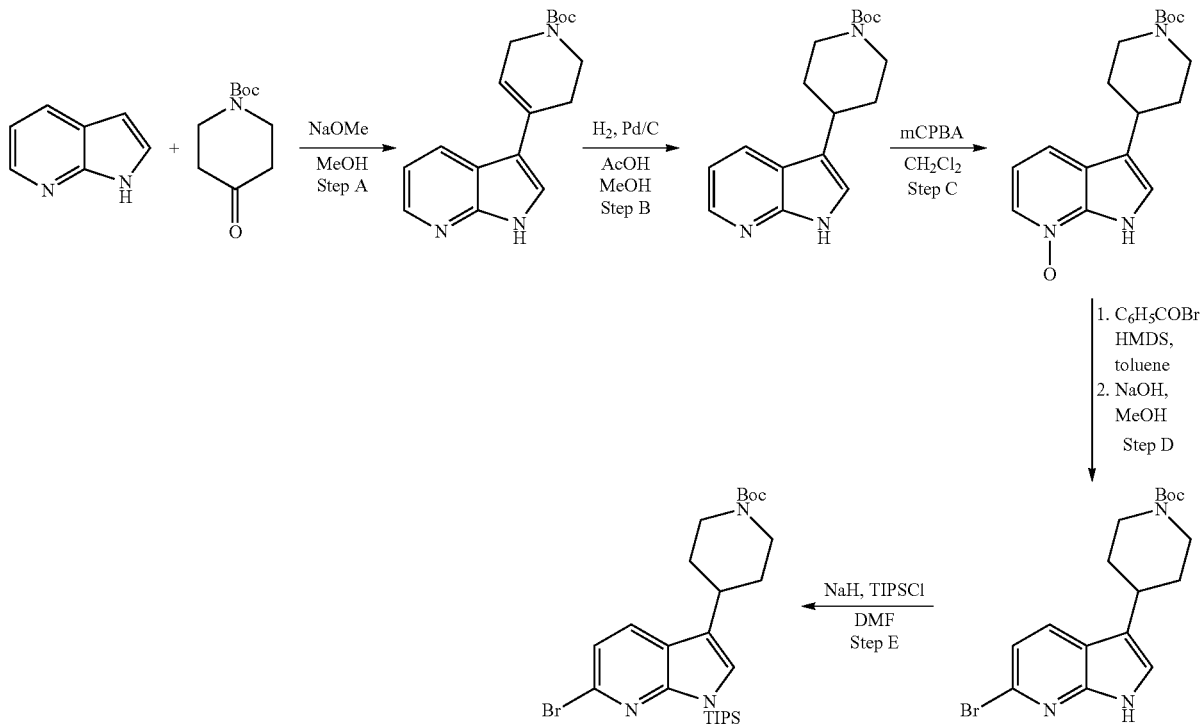

Step A

To a solution of commercially available 7-azaindole (2 g, 16.8 mmol) in methanol (20 mL) were added 1-(t-butoxycarbonyl)-4-piperidone (6.75 g, 34 mmol) and 25% methanol solution of sodium methoxide (21.6 mL, 100 mmol) and the stirred for 12 h. A saturated aqueous solution of sodium bicarbonate was added to the reaction mixture and extracted with dichloromethane. The organic phase was dried over anhydrous sodium sulfate, filtered and then concentrated. The obtained residue was purified using the Biotage flash chromatography system (methanol/dichloromethane: 3 to 10%) to afford a white compound (0.4 g, 74%).

¹H-NMR (400 MHz, CDCl₃): δ=1.47 (s, 9H), 1.61-1.65 (m, 2H), 1.96 (d, 2H), 2.86-2.90 (m, 3H), 4.21 (brs, 2H), 7.02 (t, 1H), 7.16 (s, 1H), 7.68 (d, 1H), 8.18 (d, 1H).

MS (ESI); m/z=317.96 (MH⁺)

Step D

To a solution of the title compound from Step C above (0.38 g, 1.19 mmol) in 24 ml of toluene, were added simultaneously hexamethyldisilazane (0.25 mL, 1.19 mmol) dissolved in 12 mL of toluene and benzoyl bromide (0.42 ml, 3.59 mmol) in 14 ml of toluene. The reaction mixture was stirred at room temperature for 12 h. The residue obtained after solvent evaporation was dissolved in 10 mL of methanol and treated with 3.5 mL of 1M sodium hydroxide solution. After stirring for 2 hours, a saturated aqueous solution of citric acid (10 mL) was added. The aqueous phase was extracted with ethyl acetate (100 mL). The organic phase was washed with sodium bicarbonate and water and was then dried. The residue obtained after solvent removal was purified using the Biotage flash chromatography system (methanol/dichloromethane: 1 to 5%) to give a white compound (0.185 g, 40% for two steps).

¹H-NMR (400 MHz, CDCl₃): δ=1.48 (s, 9H), 1.63-1.67 (m, 2H), 1.97 (d, 2H), 2.84-2.90 (m, 3H), 4.22 (d, 2H), 6.96 (s, 1H), 7.14 (d, 1H), 7.69 (d, 1H).

MS (ESI); m/z=381.85 (MH⁺)

Step E

The title compound from Step D above (0.1 g, 0.263 mmol) was dissolved in N,N'-dimethylformamide (6 mL) and the solution was cooled to 0° C. At 0° C. sodium hydride 95% (0.007 g, 0.289 mmol) was added in portions. After the addition was completed the mixture was stirred at room temperature for 1 hour. Then triisopropylsilylchloride (0.06 mL, 0.289 mmol) was added and the mixture was stirred at room temperature for 19 h. The mixture was diluted with water (50 mL). The aqueous phase was extracted with ethyl acetate. The organic phase was separated, dried over Na₂SO₄, filtered and the solvents were removed. The residue was purified by chromatography on silica using methanol/dichloromethane: 1 to 5% to afford the title compound as a white solid (0.1 g, 71%).

¹H-NMR (400 MHz, CDCl₃): δ=1.10-1.11 (m, 18H), 1.66 (s, 9H), 1.67-1.63 (m, 2H), 1.80-1.73 (m, 3H), 1.97 (d, 2H), 2.90-2.84 (m, 3H), 4.22 (d, 2H), 6.96 (s, 1H), 7.14 (d, 1H), 7.69 (d, 1H).

MS (ESI); m/z=537.95 (MH⁺)

Preparative Example 15

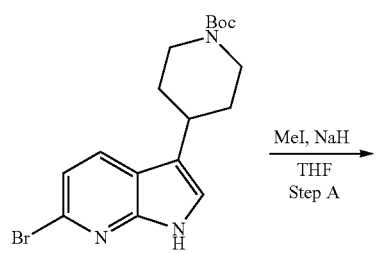

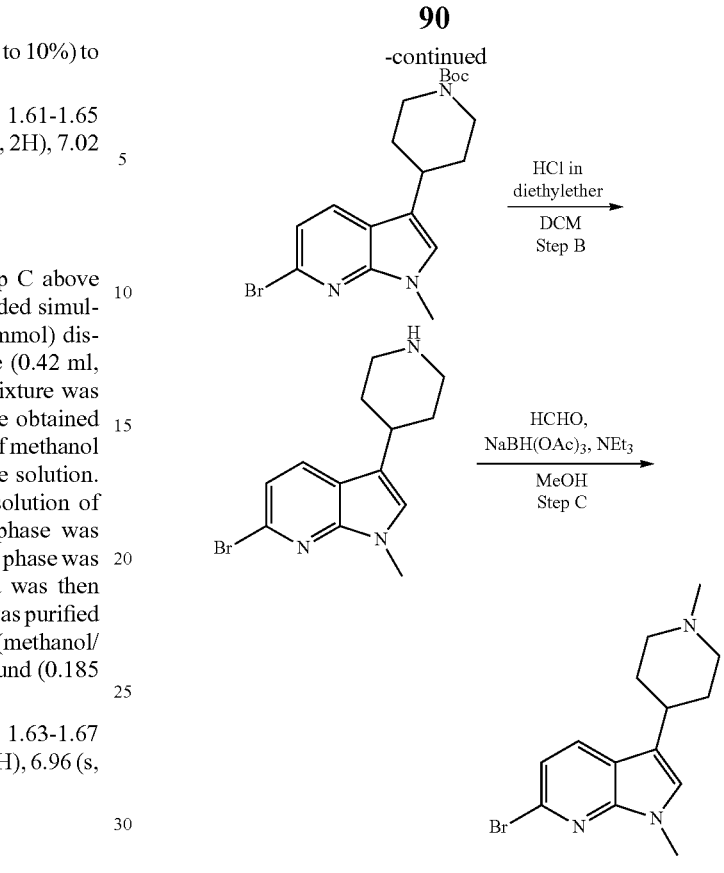

Step A

To a solution of the title compound from Preparative Example 14 Step D (1 g, 2.63 mmol) in dry tetrahydrofuran (25 ml) was added at 0° C. sodium hydride 60% (0.111 g, 2.89 mmol) portionwise. The mixture was stirred at room temperature for 30 min then methyl iodide (0.491 ml, 7.89 mmol) was added. Upon completion, which was checked by TLC plate, the solution was concentrated to dryness. The residue was purified by flash chromatography in ethylacetate/n-heptane 15% to 40% to give the compound as a white solid (0.984 g, 95%).

MS (ESI); m/z=394.48/396.48 (MH⁺)

Step B

To a solution of the title compound from Step A above (0.688 g, 1.745 mmol) in dichloromethane (50 ml) was added hydrogen chloride 2 M in diethyl ether (8.72 ml, 17.45 mmol). The resulting mixture was stirred at room temperature for 12 h. The reaction mixture was concentrated to dryness to afford a beige solid compound (0.654 g, 99%).

MS (ESI); m/z=294.60/296.60 (MH⁺)

Step C

To a solution of the title compound from Step B above (0.654 g, 2.223 mmol) in MeOH (50 ml) was added triethylamine (0.781 ml, 5.56 mmol), formaldehyde solution (0.196 ml, 2.445 mmol) and sodium triacetoxyborohydride (0.565 g, 2.67 mmol) sequentially. The resulting mixture was stirred at room temperature for 12 h. The mixture was concentrated to dryness, and then the residue was diluted with water and ethyl acetate. An extraction was performed with NaOH 1 M and brine. The organic layers were collected, dried over Na₂SO₄, filtered and concentrated to dryness to lead to the expected compound as a yellowish solid (0.411 g, 60%).

¹H-NMR (400 MHz, CDCl₃): δ=1.81 (t, J=11.6 Hz, 2H); 1.96 (d, J=11.6 Hz, 2H); 2.08 (t, J=11.2 Hz, 2H); 2.33 (s, 3H);

2.71 (t, J=11.2 Hz, 2H); 2.96 (d, J=9.6 Hz, 2H); 3.80 (s, 3H); 6.88 (s, 1H); 7.08-7.19 (m, 2H); 7.69-7.83 (m, 1H)

MS (ESI); m/z=308.59/310.59 (MH+)

Preparative example 16

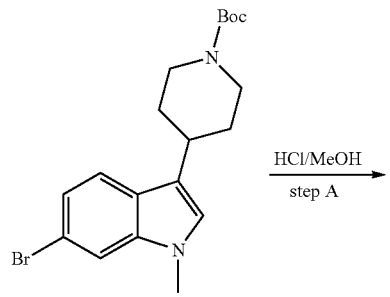

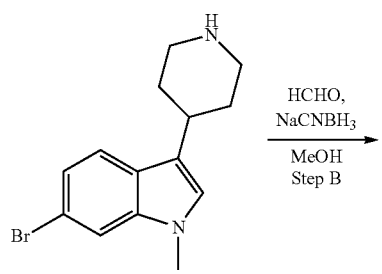

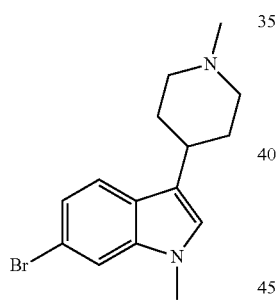

Step A

To a solution of title compound (220 mg, 0.55 mmol) in MeOH (3 mL) was added 3N HCl in MeOH (0.5 mL) and stirred the reaction mixture for overnight. The solvent was removed under reduced pressure to give the title compound (180 mg, 98%).

Step B

To a solution of compound (220 mg, 0.75 mmol) in MeOH (5 ml) was added NaCNBH₃ (200 mg, 3.1 mmol). The reaction mixture was stirred for overnight. The solvent was removed and the crude product was purified on a silica gel column using Biotage Isolera One purification system employing an MeOH/DCM gradient (1/99=>5/95) to afford the title compound (92 mg, 30%).

$^1$H-NMR (400 MHz, CDCl$_3$): 7.46 (m, 2H), 7.20 (s, 1H), 6.89 (s, 1H), 3.72 (s, 3H), 3.48 (s, 3H), 2.94 (m, 1H), 2.68-2.63 (m, 3H), 2.21-2.04 (m, 5H).

MS (ESI): m/z=307.6 (M+H).

Preparative Example 17

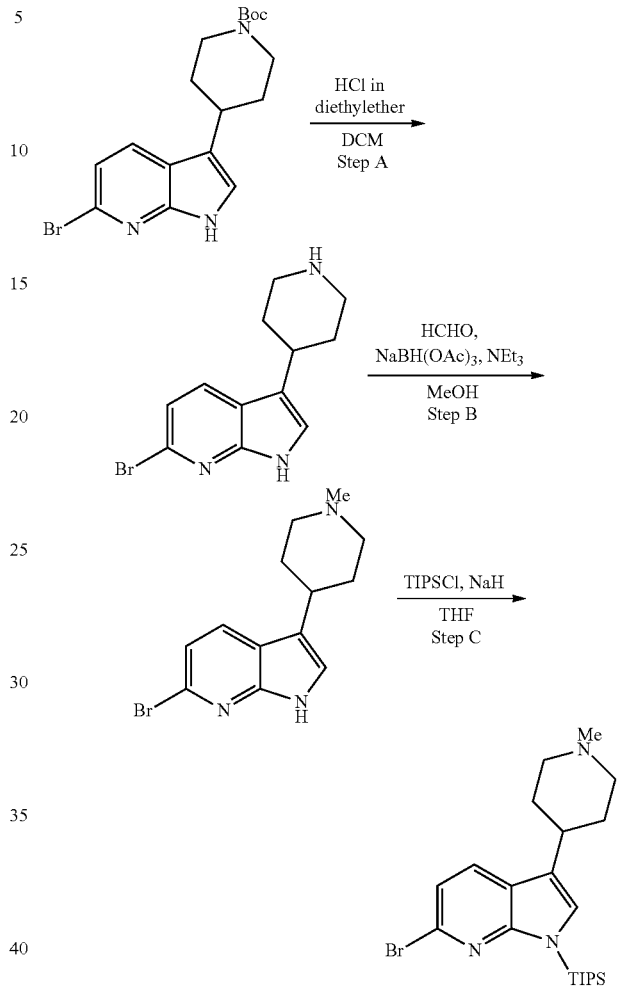

Step A

To a solution of the title compound from Preparative Example 14 Step D (0.500 g, 1.315 mmol) in dichloromethane (10 ml) was added hydrogen chloride 2 M diethyl ether (3.29 ml, 6.57 mmol). The resulting mixture was stirred at room temperature for 12 h. After completion the slurry was concentrated to dryness to give the compound as a beige solid (0.443 g, 95%).

MS (ESI); m/z=280.53/282.52 (MH+)

Step B

To a solution of the title compound from Step A above (0.443 g, 1.255 mmol) and triethylamine (0.353 ml, 2.509 mmol) in methanol (5 ml) was added formaldehyde solution (0.121 ml, 1.506 mmol) then sodium triacetoxyborohydride (30.99 g, 1.882 mmol). The resulting mixture was stirred at room temperature for 12 h. The mixture was concentrated to dryness, and then the residue was diluted with water and ethyl acetate. An extraction was performed with NaOH 1M and brine. The organic layers were collected, dried over Na₂SO₄, filtered and concentrated to dryness to lead to the expected compound as a white solid (0.328 g, 89%).

MS (ESI); m/z=294.59/296.59 (MH+)

Step C

To a solution of the title compound from Step B above (0.328 g, 1.115 mmol) in dry tetrahydrofuran (10 ml) was added sodium hydride 60% (0.045 g, 1.171 mmol) portionwise. The resulting mixture was stirred at room temperature for 30 min then triisopropylsilyl chloride (0.255 ml, 1.204 mmol) was added. The reaction mixture was further stirred at room temperature for 3 h. The reaction mixture was concentrated to dryness then the residue was purified by flash chromatography in DCM/MeOH 97:3 to 90:10 to afford the expected compound as a white amorphous solid (0.184 g, 37%).

$^1$H-NMR (400 MHz, CDCl$_3$): δ=1.00-1.23 (s, 18H); 1.69-1.87 (m, 3H); 1.95-2.12 (m, 4H); 2.25-2.40 (m, 2H); 2.47 (s, 3H); 2.70-2.89 (m, 1H); 3.08-3.23 (m, 2H); 6.99 (sl, 1H); 7.08-7.17 (m, 1H); 7.67-7.79 (m, 1H)

MS (ESI); m/z=450.63/452.63 (MH$^+$)

Preparative Example 18

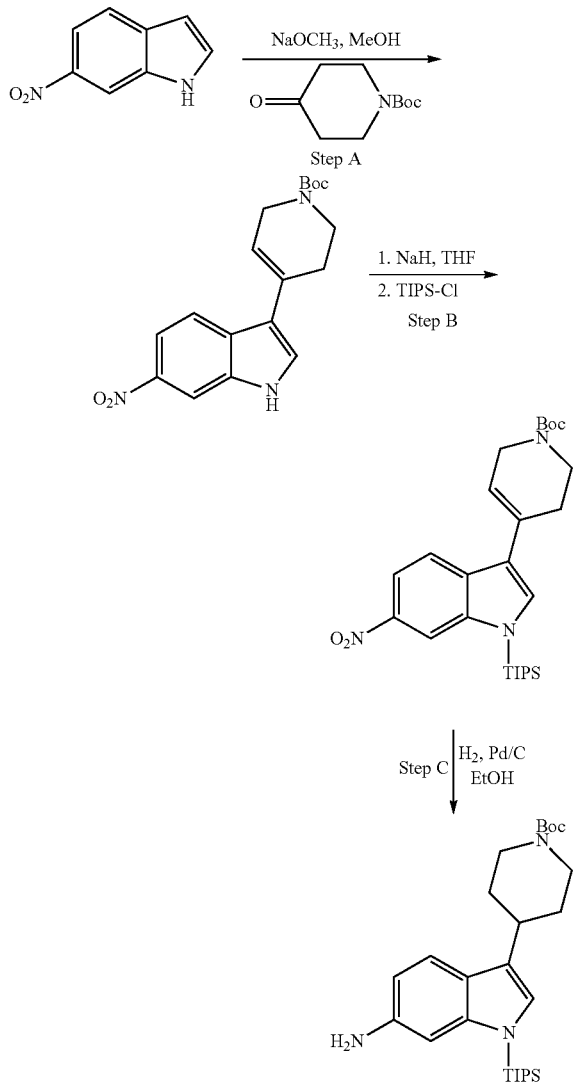

Step A

Commercially available 6-nitroindole (2.15 g, 13.27 mmol) was dissolved in methanol (10 mL) and commercially available N-Boc-4-piperidone (3.93 g, 19.8 mmol) was added. After the addition of a 25%-solution of sodium methoxide in methanol (8.22 mL, 38 mmol), the mixture was heated at ~100° C. in a sand-bath overnight. The mixture was diluted with ethyl acetate (150 mL) and washed with saturated sodium bicarbonate (40 mL) and brine (40 mL). The organic phase was separated, dried over Na$_2$SO$_4$, filtered and the solvents were removed. The residue was purified by chromatography on silica using ethyl acetate/n-heptane (40/60) to elute starting material followed by ethyl acetate/n-heptane (60/40) to afford the title compound as a yellow solid (2.56 g, 56%).

$^1$H-NMR (400 MHz, DMSO$_6$): δ=1.39 (s, 9H), 2.48-2.51 (m, 2H), 3.54 (t, 2H), 4.00-4.04 (m, 2H), 6.16-6.19 (m, 1H), 7.84-7.90 (m, 2H), 7.98 (d, 1H), 8.31 (s, 1H), 11.8 (br-s, 1H)

Step B

To a solution of the title compound from Step A above (2.2 g, 6.3 mmol) in tetrahydrofurane (50 mL) was added sodium hydride (0.18 g, 7.56 mmol). The black suspension was stirred for 10 minutes, and then triisopropylsilyl chloride (1.24 g, 6.3 mmol) was added. The reaction mixture was stirred at room temperature for 1 h. At this time, the reaction mixture was quenched with water and concentrated. The resulting residue was dissolved in EtOAc (300 mL) and washed with water and brine. The organic phase was dried over Na$_2$SO$_4$ and the solvent was evaporated under reduced pressure to afford the crude product, which was then purified on a silica gel column to afford the title compound (1.5 g, 46%).

$^1$H-NMR (400 MHz, CDCl$_3$): δ=1.17 (d, 18H), 1.52 (s, 9H), 1.73-1.79 (m, 3H), 2.59 (s, 2H), 3.72 (t, 2H), 4.17 (s, 2H), 6.16 (s, 1H), 7.46 (s, 1H), 7.88 (d, 1H), 8.06 (d, 1H), 8.47 (s, 1H)

MS (ESI) m/z: 500 (MH) 501 (M+2H).

Step C

To a solution of the title compound from Step B above (1.5 g, 3.0 mmol) in ethyl acetate (50 mL) was added 10% Pd/C. The mixture was degassed under vacuum and back filled with hydrogen. The reaction mixture was stirred under a hydrogen atmosphere overnight. The reaction mixture was filtered off and the solvent was evaporated. The residue was then purified by chromatography on silica using an ethyl acetate/n-heptane gradient (20/80->50/50) to afford the title compound as a solid (0.51 g, 36%).

$^1$H-NMR (400 MHz, CDCl$_3$): δ=1.16 (d, 18H), 1.50 (s, 9H), 1.65-1.69 (m, 5H), 2.02-2.05 (m, 2H),), 2.87-2.93 (m, 3H), 4.22-4.23 (m, 2H), 6.59 (d, 1H), 6.61 (d, 1H), 6.78 (s, 1H), 6.83 (s, 1H), 7.39 (d, 1H)

Preparative Example 19

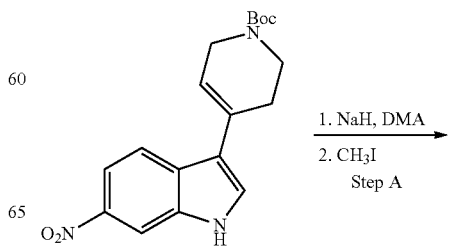

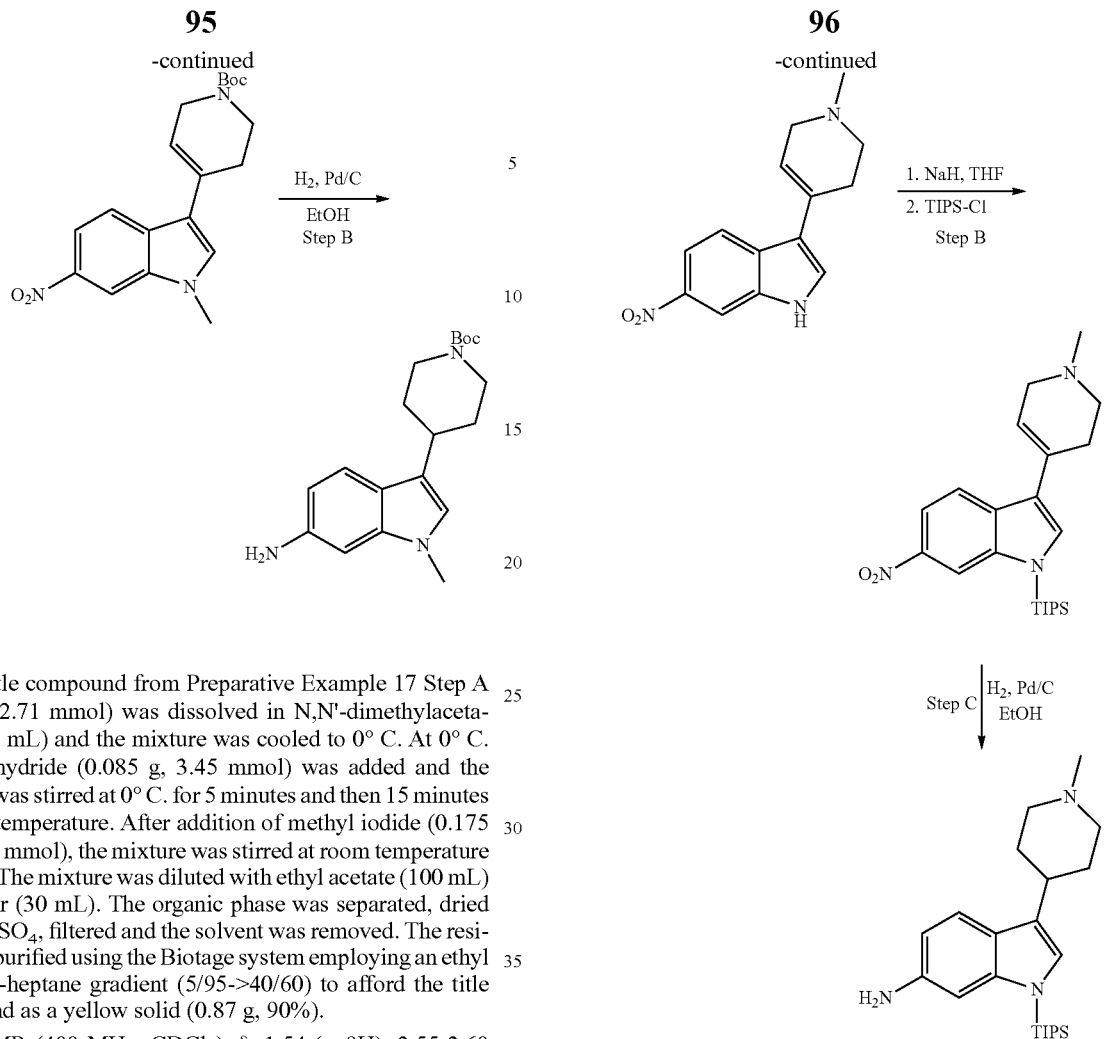

Step A

The title compound from Preparative Example 17 Step A (0.93 g, 2.71 mmol) was dissolved in N,N'-dimethylacetamide (10 mL) and the mixture was cooled to 0° C. At 0° C. sodium hydride (0.085 g, 3.45 mmol) was added and the mixture was stirred at 0° C. for 5 minutes and then 15 minutes at room temperature. After addition of methyl iodide (0.175 mL, 2.72 mmol), the mixture was stirred at room temperature for 18 h. The mixture was diluted with ethyl acetate (100 mL) and water (30 mL). The organic phase was separated, dried over $Na_2SO_4$, filtered and the solvent was removed. The residue was purified using the Biotage system employing an ethyl acetate/n-heptane gradient (5/95->40/60) to afford the title compound as a yellow solid (0.87 g, 90%).

$^1$H-NMR (400 MHz, $CDCl_3$): δ=1.54 (s, 9H), 2.55-2.60 (m, 2H), 3.70 (t, 2H), 3.90 (s, 3H), 4.14.4.17 (m, 2H), 6.15 (s, 1H), 7.30 (s, 1H), 7.90 (d, 1H), 8.04 (dd, 1H), 8.31 (d, 1H)

Step B

To a solution of the title compound from Step A above (0.87 g, 2.44 mmol) in ethanol (50 mL) was added 10% Pd/C catalyst (0.4 g). The mixture was degassed under vacuum and back filled with hydrogen. The reaction mixture was stirred under a hydrogen atmosphere overnight. The reaction mixture was filtered off and the solvent was evaporated. The residue was purified using the Biotage system employing an ethyl acetate/n-heptane gradient (5/95->100/0) to afford the title compound as a pale pink foam (0.3 g, 38%).

$^1$H-NMR (400 MHz, $CDCl_3$): δ=1.52 (s, 9H), 1.58-1.66 (m, 3H), 2.00 (d, 2H), 2.85-2.91 (m, 3H), 3.64 (s, 3H), 4.15-4.27 (br-s, 2H), 6.56-6.62 (3 H), 7.40 (d, 1H)

Preparative Example 20

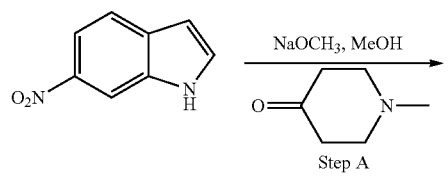

Step A

Commercially available 6-nitroindole (2.15 g, 13.27 mmol) was dissolved in methanol (15 mL) and commercially available N-methyl-4-piperidone (2.19 mL, 19.8 mmol) was added. After the addition of a 25%-solution of sodium methoxide in methanol (8.22 mL, 38 mmol), the mixture was heated at ~100° C. in a sand-bath for 30 h. The mixture was diluted with water (100 mL) and stirred at room temperature for 10 minutes. The precipitate was collected by filtration, washed with methanol (25 mL) and air-dried to afford the title compound as an orange solid (2.47 g, 72%).

$^1$H-NMR (400 MHz, $DMSO_6$): δ=2.25 (s, 3H), 2.52-2.59 (m, 4H), 3.04 (s, 2H), 6.17 (s, 1H), 7.82 (s, 1H), 7.88 (d, 1H), 7.97 (d, 1H), 8.31 (s, 1H), 11.9 (br-s, 1H)

Step B

To a solution of the title compound from Step A above (1.1 g, 4.32 mmol) in tetrahydrofurane (25 mL) was added sodium hydride (0.136 g, 5.5 mmol) at 0° C. The black suspension was stirred for 5 minutes at 0° C. and 15 minutes at room temperature. Then triisopropylsilyl chloride (0.58 mL, 4.35 mmol) was added. The reaction mixture was stirred at ~85° C. in a sand-bath for 2 h. The reaction mixture was diluted with ethyl acetate (50 mL) and washed with saturated bicarbonate (25 mL) and brine (25 mL). The organic phase was separated, dried over $Na_2SO_4$, filtered and the solvents were removed to afford a mixture of the title compound and starting material. This mixture was directly used for the next step.

Step C

To a solution of the mixture from Step B above in ethanol (30 mL) was added 10% Pd/C catalyst (0.4 g). The mixture was degassed under vacuum and back filled with hydrogen. The reaction mixture was stirred under a hydrogen atmosphere overnight. The reaction mixture was filtered off and the solvent was evaporated. The residue was then purified by chromatography on silica using dichloromethane/methanol (9/1) to afford a mixture of the title compound together with a compound where the double bound had not been reduced (0.22 g). This mixture was again hydrogenated in ethanol (15 mL) using 10% Pd/C catalyst (0.11 g) as described above. Filtration of the solution and evaporation of the solvent afforded the title compound as a colorless glass (0.2 g, 19% for 2 steps).

$^1$H-NMR (400 MHz, DMSO$_6$): δ=1.04-1.07 (m, 18H), 1.59-1.69 (m 5H), 1.88 (d, 1H), 2.13-2.18 (m, 2H), 2.26 (s, 3H), 2.57-2.66 (m, 2H), 2.90 (d, 2H), 4.58-4.67 (br-s, 2 H), 6.38 (d, 1H), 6.69-6.72 (m 2H), 7.17 (d, 1H)

Preparative Example 21

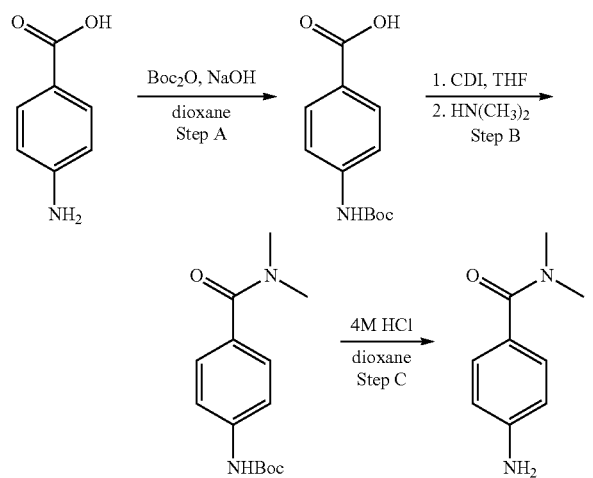

Step A

Commercially available 4-amino benzoic acid (5 g, 36 mmol) was dissolved in 1 M sodium hydroxide solution (40 mL, 40 mmol) and 1,4 dioxane (30 mL). After the addition of di-tert-butyl dicarbonate (7.85 g, 36 mmol), the mixture was stirred at room temperature over the weekend. The dioxane was removed in vacuo and the residue was diluted with water (100 mL). Then concentrated hydrochloric acid (~37%) was added until pH~3. The precipitate was collected by filtration, washed with water (100 mL) and air-dried to afford the title compound as a white solid (6.3 g, 72%).

Step B

The title compound from Step A above (0.43 g, 1.8 mmol) was suspended in tetrahydrofurane (10 mL) and treated with carbonyldiimidazole (0.37 g, 2.26 mmol). The mixture was stirred at room temperature for 1 h. To the clear solution was then added a 2 M solution of dimethylamine in tetrahydrofurane (2.25 mL, 4.5 mmol). Stirring was continued overnight and the solvents were removed. The residue was dissolved in ethyl acetate (50 mL) and washed with a solution of 10% citric acid in water (15 mL) and brine (15 ml). The organic phase was separated, dried over Na$_2$SO$_4$, filtered and the solvents were removed to afford the title compound as a colorless foam (0.46 g, 96%).

$^1$H-NMR (400 MHz, CDCl$_3$): δ=1.54 (s, 9H), 3.00-3.12 (m, 6H), 6.63 (br-s, 1H), 7.39-7.41 (m, 4H)

Step C

The title compound from Step B above (0.46 g, 1.75 mmol) was dissolved in dichloromethane (2.2 mL) and treated with a 4 M solution of hydrochloric acid in 1,4-dioxane (2.2 mL, 8.8 mmol). The mixture was stirred at room temperature for 3 h and diluted with ethyl acetate (20 mL). Saturated aqueous sodium carbonate was then added until pH~10. The organic phase was separated, dried over Na$_2$SO$_4$, filtered and the solvents were removed. The residue was purified by chromatography on silica using ethyl acetate to afford the title compound as an off-white solid (0.16 g, 55%).

$^1$H-NMR (400 MHz, CDCl$_3$): δ=3.04 (s, 6H), 3.80 (br-s, 2H), 6.67 (m, 2H), 7.31 (m, 2H)

Preparative Example 22

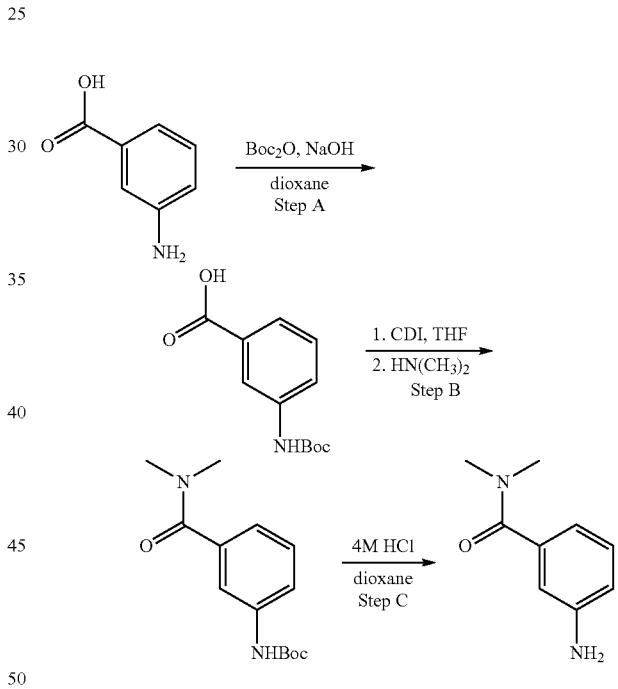

Step A

Commercially available 3-amino benzoic acid (5 g, 36 mmol) was dissolved in 1 M sodium hydroxide solution (40 mL, 40 mmol) and 1,4 dioxane (30 mL). After the addition of di-tert-butyl dicarbonate (7.85 g, 36 mmol), the mixture was stirred at room temperature over the weekend. The dioxane was removed in vacuo and the residue was diluted with water (100 mL). Then concentrated hydrochloric acid (~37%) was added until pH~3. The precipitate was collected by filtration, washed with water (100 mL) and air-dried to afford the title compound as a white solid (7.3 g, 84%).

Step B

The title compound from Step A above (0.43 g, 1.8 mmol) was suspended in tetrahydrofurane (10 mL) and treated with carbonyldiimidazole (0.37 g, 2.26 mmol). The mixture was stirred at room temperature for 1 h. To the clear solution was then added a 2 M solution of dimethylamine in tetrahydrofurane (2.25 mL, 4.5 mmol). Stirring was continued overnight and the solvents were removed. The residue was dissolved in ethyl acetate (50 mL) and washed with a solution of 10% citric acid in water (15 mL) and brine (15 ml). The organic phase was separated, dried over $Na_2SO_4$, filtered and the solvents were removed to afford the title compound as a colorless foam (0.36 g, 75%).

$^1$H-NMR (400 MHz, $CDCl_3$): δ=1.55 (s, 9H), 3.00 (s, 3H), 3.13 (s, 3H), 6.67 (br-s, 1H), 7.08 (dt, 1H), 7.32 (t, 1H), 7.40-7.48 (m, 2H),

Step C

The title compound from Step B above (0.36 g, 1.37 mmol) was dissolved in dichloromethane (2 mL) and treated with a 4 M solution of hydrochloric acid in 1,4-dioxane (2 mL, 8 mmol). The mixture was stirred at room temperature for 3 h and diluted with ethyl acetate (20 mL). Saturated aqueous sodium carbonate was then added until pH~10. The organic phase was separated, dried over $Na_2SO_4$, filtered and the solvents were removed. The residue was purified by chromatography on silica using ethyl acetate to afford the title compound as off-white solid (0.08 g, 36%).

$^1$H-NMR (400 MHz, $CDCl_3$): δ=3.00 (s, 3H), 3.11 (s, 3H), 6.70-6.74 (m, 2H), 6.77 (dt, 1H), 7.18 (t, 1H)

Preparative Example 23

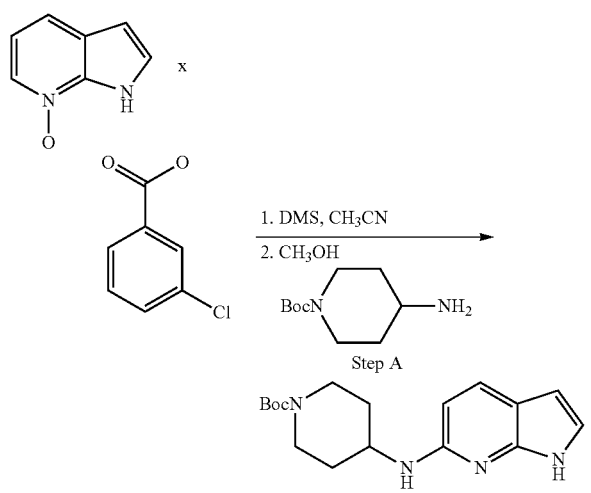

Step A

To a suspension of the title compound from Preparative Example 3 Step A (2 g, 6.92 mmol) in dry acetonitrile (15 mL) was added dimethylsulfate (0.885 g, 6.92 mmol). The reaction mixture was heated at 70° C. for 8 h. Then, the clear solution was cooled to room temperature. The solution was distributed in three sealed tubes and cooled to 0° C. under an argon atmosphere. Then a solution of 4-amino piperidine-1-carboxylicacid tert-butyl ester (0.1 g) in methanol (5 mL) was added to each of the sealed tubes and heated at 50-60° C. over 2 days. The solvent was removed and the residue was dissolved in ethyl acetate (200 mL). The organic phase was washed with dilute $Na_2CO_3$ solution, water, and brine and dried over $Na_2SO_4$. The solvent was evaporated and the crude product was purified on silica gel (EtOAc) to give the title compound (0.130 g).

$^1$H-NMR (400 MHz, $CDCl_3$): δ=1.59 (s, 9H), 2.23 (m, 2H), 3.09 (m, 2H), 3.81 (m, 1H), 4.23 (m, 2H), 4.44 (d, 1H), 6.37 (d, 1H), 6.47 (d, 1H), 7.24 (d, 1H), 7.38 (s, 1H), 8.16 (d, 1H)

Preparative Example 24

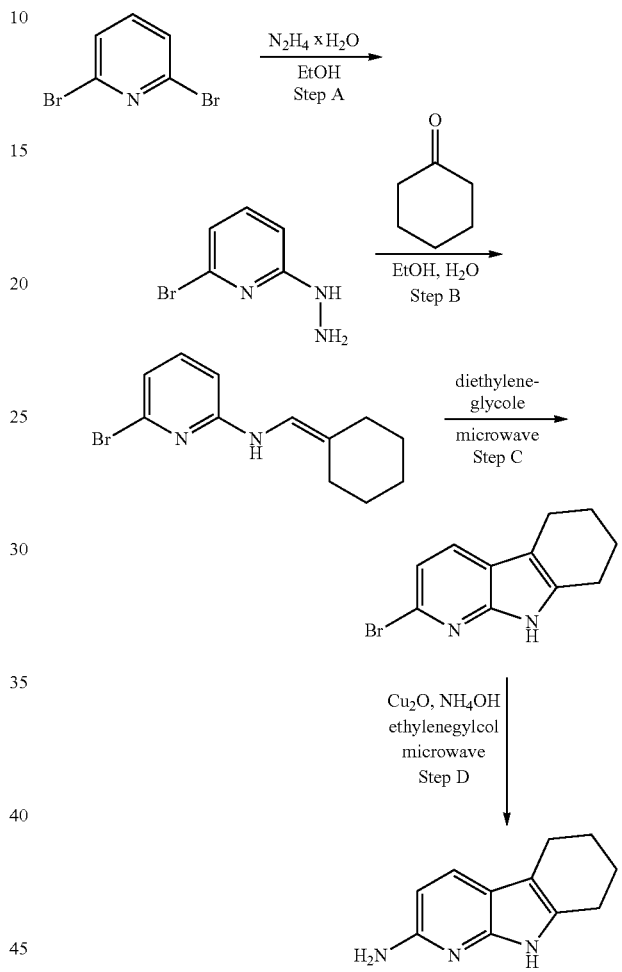

Step A

Commercially available 2,6-dibromopyridine (4.12 g, 16.6 mmol) was suspended in ethanol (40 mL) and hydrazine hydrate (10 mL, 97.6 mmol) in water (~50-60%) was added. The mixture was heated in a sand-bath at ~115° C. for 18 h. The solvent was removed and the residue was purified by chromatography on silica using ethyl acetate/n-heptane (60/40) to afford the title compound as an off-white solid (3.05 g, 93%).

$^1$H-NMR (400 MHz, $CDCl_3$): δ=3.00-3.33 (br-s, 2H), 6.00 (br-s, 1H), 6.67 (d, 1H), 6.83 (d, 1H), 7.33 (t, 1H)

Step B

The title compound from Step A above (0.84 g, 4.49 mmol) was dissolved in ethanol (16 mL) and water (4 mL). After the addition of cyclohexanone (0.54 mL, 5.1 mmol), the mixture was stirred at room temperature for 1 h. The precipitate was collected by filtration, washed with ethanol (5 mL) and air-dried to afford the title compound as a white solid (0.88 mg, 73%).

$^1$H-NMR (400 MHz, DMSO-d$_6$): δ=1.50-1.64 (m, 6H), 2.20-2.23 (m, 2H), 2.39-2.41 (m, 2H), 6.80 (d, 1H), 7.00 (d, 1H), 7.42 (t, 1H), 9.83 (s, 1H)

Step C

The title compound from Step B above (0.2 g, 0.75 mmol) was suspended in diethylene glycol (2 mL) and heated at 250° C. for 30 minutes using a Biotage Initiator microwave. The mixture was diluted with ethyl acetate (40 mL) and water (15 mL). The organic phase was separated, washed with brine (10 mL), dried over Na$_2$SO$_4$, filtered and the solvents were removed. The residue was purified employing a Biotage Isolera One system using an ethyl acetate/n-heptane (5/95->30/70) gradient to afford the title compound as an off-white solid (0.096 mg, 51%).

$^1$H-NMR (400 MHz, DMSO-d$_6$): δ=1.73-1.85 (m, 4H), 2.57 (t, 2H), 2.68 (t, 2H), 7.05 (d, 1H), 7.63 (d, 1H), 11.40 (s, 1H)

Step D

The title compound from Step C above (0.06 g, 0.24 mmol) was suspended in ethylene glycol (2 mL) and 30% ammonium hydroxide solution (3 mL). After the addition of copper (I)-oxide (0.005 g, 0.035 mmol), the mixture was heated at 150° C. for 45 minutes using a Biotage Initiator microwave. The reaction mixture was diluted with ethyl acetate (30 mL) and a mixture of water/ammonium hydroxide (10 mL, 1/1). The organic phase was separated, dried over Na$_2$SO$_4$, filtered and the solvents were evaporated. The residue was purified by PREP-TLC using dichloromethane/methanol (95/5) to afford the title compound as a brown solid (0.022 g, 50%).

$^1$H-NMR (400 MHz, DMSO-d$_6$): δ=1.67-1.78 (m, 4H), 2.46 (t, 2H), 2.55 (t, 2H), 5.26 (s, 2H), 6.12 (d, 1H), 7.34 (d, 1H), 10.30 (s, 1H)

Preparative Example 25

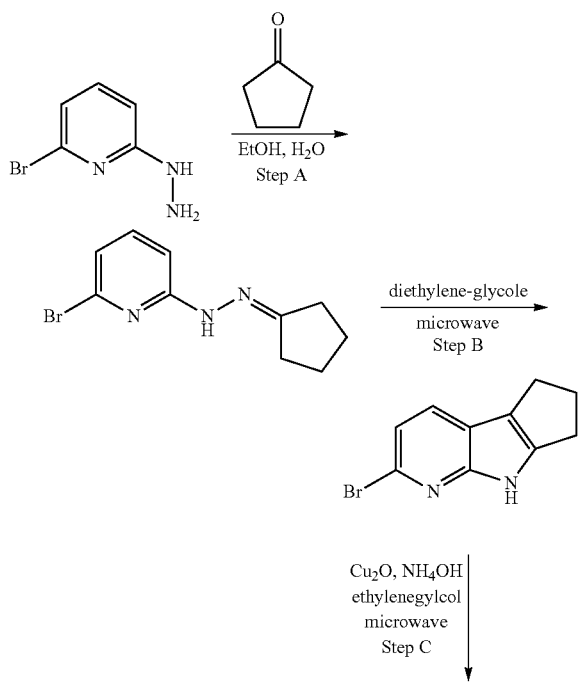

-continued

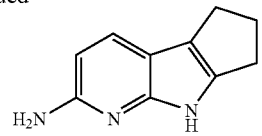

Step A

To a solution of the title compound from Preparative Example 23 Step A (1 g, 5.37 mmol) in ethanol (50 mL) was added cyclopentanone (0.45 g, 5.37 mmol) and the reaction mixture was stirred for 3 h at room temperature. At this time, the solvent was removed under reduced pressure to give the title compound (1.36 g, quantitative).

$^1$H-NMR (400 MHz, CDCl$_3$): δ=1.74-1.80 (m, 2H), 1.85-1.92 (m, 2H), 2.24 (t, 2H), 2.46 (t, 2H), 6.86 (d, 1H), 7.10 (d, 1H), 7.37 (t, 1H), 7.54 (s, 1H)

Step B

A solution of the title compound from Step B above (0.65 g, 2.55 mmol) in diethylene glycol (11 mL) was sealed in a microwavable glass tube (20 mL). Then, the reaction mixture was heated at 250° C. using microwaves for 90 minutes. The reaction mixture was cooled and poured into ethyl acetate (120 mL) and washed with water and brine. The organic phase was dried over Na$_2$SO$_4$ and the solvent was removed under reduced pressure to give the crude product, which was purified on silica gel column (dichloromethane) to give the title compound (0.120 g, 20%).

$^1$H-NMR (400 MHz, CDCl$_3$): δ=2.48-2.55 (m, 2H), 2.82 (t, 2H), 2.99 (t, 2H), 7.18 (d, 1H), 7.60 (d, 1H), 10.1 (s, 1H)

Step C

The title compound from Step C above (0.1 g, 0.42 mmol) was dissolved in diethylene glycol (2 mL) and 25% ammonium hydroxide solution (3 mL) and copper(I)-oxide (0.008 g, 0.058 mmol) was added. Then, the reaction mixture was heated at 150° C. using a Biotage Initiator microwave for 90 minutes. The reaction mixture was diluted with dichloromethane (200 mL), washed with water and brine solution. The organic phase was separated, and dried over Na$_2$SO$_4$. The residue was purified on silica gel column (1/10, methanol/dichloromethane) to afford the title compound (0.06 g, 83%).

$^1$H-NMR (400 MHz, CDCl$_3$): δ=2.46-2.49 (m, 2H), 2.78 (t, 2H), 2.87 (t, 2H), 6.36 (d, 1H), 7.55 (d, 1H), 8.35 (s, 1H)

Preparative Example 26

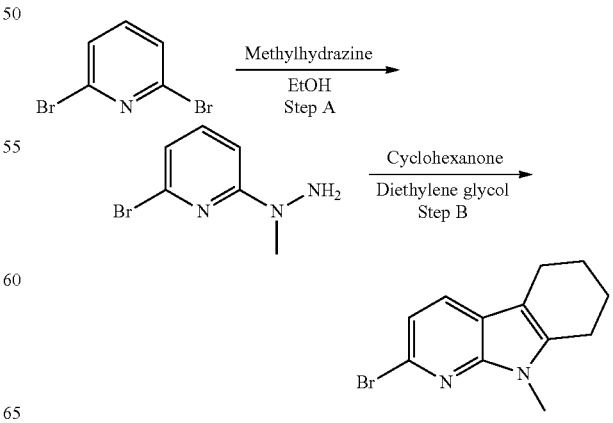

Step A

To a suspension of 2-6-dibromopyridine (5 g, 21.11 mmol) in ethanol (50 mL) was added methylhydrazine (3.33 mL, 63.3 mmol). The resulting mixture was warmed to 100° C. for 20 h. The reaction mixture was concentrated to dryness and the residue was purified by flash chromatography (2×) using ethyl acetate/n-heptane (15% to 35%). The product was obtained as a pale reddish liquid (2.1 g, 49%).

Step B

To a mixture of the title compound from Step A above (0.500 g, 2.475 mmol) and cyclohexanone (0.256 ml, 2.475 mmol) was added ethanol (Ratio: 1.000, Volume: 10.00 ml). The resulting solution was stirred at room temperature for 2 h, then the solvent was removed under vacuum. The oil was diluted with diethylene glycol (Ratio: 1.000, Volume: 10 ml) and the resulting mixture warmed by microwaves at 250° C. for 35 min. The dark solution was poured into water and filtered. The solid was purified by flash chromatography in ethyl acetate/n-heptane (10% to 30%) to afford the expected compound as a white solid (0.307 g, 47%).

$^1$H-NMR (400 MHz, CDCl$_3$): δ=1.76-2.05 (m, 4H); 2.54-2.80 (m, 4H); 3.67 (s, 3H); 7.10 (d, J=8.0 Hz, 1H); 7.54 (d, J=8.0 Hz, 1H)

MS (ESI); m/z=265.69/267.69 (MH$^+$)

Preparative Example 27

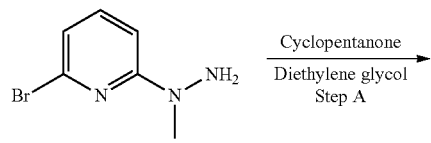

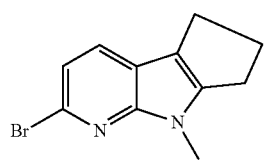

Step A

To a mixture of the title compound from Preparative Example 25 Step A (0.500 g, 2.475 mmol) and cyclopentanone (0.208 g, 2.475 mmol) was added ethanol (Ratio: 1.000, Volume: 10.00 ml). The resulting solution was stirred at room temperature for 2 h. Then the solvent was removed under vacuum. The oil was diluted with diethylene glycol (Ratio: 1.000, Volume: 10 ml) and the resulting mixture warmed by microwaves at 250° C. for 35 min.

The dark solution was poured into water and filtered. The solid was purified by flash chromatography in ethyl acetate/n-heptane (10% to 30%) to afford the expected compound as a yellowish solid (0.264 g, 42%).

MS (ESI); m/z=251.66/253.67 (MH$^+$)

Preparative Example 28

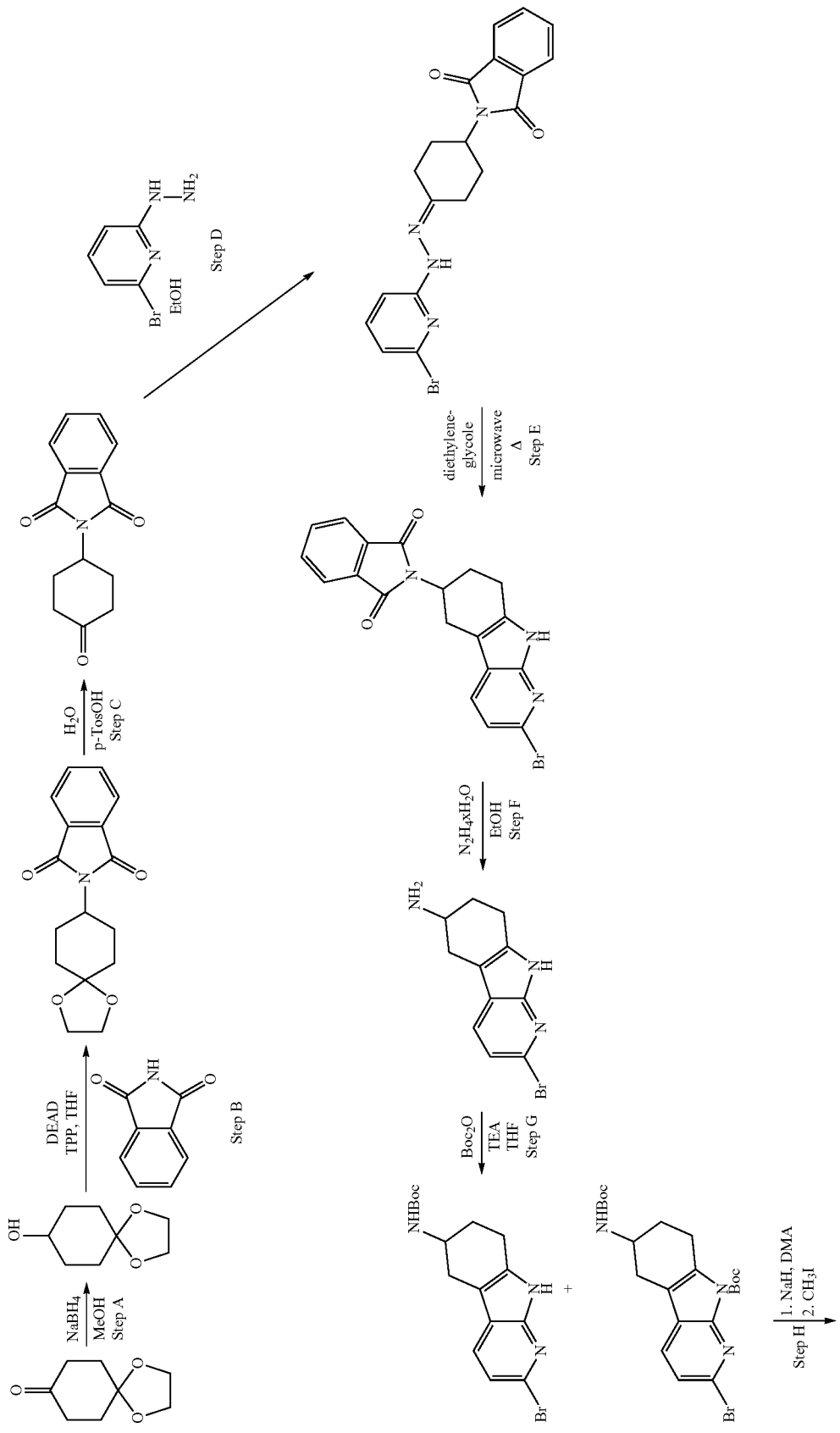

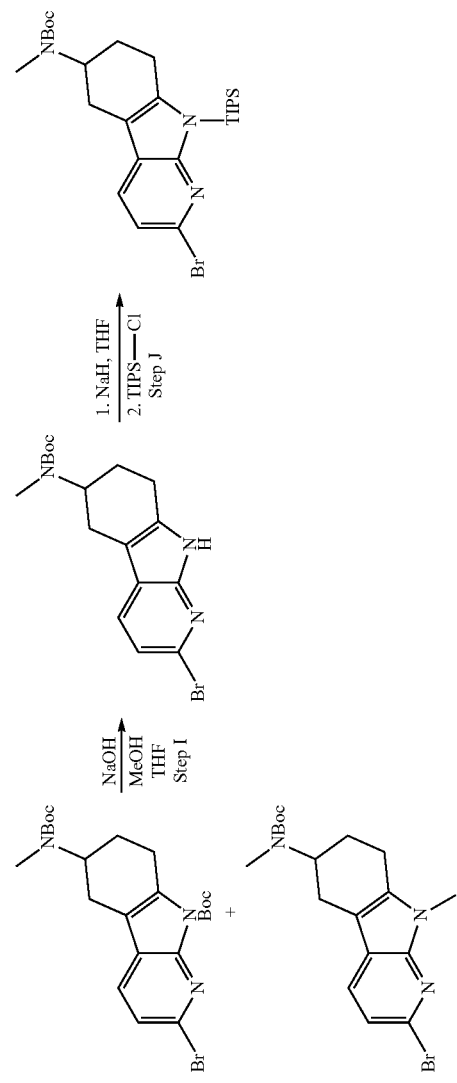

Step A

Commercially available 1,4-cyclohexadione monoethylene acetal (5 g, 32 mmol) was dissolved in methanol (65 mL) and the mixture was placed in a cold-water bath. Sodium borohydride (1.9 g, 50 mmol) was added in small portions (exotherm). After the addition was completed, the mixture was stirred at room temperature for 2 h. The solvent was removed and the residue was dissolved in ethyl acetate (150 mL), water (40 mL) and 1 M NaOH (10 mL). The organic phase was separated and the aqueous phase was extracted with ethyl acetate (4×75 mL). The combined organic phase was dried over $Na_2SO_4$, filtered and the solvent was removed to afford the title compound as a colorless liquid (4.8 g, 94%).

$^1$H-NMR (400 MHz, $CDCl_3$): δ=1.53-1.70 (m, 4H), 1.78-1.95 (m, 4H), 3.77-3.83 (m, 1H), 3.94-3.97 (m, 4H)

Step B

Triphenylphosphine (12.57 g, 48.6 mmol) and phthalimide (3.56 g, 24.22 mmol) were dissolved in tetrahydrofurane (90 mL) and the mixture was cooled to 0° C. At 0° C. a solution of the title compound from Step A above (3.84 g, 24.2 mmol) in tetrahydrofurane (90 mL) was added followed by the addition of a ~40%-solution of diethyl azodicarboxylate in toluene (19.9 mL, 48.6 mmol). The mixture was stirred at 0° C. for 10 minutes and then at room temperature overnight. The solvents were removed and the residue was purified by chromatography on silica using ethyl acetate/n-heptane (20/80) as a mobile phase to afford the title compound as an off-white solid (3.5 g, 50%).

$^1$H-NMR (400 MHz, $CDCl_3$): δ=1.61-1.76 (m, 4H), 1.85-1.90 (m, 2H), 2.50-2.62 (m, 2H), 3.93-4.02 (m, 4H), 4.18 (tt, 1H), 7.66-7.71 (m, 2H), 7.80-7.83 (m, 2H)

Step C

The title compound from Step B above (3.5 g, 12.1 mmol) was suspended in tetrahydrofurane (30 mL) and water (20 mL). After the addition of p-toluene sulfonic acid (0.13 g, 0.67 mmol), the mixture was heated at ~115° C. in a sand-bath for 2 h. The mixture was diluted with ethyl acetate (200 mL) and an aqueous solution of sodium bicarbonate was added until pH~8-9. The organic phase was separated and the aqueous phase was extracted with ethyl acetate (3×50 mL). The combined organic phase was dried over $Na_2SO_4$, filtered and the solvent was removed to afford the title compound as an off-white solid (3 g, quant.).

$^1$H-NMR (400 MHz, $CDCl_3$): δ=2.17-2.24 (m, 2H), 2.60-2.71 (m, 4H), 2.80-2.90 (m, 2H), 4.78 (tt, 1H), 7.84-7.88 (m, 2H), 7.97-8.02 (m, 2H)

Step D

The title compound from Preparative Example 23 Step A (1.54 g, 8.23 mmol) was dissolved in ethanol (50 mL) and the title compound from Step C above (2 g, 8.23 mmol) was added. The mixture was stirred at room temperature for 1 h to become a suspension. The solvent was removed to afford the title compound as an off-white solid (3.3 g, quant.).

$^1$H-NMR (400 MHz, DMSO-$d_6$): δ=2.00-2.18 (m, 3H), 2.27-2.43 (m, 2H), 2.50-2.63 (m, 2H), 3.30-3.38 (m, 1H), 4.46 (tt, 1H), 7.00 (d, 1H), 7.18 (d, 1H), 7.62 (t, 1H), 7.93-8.00 (m, 4H), 10.1 (s, 1H)

Step E

The title compound from Step D above (1 g, 2.42 mmol) was suspended in diethylene glycol (10 mL) and heated at 250° C. for 35 minutes using a Biotage Initiator microwave. The reaction mixture was diluted with ethyl acetate (100 mL) and brine (20 mL). The organic phase was separated, dried over $Na_2SO_4$, filtered and the solvent was removed. The reaction was run 2 more times as described above and the combined crude product was treated with methanol (15 mL). The precipitate was collected by filtration, washed with methanol (5 mL) and air-dried to afford the title compound as a beige solid (1.57 g, 49%).

$^1$H-NMR (400 MHz, DMSO-$d_6$): δ=2.20-2.24 (m, 1H), 2.71-2.82 (m, 1H), 2.96-3.10 (m, 3H), 3.32-3.46 (m, 1H), 4.54-4.61 (m, 1H), 7.27 (d, 1H), 7.80 (d, 1H), 7.97-8.03 (m, 4H), 11.70 (s, 1H)

Step F

The title compound from Step E above (1.57 g, 3.96 mmol) was suspended in ethanol (50 mL) and treated with a 50-60% aqueous solution of hydrazine-hydrate (12 mL, 119 mmol). The mixture was stirred at room temperature overnight to become a clear solution. The solvents were removed and the residue was treated with dichloromethane (150 mL). The mixture was sonicated for 5 minutes and then stirred at room temperature for 30 minutes. The precipitate was collected by filtration and washed with dichloromethane (15 mL). The combined filtrate was evaporated to afford the title compound as a beige solid (0.74 g, 70%).

$^1$H-NMR (400 MHz, DMSO-$d_6$): δ=1.53-1.62 (m, 1H), 1.90-1.95 (m, 1H), 2.20-2.28 (m, 1H), 2.69-2.73 (m, 2H), 2.80 (dd, 1H), 3.00-3.06 (m, 1H), 7.10 (d, 1H), 7.68 (d, 1H), 11.33-11.41 (br-s, 1H)

Step G

The title compound from Step F above (0.87 g, 3.28 mmol) was dissolved in tetrahydrofurane (60 mL) and treated with triethylamine (1.1 mL) and di-tert-butyl dicarbonate (2.7 g, 12.4 mmol). The mixture was heated at ~40° C. in a sand-bath overnight. The solvent was removed and the residue was treated with diethylether (20 mL). The precipitate was collected by filtration and the solid washed with diethylether (10 mL) to afford the mono-Boc protected intermediate as a white solid (0.86 g). The filtrate was evaporated to afford the crude title compound. The mono-Boc intermediate (0.86 g) was dissolved in tetrahydrofurane (60 mL) and treated with triethylamine (2.2 mL) and di-tert-butyl dicarbonate (5.4 g, 24.8 mmol). The mixture was stirred at room temperature overnight, the solvents were removed and the crude product was combined with the material from the initial run. Purification of the crude product on silica using a Biotage Isolera One system employing an ethyl acetate/n-heptane gradient (5/95->30/75) afforded the title compound as a white solid/foam (1.16 g, 76%).

$^1$H-NMR (400 MHz, $CDCl_3$): δ=1.44 (s, 9H), 1.69 (s, 9H), 1.84-1.92 (m, 1H), 2.07-2.15 (m, 1H), 2.50 (dd, 1H), 3.00 (dd, 1H), 3.10 (t, 2H), 4.00-4.08 (m, 1H), 4.62-4.66 (m, 1H), 7.31 (d, 1H), 7.51 (d, 1H)

Mono-Boc intermediate: $^1$H-NMR (400 MHz, DMSO-$d_6$): δ=1.38 (s, 9H), 1.69-1.75 (m, 1h), 1.93-2.00 (m, 1H), 2.41 (dd, 1H), 2.72-2.79 (m, 2H), 2.87 (dd, 1H), 3.66-3.72 (m, 1H), 7.00 (d, 1H), 7.11 (d, 1H), 7.70 (d, 1H), 11.47 (s, 1H)

Step H

The title compound from Step G above (1.16 g, 2.5 mmol) was dissolved in N,N'-dimethylacetamide (8 mL) and the mixture was cooled to 0° C. At 0° C. sodium hydride (0.07 g, 3 mmol) was added and the mixture was stirred at 0° C. for 1 h. Methyliodide (0.2 mL, 3.32 mmol) was added at 0° C. and the mixture was stirred at room temperature for 2 h. The mixture was diluted with ethyl acetate (80 mL) and brine (20 mL). The organic phase was separated, dried over $Na_2SO_4$, filtered and the solvent was removed. The residue was purified by chromatography on silica using a Biotage Isolera One system employing an ethyl acetate/n-heptane gradient (5/95->15/85) to afford the title compound as a colorless foam (0.73 g, 61%), together with starting material (0.23 g, 20%) and the corresponding $N^1$-methyl-derivative (0.053 g, 5%, white solid).

$^1$H-NMR (400 MHz, CDCl$_3$): δ=1.46 (s, 9H), 1.69 (s, 9H), 1.91-2.04 (m, 2H), 2.62-2.77 (m, 2H), 2.84 (s, 3H), 3.00-3.10 (m, 1H), 3.22 (dd, 1H), 4.24-4.46 (br-m, 1H), 7.31 (d, 1H), 7.50 (d, 1H)

N$^1$-methyl-derivative: $^1$H-NMR (400 MHz, CDCl$_3$): δ=1.46 (s, 9H), 2.00-2.10 (m, 2H), 2.70-2.90 (m, 7H), 3.70 (s, 3H), 4.21-4.50 (br-m, 1H), 7.12 (d, 1H), 7.54 (d, 1H)

Step I

The title compound from Step H above (0.88 g, 1.83 mmol) was dissolved in tetrahydrofurane (15 mL) and methanol (15 mL). After the addition of 1 M sodium hydroxide solution (15 mL, 15 mmol), the mixture was stirred at room temperature overnight. The organic solvents were removed and the residue was diluted with water (20 mL). The precipitate was collected by filtration, washed with water (5 mL) and air-dried to afford the title compound as a white solid (0.67 g, 96%).

$^1$H-NMR (400 MHz, DMSO-d$_6$): δ=1.40 (s, 9H), 1.86-1.90 (m, 1H), 1.95-2.04 (m, 1H), 2.66-2.71 (m, 2H), 2.78 (s, 3H), 2.80-2.85 (m, 2H), 4.13-4.27 (br-m, 1H), 7.18 (d, 1H), 7.75 (d, 1H), 11.55 (s, 1H)

Step J

The title compound from Step I above (0.38 g, 0.89 mmol) was suspended in tetrahydrofurane (5 mL) and the mixture was cooled to 0° C. At 0° C. sodium hydride (0.028 g, 1.15 mmol) was added and the mixture was stirred at 0° C. for 5 minutes and at room temperature for 15 minutes to become a clear solution. After the addition of triisopropylsilyl-chloride (0.12 mL, 0.9 mmol), the mixture was heated at ~85° C. in a sand bath for 1 h. The mixture was diluted with ethyl acetate (50 mL) and brine (15 mL). The organic phase was separated, dried over Na$_2$SO$_4$, filtered and the solvents were removed. The residue was purified by chromatography on silica using a Biotage Isolera One system employing an ethyl acetate/n-heptane gradient (5/95->100/0) to afford the title compound as a colorless oil (0.27 g, 52%), together with starting material (0.14 g, 39%, white solid).

$^1$H-NMR (400 MHz, CDCl$_3$): δ=1.12-1.16 (m, 18H), 1.51 (s, 9H), 1.81-1.90 (m, 3H), 1.98-2.03 (m, 2H), 2.72-2.80 (m, 2H), 2.85 (s, 3H), 2.97-3.08 (m, 2H), 4.25-4.57 (br-m, 1H), 7.12 (d, 1H), 7.48 (d, 1H)

Preparative Example 29

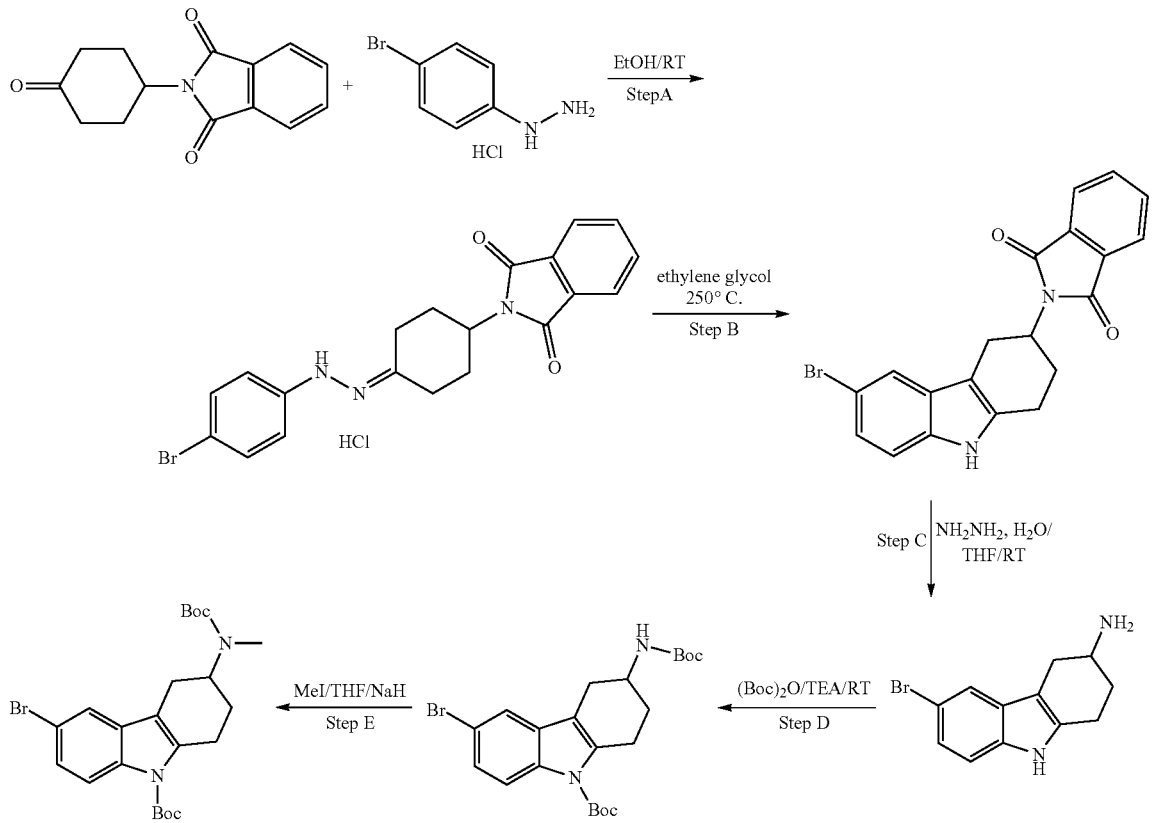

Step A

To a solution of commercially available 4-bromophenyl hydrazine (1.46 g, 6.5 mmol) in ethanol (50 mL) was added preparative example 28 step C (1.6 g, 6.5 mmol) in ethanol (15 mL). The reaction mixture was stirred for 2 h at room temperature. The solvent was removed to give the title compound as a solid (2.9 g, quantitative).

$^1$H-NMR (400 MHz, DMSO-d$_6$): δ=7.85-7.86 (m, 4H), 7.31 (d, 8.4 Hz, 2H), 7.00 (d, 2H), 4.32-4.38 (m, 1H), 3.12-3.15 (m, 1H), 2.36-2.51 (m, 2.19-2.28 (m, 2H), 1.92-2.06 (m, 3H).

Step B

A solution of the title compound from step A (2.9 g, 7.0 mmol) in diethyleneglycol (45 mL) was sealed in microwavable glass tubes (20 mL). Then, the reaction tubes were heated at 250° C. using microwaves for 55 min. The reaction was performed in three batches. The combined reaction mixture was collected and was dissolved in ethyl acetate (250 mL) and washed with water and brine. The organic phase was dried over Na$_2$SO$_4$ and the solvent was removed under reduced pressure to give crude product, which was purified on silica gel column (ethyl acetate/n-heptane 20%-40%) to give the title compound (2.1 g, 72%).

¹H-NMR (400 MHz, CDCl₃): δ=7.88-7.90 (m, 2H), 7.84 (brs, 1H), 7.75-7.78 (m, 2H), 7.53 (d, 1H); 7.22 (dd, 1H), 7.17 (d, 1H), 4.64-4.71 (m, 1H), 3.44-3.51 (m, 1H), 2.90-2.96 (m, 3H), 2.07 (m, 1H), 1.28 (brs, 1H).

Step C

To a stirred solution of the compound from step B (2 g, 5.0 mmol) in THF (50 mL) was added NH₂NH₂.H₂O (500 mg 10 mmol) and the reaction mixture was stirred overnight. The precipitate was filtered off and the filtrate was concentrated and used in the next step without further purification and characterization.

Step D

To the compound from step C (2.01 g) in THF (50 ml) was added (Boc)₂O (2 g, 9.1 mmol) and triethylamine (1 g, 10 mmol). The reaction mixture was stirred at room temperature overnight. The solvent was removed and crude product crystallized from ethyl acetate and heptanes mixture to give a mono-Boc derivative (1.15 g). The crystallized mono-Boc derivative was dissolved in THF (50 mL) and an excess of (Boc)₂O (5 g, 22.9 mmol) and triethylamine (1.5 ml) was added and the reaction mixture was stirred for 2 days. The solvent was removed and the crude product was purified on silica gel column chromatography (ethyl acetate/n-heptane 10-20%) to give the title compound (1.35 g).

¹H-NMR (400 MHz, CDCl₃): δ=7.99 (d, 1H), 7.49 (d, 1H), 7.34 (dd, 1H), 4.68 (brs, 1H), 4.09 (brs, 1H), 3.11 (brs, 2H), 2.99 (dd, 1H), 2.49 (dd, 1H), 2.10-2.12 (m, 1H), 1.89-1.96 (m, 1H), 1.68 (s, 9H), 1.48 (s, 9H).

Step E

A solution of the title compound from step D (370 mg, 0.79 mmol) in DMA (7 mL) was cooled to ice bath temperature then NaH (40 mg, 1.59 mmol) was added portionswise. The reaction mixture was stirred at room temperature for 30 min and cooled to ice bath temperature and methyl iodide (222 mg, 1.59 mmol) was added. The reaction mixture was brought to room temperature and stirred for 3 h. The reaction mixture was dissolved in dichloromethane (250 mL) and washed with water and brine and dried over Na₂SO₄. The solvent was removed and the residue was purified by silica gel column chromatography (0/100 to 15/85; EtOAc/heptane mixture) to give the title compound as a white foam (271 mg, 71%).

¹H-NMR (400 MHz, DMSO-d₆): δ=7.97 (d, 1H), 7.67 (s, 1H), 7.38 (d, 1H), 4.18-4.32 (m, 1H), 3.1-3.22 (m, 1H), 2.98-3.02 (m, 1H), 2.78 (s, 3H), 2.68-2.70 (m, 2H), 1.92-1.97 (m, 2H), 1.61 (s, 9H), 1.42 (s, 9H).

Preparative Example 30

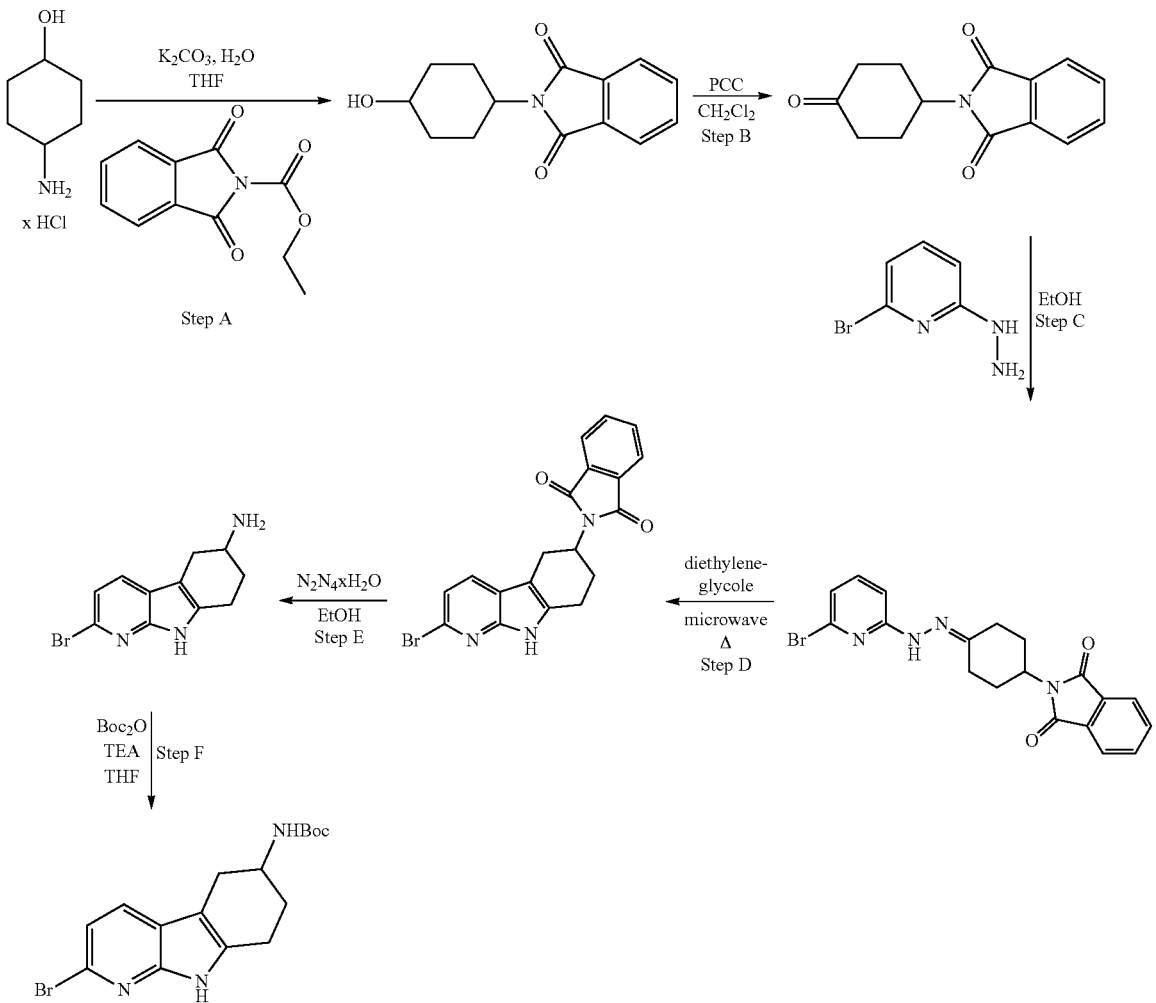

Step A

Commercially available 4-aminocyclohexanol hydrogen chloride salt (25 g, 164 mmol) was dissolved in water (350 mL). Then potassium carbonate (72 g, 328 mmol) was added, followed by a solution of commercially available N-carbethoxyphthalimide in tetrahydrofurane (300 mL). The reaction mixture was then vigorously stirred at room temperature for 3 days. Tetrahydrofurane was evaporated under reduced pressure and the remaining aqueous phase was extracted with dichloromethane (2×300 mL) until the aqueous phase was clear. The combined organic phase was dried over $Na_2SO_4$, filtered and the solvents were evaporated under reduced pressure to afford the title compound as a white solid (28 g, 69%).

$^1$H-NMR (400 MHz, $CDCl_3$): δ=1.32-1.43 (m, 2H), 1.70-1.75 (m, 2H), 2.04-2.09 (m, 2H), 2.25-2.38 (m, 2H), 3.67-3.77 (m, 1H), 4.05-4.13 (m, 1H), 7.63-7.7.68 (m, 2H), 7.76-7.7.80 (m, 2H)

Step B

The title compound from Step A above (28 g, 114 mmol) was dissolved in dichloromethane (990 mL) and pyridinium chlorochromate (33.6 g, 157 mmol) was added in portions. The reaction mixture was stirred at room temperature for 8 h. Then another batch of pyridinium chlorochromate (10.4 g, 48.6 mmol) was added in portions and stirring at room temperature was continued for 18 h. The reaction mixture was filtered through a pad of Celite and the Celite pad was washed with dichlormethane (400 mL). The combined filtrate was concentrated under reduced pressure and the residue was purified by chromatography on silica using ethyl acetate/n-heptane (60/40) as a mobile phase to afford the title compound as a white solid (24.62 g, 88%)

$^1$H-NMR (400 MHz, $CDCl_3$): δ=2.17-2.24 (m, 2H), 2.60-2.71 (m, 4H), 2.80-2.90 (m, 2H), 4.78 (tt, 1H), 7.84-7.88 (m, 2H), 7.97-8.02 (m, 2H)

Step C

The title compound from Preparative Example 23 Step A (19 g, 101 mmol) was dissolved in ethanol (570 mL) and the title compound from Step B above (24.6 g, 101 mmol) was added. The mixture was stirred at room temperature for 2 h to become a suspension. The solvent was removed to afford the title compound as an off-white solid (41.8 g, quant.).

$^1$H-NMR (400 MHz, DMSO-$d_6$): δ=2.00-2.18 (m, 3H), 2.27-2.43 (m, 2H), 2.50-2.63 (m, 2H), 3.30-3.38 (m, 1H), 4.46 (tt, 1H), 7.00 (d, 1H), 7.18 (d, 1H), 7.62 (t, 1H), 7.93-8.00 (m, 4H), 10.1 (s, 1H)

Step D

The title compound from Step C above (1.3 g, 3.15 mmol) was suspended in diethylene glycol (13 mL) and was heated at 245° C. for 35 minutes using a Biotage Initiator microwave. The reaction mixture was diluted with water (90 mL), the precipitate was collected by filtration and air dried. This reaction sequence was repeated until the title compound from Step C above (41.8 g) was consumed to afford the title compound as a grey solid (34.2 g, 85%). The crude material was directly used for the next step.

Step E

The title compound from Step D above (34.2 g, 86.36 mmol) was suspended in ethanol (1080 mL) and treated with a 50-60% aqueous solution of hydrazine-hydrate (185 mL, 1990 mmol). The mixture was stirred at room temperature for 2 days. The precipitate was separated by filtration and washed with ethanol (150 mL). The combined filtrate was concentrated to ~150 mL and extracted with dichloromethane (2×450 mL). The organic phase was dried over $Na_2SO_4$, filtered and the solvents were removed to afford the crude title compound as a dark solid (22.97 g, quant.).

Step F

The title compound from Step E above (22.97 g, 90.1 mmol) was dissolved in tetrahydrofuran (1000 mL) and treated with triethylamine (64 mL) and di-tert-butyl dicarbonate (79 g, 367 mmol). The mixture was stirred at room temperature for 18 h and the solvents were removed under reduced pressure. The residue was treated with diethylether (600 mL) and stirred at room temperature for 30 minutes. The precipitate was collected by filtration, washed with diethylether (250 mL) and air-dried to afford the title compound as a white solid (11 g, 33%):

$^1$H-NMR (400 MHz, DMSO-$d_6$): δ=1.38 (s, 9H), 1.69-1.75 (m, 1h), 1.93-2.00 (m, 1H), 2.41 (dd, 1H), 2.72-2.79 (m, 2H), 2.87 (dd, 1H), 3.66-3.72 (m, 1H), 7.00 (d, 1H), 7.11 (d, 1H), 7.70 (d, 1H), 11.47 (s, 1H)

Preparative Example 31

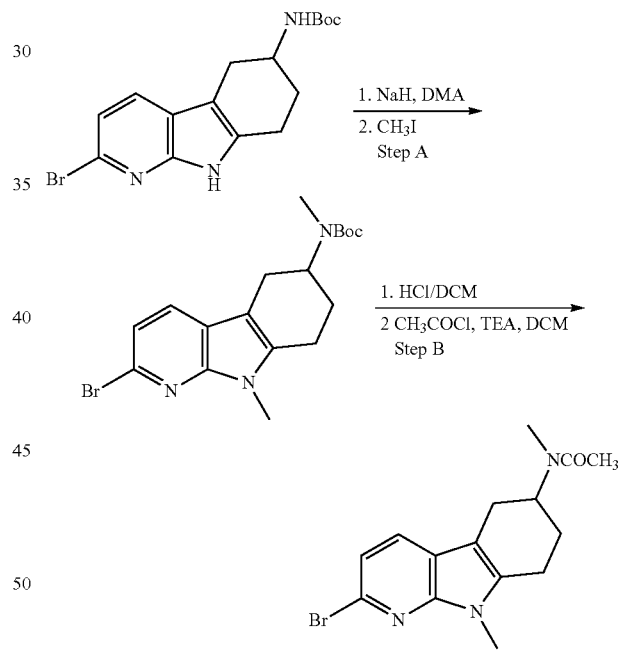

Step A

The title compound from Preparative Example 30 Step F (11 g, 30 mmol) was dissolved in N,N'-dimethylacetamide (140 mL) and the mixture was cooled to 0° C. At 0° C. sodium hydride (2.2 g, 92 mmol) was added and the mixture was stirred at 0° C. for 2 h. Then methyl iodide (9 mL, 145 mmol) was added, the mixture was stirred at 0° C. for 5 minutes. The ice bath was removed and after ~5 minutes an exotherm was observed. The reaction mixture was briefly placed in a water bath and stirred at room temperature overnight. The reaction mixture was diluted with water (700 mL) and the precipitate was collected by filtration. The solid material was further purified by chromatography on silica using dichloromethane/acetone (98/2) to afford the title compound as a white solid (10.6 g, 85%).

$^1$H-NMR (400 MHz, CDCl$_3$): δ=1.46 (s, 9H), 2.00-2.10 (m, 2H), 2.70-2.90 (m, 7H), 3.70 (s, 3H), 4.21-4.50 (br-m, 1H), 7.12 (d, 1H), 7.54 (d, 1H)

Step B

The title compound from Step A above (0.1 g, 0.253 mmol) was dissolved in dichloromethane (2 mL) and treated with a 2 M solution of hydrogen chloride (0.5 mL, 1 mmol) in diethylether. The mixture was stirred at room temperature overnight. Then triethyl amine (0.07 mL, 0.316 mmol) and acetyl chloride (0.316 mL, 1.034 mmol) were added to the reaction mixture. The stirring was continued for another 2 h, then the mixture was diluted with dichloromethane and washed with a saturated aqueous solution of sodium carbonate. The organic phase was separated, dried over Na$_2$SO$_4$, filtered and the solvents were removed to give a residue which was purified using a Biotage flash chromatography system (methanol/dichloromethane: 0->5%) to afford the title compound as a white solid (0.065 g, 75% for 2 steps).

$^1$H-NMR (400 MHz, CDCl$_3$): δ=1.99-2.03 (m, 1H), 2.12-2.19 (m, 4H), 2.67-2.73 (m, 1H), 2.81 (dd, 1H), 2.87-2.90 (m, 2H), 2.94-2.98 (m, 4H), 3.70 (d, 3H), 7.14 (dd, 1H), 7.53 (dd, 1H).

Preparative Example 32

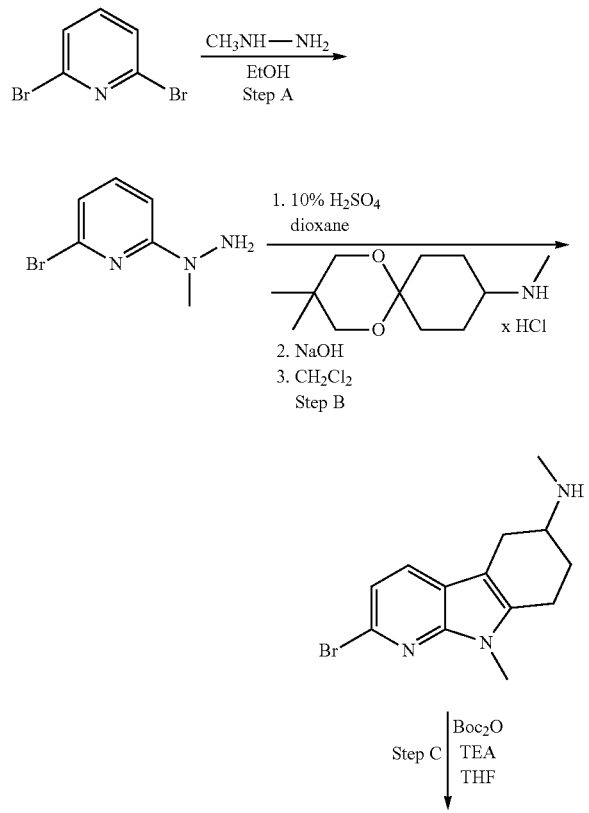

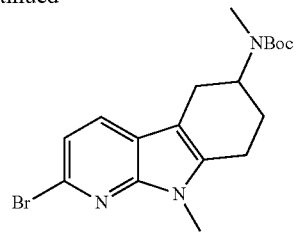

Step A

To a suspension of commercially available 2,6-dibromopyridine (10 g, 42.2 mmol) in ethanol (50 mL) was added commercially available methylhydrazine (11.11 mL, 211 mmol). The mixture was heated at 80° C. (reaction mixture temperature) for 48 h. The reaction mixture was concentrated to dryness and the residue was purified by chromatography on silica using a Biotage Isclera One purification system employing an ethyl acetate/n-heptane gradient (15/75->35/65) to afford the title compound as a reddish oil which becomes a solid by standing at room temperature (7.6 g, 89%)

$^1$H-NMR (400 MHz, CDCl$_3$): δ=3.23 (s, 3H), 4.00 (br-s, 2H), 6.70 (d, 1H), 6.82 (d, 1H), 7.27 (t, 1H)

Step B

A suspension of commercially available 4-(methylamino)cyclohexanone-2,2-dimethyltrimethylene ketal hydrochloride (3.7 g, 14.8 mmol) and the title compound from Step A above (3 g, 14.8 mmol) in dioxane (30 mL) were placed in an ice bath. To the stirred suspension was slowly added concentrated H$_2$SO$_4$ (3 mL). After the addition of H$_2$SO$_4$ was completed, the reaction mixture was heated at reflux temperature for 5 h using a sand bath (~140° C.). The reaction mixture was cooled to room temperature, the dioxane layer was discarded, and ice water (20 mL) was added. The mixture was stirred until the gummy material was dissolved. Then the pH of the reaction mixture was adjusted to pH=14 using aq. NaOH solution. The aqueous layer was extracted with dichloromethane (200 mL) and the organic phase was washed with water and brine. The organic phase was separated, dried over Na$_2$SO$_4$ and the solvent was removed under reduced pressure to afford the crude title compound as an off-white solid (4.7 g, quant.).

Step C

To a solution of the crude title compound from Step A above (4.7 g) in tetrahydrofuran (50 ml) was added triethylamine (5 mL) and di-tert-butyl dicarbonate (10 g, 45.8 mmol). The reaction mixture was stirred at room temperature overnight. Then, the reaction mixture was concentrated and the residue was dissolved in dichloromethane (200 mL). The organic phase was washed with water, brine and dried over Na$_2$SO$_4$. The organic solvent was removed under reduced pressure and the residue was purified on silica gel using a Biotage Isolera One purification system employing an ethyl acetate/n-heptane gradient (20/80->50/50) to afford the title compound as a white solid (3.55 g, 61% for 2 steps).

$^1$H-NMR (400 MHz, CDCl$_3$): δ=1.46 (s, 9H), 2.00-2.10 (m, 2H), 2.70-2.90 (m, 7H), 3.70 (s, 3H), 4.21-4.50 (br-m, 1H), 7.12 (d, 1H), 7.54 (d, 1H)

Preparative Example 33
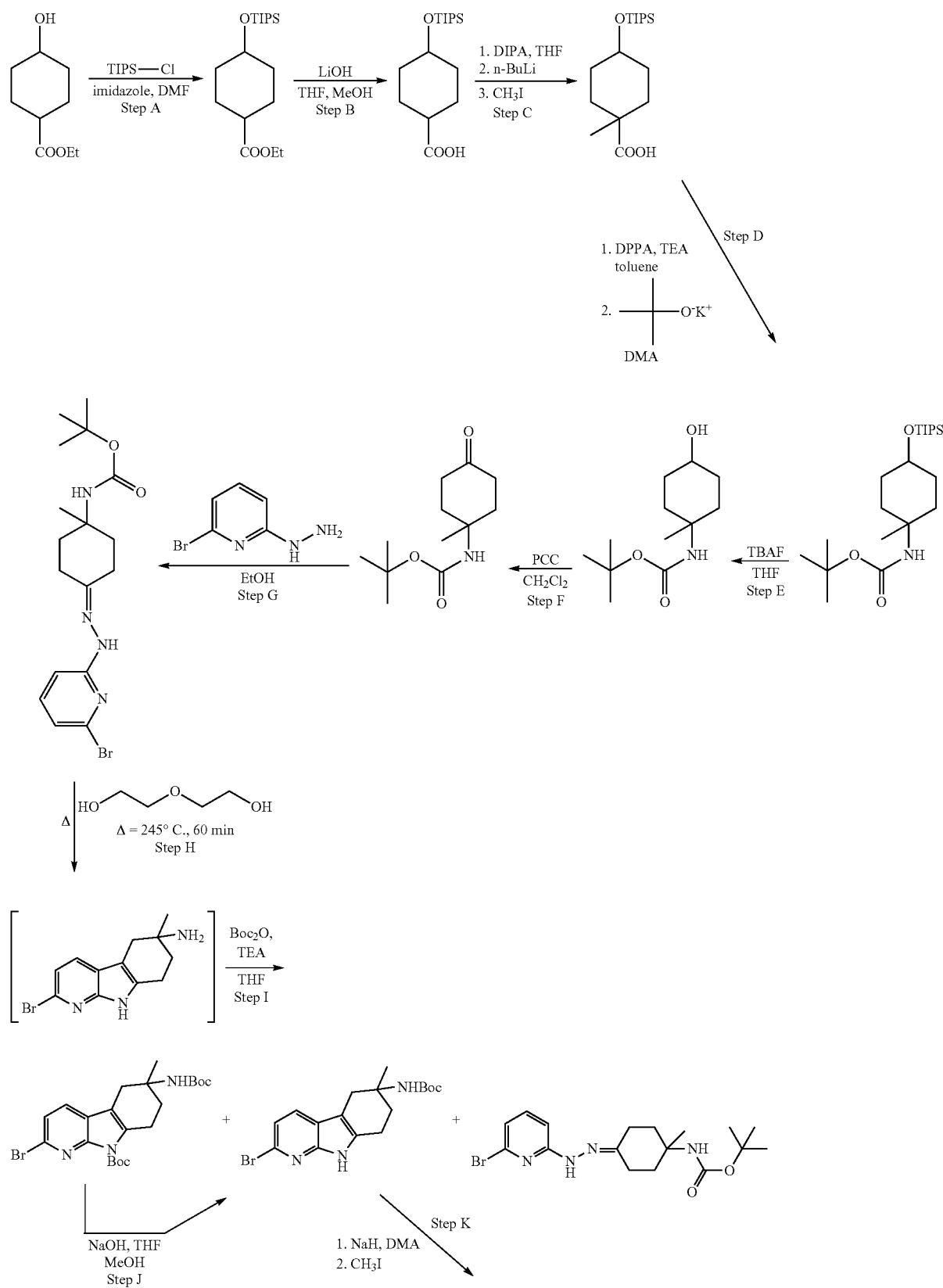

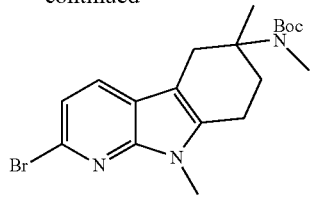

Step A

Commercially available 4-hydroxy-cyclohexane carboxylic acid ethyl ester (10.32 g, 59.92 mmol) was dissolved in N,N'-dimethylformamide (50 mL) and imidazole (8.16 g, 119.5 mmol) was added. After the addition of triisopropylsilylchloride (14.1 mL, 65.9 mmol), the reaction mixture was stirred at room temperature overnight. The reaction mixture was diluted with diethylether (150 mL) and washed with a 1 M hydrochloric acid solution (150 mL). The organic phase was separated and the aqueous phase was extracted with diethylether (150 mL). The combined organic phase was washed with 1 M hydrochloric acid solution (150 mL) and brine (150 mL). The organic phase was dried over $Na_2SO_4$, filtered and the solvents were removed to afford the crude title compound as a colorless liquid (18.7 g, 95%).

Step B

The crude title compound from Step A above (18.7 g, 65.17 mmol) was dissolved in tetrahydrofuran (90 mL) and methanol (60 mL). After the addition of lithium hydroxide hydrate (5.47 g, 130.6 mmol), the reaction mixture was heated at ~70° C. for 2 h using a sand-bath and at room temperature overnight. The solvents were removed and the residue was dissolved in water (100 mL). The pH of the reaction mixture was adjusted to pH ~3-4 using 1 M hydrochloric acid and the aqueous phase was extracted with ethyl acetate (2×200 mL). The combined organic phase was dried over $Na_2SO_4$, filtered and the solvents were removed to afford the crude title compound as a pale yellow oil (16.65 g, 97%).

Step C

Diisopropylamine (9 mL, 65 mmol) was dissolved in tetrahydrofuran (100 mL) and the mixture was cooled to 0° C. At 0° C. a 1.6 M solution of n-butyllithium in n-hexane (38.5 mL, 61.6 mmol) was added and the reaction mixture was stirred at 0° C. for 15 minutes. The reaction mixture was then cooled to -78° C. and a solution of the crude title compound from Step B above (8.3 g, 30.9 mmol) in tetrahydrofuran (30 mL) was added dropwise. After the addition was completed, the cooling bath was removed and the reaction mixture was heated at ~60° C. in a sand bath for 2 h. The reaction mixture was again cooled to -78° C. and methyliodide (2.1 ml, 34 mmol) was added. The reaction mixture was stirred at -78° C. for 2 h and then allowed to warm to room temperature overnight. The reaction mixture was poured into a mixture of diethylether (500 mL) and 1 M hydrochloric acid (500 mL). The organic phase was separated and the aqueous phase was extracted with diethylether (2×200 mL). The combined organic phase was dried over $Na_2SO_4$, filtered and the solvents were removed. The residue was purified by chromatography on silica using ethyl acetate/n-heptane/methanol (15/84/1) as a mobile phase to afford the title compound as a pale yellow oil (4.35 g, 50%) and recovered starting material as a pale yellow oil (1.51 g, 18%).

$^1$H-NMR (400 MHz, $CDCl_3$): δ=1.03 (s, 18H), 1.17-1.24 (m, 7H), 1.43-1.52 (m, 2H), 1.64-1.71 (m, 1H), 1.77-1.84 (m, 2H), 2.18-2.23 (m, 2H), 3.65-3.73 (m, 1H)

recovered starting material:

$^1$H-NMR (400 MHz, $CDCl_3$): δ=1.03 (s, 18H), 1.20-1.80 (m, 7H), 1.94-2.05 (m, 4H), 2.28-2.33 (m, 1H), 3.62-3.68 (m, 1H)

Step D

The title compound from Step C above (2.18 g, 6.92 mmol) was dissolved in toluene (25 mL) and triethylamine (1.08 mL, 7.7 mmol) was added. After the addition of diphenyl-phosphorylazide (1.63 mL, 7.54 mmol), the reaction mixture was heated at ~115° C. in a sand-bath for 1 h until the evolution of nitrogen was completed. The mixture was cooled to 0° C. and washed with saturated sodium bicarbonate (15 mL), water (15 mL) and brine (15 mL). The organic phase was separated, dried over $Na_2SO_4$, filtered and the solvents were evaporated to afford the crude isocyanate intermediate. The crude intermediate was dissolved in N,N'-dimethylacetamide (10 mL) and potassium tert-butoxide (0.8 g, 7.13 mmol) was added in portions. After the addition was completed, the reaction mixture was stirred at room temperature overnight. The reaction mixture was diluted with ethyl acetate (80 mL) and water (30 mL). The organic phase was separated and washed with water (20 mL) and brine (20 mL). The organic phase was dried over $Na_2SO_4$, filtered and the solvents were removed. The residue was purified by chromatography on silica using ethyl acetate/n-heptane (10/90) as a mobile phase to afford the title compound as a colorless oil (1.57 g, 59%).

$^1$H-NMR (400 MHz, $CDCl_3$): δ=1.16 (s, 18H), 1.37-1.45 (m, 3H), 1.43 (s, 3H), 1.56 (s, 9H), 1.58-1.66 (m, 4H), 1.82-1.88 (m, 2H), 2.13-2.20 (m, 2H), 3.76-3.81 (m, 1H), 4.48 (br-s, 1H)

Step E

The title compound from Step D above (1.45 g, 3.77 mmol) was dissolved in acetonitrile (25 mL) and a 1 M solution of tetra-butyl ammonium fluoride in tetrahydrofuran (14.8 mL, 14.8 mmol) was added. The reaction mixture was stirred at room temperature overnight and the solvents were removed. The residue was purified by chromatography on silica using ethyl acetate/n-heptane (80/20) to afford the title compound as a colorless oil (0.86 g, 99%).

$^1$H-NMR (400 MHz, $CDCl_3$): δ=1.42 (s, 3H), 1.54 (s, 9H), 1.57-1.70 (m, 3H), 1.85-1.93 (m, 3H), 2.19-2.24 (m, 2H), 3.70-3.73 (m, 1H), 4.45 (br-s, 1H)

Step F

The title compound from Step E above (0.86 g, 3.76 mmol) was dissolved in dichloromethane (40 mL) and pyridinium chlorochromate (1.18 g, 5.48 mmol) was added in portions. The reaction mixture was stirred at room temperature for 18 h, filtered through a pad of Celite and the Celite was washed with dichloromethane (20 mL). The combined filtrate was concentrated under reduced pressure and the residue was purified by chromatography on silica using ethyl acetate/n-heptane (60/40) as a mobile phase to afford the title compound as a colorless oil (0.76 g, 89%)

$^1$H-NMR (400 MHz, $CDCl_3$): δ=1.42 (s, 3H), 1.45 (s, 9H), 1.77 (dt, 2H), 2.23-2.50 (m, 6H), 4.48 (br-s, 1H)

Step G

The title compound from Preparative Example 23 Step A (0.63 g, 3.35 mmol) was dissolved in ethanol (20 mL) and the title compound from Step F above (0.76 g, 3.35 mmol) was added. The mixture was stirred at room temperature for 1 h to become a clear solution. The solvent was removed to afford the title compound as a dark yellow oil (1.33 g, quant.).

$^1$H-NMR (400 MHz, CDCl$_3$): δ=1.40 (s, 3H), 1.47 (s, 9H), 1.52-1.67 (m, 3H), 2.15-2.23 (m, 2H), 2.40-2.50 (m, 3H), 4.45 (br-s, 1H), 6.90 (d, 1H), 7.15 (d, 1H), 7.40 (t, 1H), 7.85 (br-s, 1H)

Step H

The title compound from Step G above (0.7 g, 1.76 mmol) was dissolved in diethylene glycol (10 mL) and heated at 245° C. for 60 minutes using a Biotage Initiator microwave (pressure: 10-11 bar). The reaction mixture was diluted with water (15 mL) and dichloromethane (40 mL). The organic phase was separated, dried over Na$_2$SO$_4$, filtered and the solvents were removed to afford the crude title compound as a dark oil. This procedure was repeated one more time and the combined crude material was directly used for the next step.

Step I

The crude title compound from Step H above was dissolved in tetrahydrofuran (45 mL) and treated with triethylamine (1.7 mL) and di-tert-butyl dicarbonate (2 g, 9.3 mmol). The mixture was stirred at room temperature for 18 h and the solvents were removed under reduced pressure. The residue was purified by chromatography on silica using a Biotage Isolera One purification system employing an ethyl acetate/n-heptane gradient (5/95->30/70) to afford 3 different fractions.

Fraction I: Bis-Boc derivative; yellow oil (0.15 g, 9%)

$^1$H-NMR (400 MHz, CDCl$_3$): δ=1.39 (s, 9H), 1.45 (s, 3H), 1.64 (s, 9H), 1.70-1.75 (m, 1H), 2.41-2.46 (m, 1H), 2.70 (d, 1H), 2.83 (d, 1H), 2.88-3.05 (m, 2H), 4.45 (br-s, 1H), 7.27 (d, 1H), 7.48 (d, 1H)

Fraction II: recovered title compound from Step G; yellow oil (0.13 g, 9%)

Fraction III: Mono-Boc title compound; off-white solid (0.26 g, 19%)

$^1$H-NMR (400 MHz, CDCl$_3$): δ=1.45 (s, 9H), 1.54 (s, 3H), 1.76-1.83 (m, 1H), 2.60-2.65 (m, 1H), 2.80-2.90 (m, 4H), 4.55 (s, 1H), 7.18 (d, 1H), 7.59 (d, 1H), 9.75 (br-s, 1H)

Step J

The bis-Boc derivative from Step I above (0.15 g, 0.32 mmol) was dissolved in tetrahydrofuran (2.6 mL) and methanol (2.6 mL). After the addition of 1 M aqueous sodium hydroxide solution (2.6 mL, 2.6 mmol), the reaction mixture was stirred at room temperature overnight and the solvents were evaporated. The residue was treated with water (20 mL), the precipitate was collected by filtration, washed with water (5 mL) and air-dried to afford the mono-Boc title compound from Step I as a white solid (0.09 g, 76%).

Step K

The mono-Boc title compound from Step I above (0.35 g, 0.94 mmol) was dissolved in N,N'-dimethylacetamide (5 mL) and the mixture was cooled to 0° C. At 0° C. sodium hydride (0.068 g, 2.8 mmol) was added and the mixture was stirred at 0° C. for 90 minutes. Then methyl iodide (0.27 mL, 4.45 mmol) was added at 0° C., the ice bath was removed and the reaction mixture was stirred at room temperature overnight. The reaction mixture was diluted with ethyl acetate (50 mL) and water (20 mL). The organic phase was separated and the aqueous phase was extracted with ethyl acetate (20 mL). The combined organic phase was dried over Na$_2$SO$_4$, filtered and the solvents were removed. The residue was purified by chromatography on silica using a Biotage Isolera One system employing an ethyl acetate/n-heptane gradient (5/95->30/70) to afford the title compound as a white solid (0.31 g, 81%).

$^1$H-NMR (400 MHz, CDCl$_3$): δ=1.49 (s, 3H), 1.86-1.94 (m, 1H), 2.68-2-74 (m, 3H), 2.72 (s, 3H), 3.07-3.18 (m, 2H), 3.72 (s, 3H), 7.15 (d, 1H), 7.57 (d, 1H)

Preparative Example 34

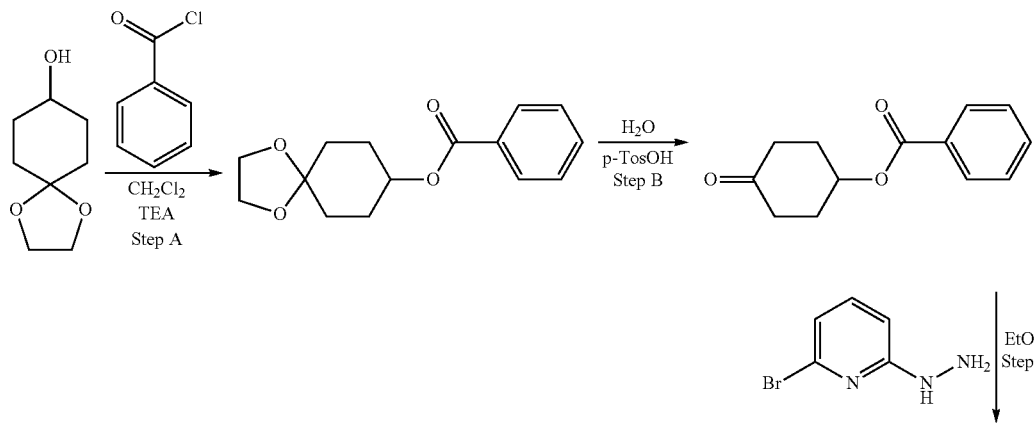

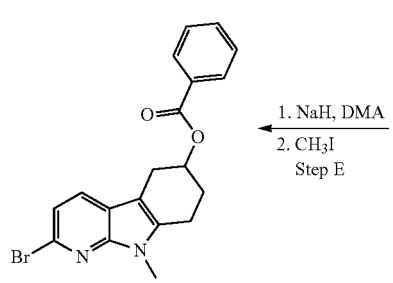
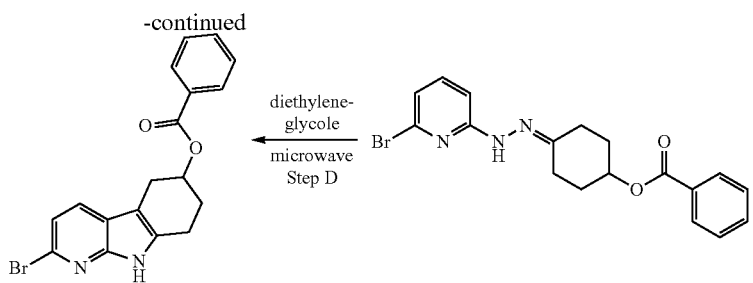
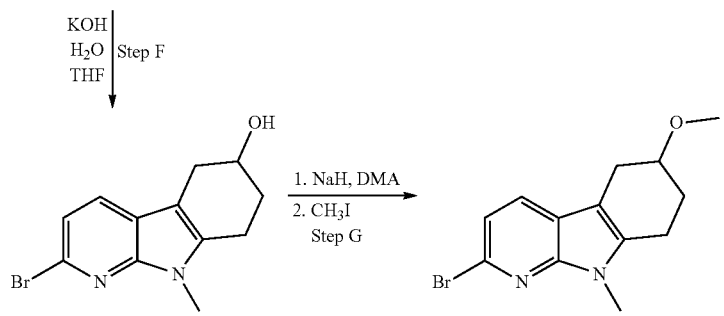

Step A

The title compound from Preparative Example 28 Step A (12 g, 75.9 mmol) was dissolved in dichloromethane (240 mL) and triethylamine (14.5 mL) was added. After the addition of benzoylchloride (12.7 g, 91.2 mmol), the reaction mixture was stirred at room temperature overnight. The reaction mixture was diluted with dichloromethane (100 mL) and washed with water (80 mL) and a 10% aqueous citric acid solution (2×80 mL). The organic phase was separated, dried over $Na_2SO_4$, filtered and the solvents were evaporated under reduced pressure to afford the crude title compound as a oil.

Step B

The crude title compound from Step A above was dissolved in tetrahydrofuran (85 mL) and water (250 mL). Then p-toluene sulfonic acid (1 g, 5.8 mmol) was added and the mixture was heated at ~115° C. in a sand bath for 4 h. The mixture was cooled to room temperature, diluted with ethyl acetate (250 mL) and the organic phase was separated. The organic phase was dried over $Na_2SO_4$, filtered and the solvents were removed. The residue was purified by chromatography on silica using ethyl acetate/n-heptane (20/80) as a mobile phase to afford the title compound as a white solid (10.7 g, 64% for 2 steps).

$^1$H-NMR (400 MHz, $CDCl_3$): δ=2.27-2.45 (m, 4H), 2.52-2.61 (m, 2H), 2.74-2.84 (m, 2H), 5.55-5.60 (m, 1H), 7.60 (t, 2H), 7.73 (t, 1H), 8.21 (d, 2H)

Step C

The title compound from Preparative Example 23 Step A (3.69 g, 19.6 mmol) was dissolved in ethanol (85 mL) and the title compound from Step B above (4.28 g, 19.6 mmol) was added. The mixture was stirred at room temperature for 1 h and the solvents were removed under reduced pressure to afford the title compound as a yellow foam (7.6 g, quant.).

$^1$H-NMR (400 MHz, $CDCl_3$): δ=2.12-2.26 (M, 4H), 2.53-2.61 (m 2H), 2.68-2.84 (m, 2H), 7.02 (d, 1H), 7.30 (d, 1H), 7.55 (t, 1H), 7.57-7.62 (m 2H), 7.71 (t, 1H), 8.17-8.22 (m, 2H)

Step D

The title compound from Step C above (0.95 g, 2.45 mmol) was dissolved in diethylene glycol (9.5 mL) and heated at 245° C. for 35 minutes using a Biotage Initiator microwave. The reaction mixture was diluted with water (25 mL) and ethyl acetate (100 mL). The organic phase was separated, washed with brine (25 mL), dried over $Na_2SO_4$, filtered and the solvents were removed. This procedure was repeated seven more times and the combined crude material was purified by chromatography on silica using dichloromethane/acetone (98/2) as a mobile phase to afford the title compound as an off-white solid (3.4 g, 46%).

$^1$H-NMR (400 MHz, $CDCl_3$): δ=2.23-2.38 (m 2H), 2.95-3.27 (m, 4H), 5.60 (5.57-5.61 (m, 1H), 7.22 (d, 1H), 7.44-7.47 (m, 2H), 7.58 (t. 1H), 7.65 (d, 1H), 8.06 (d, 2H), 9.88 (br-s, 1H)

Step E

The title compound from Step D above (3.4 g, 9.19 mmol) was dissolved in N,N'-dimethylacetamide (40 mL) and the solution was cooled to 0° C. At 0° C. sodium hydride (0.29 g, 11.95 mmol) was added in portions. The mixture was stirred at 0° C. for 1 h and methyl iodide (1.19 mL, 19.14 mmol) was added. The mixture was stirred at 0° C. for 5 minutes then at room temperature for 16 h. The reaction mixture was diluted with ethyl acetate (250 mL), 10% aqueous solution of citric acid (80 mL) and brine (50 mL). The organic phase was separated, washed with brine (50 mL), dried over $Na_2SO_4$, filtered and the solvents were removed. The residue was purified by chromatography on silica using a Biotage Isolera One purification system employing an ethyl acetate/n-heptane gradient (5/95->30/70) to afford the title compound as an off-white solid (2.42 g, 68%).

$^1$H-NMR (400 MHz, $CDCl_3$): δ=2.25-2.34 (m, 2H), 2.85-3.00 (m, 3H), 3.18 (dd, 1H), 3.75 (s, 3H), 5.52-5.57 (m, 1H), 7.15 (d, 1H), 7.42 (t, 2H), 7.53-7.57 (m, 2H), 8.00-8.04 (m, 2H)

Step F

The title compound from Step E above (0.33 g, 0.86 mmol) was dissolved in tetrahydrofuran (8 mL) and water (8 mL). After the addition of potassium hydroxide (0.75 g, 13.4 mmol), the mixture was heated at 140° C. for 30 minutes using a Biotage Initiator microwave. The reaction mixture was diluted with ethyl acetate (30 mL) and water (10 mL). The organic phase was separated, washed with brine (10 mL), dried over Na$_2$SO$_4$, filtered and the solvents were removed. This procedure was repeated six more times to afford the title compound as an off-white solid (1.74 g, 98%).

$^1$H-NMR (400 MHz, CDCl$_3$): δ=2.00-2.16 (m, 2H), 2.68 (dd, 1H), 2.75-2.80 (m, 1H), 2.88-2.93 (m, 1H), 3.06 (dd, 1H), 3.71 (s, 3H), 4.25-4.30 (m, 1H), 7.13 (d, 1H), 7.56 (d, 1H)

Step G

The title compound from Step F above (0.2 g, 0.71 mmol) was dissolved in N,N'-dimethylacetamide (3 mL) and the solution was cooled to 0° C. At 0° C. sodium hydride (0.023 g, 0.92 mmol) was added. The mixture was stirred at 0° C. for 1 h and methyl iodide (0.09 mL, 1.47 mmol) was added. The mixture was stirred at room temperature for 16 h. The reaction mixture was diluted with ethyl acetate (30 mL), 10% aqueous solution of citric acid (8 mL) and brine (5 mL). The organic phase was separated, washed with brine (5 mL), dried over Na$_2$SO$_4$, filtered and the solvents were removed. The residue was purified by chromatography on silica using a Biotage Isolera One purification system employing an ethyl acetate/n-heptane gradient (5/95->40/60->100/0) to afford the title compound as a pale orange oil which becomes a solid by standing at room temperature (0.13 g, 63%).

$^1$H-NMR (400 MHz, CDCl$_3$): δ=2.05-2.19 (m, 2H), 2.70-2.78 (m, 2H), 2.86-2.93 (m, 1H), 3.30 (dd, 1H), 3.47 (s, 3H), 3.71 (s, 3H), 3.75-3.78 (m, 1H), 7.14 (d, 1H), 7.56 (d, 1H)

Preparative Example 35

Step B

A solution of the title compound from the above step (4.4 g, 11.3 mmol) in diethyleneglycol (45 mL) was sealed in three different microwavable glass tubes (20 mL). Then, the reaction tubes were heated at 250° C. using a microwave for 55 min. The combined reaction mixture was collected and was dissolved in DCM (200 mL) and washed with water and brine. The organic phase was dried over Na$_2$SO$_4$ and the solvent was removed under reduced pressure to give crude product, which was purified on a silica gel column (ethyl acetate/n-heptane 20%-30%) to give the title compound (1.77 g, 42%).

$^1$H NMR (400 MHz, DMSO-d$_6$) δ 7.95 (d, 1H), 7.65 (t, 1H), 7.52 (dd, 1H), 7.24 (d, 1H), 7.12 (d, 1H), 5.46 (s, 1H), 3.34 (s, 3H), 3.13 (dd, 1H), 2.98-2.78 (m, 1H), 2.51 (s, 2H), 2.18 (d, 1H).

Step C

To a stirred solution of the compound from above step B (200 mg, 0.54 mmol) in THF (50 mL) was added NaH (25 mg, 1.0 mmol). The suspension was stirred for 10 min. Then the methyl iodide solution (75 mg, 0.5 mmol) was added and the reaction mixture was stirred for 1 h. The reaction mixture was quenched with water and extracted with ethyl acetate (100 mL). The organic phase was washed with brine and dried over Na$_2$SO$_4$. The solvent was removed and crude material was purified on a silica gel column (eluent: 10:90 EtOAc:heptane) to give the title compound (200 mg, 96%).

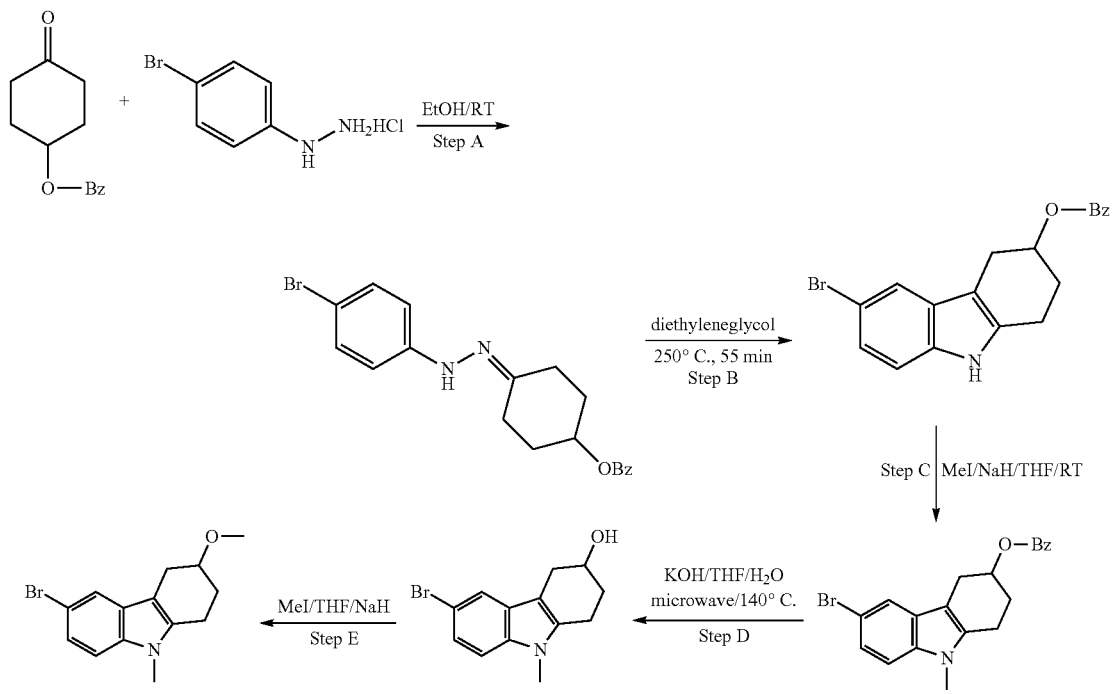

Step A

To a solution of commercially available 4-bromophenyl hydrazine (2.6 g, 11.6 mmol) in ethanol (50 mL) was added ketone derivative (2.54 g, 11.6 mmol). The reaction mixture was stirred for 2 h at room temperature. The solvent was removed to give the title compound as a solid (4.5 g, quantitative). The compound was used in the next step without any purification.

$^1$H-NMR (400 MHz, CDCl$_3$): δ=8.10-8.00 (m, 2H), 7.59-7.55 (m, 2H), 7.46-7.42 (m, 2H), 7.26-7.28 (m, 1H), 7.16 (d, 1H), 5.59-5.56 (m, 1H), 3.66 (s, 3H), 3.21 (dd, 1H), 3.01-2.92 (m, 3H), 2.33-2.27 (m, 2H).

Step D

To a solution of the compound from step C (200 mg, 0.52 mmol) in THF:H$_2$O (1:1, 8 mL) was added KOH (450 mg, 7.8 mmol). The reaction mixture was heated at 140° C. using a microwave for 30 min. The reaction mixture was extracted with ethyl acetate (150 mL) and washed with water and brine and dried over $Na_2SO_4$. The solvent was evaporated and the crude material was purified on a silica gel column (eluent: 10:90 EtOAc:heptane) to give the title compound (137 mg, 69%).

$^1$H-NMR (400 MHz, CDCl$_3$): δ=7.56 (d, 1H), 7.23 (dd 1H), 7.10 (d, 1H), 4.48-4.07 (m, 1H), 3.60 (s, 3H), 3.05 (dd, 1H), 2.89 (dt, 1H), 2.83-2.61 (m, 3H), 2.20-1.96 (m, 2H).

Step E

To a solution of the compound from above step D (130 mg, 0.46 mmol) in THF (10 mL) was added NaH (22 mg, 0.92 mmol). The suspension was stirred for 10 min at room temperature. Then the methyl iodide solution (129 mg, 0.92 mmol) was added and the reaction mixture was stirred for 1 h. Then the reaction mixture was quenched carefully with water and extracted with ethyl acetate (150 mL). The organic phase was washed with brine and dried over $Na_2SO_4$. The solvent was removed and purified on a silica gel column (eluent: 10:90 EtOAc:heptane) to give the title compound (115 mg, 85.8%).

$^1$H NMR (400 MHz, CDCl$_3$) δ 7.57 (d, 1H), 7.21 (dd, 1H), 7.09 (d, 1H), 3.87-3.72 (m, 1H), 3.59 (s, 3H), 3.46 (s, 3H), 3.03 (dd, 1H), 2.90-2.83 (m, 1H), 2.77-2.68 (m, 2H), 2.19-2.12 (m, 1H), 2.19-1.98 (m, 1H).

Preparative Example 36 to give the title compound as a solid (3.52 g, quantitative). The product was used in the next step without any further purification.

Step B

A solution of the title compound (3.5 g, 9.1 mmol) in diethyleneglycol (12 mL) was sealed in a microwavable glass tube (20 mL). Then, the reaction mixture was heated at 245° C. using a microwave for 50 min. The reaction mixture was dissolved in ethyl acetate (250 mL) and washed with water and brine. The organic phase was dried over $Na_2SO_4$ and the solvent was removed under reduced pressure, and the crude product was purified on a silica gel column (ethyl acetate/n-heptane 10%-40%) to give two regioisomers (1.17, 32%).

Regioisomer A (7-bromo-2,3,4,9-tetrahydro-1H-carbazol-3-yl benzoate) (670 mg)

$^1$H-NMR (400 MHz, CDCl$_3$): δ=8.05 (d, 1H), 7.83 (s, 1H), 7.57 (m, 1H), 7.47-7.42 (m, 2H), 7.32 (d, 1H), 7.21 (dd, 1H), 5.62-5.59 (m, 1H), 3.22 (dd, 1H), 3.10-2.76 (m, 3H), 2.56-2.07 (m, 2H).

Regioisomer B (5-bromo-2,3,4,9-tetrahydro-1H-carbazol-3-yl benzoate) (500 mg)

$^1$H-NMR (400 MHz, CDCl$_3$): δ=8.08 (d, 1H), 7.92 (s, 1H), 7.57 (m, 1H), 7.45 (t, 1H), 7.24 (t, 1H), 6.97 (t, 1H), 5.61 (m, 1H), 3.65 (dd, 1H), 3.38 (dd, 1H), 3.17-2.66 (m, 2H), 2.45-2.07 (m, 2H).

Step C

To a stirred solution of compound regiomer A from step 2 (450 mg, 1.2 mmol) in THF (15 mL) was added NaH (58 mg,

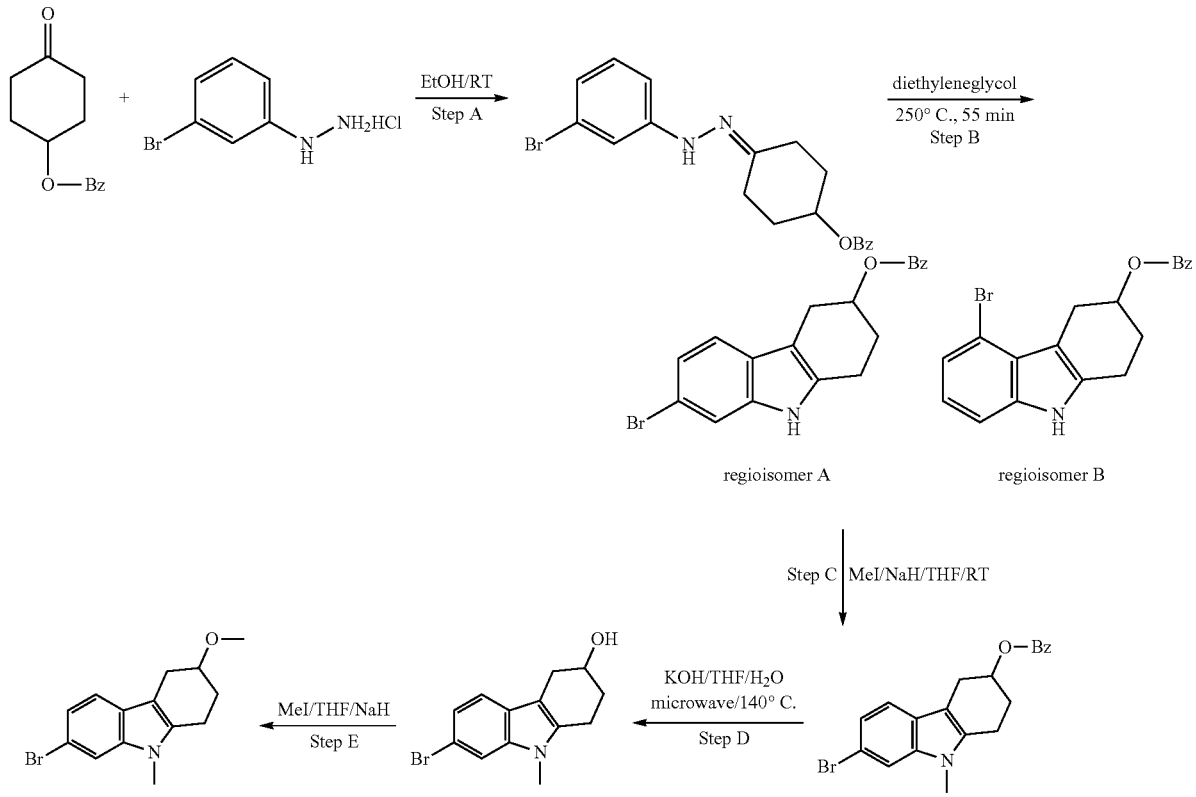

regioisomer A      regioisomer B

Step A

To a solution of commercially available 3-bromophenyl hydrazine (2 g, 9.1 mmol) in ethanol (50 mL) was added ketone derivative (2 g, 9.1 mmol). The reaction mixture was stirred for 2 h at room temperature. The solvent was removed 2.4 mmol). The suspension was stirred for 10 min. Then the methyl iodide solution (338 mg, 2.4 mmol) was added and the reaction mixture was stirred for 2 h. The reaction mixture was quenched with water and extracted with ethyl acetate (200 mL). The organic phase was washed with brine and dried over Na$_2$SO$_4$. The solvent was removed and the crude material was purified on a silica gel column (ethyl acetate/n-heptane 10%-30%) to give the title compound (357 mg, 77.6%).

$^1$H-NMR (400 MHz, CDCl$_3$): δ=8.06-8.03 (m, 1H), 7.62-7.52 (m, 1H), 7.49-7.39 (m, 2H), 7.33 (d, 1H), 7.20 (dd, 1H), 5.76-5.41 (m, 1H), 3.65 (s, 3H), 3.23 (dd, 1H), 3.13-2.73 (m, 3H), 2.56-2.11 (m, 2H).

removed and purified on a silica gel column (acetate/n-heptane 10%-40%) to give the title compound (120 mg, 71.8%).

$^1$H-NMR (400 MHz, CDCl$_3$): δ=7.40 (d, 1H), 7.32 (d, 1H), 7.18 (dd, 1H), 3.84-3.71 (m, 1H), 3.60 (s, 3H), 3.48 (s, 3H), 3.08 (dd, 1H), 2.87 (dt, 1H), 2.74-2.70 (m 2H), 2.20-2.03 (m, 2H).

Preparative Example 37

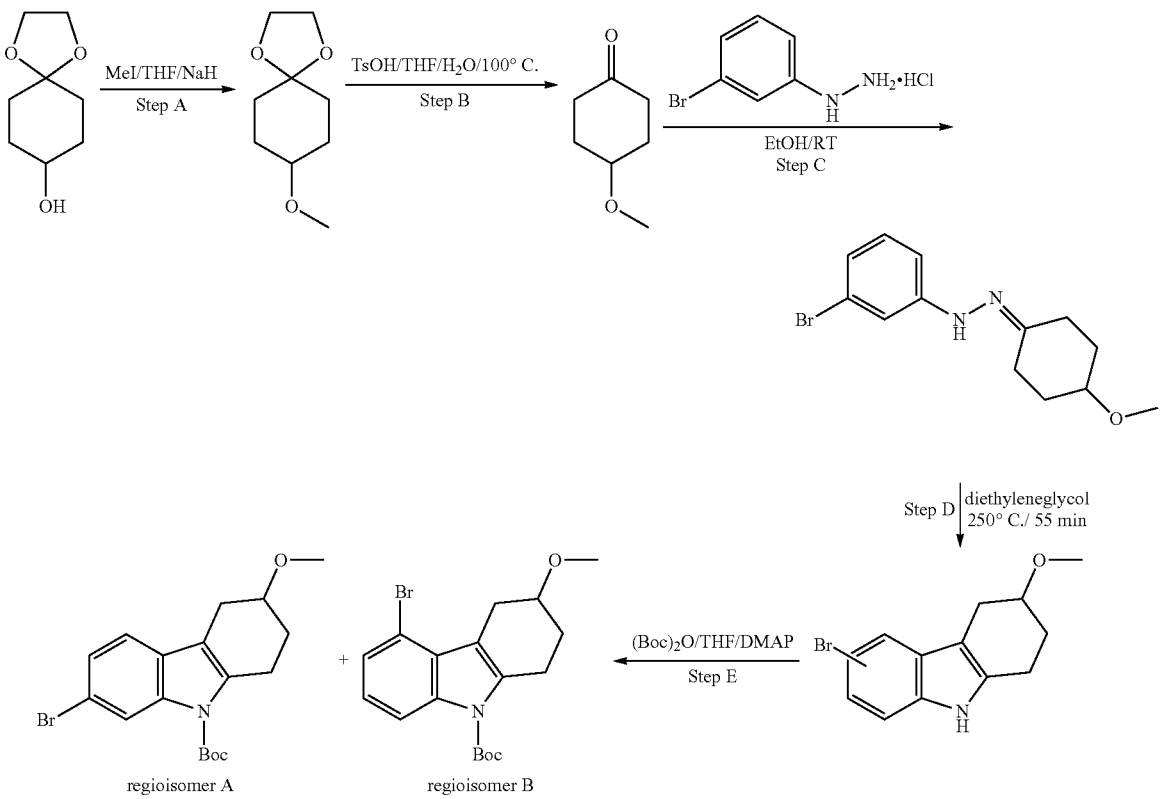

Step D

To a solution of the compound from step 3 (357 mg, 0.92 mmol) in THF:H$_2$O (1:1, 8 mL) was added KOH (450 mg, 7.8 mmol). The reaction mixture was heated at 140° C. using a microwave for 30 min. The reaction mixture was extracted with ethyl acetate (150 mL) and washed with water and brine and dried over Na$_2$SO$_4$. The solvent was evaporated and the crude material was purified on a silica gel column (ethyl acetate/n-heptane 10%-40%) to give the title compound (160 mg, 62%).

$^1$H NMR (400 MHz, CDCl$_3$) δ=7.42 (d, 1H), 7.32 (d, 1H), 7.19 (dd, 1H), 4.38-4.21 (m, 1H), 3.61 (s, 3H), 3.09 (dd, 1H), 2.82-2.70 (m, 3H), 2.16-1.96 (m, 2H).

Step E

To a solution of the compound from step 4 (160 mg, 0.57 mmol) in THF (5 mL) was added NaH (122 mg, 5.0 mmol). The suspension was stirred for 10 min at room temperature. Then the methyl iodide solution (400 mg, 2.83 mmol) was added and the reaction mixture was stirred for 4 h. Then, the reaction mixture was quenched carefully with water and extracted with ethyl acetate (150 mL). The organic phase was washed with brine and dried over Na$_2$SO$_4$. The solvent was Step A To a solution of the title compound (5 g, 31.6 mmol) in THF (100 mL) was added NaH (1.2 g, 50 mmol). The suspension was stirred for 10 min at room temperature. The methyl iodide solution (5.5 g, 39 mmol) was added slowly and the reaction mixture was stirred for 3 h. Then, the reaction mixture was quenched with water carefully, and the reaction mixture was concentrated. The residue was dissolved in EtOAc (200 mL) and washed with water and brine and dried over Na$_2$SO$_4$. The solvent was removed under reduced pressure and the residue was purified on a silica gel column using a Biotage Isolera One purification system employing an EtOAc/n-heptane gradient (15/85->50/50) to afford the title compound (4.3 g, 80%).

$^1$H-NMR (400 MHz, CDCl$_3$) δ: 3.95 (s, 3H), 3.35-3.29 (m, 5H), 1.87-1.80 (m, 4H), 1.75-1.68 (m, 2H), 1.60-1.52 (m, 2H).

Step B

To a solution of the title compound (6.4 g, 37.2 mmol) in THF:H$_2$O (1:1; 50 mL) was added p-toluene sulfonic acid (640 mg, 3.86 mmol). The reaction mixture was heated at 100° C. overnight. The reaction mixture was extracted with ethyl acetate (200 mL). The organic phase was washed with water, brine and dried over Na$_2$SO$_4$. The solvent was removed under reduced pressure and the residue was purified on a silica gel column using a Biotage Isolera One purification system employing an EtOAc/n-heptane gradient (20/80->50/50) to afford the title compound (4.2 g, 89%).

¹H-NMR (400 MHz, CDCl₃) δ: 3.64-3.62 (m, 1H), 3.42 (s, 3H), 2.62-2.54 (m, 2H), 2.31-2.26 (m, 2H), 2.14-2.06 (m, 2H), 1.99-1.92 (m, 2H).

Step C

To a solution of 4-methoxycyclohexanone (1.4 g, 10.8 mmol) from step B was added (3-bromophenyl)hydrazine hydrochloride (2.4 g, 10.8 mmol) in ethanol (50 mL). Then the reaction mixture was stirred at room temperature for 4 h. Then the solvent was removed under reduced pressure to give the title compound (3.1 g, quantitative). The product was used in the next step without any purification.

Step D

A solution of the title compound from step D (3.1 g, 10.4 mmol) in diethyleneglycol (12 mL) was sealed in microwavable glass tube (20 mL). Then, the reaction mixture was heated at 250° C. using a microwave for 50 min. The reaction mixture was dissolved in ethyl acetate (250 mL) and washed with water and brine. The organic phase was dried over Na₂SO₄ and the solvent was removed under reduced pressure, and the crude product was purified on a silica gel column using a Biotage Isolera One purification system employing an EtOAc/n-heptane gradient (20/80->30/70) to afforded a mixture of two regioisomers (1.6 g, 53%).

Step E

To a solution of the title compound from above step D (1.4 g, 4.99 mmol) in THF (30 mL) was added di-tert-butyl dicarbonate (1.3 g, 5.9 mmol) and a catalytic amount of dimethylamino pyridine (5 mg). Then, the reaction mixture was stirred for 1 h. The solvent was removed, the crude product was purified on a silica gel column using a Biotage Isolera One purification system employing an EtOAc/n-heptane gradient (5/95->25/75) to afford the two regioisomers. The fast eluting compound was regioisomer A (700 mg, 37%), and the slow eluting compound was regiomer B (1.1 g 58%).

Regioisomer A: tert-butyl 5-bromo-3-methoxy-3,4-dihydro-1H-carbazole-9(2H)-carboxylate:

¹H-NMR (400 MHz, CDCl₃) δ: 8.15 (d, 1H), 7.34 (d, 1H), 7.06 (t, 1H), 3.77-3.71 (m, 1H), 3.48 (s, 3H), 3.47-3.42 (m, 1H), 3.18-3.11 (m, 2H), 3.05-2.97 (m, 1H), 2.10-1.95 (m, 2H), 1.67 (s, 9H).

Regioisomer B: tert-butyl 7-bromo-3-methoxy-3,4-dihydro-1H-carbazole-9(2H)-carboxylate:

¹H-NMR (400 MHz, CDCl₃) δ=8.35 (d, 1H), 7.34 (dd, 1H), 7.23 (d, 1H), 3.78-3.73 (m, 1H), 3.47 (s, 3H), 3.19-3.12 (m, 1H) 3.00-2.95 (m, 2H), 2.69-2.63 (m, 1H), 2.15-2.09 (m, 1H), 2.05-1.96 (m, 1H) 1.68 (s, 9H).

Preparative Example 38

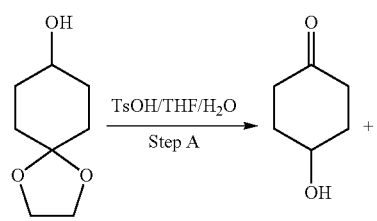

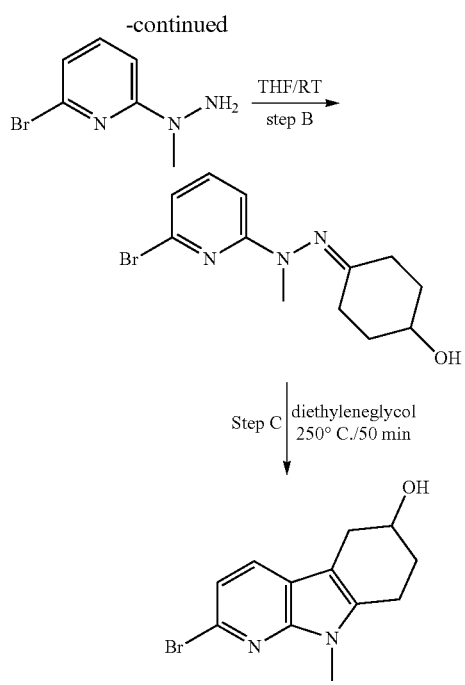

Step A

A solution of the title compound (11 g, 70 mmol) in THF:H₂O (100 mL, 1:1) was heated at 110° C. overnight. The reaction mixture was extracted with ethyl acetate (250 mL). The organic phase was washed with water and brine and dried over Na₂SO₄. The solvent was removed under reduced pressure to give the title compound (5.2 g, 65%).

Step B

To a solution of 2-bromo-6-(1-methylhydrazinyl)pyridine (5.2 g, 25.7 mmol) in THF (50 mL) was added 4-hydroxycyclohexanone (3.1 g, 27.1 mmol). The reaction mixture was stirred for 1 h. The solvent was removed under reduced pressure to give an oily compound (7.6 g, quantitative). The compound was used in the next step without any purification.

Step C

A solution of the title compound from step B (7.65 g, 25.7 mmol) in diethyleneglycol (45 mL) was sealed in microwavable glass tubes (20 mL). The reaction tubes were heated at 250° C. using a microwave for 55 min. The reaction was performed in 3 batches. The combined reaction mixture was collected and was dissolved in ethyl acetate (250 mL) and washed with water and brine. The organic phase was dried over Na₂SO₄ and the solvent was removed under reduced pressure to give crude product, which was purified on a silica gel column (ethyl acetate/n-heptane 20%-40%) to give the title compound (3.6, 50%).

¹H-NMR (400 MHz, CDCl₃) δ 7.58 (d, J=8.0 Hz, 1H), 7.16 (d, J=8.0 Hz, 1H), 4.29-4.28 (m, 1H), 3.69 (s, 3H), 3.08 (dd, J=15.4, 4.2 Hz, 1H), 2.93-2.85 (m, 1H), 2.80-2.66 (m, 2H), 2.17-1.99 (m, 3H).

Preparative Example 39

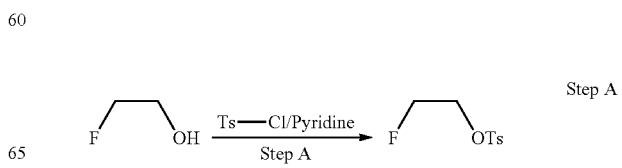

To a solution of 2-fluoroethanol (0.32 mL, 5 mmol) in pyridine and toluene (5 mL, 1:1) mixture was added p-toluenesulfonyl chloride at 0° C. The reaction mixture was stirred overnight. The reaction mixture was dissolved in EtOAc (150 mL) and washed with water and brine and dried over $Na_2SO_4$. The solvent was removed under reduced pressure, and the crude product was purified on a silica gel column using Biotage Isolera One purification system employing EtOAc/n-heptane (5/95=>30/70) to give the title compound as a colorless liquid (1.54 g, 67%).

$^1$H NMR (400 MHz, $CDCl_3$) δ=7.85 (m, 2H), 7.40 (m, 2H), 4.65 (m, 1H), 4.55 (m, 1H), 4.35 (m, 1H), 4.25 (m, 1H), 2.48 (s, 3H).

Preparative Example 40

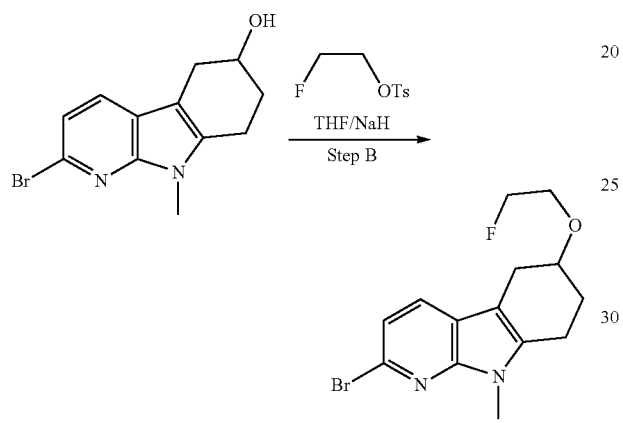

Step A

To a solution of the title compound from preparative example 38 step C (150 mg, 0.53 mmol) in THF (15 mL) was added NaH (25 mg, 1.06 mmol) and the suspension was stirred for 5 min. Then, the solution of the compound (116 mg, 0.53 mmol) from step A was added. The reaction mixture was heated at 100° C. for overnight. The reaction mixture was dissolved in EtOAc (100 ml), and washed with water and brine and dried over $Na_2SO_4$. The product was purified on a silica gel column using Biotage Isolera One purification system employing an EtOAc/n-heptane gradient (10/90=>20/80) to afford the title compound (78 mg, 45%).

$^1$H NMR (400 MHz, $CDCl_3$) δ 7.57 (d, 1H), 7.15 (d, 1H), 4.72-4.61 (m, 1H), 4.67 (t, 1H), 4.55 (t, 1H), 3.97-3.91 (m, 1H), 3.90 (t, 1H), 3.83 (t, H) 3.71 (s, 3H), 3.07 (dd, 1H), 2.93-2.88 (m, 1H), 2.80-2.72 (m, 2H), 2.22-2.20 (m, 1H), 2.14-2.05 (m, 1H).

Preparative Example 41

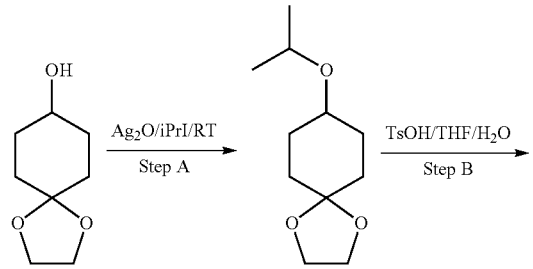

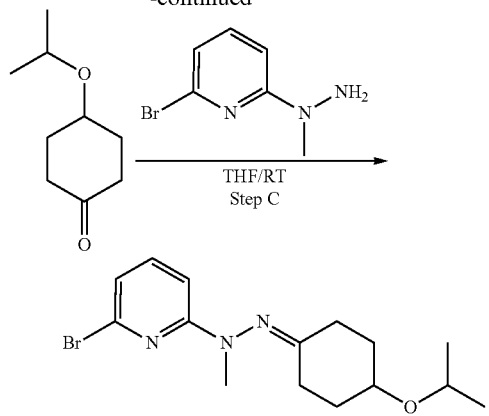

Step A

To a solution of the title compound (5.6 g, 35.4 mmol) in 2-iodopropane (28 mL) was added $Ag_2O$ (16 g, 69.2 mmol) and the reaction mixture was stirred for 4 days. Then the reaction mixture was diluted with diethyl ether and filtered off and the filtrate was concentrated under reduced pressure and the crude product was purified on a silica gel column using Biotage Isolera One purification system employing an EtOAc/n-heptane gradient (5/95=>20/80) to afford the title compound (2.6 g, 57% based on starting material recovery).

$^1$H NMR (400 MHz, $CDCl_3$) δ 3.95 (s, 4H), 3.80-3.59 (m, 1H), 3.48 (s, 1H), 1.81 (d, 4H), 1.76-1.61 (m, 3H), 1.56 (d, 2H), 1.15 (d, 6H).

Step B

To a solution of the title compound from step A (3 g, 15.0 mmol) in THF:$H_2O$ (20 mL, 1:1) was added p-toluene sulfonic acid (0.5 g, 3 mmol) and the reaction mixture was heated at 100° C. overnight. The reaction mixture was extracted with EtOAc (200 mL). The organic phase was washed with water and brine and dried over $Na_2SO_4$. The solvent was removed and the crude product was purified on a silica gel column using Biotage Isolera One purification system employing an EtOAc/n-heptane gradient (20/80=>50/50) to afford the title compound (2.1 g, 91%).

$^1$H-NMR (400 MHz, $CDCl_3$) δ 3.78 (d, 1H), 2.61 (s, 1H), 2.29 (s, 1H), 2.18-1.80 (m, 2H), 1.35-1.07 (m, 4H).

Step C

To a solution of commercially available 2-bromo-6-(1-methylhydrazinyl)pyridine (620, 3.06 mmol) in THF (5 mL) was added ketone derivative from step B (0.62 g, 3.06 mmol). The reaction mixture was stirred for 2 h at room temperature. The solvent was removed to give the title compound as an oily material (1 g, quantitative). The product was used in the next step without any further purification

Step D

A solution of the title compound from step C (1 g, 3.9 mmol) in diethyleneglycol (12 mL) was sealed in a microwavable glass tube (20 mL). Then, the reaction mixture was heated at 245° C. using a microwave for 50 min. The reaction mixture was dissolved in ethyl acetate (250 mL) and washed with water and brine. The organic phase was dried over Na$_2$SO$_4$ and the solvent was removed under reduced pressure, and the crude product was purified on a silica gel column using Biotage Isolera One purification system by employing an EtOAc/n-heptane gradient (10/90=>50/50) to afford the title compound (258 mg, 26%).

$^1$H-NMR (400 MHz, CDCl$_3$) δ 7.57 (d, 1H), 7.14 (d, 1H), 3.99-3.79 (m, 2H), 3.71 (s, 3H), 3.11-2.98 (m, 1H), 2.90 (dt, 1H), 2.79-2.72 (m, 1H), 2.69-2.62 (m, 1H), 2.20-2.11 (m, 1H), 2.08-1.93 (m, 1H), 1.23 (d, 3H), 1.22 (d, 3H).

Step A

To a solution of commercially available 3-bromophenyl hydrazine (2.74 g, 12.2 mmol) in ethanol (100 mL) was added ketone derivative (3 g, 12.2 mmol) in ethanol (50 mL). The reaction mixture was stirred for 5 h at room temperature. The solvent was removed to give the title compound as a solid (5 g, quantitative). The product was used in the next step without any purification.

Step B

A solution of the title compound from step A (5 g, 12.1 mmol) in diethyleneglycol (12 mL) was sealed in microwavable glass tube (20 mL). Then, the reaction mixture was heated at 245° C. using microwaves for 50 min. The reaction was performed in 3 batches. The combined reaction mixture was dissolved in ethyl acetate (250 mL) and washed with water and brine. The organic phase was dried over Na$_2$SO$_4$ and the solvent was removed under reduced pressure, and the crude product was purified on a silica gel column using Biotage Isolera One purification system employing an

Preparative Example 42

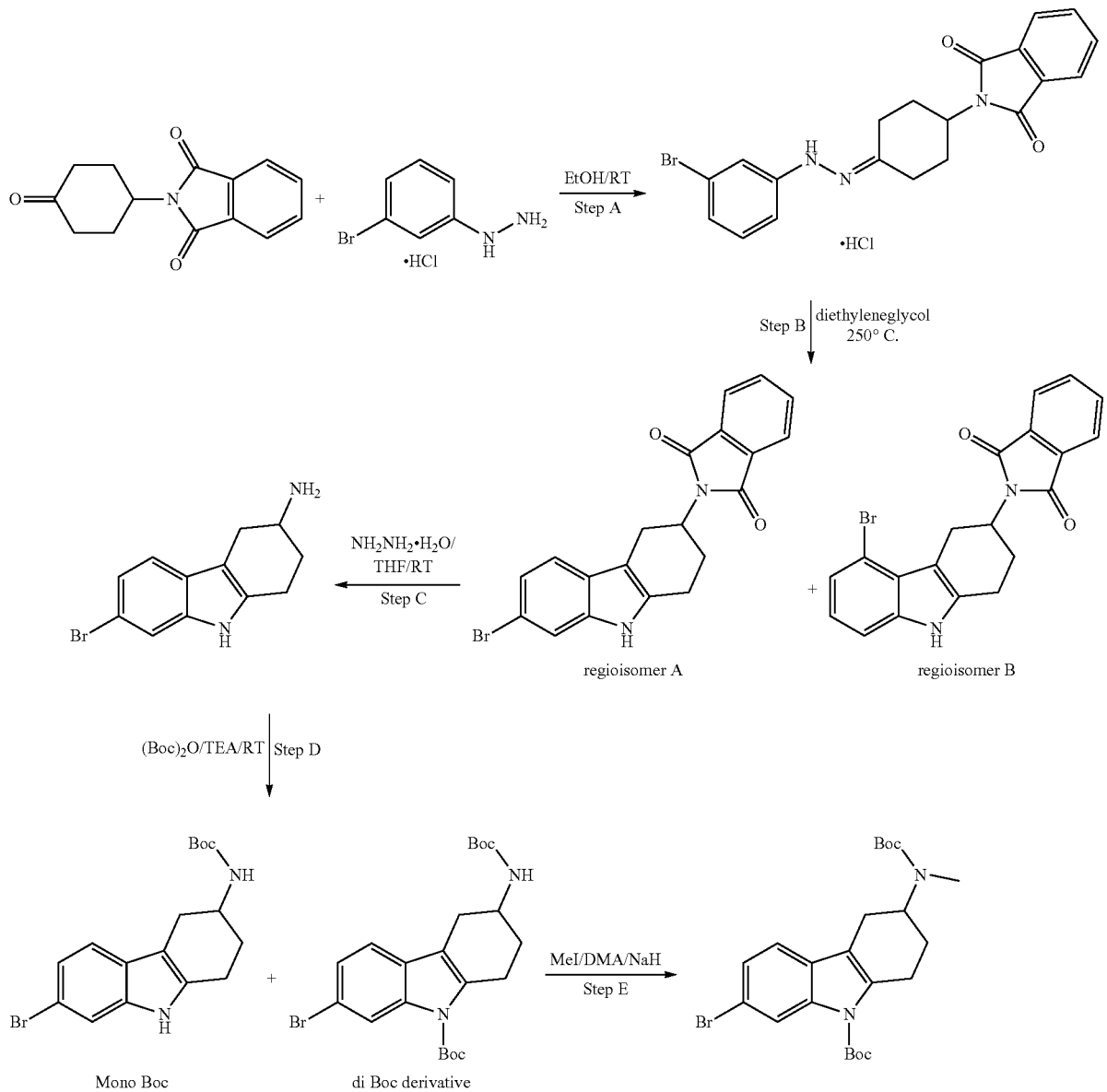

EtOAc/n-heptane gradient (10/90=>55/45) to afford the title compounds as two regioisomers (3.3 g, 70%).

Regioisomer A (1.9 g) (2-(7-bromo-2,3,4,9-tetrahydro-1H-carbazol-3-yl)isoindoline-1,3-dione)

$^1$H NMR (400 MHz, CDCl$_3$) δ 7.89 (m, 2H), 7.82-7.65 (m, 2H), 7.46 (s, 1H), 7.2-7.26 (m, 1H), 7.19 (d, 1H), 4.71-4.66 (m, 1H), 3.52-3.46 (m, 1H), 3.00-2.91 (m, 4H), 2.11-2.07 (m, 1H).

Regioisomer B (1.4 g) (2-(5-bromo-2,3,4,9-tetrahydro-1H-carbazol-3-yl)isoindoline-1,3-dione)

$^1$H NMR (400 MHz, CDCl$_3$) δ 7.82 (dd, 2H), 7.70 (dd, 2H), 7.18 (d, 1H), 7.10 (d, 1H), 6.86 (t, 1H), 4.57 (m, 1H), 3.63-3.57 (m, 1H), 3.53-3.25 (m, 1H), 3.08-2.69 (m, 3H), 1.99 (d, 1H).

Step C

To a stirred solution of compound regioisomer A from above step B (980 mg, 2.48 mmol) in THF (25 mL) was added NH$_2$NH$_2$ (2 mL). The reaction mixture was stirred for 2 days. The solid was filtered off. The filtrate was concentrated under reduced pressure, and the crude product was dissolved in DCM (200 mL). The organic phase was washed with water and brine and dried over Na$_2$SO$_4$. The solvent was removed under reduced pressure, the crude product was used in the next step without any further purification.

Step D

To the crude product from the above step (1.1 g) in THF (25 ml) was added (Boc)$_2$O (4.5 g, 20.6 mmol) and triethylamine (2.5 mL). The reaction mixture was stirred at room temperature overnight. The solvent was removed and the crude product was purified on a silica gel column using Biotage Isolera One purification system employing an EtOAc/n-heptane gradient (20/80=>50/50) to afford fast eluting compound as di-Boc-(650 mg) and slow eluting compound as mono-Boc-(830 mg) protected compound.

Di-Boc:(650 mg)

tert-butyl 7-bromo-3-(tert-butoxycarbonylamino)-3,4-dihydro-1H-carbazole-9(2H)-carboxylate $^1$H NMR (400 MHz, CDCl$_3$) δ 8.35 (d, 1H), 7.35 (dd, 1H), 7.23 (d, 1H), 4.68 (s, 1H), 4.10 (s, 1H), 3.09-3.01 (m, 3H), 2.53 (dd, 1H), 2.13-2.00 (m, 1H), 2.03-1.75 (m, 1H), 1.69 (s, 9H), 1.48 (s, 9H).

Mono-Boc: (830 mg)

tert-butyl 7-bromo-2,3,4,9-tetrahydro-1H-carbazol-3-ylcarbamate $^1$H NMR (400 MHz, CDCl$_3$) δ 7.45 (d, 1H), 7.30 (d, 3H), 7.20 (dd, 1H), 4.70 (s, 1H), 4.12 (s, 1H), 3.08 (dd, 1H), 2.85-2.81 m, 3H), 2.57 (dd, 2H), 2.15-2.12 (m, 1H), 2.01-1.93 (m, 1H), 1.48 (s, 9H).

Step E

A solution of di-Boc protected compound from the above step (630 mg, 1.35 mmol) in DMA (5 mL) was cooled to ice bath temperature and NaH (65 mg, 2.7 mmol) was added portionswise. The suspension was stirred at room temperature for 5 min and methyl iodide solution (380 mg, 2.7 mmol) was added. The reaction mixture was stirred at room temperature for 2 h. The reaction mixture was dissolved in dichloromethane (250 mL) and washed with water and brine and dried over Na$_2$SO$_4$. The solvent was removed and the crude product was purified on a silica gel column using Biotage Isolera One purification system employing an EtOAc/n-heptane gradient (20/80=>50/50) to afford the title compound (435 mg, 67%).

$^1$H-NMR (400 MHz, CDCl$_3$) δ 8.34 (s, 1H), 7.35 (d, 1H), 7.23 (d, 1H), 4.50 (m, 1H), 3.28-3.24 (m, 1H), 3.08-3.0 (m, 1H), 2.87 (s, 3H), 2.75 (m, 2H), 1.98 (dd, 3H), 1.68 (s, 9H), 1.50 (s, 9H).

Preparative Example 43

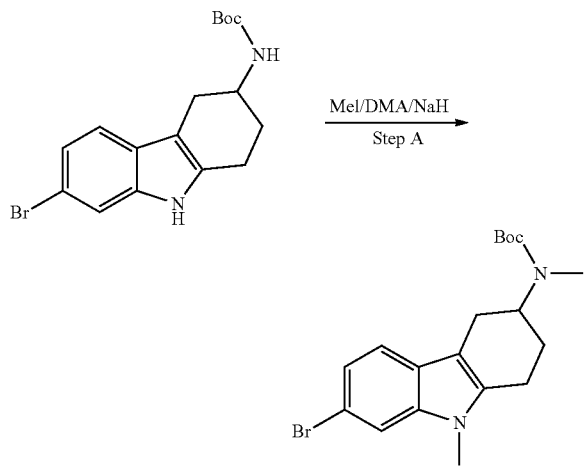

Step A

To a solution of monoprotected compound from preparative example 41 step D (750 mg, 2.05 mmol) in DMA (5 mL) was added NaH (65 mg, 2.7 mmol) portionswise. The suspension was stirred at room temperature for 5 min and methyl iodide solution (380 mg, 2.7 mmol) was added. The reaction mixture was stirred at room temperature for 1 h. The reaction mixture was dissolved in dichloromethane (150 mL) and washed with water and brine and dried over Na$_2$SO$_4$. The solvent was removed and the crude product was purified on a silica gel column using Biotage Isolera One purification system employing an EtOAc/n-heptane gradient (20/80=>50/50) to afford the title compound (455 mg, 56%).

$^1$H NMR (400 MHz, CDCl$_3$) δ=7.40 (d, 1H), 7.31 (d, 1H), 7.18 (d, 1H), 4.50-4.33 (m, 1H), 3.59 (s, 3H), 2.88-2.74 (m, 7H), 2.08 (brs, 2H), 1.50 (s, 9H).

Preparative Example 44

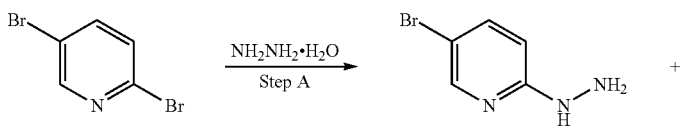

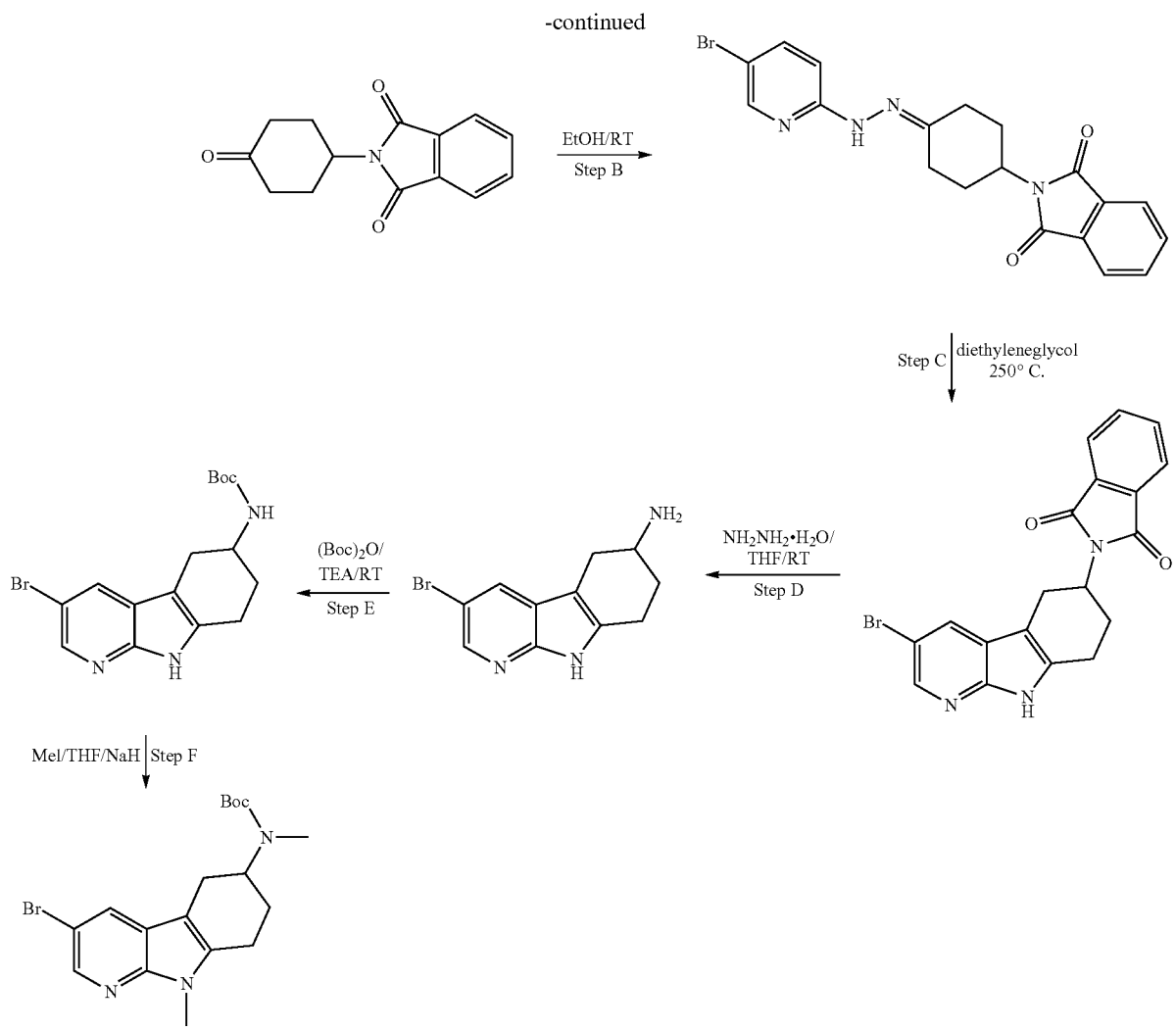

Step A

To a solution of 2,5-dibromopyridine (15 g, 64 mmol) was added NH$_2$NH$_2$·H$_2$O (20 mL). The reaction mixture was refluxed for 2 days. The solvent was removed under reduced pressure, and the crude product was dissolved in DCM (200 mL) and washed with water and brine and dried over Na$_2$SO$_4$. The solvent was removed and the crude product was purified on a silica gel column using Biotage Isolera One purification system employing an EtOAc/n-heptane gradient (20/80=>50/50) to afford the title compound (5.1 g, 59% based on starting material recovery).

$^1$H NMR (400 MHz, CDCl$_3$) δ 8.16 (s, 1H), 7.56 (d, 1H), 6.69 (d, 1H), 6.04 (brs, 1H), 3.7 (brs, 2H).

Step B

To a solution of the title compound from above step A (1.5 g, 6.7 mmol) in ethanol (100 mL) was added ketone derivative (1.6 g, 6.7 mmol) in ethanol (50 mL). The reaction mixture was stirred for 5 h at room temperature. The solvent was removed to give the title compound as a solid (3.1, quantitative). The product was used in the next step without any purification.

Step C

A solution of the title compound from above step B (3.7 g, 8.9 mmol) in diethyleneglycol (12 mL) was sealed in a microwavable glass tube (20 mL). Then, the reaction mixture was heated at 245° C. using a microwave for 50 min. The reaction was performed in 3 batches. The combined reaction mixture was dissolved in ethyl acetate (250 mL) and washed with water and brine. The organic phase was dried over Na$_2$SO$_4$ and the solvent was removed under reduced pressure, and the crude product was purified on a silica gel column using Biotage Isolera One purification system employing an EtOAc/n-heptane gradient (20/80=>70/30) to afford the title compounds as two regioisomers (1 g, 28.5%). The product was used in the next step without any characterization.

Step D

To a stirred solution of compound from above step C (1.2 mg, 3.0 mmol) in THF (50 mL) was added NH$_2$NH$_2$ (5 mL). The reaction mixture was stirred for 2 days. The solid was filtered off. The filtrate was concentrated under reduced pressure, and the crude product was dissolved in DCM (200 mL). The organic phase was washed with water and brine and dried over Na$_2$SO$_4$. The solvent was removed under reduced pressure, the crude product (890 mg) was used in the next step without any further purification.

Step E

To the crude product from above step D (0.89 g) in THF (20 mL) was added (Boc)$_2$O (2 g, 9.1 mmol) and triethylamine (5 mL). The reaction mixture was stirred at room temperature overnight. The solvent was removed and the crude product was purified on a silica gel column using Biotage Isolera One purification system employing an EtOAc/n-heptane gradient (20/80=>60/40) to afford the title compound (0.77 g, 24% overall yield from 3 steps).

¹H NMR (400 MHz, CDCl₃) δ 11.50 (s, 1H), 8.12 (d 1H), 7.98 (d 1H), 7.01 (d, 1H), 3.78-3.69 (m, 1H), 3.32 (s, 3H), 2.91-2.86 (m, 1H), 2.77-2.70 (m, 2H), 2.47-2.41 (m, 1H), 2.01-1.97 (m, 1H), 1.79-1.69 (m, 1H), 1.41 (s, 9H).

Step F

To a solution of Boc-protected compound from above step E (700 mg, 1.9 mmol) in DMA (10 mL) was added NaH (180 mg, 7.5 mmol) portionswise. The suspension was stirred at room temperature for 10 min and methyl iodide solution (1.2 g, 8 mmol) was added. The reaction mixture was stirred at room temperature for 2 h. The reaction mixture was dissolved in ethyl acetate (250 mL) and washed with water and brine and dried over Na₂SO₄. The solvent was removed and the crude product was purified on a silica gel column using Biotage Isolera One purification system employing an EtOAc/n-heptane gradient (25/75=>80/20) to afford the title compound (435 mg, 67%).

¹H NMR (400 MHz, DMSO) δ 8.20 (d, 1H), 8.06 (d, 1H), 4.26 (m, 1H), 3.65 (s, 3H), 3.00-2.88 (m, 2H), 2.79 (s, 3H), 2.73-2.70 (m, 2H), 2.04-1.99 (m, 2H), 1.42 (s, 9H).

Preparative Example 45

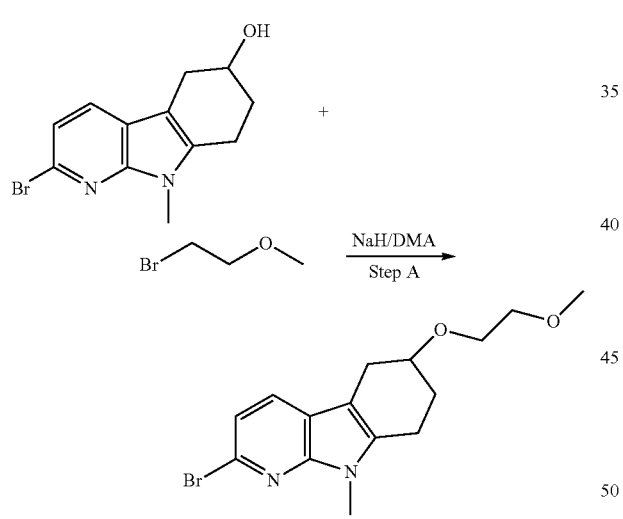

Step A

To a solution of the title compound (0.25 g, 0.88 mmol) in DMA (5 mL) was added NaH (60 mg, 2.5 mmol) and the suspension was stirred for 5 min. Then, the solution of 1-bromo-2-methoxyethane (245 mg, 1.77 mmol) was added. The reaction mixture was stirred for 3 h at 50° C. on a sand bath. The reaction mixture was dissolved in EtOAc (150 mL), and washed with water and brine and dried over Na₂SO₄. The product was purified on a silica gel column using Biotage Isolera One purification system by employing an EtOAc/n-heptane gradient (20/80=>80/20) to afford the title compound (0.255 g, 85%).

¹H NMR (400 MHz, CDCl₃) δ 7.56 (d, 1H), 7.14 (d, 1H), 3.91-3.85 (m, 1H), 3.77-3.74 (m, 2H), 3.70 (s, 3H), 3.59 (t, 2H), 3.42 (s, 3H), 3.07 (dd, 1H), 2.93-2.86 (m, 1H), 2.78-2.69 (m, 2H), 2.24-2.21 (m, 1H), 2.10-2.01 (m, 1H).

Preparative Example 46

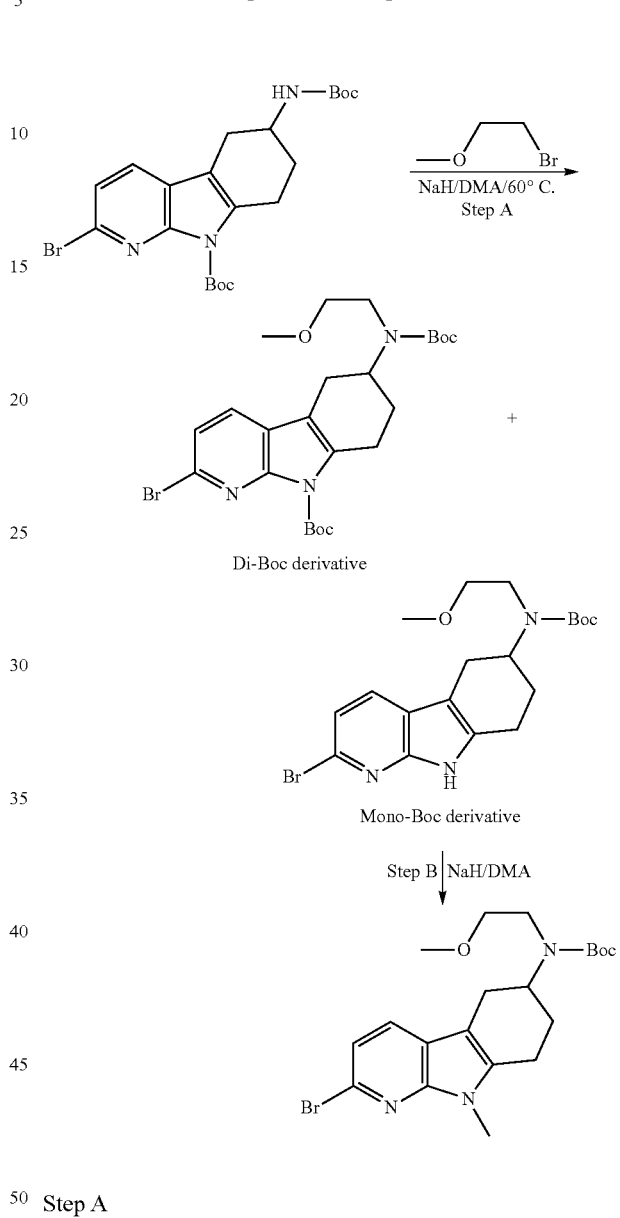

Step A

To a solution of the title compound from preparative example 28 step G (400 mg, 0.858 mmol) in DMA (5 mL) was added NaH (31 mg, 1.29 mmol). The suspension was stirred for 5 min at room temperature and 1-bromo-2-methoxyethane (120 mg, 0.869 mmol) was added. The reaction mixture was heated at 50° C. overnight. The reaction mixture was cooled, and dissolved in ethyl acetate (150 mL) and washed with water and brine and dried over Na₂SO₄. The solvent was removed under reduced pressure and the crude product was purified on a silica gel column using Biotage Isolera One purification system employing an EtOAc/n-heptane gradient (1/99=>20/80) to afford the title compound (150 mg, 41%).

¹H-NMR (400 MHz, CDCl₃) δ 7.50 (d, 1H), 7.10 (d, 1H), 4.69 (d, 1H), 4.38-4.14 (m, 2H), 4.04 (s, 1H), 3.65 (t, 2H), 3.24 (s, 3H), 3.01 (dd, 1H), 2.85-2.82 (m, 1H), 2.50 (dd, 1H), 2.19-2.06 (m; 1H), 1.95-1.86 (m, 1H), 1.42 (s, 9H)

Step B

To a solution of mono-Boc derivative from the above step (80 mg, 0.188 mmol) in DMA (2 mL) was added NaH (7 mg, 0.28 mmol). To this suspension methyl iodide (39 mg, 0.28 mmol) was added. The reaction mixture was stirred for 2 h. Then the reaction mixture was dissolved in ethyl acetate (150 mL) and washed with water and brine and dried over $Na_2SO_4$. The solvent was removed and the crude product was purified on a silica gel column using Biotage Isolera One purification system employing an EtOAc/n-heptane gradient (10/90=>60/40) to afford the title compound (70 mg, 85%).

$^1$H-NMR (400 MHz, CDCl$_3$) δ 7.53 (d 1H), 7.13 (d 1H), 4.49-4.24 (m, 4H), 3.70-3.67 (m, 2H), 3.27 (s, 3H), 3.27-2.70 (m, 6H), 2.04-2.03 (m, 2H), 1.48 (s, 9H).

Preparative Example 47

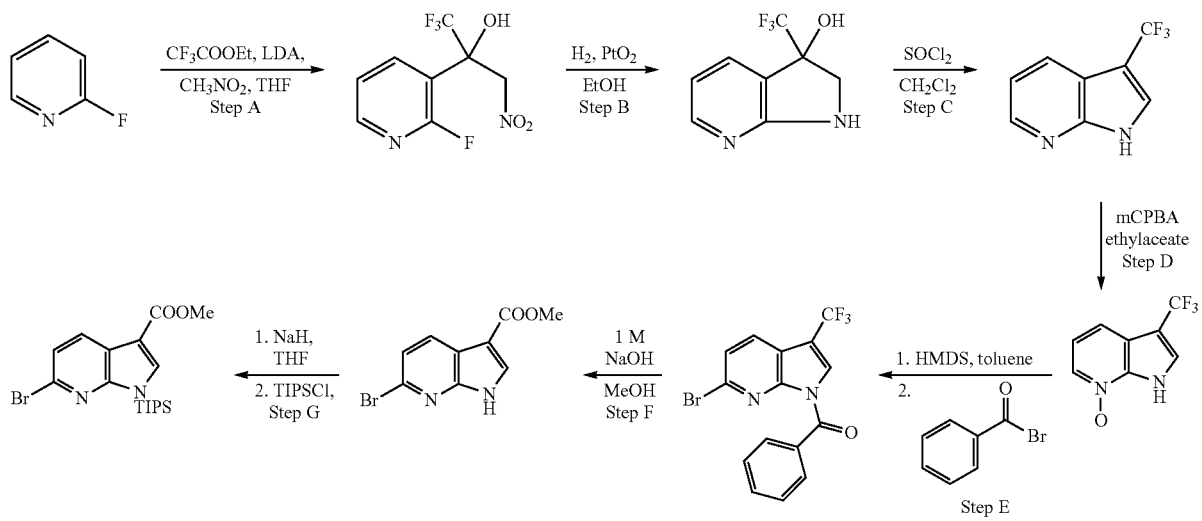

was removed under reduced pressure. The title compound was obtained after chromatographic purification using a gradient of dichloromethane/methanol (98/2 to 9/1) to afford the title compound (1.2 g, 34%).

MS (ESI); m/z=204.86 (MH$^+$)

Step C

To a solution of the title compound from Step B above (1.2 g, 5.88 mmol) in tetrahydrofuran (15 mL) and pyridine (0.951 mL, 11.76 mmol) was added thionyl chloride (0.858 mL, 11.76 mmol) at 0° C. The resulting mixture was stirred at room temperature for 24 h. The reaction mixture was poured into ice water. The mixture was neutralized (pH 6) with a saturated solution of sodium carbonate. The aqueous layer was extracted with dichloromethane. The organic layers were collected, dried over $Na_2SO_4$, filtered and concentrated to dryness. The residual pyridine was removed by addition of toluene and concentration to dryness 3 times to afford the title compound as a brown solid (1.13 g, 100%).

MS (ESI); m/z=186.88 (MH$^+$)

Step D

To a solution of 3-chloroperbenzoic acid (1.571 g, 9.11 mmol) in tetrahydrofuran (50 mL) was added at 0° C. the title compound from Step C above (1.130 g, 6.07 mmol) in portions. The resulting solution was stirred at room temperature for 4 h. The reaction mixture was concentrated to dryness. The crude product was triturated in diethyl ether and then filtered (this was repeated several times). The mother liquor was concentrated to dryness and purified by flash chromatography using dichloromethane/methanol to afford the title compound (1.37 g, 67%).

MS (ESI); m/z=202.84 (MH$^+$)

Step E

To a solution of the title compound from Step D above (0.513 g, 1.430 mmol) in dry toluene (30 mL) was added at the same time a solution of hexamethyldisilazane (0.6 mL, 2.86 mmol) in toluene and a solution of benzoyl bromide (0.421 mL, 3.58 mmol) in toluene. The resulting mixture was stirred at room temperature for 3 h. The reaction mixture was concentrated to dryness. The residue was purified by flash chromatography using ethyl acetate/n-heptane (15/85 to 35/65) to afford the title compound as a white solid (0.190 g, 36%).

Step A

To a solution of LDA solution 1.8 M (33.0 mL, 59.3 mmol) in tetrahydrofuran (150 mL) at −75° C. was added commercially available 2-fluoropyridine (4.25 mL, 49.4 mmol). The mixture was stirred for 4 h at this temperature. To the resulting suspension, ethyl trifluoroacetate (7.08 mL, 59.3 mmol) was added, during which the internal temperature should not rise above −45° C. The reaction mixture was warmed to room temperature. Nitromethane (5.31 mL, 99 mmol) was added and the reaction mixture was stirred at room temperature overnight. The slurry was diluted with ethyl acetate (100 mL) and 50 mL of 1.2 M HCl. The organic layer was separated, dried over $Na_2SO_4$, filtered and concentrated to dryness. The residue was suspended in dichloromethane and filtered to afford the title compound as white crystals (6.14 g). The mother liquor was concentrated to dryness and purified by flash chromatography in ethyl acetate/n-heptane (20/80 to 35/65) yielding additional material (4.45 g). The overall yield was 10.59 g (84%).

Step B

The title compound from step A above (4.45 g, 17.51 mmol) was dissolved in ethanol (50 mL) and stirred under hydrogen (0.141 g, 70.0 mmol) with platinum(IV) oxide hydrate (0.398 g, 1.751 mmol). After the consumption of the theoretical amount of hydrogen, the solution was filtered, and the filtrate was refluxed overnight. Subsequently, the solvent Step F To a solution of the title compound from Step E above (0.19 g, 0.515 mmol) in methanol (10 ml) was added a 1 M aqueous solution of sodium hydroxide (1.544 mL, 1.544 mmol). The resulting solution was stirred at room temperature for 10 h. The methanol was then removed under reduced pressure. The residue was dissolved in ethyl acetate and saturated sodium bicarbonate. The organic layer was separated, dried over $Na_2SO_4$ and concentrated to dryness to afford the title compound as a white solid (0.122 g, 89%).

Step G

To a solution of the title compound from Step F above (0.122 g, 0.460 mmol) in dry tetrahydrofuran (10 ml) was added at 0° C. sodium hydride 60% (0.019 g, 0.483 mmol) in portions. The reaction mixture was stirred at room temperature for 20 minutes and then triisopropylsilyl chloride (0.099 mL, 0.460 mmol) was added. The resulting mixture was stirred at room temperature for 2 h. The reaction mixture was concentrated to dryness. The residue was diluted with ethyl acetate. An extraction was performed with saturated bicarbonate and brine. The organic layers were collected, dried over $Na_2SO_4$, filtered and concentrated to dryness. The crude product was purified by flash chromatography using ethyl acetate/n-heptane (15/85 to 40/60) to afford the title compound as a white solid (0.188 g, 99%).

$^1$H NMR (400 MHz, $CDCl_3$): δ=1.12 (d, 18H); 1.82 (h, 3H); 3.91 (s, 3H); 7.31 (d, 1H); 7.94 (s, 1H); 8.21 (d, 1H)

$^{13}$C NMR Dept135 (400 MHz, $CDCl_3$): δ=11.89; 17.99; 51.31; 121.62; 131.43; 137.75

Preparative Example 48

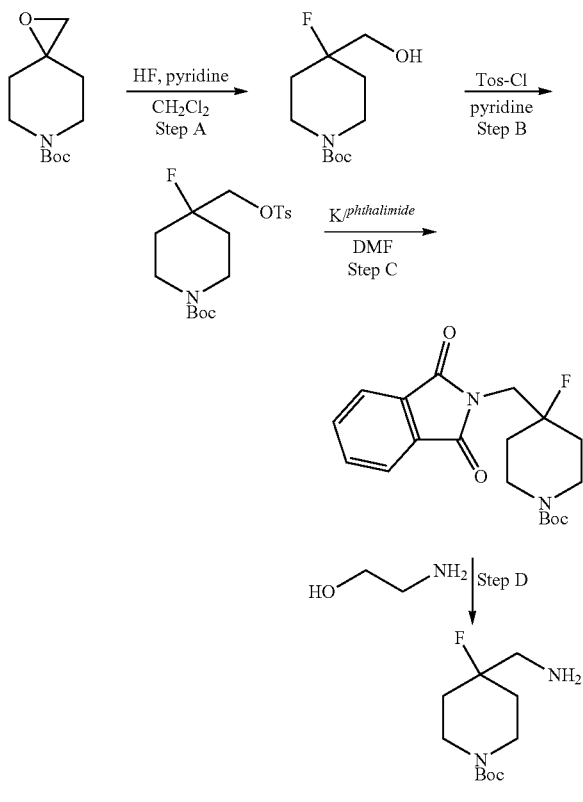

Step A

A mixture of 0.6 mL of a ~70% solution of hydrogen fluoride in pyridine and dichloromethane (10 mL) was cooled to −10° C., and a solution of commercially available epoxide (2 g, 9.38 mmol) in dichloromethane (10 mL) was added dropwise. Then the mixture was stirred at room temperature for 4 h, diluted with dichloromethane and washed with a saturated aqueous solution of sodium carbonate. The organic phase was separated, dried over $Na_2SO_4$, filtered and the solvents were removed to give a residue which was purified by chromatography on silica using an ethyl acetate/n-heptane gradient (20/80->50/50) to afford the title compound as a yellow oil (1.44 g, 66%).

$^1$H-NMR (400 MHz, $CDCl_3$): δ=1.44 (s, 9H), 1.47-1.63 (m, 2H), 1.85 (m, 2H), 3.08 (m, 2H), 3.56 (s, 1H), 3.61 (s, 1H), 3.92 (brs, 2H).

MS (ESI); m/z=233.98 (MH$^+$)

Step B

The title compound from Step A above (1.44 g, 6.17 mmol) was dissolved in pyridine (6 mL) and the solution was cooled to 0° C. p-Toluenesulfonyl chloride (1.29 g, 6.79 mmol) was added and the mixture was stirred at room temperature for 4 h. The reaction mixture was diluted with dichloromethane (250 mL) and washed with water (50 mL). The organic phase was dried over $Na_2SO_4$, filtered and the solvent was removed. The residue was purified using a Biotage flash chromatography system (ethyl acetate/n-heptane: 20/80->50/50) to afford the title compound as a yellow oil (2.2 g, 92%).

$^1$H-NMR (400 MHz, $CDCl_3$): δ=1.47 (s, 9H), 1.49-1.63 (m, 4H), 1.80 (m, 2H), 2.46 (s, 3H), 3.03 (m, 2H), 3.96 (brs, 2H), 7.36 (d, 2H), 7.79 (d, 2H).

Step C

The title compound from Step B above (2.2 g, 5.68 mmol) was dissolved in N,N'-dimethylformamide (22 mL). Potassium phthalimide (1.052 g, 5.68 mmol) was added and the mixture was heated at 150° C. for 12 h. After cooling to room temperature, water (100 mL) was added and the mixture was extracted with ethyl acetate (3×250 mL). The organic phase was dried over $Na_2SO_4$, filtered and the solvent was removed to afford the title compound as a white solid (2.45 g) which was directly used for the next step.

MS (ESI); m/z=362.9 (MH$^+$)

Step D

The title compound from Step C above (2.45 g) was suspended in ethanolamine (6 mL). The mixture was heated at 60° C. for 2.5 h. After cooling to room temperature, water (50 mL) was added and the mixture was extracted with ethyl acetate (3×250 mL). The organic phase was dried over $Na_2SO_4$, filtered and the solvent was removed. The residue was purified using a Biotage flash chromatography system (methanol/dichloromethane:20/80->50/50) to afford the title compound as a yellow oil (0.67 g, 46% for 3 steps).

$^1$H-NMR (400 MHz, $CDCl_3$): δ=1.44 (s, 9H), 1.56 (m, 4H), 1.84 (m, 2H), 3.06 (m, 2H), 3.94 (brs, 2H).

MS (ESI): m/z=177.04 (M-t-Bu+H$^+$), 217.96 (M-Me+H$^+$), 233.01 (M+H$^+$)

Preparative Example 49

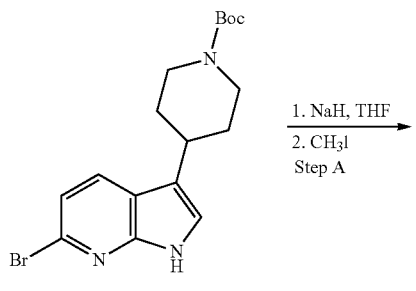

Step A

To a solution of the title compound from Preparative Example 14, Step D (1 g, 2.63 mmol) in dry tetrahydrofuran (25 ml) was added at 0° C. sodium hydride (0.111 g, 2.89 mmol, 60% in mineral oil) in portions. The mixture was stirred at room temperature for 30 minutes, then methyl iodide (0.491 ml, 7.89 mmol) was added. The solution was concentrated to dryness. The residue was purified by flash chromatography in ethyl acetate/n-heptane (15% to 40%) to afford the title compound as a white solid (0.98 g, 95%).

MS ESI: 394.48/396.48 (M+H)

Preparative Example 50

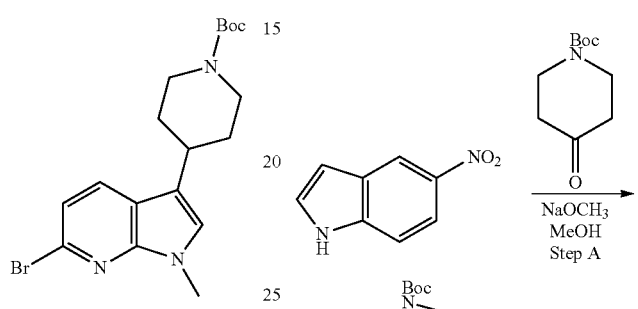

Step A 1,2-dimethoxyethane (3 mL) was added to a mixture of the title compound from Preparative Example 3 (0.021 g, 0.156 mmol), the title compound from Preparative Example 1, Step D (0.050 g, 0.141 mmol), tris(dibenzylideneacetone)dipalladium chloroform complex (0.013 g, 0.014 mmol), 4,5-bis(diphenylphosphino)-9,9-dimethylxanthene (Xantphos, 0.008 g, 0.014 mmol) and cesium carbonate (0.09 g, 0.283 mmol). The reaction mixture was degassed for 3 minutes at room temperature under argon and subjected to sonication. The vial was then warmed to 100° C. for 1 h. The reaction mixture was extracted with ethyl acetate and brine. The organic layers were collected, dried over Na$_2$SO$_4$, filtered and concentrated to dryness. The residue was purified by flash chromatography using an ethyl acetate/n-heptane mixture to afford the title compound as a white solid (0.07 g, 12%).

MS ESI: 406.06 (M+H)

Preparative Example 51

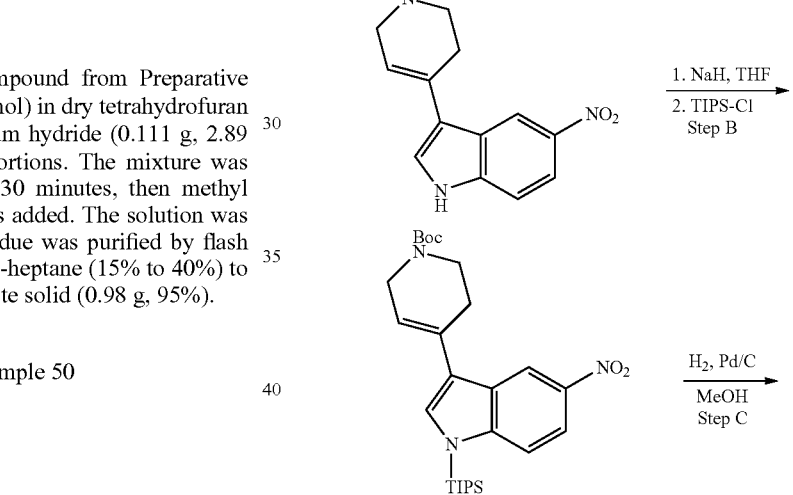

Step A

To a solution of commercially available 5-nitro-indole (3.4 g, 20.9 mmol) and 1-Boc-4-piperidone (6 g, 31.3 mmol) in methanol (50 mL) was added (28%) sodium methoxide in methanol (10 mL) and the reaction mixture was heated at 80° C. for 2 d. The precipitated product was filtered off and dried to afford the title compound as a yellow solid (5.1 g, 72%)

$^1$H-NMR (400 MHz, DMSO-d$_6$): δ=1.42 (s, 9H), 3.2 (m, 2H), 3.56 (t, 2H), 4.0 (m, 2H), 6.17 (s, 1H), 7.54 (d, 1H), 7.69 (s, 1H), 8.00 (d, 1H), 8.69 (s, 1H)

Step B

To a solution of the title compound from Step A above (4 g, 11.6 mmol) in tetrahydrofurane (150 mL) was added sodium hydride (0.42 g, 17.4 mmol) in portions. The dark red colored suspension was stirred at room temperature for 10 minutes. Then triisopropylsilyl chloride (2.23 g, 11.6 mmol) was added and the reaction mixture was stirred at room temperature overnight. The reaction mixture was quenched with water and the solvents were removed. The residue was suspended in ethyl acetate (200 mL) and the starting material was removed by filtration. The filtrate was concentrated and the residue was purified on a silica gel column (ethyl acetate/n-heptane (20/80)–>(60/40)) to afford the title compound (2 g, 66%).

$^1$H-NMR (400 MHz, DMSO-d$_6$): δ=1.14 (d, 18H), 1.51 (s, 9H), 1.67-1.71 (m, 3H), 3.69-3.75 (m, 4H), 4.17 (s, 2H), 6.18 (s, 1H), 7.30 (s, 1H), 7.49 (d, 1H), 8.06 (d, 1H), 8.78 (s, 1H)

Step C

To a solution of the title compound from Step B above (2 g, 4 mmol) in ethyl acetate (150 mL) was added 10% Pd/C (0.5 g). The flask was evacuated and back filled with hydrogen gas. Then, the reaction mixture was stirred under hydrogen atmosphere overnight. The reaction mixture was filtered off and dried to afford the crude product, which was purified by a silica gel column using ethyl acetate/n-heptane (20/80->50/50) to afford the title compound (1.31 g, 69%).

$^1$H-NMR (400 MHz, CDCl$_3$): δ=1.14 (d, 18H), 1.51 (s, 9H), 1.61-1.69 (m, 5H), 2.02-2.05 (m, 2H), 2.89-2.91 (m, 3H), 4.23-4.24 (m, 2H), 6.68-6.70 (m, 1H), 6.92 (s, 1H), 6.99 (d, 1H), 7.30 (d, 1H)

Preparative Example 52

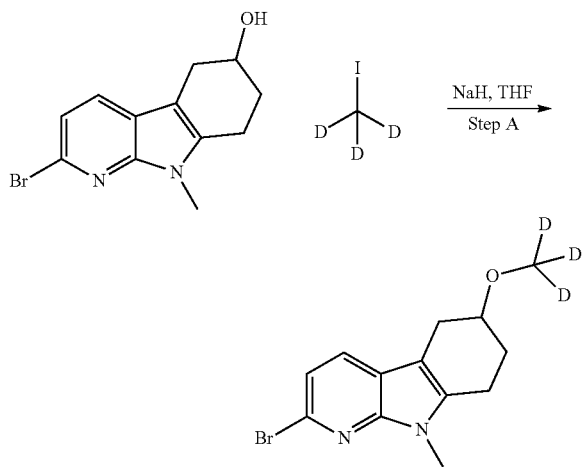

Step A

To a solution of the title compound from preparative example 33 step F (0.150 g, 0.534 mmol) in dry tetrahydrofuran (Volume: 10 ml) was added sodium hydride 60% (0.022 g, 0.560 mmol) portionwise. After 30 min at room temperature d3-iodomethane (0.040 ml, 0.640 mmol) was added dropwise. The resulting mixture was stirred at room temperature for 12 h. The reaction mixture was concentrated to dryness. The residue was purified by flash chromatography in ethyl acetate/n-heptane 15% to 50% to afford the expected compound as a yellowish solid (0.95 g, 60%).

MS (ESI); m/z=298.65/300.68 (MH$^+$)

Preparative Example 53

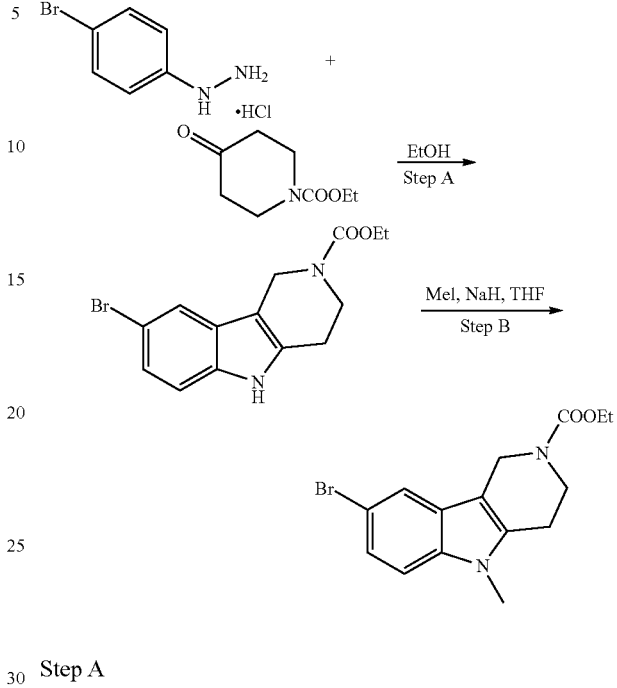

Step A

To stirred ethanol (45 mL) was added ethyl carbethoxy-4-piperidone (8.81 mL, 58.4 mmol) and 4-bromophenylhydrazine hydrochloride (13.06 g, 58.4 mmol). The resulting mixture was warmed to 140° C. for 2 h, then stirred at room temperature overnight. The slurry was filtered and rinsed with EtOH/water 1:1. The cake was dried at 120° C. for 1 h to afford the title compound as an off-white solid (12.75 g, 67%).

MS (ESI); m/z=323.54/325.54 (MH$^+$)

Step B

To a solution of the title compound from step A (2.5 g, 7.74 mmol) in tetrahydrofuran (75 mL) was added sodium hydride 60% (0.311 g, 8.12 mmol) portionwise at 0° C. After 30 min at room temperature, iodomethane (0.532 mL, 8.51 mmol) was added dropwise and the resulting mixture was stirred at room temperature for 4 h. The reaction mixture was concentrated to dryness. The residue was purified by flash chromatography in ethyl acetate/n-heptane (15 to 35%) to afford the title compound as a white solid (2.52 g, 97%).

MS (ESI); m/z=337.66/339.61 (MH$^+$)

Preparative Example 54

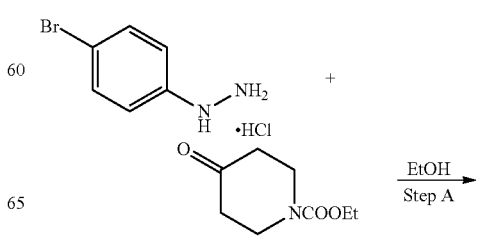

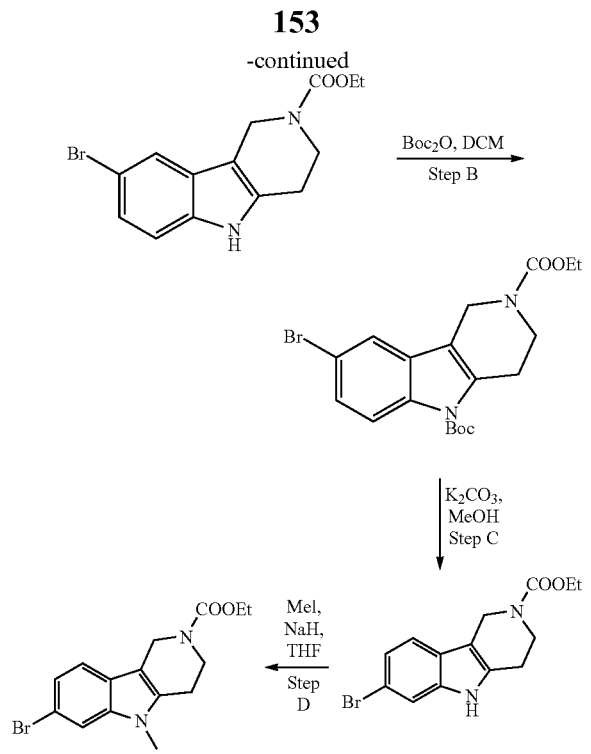

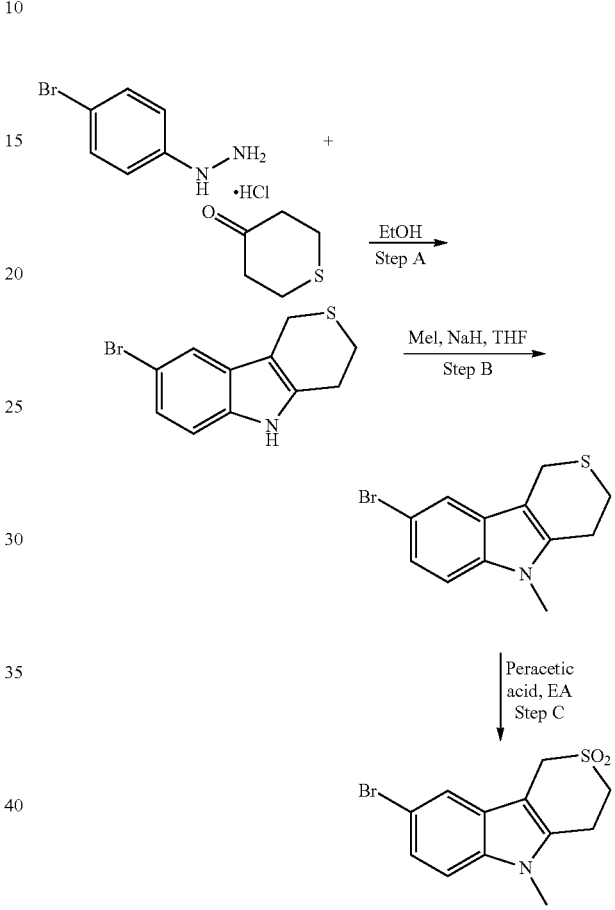

Step A

To stirred ethanol (45 mL) was added ethyl carbethoxy-4-piperidone (4.41 mL, 29.2 mmol) and 3-bromophenylhydrazine hydrochloride (6.53 g, 29.2 mmol). The resulting mixture was warmed to 140° C. for 12 h, then stirred at room temperature overnight. The slurry was filtered and rinsed with EtOH/water 1:1 to afford the title product as a mixture of 2 isomers (2.98 g, 32%).

Step B

To a solution of the title compound from step A (2.979 g, 9.22 mmol) in dichloromethane (150 mL) was added DMAP (0.056 g, 0.461 mmol) and then Boc$_2$O (2.68 mL, 11.52 mmol). The resulting solution was stirred at room temperature for 2 h. The reaction mixture was concentrated to dryness. The residue was purified by flash chromatography (2×) using ethyl acetate/n-heptane (10% to 20%) to afford the title compound as a white solid (1.82 g, 47%).

$^1$H-NMR (400 MHz, CDCl$_3$): δ=1.30 (t, J=8.0 Hz, 3H); 1.66 (s, 9H); 3.08 (sl, 2H); 3.79 (sl, 2H); 4.20 (q, J=8.0 Hz, 2H); 4.59 (s, 2H); 7.23 (d, J=8.0 Hz, 1H); 7.34 (dd, J1=1.6 Hz, J2=8.0 Hz, 1H); 8.36 (sl, 1H)

Step C

To a suspension of the title compound from Step B (1 g, 2.362 mmol) in methanol (25 mL) was added potassium carbonate (0.979 g, 7.09 mmol). The resulting mixture was refluxed for 3 h. The reaction mixture was concentrated to dryness. The residue was extracted with ethyl acetate and brine. The organic layers were collected, dried over Na$_2$SO$_4$, filtered and concentrated to dryness. The crude product was purified by flash chromatography in ethyl acetate/n-heptane mixture to afford the title compound as a white solid (0.746 g, 98%).

MS (ESI); m/z=323.60/325.61 (MH$^+$)

Step D

To a solution of the title compound from Step C (0.746 g, 2.308 mmol) in dry tetrahydrofuran (25 mL) was added at 0° C. sodium hydride 60% (0.101 g, 2.424 mmol) portionwise. After 30 min stirring at room temperature, iodomethane (0.166 mL, 2.65 mmol) was added dropwise. The resulting mixture was stirred at room temperature for 4 h. The resulting mixture was concentrated to dryness and the crude product was purified by flash chromatography in ethyl acetate/n-heptane mixture to afford the expected compound as a white solid (0.657 g, 84%).

MS (ESI); m/z=337.66/339.56 (MH$^+$)

Preparative Example 55

Step A

To a mixture of (4-bromophenyl)hydrazine, HCl (1 g, 4.47 mmol) and dihydro-2H-thiopyran-4(3H)-one (0.520 g, 4.47 mmol) was added absolute ethanol (Volume: 20 ml). The resulting slurry was stirred at room temperature for 2 h. The resulting slurry was concentrated to dryness to lead to the corresponding hydrazone. The solid was partitioned in microwave vials and suspended in ethanol (Volume: 15 ml). The resulting slurry was warmed by microwaves to 125° C. for 25 min. The reaction mixture was dropped into water under vigorous stirring. The resulting beige suspension was filtered and then dried under air overnight. The crude product was crystallized in ethanol. The remaining product in the mother liquor was recovered by flash chromatography in DCM/MeOH 2% to 5%. It afforded the title compound as a white solid (4.16 g, 87%).

$^1$H-NMR (400 MHz, CDCl$_3$): δ=3.02 (s, 4H); 3.82 (s, 2H); 7.16 (d, J=8.4 Hz, 1H); 7.24 (dd, J1=1.6 Hz, J2=8.4 hz, 1H); 7.58 (d, J=2.0 hz, 1H); 7.82 (sl, 1H)

$^{13}$C-NMR (400 MHz, CDCl$_3$): δ=22.53; 25.17; 25.57; 111.89; 120.28; 124.42

Step B

To a solution of the title compound from Step A (0.809 g, 3.02 mmol) in dry tetrahydrofuran (Volume: 50 ml) was added at 0° C. sodium hydride 60% (0.139 g, 3.32 mmol). The resulting mixture was stirred at room temperature for 30 min, then iodomethane (0.283 ml, 4.53 mmol) was added. The resulting solution was stirred at room temperature for 12 h. The mixture was concentrated to dryness and the crude product was purified by flash chromatography in ethyl acetate/n-heptane 10-30% to afford the title compound as a yellow solid (0.811 g, 95%).

Step C

To a solution of the title compound from Step B (0.5 g, 1.772 mmol) in ethyl acetate (Volume: 4 ml) was added peracetic acid (0.706 ml, 3.72 mmol) dropwise at 0° C. The light yellow slurry was stirred at room temperature for 4 h. The reaction mixture was concentrated to dryness. The crude product was purified by flash chromatography in ethyl acetate/n-heptane 40% to 65% to afford the expected compound as a yellowish solid (0.320 g, 57%).

$^1$H-NMR (400 MHz, DMSO-d6): δ=3.31 (t, J=6.4 Hz, 2H); 3.52 (t, J=6.4 Hz, 2H); 3.66 (s, 3H); 4.46 (s, 2H); 7.26 (dd, J1=2.0 Hz, J2=8.8 Hz, 1H); 7.43 (d, J=8.8 hz, 1H); 7.68 (d, J=2.0 Hz, 1H)

Preparative Example 56

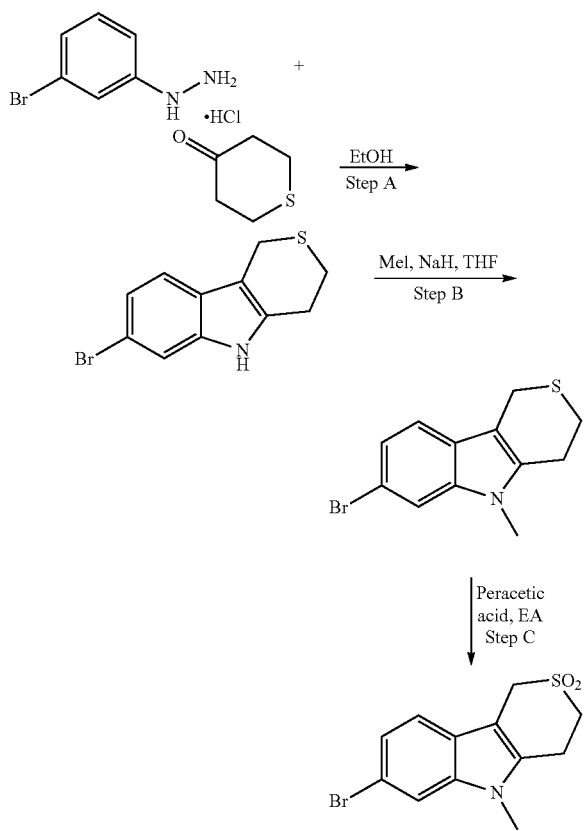

Step A

To a mixture of (3-bromophenyl)hydrazine, HCl (1 g, 4.47 mmol) and dihydro-2H-thiopyran-4(3H)-one (0.520 g, 4.47 mmol) was added absolute ethanol (Volume: 20 ml). The resulting slurry was stirred at room temperature for 2 h. The resulting slurry was concentrated to dryness to lead to the corresponding hydrazone. The solid was partitioned in microwave vials and suspended in ethanol (Volume: 15 ml). The resulting slurry was warmed by microwaves to 125° C. for 25 min. The mixture was dropped into water under vigorous stirring. An extraction in DCM was performed with HCl 1M and water. The organic layers were collected, dried over Na$_2$SO$_4$, filtered and concentrated to dryness. The crude product was purified by flash chromatography in DCM/MeOH 95:5 to afford the title compound as a beige solid (0.328 g, 27%).

$^1$H-NMR (400 MHz, CDCl$_3$): δ=3.02 (s, 4H); 3.84 (s, 2H); 7.13-7.38 (m, 2H); 7.43 (s, 1H); 7.78 (sl, 1H)

Step B

To a solution of the title compound from Step A (0.298 g, 1.111 mmol) in dry tetrahydrofuran (Volume: 20 ml) was added at 0° C. sodium hydride 60% (0.0488 g, 1.167 mmol). The resulting mixture was stirred at room temperature for 30 min then iodomethane (0.076 ml, 1.222 mmol) was added. The resulting solution was stirred at room temperature for 12 h. The mixture was concentrated to dryness and the crude product was purified by flash chromatography in ethyl acetate/n-heptane 10-30% to afford the title compound as a white solid (0.310 g, 99%).

Step C

To a solution of the title compound from Step B (0.3 g, 1.063 mmol) in ethyl acetate (Ratio: 1.000, Volume: 20 ml) was added a solution of peracetic acid (0.403 ml, 2.126 mmol) in ethyl acetate (Ratio: 1.000, Volume: 20.00 ml) dropwise at room temperature. The resulting mixture was stirred at room temperature for 12 h. The reaction mixture was extracted with water and a saturated solution of Na$_2$CO$_3$. The organic layers were collected, dried over Na$_2$SO$_4$, filtered and concentrated to dryness. The residue was purified by flash chromatography in ethyl acetate/n-heptane 40% to 65% to afford the expected compound as a white solid (0.160 g, 48%).

$^1$H-NMR (400 MHz, CDCl$_3$): δ=3.35 (sl, 4H); 3.62 (s, 3H); 4.33 (sl, 2H); 7.21 (sl, 2H); 7.42 (s, 1H)

Preparative Example 57

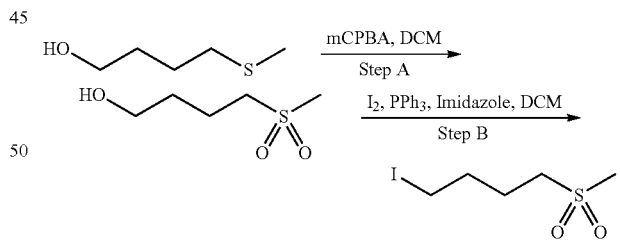

Step A

To an ice-cooled solution of 4-(methylthio)butan-1-ol (2.5 g, 20.80 mmol) in dry dichloromethane (Volume: 250 ml) was added meta-chloroperoxybenzoic acid (mCPBA; 9.32 g, 41.6 mmol) portionwise. The resulting mixture was stirred at room temperature for 20 h. The solution was concentrated to dryness. The residue was dissolved in a mixture of diethyl ether and water. The benzoic acid was extracted in diethyl ether. The water layer was concentrated to dryness. The residue was diluted with DCM and the concentrated solution was loaded on a samplet. The crude product was purified by flash chromatography in DCM/MeOH 3 to 10% to afford the title compound as a colorless oil (2.95 g, 93%).

¹H-NMR (400 MHz, CDCl₃): δ=1.59-1.75 (m, 2H); 1.85-2.01 (m, 2H); 2.67 (sl, 1H); 2.90 (s, 3H); 3.06 (dd, J1=J2=8.0 Hz, 2H); 3.64 (q, J=5.6 Hz, 2H)

¹³C-NMR Dept135 (400 MHz, CDCl₃): δ=22.17; 33.89; 43.46; 57.39; 64.50

Step B

To a mixture of the title compound from step A (2.95 g, 19.38 mmol), triphenylphosphine (7.62 g, 29.1 mmol) and imidazole (1.979 g, 29.1 mmol) in dichloromethane (Volume: 250 ml) was added a solution of iodine (7.38 g, 29.1 mmol) dropwise. The resulting solution was stirred at room temperature for 24 h. The reaction mixture was concentrated to half, then water was added. The slurry was filtered and the extraction was performed with a solution of Na₂SO₃. The organic layers were collected, dried over Na₂SO₄, filtered and concentrated to dryness. The residue was purified by flash chromatography in ethyl acetate/n-heptane 40% to 60% to afford the expected compound as a white solid (1.2 g, 24%).

¹H-NMR (400 MHz, CDCl₃): δ=1.93-2.10 (m, 4H); 2.94 (s, 3H); 3.05 (t, J=7.6 Hz, 2H); 3.23 (t, J=6.2 Hz, 2H)

¹³C-NMR Dept135 (400 MHz, CDCl₃): δ=4.84; 23.47; 31.56; 40.66 (CH3); 53.45

Preparative Example 58

Following the procedure described in Preparative Example 54, except using the propyl-derivatives indicated in the scheme below, the following compound was prepared.

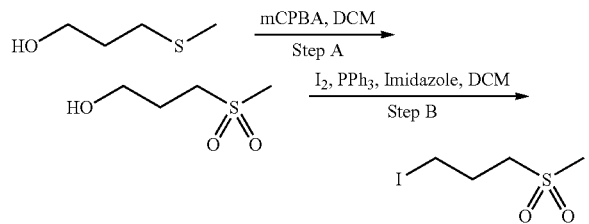

Yield: 72%

¹H-NMR (400 MHz, CDCl₃): δ=2.26-2.40 (m, 2H); 2.91 (s, 3H); 3.12 (t, J=7.6 Hz, 2H); 3.28 (t, J=6.8 Hz, 2H)

¹³C-NMR (400 MHz, CDCl₃): δ=3.11; 26.00; 41.11 (CH3); 55.21

Preparative Example 59

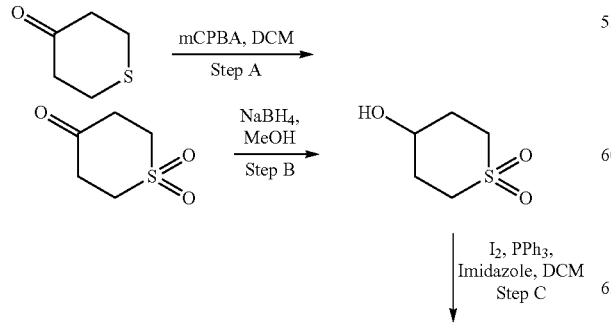

-continued

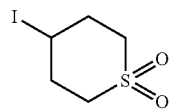

Step A

To a mixture of dihydro-2H-thiopyran-4(3H)-one (5 g, 43.0 mmol) in acetone (Volume: 100 ml) was added OXONE (52.9 g, 86 mmol). The resulting mixture was stirred vigorously at room temperature for 12 h. The slurry was filtered and the solid was rinsed with acetone. The organic layer was concentrated to dryness to afford the title compound as a white solid (5.83 g, 91%).

Step B

To a mixture of the title compound from step A (2 g, 13.50 mmol) in methanol (Volume: 50 ml) was added at 0° C. sodium borohydride (0.511 g, 13.50 mmol). The resulting mixture was stirred at room temperature for 1 h. The solution was concentrated to dryness. The residue was purified by flash chromatography in DCM/MeOH 0% to 5% to afford the title compound as a white solid (1.74 g, 86%).

¹³C-NMR Dept135 (400 MHz, CDCl₃): δ=31.18; 46.74; 62.57

Step C

To a mixture of the title compound from step B (1.0 g, 6.66 mmol), triphenylphosphine (2.62 g, 9.99 mmol) and imidazole (0.680 g, 9.99 mmol) in dichloromethane (Volume: 50 ml) was added a solution of iodine (2.53 g, 9.99 mmol) dropwise. The resulting solution was stirred at room temperature for 24 h. The reaction mixture was filtered, then concentrated to dryness. The residue was purified by flash chromatography in ethyl acetate/n-heptane 40% to 75% to afford the expected compound as a white solid (0.684 g, 39%).

¹H-NMR (400 MHz, CDCl₃): δ=2.40-2.53 (m, 4H); 2.93-3.06 (m, 2H); 3.25-3.42 (m, 2H); 4.56-4.70 (m, 1H)

¹³C-NMR Dept135 (400 MHz, CDCl₃): δ=24.74; 35.35; 50.40

Preparative Example 60

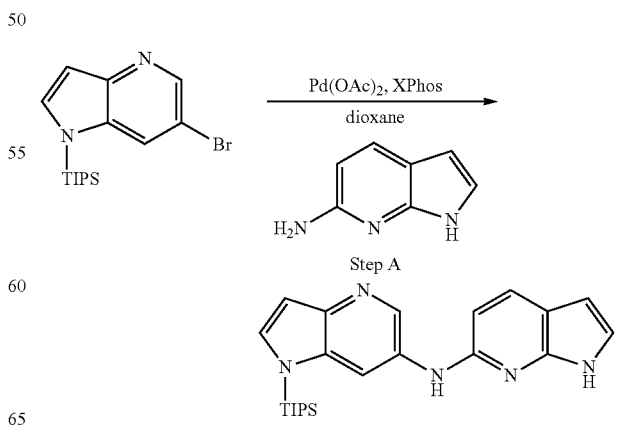

Step A

Step A

An oven-dried Schlenk flask was evacuated and back filled with argon gas. The procedure was repeated for 3-4 times. At room temperature dioxane (3 mL) was added by a syringe and degassed by bubbling argon through the mixture. Then 2-dicyclohexylphosphino-2',4',6'-triisopropylbiphenyl (XPhos, 0.054 g, 0.112 mmol) and palladium(II) acetate (0.009 g, 0.037 mmol) were added together. The mixture was heated at 110° C. for 1 minute. The reaction mixture became a clear red color solution. Then the title compound from Preparative Example 3 (0.050 g, 0.375 mmol), commercially available 6-bromo-1-(triisopropylsilyl)-1H-pyrrolo[3,2-b]pyridine (0.132 g, 0.375 mmol) and sodium tert butoxide (0.12 g, 1.25 mmol) were added together under an argon atmosphere. The reaction mixture was heated at 110° C. for 2 h. The reaction mixture was diluted with ethyl acetate (150 mL). The organic phase was washed with water, brine, and was dried over $Na_2SO_4$. The solvent was removed and the residue was purified by chromatography on silica using ethyl acetate to afford the title compound (0.045 g, 30%).

$^1$H-NMR (400 MHz, $CDCl_3$): δ=1.13 (d, 18H), 1.61-1.68 (m, 3H), 6.35 (dd, 1H), 6.60 (d, 1H), 6.80 (d, 1H), 6.94 (dd, 1H), 7.10 (brs, 1H), 7.39 (d, 1H), 7.73 (d, 1H), 8.20 (s, 1H), 8.54 (s, 1H), 9.27 (s, 2H)

Preparative Examples 61 to 140

Following the Pd-coupling procedure described in Preparative Example 57, except using the bromo-derivatives and amines indicated in the table below, the following compounds were prepared.

TABLE 1

| Bromo-derivative | Amine | Product Preparative Example | 1. Yield<br>2. ¹H-NMR (CDCl₃)<br>3. MS (ESI) m/z |
|---|---|---|---|
| 2-bromopyridine | 7-azaindol-6-amine | 61 | 1. 39%<br>2. δ 10.6 (s, 1H), 9.31 (s, 1H), 8.3 (d, 1H), 7.86 (d, 1H), 7.75 (d, 1H), 7.64 (t, 1H), 7.20 (m, 1H), 7.08 (d, 1H), 6.87 (dd, 1H), 6.45 (dd, 1H) |
| 1-bromo-4-fluorobenzene | 7-azaindol-6-amine | 62 | 1. 47%<br>2. δ = 8.63 (brs, 1H), 7.42 (dd, 2H), 7.06 (m, 2H), 6.58 (d, 1H), 6.41 (brs, 2H). |
| 5-bromo-1-TIPS-7-azaindole | 7-azaindol-5-amine | 63 | 1. 6%<br>2. δ = 8.37 (d, 1H), 8.04 (d, 1H), 7.75 (d, 1H), 7.32 (d, 1H), 7.01 (s, 1H), 6.96 (brs, 1H), 6.59 (d, 1H), 6.52 (d, 1H), 6.41 (brs, 1H), 6.37 (dd, 1H), 1.90 (m 3H), 1.16 (d, 18H). |
| 6-bromo-1-TIPS-7-azaindole | indol-6-amine | 64 | 1. 14%<br>2. δ = 8.89 (s, 1H), 7.76 (s, 1H), 7.73 (d, 1H), 7.60 (d, 1H), 7.24 (d, 1H), 7.04 (dd, 1H), 6.95 (d, 1H), 6.68 (d, 1H), 6.62 (d, 1H), 6.38 (d, 1H), 1.71 (m, 3H), 1.19 (d, 18H). |

TABLE 1-continued
| Bromo-derivative | Amine | Product Preparative Example | 1. Yield 2. ¹H-NMR (CDCl₃) 3. MS (ESI) m/z |
|---|---|---|---|
| 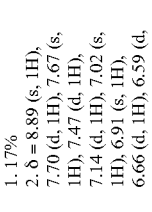 | 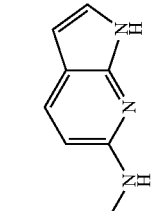 | 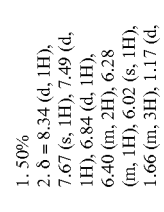 65 | 1. 17% 2. δ = 8.89 (s, 1H), 7.70 (d, 1H), 7.67 (s, 1H), 7.47 (d, 1H), 7.14 (d, 1H), 7.02 (s, 1H), 6.91 (s, 1H), 6.66 (d, 1H), 6.59 (d, 1H), 6.48 (s, 1H), 6.35 (d, 1H), 1.68-1.76 (m, 3H), 1.17 (d, 18H). 3. 405 |
| 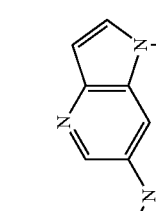 | 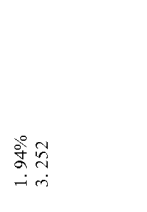 | 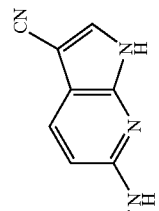 66 | 1. 50% 2. δ = 8.34 (d, 1H), 7.67 (s, 1H), 7.49 (d, 1H), 6.84 (d, 1H), 6.40 (m, 2H), 6.28 (m, 1H), 6.02 (s, 1H), 1.66 (m, 3H), 1.17 (d, 18H). |
| 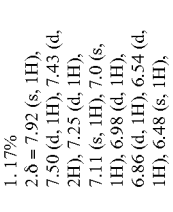 | 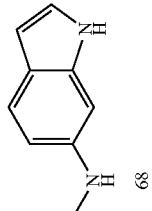 | 67 | 1. 94% 3. 252 |
| | | 68 | 1. 17% 2. δ = 7.92 (s, 1H), 7.50 (d, 1H), 7.43 (d, 2H), 7.25 (d, 1H), 7.11 (s, 1H), 7.0 (s, 1H), 6.98 (d, 1H), 6.86 (d, 1H), 6.54 (d, 1H), 6.48 (s, 1H), 1.70 (m, 3H), 1.14 (d, 18H). 3. 404 |

TABLE 1-continued
| Bromo-derivative | Amine | Product Preparative Example | 1. Yield 2. ¹H-NMR (CDCl₃) 3. MS (ESI) m/z |
|---|---|---|---|
| 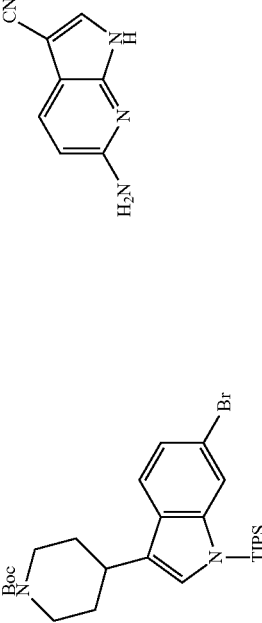 | 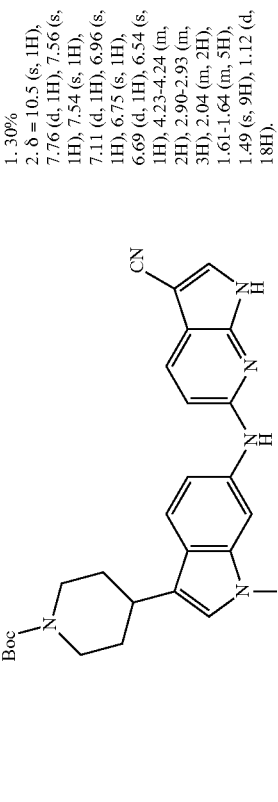 | 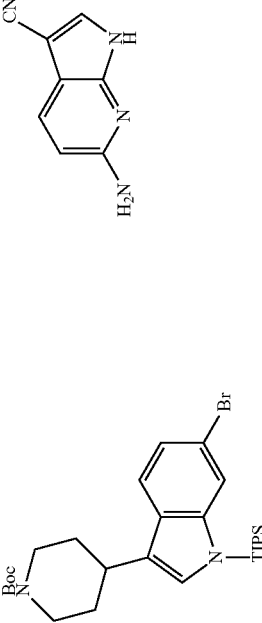 69 | 1. 30% 2. δ = 10.5 (s, 1H), 7.76 (d, 1H), 7.56 (s, 1H), 7.54 (s, 1H), 7.11 (d, 1H), 6.96 (s, 1H), 6.75 (s, 1H), 6.69 (d, 1H), 6.54 (s, 1H), 4.23-4.24 (m, 2H), 2.90-2.93 (m, 3H), 2.04 (m, 2H), 1.61-1.64 (m, 5H), 1.49 (s, 9H), 1.12 (d, 18H). |
| | | 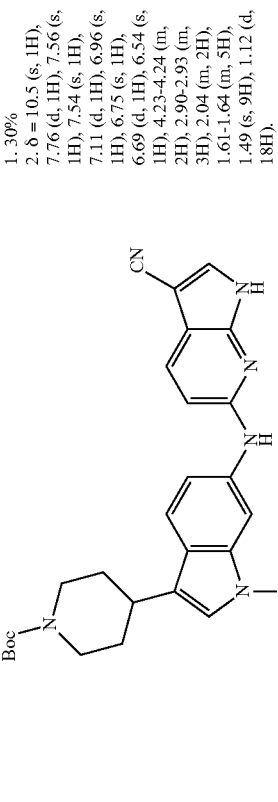 70 | 1. 17.6% 2. δ = 8.62 (brs, 1H), 7.84 (d, 1H), 7.76 (d, 1H), 7.72 (d, 1H), 7.50 (s, 1H), 7.43 (s, 1H), 7.09 (s, 1H), 6.64 (d, 1H), 6.44 (d, 1H), 4.13-4.15 (m, 2H), 3.1-3.2 (m, 2H), 2.8-2.9 (m, 2H), 2.0-2.1 (m, 2H), 1.55-1.60 (m, 2H), 1.41 (s, 9H), 1.08 (d, 18H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (Boc-piperidine-pyrrolopyridine with Br, TIPS) | (tetrahydro-β-carboline, H₂N-) | 71 | 1. 13%<br>2. δ = 8.37 (s, 1H), 8.10 (s, 1H), 7.93 (s, 1H), 7.54 (d, 1H) 7.09 (s, 1H) 6.51 (d, 1H), 6.44 (s, 1H), 4.20-4.22 (m, 2H), 3.16-3.22 (m, 1H), 2.90-2.96 (m, 2H), 2.61-2.68 (m, 4H), 2.13 (m, 2H), 1.83-1.88 (4H), 1.60-1.66 (m, 5H) 1.47 (s, 9H), 1.12 (d, 18H). |
| (Boc-piperidine-indole with Br, TIPS) | (indole-NH₂, Boc-piperidine, TIPS) | 72 | 1. 75%<br>2. δ = 7.47 (d, 1H), 7.40 (d, 1H), 7.30 (d, 1H), 7.04 (d, 1H), 7.00 (d, 1H), 6.98 (d, 1H), 6.96 (s, 1H), 6.88 (d, 1H), 6.86 (d, 1H), 6.81 (s, 1H) 4.23 (m, 4H), 2.88-2.91 (m, 6H), 2.02-2.07 (m, 4H), 1.64-1.68 (m, 8H), 1.54 (s, 9H), 1.52 (s, 9H), 1.17 (d, 18H), 1.06 (d, 18H).<br>3. 927 |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (structure) | (structure) | 73 | 1. 30%<br>2. δ = 8.56 (brs, 1H), 8.28 (s, 1H), 8.0 (s, 1H), 7.61 (d, 1H), 7.04 (s, 1H), 6.78 (s, 1H), 6.47 (d, 1H), 4.23-4.25 (m, 2H), 2.87-2.92 (m, 2H), 2.69-2.71 (m, 2H), 2.63 (bs, 2H) 1.84-1.99 (m, 12H), 1.52 (s, 9H), 1.13 (d, 18H)<br>3. 643 |
| (structure) | (structure) | 74 | 1. 18%<br>2. δ = 9.4 (brs, 1H), 8.52 (brs, 1H), 8.27 (d, 1H), 7.60 (d, 1H), 7.50 (s, 1H), 7.01-7.04 (m, 2H), 6.70 (d, 1H), 4.20-4.25 (m, 2H), 2.89-3.0 (m, 5H), 2.63-2.64 (m, 2H), 2.18-2.24 (m, 2H), 2.04-2.07 (m, 2H), 1.65-1.70 (m 6H), 1.51 (s, 9H), 1.15 (d, 18H). |
| (structure) | (structure) | 75 | 1. 21%<br>2. δ = 8.33 (s, 1H), 7.65 (d, 1H), 7.53 (d, 1H), 7.42 (d, 1H), 7.98 (dd, 1H), 6.98 (s, 1H), 6.58 (d, 1H), 6.35 (s, 1H), 4.20-4.25 (m, 2H), 2.84-2.92 (m, 4H), 2.77 (t, 2H), 2.45-2.49 (m, 2H), 2.01-2.05 (m, 2H), 1.63-1.72 (m, 6H), 1.49 (s, 9H), 1.15 (d, 18H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 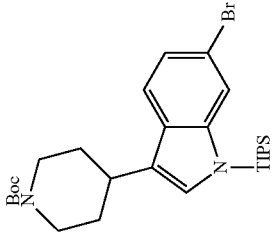 | 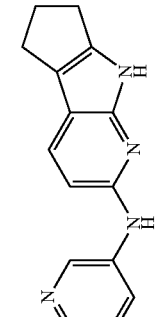 | 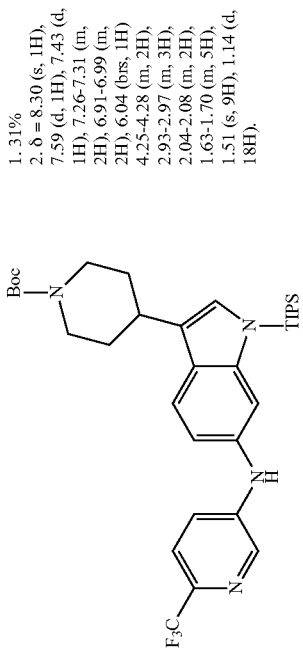<br>76 | 1. 31%<br>2. δ = 8.30 (s, 1H), 7.59 (d, 1H), 7.43 (d, 1H), 7.26-7.31 (m, 2H), 6.91-6.99 (m, 2H), 6.04 (brs, 1H), 4.25-4.28 (m, 2H), 2.93-2.97 (m, 3H), 2.04-2.08 (m, 2H), 1.63-1.70 (m, 5H), 1.51 (s, 9H), 1.14 (d, 18H). |
| 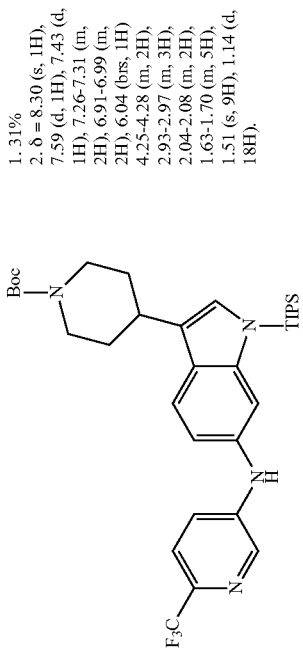 | 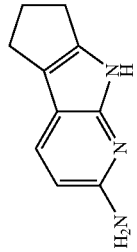 | 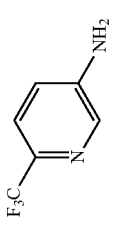<br>77 | 1.<br>2. δ = 8.4 (brs, 1H), 8.22 (d, 1H), 8.06 (d, 1H), 7.56 (d, 1H), 7.03 (s, 1H), 6.50 (d, 1H), 4.21-4.27 (m, 2H), 2.85-2.92 (m, 6H), 2.77-2.81 (m, 2H), 2.42-2.50 (m, 2H), 1.99-2.02 (m, 2H), 1.68-1.73 (m, 3H), 1.49 (s, 9H), 1.13 (d, 18H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 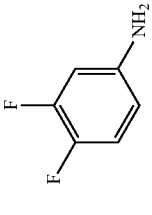 | 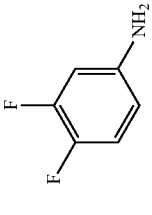 | 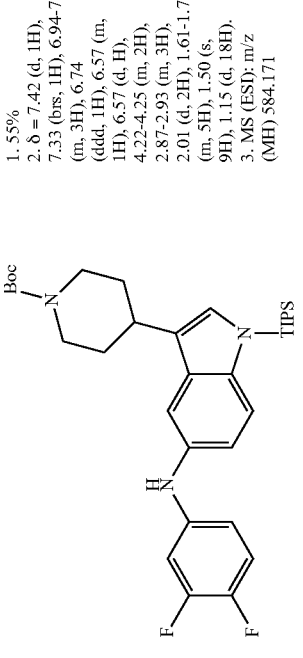<br>78 | 1. 75%<br>2. δ = 7.54 (d, 1H), 7.25 (s, 1H), 7.00-7.04 (m, 1H), 6.93 (s, 1H), 6.82-6.87 (m, 1H), 6.61-6.66 (m, 1H), 5.64 (brs, 1H), 42.4-4.25 (m, 2H), 2.92-2.95 (m, 3H), 2.04-2.07 (m 2H), 1.61-1.67 (m, 5H), 1.51 (s, 9H), 1.14 (d, 18H).|
| | 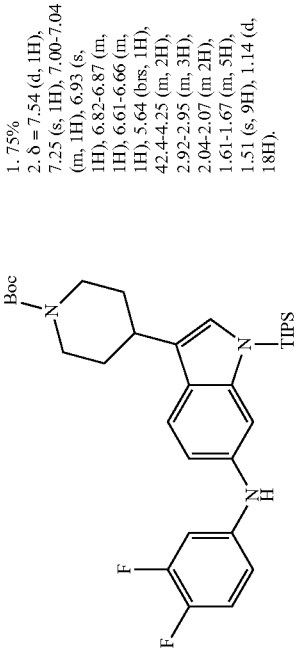 | 79 | 1. 55%<br>2. δ = 7.42 (d, 1H), 7.33 (brs, 1H), 6.94-7.03 (m, 3H), 6.74 (ddd, 1H), 6.57 (m, 1H), 6.57 (d, H), 4.22-4.25 (m, 2H), 2.87-2.93 (m, 3H), 2.01 (d, 2H), 1.61-1.72 (m, 5H), 1.50 (s, 9H), 1.15 (d, 18H).<br>3. MS (ESI): m/z (MH) 584.171 |

TABLE 1-continued
| Bromo-derivative | Amine | Product Preparative Example | 1. Yield 2. ¹H-NMR (CDCl₃) 3. MS (ESI) m/z |
|---|---|---|---|
| 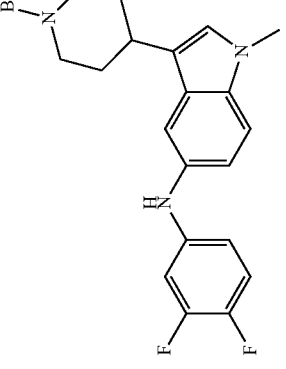 | 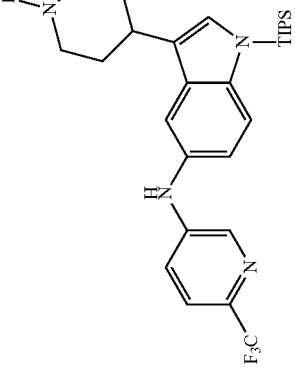 | 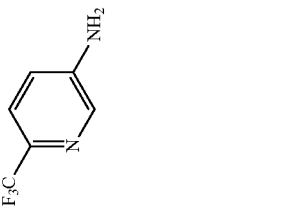 80 | 1. 22%. 2. δ = 8.30 (s, 1H), 7.43-7.49 (m, 3H), 7.22 (d, 1H), 7.03 (s, 1H), 6.98 (d, 1H), 6.03 (s, 1H), 4.24-4.25 (m, 2H), 2.87-2.94 (m, 3H), 2.01-2.04 (m, 2H), 1.66-1.73 (m, 5H), 1.50 (s, 9H), 1.17 (d, 18H). 3. 617.16 |
| 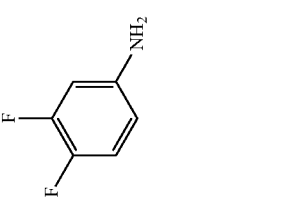 | | 81 | 1. 71% 2. δ = 7.37 (s, 1H), 7.26 (d, 1H), 7.04 (d, 1H), 6.97 (abq, 1H), 6.84 (s, 1H), 6.68 (ddd, 1H), 6.53 (d, 1H), 5.61 (brs, 1H), 4.24 (brs, 2H), 3.77 (s, 3H), 2.86-2.95 (m, 3H), 2.0-2.03 (m, 2H), 1.86-1.89 (m, 2H), 1.50 (s, 9H). 3. 442 |

TABLE 1-continued
| Bromo-derivative | Amine | Product Preparative Example | 1. Yield 2. ¹H-NMR (CDCl₃) 3. MS (ESI) m/z |
|---|---|---|---|
| 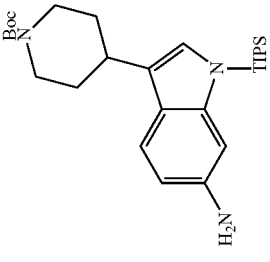 | 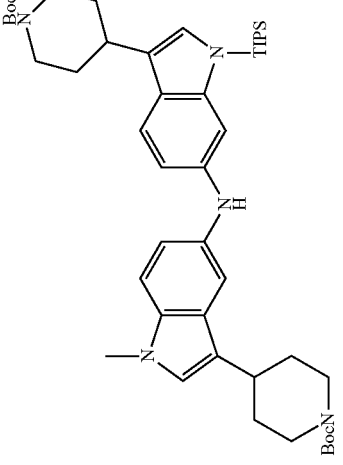 | 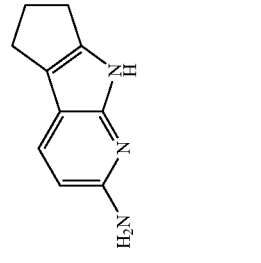 82 | 1. 78% 3. 785.41 |
| 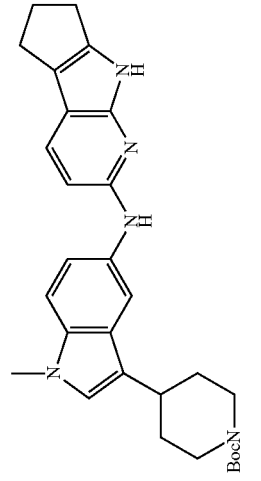 | 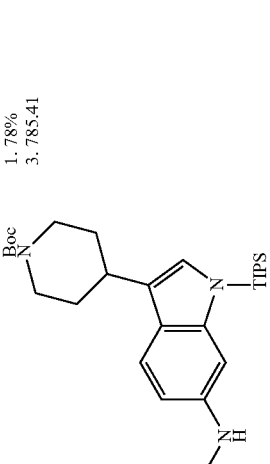 | 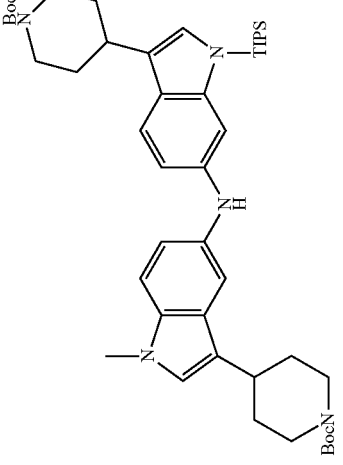 83 | 1. 17% 2. δ = 8.48 (s, 1H), 7.67 (s, 1H), 7.52 (d, 1H), 7.25 (d, 1H), 7.17 (d, 1H), 6.81 (s, 1H), 6.52 (d, 1H), 6.33 (s, 1H), 4.17-4.22 (brs, 2H), 3.76 (s, 3H), 2.76-2.91 (m, 5H), 2.44-2.47 (m, 2H), 1.99-2.07 (m, 2H), 1.65-1.71 (m, 2H), 1.49 (s, 9H), 3. 486 |

TABLE 1-continued

| Bromo-derivative | Amine | Product Preparative Example | 1. Yield 2. ¹H-NMR (CDCl₃) 3. MS (ESI) m/z |
|---|---|---|---|
| 5-bromo-3-(1-methylpiperidin-4-yl)-1-TIPS-indole | 3,4-difluoroaniline | 84: N-(3,4-difluorophenyl)-3-(1-methylpiperidin-4-yl)-1-TIPS-1H-indol-5-amine | 1. 51% 2. δ = 7.41 (d, 1H), 7.35 (s, 1H), 6.93-7.02 (m, 3H), 6.74 (ddd, 1H), 6.56-6.58 (m, 1H), 5.57 (s, 1H), 2.99 (d, 2H), 2.71-2.78 (m, 1H), 2.37 (s, 3H), 2.15 (t, 1H), 2.04 (d, 2H), 1.85-1.88 (m, 2H), 1.64-1.71 (m, 3H), 1.14 (d, 18H). 3. 499 |
| 6-bromo-3-(1-methylpiperidin-4-yl)-1-TIPS-indole | 3,4-difluoroaniline | 85: N-(3,4-difluorophenyl)-3-(1-methylpiperidin-4-yl)-1-TIPS-1H-indol-6-amine | 1. 47% 2. δ = 7.54 (d, 1H), 7.25 (s, 1H), 6.96-7.03 (m, 2H), 6.77-6.86 (m, 2H), 6.60-6.61 (m, 1H), 5.63 (s, 1H), 3.00 (d, 2H), 2.76-2.82 (m, 1H), 2.38 (s, 3H), 2.17 (t, 2H), 2.07-2.10 (m, 2H), 1.87-1.93 (m, 2H), 1.58-1.66 (m, 3H), 1.13 (d, 18H). |

TABLE 1-continued

| Bromo-derivative | Amine | Product Preparative Example | 1. Yield 2. ¹H-NMR (CDCl₃) 3. MS (ESI) m/z |
|---|---|---|---|
| | | 86 | 1. 79% 3. 841, 842 |
| | | 87 | 1. 48% 3. 841, 842 |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 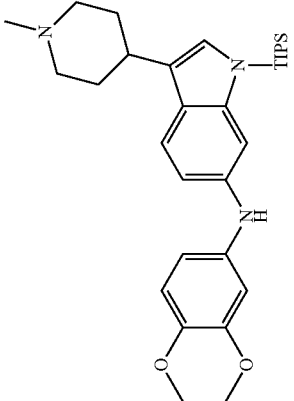 | 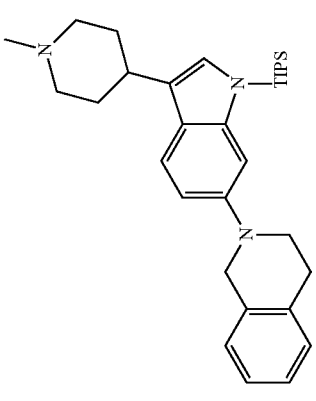 | 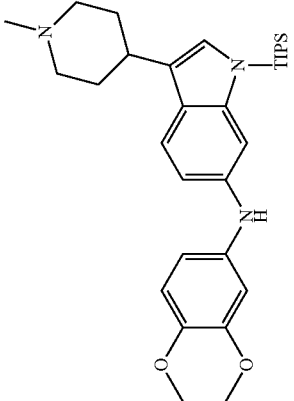\n88 | 1. 63%<br>2. δ = 7.49 (d, 1H), 7.14 (s, 1H), 6.90 (s, 1H), 6.84 (d, 1H), 6.78 (d, 1H), 6.66 (s, 1H), 6.59 (d, 1H), 5.50 (s, 1H), 3.87 (s, 3H), 3.83 (s, 3H), 3.02 (d, 2H), 2.78 (m, 1H), 2.40 (s, 3H), 2.17-2.22 (m, 2H), 2.07-2.10 (m, 2H), 1.88-1.91 (m, 2H), 1.56-1.63 (m, 3H), 1.11 (d, 18H).<br>3. 523 |
| 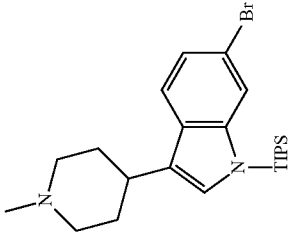 | 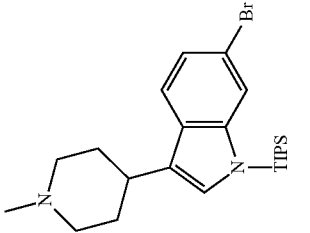 | 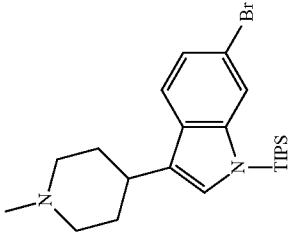\n89 | 1. 45%<br>3. 501 |

TABLE 1-continued

| Bromo-derivative | Amine | Product Preparative Example | 1. Yield 2. ¹H-NMR (CDCl₃) 3. MS (ESI) m/z |
|---|---|---|---|
| 1,2,3,4-tetrahydroisoquinoline (NH) | 6-bromo-3-(1-Boc-piperidin-4-yl)-1-TIPS-indole | 90 | 1. 45% 3. 587 |
| 5-amino-3-(1-Boc-piperidin-4-yl)-1-TIPS-indole | 2-bromo-6-(N-Boc-N-methylamino)-9-methyl-tetrahydro-β-carboline | 91 | 1. 55% 2. (DMSO-d₆): δ = 8.73 (s, 1H), 8.63 (s, 1H), 7.56 (d, 1H), 7.35 (d, 1H), 7.09 (d, 1H), 7.04 (s, 1H), 6.52 (d, 1H), 4.10-4.13 (m, 3H), 3.65 (s, 3H), 2.67-2.91 (m, 10H), 1.93-2.01 (m, 4H), 1.63-1.75 (m, 5H), 1.42 (s, 18H), 1.08 (d, 18H). 3. 785 |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (Boc-piperidine-indole-TIPS with Br) | (1-aminoindane) | 92 | 1. 29%<br>2. (CDCl₃) δ 7.45-7.40 (m, 2H), 7.32-7.21 (m, 3H), 6.80-6.78 (m, 2H), 6.59 (d, 1H), 5.02 (t, 1H), 4.27-4.22 (m, 2H), 3.87 (s, 1H), 3.10-3.03 (m, 1H), 2.98-2.89 (m, 5H), 2.59-2.51 (m, 1H), 2.07-2.04 (m, 6H), 1.69-1.58 (m, 3H), 1.51 (s, 9H), 1.15 (d, 18H). |
| (Boc-N-methyl tetrahydro-pyrido-indole with Br) | (3,4-dimethoxyaniline) | 93 | 1. 51%<br>2. (CDCl₃) δ 7.56 (d, 1H), 7.32 (s, 1H), 6.88-6.84 (m, 2H), 6.51 (d, 1H), 4.58-4.46 (s, 1H), 3.92 (s, 3H), 3.90 (s, 3H), 3.67 (s, 3H), 2.87-2.72 (s, 3H), 2.06-2.04 (m, 2H), 1.66-1.58 (s, 1H), 1.50 (s, 9H). |
| (Boc-N-methyl tetrahydro-pyrido-indole with Br) | (3-fluoro-4-methoxyaniline) | 94 | 1. 22%<br>2. (CDCl₃) δ 7.57-7.53 (m, 2H), 7.06 (d, 1H), 6.95-6.91 (m, 1H), 6.50 (d, 1H), 6.39 (s, 1H), 4.44-4.42 (m, 1H), 3.90 (s, 3H), 3.66 (s, 3H), 2.87 (s, 6H), 2.2.82-2.78 (m, 1H), 2.05 (s, 2H), 1.51 (s, 9H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 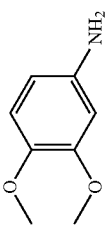 | 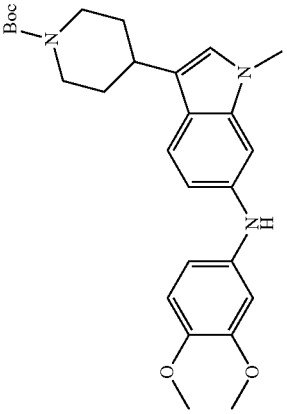 | 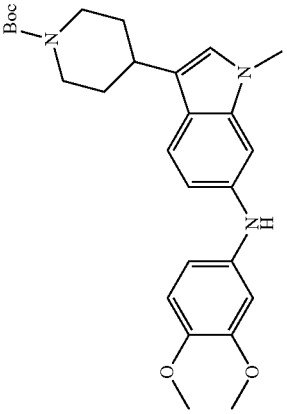<br>95 | 1. 65%<br>2. (DMSO-d₆) δ 7.49 (d, 1H), 7.04 (d, 1H), 6.95 (s, 1H), 6.92 (d, 1H), 6.83 (dd, 1H), 6.79 (d, 1H), 6.70 (dd, 1H), 4.11 (d, 2H), 3.78 (s, 3H), 3.76 (s, 3H), 3.66 (s, 3H), 2.99-2.94 (m, 3H), 1.99 (d, 2H), 1.49 (s, 11H).<br>3. 466.7 (M + H). |
| 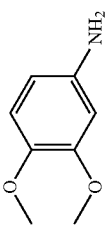 | 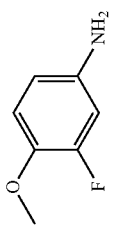 | 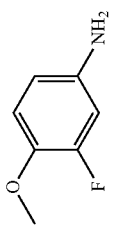<br>96 | 1. 75%<br>2. (CDCl₃); δ = 7.51 (d, 1H), 6.98-6.75 (m, 6H), 4.25 (m, 2H), 3.87 (s, 3H), 3.67 (s, 3H), 2.97-2.87 (m, 2H), 2.04-2.01 (m, 2H), 1.74-1.62 (m, 3H), 1.51 (s, 9H).<br>3. 454.61 (M + H). |
| 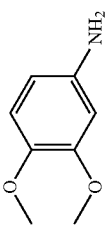 | 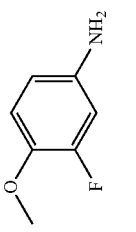 | 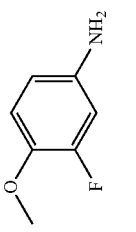<br>97 | 1. 46%<br>2. (CDCl₃) δ 7.62 (d, 1H), 7.31 (s, 1H), 7.03 (s, 1H), 6.99-6.89 (m, 1H), 6.80-6.78 (m, 1H), 5.64 (s, 1H), 5.64 (s), 3.97 (s, 3H), 3.16-3.13 (m, 2H), 2.93-2.90 (m, 1H), 2.33-2.31 (m, 2H), 2.21-2.18 (m, 2H), 2.03-2.0 (m, 2H), 1.73-1.69 (m, 3H), 1.23 (d, 18H).<br>3. 510.68 (M + H). |

TABLE 1-continued

| Bromo-derivative | Amine | Product Preparative Example | 1. Yield  2. ¹H-NMR (CDCl₃)  3. MS (ESI) m/z |
|---|---|---|---|
| (5-bromo-3-(1-methylpiperidin-4-yl)-1-TIPS-indole) | 3,4-dimethoxyaniline | 98 | 1. 56%  2. (CDCl₃) δ 7.60 (s, 1H), 7.37 (d, 1H), 7.01 (s, 1H), 6.85-6.80 (m, 2H), 6.72 (s, 1H), 6.52-6.50 (m, 1H), 3.71 (s, 3H), 3.68 (s, 3H), 3.15-3.08 (m, 2H), 2.79-2.68 (m, 2H), 2.01-1.97 (m, 2H), 1.84-1.78 (m, 2H), 1.76-1.65 (m, 2H), 1.09 (d, 18H). |
| (5-bromo-3-(1-methylpiperidin-4-yl)-1-TIPS-indole) | 3-fluoro-4-methoxyaniline | 99 | 1. 45%  2. (CDCl₃); δ = 7.40 (d, 1H), 7.30 (s, 1H), 7.00 (s, 1H), 6.94-6.83 (m, 2H), 6.78 (d, 1H), 6.66 (d, 1H), 3.86 (s, 3H), 3.12 (d, 2H), 2.78 (t, 1H), 2.44 (s, 3H), 2.29 (t, 2H), 2.10-1.91 (m, 4H), 1.71-1.63 (m, 3H), 1.14 (d, 18H).  3. 510.7 (M + H) |

TABLE 1-continued
| Bromo-derivative | Amine | Product Preparative Example | 1. Yield 2. ¹H-NMR (CDCl₃) 3. MS (ESI) m/z |
|---|---|---|---|
| | | 100 | 1. 39% 2. (CDCl₃): δ = 7.70 (d, 1H), 7.47 (d, 1H), 6.94-6.78 (m, 2H), 6.78 (s, 1H), 6.50 (d, 1H), 6.15 (s, 1H), 4.24-4.23 (m 1H), 3.91 (s, 3H), 2.90-2.80 (m, 3H), 2.02-1.99 (m, 2H), 1.86-1.78 (m, 3H), 1.69-1.66 (m, 2H), 1.51 (s, 9H), 1.11 (d, 18H). 3. 597.67 (M + H). |
| | | 101 | 1. 39% 2. (CDCl₃): δ = 7.76-7.73 (m, 1H) 7.55 (brs, 1H), 7.07 (brs, 1H), 6.97-6.95 (m, 1H), 6.69 (s, 1H), 6.52-6.50 (m, 1H), 4.23-4.20 (m, 2H), 3.91 (s, 3H), 3.79 (s, 3H), 2.89-2.87 (m, 4H), 2.00-1.97 (m, 2H), 1.66-1.63 (m, 2H), 1.50 (s, 9H) |
| | | 102 | 1. 50% 3. 380.7 (M + H). |
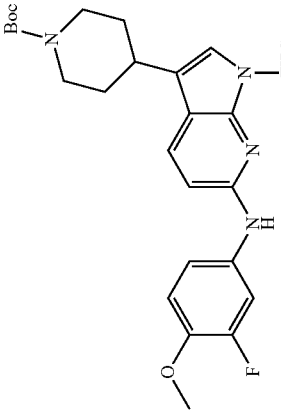

TABLE 1-continued
| Bromo-derivative | Amine | Product Preparative Example | 1. Yield 2. ¹H-NMR (CDCl₃) 3. MS (ESI) m/z |
|---|---|---|---|
| 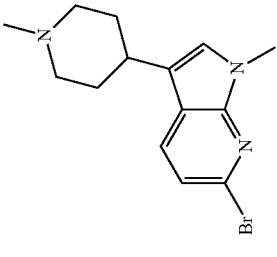 | 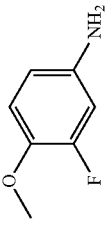 | 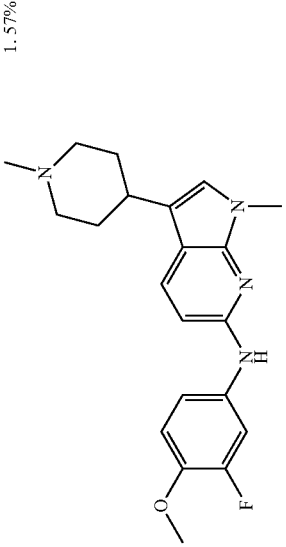 103 | 1. 57% |
| 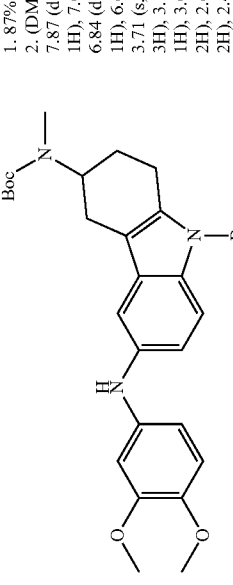 | 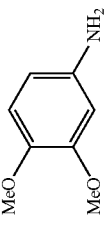 | 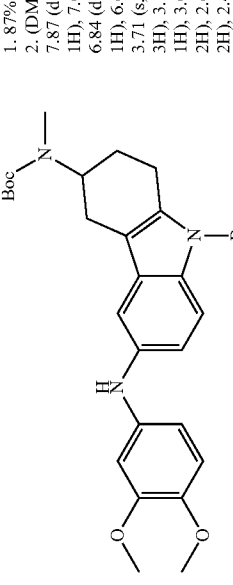 104 | 1. 87%<br>2. (DMSO-d₆): δ = 7.87 (d, 1H), 7.77 (s, 1H), 7.02 (s, 1H), 6.84 (d, 1H), 6.68 (s, 1H), 6.62 (d, 1H), 3.71 (s, 3H), 3.70 (s, 3H), 3.15-3.17 (m, 1H), 3.07-2.83 (m, 2H), 2.68-2.55 (m, 2H), 2.43-2.29 (m, 1H), 2.10-1.85 (m, 2H), 1.85-1.66 (m, 2H), 1.61 (s, 9H) 1.42 (s, 9H).<br>3. 552.69 (M + H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 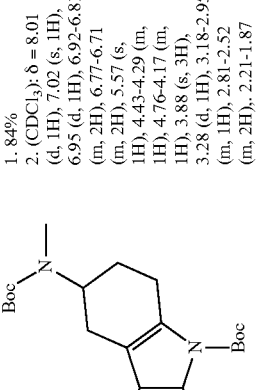 | 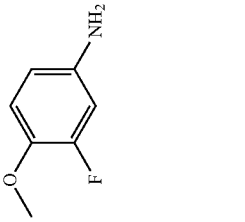 | 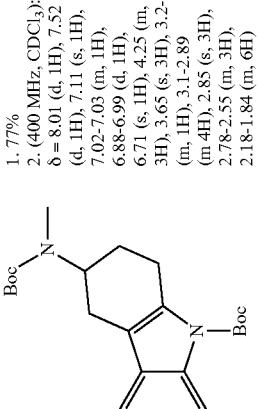　105 | 1. 84%<br>2. (CDCl₃): δ = 8.01 (d, 1H), 7.02 (s, 1H), 6.95 (d, 1H), 6.92-6.81 (m, 2H), 6.77-6.71 (m, 2H), 5.57 (s, 1H), 4.43-4.29 (m, 1H), 4.76-4.17 (m, 1H), 3.88 (s, 3H), 3.28 (d, 1H), 3.18-2.95 (m, 1H), 2.81-2.52 (m, 2H), 2.21-1.87 (m, 2H), 1.68 (s, 9H), 1.5 (s, 9H).<br>3. 440.68 (M + H). |
| 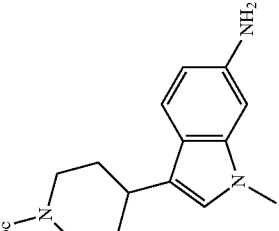 | 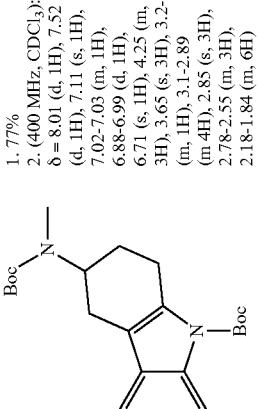 | 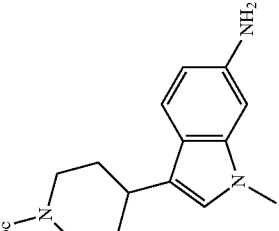　106 | 1. 77%<br>2. (400 MHz, CDCl₃): δ = 8.01 (d, 1H), 7.52 (d, 1H), 7.11 (s, 1H), 7.02-7.03 (m, 1H), 6.88-6.99 (d, 1H), 6.71 (s, 1H), 4.25 (m, 3H), 3.65 (s, 3H), 3.2-3.3 (m, 1H), 3.1-2.89 (m, 4H), 2.85 (s, 3H), 2.78-2.55 (m, 3H), 2.18-1.84 (m, 6H), 1.68 (s, 9H), 1.52 (s, 9H), 1.50 (s, 9H).<br>3. 728.74 (M + H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
|  |  | 107 | 1. 59%<br>2. (CDCl₃): δ = 7.89 (d, 1H), 6.61-6.57 (m, 2H), 4.32 (m, 1H), 3.34-3.24 (m, 2H), 3.02 (m, 1H), 2.86 (s, 3H), 2.65-2.72 (m, 2H), 2.32 (s, 3H), 2.09-2.18 (m, 6H), 1.95-1.99 (m, 4H), 1.66 (s, 9H), 1.50 (s, 9H).<br>3. 513.71 (M + H). |
|  | 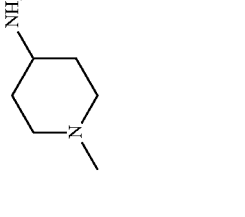 | 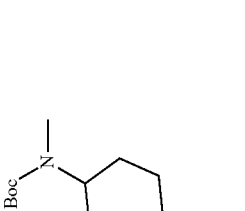108 | 1. 40%<br>2. (CDCl₃) δ 8.04 (s, 1H), 7.54 (d, 1H), 7.45-7.36 (m, 2H), 7.28-7.27 (m, 1H), 7.08 (d, 1H), 6.98-6.88 (m, 2H), 5.76 (s, 1H), 4.14 (d, 1H), 3.13-3.11 (m, 2H), 2.88-2.77 (m, 1H), 2.46 (s, 3H), 2.29-2.24 (m, 2H), 2.14-1.99 (m, 4H), 1.63-1.59 (m, 3H), 1.13 (d, 18H).<br>3. 503.65 (M + H). |
| | | 109 | 1. 48%<br>2. (DMSO-d₆) δ 8.60 (s, 1H), 8.07 (s, 1H), 7.58 (d, 1H), 7.47 (d, 1H), 7.36 (s, 1H), 7.12 (d, 1H), 7.07 (s, 1H), 6.95 (s, 1H), 6.84 (d, 1H), 4.05 (m 1H), 3.63 (s, 3H), 3.07-2.70 (m, 3H), 1.95-1.92 (m, 2H), 1.44 1.42 (m, 2H), 1.40 (s, 9H).<br>3. 447.7 (M + H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| [Bromo-derivative: 6-bromo-3-(1-Boc-piperidin-4-yl)-1-methylindole] | [4-fluoro-3-methoxyaniline] | [Product 110: N-(4-fluoro-3-methoxyphenyl)-3-(1-Boc-piperidin-4-yl)-1-methyl-1H-indol-6-amine] | 1. 73%<br>2. (CDCl₃) δ 7.54 (d, 1H), 7.03-6.93 (m, 2H), 6.87 (dd, 1H), 6.78-6.70 (m, 2H), 6.55 (ddd, 1H), 5.71 (s, 1H), 4.27 (s, 1H), 3.84 (s, 3H), 3.68 (s, 3H), 2.99-2.92 (m, 4H), 2.05 (d, 2H), 1.76-1.64 (m, 2H), 1.53 (s, 9H).<br>3. 454.69 (M + H). |
| [Bromo-derivative: 6-bromo-3-(1-methylpiperidin-4-yl)-1-TIPS-indole] | [3,4,5-trifluoroaniline] | [Product 111] | 1. 80%<br>2. (CDCl₃) δ 7.57 (d, 1H), 7.27 (d, 1H), 6.99 (s, 1H), 6.88-6.85 (m, 1H), 6.52-6.48 (m, 1H), 5.71 (s, 1H), 3.16-3.13 (m, 2H), 2.88-2.82 (m, 1H), 2.47 (s, 3H), 2.33 (t, 2H), 2.13-1.99 (m, 4H), 1.67-1.60 (m, 3H), 1.14 (d, 18H).<br>3. 516.67 (M + H). |
| [Bromo-derivative: 6-bromo-3-(1-methylpiperidin-4-yl)-1-TIPS-indole] | [4-fluoro-3-methoxyaniline] | [Product 112] | 1. 74%<br>2. ¹H NMR (400 MHz, CDCl₃) δ 7.54 (d, 1H), 7.20 (d, 1H), 6.98-6.85 (m, 2H), 6.63 (dd, 1H), 6.52-6.48 (m, 1H), 5.58 (s, 1H), 3.83 (s, 3H), 3.04-3.01 (m, 2H), 2.80 (tt, 1H), 2.39 (s, 3H), 2.21-2.05 (m, 4H), 1.94-1.85 (m, 2H), 1.65-1.58 (m, 3H), 1.13 (d, 18H).<br>3. 510.75 (M + H). |

TABLE 1-continued

| Bromo-derivative | Amine | Product Preparative Example | 1. Yield 2. ¹H-NMR (CDCl₃) 3. MS (ESI) m/z |
|---|---|---|---|
| (structure) | (structure) | 113 | 1. 76% 3. 455.66 (M + H) |
| (structure) | (structure) | 114 | 1. 80% 2. (CDCl₃): δ = 8.03 (d, 1H), 7.06 (d, 1H), 6.97 (dd, 2H), 6.67 (dd, 1H), 6.55-6.51 (m, 1H), 5.58 (brs, 1H), 4.66-4.28 (m, 1H), 3.84 (s, 3H), 3.28 (dd, 1H), 3.18-2.97 (m, 1H), 2.86 (s, 3H), 2.80-2.56 (m, 1H), 2.19-1.89 (m, 1H), 1.68 (s, 9H), 1.5 (s, 9H). 3. 540.68 (M + H) |
| (structure) | (structure) | 115 | 1. 74% 2. (CDCl₃): δ = 7.57 (d, 1H), 7.54 (d, 1H), 7.05-7.0 (m, 1H), 6.95 (s, 1H), 6.65 (d, 1H), 6.43 (s, 1H), 3.73 (s, 3H), 3.66 (s, 3H), 3.02-2.99 (m, 2H), 2.87 (s, 3H), 2.83-2.77 (m, 2H), 2.37 (s, 3H), 2.19-2.04 (m, 6H), 1.88-1.83 (m, 2H), 1.83-1.65 (m, 5H), 1.51 (s, 9H), 1.13 (d, 18H). 3. 699.68 (M + H) |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (structure) | (structure) | (structure) 116 | 1. 46%<br>3. 752.7 (M + H) |
| (structure) | (structure) | (structure) 117 | 1. 84%<br>2. (CDCl₃): δ = 7.45 (d, 2H), 7.07 (s, 2H), 6.96 (d, 2H), 6.88 (s, 2H), 5.63 (brs 1H), 3.07-3.05 (m, 4H), 2.83-2.80 (m, 2H), 2.42 (s, 6H), 2.26-2.21 (m, 4H), 1.95-1.92 (m, 4H), 1.61-1.57 (m, 6H), 1.11 (d, 36H).<br>3. 754.7 (M + H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (Boc-N-tetrahydrocarbazole-Boc, 7-Br) | 3,4-dimethoxyaniline | 118 | 1. 75%<br>2. (CDCl₃) δ 7.86 (d, 1H), 7.24 (d, 1H), 6.92-6.90 (m, 1H), 6.82 (d, 1H), 6.77 (d, 1H), 6.67 (dd, 1H), 5.59 (s, 1H), 4.52-4.32 (m, 1H), 3.88 (s, 3H), 3.86 (s, 3H), 3.25 (dd, 1H), 3.11-2.98 (m, 1H), 2.87 (s, 3H), 2.83-2.60 (m, 3H), 2.05-1.86 (m, 2H), 1.60 (s, 9H), 1.51 (s, 9H).<br>3. 552.67 (M + H) |
| (MeO-tetrahydrocarbazole-NMe, 7-Br) | 3,4-dimethoxyaniline | 119 | 1. 88% |
| (MeO-tetrahydrocarbazole-NMe, 7-Br) | 3-methoxy-4-fluoroaniline | 120 | 1. 60%.<br>2. (DMSO-d₆) δ 7.26 (d, 1H), 7.07 (s, 1H), 7.01-6.89 (m, 1H), 6.86 (d, 1H), 6.64 (d, 1H), 6.39 (d, 1H), 3.82-3.58 (m, 3H), 3.55 (s, 3H), 3.31 (s, 3H), 2.91 (dd, 1H), 2.85-2.61 (m, 3H), 2.09-2.05 (m, 1H), 1.88-1.82 (m, 1H).<br>3. 355.72 (M + H) |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| | | 121 | 1. 66%<br>2. (CDCl₃): δ 7.37 (d, 1H), 6.96 (d, 1H), 6.84-6.79 (m, 2H), 6.71 (d, 1H), 6.60 (dd, 1H), 5.57-5.55 (m, 1H), 3.87 (s, 3H), 3.82 (s, 2H), 3.77-3.69 (m, 1H), 3.13 (dd, 1H), 2.89-2.86 (m, 1H), 2.76-2.70 (m, 2H), 2.22-2.18 (m, 1H), 2.05-2.02 (m, 1H).<br>3. |
| | | 122 | 1. 79%<br>2. (400 MHz, CDCl₃): δ = 7.41 (d, 1H), 7.01 (s, 1H), 6.95 (dd, 1H), 6.87 (dd, 1H), 6.67 (dd, 1H), 6.55-6.41 (m, 1H), 5.62 (s, 1H), 3.81 (s, 3H), 3.79-3.77 (m, 1H), 3.56 (s, 3H), 3.50 (s, 3H), 3.13 (dd, 1H), 2.91-2.86 (m, 1H), 2.80-2.72 (m, 2H), 2.23-2.19 (m, 1H), 2.08-2.03 (m, 1H). |
| | | 123 | 1. 48%<br>2. (CDCl₃) δ: 7.20 (s, 1H), 7.17 (s, 1H), 6.95 (m, 1H), 6.71 (d, 1H), 6.57 (brs, 1H), 6.39 (brs, 1H), 5.91 (brs, 2H), 3.79-3.74 (m, 1H), 3.66 (brs, 2H), 3.48 (s, 3H), 3.09-3.06 (m, 1H), 2.92-2.86 (m, 1H), 2.80-2.69 (m, 2H), 2.23-2.17 (m, 1H), 2.09-2.00 (m, 1H). |

TABLE 1-continued

| Bromo-derivative | Amine | Product Preparative Example | 1. Yield 2. ¹H-NMR (CDCl₃) 3. MS (ESI) m/z |
|---|---|---|---|
| (bromo-methoxy-tetrahydrocarbazole, N-methyl) | (2,3-dihydro-1,4-benzodioxin-6-amine) | 124 | 1. 48% |
| (bromo-methoxy-tetrahydrocarbazole, N-Boc) | (2,3-dihydro-1,4-benzodioxin-6-amine) | 125 | 1. 78% 2. (DMSO-d₆) δ 7.85 (s, 1H), 7.77 (s, 1H), 7.24 (d, 1H), 6.86 (dd, 1H), 6.75 (d, 1H), 6.68-6.48 (m, 2H), 4.20 (dd, 4H), 3.68 (m, 1H), 3.33 (s, 4H), 3.02-2.90 (m, 2H), 2.03-2.0 (m, 1H), 1.84-1.83 (m, 1H), 1.57 (s, 9H). |
| (bromo-(2-fluoroethoxy)-tetrahydro-pyrido-indole, N-methyl) | (3,4-difluoroaniline) | 126 | 1. 98% 2. (CDCl₃) δ 7.81-7.67 (m, 1H), 7.61 (d, 1H), 7.15-6.95 (m, 2H), 6.51 (d, 1H), 6.35 (s, 1H), 4.68 (s, 1H), 4.56 (s, 1H), 3.91 (s, 2H), 3.83 (s, 1H), 3.68 (s, 3H), 3.10 (d, 1H), 2.94-2.92 (m, 1H), 2.86-2.63 (m, 2H), 2.25-2.19 (m, 1H), 2.09-1.96 (m, 1H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| (bromo-derivative structure) | 3,4-dimethoxyaniline | 127 | 1. 70% |
| (bromo-derivative structure) | 2,3-dihydro-1,4-benzodioxin-6-amine | 128 | 1. 52%<br>2. (CDCl₃) δ 7.55 (d, 1H), 7.15 (d, 1H), 6.89-6.78 (m, 2H), 6.55 (d, 1H), 6.24 (s, 1H), 4.68 (t, 1H), 4.56 (t, 1H), 4.37-4.23 (m, 4H), 3.91-3.88 (m, 2H), 3.84-3.81 (m, 1H), 3.66 (s, 3H), 3.08 (dd, 1H), 2.89 (dt, 1H), 2.85-2.61 (m, 2H), 2.31-2.17 (m, 1H), 2.11-1.93 (m, 2H). |
| (bromo-derivative structure) | 3,4-dimethoxyaniline | 129 | 1. 82%<br>2. (CDCl₃) δ 7.56 (d, 1H), 7.33 (s, 1H), 6.87 (m, 2H), 6.51 (d, 1H), 6.30 (brs, 1H), 3.91 (m, 2H), 3.90 (s, 3H), 3.05-3.01 (m, 1H), 2.87-2.76 (m, 1H), 2.62-2.58 (m, 1H), 2.19-2.17 (m, 1H), 1.94 (m, 1H), 1.24 (s, 3H), 1.23 (s, 3H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 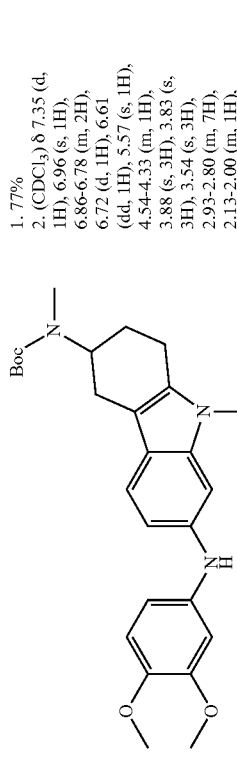 | 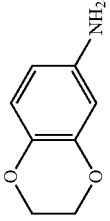 | 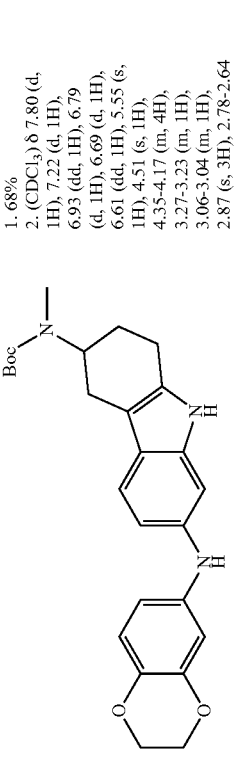 130 | 1. 68%<br>2. (CDCl₃) δ 7.80 (d, 1H), 7.22 (d, 1H), 6.93 (dd, 1H), 6.79 (d, 1H), 6.69 (d, 1H), 6.61 (dd, 1H), 5.55 (s, 1H), 4.51 (s, 1H), 4.35-4.17 (m, 4H), 3.27-3.23 (m, 1H), 3.06-3.04 (m, 1H), 2.87 (s, 3H), 2.78-2.64 (m, 2H), 2.04-1.84 (m, 2H), 1.62 (s, 9H), 1.50 (s, 9H). |
|  | 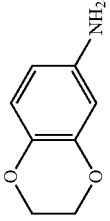 | 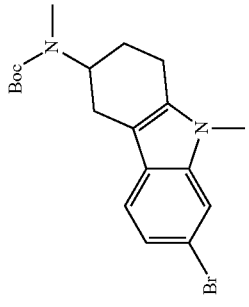 131 | 1. 77%<br>2. (CDCl₃) δ 7.35 (d, 1H), 6.96 (s, 1H), 6.86-6.78 (m, 2H), 6.72 (d, 1H), 6.61 (dd, 1H), 5.57 (s, 1H), 4.54-4.33 (m, 1H), 3.88 (s, 3H), 3.83 (s, 3H), 3.54 (s, 3H), 2.93-2.80 (m, 7H), 2.13-2.00 (m, 1H), 1.74 (s, 1H), 1.51 (s, 9H). |
| | | 132 | 1. 80%<br>2. (CDCl₃) δ 8.10 (s, 1H), 7.53 (s, 1H), 6.98 (dd, 1H), 6.61 (ddd, 1H), 6.59-6.49 (m, 1H), 5.62 (s, 1H), 4.44-4.36 (m, 1H), 3.74 (s, 3H), 2.93-2.75 (m, 7H), 2.08 (s, 2H), 1.50 (s, 9H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| | | 133 | 1. 62%<br>2. (CDCl₃) δ 8.10 (d, 1H), 7.49 (s, 1H), 6.77 (d, 1H), 6.55 (d, 1H), 6.46 (dd, 1H), 5.45 (s, 1H), 4.42-4.33 (m, 1H), 3.85 (s, 3H), 3.81 (s, 3H), 3.72 (s, 3H), 2.91-2.58 (m, 7H), 2.10-2.06 (s, 1H), 1.87-1.80 (m, 1H), 1.50 (s, 9H). |
| | | 134 | 1. 98% |
| | | 135 | 1. 94%<br>2. (CDCl₃) δ 8.17 (d, 1H), 7.61 (d, 1H), 6.85 (d, 1H), 6.63-6.46 (m, 3H), 5.47 (brs, 1H), 4.61 (brs, 1H), 4.41-4.27 (m, 5H), 3.82 (s, 3H), 3.01-2.84 (m, 9H), 1.60 (s, 9H). |

TABLE 1-continued

| Bromo-derivative | Amine | Product Preparative Example | 1. Yield<br>2. ¹H-NMR (CDCl₃)<br>3. MS (ESI) m/z |
|---|---|---|---|
| | | 136 | 1. 74% |
| | | 137 | 1. 90%<br>2. (CDCl₃) δ 7.43 (d, 1H), 7.38 (s, 1H), 7.06 (s, 1H), 6.93-6.87 (m, 2H), 6.73-6.63 (m, 2H), 4.37-4.35 (m, 4H), 3.65 (s, 4H), 3.04-2.89 (m, 8H), 2.15-2.13 (m, 1H), 2.02-1.91 (m, 2H), 1.60 (s, 9H). |
| | | 138 | 1. 74%<br>2. (CDCl₃) δ 7.39 (d, 1H), 7.04-6.9 (m, 2H), 6.87 (d, 1H), 6.79 (ddd, 1H), 6.67-6.53 (m, 1H), 5.64 (s, 1H), 4.54-4.36 (m, 1H), 3.58 (s, 3H), 3.06-2.65 (m, 8H), 2.06 (d, 2H), 1.51 (s, 9H). |

TABLE 1-continued
| Bromo-derivative | Amine | Product Preparative Example | 1. Yield<br>2. ¹H-NMR (CDCl₃)<br>3. MS (ESI) m/z |
|---|---|---|---|
| 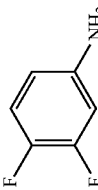 | 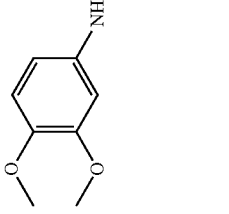 | 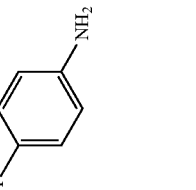<br>139 | 1. 89%<br>2. ¹H NMR (400 MHz, CDCl₃) δ 7.78 (ddd, 1H), 7.58 (d, 1H), 7.07 (dd, 1H), 7.02-6.93 (m, 1H), 6.51 (d, 1H), 6.40 (s, 1H), 4.57-4.23 (m, 3H), 3.74 (s, 2H), 3.51 (s, 2H), 3.38-3.35 (m, 3H), 2.94-2.75 (m, 8H), 2.05-2.03 (m, 2H), 1.51 (s, 9H). |
| 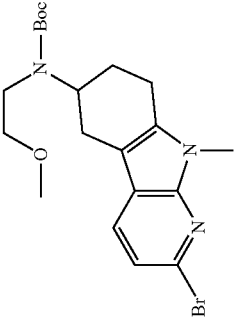 | 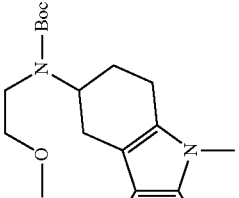 | 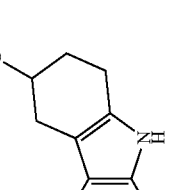<br>140 | 1. 73%<br>2. (CDCl₃) δ 7.55-7.53 (m, 1H), 7.40 (s, 1H), 6.86 (s, 2H), 6.52-6.50 (m, 1H), 6.28 (s, 1H), 4.35-4.21 (m, 3H), 3.92 (s, 3H), 3.90 (s, 3H), 3.70 (s, 2H), 3.51 (s, 2H), 3.32 (s, 3H), 2.92-2.78 (m, 6H), 2.07-2.04 (m, 2H), 1.51 (s, 9H). |
| 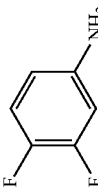 | 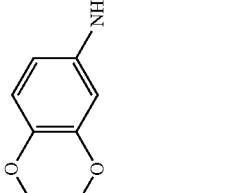 | 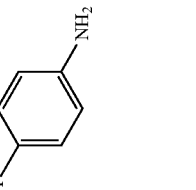<br>141 | 1. 98%<br>2. (CDCl₃): δ 7.37 (d, 2H), 6.94-6.86 (m, 5H), 3.80-3.73 (m, 1H), 3.56 (s, 3H), 3.49 (s, 3H), 3.11-2.75 (m, 4H), 2.22-2.19 (m, 1H), 2.17-1.99 (m, 1H). |

Preparative Example 142

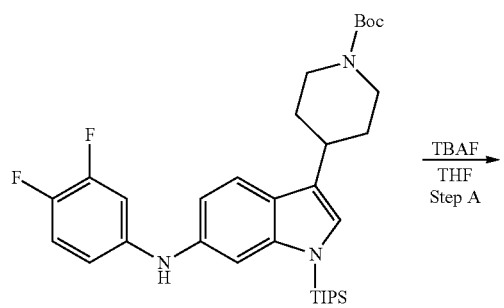

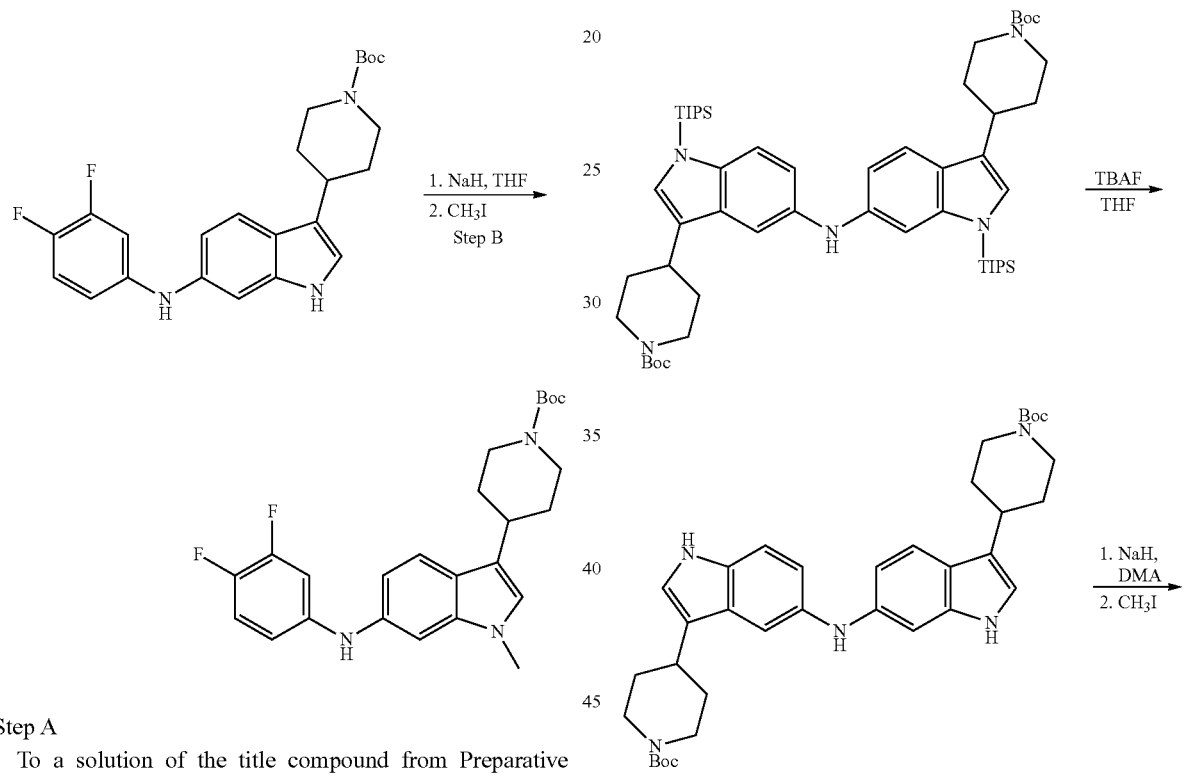

Step A

To a solution of the title compound from Preparative Example 75 (0.120 g, 0.2 mmol) in THF (1 mL) was added tetra-butyl ammonium (0.052 g, 0.2 mmol). The reaction mixture was stirred for 1 h. Then the reaction mixture was concentrated. The crude product was purified using a silica gel column (1:1, EtOAc:heptane) to afford the title compound (0.08 g, 94%).

$^1$H-NMR (400 MHz, CDCl$_3$): δ=1.48 (s, 9H), 1.68-1.71 (m, 2H), 2.01-2.17 (m, 2H), 2.89-2.95 (m, 3H), 4.23-4.25 (m, 2H), 6.65 (m, 1H), 6.83-6.89 (m, 2H), 6.98-6.99 (m, 1H), 7.10 (s, 1H), 7.52 (d, 1H), 7.91 (s, 1H)

Step B

To a solution of the title compound from Step A above (0.08 g, 0.187 mmol) in THF (3 mL) was added sodium hydride (0.007 g, 0.28 mmol) followed by addition of methyl iodide (0.026 g, 0.187 mmol) and the resulting reaction mixture was stirred for 1 h. Then, the reaction mixture was quenched with water and extracted with ethyl acetate (3×50 mL). The organic phase was washed with brine and dried over Na$_2$SO$_4$ and the solvent was removed under reduced pressure. The crude product was purified on a silica gel column (EtOAc:heptane; 40:60) to afford the title compound (0.025 g, 30%).

$^1$H-NMR (400 MHz, CDCl$_3$): δ=1.51 (s, 9H), 1.66-1.72 (m, 2H), 2.02-2.05 (m, 2H), 2.88-2.99 (m, 3H), 3.70 (s, 3H), 4.24-4.27 (m, 2H), 6.66 (d, 1H), 6.77 (s, 1H), 6.81-6.88 (m, 2H), 6.99-7.06 (m, 2H), 7.54 (d, 1H)

Preparative Examples 143 and 144

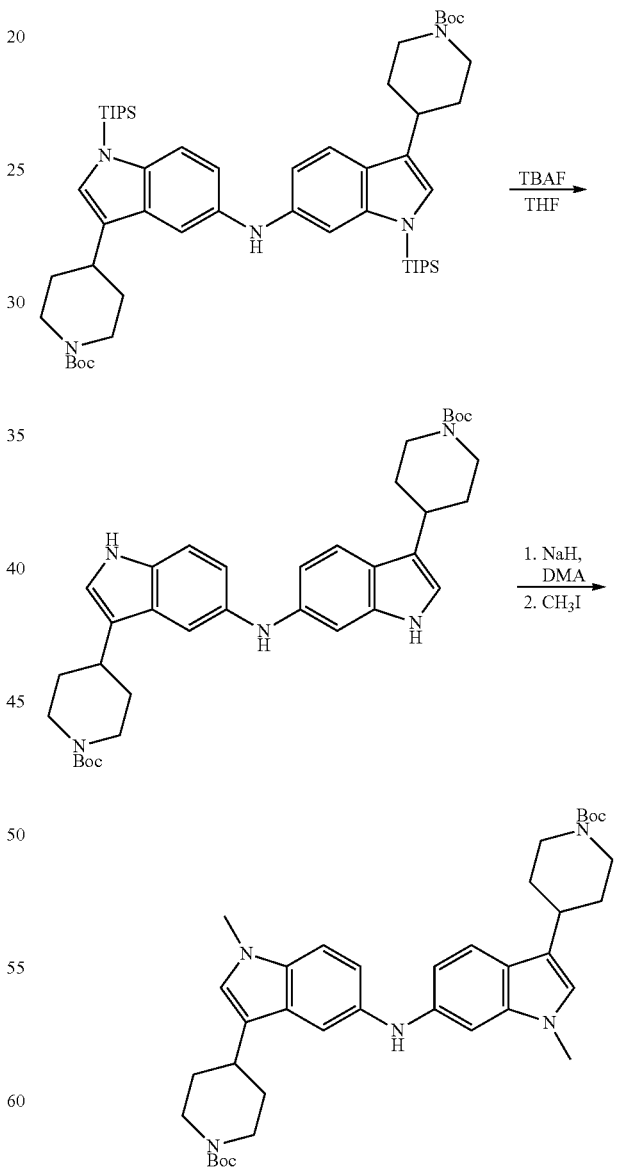

143

+

225

-continued

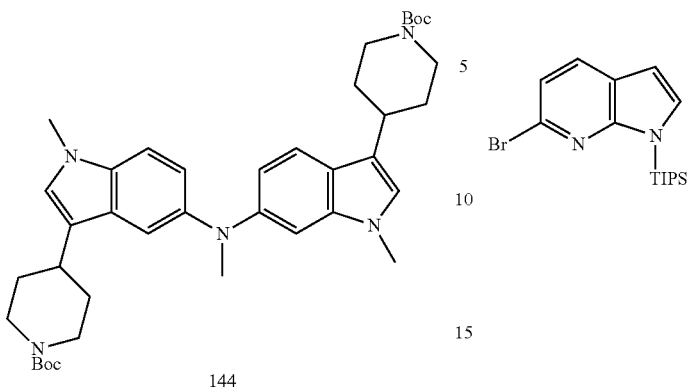

144

Step A

To a solution of the title compound from Preparative Example 69 (0.3 g, 0.323 mmol) in THF (3 mL) was added tetrabutylammonium fluoride (0.08 g, 0.323 mmol) and the reaction mixture was stirred at room temperature for 1 h. The solvent was removed and the residue was purified on a silica gel column (EtOAc to heptane; 20-100%) to afford the title compound (0.127 g, 64%).

$^1$H-NMR (400 MHz, DMSO-d$_6$): δ=1.49 (s, 9H), 1.51 (s, 9H), 1.66 (m, 4H), 2.06 (m, 4H), 2.90 (m, 4H), 4.23 (m, 4H), 6.80 (d, 1H), 6.83 (dd, 1H), 6.94 (d, 1H), 6.96 (d, 1H), 7.07 (dd, 1H), 7.30 (d, 1H), 7.42 (d, 1H), 7.50 (d, 1H), 7.75 (s, 1H), 7.99 (s, 1H)

ESI MS (MH): 614

Step B

To a solution of the title compound from Step A above (0.05 g, 0.081 mmol) in THF (5 mL) was added sodium hydride (0.004 g, 0.16 mmol) followed by methyl iodide (0.022 g, 0.15 mmol). The reaction mixture was stirred overnight at room temperature. Then the reaction mixture was quenched with a drop of methanol, and the solvents were removed. The crude mixture was purified on a silica gel column to afford the dimethylated title compound (0.021 g) and the trimethylated title compound (0.010 g).

dimethylated compound 143, ESI MS (MH): 642 (M+H), 643 (M+2H), 644 (M+3H)

trimethylated compound 144, ESI MS (MH): 656 (M+H) 657 (M+2H), 658 (M+3H)

226

Preparative Example 145

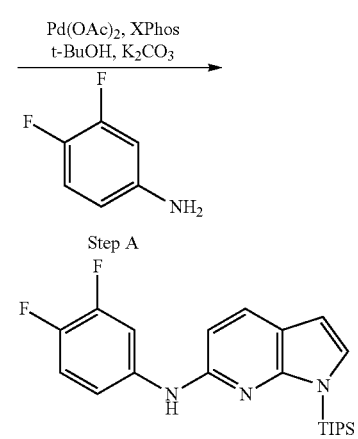

Step A

Tert-butanol (2 mL) was degassed by sonication for 1 min while a stream of argon was passed through the solution. To the degassed tert-butanol (1 mL) was added palladium(II) acetate (0.003 g, 0.0127 mmol) and 2-dicyclohexylphosphino-2',4',6'-triisopropylbiphenyl (XPhos, 0.018 g, 0.038 mmol). This mixture was heated at ~100° C. in a sand-bath for 1 min to generate the catalyst. To the faint red catalyst solution was then added a solution of the title compound from Preparative Example 1, Step D (0.045 g, 0.127 mmol) and commercially available 3,4-difluoro aniline (0.019 g, 0.15 mmol) in degassed tert-butanol (1 mL). After the addition of potassium carbonate (0.039 g, 0.28 mmol), the mixture was heated in a sand-bath at ~110° C. for 3 h. The mixture was diluted with ethyl acetate (30 mL), water (10 mL) and brine (10 mL). The organic phase was separated, dried over Na$_2$SO$_4$, filtered and the solvents were removed. The residue was purified by chromatography on silica using ethyl acetate/n-heptane (20/80) to afford the title compound as an off-white solid (0.045 g, 87%).

$^1$H-NMR (400 MHz, CDCl$_3$): δ=1.12-1.16 (m, 18H), 1.80-1.90 (m, 3H), 6.22 (br-s, 1H), 6.47 (d, 1H), 6.53 (d, 1H), 6.90-6.94 (m, 1H), 7.06 (t, 1H), 7.10 (d, 1H), 7.60-7.67 (m, 1H), 7.75 (d, 1H)

Preparative Examples 146 to 256

Following the Pd-coupling procedure as described in Preparative Example 145, except using the bromo-derivatives and amines indicated in the table below, the following compounds were prepared.

TABLE 2
| Bromo derivative | Amine derivative | Product Preparative Example | 1. Yield 2. $^1$H-NMR (CDCl$_3$) 3. MH$^+$ (ESI) |
|---|---|---|---|
| 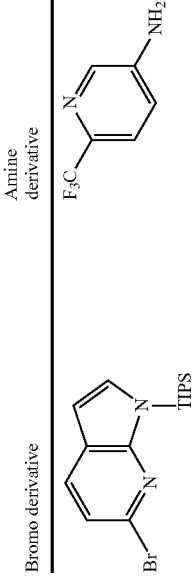 | 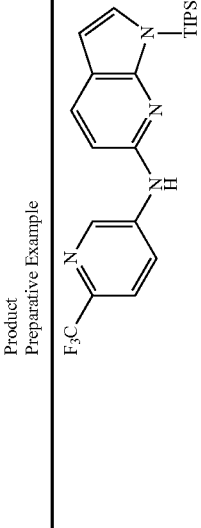 | 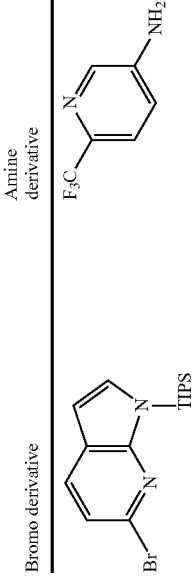 146 | 1. 77% 2. δ = 1.13-1.16 (m, 18H), 1.80-1.88 (m, 3H), 6.52 (d, 1H), 6.55 (br-s, 1H), 6.66 (d, 1H), 7.17 (d, 1H), 7.58 (d, 1H), 7.83 (d, 1H), 8.32-8.37 (m, 1H), 8.51 (d, 1H) |
| 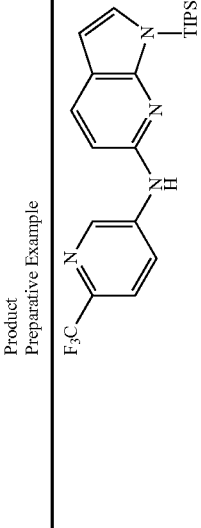 | 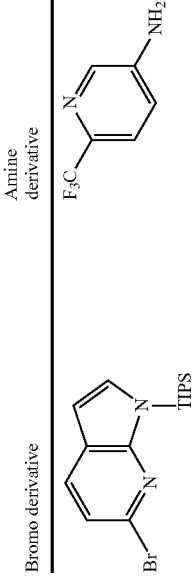 | 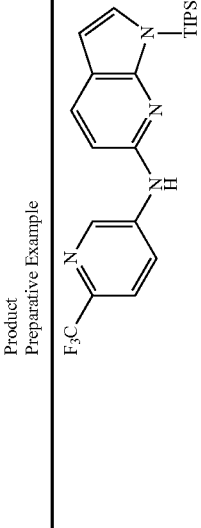 147 | 1. 91% 2. δ = 1.13-1.17 (m, 18H), 1.84-1.93 (m, 3H), 6.37-6.42 (m, 2H), 6.49 (d, 1H), 6.57 (d, 1H), 7.07-7.12 (m, 2H), 7.15 (d, 1H), 7.79 (d, 1H) |
| | | 148 | 1. 90% 2. δ = 1.12-1.16 (m, 18H), 1.80-1.88 (m, 3H), 3.00 (s, 3H), 3.12 (s, 3H), 6.35 (br-s, 1H), 6.47 (d, 1H), 6.63 (d, 1H), 6.99 (d, 1H), 7.10 (d, 1H), 7.32 (t, 1H), 7.41-7.44 (m, 1H), 7.52-7.56 (m, 1H), 7.76 (d, 1H) |

TABLE 2-continued

| Bromo derivative | Amine derivative | Product Preparative Example | 1. Yield<br>2. ¹H-NMR (CDCl₃)<br>3. MH⁺ (ESI) |
|---|---|---|---|
| (6-bromo-7-azaindole-TIPS) | 4-amino-N,N-dimethylbenzamide | 149 | 1. 83%<br>2. δ = 1.12-1.17 (m, 18H), 1.84-1.92 (m, 3H), 3.10 (s, 6H), 6.43 (br-s, 1H), 6.49 (d, 1H), 6.64 (d, 1H), 7.11 (d, 1H), 7.39-7.51 (m, 4H), 7.77 (d, 1H) |
| (bromo-tetrahydrocarbazole-NBoc-TIPS) | 3,4-difluoroaniline | 150 | 1. 66%<br>2. δ = 1.08-1.15 (m, 18H), 1.50 (s, 9H), 1.91-2.03 (m, 5H), 2.70-2.88 (m, 5H), 2.93-3.05 (m, 2H), 4.25-4.56 (br-m, 1H), 6.07 (br-s, 1H), 6.54 (d, 1H), 6.88-6.92 (m, 1H), 7.08 (q, 1H), 7.25-7.31 (m, 1H), 7.55 (d, 1H) |
| (bromo-tetrahydrocarbazole-NBoc-TIPS) | 5-amino-2-(trifluoromethyl)pyridine | 151 | 1. 61%<br>2. δ = 1.10-1.15 (m, 18H), 1.51 (s, 9H), 1.93-2.04 (m, 5H), 2.70-2.88 (m, 5H), 2.96-3.04 (m, 2H), 4.25-4.54 (br-m, 1H), 6.40 (s, 1H), 6.68 (d, 1H), 7.55 (d, 1H), 7.62 (d, 1H), 7.97-8.02 (m, 1H), 8.50 (d, 1H) |

TABLE 2-continued

| Bromo derivative | Amine derivative | Product Preparative Example | 1. Yield 2. $^1$H-NMR (CDCl$_3$) 3. MH$^+$ (ESI) |
|---|---|---|---|
| | | 152 | 1. 96% 2. δ = 1.51 (s, 9H), 2.04-2.11 (m, 2H), 2.70-2.91 (m, 7H), 3.66 (s, 3H), 4.25-4.55 (br-m, 1H), 6.38 (br-s, 1H), 6.51 (d, 1H), 6.98-7.03 (m, 1H), 7.10 (q, 1H), 7.60 (d, 1H), 7.71-7.77 (m, 1H) |
| | | 153 | 1. 62% 2. δ = 1.11-1.15 (m, 18H), 1.52 (s, 9H), 1.95-2.02 (m, 5H), 2.70-2.80 (m, 2H), 2.87 (s, 3H), 2.94-3.03 (m, 2H), 4.25-4.55 (m, 1H), 6.15 (br-s, 1H), 6.54 (d, 1H), 6.96-7.02 (m, 1H), 7.60 (d, 1H), 7.77-7.84 (m, 1H) |
| | | 154 | 1. 94% 2. δ = 1.53 (s, 9H), 2.00-2.06 (m, 2H), 2.75-2.90 (m, 7H), 3.72 (s, 3H), 4.25-4.55 (m, 1H), 6.48-6.51 (m, 2H), 6.95-7.01 (m, 1H), 7.64 (d, 1H), 8.62-8.68 (m, 1H) |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 155 | 1. 96% 2. δ = 1.51 (s, 9H), 2.00-2.04 (m, 2H), 2.72-2.90 (m, 7H), 3.65 (s, 3H), 4.25-4.50 (m, 1H), 6.36 (t, 1H), 6.51-6.54 (m, 2H), 7.13-7.17 (m, 2H), 7.60 (d, 1H) |
| | | 156 | 1. 96% 2. δ = 1.51 (s, 9H), 1.97-2.04 (m, 2H), 2.68-2.90 (m, 7H), 3.65 (s, 3H), 4.25-4.50 (m, 1H), 6.38 (br-s, 1H), 6.45 (d, 1H), 7.26-7.30 (m, 2H), 7.60 (d, 1H) |
| | | 157 | 1. 79% 2. δ = 1.12-1.18 (m, 36H), 1.51 (s, 18H), 1.63-1.72 (m, 2H), 1.90-2.00 (m, 6H), 2.04-2.12 (m, 2H), 2.75-3.06 (m, 12H), 4.18-4.53 (br-m, 3H), 6.15 (br-s, 1H), 6.68 (d, 1H), 6.93 (s, 1H), 7.02 (d, 1H), 7.35 (s, 1H), 7.46 (d, 1H), 7.55 (d, 1H) |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 158 | 1. 22% 3. 802 |
| | | 159 | 1. 76% 3. 688 |
| | | 160 | 1. 92% 3. 593 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 161 | 1. 66% 3. 589 |
| | | 162 | 1. 32% 3. 592 |
| | | 163 | 1. 72% 3. 492 |

TABLE 2-continued
| Bromo derivative | Amine derivative | Product Preparative Example | 1. Yield<br>2. ¹H-NMR (CDCl₃)<br>3. MH⁺ (ESI) |
|---|---|---|---|
| 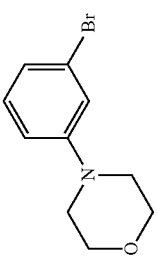 | 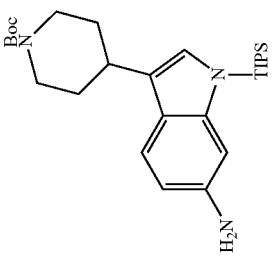 | 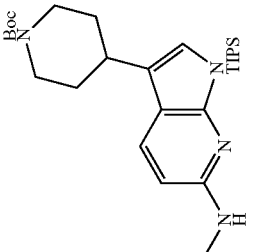<br>164 | 1. 42%<br>3. 633 |
| 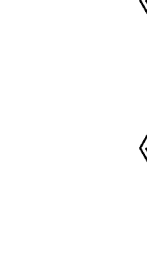 | 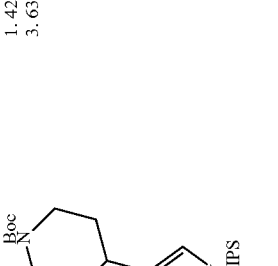 | <br>165 | 1. 99%<br>3. 927 |
| 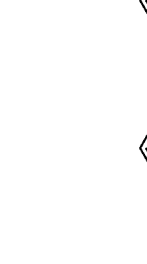 | 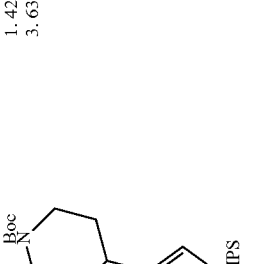 | <br>166 | 1. 92%<br>2. 670 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (Boc-piperidinyl-TIPS-pyrrolopyridine-Br) | 3,4-difluoroaniline | 167 | 1. 61% 3. 585 |
| (Boc-piperidinyl-TIPS-pyrrolopyridine-Br) | 6-(trifluoromethyl)pyridin-3-amine | 168 | 1. 58% 3. 618 |
| (Boc-piperidinyl-TIPS-pyrrolopyridine-Br) | (Boc-piperidinyl-TIPS-indol-6-amine) | 169 | 1. 55% 3. 926 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 170 | 1. 70% 3. 547 |
| | | 171 | 1. 90% 3. 588 |
| | | 172 | 1. 98% 3. 443 |

TABLE 2-continued
| Bromo derivative | Amine derivative | Product Preparative Example | 1. Yield 2. ¹H-NMR (CDCl₃) 3. MH⁺ (ESI) |
|---|---|---|---|
|  | 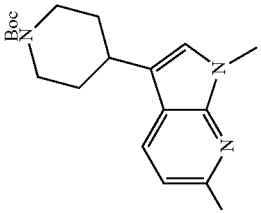 | 173 | 1. 98% 3. 450.99 |
| 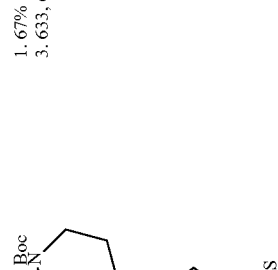 | 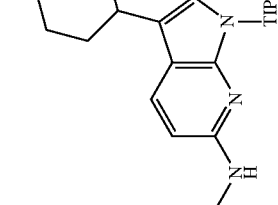 | 174 | 1. 67% 3. 633, 634 |
| 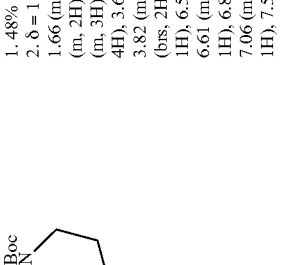 | 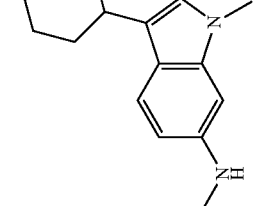 | 175 | 1. 48% 2. δ = 1.50 (s, 9H), 1.66 (m, 2H), 2.02 (m, 2H), 2.86-2.97 (m, 3H), 3.12 (m, 4H), 3.64 (s, 3H), 3.82 (m, 4H), 4.23 (brs, 2H), 6.44 (dd, 1H), 6.56 (dd, 1H), 6.61 (m, 1H), 6.71 (s, 1H), 6.89 (dd, 1H), 7.06 (m, 1H), 7.14 (t, 1H), 7.51 (d, 1H), 3. 492 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| [Boc-piperidine-pyrrolopyridine-Br with TIPS] | [tetrahydrocarbazole-NH₂ pyridine] | 176 | 1. 33% 3. 643.25 |
| [6-bromoindole-TIPS] | [6-aminoindole] | 177 | 1. 77% 2. 404 |
| [Boc-piperidine-methylpyrrolopyridine-Br] | [4-morpholinoaniline] | 178 | 1. 28% 2. 492 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (6-bromo-3-(1-Boc-piperidin-4-yl)-1-TIPS-indole) | (4-morpholinoaniline) | 179 | 1. 82% 2. 633 |
| (3-(1-methylpiperidin-4-yl)-6-bromo-1-methylindole, shown with amine) | (3-(1-methylpiperidin-4-yl)-1-methyl-6-aminoindole) | 180 | 1. 25% 2. (MeOD) δ = 1.78-1.87 (m, 2H), 2.01-2.05 (m, 2H), 2.40-2.45 (m, 5H), 2.80 (m, 1H), 2.99 (brs, 4H), 3.08-3.10 (m, 2H), 3.56 (s, 3H), 3.72 (brs, 4H), 6.37 (d, 1H), 6.57 (d, 1H), 6.62 (s, 1H), 6.77 (s, 1H), 6.83 (d, 1H), 7.01-7.05 (m, 2H9, 7.41 (d, 1H). 3. 405.75 |
| (6-bromo-3-(dimethylamino)-1-TIPS-tetrahydrocarbazole) | (4-morpholinoaniline) | 181 | 1. 61% 3. 547 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (bromo-tetrahydrocarbazole with dimethylamino, TIPS) | 4-(4-methylpiperazin-1-yl)aniline | 182 | 1. 66% 3. 560 |
| (bromo-benzodioxepine) | (1-methylpiperidin-4-yl indole with TIPS, 6-amino) | 183 | 1. 61% 3. 534 |
| (bromo-methyl-benzoxazine) | (1-methylpiperidin-4-yl indole with TIPS, 6-amino) | 184 | 1. 48% 3. 533 |

TABLE 2-continued
| Bromo derivative | Amine derivative | Product Preparative Example | 1. Yield 2. $^1$H-NMR (CDCl$_3$) 3. MH$^+$ (ESI) |
|---|---|---|---|
| 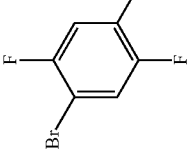 | 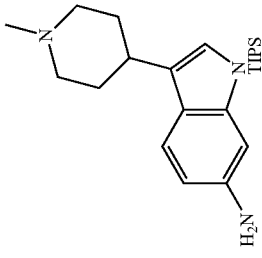 | 185 | 1. 52% |
| 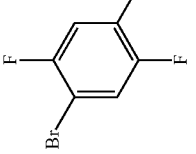 | 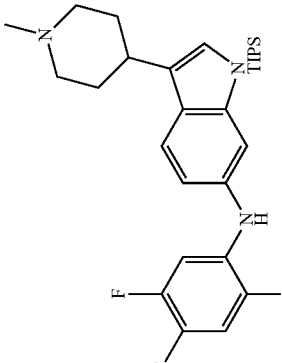 | 186 | 1. 83% 3. 505 |
| 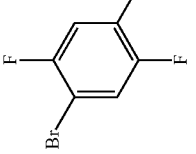 | 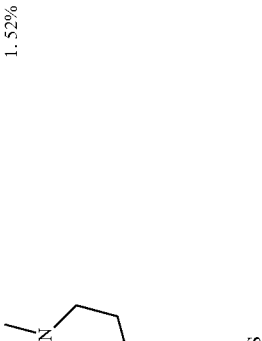 | 187 | 1. 91% 2. (CD$_2$Cl$_2$) δ = 1.80 (m, 2H), 1.90 (m, 2H), 2.57-2.62 (m, 4H), 3.80 (s, 3H), 3.84 (s, 6H), 6.47-6.48 (s, 1H), 6.82 (brs, 1H), 6.88 (m, 2H), 7.76-7.77 (m, 1H), 9.59 (s, H). 3. 338 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (Bromo derivative structure) | (Morpholine-phenyl amine) | 188 | 1. 45% 3. 492 |
| (Bromo derivative structure) | (N-methylpiperazine-phenyl amine) | 189 | 1. 69% 2. (CD₂Cl₂) δ = 1.44 (s, 9H), 1.96-1.98 (m, 2H), 2.29 (s, 3H), 2.53-2.56 (m, 5H), 2.86-2.88 (m, 2H), 2.80 (m, 4H), 3.10 (m, 4H), 3.56 (s, 3H), 6.41-6.43 (d, 2H), 6.86-6.88 (d, 2H), 7.37-7.39 (d, 2H), 7.47-7.49 (d, 1H). 3. 505 |
| (Bromo derivative structure) | (benzodioxepine amine) | 190 | 1. 92% 2. δ = 1.48 (s, 9H), 2.02-2.03 (m, 2H), 2.18 (m, 2H), 2.76 (m, 2H), 2.85 (s, 3H), 3.64 (s, 3H), 4.16-4.21 (m, 5H), 6.54 (d, 1H), 6.93 (m, 1H), 6.98 (m, 1H), 7.17 (brs, 1H), 7.52 (brs, 1H). 3. 479 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 191 | 1. 45% 3. 478 |
| | | 192 | 1. 53% 3. 478 |
| | | 193 | 1. 98% 3. 533 |

TABLE 2-continued

| Bromo derivative | Amine derivative | Product Preparative Example | 1. Yield
2. ¹H-NMR (CDCl₃)
3. MH⁺ (ESI) |
|---|---|---|---|
| (6-bromo-TIPS-tetrahydrocarbazole with NMe₂) | 3,4-dimethoxyaniline | 194 | 1. 60% |
| (bromo-N-methyl-pyridoindole with NCOCH₃/NMe) | 4-morpholinoaniline | 195 | 1. 93%
3. 434 |
| (bromo-N-methyl-tetrahydro-pyridoindole) | 4-morpholinoaniline | 196 | 1. 70%
2. (DMSO-d₆) δ = 1.75-1.76 (m, 2H), 1.83-1.85 (m, 2H), 2.55-2.56 (m, 2H), 2.65-2.66 (m, 2H), 2.99-3.01 (m, 4H), 3.57 (s, 3H), 3.72-2.74 (m, 4H), 6.45 (d, 1H), 6.87-6.90 (m, 2H), 7.52 (d, 1H), 7.66 (m, 2H), 8.58 (s, 1H).
3. 363 |

TABLE 2-continued
| Bromo derivative | Amine derivative | Product Preparative Example | 1. Yield 2. ¹H-NMR (CDCl₃) 3. MH⁺ (ESI) |
|---|---|---|---|
|  |  |  197 | 1. 75% 2. (DMSO-d₆) δ = 1.75-1.76 (m, 2H), 1.83-1.84 (m, 2H), 2.24 (s, 3H), 2.54-2.56 (m, 2H), 2.66 (m, 2H), 3.03 (m, 4H), 3.56 (s, 3H), 6.45 (d, 1H), 6.86-6.88 (m, 2H), 7.51 (d, 1H), 7.63-7.65 (m, 2H), 8.56 (s, 1H). 3. 376 |
| |  | 198 | 1. 95% 2. (DMSO-d₆) δ = 1.75-1.78 (m, 2H), 1.85-1.87 (m, 2H), 2.55-2.58 (m, 2H), 2.67-2.70 (m, 2H), 3.59 (s, 3H), 4.53 (s, 2H), 6.49 (d, 1H), 6.79 (d, 1H), 7.22 (dd, 1H), 7.57 (d, 1H), 7.73 (d 1H), 8.82 (s, 1H), 10.5 (s, 1H). 3. 349 |
| |  | 199 | 1. 78% 2. (DMSO-d₆) δ = 1.75-1.78 (m, 2H), 1.84-1.87 (m, 2H), 2.55-2.57 (m, 2H), 2.67-2.70 (m, 2H), 3.63 (s, 3H), 4.48 (s, 2H), 6.48 (d, 1H), 6.84 (d, 1H), 7.09 (dd, 1H), 7.54 (d, 1H), 7.74 (d 1H), 8.76 (s, 1H), 10.83 (s, 1H). 3. 349 |

TABLE 2-continued
| Bromo derivative | Amine derivative | Product Preparative Example | 1. Yield 2. ¹H-NMR (CDCl₃) 3. MH⁺ (ESI) |
|---|---|---|---|
|  |  |   200 | 1. 71% 2. (DMSO-d₆) δ = 1.74-1.78 (m, 2H), 1.84-1.86 (m, 2H), 2.54-2.57 (m, 2H), 2.66-2.68 (m, 2H), 3.57 (s, 3H), 5.93 (s, 2H), 6.47 (d, 1H), 7.08 (dd, 1H), 7.55 (d, 1H), 7.66 (d, 1H), 8.73 (s, 1H). 3. 322 |
|  |  | 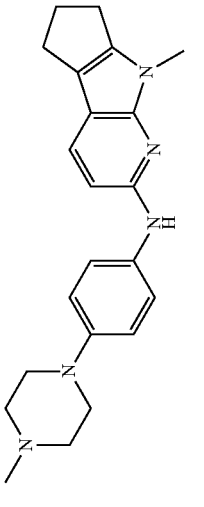  201 | 1. 78% 2. (DMSO-d₆) δ = 1.76-1.77 (m, 2H), 1.84-1.85 (m, 2H), 2.04 (s, 3H), 2.55-2.57 (m, 2H), 2.66-2.68 (m, 2H), 2.96-2.98 (m, 2H), 3.03-3.05 (m, 2H), 3.55-3.59 (m, 7H), 6.46 (d, 1H), 6.91 8d, 1H), 7.53 (d, 1H), 7.67 (d, 2H), 8.59 (s, 1H). 3. 404 |
|  |  |  202 | 1. 67% 2. (DMSO-d₆) δ = 2.22 (s, 3H), 2.35-2.42 (m, 2H), 2.45-2.47 (m, 4H), 2.70-2.73 (m, 2H), 2.82-2.85 (m, 2H), 3.02-3.04 (m, 4H), 3.63 (s, 3H), 6.47 (d, 1H), 6.88 (d, 1H), 7.50 (d, 1H), 7.63 (d, 2H), 8.55 (s, 1H). 3. 362 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 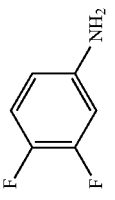 | 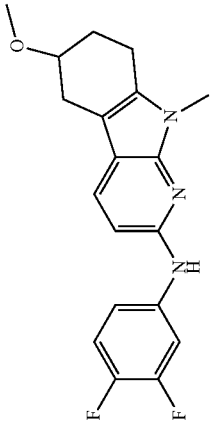 | 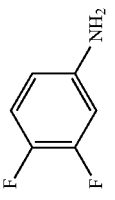 203 | 1. 74% 2. δ = 2.02-2.10 (m, 1H), 2.17-2.22 (m, 1H), 2.65-2.79 (m, 2H), 2.86-2.94 (m, 1H), 3.03 (dd, 1H), 3.48 (s, 3H), 3.67 (s, 3H), 3.75-3.78 (m, 1H), 6.36 (br-s, 1H), 6.51 (d, 1H), 6.90-7.11 (m, 2H), 7.62 (d, 1H), 7.71 (ddd, 1H) |
| 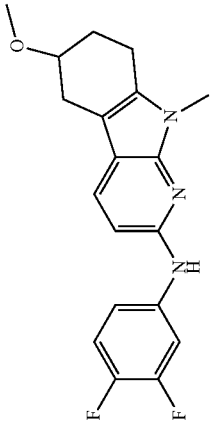 | 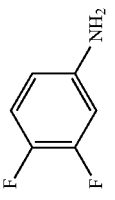 | 204 | Not characterized as free base |
| | | 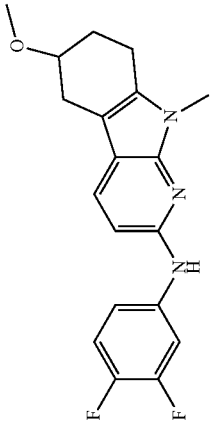 205 | 1. 40% 2. δ = 1.96-2.23 (m, 2H); 2.59-2.77 (m, 2H); 2.77-2.90 (m, 1H); 2.92-3.05 (d, J = 14.4 Hz, 1H); 3.45 (s, 3H); 3.66-3.82 (m, 4H); 4.26 (s, 4H); 6.52 (d, J = 7.6 Hz, 1H); 6.82 (sl, 2H); 7.01 (s, 1H); 7.61 (d, J = 7.2 Hz, 1H) 3. 366.70 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 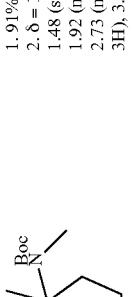 | | 206 | 1. 91% 2. δ = 1.46 (s, 3H), 1.48 (s, 9H), 1.85-1.92 (m, 1H), 2.65-2.73 (m, 3H), 2.73 (s, 3H), 3.01-3.04 (m, 1H), 3.13 (d, 1H), 3.66 (s, 3H), 6.30 (br-s, 1H), 6.48 (d, 1H), 6.96-7.08 (m, 2H), 7.58 (d, 1H), 7.70 (ddd, 1H) |
|  | | 207 | 1. 78% 2. δ = 1.48 (s, 3H), 1.50 (s, 9H), 1.85-1.92 (m, 1H), 2.66-2.73 (m, 3H), 2.75 (s, 3H), 3.02-3.08 (m, 1H), 3.13 (d, 1H), 3.66 (s, 3H), 3.87 (s, 3H), 3.92 (s, 3H), 6.25 (br-s, 1H), 6.52 (d, 1H), 6.83-6.90 (m, 2H), 7.34 (dd, 1H), 7.54 (d, 1H) |
|  | | 208 | 1. 99% 2. 606.17 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| [Boc-piperidinyl-TIPS-pyrrolopyridine-Br structure] | [aminoindane structure] | [product 209] | 1. 90% 2. 588.17 |
| [5-bromo-benzo[d][1,3]dioxole structure] | [Boc-piperidinyl-N-Me-indole-NH₂ structure] | [product 210] | 1. 48% 2. 449.98 |
| [Me-piperidinyl-TIPS-pyrrolopyridine-Br structure] | [Me-piperidinyl-TIPS-indole-NH₂ structure] | [product 211] | 1. 75% 2. 755.77 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 212 | 1. 2. 365.71 |
| | | 213 | 1. 2. 379.74 |
| | | 214 | 1. 89% 2. 613.76 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| | | 215 | 1. 2. 357.73 |
| | | 216 | 1. 2. 390.75 |
| | | 217 | 1. 82% 2. 506.72 |

TABLE 2-continued
| Bromo derivative | Amine derivative | Product Preparative Example | 1. Yield 2. ¹H-NMR (CDCl₃) 3. MH⁺ (ESI) |
|---|---|---|---|
|  | 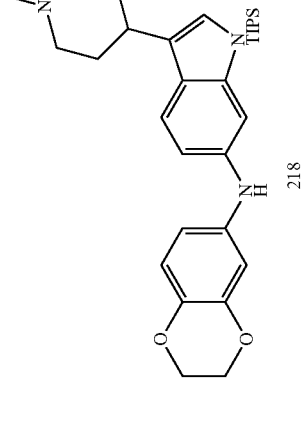 | 218 | 1. 82% 2. 520.74 |
| 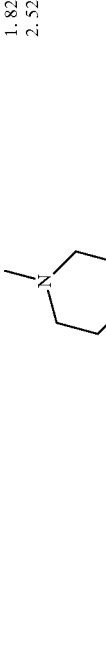 | 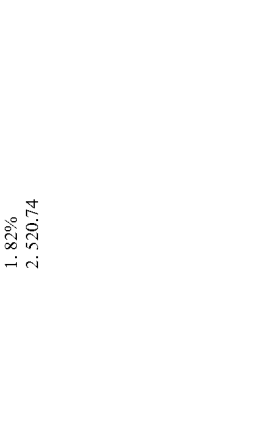 | 219 | 1. 88% 2. 617.70 |
|  | 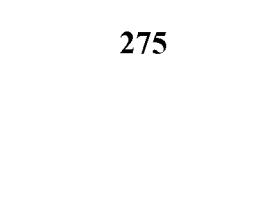 | 220 | 1. 71% 2. 480.73 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 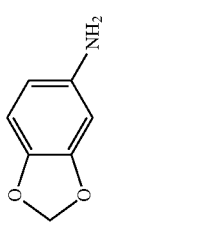 | 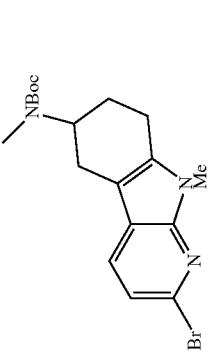 | 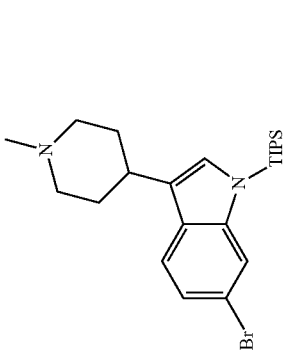 221 | 1. 67% 2. 516.73 |
| 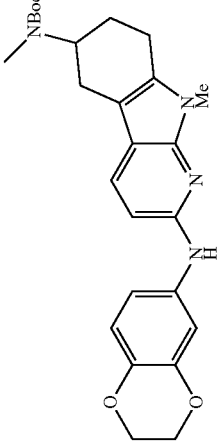 | 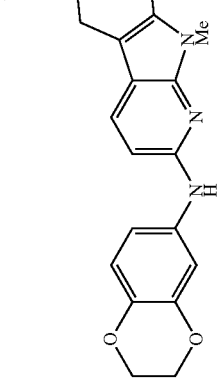 | 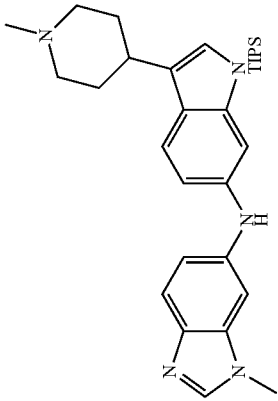 222 | 1. 109% 2. 464.56 |
| 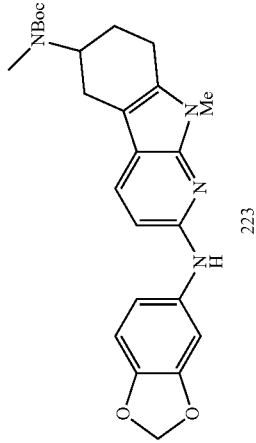 | 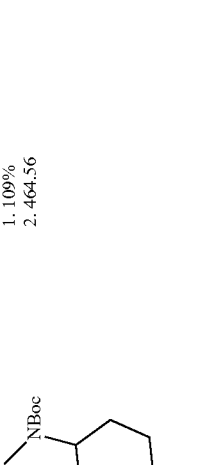 | 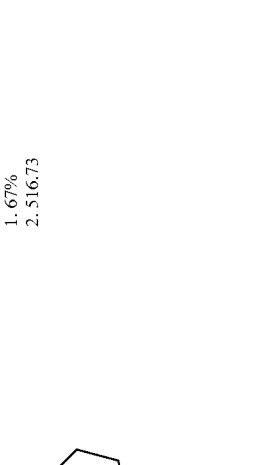 223 | 1. 95% 2. 451.60 |

TABLE 2-continued

| Bromo derivative | Amine derivative | Product Preparative Example | 1. Yield  2. ¹H-NMR (CDCl₃)  3. MH⁺ (ESI) |
|---|---|---|---|
| (bromo pyridoindole with NBoc) | (tetrahydroisoquinoline, N-Me, NH₂) | 224 | 1. 85%  2. 476.71 |
| (bromo pyridoindole with NBoc) | (N-methylbenzimidazole-NH₂) | 225 | 1. 92%  2. 461.73 |
| (bromo pyridoindole with NBoc) | (3-methoxy-4-methylaniline) | 226 | 1. 97%  2. 451.71 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (7-bromo, N-methyl tetrahydro-β-carboline-NCOOEt) | 3,4-difluoroaniline | 227 | 1. 29% 2. 1.31 (t, J = 7.2 Hz, 3H); 2.86 (t, J = 6.0 hz, 2H); 3.65 (s, 3H); 3.89 (t, J = 6.0 hz, 2H); 4.20 (q, J = 7.2 hz, 2H); 4.63 (s, 2H); 6.58–6.67 (m, 1H); 6.67–6.78 (m, 1H); 6.92–7.07 (m, 2H); 7.16 (d, J = 1.6 Hz, 1H); 7.30 (d, J = 8.8 hz, 1H) 3. 386.70 |
| (7-bromo, N-methyl tetrahydro-β-carboline-NCOOEt) | 2,3-dihydro-1,4-benzodioxin-6-amine | 228 | 1. 69% 2. 408.75 |
| (7-bromo, N-methyl tetrahydro-β-carboline-NCOOEt) | 2,3-dihydro-1,4-benzodioxin-6-amine | 229 | 1. 44% 2. 408.70 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 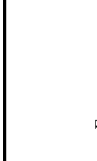 | 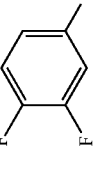 |  230 | 1. 66% 2. 386.76 |
|  | 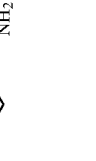 | 232 | 1. 79% 2. 1.22 (s, 3H); 1.24 (s, 3H); 1.87-2.03 (m, 1H); 2.12-2.24 (m, 1H); 2.61 (dd, J1 = 8.0 Hz, J2 = 14.8 Hz, 1H); 2.69-2.83 (m, 1H); 2.89 (dt, J1 = 5.2 Hz, J2 = 16.4 Hz, 1H); 3.04 (dd, J1 = 4.8 Hz, J2 = 14.8 Hz, 1H); 3.65 (s, 3H); 3.79-3.93 (m, 2H); 4.23-4.36 (m, 4H); 6.22 (sl, 1H); 6.54 (d, J = 8.0 Hz, 1H); 6.78-6.90 (m, 2H); 7.10-7.19 (m, 1H); 7.55 (d, J = 8.4 Hz, 1H) 3. 394.70 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (6-methoxy-9-methyl-2-bromo-tetrahydropyrido[2,3-b]indole) | 4-morpholinoaniline | 233 | 1. 93% 2. 1.75-1.91 (m, 1H); 2.02-2.16 (m, 1H); 2.42-2.50 (m, 1H); 2.63-2.84 (m, 2H); 2.93 (dd, J1 = 4.8 Hz, J2 = 15.2 Hz, 1H); 3.01 (t, J = 4.4 Hz, 4H); 3.33 (s, 3H); 3.57 (s, 3H); 3.60-3.69 (m, 1H); 3.73 (t, J = 4.4 Hz, 4H); 6.47 (d, J = 8.4 Hz, 1H); 6.89 (d, J = 8.8 Hz, 2H); 7.54 (d, J = 8.4 Hz, 1H); 7.66 (d, J = 8.8 Hz, 2H); 8.60 (s, 1H). 3. 393.70 |
| (6-(trideuteromethoxy)-9-methyl-2-bromo-tetrahydropyrido[2,3-b]indole) | 2,3-dihydro-1,4-benzodioxin-6-amine | 234 | 1. 56% 2. 1.95-2.06 (m, 1H); 2.12-2.25 (m, 1H); 2.60-2.80 (m, 2H); 2.81-2.93 (m, 1H); 3.04 (dd, J1 = 4.8 Hz, J2 = 14.8 Hz, 1H); 3.65 (s, 3H); 3.69-3.79 (m, 1H); 4.21-4.34 (m, 4H); 6.22 (s, 1H); 6.54 (d, J = 8.4 Hz, 1H); 6.77-6.89 (m, 2H); 7.13 (d, J = 2.0 Hz, 1H); 7.55 (d, J = 8.4 Hz, 1H). 3. 369.70 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 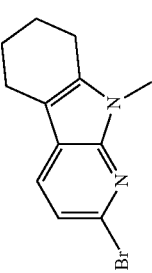 | 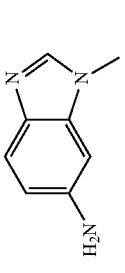 | 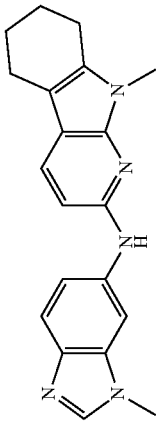 235 | 1. 62% 2. 1.70-1.94 (m, 4H); 2.54-2.62 (m, 2H); 2.64-2.75 (m, 2H); 3.65 (s, 3H); 3.80 (s, 3H); 6.57 (d, J = 8.4 Hz, 1H); 7.20 (dd, J1 = 2.0 Hz, J2 = 8.8 Hz, 1H); 7.49 (d, J = 8.4 Hz, 1H); 7.58 (d, J = 8.0 Hz, 1H); 7.99 (s, 1H); 8.59 (d, J = 2.0 hz, 1H); 8.95 (s, 1H) 3. 332.74 |
| 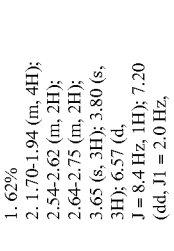 | 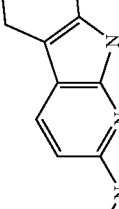 | 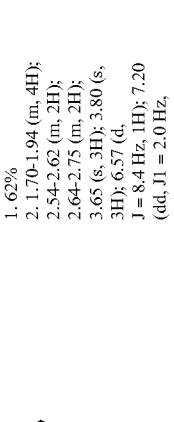 236 | 1. 80% 2. 1.79-2.03 (m, 4H); 2.49 (s, 3H); 2.62-2.77 (m, 5H); 2.91 (t, J = 6.0 Hz, 2H); 3.47 (s, 1H); 3.60 (s, 2H); 3.65 (s, 3H); 6.35 (sl, 1H); 6.60 (d, J = 8.4 hz, 1H); 7.05 (d, J = 8.0 Hz, 1H); 7.13-7.24 (m, 2H); 7.58 (d, J = 8.0 hz, 1H) 3. 347.77 |
| 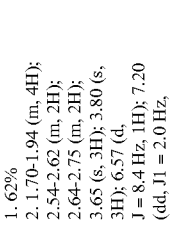 | 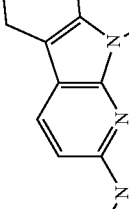 | 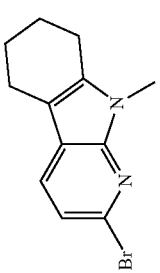 237 | 1. 48% 2. 2.33-2.52 (m, 2H); 2.72-2.93 (m, 4H); 3.67 (s, 3H); 4.15-4.33 (m, 4H); 6.17 (s, 1H); 6.62 (d, J = 8.4 Hz, 1H); 6.73-6.86 (m, 2H); 7.10 (d, J = 2.0 Hz, 1H); 7.50 (d, J = 8.4 Hz, 1H) 3. 322.73 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 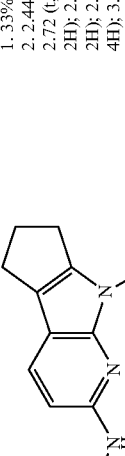 | 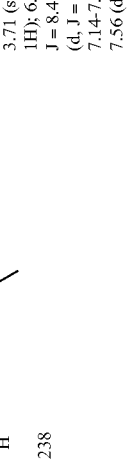 | 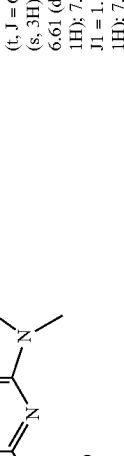 238 | 1. 33% 2. 2.44-2.54 (m, 5H); 2.72 (t, J = 6.0 Hz, 2H); 2.80-2.86 (m, 2H); 2.86-2.94 (m, 4H); 3.60 (s, 2H); 3.71 (s, 3H); 6.31 (sl, 1H); 6.60 (d, J = 8.4 hz, 1H); 7.06 (d, J = 8.4 Hz, 1H); 7.14-7.25 (m, 2H); 7.56 (d, J = 8.4 hz, 1H) 3. 333.77 |
| 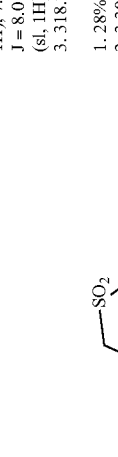 | 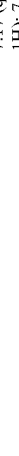 | 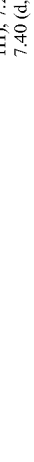 239 | 1. 28% 2. 2.49 (p, J = 6.8 Hz, 2H); 2.82 (t, J = 6.8 Hz, 2H); 2.90 (t, J = 6.8 hz, 2H); 3.76 (s, 3H); 3.90 (s, 3H); 6.61 (d, J = 8.4 Hz, 1H); 7.27 (dd, J1 = 1.2 Hz, J2 = 8.4 Hz, 1H); 7.56 (t, J = 8.0 Hz, 2H); 8.03 (sl, 1H); 8.44 (sl, 1H) 3. 318.73 |
| | | 240 | 1. 28% 2. 3.30 (sl, 2H); 3.50 (sl, 2H); 3.65 (s, 3H); 4.45 (s, 2H); 6.60 6.71 (m, 1H); 6.73-6.86 (m, 1H); 6.95 (d, J = 7.6 Hz, 1H); 7.17 (q, J = 9.2 Hz, 1H); 7.21 (s, 1H); 7.40 (d, J = 7.6 Hz, 1H); 7.98 (sl, 1H) 3. 363.73 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (bromo-N-methyl tetrahydrothiopyrano-indole SO₂) | benzodioxin-NH₂ | 241 | 1. 45% 2. 3.28 (t, J = 6.4 Hz, 2H); 3.49 (t, J = 6.4 Hz, 2H); 3.63 (s, 3H); 4.14 (d, J = 5.2 Hz, 2H); 4.17 (d, J = 5.2 Hz, 2H); 4.39 (s, 2H); 6.41-4.50 (m, 2H); 6.67 (d, J = 9.2 Hz, 1H); 6.88 (dd, J1 = 2.0 hz, J2 = 8.8 Hz, 1H); 7.07 (d, J = 2.0 hz, 1H); 7.32 (d, J = 8.8 hz, 1H); 7.50 (sl, 1H) 3. 385.71 |
| (same bromo) | 3-methoxy-4-methyl-aniline | 242 | 1. 69% 2. 2.03 (s, 3H); 3.28 (t, J = 6.4 Hz, 2H); 3.49 (t, J = 6.4 Hz, 2H); 3.64 (s, 3H); 3.69 (s, 3H); 4.40 (s, 2H); 6.44 (dd, J1 = 2.0 Hz, J2 = 8.0 Hz, 1H); 6.55 (d, J = 2.0 Hz, 1H); 6.87 (d, J = 8.0 Hz, 1H); 6.94 (dd, J1 = 2.0 hz, J2 = 8.8 Hz, 1H); 7.17 (d, J = 2.0 Hz, 1H); 7.34 (d, J = 8.4 Hz, 1H); 7.71 (s, 1H) 3. 371.72 |
| (same bromo) | 6-trifluoromethyl-pyridin-3-amine | 243 | 1. 71% 2. 3.42 (t, J = 6.0 Hz, 2H); 3.48 (t, J = 6.0 Hz, 2H); 3.72 (s, 3H); 4.40 (s, 2H); 7.11 (dd, J1 = 2.0 Hz, J2 = 8.4 Hz, 1H); 7.27-7.36 (m, 2H); 7.40 (d, J = 8.8 Hz, 1H); 7.49 (d, J = 8.8 Hz, 1H); 8.20 (d, J = 2.8 Hz, 1H) 3. 396.67 |

TABLE 2-continued

| Bromo derivative | Amine derivative | Product Preparative Example | 1. Yield<br>2. ¹H-NMR (CDCl₃)<br>3. MH⁺ (ESI) |
|---|---|---|---|
| 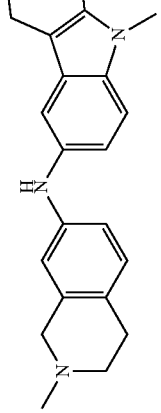 | 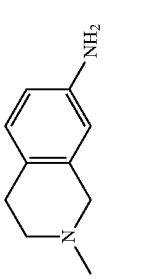 | 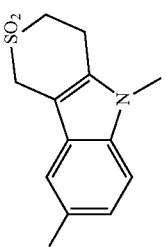<br>244 | 1. 67%<br>2. 2.43 (s, 3H); 2.73 (t, J = 6.0 Hz, 2H); 2.85 (t, J = 6.0 Hz, 2H); 3.37 (t, J = 6.0 Hz, 2H); 3.45 (t, J = 6.0 Hz, 2H); 3.51 (s, 2H); 3.66 (s, 3H); 4.33 (s, 2H); 6.66 (s, 1H); 6.80 (dd, J1 = 2.0 Hz, J2 = 8.0 hz, 1H); 6.94 (d, J = 8.4 Hz, 1H); 7.01 (dd, J1 = 1.6 Hz, J2 = 8.4 Hz, 1H); 7.08-7.15 (m, 1H); 7.27 (d, J = 8.8 hz, 1H)<br>3. 396.74 |
| 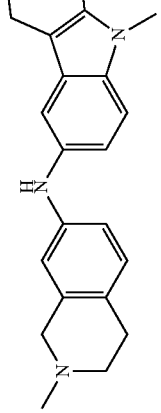 | 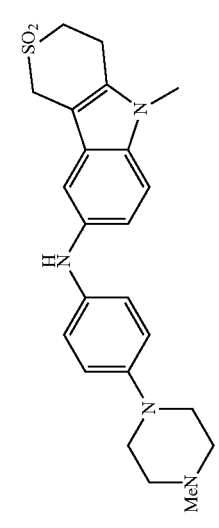 | 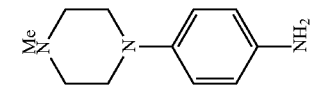<br>245 | 1. 14%<br>2. 3.40 (t, J = 6.0 Hz, 2H); 3.48 (t, J = 6.0 Hz, 2H); 3.71 (s, 3H); 3.94 (s, 3H); 4.39 (s, 2H); 7.05-7.16 (m, 2H); 7.23 (d, J = 8.8 Hz, 1H); 7.32 (s, 1H); 7.39 (d, J = 8.4 Hz, 1H); 7.58 (d, J = 8.4 Hz, 1H); 8.07 (s, 1H)<br>3. 381.70 |
| (same bromo derivative) | (Me-piperazinyl aniline) | (product 246) | 1. 67%<br>2. 2.22 (s, 3H); 2.45 (t, J = 4.8 Hz, 4H); 2.99 (t, J = 4.8 Hz, 4H); 3.27 (t, J = 6.4 Hz, 2H); 3.49 (t, J = 6.4 Hz, 2H); 3.62 (s, 3H); 4.38 (s, 2H); 6.78-6.84 (m, 2H); 6.84-6.94 (m, 3H); 7.05 (sl, 1H); 7.30 (d, J = 8.4 Hz, 1H); 7.46 (sl, 1H)<br>3. 425.72 |

TABLE 2-continued

| Bromo derivative | Amine derivative | Product Preparative Example | 1. Yield 2. ¹H-NMR (CDCl₃) 3. MH⁺ (ESI) |
|---|---|---|---|
| (bromo-tetrahydrothiopyrano-N-methyl-indole SO₂) | 5-amino-2-fluoropyridine | 247 | 1. 45% 2. 3.29 (t, J = 6.0 Hz, 2H); 3.50 (t, J = 6.0 Hz, 2H); 3.65 (s, 3H); 4.43 (s, 2H); 6.90-7.00 (m, 2H); 7.19 (d, J = 1.6 hz, 1H); 7.39 (d, J = 8.8 Hz, 1H); 7.44-7.52 (m, 1H); 7.79 (sl, 1H); 8.03 (s, 1H) 3. 346.77 |
| (same bromo derivative) | 4-morpholinoaniline | 248 | 1. 74% 2. 2.96 (t, J = 4.4 Hz, 4H); 3.27 (t, J = 6.0 Hz, 2H); 3.48 (t, J = 6.0 Hz, 2H); 3.62 (s, 3H); 3.72 (t, J = 4.4 Hz, 4H); 4.37 (s, 2H); 6.78-6.95 (m, 5H); 7.06 (sl, 1H); 7.30 (d, J = 8.8 hz, 1H); 7.48 (sl, 1H) 3. 412.69 |
| 5-bromo-benzo[1,3]dioxole | aniline | 249 | 1. 73% 2. 5.95 (s, 2H); 6.55 (dd, J1 = 2.0 Hz, J2 = 8.4 Hz, 1H); 6.69 (d, J = 2.0 Hz, 1H); 6.74 (t, J = 7.2 Hz, 1H); 6.81 (d, J = 8.4 Hz, 1H); 6.90-6.99 (m, 2H); 7.12-7.23 (m; 2H); 7.91 (sl, 1H) 3. 214.82 |

TABLE 2-continued
| Bromo derivative | Amine derivative | Product Preparative Example | 1. Yield<br>2. ¹H-NMR (CDCl₃)<br>3. MH⁺ (ESI) |
|---|---|---|---|
| 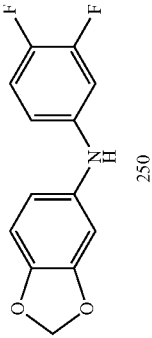 | 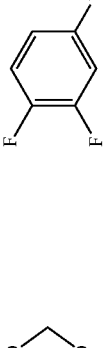 | 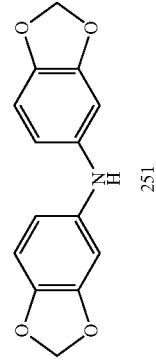<br>250 | 1. 54%<br>2. 5.95 (s, 2H), 6.52 (dd, J1 = 2.0 Hz, J2 = 8.0 Hz, 1H); 6.54-6.59 (m, 1H); 6.63 (d, J = 2.0 Hz, 1H); 6.68-6.75 (m, 1H); 6.75 (d, J = 6.0 Hz, 1H); 6.99 (q, J = 8.0 Hz, 1H)<br>3. 250.69 |
| 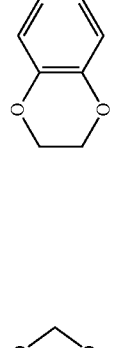 |  | 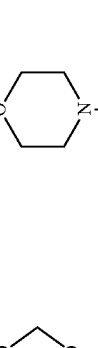<br>251 | 1. 60%<br>2. 5.92 (s, 4H), 6.42 (dd, J1 = 2.0 Hz, J2 = 8.4 Hz, 2H); 6.58 (d, J = 2.0 Hz, 2H); 6.77 (d, J = 8.4 Hz, 2H) (2 d overlap); 7.67 (sl, 1H)<br>3. 258.71 |
| | | 252 | 1. 66%<br>2. 2.99 (t, J = 4.8 Hz, 4H); 3.72 (t, J = 4.8 Hz, 4H); 5.91 (s, 2H); 6.40 (dd, J1 = 2.0 Hz, J2 = 8.0 Hz, 1H); 6.55 (d, J = 2.0 Hz, 1H); 6.74 (d, J = 8.0 Hz, 1H); 6.85 (d, J = 9.2 Hz, 2H); 6.92 (d, J = 9.2 Hz, 2H); 7.58 (s, 1H)<br>3. 299.71 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 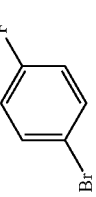 | 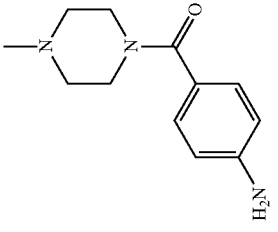 | 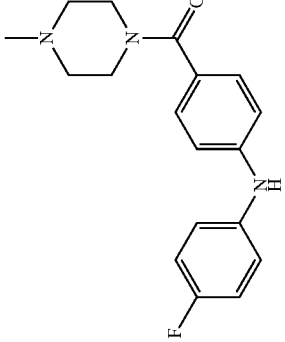 253 | 1. 69% 2. 2.35 (s, 3H); 2.43-2.55 (m, 4H); 3.60-3.75 (m, 4H); 6.98-7.09 (m, 4H); 7.12-7.21 (m, 2H); 7.32 (dt, J1 = 2.2 Hz, J2 = 8.8 Hz, 2H) 3. 314.75 |
| 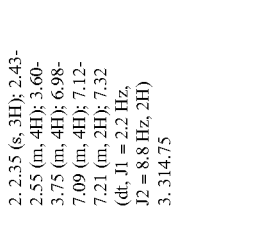 | 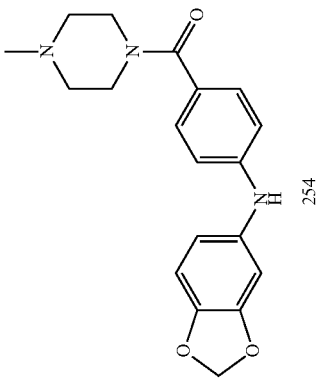 | 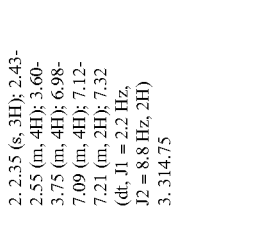 254 | 1. 76% 2. 2.34 (s, 3H); 2.42-2.54 (m, 4H); 3.58-3.76 (m, 4H); 5.93 (s, 2H); 6.64 (dd, J1 = 2.0 Hz, J2 = 8.0 Hz, 1H); 6.72 (d, J = 2.4 Hz, 1H); 6.77 (d, J = 8.4 Hz, 1H); 6.95 (d, J = 8.8 Hz, 2H); 7.29 (d, J = 8.8 Hz, 2H) 3. 340.70 |

TABLE 2-continued
| Bromo derivative | Amine derivative | Product Preparative Example | 1. Yield 2. ¹H-NMR (CDCl₃) 3. MH⁺ (ESI) |
|---|---|---|---|
| 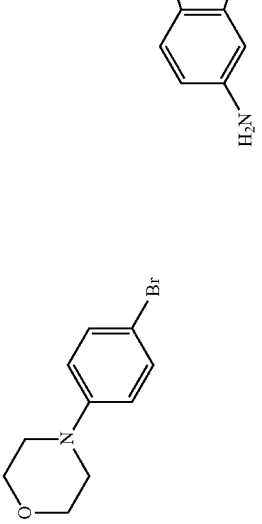 | 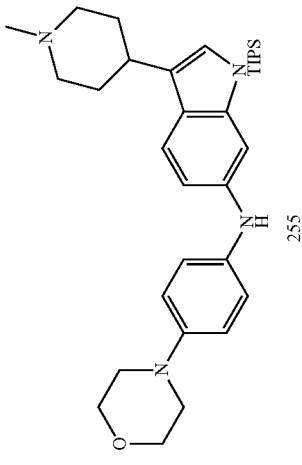 | 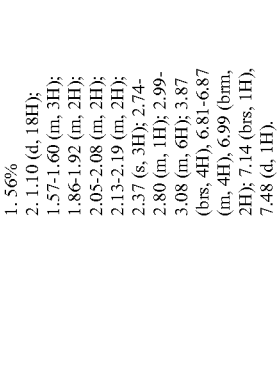 255 | 1. 56% 2. 1.10 (d, 18H); 1.57-1.60 (m, 3H); 1.86-1.92 (m, 2H); 2.05-2.08 (m, 2H); 2.13-2.19 (m, 2H); 2.37 (s, 3H); 2.74-2.80 (m, 1H); 2.99-3.08 (m, 6H); 3.87 (brs, 4H), 6.81-6.87 (m, 4H), 6.99 (bm, 2H); 7.14 (brs, 1H), 7.48 (d, 1H). 3. 547.66 |
| 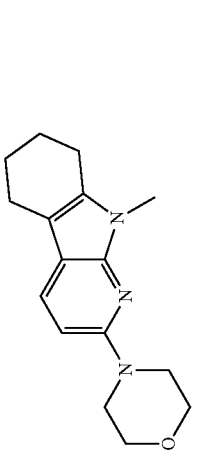 | | 256 | 1. 49% 2. 1.82-1.86 (m, 2H); 1.90-1.94 (m, 2H); 2.63-2.69 (m, 4H); 3.50-3.52 (m, 4H); 3.61 (s, 3H); 3.88-3.90 (m, 4H); 6.46 (d, 1H); 7.59 (d, 1H). |

Preparative Example 258

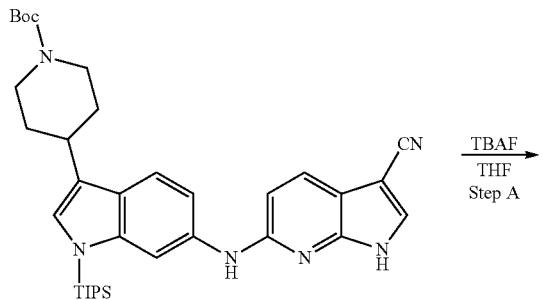

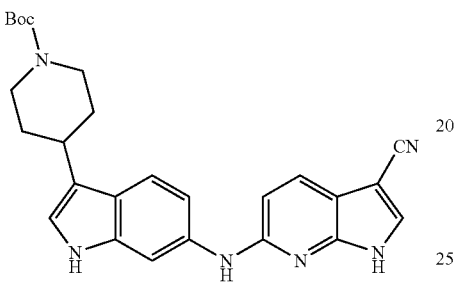

Step A

To a solution of the title compound from Preparative Example 66 (0.056 g, 0.091 mmol) in THF (1 mL) was added tetrabutylammonium fluoride (0.024 g, 0.091 mmol) and the reaction mixture was stirred at room temperature for 30 minutes. The reaction mixture was concentrated and the residue was purified on a silica gel column (25%-100% EtOAc/heptanes:isocratic mixture) to afford the title compound (0.026 g, 63%).

$^1$H-NMR (400 MHz, CDCl$_3$): δ=1.40 (s, 9H), 1.50 (m, 2H), 1.94 (m, 2H), 2.89 (m, 2H), 4.1 (m, 2H), 6.76 (d, 1H), 6.96 (d, 1H), 7.16 (dd, 1H), 7.43 (d, 1H), 7.94 (d, 1H), 8.96 (s, 1H), 10.5 (s, 1H), 12.2 (s, 1H)

Preparative Example 259

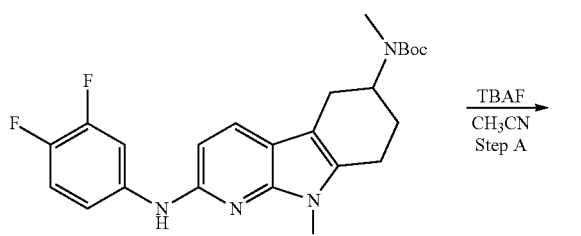

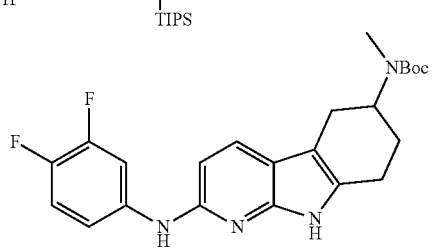

Step A

The title compound from Preparative Example 150 (0.049 g, 0.08 mmol) was dissolved in acetonitrile (1 mL) and dichloromethane (1 mL) and treated with a 1 M solution of tetrabutylammonium fluoride (0.1 mL, 0.1 mmol, 1.25 eq. per TIPS-group) in tetrahydrofurane. The mixture was stirred at room temperature for 1 h and the solvents were removed. The residue was purified by chromatography on silica using dichloromethane/acetone (95/5) to afford the title compound as a pale yellow glass (0.029 g, 82%).

$^1$H-NMR (400 MHz, CDCl$_3$): δ=1.49 (s, 3H), 1.94-2.08 (m, 2H), 2.70-2.95 (m, 7H), 4.25-4.56 (br-m, 1H), 6.33 (br-s, 1H), 6.56 (d, 1H), 6.92-7.03 (m, 1H), 7.06 (q, 1H), 7.55-7.66 (m, 2H), 8.04 (br-s, 1H)

Preparative Example 260

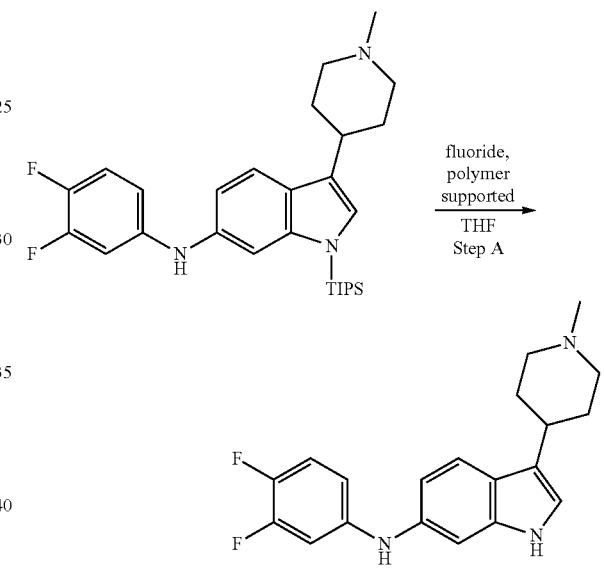

Step A

To a solution of the title compound from Preparative Example 82 (0.150 g, 0.3 mmol) in THF (5 mL) was added fluoride, polymer supported (Aldrich 387789) (0.4 g). The mixture was agitated overnight, filtered and the solvent was evaporated. The solvent was filtered off and concentrated, and the residue was purified on a silica gel column (methanol to dichloromethane; 5 to 15%) to afford the title compound (0.075 g, 73%).

$^1$H-NMR (400 MHz, DMSO-d$_6$): δ=1.66-1.69 (m, 2H), 1.89-1.92 (m, 2H), 1.99-2.04 (m, 2H), 2.20 (s, 3H), 2.63-2.69 (m, 1H), 2.84-2.87 (m, 2H), 6.72-6.77 (m, 2H), 6.85-6.90 (m, 1H), 6.96 (s, 1H), 7.07 (s, 1H), 7.20 (abq, 1H), 7.44 (d, 1H), 8.09 (s, 1H), 10.5 (s, 1H)

Preparative Examples 261 to 330

Following a procedure similar to that described in Preparative Examples 258(A), 259 (B), 260(C), except using the compounds from the Preparative Examples indicated in the table below, the following compounds were prepared.

TABLE 3

| Starting Material Preparative Example | Product Preparative Example | 1. Yield  2. ¹H-NMR (CDCl₃)  3. MH⁺ (ESI)  4. Deprotection |
|---|---|---|
| 151 | 261 | 1. 84%  2. δ = 1.50 (s, 9H), 1.96-2.05 (m, 2H), 2.70-2.95 (m, 7H), 4.25-4.55 (br-m, 1H), 6.60 (d, 1H), 6.70-6.76 (br-s, 1H), 7.60 (d, 1H), 7.63-7.67 (m, 1H), 8.11 (br-s, 1H), 8.29 (d, 1H), 8.72 (s, 1H)  4. B |
| 153 | 262 | 1. 83%  2. δ = 1.56 (s, 9H), 2.08-2.17 (m, 2H), 2.79-3.03 (m, 7H), 4.41-4.65 (m, 1H), 6.54 (br-s, 1H), 6.62 (d, 1H), 7.03-7.11 (m, 1H), 7.70 (d, 1H), 8.16 (br-s, 1H), 8.53-8.59 (m, 1H)  4. B |
| 157 | 263 | 1. 69%  2. δ = 1.51 (s, 18H), 1.94-2.07 (m, 4H), 2.65-3.00 (m, 12H), 4.15-4.55 (br-m, 3H). 6.50 (br-s, 1H), 6.63 8d, 1H), 6.89 (s, 1H), 7.00 (d, 1H), 7.52-7.57 (m, 2H), 7.95 (br-s, 1H), 8.22 (br-s, 1H)  4. B |
| 158 | 264 | 1. 74%  2. (CD₃OD) δ = 1.50 (s, 9H); 1.64 (dq, 3H); 2.05 (d, 2H); 2.9-3.1 (m, 3H); 3.88 (s, 3H); 4.20 (d, 2H); 6.74 (d, 1H); 6.93 (s, 1H); 7.09 (dd, 1H); 7.49 (d, 1H); 7.71 (s, 1H); 7.81 (d, 1H); 8.10 (d, 1H)  3. 490  4. B |
| 67 | 265 | 1. 83%  2. δ = 8.41 (d, 1H), 8.13 (d, 1H), 7.78 (d, 1H), 7.74 (d, 1H), 7.49 (s, 1H), 7.44 (s, 1H) 7.06 (s, 1H), 6.66 (d, 1H), 6.45 (d, 1H), 4.12-4.15 (m, 2H), 3.10-3.15 (s, 2H), 2.86-2.91 (m, 2H), 1.99-2.07 (m, 2H), 1.54-1.63 (m, 2H), 1.42 (s, 9H).  4. A |

TABLE 3-continued

| Starting Material Preparative Example | Product Preparative Example | 1. Yield  2. ¹H-NMR (CDCl₃)  3. MH⁺ (ESI)  4. Deprotection |
|---|---|---|
| 68 | 266 | 1. 63%  3. 487  4. A |
| 69 | 267 | 1. 64%  2. (DMSO-d₆): δ = 7.99 (s, 1H), 7.75 (s, 1H), 7.50 (d, 1H), 7.42 (d, 1H), 7.30 (d, 1H), 7.07 (dd, 1H), 6.96 (d, 1H), 6.94 (d, 1H), 6.83 (dd, 1H), 6.80 (d 1H), 4.23 (m, 4H), 2.90 (m, 4H), 2.06 (m, 4H), 1.66 (m, 4H), 1.51 (s, 9H), 1.49 (s, 9H).  3. 614  4. A |
| 159 | 268 | 1. 72%  4. B |
| 160 | 269 | 1. 57%  3. 437  4. B |

TABLE 3-continued
| Starting Material Preparative Example | Product Preparative Example | 1. Yield<br>2. $^1$H-NMR (CDCl$_3$)<br>3. MH$^+$ (ESI)<br>4. Deprotection |
|---|---|---|
| 161 | 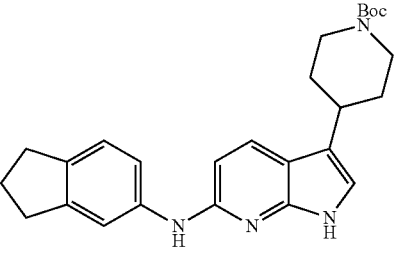<br>270 | 1. 74%<br>3. 433<br>4. B |
| 162 | 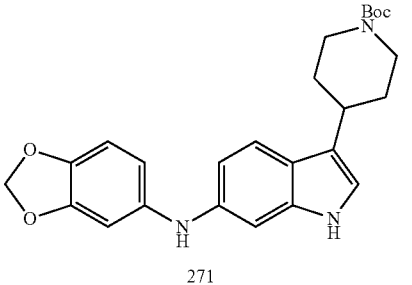 [SMILES: CC(C)(C)OC(=O)N1CCC(c2c[nH]c3cc(Nc4ccc5c(c4)OCO5)ccc23)CC1]<br>271 | 1. 58%<br>3. 436<br>4. B |
| 176 | 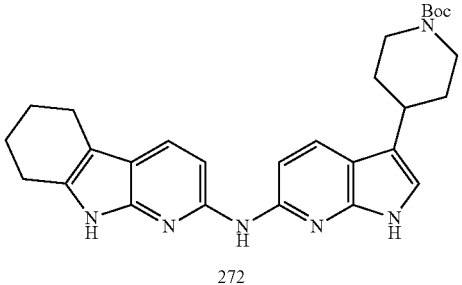 [SMILES: CC(C)(C)OC(=O)N1CCC(c2c[nH]c3nc(Nc4ccc5c6c([nH]c5n4)CCCC6)ccc23)CC1]<br>272 | 1. 97%<br>3. 487<br>4. B |
| 70 | 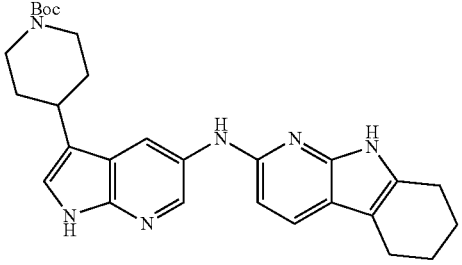<br>273 | 1. 35%<br>3. 387<br>4. A |
| 71 | 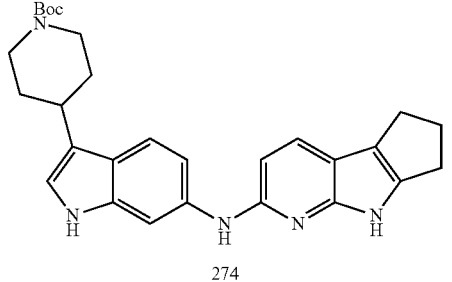 [SMILES: CC(C)(C)OC(=O)N1CCC(c2c[nH]c3cc(Nc4ccc5c6c([nH]c5n4)CCC6)ccc23)CC1]<br>274 | 1. 59%<br>2. δ = 8.56 (s, 1H), 7.96 (s, 1H), 7.53-7.58 (m, 2H), 6.98 (d, 1H), 6.88 (s, 1H), 6.64 (d, 1H), 6.53 (s, 1H), 4.24-4.25 (m 2H), 2.91-2.96 (m 4H), 2.77-2.85 (m, 4H), 2.45-2.48 (m, 2H), 1.67-1.69 (m 2H), 1.51 (s, 9H).<br>4. A |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 72 | 275 | 1. 36%<br>2. δ = 8.38 (brs, 1H), 7.97 (brs, 1H), 7.69 (s, 1H), 7.53 (d, 1H), 7.33 (d, 1H), 7.15 (d, 1H), 6.97 (s, 1H), 6.54 (d, 1H), 6.37 (s, 1H), 4.23-4.25 (m, 2H), 2.78-2.94 (m, 7H), 2.45-2.49 (m, 2H), 2.01-2.04 (m, 2H), 1.76-1.79 (m, 2H), 1.49 (s, 9H).<br>4. A |
| 165 | 276 | 1. 67%<br>3. 615<br>4. B |
| 73 | 277 | 1. 86%<br>2. δ = 8.63 (d, 1H), 8.02 (s, 1H), 7.62 (d, 1H), 7.46 (d, 1H), 7.31 (d, 1H), 6.95-6.99 (m, 2H), 6.1 (brs, 1H), 4.25-4.28 (m, 2H), 2.89-2.99 (m, 3H), 2.04-2.08 (m, 2H), 1.67-1.71 (m, 2H), 1.51 (s, 9H).<br>4. A |
| 166 | 278 | 1. 52%<br>3. 514<br>4. B |
| 74 | 279 | 1. 86%<br>2. δ = 9.51 (brs, 1H), 9.34 (brs, 1H), 8.3 (brs, 1H), 7.57 (d, 1H), 6.86 (s, 1H), 6.49 (s, 1H), 6.47 (s, 1H), 4.11-4.18 (m, 2H), 2.76-2.85 (m, 9H), 2.44-2.47 (m, 2H) 1.86-1.89 (m, 2H), 1.48 (s, 9H).<br>4. A |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 75 | 280 | 1. 70%<br>2. δ = 7.91 (s, 1H), 7.52 (d, 1H), 7.10 (s, 1H), 6.98-6.99 (m, 1H), 6.83-6.89 (m, 2H), 6.65 (m, 1H), 4.23-4.25 (m, 2H), 2.89-2.95 (m, 3H), 2.01-2.17 (m, 2H), 1.68-1.71 (m, 2H), 1.48 (s, 9H).<br>4. A |
| 76 | 281 | 1. 90%<br>2. δ = 7.99 (brs, 1H), 7.39 (brs, 1H), 7.34 (d, 1H), 6.98-7.03 (m, 4H), 6.69-6.72 (m, 1H), 6.55-6.57 (m, 1H), 4.22-4.26 (m, 2H), 2.86-2.93 (m, 3H), 2.01-2.05 (m, 2H), 1.58-1.70 (m, 2H), 1.50 (s, 9H).<br>3. 430<br>4. A |
| 77 | 282 | 1. 90%<br>2. δ = 8.47 (brs, 1H), 8.26 (s, 1H), 7.41-7.44 (m, 2H), 7.35 (d, 1H), 7.14 (d, 1H), 7.00-7.04 (m, 2H), 6.12 (s, 1H), 4.21-4.22 (m, 2H), 2.87-2.91 (m, 3H), 1.97-12.0 (m, 2H), 1.61-1.64 (m, 2H), 1.48 (s, 9H).<br>4. A |
| 79 | 283 | 1. 60%<br>2. δ = 7.74 (brs, 1H), 7.47 (d, 1H), 7.45 (s, 1H), 7.24 (d, 1H), 7.09 (d, 1H), 6.97 (s, 1H), 6.81-6.84 (m, 2H), 4.22-4.23 (m, 4H), 3.73 (s, 3H), 2.87-2.94 (m, 6H), 1.99-2.07 (m, 4H), 1.61-1.71 (m, 6H), 1.51 (s, 9H), 1.49 (s, 9H).<br>3. 628<br>4. A |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 167 | 284 | 1. 68%<br>3. 429<br>4. B |
| 168 | 285 | 1. 72%<br>3. 462<br>4. B |
| 164 | 286 | 1. 84%<br>2. δ = 1.49 (s, 9H), 1.65 (m, 2H), 2.01-2.04 (m, 2H), 2.86-2.96 (m, 3H), 3.1 (m, 4H), 3.81 (M, 4H), 4.22 (brs, 2H), 6.44 (d, 1H), 6.55 (d, 1H), 6.60 (s, 1H), 6.84 (s, 1H), 6.89 (d, 1H), 7.10-7.14 (m, 2H), 7.51 (d, 1H), 8.04 (brs, 1H).<br>3. 477<br>4. B |
| 169 | 287 | 1. 61%<br>3. 614<br>4. B |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 83 | 288 | 1. 92%<br>3. 528<br>4. C |
| 170 | 289 | 1. 98%<br>2. 391<br>4. C |
| 81 | 290 | 1. 92%<br>2. δ = 8.23 (s, 1H), 7.39 (s, 1H), 7.32 (d, 1H), 6.94-7.01 (m, 3H), 6.68 (ddd, 1H), 6.52-6.54 (m, 1H), 5.58 (s, 1H), 2.99 (d, 2H), 2.74-2.80 (m, 1H), 2.36 (s, 3H), 2.14 (t, 2H), 2.03 (d, 2H), 1.84-1.91 (m 2H).<br>4. C |
| 171 | 291 | 1. 83%<br>3. 433<br>4. B |

TABLE 3-continued
| Starting Material Preparative Example | Product Preparative Example | 1. Yield  2. ¹H-NMR (CDCl₃)  3. MH⁺ (ESI)  4. Deprotection |
|---|---|---|
| 85 | 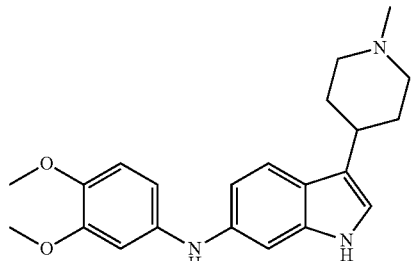  292 | 1. 73%  2. δ = 8.00 (s, 1H), 7.51 (d, 1H), 7.01 (d, 1H), 6.86 (d, 1H), 6.83 (d, 1H), 6.79 (d, 1H), 6.71 (d, 1H), 6.63 (dd, 1H), 5.55 (s, 1H), 3.87 (s, 3H), 3.83 (s, 3H), 3.06 (m, 2H), 2.82 (ttt, 1H), 2.43 (s, 3H), 2.32-2.87 (t, 2H), 2.07-2.10 (m, 2H), 1.93-2.00 (m, 2H).  3. 366  4. C |
| 84 | 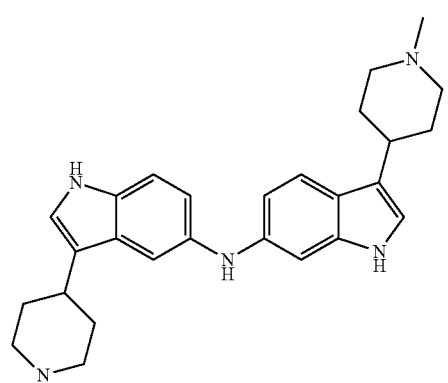  293 | 1. 43%  3. 528  4. C |
| 174 | 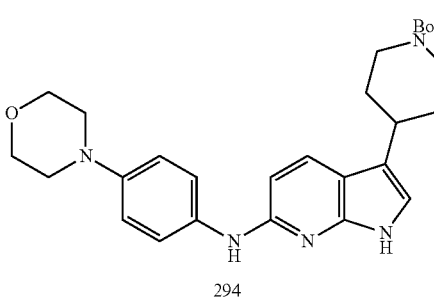  294 | 1. 81%  3. 478  4. A |
| 87 | 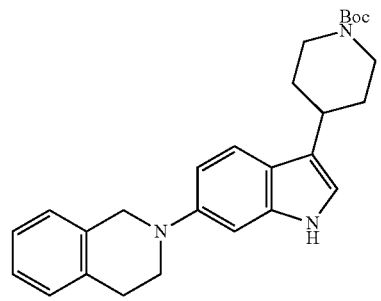  295 | 1. 41%  3. 433  4. A |

TABLE 3-continued

| Starting Material Preparative Example | Product Preparative Example | 1. Yield  2. ¹H-NMR (CDCl₃)  3. MH⁺ (ESI)  4. Deprotection |
|---|---|---|
| 179 | 296 | 1. 56%  3. 477  4. A |
| 88 | 297 | 1. 80%  2. (DMSO-d₆): δ = 10.55 (s, 1H), 8.62 (s, 1H), 8.59 (s, 1H), 7.88 (m, 1H), 7.54 (d, 1H), 7.21 (d, 1H), 7.05 (d, 1H), 7.03 (s, 1H); 6.50 (d, 1H), 4.10-4.12 (m, 3H), 3.64 (s, 3H), 2.67-2.91 (m, 10H), 1.92-1.2.01 (m, 4H), 1.58-1.64 (m, 2H), 1.42 (s, 18H)  3. 629  4. A |
| 181 | 298 | 1. 56%  2. (CD₂Cl₂): δ = 1.71-1.82 (m, 1H), 2.14-2.17 (m, 1H), 2.37 (s, 6H), 2.53-2.58 (m, 1H), 2.73-2.84 (m, 4H), 3.01 (brm, 4H), 3.80 (brm, 4H), 5.48 (s, 1H), 6.80-6.82 (m, 3H), 6.90-6.92 (m, 2H), 7.09 (s, 1H), 7.15 (d, 1H), 8.09 (s, 1H).  3. 391.67  4. C |
| 182 | 299 | 1. 70%  4. C |

TABLE 3-continued
| Starting Material Preparative Example | Product Preparative Example | 1. Yield<br>2. $^1$H-NMR (CDCl$_3$)<br>3. MH$^+$ (ESI)<br>4. Deprotection |
|---|---|---|
| 183 | 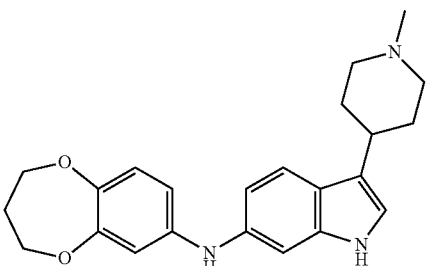<br>300 | 1. 99%<br>3. 378<br>4. C |
| 184 | 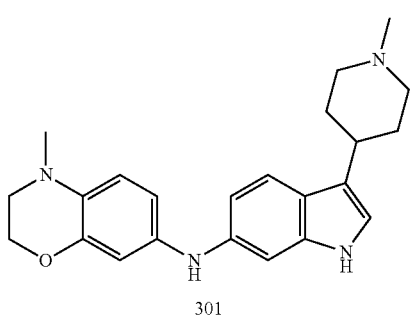 [SMILES: CN1CCC(c2c[nH]c3cc(Nc4ccc5c(c4)OCCN5C)ccc23)CC1]<br>301 | 1. 52%<br>3. 377<br>4. C |
| 185 | 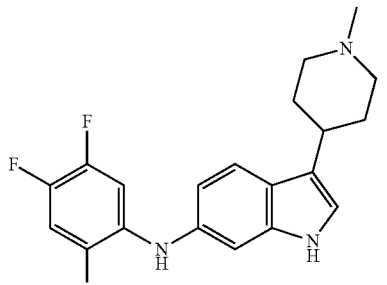<br>302 | 1. 86%<br>2. (CD$_2$Cl$_2$/MeOD): δ = 1.19 (s, 3H), 1.93-2.02 (m, 2H), 2.19-2.22 (m, 2H), 2.35-2.40 (m, 2H), 2.94-3.00 (m, 1H), 3.14-3.16 (m, 2H), 7.03 (d, 1H), 7.13 (m, 3H), 7.31 (brs, 1H), 7.72 (d, 1H).<br>3. 360<br>4. C |
| 193 | 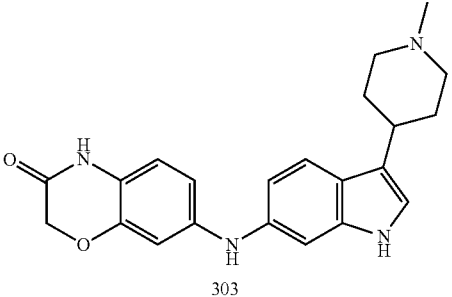<br>303 | 1. 31%<br>4. C |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 194 | 304 | 1. 67%<br>3. 366.78<br>4. C |
| 153 | 305 | 1. 83%<br>2. δ = 1.56 (s, 9H), 2.08-2.17 (m, 2H), 2.79-3.03 (m, 7H), 4.41-4.65 (m, 1H), 6.54 (br-s, 1H), 6.62 (d, 1H), 7.03-7.11 (m, 1H), 7.70 (d, 1H), 8.16 (br-s, 1H), 8.53-8.59 (m, 1H)<br>4. B |
| 89 | 306 | 1. 73%<br>2. ¹H-NMR (400 MHz, CDCl₃): δ = 8.00 (s, 1H), 7.51 (d, J = 8.4 Hz, 1H), 7.01 (d, J = 1.6 Hz, 1H), 6.86 (d, J = 1.6 Hz, 1H), 6.83 (d, J = 2.0 Hz, 1H), 6.79 (d, J = 8.4 Hz, 1H), 6.71 (d, J = 2.4 Hz, 1H), 6.63 (dd, J = 2.4 Hz, J = 8.4 Hz, 1H), 5.55 (s, 1H), 3.87 (s, 3H), 3.83 (s, 3H), 3.06 (m, 2H), 2.82 (ttt, 1H), 2.43 (s, 3H), 2.32-2.87 (t, J = 10.4 Hz, 2H), 2.07-2.10 (m, 2H), 1.93-2.00 (m, 2H).<br>4. C |
| 90 | 307 | 1. 80%<br>4. C |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 91 | 308 | 1. 43%<br>2. ¹H-NMR (400 MHz, CDCl₃): δ = 8.0 (s, 1H), 7.88 (s, 1H), 7.47 (d, 1H), 7.41 (s, 1H), 7.30 (d, 1H), 7.05 (d, 1H), 6.94 (d, 1H), 6.82 (s, 1H), 5.64 (brs, 1H), 4.22-4.24 (m, 2H), 3.26-3.28 (m, 2H), 2.87-2.93 (m, 5H), 2.48-2.58 (m, 5H), 2.15-2.20 (m, 2H), 2.00-2.03 (m, 2H), 1.66-1.69 (m, 2H), 1.49 (s, 9H).<br>4. C |
| 92 | 309 | 1. 68%<br>2. (CDCl₃) δ 7.76 (s, 1H), 7.46-7.41 (m, 2H), 7.32-7.26 (m, 2H), 7.24-7.21 (m, 1H), 6.77 (s, 1H), 6.72 (s, 1H), 6.60 (d, 1H), 5.07 (t, 1H), 4.29-4.22 (m, 2H), 3.09-3.02 (m, 1H), 2.97-2.89 (m, 4H), 2.68-2.58 (m, 1H), 2.09-2.02 (m), 1.98 (dd, 1H), 1.77-1.62 (m), 1.52 (s).<br>4. A |
| 97 | 310 | 1. 55%<br>2. ¹H-NMR (400 MHz, CDCl₃) δ 8.01 (s, 1H), 7.55 (d, 1H), 7.06 (d, 1H), 6.90-6.81 (m, 2H), 6.79-6.69 (m, 1H), 5.56 (s, 1H), 3.87 (s, 3H), 3.02 (d, 2H), 2.83-2.77 (m, 1H), 2.38 (s, 3H), 2.19-2.06 (m, 2H), 2.13-2.06 (m, 2H), 1.92-1.85 (m, 2H).<br>4. C |
| 98 | 311 | 1. 77%<br>2. ¹H-NMR (400 MHz, DMSO-d₆) δ 10.58 (s), 7.48 (s, 1H), 7.24-722 (m, 1H), 7.01 (s, 1H), 6.83 (d, J = 8.8 Hz, 1H), 6.78 (d, J = 8.6 Hz, 1H), 6.65 (s, 1H), 6.46-6.42 (m, 1H), 3.68 (s, 3H), 3.67 (s, 3H), 2.85 (d, J = 10.6 Hz, 2H), 2.68-2.59 (m, 1H), 2.20 (s, 3H), 2.04-1.98 (m, 2H), 1.93-1.84 (m, 2H), 1.72-1.68 (m, 2H).<br>4. C |

TABLE 3-continued
| Starting Material Preparative Example | Product Preparative Example | 1. Yield<br>2. $^1$H-NMR (CDCl$_3$)<br>3. MH$^+$ (ESI)<br>4. Deprotection |
|---|---|---|
| 256 | 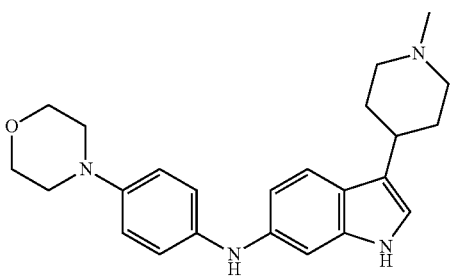<br>312 | 1. 50%<br>3. 391<br>4. A |
| 99 | 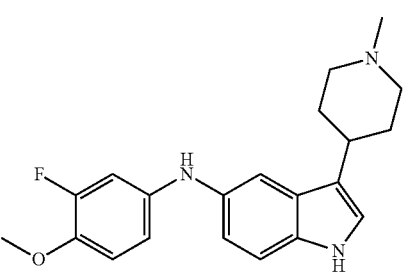<br>313 | 1.<br>3.<br>4. C |
| 100 | 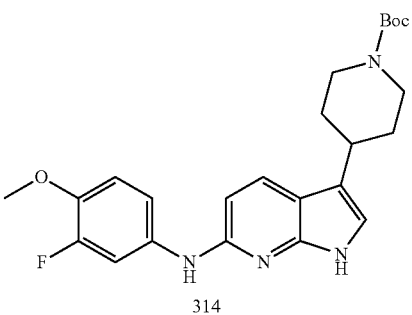<br>314 | 1. 76%<br>2. (CDCl$_3$) δ 8.28 (s, 1H), 7.77 (d, J = 8.5 Hz, 1H), 7.47-7.43 (m, 1H), 7.04 (d, J = 8.7 Hz, 1H), 6.96-6.92 (m, 1H), 6.77 (s, 1H), 6.54 (d, J = 8.5 Hz, 1H), 6.30 (s, 1H), 4.30-4.25 (m, 2H), 3.90 (s, 3H), 2.92-2.86 (m, 3H), 2.01 (d, J = 12.7 Hz, 2H), 1.68-1.66 (m, 2H), 1.51 (m, 9H).<br>4. A |
| 108 | 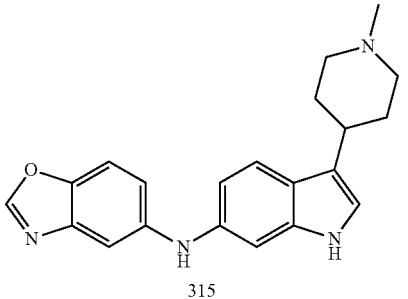<br>315 | 1. 55%<br>4. A |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 111 | 316 | 1. 80%<br>2. (CDCl₃) δ 7.97 (s, 1H), 7.62 (d, 1H), 7.15 (d, 1H), 6.98 (d, 1H), 6.88 (dd, 1H), 6.53 (dd, 2H), 5.68 (s, 1H), 3.03 (d, 2H), 2.89-2.72 (m, 1H), 2.39 (s, 3H), 2.21-2.07 (m, 4H), 1.93-1.85 (m, 2H).<br>4. C |
| 112 | 317 | 1. 73%<br>2. ¹H NMR (400 MHz, CDCl₃) δ 7.89 (s, 1H), 7.56 (d, J = 8.4 Hz, 1H), 7.09 (d, J = 1.8 Hz, 1H), 7.00-6.84 (m, 2H), 6.70 (dd, J = 7.4, 2.6 Hz, 1H), 6.57-6.51 (m, 1H), 5.60 (s, 1H), 3.84 (s, 3H), 3.14-3.11 (m, 2H), 2.88-2.82 (m, 1H), 2.46 (s, 3H), 2.30 (s, 2H), 2.13-2.10 (m, 2H), 2.04-1.98 (m, 2H).<br>4. C |
| 115 | 318 | 1. 73%<br>2. (CDCl₃): δ 8.15 (s, 1H), 7.58-7.56 (m, 2H), 7.04 (d, 1H), 6.89 (s, 1H), 6.63 (d, J = 8.4 Hz, 1H), 6.47 (s, 1H), 3.64 (s, 3H), 3.02 2.99 (m, 2H), 2.87-2.77 (m, 9H), 2.37 (s, 3H), 2.19-2.06 (m, 8H) 1.51 (s, 9H).<br>4. C |
| 116 | 319 | 1. 68%<br>2. ¹H-NMR (400 MHz, CDCl₃): δ = 7.48 (d, = 8.4 Hz, 2H), 7.4 (s, 2H), 6.97 (d, 2H), 6.94 (s, 2H), 6.77 (d, 2H), 3.49-3.46 (m, 4H), 3.13-3.07 (m, 4H), 2.98-2.97 (m, 2H), 2.12-2.11 (m, 4H), 1.94-1.87 (m, 4H).<br>4. C |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 117 | 320 | 1. 80%<br>2. (CDCl₃): δ = 8.06 (brs, 2H), 7.52 (d, 2H), 7.06 (s, 2H), 6.85 (d, 2H), 6.78 (s, 2H), 5.68 (s, 2H), 3.00-2.98 (m, 4H), 2.80-2.77 (m, 2H), 2.35 (s, 6H), 2.19-2.03 (m, 8H), 1.89-1.83 (m, 4H).<br>4. C |
| 208 | 321 | 4. A |
| 209 | 322 | 1. 83%<br>2. 432.60<br>4. A |
| 219 | 323 | 1. 77%<br>2. 461.75<br>4. A |
| 214 | 324 | 1. 71%<br>2. δ = 1.97-2.18 (m, 4H); 2.18-2.40 (m, 4H); 2.94 (s, 3H); 2.96 (s, 3H); 3.09-3.31 (m, 6H); 3.64 (t, J = 12.4 Hz, 4H); 3.89 (s, 3H); 6.73 (d, J = 8.8 Hz, 1H); 7.06-7.13 (m, 2H), 7.23 (s, 1H); 7.45-7.51 (m, 1H); 7.75-7.82 (m, 1H); 8.33 (d, J = 8.8 Hz, 1H)<br>3. 457.79<br>4. C |

TABLE 3-continued

| Starting Material Preparative Example | Product Preparative Example | 1. Yield<br>2. ¹H-NMR (CDCl₃)<br>3. MH⁺ (ESI)<br>4. Deprotection |
|---|---|---|
| 218 | 325 | 1. 51%<br>2. δ = 2.07 (dq, J1 = 2.8 Hz, J2 = 12.8 Hz, 2H); 2.29 (d, J = 14.0 Hz, 2H); 2.93 (s, 3H); 3.14-3.28 (m, 3H); 3.63 (d, J = 12.0 Hz, 2H); 4.28 (s, 4H); 6.88-7.04 (m, 4H); 7.08 (d, J = 8.0 Hz, 1H); 7.301 (s, 1H); 7.78-7.88 (m, 1H)<br>3. 364.74<br>4. C |
| 221 | 326 | 1. 76%<br>2. 2.07 (dq, J1 = 3.6 Hz, J2 = 13.2 Hz, 2H); 2.32 (d, J = 13.2 Hz, 2H); 2.93 (s, 3H); 3.10-3.28 (m, 3H); 3.56-3.69 (m, 2H); 3.96 (s, 3H); 6.97 (d, J = 8.4 Hz, 1H); 7.06 (s, 1H); 7.25 (s, 1H); 7.28 (s, 1H); 7.29 (d, J = 8.8 Hz, 1H); 7.61 (m, 2H); 9.10 (s, 1H)<br>3. 360.68<br>4. C |
| 220 | 327 | 1. 76%<br>2. 2.55-2.71 (m, 4H); 3.05 (s, 3H); 3.42-3.55 (m, 1H); 3.55-3.69 (m, 2H); 4.00 (d, J = 11.6 Hz, 2H); 7.30 (d, J = 8.4 Hz, 1H); 7.51 (s, 1H); 7.53-7.63 (m, 5H); 8.10 (d, J = 8.4 Hz, 1H); 11.18 (sl, 2H)<br>3. 324.73<br>4. C |
| 217 | 328 | 4. C |
| 66 | 329 | 4. A |

TABLE 3-continued

| Starting Material Preparative Example | Product Preparative Example | 1. Yield 2. ¹H-NMR (CDCl₃) 3. MH⁺ (ESI) 4. Deprotection |
|---|---|---|
| 211 | 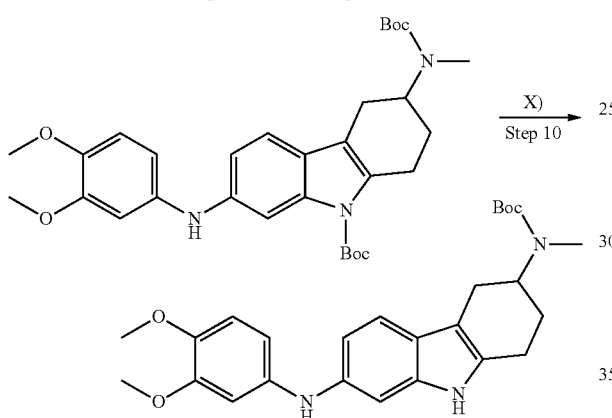<br>330 | 4. C |

Preparative Example 331

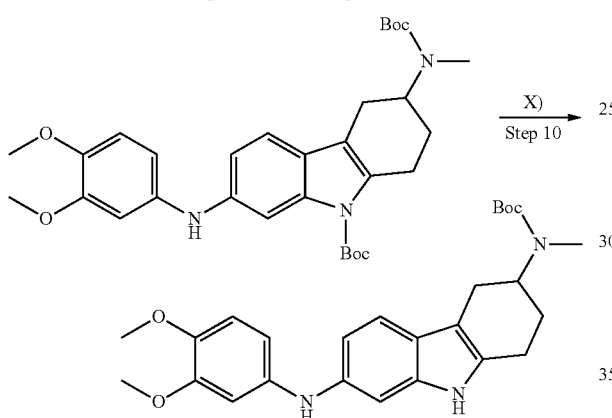

Preparative Example 332

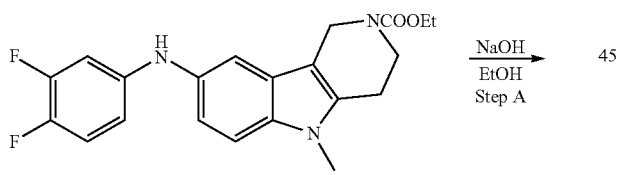

Step A

To a solution of the title compound from preparative example 227 (0.127 g, 0.330 mmol) in absolute ethanol (Volume: 10 ml) was added sodium hydroxide (0.132 g, 3.30 mmol). The resulting mixture was warmed by microwaves to 180° C. for 20 min. The solution was concentrated to dryness. The product was extracted with ethyl acetate and brine. The organic layers were collected, dried over Na₂SO₄, filtered and concentrated to dryness. The residue was purified by flash chromatography in DCM/MeOH to afford the title compound as a reddish solid (0.070 g, 68%).

MS (ESI); m/z=314.71 (MH⁺)

Preparative Examples 333 to 335

Following the deprotection procedure described in Preparative Example 332, except using the carbamate-derivatives indicated in the table below, the following compounds were prepared.

TABLE 4

| Starting Material Preparative Example | Product Preparative Example | 1. Yield (%) 2. MS ESI (MeOH) 3. 1H NMR (CDCl3) |
|---|---|---|
| 230 | 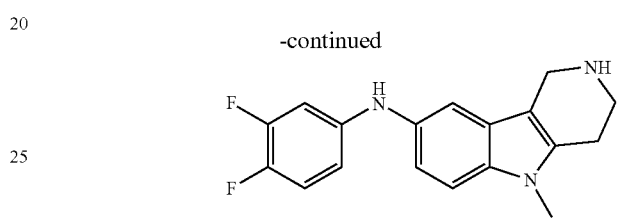<br>333 | 1. 94%<br>2. 314.81 |

TABLE 4-continued

| Starting Material Preparative Example | Product Preparative Example | 1. Yield (%) 2. MS ESI (MeOH) 3. 1H NMR (CDCl3) |
|---|---|---|
| 229 | 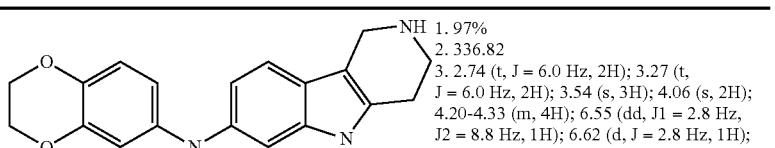 334 | 1. 97% 2. 336.82 3. 2.74 (t, J = 6.0 Hz, 2H); 3.27 (t, J = 6.0 Hz, 2H); 3.54 (s, 3H); 4.06 (s, 2H); 4.20-4.33 (m, 4H); 6.55 (dd, J1 = 2.8 Hz, J2 = 8.8 Hz, 1H); 6.62 (d, J = 2.8 Hz, 1H); 6.78 (d, J = 8.4 Hz, 1H); 6.81 (dd, J1 = 1.6 Hz, J2 = 10.0 Hz, 1H); 6.98 (d, J = 1.6 Hz, 1H); 7.30 (d, J = 8.4 Hz, 1H) |
| 228 | 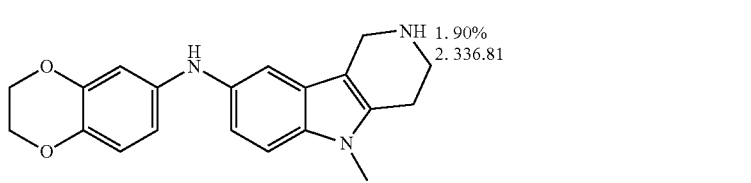 335 | 1. 90% 2. 336.81 |

Example 1

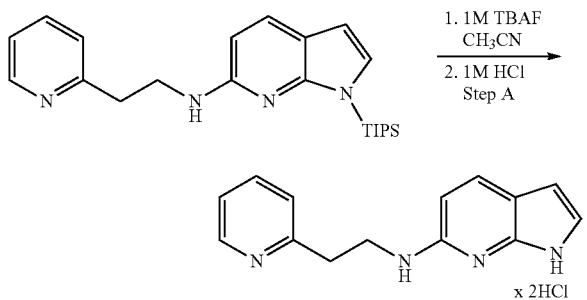

Step A

The title compound from Preparative Example 1 (0.048 g, 0.125 mmol) was dissolved/suspended in acetonitrile (1 mL) and treated with a 1 M solution of tetrabutylammonium fluoride (0.15 mL, 0.15 mmol) in tetrahydrofurane. The mixture was stirred at room temperature for 1 h and the solvents were removed. The residue was purified by PREP-TLC using ethyl acetate to afford the free base as an orange oil. This material was treated with a 1 M aqueous solution of hydrogen chloride (3 mL). The solvent was removed using a freeze dryer to afford the title compound as a pale yellow solid (0.028 g, 73%).

$^1$H-NMR (400 MHz, D$_2$O): δ=3.32 (t, 2H), 3.78 (t, 2H), 6.41-6.44 (m, 2H), 7.02 (d, 1H), 7.79 (t, 1H), 7.87 (d, 1H), 8.00 (d, 1H), 8.38 (t, 1H), 8.53 (d, 1H)

MS (ESI); m/z=239.83 (MH$^+$).

Examples 2 to 23

Following a similar procedure as that described in Example 1, except using the compounds from the Preparative Examples indicated in the table below, the following compounds were prepared. For preparative examples without TIPS-protecting group only the aqueous hydrogen chloride treatment was conducted. For Examples 19 to 23 polymer supported fluorine was used for the cleavage of the TIPS-protecting group.

All Example compounds below were obtained as their HCl-salts unless indicated otherwise.

TABLE 5

| Example | Preparative Example | Product | 1. Yield 2. $^1$H-NMR (DMSO-d$_6$/D$_2$O) 3. MH$^+$ (ESI) |
|---|---|---|---|
| 2 | 2 | 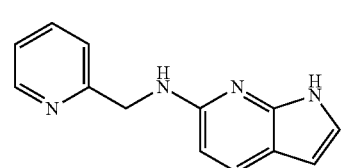 | 1. 67% 2. δ = 5.07 (s, 2H), 6.50-6.55 (m, 2H), 7.13 (s, 1H), 7.91 (t, 1H), 8.00 (d, 1H), 8.13 (d, 1H), 8.49 (t, 1H), 8.68 (d, 1H) 3. 224.91 |

TABLE 5-continued

| Example | Compound Preparative Example | Product | 1. Yield 2. ¹H-NMR (DMSO-d₆/D₂O) 3. MH⁺ (ESI) |
|---|---|---|---|
| 3 | 145 | 3,4-difluoro-N-(1H-pyrrolo[2,3-b]pyridin-6-yl)aniline | 1. 69% 2. δ = 6.30 (d, 1H), 6.59 (d, 1H), 7.10 (d, 1H), 7.26-7.30 (d, 2H), 7.78 (d, 1H), 8.14-8.21 (m, 1H) 3. 247.86 |
| 4 | 146 | N-(6-(trifluoromethyl)pyridin-3-yl)-1H-pyrrolo[2,3-b]pyridin-6-amine | 1. 66% 2. δ = 6.34 (d, 1H), 6.70 (d, 1H), 7.17 (d, 1H), 7.72 (d, 1H), 7.86 (d, 1H), 8.52 (dd, 1H), 8.99 (d, 1H) 3. 279.87 |
| 5 | 149 | N,N-dimethyl-4-(1H-pyrrolo[2,3-b]pyridin-6-ylamino)benzamide | 1. 63% 2. 2.98 (s, 6H), 6.33 (d, 1H), 6.68 (d, 1H), 7.12-7.14 (m, 1H), 7.36 (d, 2H), 7.78 (d, 2H), 7.85 (d, 1H) 3. 282.93 |
| 6 | 147 | 3,5-difluoro-N-(1H-pyrrolo[2,3-b]pyridin-6-yl)aniline | 1. 67% 2. δ = 6.32 (d, 1H), 6.58 (dt, 1H), 6.63 (d, 1H), 7.14 (d, 1H), 7.51-7.56 (m, 2H), 7.82 (d, 1H) 3. 247.87 |
| 7 | 148 | N,N-dimethyl-3-(1H-pyrrolo[2,3-b]pyridin-6-ylamino)benzamide | 1. 57% 2. δ = 2.93-3.00 (m, 6H), 6.33 (d, 1H), 6.66 (d, 1H), 6.89 (d, 1H), 7.10-7.12 (m, 1H), 7.33 (t, 1H), 7.72 (dd, 1H), 7.79-7.81 (m, 1H), 7.84 (d, 1H) |
| 8 | 47 | N-(1H-pyrrolo[2,3-b]pyridin-6-yl)-1H-pyrrolo[2,3-b]pyridin-6-amine free base | 1. 48% 2. (CD₃OD) δ = 6.49 (m, 1H); 6.69 (m, 2H); 7.40 (m, 2H); 7.80 (m, 1H); 8.11 (m, 2H) 3. 249.89 |
| 9 | 58 | N-(pyridin-2-yl)-1H-pyrrolo[2,3-b]pyridin-6-amine | 1. 74% 2. (DMSO-d₆): δ 8.37 (d, 1H), 8.18 (td, 1H), 8.12 (d, 1H), 7.54 (d, 1H), 7.44 (t, 1H), 7.25 (t, 1H), 7.0 (d, 1H), 6.91 (s, 1H), 6.48 (dd, 1H). |
| 10 | 59 | N-(4-fluorophenyl)-1H-pyrrolo[2,3-b]pyridin-6-amine | 1. 64% 2. (DMSO-d₆): δ = 11.18 (s, 1H), 8.91 (s, 1H), 7.79 (d, 1H), 7.78 (d, 1H), 7.73 (d, 1H), 7.06-7.10 (m, 3H), 6.55 (d, 1H), 6.26 (m, 1H) |

TABLE 5-continued

| Example | Compound Preparative Example | Product | 1. Yield<br>2. ¹H-NMR (DMSO-d₆/D₂O)<br>3. MH⁺ (ESI) |
|---|---|---|---|
| 11 | 60 | (7-azaindole–NH–7-azaindole) | 1. 73%<br>2. (DMSO-d₆): δ = 12.4 (s, 1H), 11.3 (s, 1H), 8.84 (s, 1H), 8.70 (s, 1H), 7.93 (d, 1H), 7.66 (t, 1H), 7.14 (t, 1H), 6.71 (d, 1H), 6.67 (m, 1H), 6.63 (dd, 1H) |
| 12 | 61 | (indole–NH–7-azaindole) | 1. 50%<br>3. 248.9 |
| 13 | 57 | (4-azaindole–NH–7-azaindole) | 1. 71%<br>3. 250 |
| 14 | 63 | (3,5-difluorophenyl–NH–4-azaindole) | 1. 81%<br>2. 246 |
| 15 | 64 | (4-fluorophenyl–NH–3-cyano-7-azaindole) | 1. 73%<br>3. 252 |
| 16 | 65 | (indole–NH–indole) | 1. 54%<br>3. 248 |
| 17 | 177 | (indole–NH–6-azaindole) | 1. 84%<br>2. (DMSO-d₆): δ = 6.30 (s, 2H); 6.80 (dd, 2H); 7.05–7.18 (m, 4H), 7.37 (d, 2H); 7.68 (s, 1H); 10.71 (s, 2H) |
| 18 | 62 | (indole–NH–7-azaindole) | 1. 58%<br>3. 248 |

TABLE 5-continued

| Example | Compound Preparative Example | Product | 1. Yield  2. ¹H-NMR (DMSO-d₆/D₂O)  3. MH⁺ (ESI) |
|---|---|---|---|
| 19 | 292 | (3,4-dimethoxyphenyl)-NH-(6-indolyl), 3-(1-methylpiperidin-4-yl) | 1. 62%  2. (DMSO-d₆) δ = 10.5 (s, 1H) 7.49 (d, 1H), 7.02 (d, 1H), 6.93 (s, 1H), 6.82 (d, 1H), 6.75 (dd, 1H), 6.70 (d, 1H), 6.59 (dd, 1H), 3.71 (s, 3H), 3.69 (s, 3H), 3.50-3.57 (m, 2H), 3.13-3.17 (m, 2H), 2.94-2.96 (t, 1H), 2.78 (d, 3H), 2.10-2.13 (m, 2H), 1.97-2.00 (2H).  3. 366 |
| 20 | 170 | (3-morpholinophenyl)-NH-(6-indolyl), 3-(1-methylpiperidin-4-yl) | 1. 55%  2. δ = 1.97 (m, 2H), 2.33 (d, 2H), 2.92 (s, 3H), 3.17-3.23 (m, 3H), 3.62-3.64 (m, 6H), 4.08 (m, 4H), 6.99 (d, 2H), 7.13 (m, 2H), 7.19 (s, 1H), 7.30 (s, 1H), 7.42 (m, 1H), 7.66 (d, 1H).  3. 390.98 |
| 21 | 81 | (3,4-difluorophenyl)-NH-(5-indolyl), 3-(1-methylpiperidin-4-yl) | 1. 70%  2. δ = 10.9 (s, 1H), 7.39-7.46 (m, 2H), 7.22-7.29 (m, 2H), 6.98 (m, 1H), 6.79 (ddd, 1H), 6.69 (m, 1H), 3.56 (d, 2H), 3.17-3.26 (m, 2H), 3.05-3.1 (t, 1H), 2.88 (s, 3H), 2.20 (m, 2H), 2.03-2.06 (m, 2H).  3. 341, 342 |
| 22 | 82 | (3,4-difluorophenyl)-NH-(6-indolyl), 3-(1-methylpiperidin-4-yl) | 1. 83%  2. (DMSO-d₆): δ = 10.6 (s, 1H), 7.56 (d, 1H), 7.17 (m, 1H), 7.09 (s, 1H), 7.00 (s, 1H), 6.89 (ddd, 1H), 6.73-6.79 (m, 1H), 3.44-3.47 (m, 2H), 3.08-3.13 (m, 2H), 2.95-2.97 (m, 1H), 2.75 (d, 3H), 2.07 (m, 4H).  3. 341, 342 |
| 23 | 86 | 6-(1,2,3,4-tetrahydroisoquinolin-2-yl)-3-(1-methylpiperidin-4-yl)-1H-indole | 1. 68%  3. 345 |

Example 24

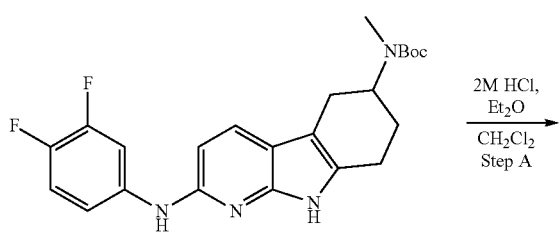

Step A

The title compound from Preparative Example 259 (0.03 g, 0.07 mmol) was dissolved in dichloromethane (1 mL) and treated with a 2 M solution of hydrogen chloride (1 mL) in diethylether. The mixture was stirred at room temperature overnight and the precipitate was collected by filtration. The solids were washed with diethylether (5 mL) and then dried under reduced pressure to afford the title compound as an off-white solid (0.021 g, 75%).

$^1$H-NMR (400 MHz, D$_2$O): δ=1.93-2.05 (m, 1H), 2.20-2.59 (m, 1H), 2.65-2.80 (m, 6 H), 3.10 (dd, 1H), 3.48-3.55 (m, 1H), 6.64 (d, 1H), 6.94-7.02 (m, 1H), 7.15-7.21 (m, 2H), 7.90 (d, 1H)

MS (ESI); m/z=328.95 (MH$^+$).

Examples 25 to 203

Following a similar procedure as that described in Example 24, except using the compounds from the Preparative Examples indicated in the table below, the following compounds were prepared. In case no precipitate was formed, the solvents were removed and the residue was dissolved in water (5 mL). Evaporation of the aqueous solution using a freeze dryer afforded the title compounds. All Example compounds below were obtained as their HCl-salts, except indicated otherwise.

TABLE 6

| Example | Compound Preparative Example | Product | 1. Yield<br>2. $^1$H-NMR (D$_2$O)<br>3. MH$^+$ (ESI) |
|---|---|---|---|
| 25 | 261 | | 1. 78%<br>2. δ = 1.88-1.95 (m, 1H), 2.20-2.23 (m, 1H), 2.60-2.75 (m, 6H), 3.03 (dd, 1H), 3.39-3.44 (m, 1H), 6.60 (d, 1H), 7.51 (d, 1H), 7.72-7.77 (m, 2H), 8.32 (s, 1H)<br>3. 361.94 |
| 26 | 152 | | 1. 75%<br>2. δ = 1.94-2.03 (m, 1H), 2.22-2.30 (m, 1H), 2.65-2.80 (m, 6H), 3.08 (dd, 1H), 4.43-3.50 (m, 4H), 6.55 (d, 1H), 6.91-6.97 (m, 1H), 7.10-7.20 (m, 2H), 7.81 (d, 1H)<br>3. 342.97 |
| 27 | 262 | | 1. 62%<br>2. δ = 1.95-2.02 (m, 1H), 2.22-2.26 (m, 1H), 2.65-2.69 (m, 1H), 2.69 (s, 3H), 2.75-2.80 (m, 2H), 3.10 (dd, 1H), 3.47-3.51 (m, 1H), 6.55 (d, 1H), 7.10-7.16 (m, 1H), 7.40-7.46 (m, 1H), 7.85 (d, 1H)<br>3. 347.58 |

TABLE 6-continued

| Example | Compound Preparative Example | Product | 1. Yield<br>2. ¹H-NMR (D₂O)<br>3. MH⁺ (ESI) |
|---|---|---|---|
| 28 | 154 | | 1. 87%<br>2. (DMSO-d₆/D₂O); δ = 1.85-1.91 (m, 1H), 2.20-2.26 (m, 1H), 2.60-2.64 (m, 1H), 2.63 (s, 3H), 2.71-2.80 (m, 2H), 3.10 (dd, 1H), 3.35-3.40 (m, 1H), 3.52 (s, 3H), 6.65 (d, 1H), 7.27-7.35 (m, 1H), 7.65 (d, 1H), 8.53-8.60 (m, 1H)<br>3. 361.56 |
| 29 | 155 | | 1. 79%<br>2. (DMSO-d₆/D₂O); δ = 1.85-1.91 (m, 1H), 2.22-2.27 (m, 1H), 2.58-2.64 (m, 1H), 2.63 (s, 3H), 2.73-2.87 (m, 2H), 3.10 (dd, 1H), 3.35-3.40 (m, 1H), 3.54 (s, 3H), 6.45-6.51 (m, 1H), 6.55 (d, 1H), 7.40-7.46 (m, 2H), 7.65 (d, 1H)<br>3. 343.59 |
| 30 | 156 | | 1. 78%<br>2. (DMSO-d₆/D₂O); δ = 1.85-1.91 (m, 1H), 2.21-2.26 (m, 1H), 2.58-2.64 (m, 1H), 2.63 (s, 3H), 3.08 (dd, 1H), 3.33-3.39 (m, 1H), 3.53 8s, 3H), 6.50 (d, 1H), 7.55-7.60 (m, 2H), 7.65 (d, 1H)<br>3. 361.56 |
| 31 | 263 | | 1. 68%<br>2. δ =1.81-2.04 (m 3H), 2.18-2.23 (m, 3H), 2.65-2.82 (m, 6H), 3.10-3.17 (m, 4H), 3.42-3.52 (m, 3H), 6.64 (d, 1H), 7.01 (d, 1H), 7.21 (s, 1H), 7.38 (s, 1H), 7.68 (d, 1H), 7.94 (d, 1H)<br>3. 415.03 |
| 32 | 264 | | 1. 76%<br>2. δ = 1.58-1.77 (m, 2H); 1.94-2.13 (m, 2H); 2.81 (sl, 1H); 3.02 (t, 2H); 3.39 (d, 2H); 3.71 (s, 3H); 6.49 (d, 1H); 6.72 (s, 1H); 6.91 (s, 1H); 7.06 (s, 1H); 7.31 (s, 1H); 7.45 (s, 1H); 7.89 (d, 1H)<br>3. 389.86 |
| 33 | 339 | | 1.<br>2. (DMSO-d₆): δ = 12.2 (s, 1H), 10.66 (s, 1H), 8.94 (brs, 2H), 7.95 (d, 1H), 7.80 (s, 1H), 7.78 (s, 1H), 7.53 (d, 1H), 7.20 (dd, 1H), 6.97 (s, 1H), 6.79 (d, 1H), 4.7 (m, 2H), 3.37 (m, 2H), 3.02 (m, 2H), 2.07 (m, 2H), 1.94 (m, 2H). |

TABLE 6-continued

| Example | Compound Preparative Example | Product | 1. Yield<br>2. ¹H-NMR (D₂O)<br>3. MH⁺ (ESI) |
|---|---|---|---|
| 34 | 265 | | 2. (DMSO-d₆): δ = 8.61 (s, 1H), 8.06 (s, 1H), 7.97 (d, J = 8.8 Hz, 1H), 7.65 (s, H), 7.57 (s, 1H), 7.51 (s, 1H), 7.31 (d, 1H), 6.62 (d, 1H), 6.42 (d, 1H), 3.55 (m, 2H), 3.2 (m, 2H), 3.1 (m, 1H), 2.26 (m, 2H), 1.84-1.91 (m, 2H). |
| 35 | 266 | | 1. 91%<br>3. 386 |
| 36 | 267 | | 1. 71%<br>3. 414 |
| 37 | 268 | | 1. 99%<br>2. (CD₃OD): δ = 1.88-2.36 (m, 8H); 3.12-3.30 (m, 5H); 3.45 (d, 2H); 3.53 (d, 2H); 3.83 (d, 2H); 6.81 (d, 1H); 7.03 (s, 1H); 8.34 (d, 1H) |
| 38 | 142 | | 1. quant.<br>2. (CDCl₃): δ = 8.86 (brs, 1H), 8.72 (brs, 1H), 7.55 (d, 1H), 7.20 (ABq, 1H), 7.09 (s, 1H), 7.09 (s, 1h), 6.90-6.98 (m, 1H), 6.81 (d, 1H), 6.77 (d, 1H), 3.66 (s, 3H), 3.34-3.37 (m, 2H), 3.0-3.08 (m, 3H), 2.05-2.08 (m, 2H), 1.84-1.93 (m, 2H). |

TABLE 6-continued
| Example | Compound Preparative Example | Product | 1. Yield<br>2. $^1$H-NMR<br>($D_2O$)<br>3. MH+ (ESI) |
|---|---|---|---|
| 39 | 269 | 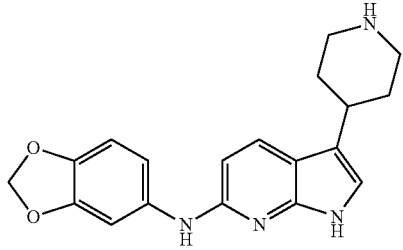 [SMILES: c1cc2c(cc1Nc1ccc3c(C4CCNCC4)c[nH]c3n1)OCO2] | 1. 70%<br>2. (CD$_3$OD): δ = 1.89-2.05 (m, 2H); 2.25 (d, 2H); 3.13-3.28 (m, 3H); 3.52 (d, 2H); 6.08 (s, 2H); 6.76 (d, 1H); 6.87-7.06 (m, 3H); 8.37 (d, 1H) |
| 40 | 270 | 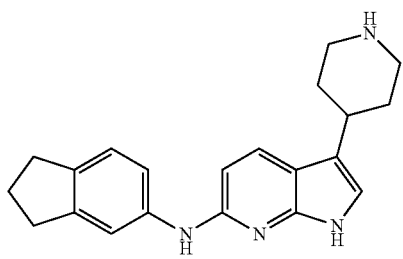 [SMILES: c1cc2c(cc1Nc1ccc3c(C4CCNCC4)c[nH]c3n1)CCC2] | 1. 98%<br>2. (CD$_3$OD): δ = 1.89-2.05 (m, 2H); 2.17 (d, 2H); 2.25 (d, 2H); 2.99 (q, J = 7.6 Hz, 4H); 3.13-3.28 (m, 3H); 3.52 (d, 2H); 6.79 (d, 1H); 7.03 (s, 1H); 7.16 (d, 1H); 7.28 (s, 1H); 7.39 (d, 1H); 8.36 (d, 1H) |
| 41 | 271 | 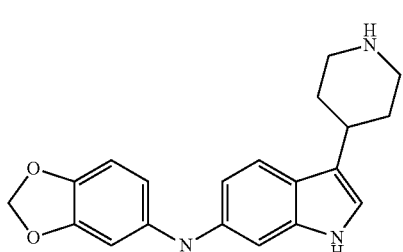 | 1. 56 %<br>2. (CD$_3$OD): δ = 1.93-2.09 (m, 2H); 2.27 (d, 2H); 3.16-3.30 (m, 4H); 3.52 (d, 2H); 6.05 (s, 2H); 6.95 (s, 2H); 7.08 (d, 1H); 7.27 (s, 1H); 7.48 (s, 1H); 7.77-7.85 (m, 2H) |
| 42 | 163 | 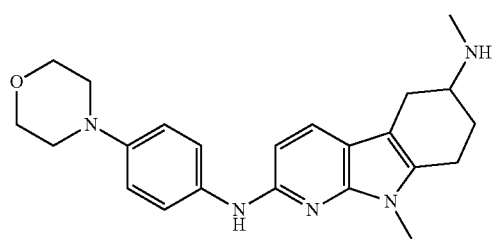 [SMILES: CNC1CCc2c(c3ccc(Nc4ccc(N5CCOCC5)cc4)nc3n2C)C1] | 1. 81%<br>2. δ = 2.11-2.13 (m, 1H), 2.36-2.39 (m, 1H), 2.82 (s, 3H), 2.84-2.87 (m, 2H), 3.21 (d, 1H), 3.59-3.64 (m, 5H), 3.74 (brs, 4H), 4.15 (brs, 4H), 6.78 (d, 1H), 7.6 (brs, 4H), 7.98 (d, 1H)<br>3. 391.95 |
| 43 | 22 | 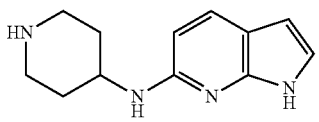 [SMILES: c1cc2ccc(NC3CCNCC3)nc2[nH]1] | 1. 70%<br>2. (DMSO-d$_6$): δ = 4.00-4.02 (m, 1H), 3.32-3.35 (m, 2H), 2.97-3.04 (m, 2H), 2.02-2.06 (m, 2H), 1.86-1.92 (m, 2H) |
| 44 | 272 | 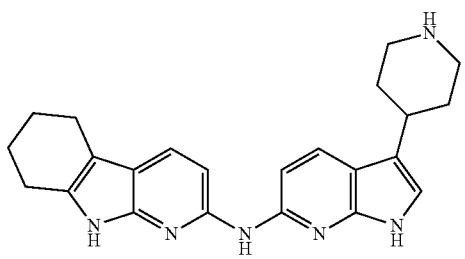 [SMILES: c1cc2c(C3CCNCC3)c[nH]c2nc1Nc1ccc2c3c([nH]c2n1)CCCC3] | 1. 83%<br>2. δ = 1.61 (m, 2H), 1.81-1.92 (m, 4H), 2.19-2.26 (m, 4H), 2.45 (m, 2H), 3.16 (m, 3H), 3.54 (d, 2H), 6.50-6.57 (m, 2H), 7.01 (s, 1H), 7.57 (d, 1H), 7.94 (d, 1H)<br>3. 387.00 |

TABLE 6-continued

| Example | Compound Preparative Example | Product | 1. Yield<br>2. ¹H-NMR (D₂O)<br>3. MH⁺ (ESI) |
|---|---|---|---|
| 45 | 273 | | 1. 61%<br>3. 387 |
| 46 | 274 | | 1. 90%<br>2. δ = 7.83 (d, 1H), 7.64 (d, 1H), 7.32 (s, 1H), 7.17 (s, 1H), 6.95 (d, 1H), 6.56 (d, 1H), 3.44-3.47 (m, 2H) 3.08-3.13 (m, 3H), 2.68-2.71 (m, 2H), 2.60-2.63 (m, 2H), 2.33-2.36 (m, 2H), 2.21-2.22 (m, 2H), 1.81-1.89 (m, 2H). |
| 47 | 275 | | 1. 98%<br>3. 372 |
| 48 | 276 | | 1. 72%<br>2. (DMSO-d₆): δ = 1.86-2.13 (m, 9H); 2.92-3.13 (m, 7H); 3.26-3.43 (m, 5H); 6.69 (d, 1H); 6.89 (s, 1H); 7.08 (s, 1H); 7.12 (d, 1H); 7.64 (d, 1H); 7.65 (s, 1H); 8.02-8.20 (m, 1H); 9.04 (sl, 4H); 10.88 (s, 1H); 11.11 (s, 1H) |
| 49 | 277 | | 1. 76%<br>2. δ = 8.02 (brs, 1H), 7.47 (d, 1H), 7.38 (d, 1H), 7.24 (brs, 1H), 7.09 (brs, 1H), 7.03 (brs, 1H), 6.79 (brs, 1H), 3.41-3.44 (m, 2H), 2.99-3.09 (m, 3H), 2.11-2.15 (m, 2H), 1-77-1.83 (m, 2H). |

TABLE 6-continued

| Example | Compound Preparative Example | Product | 1. Yield  2. ¹H-NMR (D₂O)  3. MH⁺ (ESI) |
|---|---|---|---|
| 50 | 278 | | 1. 97%  2. (CD₃OD): δ = 1.58 (q, 2H); 1.97 (dq, 2H); 2.08-2.19 (m, 3H); 2.45 (d, 2H); 3.06 (t, 2H); 3.13-3.27 (m, 3H); 3.39-3.58 (m, 6H); 6.73 (d, 1H); 7.01 (s, 1H); 8.30 (d, 1H) |
| 51 | 279 | | 1. 71%  2. δ = 8.33 (s, 1H), 8.30 (s, 1H), 7.82 (d, 1H), 7.42 (s, 1H), 6.54 (d, 1H) 3.45-3.48 (m, 2H), 3.08-3.14 (m, 3H), 2.71-2.74 (m, 2H), 2.60-2.62 (m, 2H), 2.35-2.38 (m, 2H), 2.18-2.22 (m, 2H), 1.84-1.90 (m, 2H). |
| 52 | 280 | | 1. 82%  2. (DMSO-d₆): δ = 10.6 (s, 1H), 8.88 (brs, 1H), 8.72 (brs, 1H), 7.56 (d, 1H), 7.23 (abq, 1H), 7.10 (s, 1H), 7.01 (s, 1H), 6.90 (ddd, 1H), 6.74-6.80 (m, 2H), 3.33-3.36 (m, 2H), 3.03-3.17 (m, 3H), 2.06-2.09 (m, 2H), 1.89-1.91 (m, 2H).  3. (M + H): 327 |
| 53 | 143 | | 1. 46%  3. 442, (M/2 + H) 221 |
| 54 | 144 | | 1. 32%  3. 456, (M/2 + H) 228 |

TABLE 6-continued

| Example | Compound Preparative Example | Product | 1. Yield  2. ¹H-NMR (D₂O)  3. MH⁺ (ESI) |
|---|---|---|---|
| 55 | 281 | | 1. 50%  2. (DMSO-d₆/D₂O): δ = 7.32-7.34 (m, 2H), 7.11-7.18 (m, 2H), 6.87 (d, 1H), 6.70 (ddd, 1H), 6.59 (d, 1H) 3.32 (d, 2H), 3.00-3.06 (m, 3H), 2.05 (d, 1H), 1.77-1.87 (m, 2H).  3. ESI MS (MH) 327.93 |
| 56 | 282 | | 1. 76%  2. δ = 8.02 (brs, 1H), 7.47 (d, 1H), 7.38 (d, 1H), 7.24 (brs, 1H), 7.09 (brs, 1H), 7.03 (brs, 1H), 6.79 (brs, 1H), 3.41-3.44 (m, 2H), 2.99-3.09 (m, 3H), 2.11-2.15 (m, 2H), 1-77-1.83 (m, 2H). |
| 57 | 78 | | 1. 80%  2. (DMSO-d₆/D₂O): δ = 7.43-7.46 (m, 2H), 7.22 (ABq, 1H), 7.17 (s, 1H), 7.02 (d, 1H), 6.81 (ddd, 2H), 6.69 (d, 1H), 3.79 (s, 3H), 3.41-3.44 (m, 2H), 3.09-3.15 (m, 3H), 2.14-2.17 (m, 2H), 1.86-1.95 (m, 2H) |
| 58 | 283 | | 1. 83%  3. 472.21 |
| 59 | 80 | | 1. 88%  2. (DMSOd₆): δ = 7.84 (d, 1H), 7.56 (s, 1H), 7.43 (d, 1H), 7.12-7.15 (m, 2H), 6.52 (d, 1H), 3.70 (s, 3H), 3.44-3.49 (m, 2H), 3.06-3.12 (m, 3H), 2.73 (brs, 2H), 2.66 (m, 2H), 2.39 (m, 2H), 2.16 (m, 2H), 1.78-1.85 (m 2H).  3. 386.01 |

TABLE 6-continued

| Example | Compound Preparative Example | Product | 1. Yield 2. ¹H-NMR (D₂O) 3. MH⁺ (ESI) |
|---|---|---|---|
| 60 | 284 | | 1. 78% 2. (CD₃OD): δ = 1.99 (q, 2H); 2.26 (d, 2H); 3.15-3.29 (m, 3H); 3.53 (d, 2H); 6.83 (d, 1H); 7.10 (s, 1H); 7.25 (d, 1H); 7.42 (q, 1H); 7.47-7.57 (m, 1H); 8.40 (d, 1H) |
| 61 | 285 | | 1. 81% 2. (CD₃OD): δ = 1.90-2.10 (m, 2H); 2.85 (d, 2H); 3.14-3.28 (m, 3H); 3.53 (d, 2H); 6.89 (d, 1H); 7.13 (s, 1H); 7.82 (d, 1H); 8.17-8.30 (m, 1H); 8.37 (d, 1H); 8.94 (s, 1H) |
| 62 | 286 | | 1. 53% 2. δ = 1.91 (m, 2H), 2.26 (d, 2H), 3.18 (m, 3H), 3.55 (m, 2H), 3.60 (m, 4H), 4.05 (m, 4H), 6.95-6.98 (m, 2H), 7.10 (m, 2H), 7.17 (brs, 1H), 7.27 (brs, 1H), 7.39 (brs, 1H), 7.64 (d, 1H). 3. 376.98 |
| 63 | 287 | | 1. 99% 2. (DMSO-d₆): δ = 1.85-2.00 (m, 4H); 2.07 (d, 4H); 2.92-3.13 (m, 6H); 3.33 (d, 4H); 6.87 (d, 2H); 7.00 (s, 2H); 7.20 (s, 2H); 7.56 (d, 2H); 8.88-9.20 (m, 4H); 10.72 (s, 2H) |
| 64 | 288 | | 1. 56% 3. 428.6 |

TABLE 6-continued
| Example | Compound Preparative Example | Product | 1. Yield  2. $^1$H-NMR ($D_2O$)  3. MH$^+$ (ESI) |
|---|---|---|---|
| 65 | 291 | 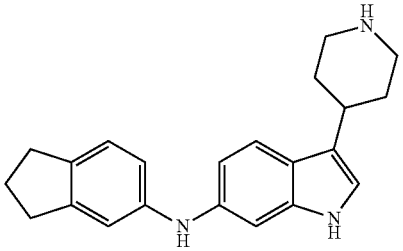 [SMILES: c1cc2c(cc1Nc1ccc3c(C4CCNCC4)c[nH]c3c1)CCC2] | 1. 67%  2. (CD$_3$OD): δ = 1.93-2.08 (m, 2H); 2.13 (p, 2H); 2.28 (d, 2H); 2.95 (t, 4H); 3.15-3.30 (m, 3H); 3.52 (d, 2H); 7.09 (d, 1H); 7.22 (d, 1H); 7.25-7.33 (m, 2H); 7.37 (d, 1H); 7.50 (sl, 1H); 7.82 (d, 1H) |
| 66 | 173 | 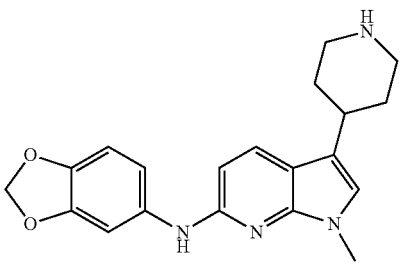 [SMILES: Cn1cc(C2CCNCC2)c2ccc(Nc3ccc4c(c3)OCO4)nc21] | 1. 78%  2. (CD$_3$OD): δ = 1.91-2.09 (m, 2H); 2.21 (d, 2H); 3.09-3.26 (m, 3H); 3.51 (d, 2H); 3.90 (s, 3H); 6.05 (s, 2H); 6.67 (d, 1H); 6.81-6.96 (m, 3H); 7.05 (s, 1H); 8.33 (d, 1H) |
| 67 | 172 | 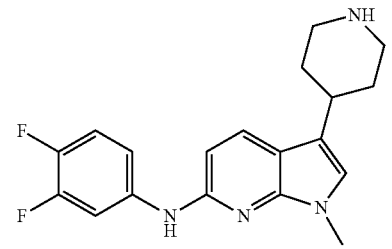 [SMILES: Cn1cc(C2CCNCC2)c2ccc(Nc3ccc(F)c(F)c3)nc21] | 1. 67%  2. (CD$_3$OD): δ = 1.91-2.08 (m, 2H); 2.24 (d, 2H); 3.13-3.28 (m, 3H); 3.52 (d, 2H); 3.88 (s, 3H); 6.79 (d, 1H); 7.12 (s, 1H); 7.26 (m, 1H); 7.35 (q, 1H); 7.58 (sl, 1H); 8.32 (m, 1H) |
| 68 | 293 | 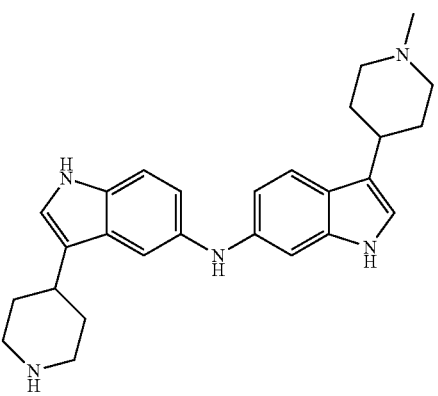 [SMILES: CN1CCC(c2c[nH]c3cc(Nc4ccc5[nH]cc(C6CCNCC6)c5c4)ccc23)CC1] | 1. 74%  3. 428 |
| 69 | 294 | 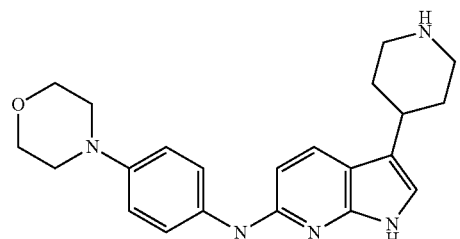 | 1. 98%  2. δ = 1.92 (m, 2H), 2.82 (m, 2H), 3.20 (m, 3H), 3.53 (m, 6H), 4.07 (brs, 4H), 6.82 (d, 1H), 7.09 (s, 1H), 7.50 (m, 4H), 8.22 (d, 1H)  3. 378.66 (MH), 379.68 (M + 2) |

TABLE 6-continued
| Example | Compound Preparative Example | Product | 1. Yield<br>2. $^1$H-NMR (D$_2$O)<br>3. MH$^+$ (ESI) |
|---|---|---|---|
| 70 | 175 | 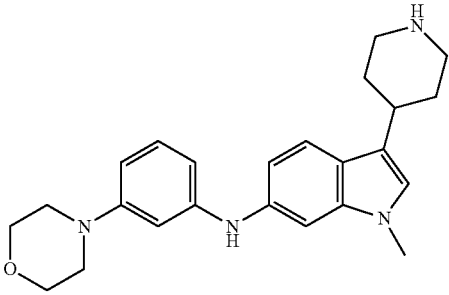 [SMILES: Cn1cc(C2CCNCC2)c2ccc(Nc3cccc(N4CCOCC4)c3)cc21] | 1. 96%<br>2. δ = 1.90 (m, 2H), 2.25 (m, 2H), 3.21 (m, 3H), 3.53 (m, 2H), 3.60 (m, 4H), 3.67 (s, 3H), 4.06 (m, 4H), 6.97 (m, 2H), 7.08-7.12 (m, 3H), 7.21 (brs, 1H), 7.40 (brs, 1H), 7.64-7.66 (m, 1H)<br>3. 391.64 (MH), 392.66 (M + 2) |
| 71 | 178 | 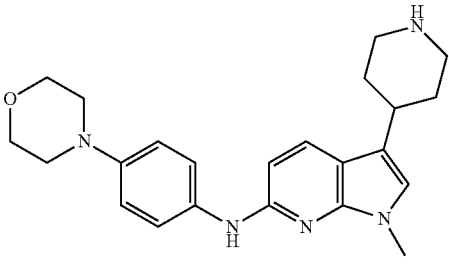 [SMILES: Cn1cc(C2CCNCC2)c2ccc(Nc3ccc(N4CCOCC4)cc3)nc21] | 1. 72%<br>2. δ = 1.90 (m, 2H), 2.24 (m, 2H), 3.19 (m, 3H), 3.54 (m, 2H), 3.72 (s, 3H), 3.76 (m, 4H), 4.14 (m, 4H), 6.79 (m, H), 7.05 (s, 1H), 7.63-7.59 (m, 4H), 8.14 (d, 1H).<br>3. 392.58 (MH) |
| 72 | 295 | 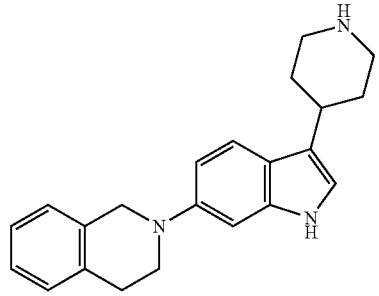 [SMILES: c1ccc2c(c1)CCN(c1ccc3c(C4CCNCC4)c[nH]c3c1)C2] | 1. 78%<br>2. 332 |
| 73 | 296 | 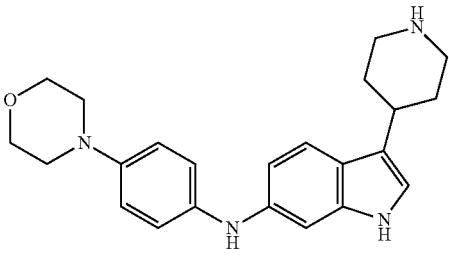 [SMILES: c1cc(N2CCOCC2)ccc1Nc1ccc2c(C3CCNCC3)c[nH]c2c1] | 1. 75%<br>3. 378 |
| 74 | 297 | 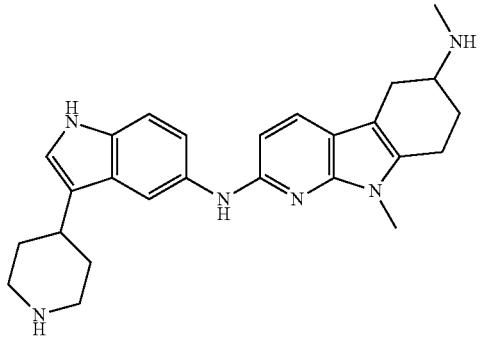 [SMILES: CNC1CCc2c(c3ccc(Nc4ccc5[nH]cc(C6CCNCC6)c5c4)nc3n2C)C1] | 1. 80%<br>2. (DMSO-d$_6$/D$_2$O): δ = 8.27 (s, 1H), 7.85 (s, 1H), 7.61 (d, 1H), 7.28 (d, 1H), 7.12 (d, 1H), 7.07 (s, 1H), 6.50 (s, 1H), 3.59 (s, 3H), 3.35-3.39 (m, 3H), 3.02-3.08 (m, 4H), 2.75-2.80 (m, 3H), 2.62 (s, 3H), 2.18-2.29 (m, 3H), 1.81-1.92 (m, 3H).<br>3. 429 |

TABLE 6-continued

| Example | Compound Preparative Example | Product | 1. Yield<br>2. ¹H-NMR (D₂O)<br>3. MH⁺ (ESI) |
|---|---|---|---|
| 75 | 180 | | 1. 94%<br>2. δ = 1.90 (m, 2H), 2.25 (m, 2H), 3.21 (m, 3H), 3.53 (m, 2H), 3.60 (m, 4H), 3.67 (s, 3H), 4.06 (m, 4H), 6.97 (m, 2H), 7.08-7.12 (m, 3H), 7.21 (brs, 1H), 7.40 (brs, 1H), 7.64-7.66 (m, 1H)<br>3. 405 |
| 76 | 298 | | 1. 70%<br>3. 391 |
| 77 | 299 | | 1. 77%<br>3. 404 |
| 78 | 300 | | 1. 63%<br>3. 378 |
| 79 | 302 | | 1. 57%<br>2. δ = 1.76-1.85 (m, 2H), 2.07-2.11 (m, 2H), 2.76 (s, 3H), 2.84 (m, 3H), 3.43-3.45 (d, 2H), 6.76 (d, 1H), 6.88-6.92 (m, 2H), 7.03 (brs, 2H), 7.39 (d, 1H).<br>3. 360 |

TABLE 6-continued

| Example | Compound Preparative Example | Product | 1. Yield  2. ¹H-NMR (D₂O)  3. MH⁺ (ESI) |
|---|---|---|---|
| 80 | 186 | | 1. 72%  2. δ = 1.16 (m, 1H), 1.22 (m, 1H), 2.13 (m, 1H), 2.37 (m, 1H), 2.81 (s, 3H), 2.89 (m, 2H), 2.86 (s, 3H), 3.16-3.20 (m, 2H), 3.20-3.27 (m, 2H), 3.54 (m, 1H), 3.64 (m, 1H), 3.67 (s, 3H), 3.85-3.88 (m, 2H), 6.79-6.81 (m, 1H), 7.01-7.04 (m, 3H), 7.43 (m, 1H), 8.05-8.07 (m, 1H). |
| 81 | 187 | | 1. 56%  2. (CD₂Cl₂) δ = 1.80 (m, 2H), 1.90 (m, 2H), 2.57-2.62 (m, 4H), 3.80 (s, 3H), 3.84 (s, 6H), 6.47-6.48 (s, 1H), 6.82 (brs, 1H), 6.88 (m, 2H), 7.76-7.77 (m, 1H), 9.59 (s, H).  3. 338 |
| 82 | 188 | | 1. 45%  3. 392 |
| 83 | 189 | | 1. 99%  2. δ = 2.12 (m, 1H), 2.36-2.38 (m, 1H), 2.80 (s, 3H), 2.84-2.88 (m, 2H), 2.98 (s, 3H), 3.19-3.23 (m, 3H), 3.30 (m, 2H), 3.54 -3.56 (m, 7H), 3.86-3.87 (m, 2H), 6.69 (d, 1H), 7.20 (m, 2H), 7.36 (m, 2H), 8.02 (d, 1H).  3. 405 |
| 84 | 190 | | 1. 38%  3. 379 |
| 85 | 191 | | 1. 99%  2. (DMSO-d₆) δ = 1.94-2.01 (m, 1H), 2.23-2.36 (m, 1H), 2.64 (m, 3H), 2.69-2.92 (m, 3H), 3.10 (dd, 1H), 3.39-3.43 (m, 1H), 3.61 (s, 3H), 4.53 (s, 2H), 6.55 (d, 1H), 6.80 (d, 1H), 7.23 (dd, 1H), 7.63 (d, 1H), 7.73 (d, 1H9, 9.13-9.20 (m, 2H), 10.55 (s, 1H).  3. 378 |

TABLE 6-continued

| Example | Compound Preparative Example | Product | 1. Yield<br>2. ¹H-NMR (D₂O)<br>3. MH⁺ (ESI) |
|---|---|---|---|
| 86 | 192 | [structure] | 1. 90%<br>3. 378 |
| 87 | 303 | [structure] | 1. 20%<br>2. (DMSO-d₆/MeOD) δ = 1.88-1.96 (m, 2H), 2.15-2.18 (m, 2H), 2.92 (s, 3H), 2.99 (m, 1H), 3.05-3.11 (m, 2H), 3.47-3.50 (m, 2H), 6.59 (m, 2H), 6.66-6.72 (m, 2H), 6.88 (brs, 1H9, 7.02 (brs, 1H), 7.41 (d, 1H).<br>3. 377 |
| 88 | 304 | [structure] | 1. 36%<br>3. 366 |
| 89 | 206 | [structure] | 1. 76%<br>2. (DMSO-d₆/D₂O): δ = 1.29 (s, 3H), 2.00-2.05 (m, 2H), 2.56 (s, 3H), 2.75-2.85 (m, 4H), 3.60 (s, 3H), 6.55 (d, 1H), 7.22-7.36 (m, 2H), 7.65 (d, 1H), 8.13 (ddd, 1H)<br>3. 357.81 |
| 90 | 207 | [structure] | 1. 88%<br>2. (DMSO-d₆/D₂O): δ = 1.30 (s, 3H), 2.00-2.05 (m, 2H), 2.56 (s, 3H), 2.75-2.85 (m, 4H), 3.57 (s, 3H), 3.66 (s, 3H), 3.76 (s, 3H), 6.50 (d, 1H), 6.85 (d, 1H), 7.08 (dd, 1H), 7.61 (d, 1H), 7.75 (d, 1H)<br>3. 382.83 |
| 91 | 292 | [structure] | 1. 83%<br>2. ¹H-NMR (400 MHz, DMSO-d₆): δ = 10.5 (s, 1H), 7.49 (d, 1H), 7.02 (d, 1H), 6.93 (s, 1H), 6.82 (d, 1H), 6.75 (dd, 1H), 6.70 (d, 1H), 6.60 (dd, 1H), 3.71 (s, 3H), 3.69 (s, 3H), 3.13-3.17 (m, 2H), 3.50-3.57 (m, 2H), 2.94-2.96 (t, 1H), 2.78 (d, 3H), 2.10-2.13 (m, 2H), 1.97-2.00 (2H). |

TABLE 6-continued

| Example | Compound Preparative Example | Product | 1. Yield  2. $^1$H-NMR ($D_2O$)  3. MH$^+$ (ESI) |
|---|---|---|---|
| 92 | 297 | | 1. 80%  2. (DMSO-d$_6$+D$_2$O): δ = 8.27 (s, 1H), 7.85 (s, 1H), 7.61 (d, 1H), 7.28 (d, 1H), 7.12 (d, 1H), 7.07 (s, 1H), 6.50 (s, 1H), 3.59 (s, 3H), 3.35-3.39 (m, 3H), 3.02-3.08 (m, 4H), 2.75-2.80 (m, 3H), 2.62 (s, 3H), 2.18-2.29 (m, 3H), 1.81-1.92 (m, 3H). |
| 93 | 293 | | 1. 92%  2. (DMSO-d$_6$): δ = 7.48 (d, 1H), 7.41 (s, 1H), 7.32 (d, 1H), 7.12 (s, 1H), 7.02 (s, 1H), 6.95 (s, 1H), 6.93 (s, 1H), 6.76 (d, 1H) 3.46-3.46 (m, 2H), 3.32-3.36 (m, 2H), 3.00-3.10 (m, 6H), 2.79 (s, 3H), 2.08-2.13 (m, 4H), 1.18-1.93 (m, 4H). |
| 94 | 309 | | 1. 99%  2. (DMSO-d$_6$) δ 7.75 (d, 1H), 7.37-7.34 (m, 2H), 7.26 (s, 1H), 7.20 (brs, 2H), 7.03-7.01 (m, 2H), 5.15 (dd, 1H), 3.37-3.34 (m, 2H), 3.13-2.92 (m, 5H), 2.88-2.80 (m, 1H), 2.36-2.26 (m, 1H), 2.20-2.09 (m, 3H), 1.87-1.77 (m, 2H). |
| 95 | 93 | | 1. 91%.  2. (DMSO-d$_6$) δ 9.28-9.16 (m, 1H), 7.78 (s, 1H), 7.63 (d, 1H), 7.14 (d, 1H), 6.88 (d, 1H), 6.55 (d, 1H), 3.80 (s, 3H), 3.71 (s, 3H), 3.62 (s, 3H), 3.41-3.36 (m, 1H), 3.13-3.09 (m, 1H), 2.92-2.88 (m, 1H), 2.80-2.70 (m, 2H), 2.65-2.62 (m, 5H), 2.36-2.33 (m, 1H), 2.03-1.93 (m, 1H). |
| 96 | 94 | | 1. 60%  2. (DMSO-d$_6$) δ 7.95 (dd, 1H), 7.64 (d, 1H), 7.46-7.34 (m, 1H), 7.11-7.39 (m 1H), 6.56 (d, 1H), 3.79 (s, 3H), 3.62 (s, 3H), 3.45-3.39 (m, 1H), 3.13-3.08 (m, 1H), 2.92-2.88 (m, 1H), 2.82-2.70 (m, 1H), 2.65-2.62 (m, 3H), 2.37-2.33 (m, 1H). |

TABLE 6-continued

| Example | Compound Preparative Example | Product | 1. Yield 2. ¹H-NMR (D₂O) 3. MH⁺ (ESI) |
|---|---|---|---|
| 97 | 95 | (3,4-dimethoxyphenyl)-NH-(1-methyl-3-(piperidin-4-yl)-1H-indol-6-yl)amine | 1. quantitative 2. (DMSO + D₂O) δ 7.46 (d, 1H), 6.89-6.60 (m, 6H), 3.68 (s, 3H), 3.58 (s, 3H), 3.35-3.33 (m, 2H), 3.05-2.99 (m, 3H), 2.07-2.04 (m, 2H), 1.85-1.79 (m, 2H). |
| 98 | 96 | (3-fluoro-4-methoxyphenyl)-NH-(1-methyl-3-(piperidin-4-yl)-1H-indol-6-yl)amine | 1. 86% 2. (DMSO-d₆) δ 7.49 (d, 1H), 7.00-6.75 (m, 6H), 3.72 (s, 3H), 3.58 (s, 3H), 3.33 (d, 2H), 3.02 (t, 4H), 2.08 (d, 3H), 1.79 (dd, 3H). |
| 99 | 310 | (3-fluoro-4-methoxyphenyl)-NH-(3-(1-methylpiperidin-4-yl)-1H-indol-6-yl)amine | 1. 65% 2. (DMSO-d₆): δ 7.48 (d, 1H), 7.13-6.91 (m, 3H), 6.86-6.68 (m, 3H), 3.73 (s, 3H), 3.47 (d, 2H), 3.15-2.96 (m, 3H), 2.78 (s, 3H), 2.14-2.11 (m, 2H), 1.93-1.83 (m, 2H). |
| 100 | 311 | (3,4-dimethoxyphenyl)-NH-(3-(1-methylpiperidin-4-yl)-1H-indol-5-yl)amine | 1. 65% 2. (DMSO-d₆) δ 7.32 (d, 2H), 7.10 (s, 1H), 6.91 (d, 1H), 6.82 (s, 1H), 6.69 (s, 1H), 3.66 (s, 6H), 3.47-3.44 (m, 2H), 3.15-2.95 (m, 3H), 2.77 (s, 3H), 2.13-2.10 (m, 3H), 1.90-1.81 (m, 2H). |
| 101 | 313 | (3-fluoro-4-methoxyphenyl)-NH-(3-(1-methylpiperidin-4-yl)-1H-indol-5-yl)amine | 1. 59% 2. (DMSO-d₆): δ 7.30 (d, 1H), 7.08 (s, 1H), 6.98-6.93 (m, 1H), 6.86 (d, 1H), 6.69-6.63 (m, 2H), 5.61 (s, 1H), 3.70 (s, 3H), 3.46 (d, 2H), 3.11-2.94 (m, 3H), 2.77 (s, 3H), 2.13-2.10 (m, 2H), 1.89-1.80 (m, 2H). |

TABLE 6-continued

| Example | Compound Preparative Example | Product | 1. Yield<br>2. ¹H-NMR (D₂O)<br>3. MH⁺ (ESI) |
|---|---|---|---|
| 102 | 314 | | 1. 69%<br>2. (DMSO-d₆) δ 11.06 (s, 1H), 8.92 (brs, 1H), 7.99-7.90 (m, 2H), 7.27-7.24 (m, 1H), 7.10-7.05 (m, 1H), 6.88 (d, 1H), 6.58-6.55 (m, 1H), 3.80 (s, 3H), 3.38-3.32 (m, 2H), 3.02-2.96 (m, 3H), 2.06-2.03 (m, 2H), 1.96-1.90 (m, 2H). |
| 103 | 101 | | 1. 80%<br>2. (DMSO-d₆): δ 7.96-7.92 (m, 1H), 7.85-7.82 (m, 1H), 7.39-7.37 (m, 1H), 7.09-7.07 (m, 1H), 6.92 (s, 1H), 6.54-6.53 (m, 1H), 3.81 (s, 3H), 3.68 (s, 3H), 3.35-3.32 (m, 2H), 3.05-2.99 (m, 3H), 2.08-2.04 (m, 2H), 1.83-1.80 (m, 2H). |
| 104 | 102 | | 1. 84%<br>2. (CDCl₃) δ 7.53 (d, 1H), 6.95 (d, 1H), 6.82 (dd, 2H), 6.75 (d, 1H), 6.72 (s, 1H), 6.64 (dd, 1H), 3.88 (s, 3H), 3.83 (s, 3H), 3.65 (s, 3H), 3.02-2.99 (m, 2H), 2.81-2.72 (m, 1H), 2.36 (s, 3H), 2.19-2.04 (m, 6H), 1.90-1.83 (m, 2H). |
| 105 | 103 | | 1. 70%<br>2. (CDCl₃): δ 9.00 (s, 1H), 8.00-7.97 (m, 1H), 7.79 (s, 1H), 7.39 (s, 1H), 7.11-7.09 (m, 1H), 6.91 (s, 1H), 6.54 (s, 1H), 3.79 (s, 3H), 3.71 (s, 3H), 3.0-2.95 (m, 2H), 2.69 (m, 1H), 2.51 (s, 3H), 2.34-2.25 (m, 2H), 1.92-1.90 (m, 2H), 1.72-1.70 (m, 2H). |
| 106 | 104 | | 1. 42%<br>2. (DMSO-d₆ + D₂O): δ 7.20 (d, 1H), 7.07 (s, 1H), 6.79-6.81 (m, 2H), 6.61 (s, 1H), 6.48 (d, 1H), 3.66 (s, 3H), 3.65 (s, 3H), 3.42-3.41 (m, 1H), 3.09-3.04 (m, 1H), 2.8 (m, 2H), 2.22-2.20 (m, 2H), 1.88-1.87 (m, 1H). |
| 107 | 105 | | 1. 61%<br>2. (DMSO-d₆ + D₂O): δ = 7.21 (d, 1H), 7.13-7.07 (m, 1H), 6.96 (t, 1H), 6.79 (d, 1H), 6.69 (dd, 2H), 3.71 (s, 3H), 3.44-3.39 (m, 1H) 3.08 (dd, 1H), 2.81 (m, 1H), 2.65 (s, 3H), 2.62-2.51 (m 1H), 2.26-2.22 (m, 1H), 1.92-1.83 (m, 1H). |

TABLE 6-continued
| Compound Preparative Example | Product | 1. Yield 2. ¹H-NMR (D₂O) 3. MH⁺ (ESI) |
|---|---|---|
| 108 | 106 | 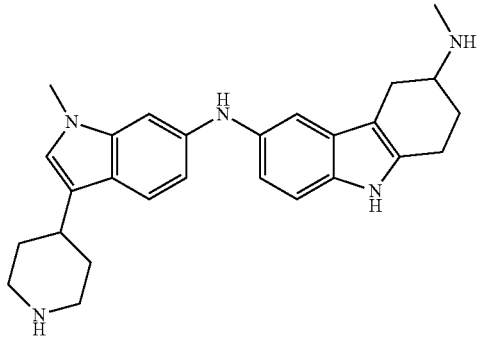 [SMILES: CNC1CCc2[nH]c3ccc(Nc4ccc5c(C6CCNCC6)cn(C)c5c4)cc3c2C1] | 1. 78% 2. (DMSO-d₆): δ = 7.50-7.52 (m, 1H), 7.27-7.21 (m, 2H), 7.02 (m, 1H), 6.91-6.94 (m, 2H), 6.81-6.83 (m, 1H), 3.58 (s, 3H), 3.47-3.24 (m, 4H), 3.10-2.99 (m, 4H), 2.82 (m, 1H), 2.65 (s, 3H), 2.21-2.24 (m, 1H), 2.06-2.09 (m, 2H), 1.75-1.95 (m, 4H). |
| 109 | 107 | 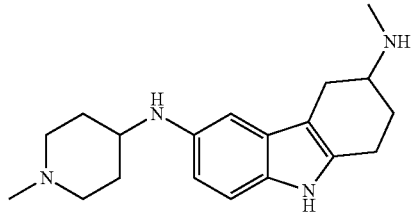 [SMILES: CNC1CCc2[nH]c3ccc(NC4CCN(C)CC4)cc3c2C1] | 1. quantitative 2. (DMSO-d₆): δ = 7.43-7.42 (m, 2H), 7.07-7.06 (m, 1H), 3.71-3.66 (m, 1H), 3.49-3.46 (m, 2H), 3.38-3.36 (m, 2H), 3.16-3.13 (m, 1H), 3.00-2.99 (m, 2H), 2.86 (m, 2H), 2.75 (m, 4H), 2.67 (m, 2H), 2.29-2.26 (m, 1H), 2.10-2.07 (m, 2H), 1.94-1.92 (m, 2H). |
| 110 | 315 | 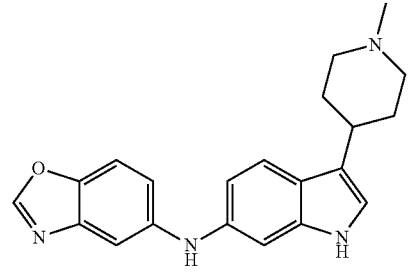 [SMILES: CN1CCC(c2c[nH]c3cc(Nc4ccc5ocnc5c4)ccc23)CC1] | 1. 61% 2. (DMSO-d₆) δ 7.47 (d, 1H), 6.98-6.88 (m, 6H), 6.72-6.70 (m, 1H), 3.48-3.45 (m, 2H), 3.11-2.98 (m, 3H), 2.14-2.11 (m, 2H), 2.89-1.83 (m, 2H). |
| 111 | 109 | 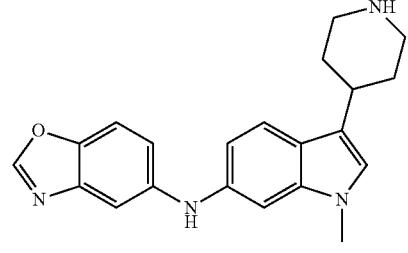 [SMILES: Cn1cc(C2CCNCC2)c2ccc(Nc3ccc4ocnc4c3)cc21] | 1. 58% 3. 347.67 (M + H). |
| 112 | 110 | 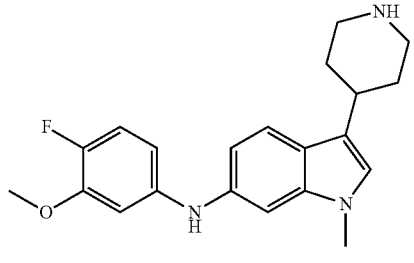 [SMILES: COc1cc(Nc2ccc3c(C4CCNCC4)cn(C)c3c2)ccc1F] | 1. 68% 2. (DMSO-d₆) δ δ 7.50-7.48 (m, 1H), 7.01.6.93 (m, 2H), 6.80-6.75 (m, 3H), 6.56-6.54 (m, 1H)), 3.74 (s, 3H), 3.60 (s, 3H), 3.39-3.24 (m, 2H), 3.12-2.96 (m, 3H), 2H, 2.17-2.00 (m, 2H), 1.91-1.69 (m, 2H). |

TABLE 6-continued

| Example | Compound Preparative Example | Product | 1. Yield  2. ¹H-NMR (D₂O)  3. MH⁺ (ESI) |
|---|---|---|---|
| 113 | 316 | (structure: 3,4,5-trifluorophenyl-NH-indole with 1-methylpiperidin-4-yl substituent) | 1. 74%  2. (CDCl₃): δ 7.57 (d, 1H), 7.13 (s, 1H), 7.04 (s, 1H), 6.81-6.78 (m, 1H), 6.68-6.64 (m, 1H), 3.83 (s, 3H), 3.49-3.46 (m, 2H), 3.17-3.01 (m, 2H), 2.79 (s, 3H), 2.15-2.12 (m, 2H), 1.90-1.87 (m, 2H). |
| 114 | 317 | (structure: 4-fluoro-3-methoxyphenyl-NH-indole with 1-methylpiperidin-4-yl substituent) | 1. 64%  2. (DMSO-d₆) δ 7.50 (d, J = 8.5 Hz, 1H), 7.08 (d, 1H), 7.04-6.95 (m, 2H), 6.79-6.73 (m, 2H), 6.55-6.50 (m, 1H), 3.75 (s, 3H), 3.50-3.47 (m, 2H), 3.14 (t, 2H), 2.98 (t, 1H), 2.79 (s, 3H), 2.12 (d, 2H), 1.97-1.88 (m, 2H). |
| 115 | 113 | (structure: tetrahydro-β-carboline with 4-fluoro-3-methoxyphenylamino and methylamino) | 1. 76%  2. (DMSO-d₆): δ 8.02-8.00 (m, 1H), 7.65 (d, 1H), 7.06 (m, 2H), 6.54-6.52 (m, 1H), 3.97 (s, 3H), 3.81 (s, 3H), 3.69 (s, 3H), 3.59-3.41 (m, 1H), 3.12-3.08 (m, 1H), 2.91-2.85 (m, 2H), 2.65 (s, 3H), 2.33-2.27 (m, 1H), 1.99-1.85 (m, 1H) |
| 116 | 114 | (structure: tetrahydrocarbazole with 4-fluoro-3-methoxyphenylamino and methylamino) | 1. 80%  2. (DMSO-d₆): δ = 10.75 (s, 1H), 9.16 (s, 1H), 7.21 (d, 1H), 7.12 (d, 1H), 6.97 (dd, 1H), 6.83 (dd, 1H), 6.68 (dd, 1H), 6.47-6.36 (m, 1H), 3.74 (s, 3H), 3.41-3.50 (m, 1H), 3.13-3.08 (dd, 1H), 2.82 (s, 1H), 2.69-2.63 (m, 4H), 2.31-2.29 (m, 1H), 2.01-1.19 (m, 1H). |
| 117 | 318 | (structure: bis-indole system with 1-methylpiperidin-4-yl and methylamino groups) | 1. 70%  3. 443.74 (M + H). |

TABLE 6-continued
| Example | Compound Preparative Example | Product | 1. Yield<br>2. $^1$H-NMR (D$_2$O)<br>3. MH$^+$ (ESI) |
|---|---|---|---|
| 118 | 319 | 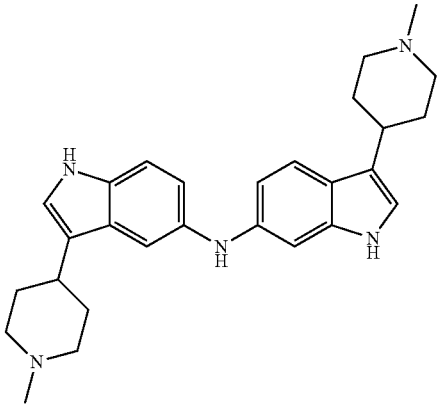 [SMILES: CN1CCC(c2c[nH]c3cc(Nc4ccc5[nH]cc(C6CCN(C)CC6)c5c4)ccc23)CC1] | 1. 60%.<br>2. (DMSO-d$_6$): δ = 7.48 (d, 2H), 7.4 (s, 2H), 6.97 (d, 2H), 6.94 (s, 2H), 6.77 (d, 2H), 3.49-3.46 (m, 4H), 3.13-3.07 (m, 4H), 2.98-2.97 (m, 2H), 2.12-2.11 (m, 4H), 1.94-1.87 (m, 4H).<br>3. 442.75 (M + H). |
| 119 | 320 | 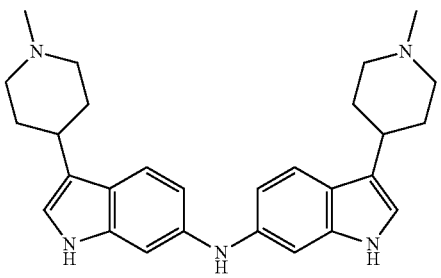 [SMILES: CN1CCC(c2c[nH]c3cc(Nc4ccc5c(C6CCN(C)CC6)c[nH]c5c4)ccc23)CC1] | 1. 80%<br>2. (400 MHz, CDCl$_3$): δ = 8.06 (brs, 2H), 7.52 (d, 2H), 7.06 (s, 2H), 6.85 (d, 2H), 6.78 (s, 2H), 5.68 (s, 2H), 3.00-2.98 (m, 4H), 2.80-2.77 (m, 2H), 2.35 (s, 6H), 2.19-2.03 (m, 8H), 1.89-1.83 (m, 4H). |
| 120 | 118 | 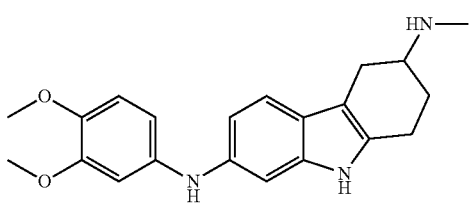 | 1. 78%<br>2. (DMSO-d$_6$) δ 10.58 (s, 1H), 9.15 (s, 1H), 7.24 (d, 1H), 7.01 (s, 1H), 6.84 (d, 1H), 6.85-6.71 (m, 2H), 6.60 (d, 1H), 4.08 (s, 1H), 3.70 (s, 6H), 3.15-3.09 (m, 1H), 2.80-2.77 (m, 1H), 2.65 (m, 3H), 2.30-2.29 (m, 1H), 1.99-1.92 (m, 1H). |
| 121 | 119 | 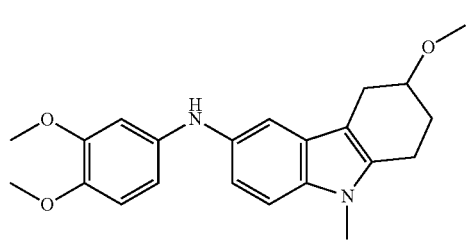 | 1. 45%<br>2. (CDCl$_3$): δ = 7.26 (d, 1H), 6.88-6.66 (m, 5H), 3.67-3.73 (m 6H), 3.55 (s, 3H), 3.31 (s, 3H), 2.92-2.88 (m, 1H), 2.77-2.68 (m, 2H), 2.08-2.08 (m, 1H), 1.91-1.81 (m, 1H). |
| 122 | 120 | 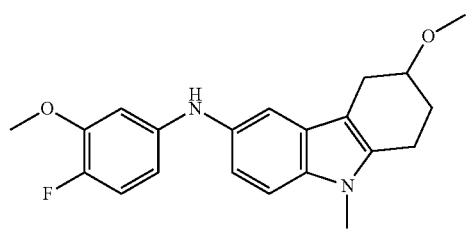 | 1. 51%<br>2. (DMSO-d$_6$) δ 7.26 (d, 1H), 7.08 (s, 1H), 7.01-6.89 (m, 1H), 6.86 (d, 1H), 6.64 (d, 1H), 6.39 (d, 1H), 3.82-3.58 (m, 3H), 3.55 (s, 3H), 3.31 (s, 3H), 2.91 (dd, 1H), 2.85-2.61 (m, 3H), 2.09-2.05 (m, 1H), 1.88-1.82 (m, 1H). |

TABLE 6-continued

| Example | Compound Preparative Example | Product | 1. Yield  2. ¹H-NMR (D₂O)  3. MH⁺ (ESI) |
|---|---|---|---|
| 123 | 121 | (structure) | 1. 79%  2. (CDCl₃): δ = 7.37 (d, 1H), 6.96 (d, 1H), 6.84-6.79 (m, 2H), 6.71 (d, 1H), 6.60 (dd, 1H), 5.57-5.55 (m, 1H), 3.87 (s, 3H), 3.82 (s, 3H), 3.77-3.69 (m, 1H), 3.13 (dd, 1H), 2.89-2.86 (m, 1H), 2.76-2.70 (m, 2H), 2.22-2.18 (m, 1H), 2.05-2.02 (m, 1H). |
| 124 | 122 | (structure) | 1. 79%  3. 355.7 (M + H) |
| 125 | 123 | (structure) | 1. 75%  2. (DMSO-d₆) δ 7.27 (d, 1H), 7.09 (s, 1H), 6.87 (s, 1H), 6.76 (s, 1H), 6.60 (s, 1H), 6.45 (s, 1H), 5.91 (s, 2H), 3.58 (s, 3H), 3.33 (s, 3H), 3.09-3.06 (m, 1H), 2.93-2.86 (m, 1H), 2.80-2.69 (m, 2H), 2.24-2.17 (m, 1H), 2.09-2.00 (m, 1H). |
| 126 | 124 | (structure) | 1. 82%  2. (DMSO-d₆) δ 7.29 (s, 1H), 7.27 (s, 1H), 7.10 (s, 1H), 6.87 (s, 1H), 6.72 (s, 1H), 6.53 (s, 1H), 4.19 (brs, 4H), 3.68-3.67 (m, 1H), 3.58 (brs, 2H), 2.92 (brs, 1H), 2.83-2.69 (m, 2H), 2.10-2.08 (m, 1H), 1.92-1.83 (m, 1H). |
| 127 | 125 | (structure) | 1. 46%  2. (CDCl₃) δ 7.58 (s, 1H), 7.34 (d, 1H), 6.97 (s, 1H), 6.89-6.69 (m, 2H), 6.62 (s, 1H), 6.54 (s, 1H), 4.25 (s, 5H), 3.76 (brs, 1H), 3.49 (s, 3H), 3.09 (brs, 1H), 2.82-2.70 (m, 3H), 2.16 (m, 1H), 2.01-1.99 (m, 1H). |
| 128 | 126 | (structure) | 1. 65%  2. (CDCl₃) δ 8.15-8.10 (m, 1H), 7.63 (d, 1H), 7.34-7.23 (m, 2H), 6.52 (d, 1H), 4.57 (s, 1H), 4.56 (s, 1H), 3.7 (s, 1H), 3.58 (s, 3H), 2.97-2.93 (m, 1H), 2.76-2.71 (m, 2H), 2.06 (s, 1H), 1.87 (s, 1H), 1.21-1.14 (m, 2H). |

TABLE 6-continued

| Example | Compound Preparative Example | Product | 1. Yield  2. $^1$H-NMR (D$_2$O)  3. MH$^+$ (ESI) |
|---|---|---|---|
| 129 | 127 | | 1. 65%  2. $^1$H NMR (400 MHz, DMSO) δ 7.68 (d, J = 8.0 Hz, 1H), 7.60 (s, 1H), 7.04 (s, 1H), 6.89 (d, J = 8.2 Hz, 1H), 6.52 (d, J = 7.2 Hz, 1H), 4.57 (s, 1H), 4.45 (s, 1H), 3.85 (s, 3H), 3.77 (s, 3H), 3.70 (s, 3H), 3.59 (s, 3H), 2.94 (d, J = 14.7 Hz, 1H), 2.74 (m, 2H), 2.07-2.04 (s, 1H), 1.95- 1.83 (m, 1H). |
| 130 | 128 | | 1. 68%  (DMSO-d$_6$) δ 7.59-7.57 (m, 2H), 7.04 (dd, J = 8.7, 2.4 Hz, 1H), 6.75 (d, J = 8.8 Hz, 1H), 6.49 (d, J = 8.4 Hz, 1H), 4.60 (t, J = 4.0 Hz, 1H), 4.48 (t, J = 4.0 Hz, 1H), 4.31-4.16 (m, 4H), 3.86-3.80 (m, 2H), 3.73-3.73 (m, 1H) 2.97 (dd, J = 15.1, 4.5 Hz, 1H), 2.83-2.68 (m, 2H), 2.18-2.06 (m, 1H), 2.12-2.10 (m, 1H) 1.93-1.86 (m, 1H). |
| 131 | 129 | | 1. 65%  2. (DMSO-d$_6$) δ 7.80 (s, 1H), 7.58 (d, J = 8.3 Hz, 1H), 7.11 (d, J = 8.6 Hz, 1H), 6.87 (d, J = 8.8 Hz, 1H), 6.49 (d, J = 8.4 Hz, 1H), 3.85-3.78 (m, 6H), 3.71 (s, 3H), 3.60 (s, 3H), 3.49 (s, 3H), 2.93-2.76 (m, 1H), 2.71-2.65 (m, 2H), 2.46-2.40 (m, 1H), 2.07-1.99 (m, 1H), 1.86 (m, 1H), 1.12 (d, J = 2.8 Hz, 3H), 1.11 (d, J = 2.8 Hz, 3H). |
| 132 | 130 | | 1. 94%  2. $^1$H NMR (400 MHz, DMSO) δ 10.58 (s, 1H), 9.18 (s, 1H), 7.23 (d, J = 8.3 Hz, 1H), 6.98 (s, 1H), 6.82-6.64 (m, 2H), 6.62-6.34 (m, 2H), 4.21-4.16 (m, 5H), 3.41-3.36 (m, 1H), 3.10 (dd, J = 14.8, 4.7 Hz, 1H), 2.79 (s, 1H), 2.73-2.63 (m, 4H), 2.51 (s, 3H), 2.36-2.27 (m, 1H), 2.02-1.90 (m, 1H). |
| 133 | 131 | | 1. 84%  2. (DMSO-d$_6$) δ 9.06 (s, 1H), 7.26 (d, J = 8.3 Hz, 1H), 7.02 (s, 1H), 6.83 (d, J = 8.6 Hz, 1H), 6.76 (d, J = 8.4 Hz, 1H), 6.71 (d, J = 2.2 Hz, 1H), 6.60 (dd, J = 8.5, 2.3 Hz, 1H), 3.70 (s, 3H), 3.69 (s, 3H), 3.69-3.68 (m, 1H), 3.51 (s, 3H), 3.41 (m, 1H), 3.11 (dd, J = 14.4, 4.8 Hz, 1H), 2.91-2.87 (m, 1H), 2.76-2.64 (m, 1H), 2.66 (s, 3H), 2.37-2.28 (m, 1H), 2.01-1.90 (m, 1H). |

TABLE 6-continued

| Example | Compound Preparative Example | Product | 1. Yield  2. ¹H-NMR (D₂O)  3. MH⁺ (ESI) |
|---|---|---|---|
| 134 | 132 | (3,4-difluorophenyl)amino-substituted tetrahydropyrido-indole with N-methyl and NHMe | 1. 78%  2. (DMSO-d₆) δ 9.19 (s, 1H), 8.03 (d, J = 2.3 Hz, 1H), 7.71 (s, 1H), 7.22 (dd, J= 19.8, 9.2 Hz, 1H), 6.79 (ddd, J = 13.2, 7.0, 2.5 Hz, 1H), 6.65 (d, J = 9.0 Hz, 1H), 3.68 (s, 3H), 344-3.38 (m, 1H), 3.17 (dd, J = 15.1, 4.8 Hz, 1H), 3.00-2.96 (m, 1H), 2.87-2.72 (m, 2H), 2.65 (t, J = 5.0 Hz, 3H), 2.38-2.34 (s, 1H), 2.06-1.96 (m, 1H). |
| 135 | 133 | (3,4-dimethoxyphenyl)amino-substituted tetrahydropyrido-indole with N-methyl and NHMe | 1. 76%  2. (DMSO-d₆)) δ 9.29 (s, 1H), 7.98 (d, J = 1.9 Hz, 1H), 7.71 (s, 1H), 6.84 (d, J = 8.6 Hz, 1H), 6.65 (d, J = 2.2 Hz, 1H), 6.53 (dd, J = 8.5, 2.2 Hz, 1H), 3.70 (s, 9H), 3.43 (s, 1H), 3.23-3.08 (m, 1H), 2.99-2.95 (m, 1H), 2.85-2.62 (m, 2H), 2.64 (t, J = 5.1 Hz, 2H), 2.38-2.35 (m, 2H), 2.05-1.96 (m 1H). |
| 136 | 134 | (3,4-difluorophenyl)amino-substituted tetrahydropyrido-indole with N-methyl and O-CH₂CH₂OMe | 1. 54%  2. (DMSO-d₆) δ 9.20 (brs, 1H), 8.18 (ddd, J = 14.5, 7.5, 2.5 Hz, 1H), 7.64 (d, J = 8.3 Hz, 1H), 7.38-7.26 (m, 3H), 6.54 (d, J = 8.3 Hz, 1H), 3.80-3.76 (m, 2H), 3.46 (t, J = 4.0 Hz, 2H), 3.26 (s, 3H), 2.96 (dd, J = 15.2, 4.5 Hz, 1H), 2.89-2.63 (m, 3H), 2.12-2.08 (m, 1H), 1.91-1.82 (m, 1H). |
| 137 | 135 | (2,3-dihydrobenzo[1,4]dioxin-6-yl)amino-substituted tetrahydropyrido-indole with N-methyl and NHMe | 1. 83%  2. (DMSO-d₆) δ 9.25 (s, 1H), 7.96 (d, J = 2.2 Hz, 1H), 7.67 (d, J = 1.9 Hz, 1H), 6.73 (d, J = 9.3 Hz, 1H), 6.60-6.28 (m, 2H), 4.20-4.16 (m, 4H), 3.69 (s, 3H), 3.43 (s, 1H), 3.15 (dd, J = 14.8, 5.0 Hz, 1H), 2.87-2.94 (m, 1H), 2.87-2.73 (m, 1H), 2.64 (t, J = 5.2 Hz, 2H), 2.37-2.36 (m, 1H), 2.05-1.95 (m, 1H). |
| 138 | 136 | (4-fluoro-3-methoxyphenyl)amino-substituted tetrahydropyrido-indole with N-methyl and NHMe | 1. 73%  2. (DMSO-d₆) δ 9.20 (s, 1H), 8.02 (d, J = 2.3 Hz, 1H), 7.70 (d, J = 2.1 Hz, 1H), 7.01 (dd, J = 11.4, 8.8 Hz, 1H), 6.68 (dd, J = 7.6, 2.5 Hz, 1H), 6.55-6.26 (m, 1H), 3.76 (s, 3H), 3.68 (s, 3H), 3.44-3.41 (m, 1H), 3.18-3.14 (m, 1H), 2.99-2.88 (m, 1H), 2.84-2.71 (m, 2H), 2.38-2.35 (d, J = 12.9 Hz, 1H), 2.05-21.96 (m, 1H). |

TABLE 6-continued

| Example | Compound Preparative Example | Product | 1. Yield<br>2. ¹H-NMR (D₂O)<br>3. MH⁺ (ESI) |
|---|---|---|---|
| 139 | 137 | [structure] | 1. 68%<br>3. 364.8 (M + H) |
| 140 | 138 | [structure] | 1. 71%<br>2. (DMSO-d₆) δ 9.03 (s, 1H), 7.29 (d, J = 8.3 Hz, 1H), 7.21-7.10 (m, 1H), 7.05 (s, 1H), 6.82 (ddd, J = 13.5, 7.0, 2.6 Hz, 1H), 6.77 (dd, J = 8.3, 1.5 Hz, 1H), 6.77-6.36 (m, 1H), 3.51 (s, 3H), 3.41-3.35 (m, 1H), 3.09 (dd, J = 14.8, 4.6 Hz, 1H), 2.88-2.84 (m, 1H), 2.75-2.65 (m, 2H), 2.30-2.27 (m, 1H), 1.97-1.87 (m, 1H). |
| 141 | 139 | [structure] | 1. 67%<br>2. (DMSO-d₆) δ 8.10 (dd, J = 13.5, 7.3 Hz, 1H), 7.64 (d, J = 8.3 Hz, 1H), 7.22 (d, J = 5.6 Hz, 2H), 6.53 (d, J = 8.4 Hz, 1H), 4.21-4.11 (m, 2H), 3.61 (t, J = 5.0 Hz, 2H), 3.40-3.35 (m, 1H), 3.18 (s, 3H), 3.11-3.06 (m, 1H), 2.89-2.72 (m, 3H), 2.67-2.55 (m, 4H), 2.31-2.21 (m, 1H), 1.89-1.82 (m, 1H). |
| 142 | 140 | [structure] | 1. 78%<br>2. (DMSO) δ 8.97 (s, 1H), 7.90 (d, J = 2.2 Hz, 1H), 7.62 (d, J = 8.4 Hz, 1H), 7.02 (dd, J = 8.6, 2.2 Hz, 1H), 6.86 (d, J = 8.7 Hz, 1H), 6.55 (d, J = 8.4 Hz, 1H), 4.32-4.17 (m, 3H), 3.80 (s, 3H), 3.71 (s, 2H), 3.63 (t, J = 5.8 Hz, 1H), 3.49-3.33 (m, 1H), 3.23 (s, 3H), 3.10 (dd, J = 14.8, 4.9 Hz, 1H), 2.96-2.91 (m, 1H), 2.83-2.78 (m, 1H), 2.44-2.24 (m, 1H), 2.03-1.85 (m, 1H). |
| 143 | 321 | [structure] | 1. 81%<br>2. δ = 1.76 (sl, 1H); 1.86-2.15 (m, 5H); 3.00 (m, 3H); 3.32 (d, J = 13.2 Hz, 2H); 3.52-3.68 (m, 2H); 6.72 (d, J = 8.8 Hz, 1H); 6.93 (s, 1H); 7.15 (t, J = 8.0 Hz, 1H); 7.22 (t, J = 8.0 Hz, 1H); 7.53 (d, J = 7.6 Hz, 1H); 7.77 (s, 1H); 8.09 (d, J = 8.4 Hz, 1H); 9.11 (sl, 2H); 10.04 (s, 1H); 11.20 (s, 1H)<br>3. 350.71 |

TABLE 6-continued
| Example | Compound Preparative Example | Product | 1. Yield 2. ¹H-NMR (D₂O) 3. MH⁺ (ESI) |
|---|---|---|---|
| 144 | 291 | 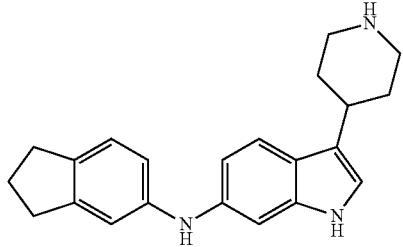 [SMILES: c1cc2c(cc1Nc1ccc3c(C4CCNCC4)c[nH]c3c1)CCC2] | 1. 66% 2. 1.93-2.08 (m, 2H); 2.13 (p, J = 7.2 Hz, 2H); 2.28 (d, J = 13.6 Hz, 2H); 2.95 (t, J = 7.2 Hz, 4H); 3.15-3.30 (m, 3H); 3.52 (d, J = 12.8 Hz, 2H); 7.09 (d, J = 8.0 Hz, 1H); 7.22 (d, J = 7.6 Hz, 1H); 7.25-7.33 (m, 2H); 7.37 (d, J = 8.0 Hz, 1H); 7.50 (sl, 1H); 7.82 (d, J = 8.4 Hz, 1H) 3. 332.67 |
| 145 | 210 | 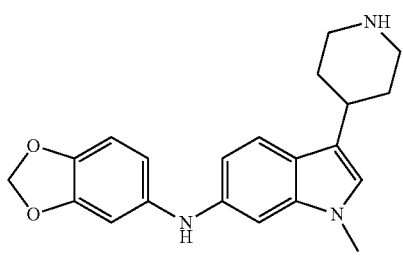 [SMILES: Cn1cc(C2CCNCC2)c2ccc(Nc3ccc4c(c3)OCO4)cc21] | 1. 26% 2. 1.87-2.08 (m, 2H); 2.28 (d, J = 13.2 Hz, 2H); 3.16-3.29 (m, 3H); 3.33 (s, 3H); 3.52 (d, J = 12.8 Hz, 2H); 3.81 (sl, 2H); 5.83-6.35 (sl, 2H); 6.70-7.25 (sl, 3H); 7.74-7.82 (m, 1H) 3. 349.91 |
| 146 | 173 | 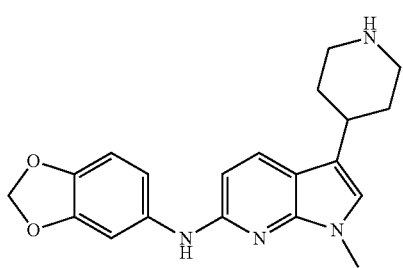 [SMILES: Cn1cc(C2CCNCC2)c2ccc(Nc3ccc4c(c3)OCO4)nc21] | 1. 78% 2. 1.91-2.09 (m, 2H); 2.21 (d, J = 13.6 Hz, 2H); 3.09-3.26 (m, 3H); 3.51 (d, J = 12.8 Hz, 2H); 3.90 (s, 3H); 6.05 (s, 2H); 6.67 (d, J = 9.2 Hz, 1H); 6.81-6.96 (m, 3H); 7.05 (s, 1H); 8.33 (d, J = 9.2 Hz, 1H) 3. 351.61 |
| 147 | 172 | 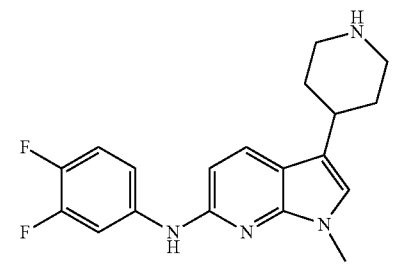 [SMILES: Cn1cc(C2CCNCC2)c2ccc(Nc3ccc(F)c(F)c3)nc21] | 1. 67% 2. 1.91-2.08 (m, 2H); 2.24 (d, J = 13.6 Hz, 2H); 3.13-3.28 (m, 3H); 3.52 (d, J = 12.8 Hz, 2H); 3.88 (s, 3H); 6.79 (d, J = 10.0 Hz, 1H); 7.12 (s, 1H); 7.26 (m, 1H); 7.35 (q, J = 8.8 Hz, 1H); 7.58 (sl, 1H); 8.32 (m, 1H) 3. 343.61 |
| 148 | 330 | 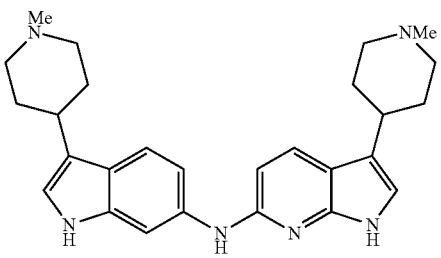 [SMILES: CN1CCC(c2c[nH]c3cc(Nc4ccc5c(C6CCN(C)CC6)c[nH]c5n4)ccc23)CC1] | 1. 59% 2. 2.99-2.21 (m, 4H); 2.22-2.40 (m, 4H); 2.95 (s, 3H); 2.97 (s, 3H); 3.11-3.31 (m, 6H); 3.65 (t, J = 11.2 Hz, 4H); 6.81 (d, J = 8.8 Hz, 1H); 7.01 (s, 1H); 7.08 (dd, J1 = 1.6 Hz, J2 = 8.4 Hz, 1H); 7.26 (s, 1H); 7.47 (d, J = 1.6 Hz, 1H); 7.85 (d, J = 8.4 Hz, 1H); 8.39 (d, J = 8.8 Hz, 1H) 3. 443.73 |

TABLE 6-continued

| Example | Compound Preparative Example | Product | 1. Yield 2. ¹H-NMR (D₂O) 3. MH⁺ (ESI) |
|---|---|---|---|
| 149 | 212 | | 1. 70% 2. 2.02 (q, J = 13.6 Hz, 2H); 2.28 (d, J = 14.4 Hz, 2H); 2.94 (s, 3H); 3.07-3.28 (m, 3H); 3.64 (d, J = 12.4 Hz, 2H); 3.85 (s, 3H); 6.03 (s, 2H); 6.66 (d, J = 8.8 Hz, 1H); 6.85-6.99 (m, 2H); 7.00-7.15 (m, 2H); 8.16-8.32 (m, 1H) 3. 365.71 |
| 150 | 213 | | 1. 70% 2. 1.95-2.13 (m, 2H); 2.28 (d, J = 13.2 Hz, 2H); 2.94 (s, 3H); 3.08-3.29 (m, 3H); 3.63 (d, J = 12.4 Hz, 2H); 3.86 (s, 3H); 4.30 (s, 4H); 6.68 (d, J = 8.8 Hz, 1H); 6.84-6.97 (m, 2H); 7.00 (d, J = 2.0 Hz, 1H); 7.06 (s, 1H); 8.28 (d, J = 8.8 Hz, 1H) 3. 379.74 |
| 151 | 216 | | 1. 72% 2. 1.96-2.15 (m, 2H); 2.28 (d, J = 13.6 Hz, 2H); 2.94 (s, 3H); 3.08-3.29 (m, 3H); 3.63 (d, J = 12.0 Hz, 2H); 3.86 (s, 3H); 6.75 (d, J = 8.8 Hz, 1H); 7.08 (s, 1H); 7.22-7.37 (m, 2H); 7.62-7.77 (m, 1H); 8.23 (d, J = 8.8 Hz, 1H) 3. 357.73 |
| 152 | 217 | | 1. 70% 2. 1.98-2.15 (m, 2H); 2.28 (d, J = 14.0 Hz, 2H); 2.94 (s, 3H); 3.05-3.29 (m, 8H); 3.41-3.55 (m, 1H); 3.64 (d, J = 11.6 Hz, 2H); 3.75-3.85 (m, 1H); 3.87 (s, 3H); 4.40 (d, J = 15.2 Hz, 1H); 4.61 (d, J = 15.2 Hz, 1H); 6.81 (d, J = 8.4 Hz, 1H); 7.09 (s, 1H); 7.35 (d, J = 8.4 Hz, 1H); 7.46 (d, J = 8.4 Hz, 1H); 7.49 (s, 1H); 8.28 (d, J = 8.4 Hz, 1H) 3. 390.75 |
| 153 | 328 | | 1. 40% 2. 2.05 (dq, J1 = 3.2 Hz, J2 = 12.4 Hz, 2H); 2.30 (d, J = 14.4 Hz, 2H); 2.94 (s, 3H); 3.14-3.28 (m, 3H); 3.63 (d, J = 12.4 Hz, 2H); 6.04 (sl, 2H); 6.92 (d, J = 10.8 Hz, 2H); 7.05 (sl, 1H); 7.26 (sl, 1H); 7.75-7.83 (m, 1H) 3. 350.73 |

TABLE 6-continued

| Compound Preparative Example | Preparative Example | Product | 1. Yield 2. ¹H-NMR (D₂O) 3. MH⁺ (ESI) |
|---|---|---|---|
| 154 | 323 | | 1. 49% 2. 2.07 (q, J = 12.8 Hz, 2H); 2.31 (d, J = 14.4 Hz, 2H); 2.95 (s, 3H); 3.09 (sl, 2H); 3.13-3.29 (m, 3H); 3.50 (t, J = 6.4 Hz, 2H); 3.63 (d, J = 11.6 Hz, 2H); 4.32 (s, 2H); 6.96 (d, J = 6.8 Hz, 1H); 7.05 (s, 1H); 7.08-7.18 (m, 2H); 7.21 (d, J = 6.8 Hz, 1H); 7.31 (s, 1H); 7.65 (d, J = 7.6 Hz, 1H) 3. 361.67 |
| 156 | 222 | | 1. 81% 2. 2.04-2.19 (m, 1H); 2.35-2.50 (m, 1H); 2.73-2.86 (m, 1H); 2.83 (s, 3H); 2.87-3.04 (m, 2H); 3.25 (dd, J1 = 3.6 Hz, J2 = 15.6 Hz, 1H); 3.51-3.64 (m, 1H); 3.75 (s, 3H); 4.28 (s, 4H); 6.65 (d, J = 8.4 Hz, 1H); 6.80-7.00 (m, 3H); 8.06 (d, J = 8.8 Hz, 1H) 3. 365.70 |
| 157 | 223 | | 1. 84% 2. 1.88-2.06 (m, 1H), 2.33 (dl, J = 11.2 Hz, 1H); 2.57-2.67 (m, 3H); 2.67-2.81 (m, 2H); 2.88 (dl, J = 16.8 Hz, 1H); 3.09 (dd, J1 = 4.4 Hz, J2 = 14.8 Hz, 1H); 3.31-3.46 (m, 1H); 3.60 (s, 3H); 5.95 (s, 2H); 6.55 (d, J = 8.4 Hz, 1H); 6.83 (d, J = 8.4 Hz, 1H); 7.09 (d, J = 8.4 Hz, 1H); 7.61 (s, 1H); 7.64 (d, J = 8.4 Hz, 1H); 9.21-9.45 (sl, 2H) 3. 351.72 |
| 158 | 224 | | 1. 92% 2. 2.06-2.28 (m, 1H); 2.31-2.56 (m, 1H); 2.85 (s, 3H); 2.93-3.25 (m, 7H); 3.42-3.70 (m, 2H); 3.82 (s, 3H); 4.42 (s, 1H); 4.63 (s, 1H); 6.84 (sl, 1H); 7.27-7.53 (m, 3H); 8.14 (sl, 1H) 3. 376.78 |
| 159 | 225 | | 1. 74% 2. 1.89-2.09 (m, 1H); 2.18-2.37 (m, 1H); 2.60-2.75 (m, 4H); 2.76-2.95 (m, 2H); 2.99-3.16 (m, 1H); 3.37-3.57 (m, 1H); 3.67 (s, 3H); 4.01 (s, 1H); 6.59 (d, J = 8.4 Hz, 1H); 7.51 (dd, J1 = 2.0 Hz, J2 = 8.8 Hz, 1H); 7.62 (t, J = 8.4 Hz, 2H); 8.96 (d, J = 2.0 Hz, 1H); 9.14 (s, 1H) 3. 361.71 |

TABLE 6-continued

| Example | Compound Preparative Example | Product | 1. Yield 2. $^1$H-NMR (D$_2$O) 3. MH$^+$ (ESI) |
|---|---|---|---|
| 160 | 226 | 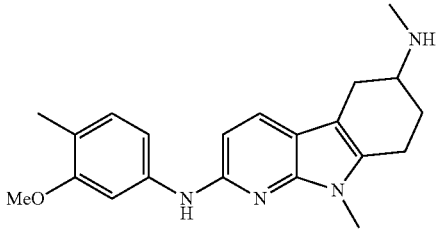 [SMILES: CNC1CCc2c(c3ccc(Nc4ccc(C)c(OC)c4)nc3n2C)C1] | 1. 99% 2. 1.88-2.02 (m, 1H); 2.08 (s, 3H); 2.32 (d, J= 13.2 Hz, 1H); 2.65 (t, J = 5.2 Hz, 3H); 2.68-2.96 (m, 3H); 3.11 (dd, J1 = 5.2 Hz, J2 = 15.2 Hz, 1H); 3.37-3.47 (m, 1H); 3.62 (s, 3H); 3.82 (s, 3H); 6.57 (d, J = 8.8 Hz, 1H); 6.98 (d, J = 8.4 Hz, 1H); 7.03 (dd, J1 = 2.0 Hz, J2 = 8.0 Hz, 1H); 7.64 (d, J = 8.4 Hz, 1H); 7.86 (d, J = 2.0 Hz, 1H); 8.89-8.08 (m, 2H) 3. 351.73 |
| 162 | 312 | 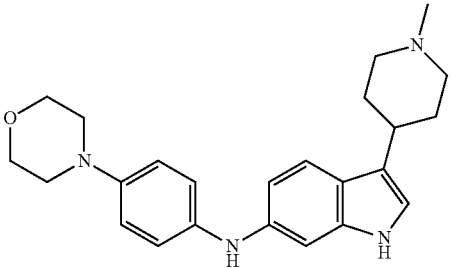 [SMILES: CN1CCC(c2c[nH]c3cc(Nc4ccc(N5CCOCC5)cc4)ccc23)CC1] | 1. 74% 3. 391.76 |
| 163 | 256 | 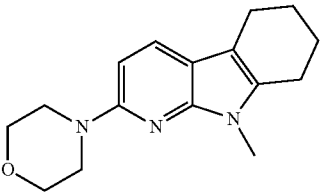 Free base | Analytical data as described for the corresponding preparative example not included in the claims |
| 164 | 195 | 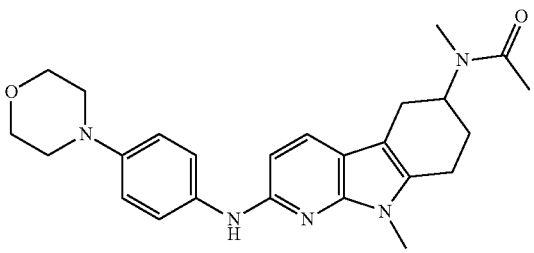 Free base | Analytical data as described for the corresponding preparative example |
| 165 | 196 | 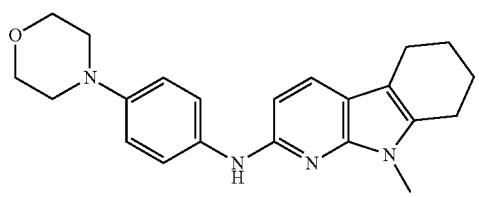 Free base | Analytical data as described for the corresponding preparative example |

TABLE 6-continued

| Example | Compound Preparative Example | Product | 1. Yield  2. ¹H-NMR (D$_2$O)  3. MH⁺ (ESI) |
|---|---|---|---|
| 166 | 197 | 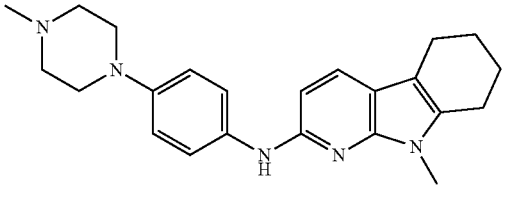 Free base | Analytical data as described for the corresponding preparative example |
| 167 | 198 | 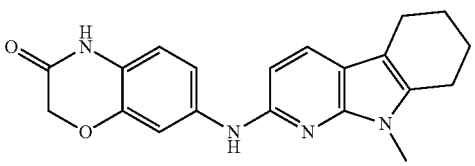 Free base | Analytical data as described for the corresponding preparative example |
| 168 | 199 | 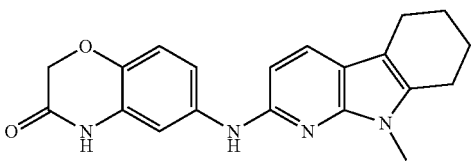 Free base | Analytical data as described for the corresponding preparative example |
| 169 | 200 | 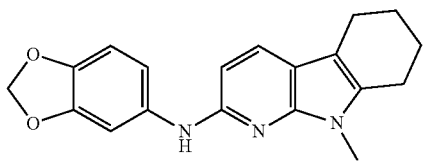 Free base | Analytical data as described for the corresponding preparative example |
| 170 | 201 | 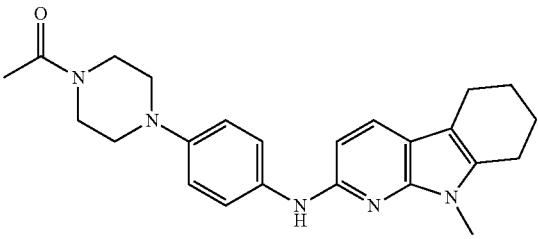 Free base | Analytical data as described for the corresponding preparative example |
| 171 | 202 | 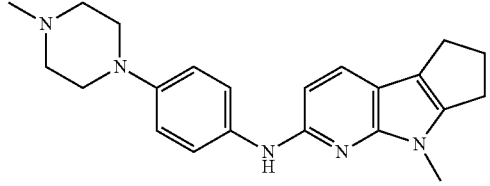 Free base | Analytical data as described for the corresponding preparative example |
| 172 | 235 | 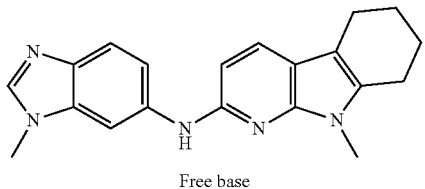 Free base | Analytical data as described for the corresponding preparative example |

TABLE 6-continued

| Example | Compound Preparative Example | Product | 1. Yield 2. ¹H-NMR ($D_2O$) 3. MH⁺ (ESI) |
|---|---|---|---|
| 173 | 237 | 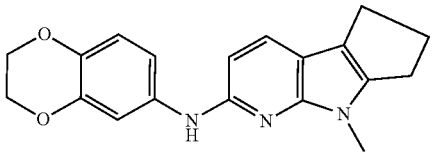 Free base | Analytical data as described for the corresponding preparative example |
| 174 | 238 | 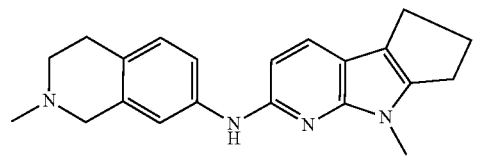 Free base | Analytical data as described for the corresponding preparative example |
| 175 | 239 | 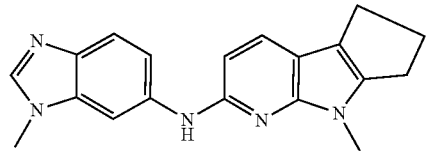 Free base | Analytical data as described for the corresponding preparative example |
| 176 | 240 | 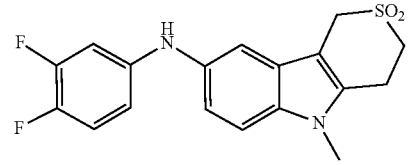 Free base | Analytical data as described for the corresponding preparative example |
| 177 | 241 | 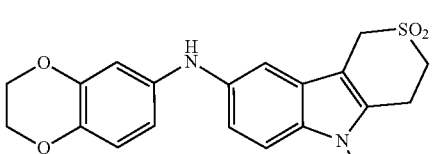 Free base | Analytical data as described for the corresponding preparative example |
| 178 | 242 | 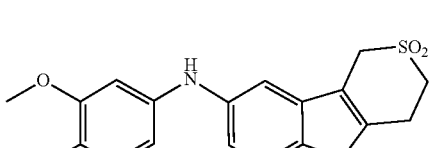 Free base | Analytical data as described for the corresponding preparative example |
| 179 | 243 | 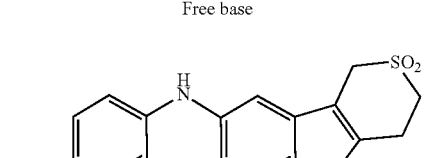 Free base | Analytical data as described for the corresponding preparative example |

TABLE 6-continued

| Example | Compound Preparative Example | Product | 1. Yield  2. $^1$H-NMR ($D_2O$)  3. MH$^+$ (ESI) |
|---|---|---|---|
| 180 | 244 | 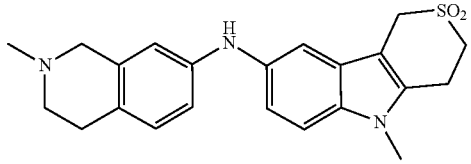<br>Free base | Analytical data as described for the corresponding preparative example |
| 181 | 245 | 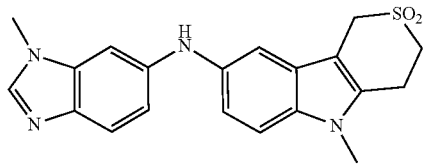<br>Free base | Analytical data as described for the corresponding preparative example |
| 182 | 246 | 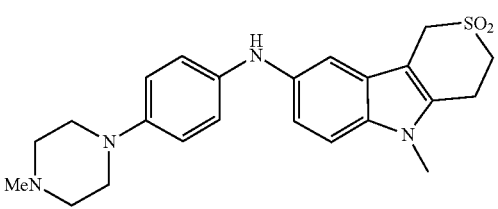<br>Free base | Analytical data as described for the corresponding preparative example |
| 183 | 247 | 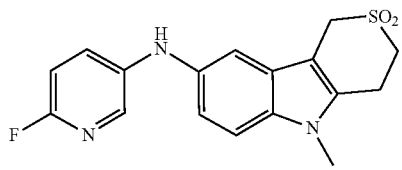<br>Free base | Analytical data as described for the corresponding preparative example |
| 184 | 248 | 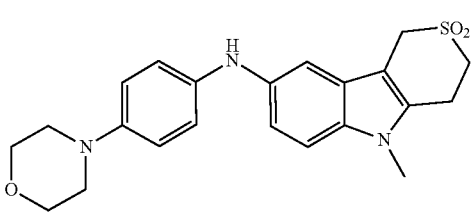<br>Free base | Analytical data as described for the corresponding preparative example |
| 185 | 249 | 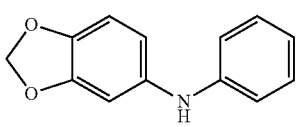<br>Free base | Analytical data as described for the corresponding preparative example not included in the claims |
| 186 | 250 | 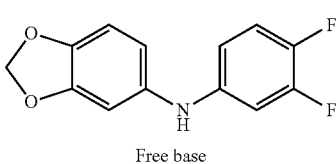<br>Free base | Analytical data as described for the corresponding preparative example not included in the claims |

TABLE 6-continued

| Example | Compound Preparative Example | Product | 1. Yield 2. ¹H-NMR (D₂O) 3. MH⁺ (ESI) |
|---|---|---|---|
| 187 | 251 | | Analytical data as described for the corresponding preparative example not included in the claims |
| 188 | 252 | | Analytical data as described for the corresponding preparative example not included in the claims |
| 189 | 253 | | Analytical data as described for the corresponding preparative example not included in the claims |
| 190 | 254 | | Analytical data as described for the corresponding preparative example not included in the claims |
| 191 | 141 | | |

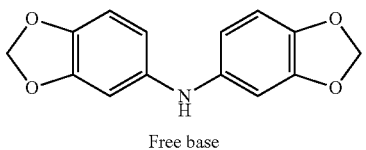

TABLE 6-continued
| Example | Compound Preparative Example | Product | 1. Yield  2. ¹H-NMR (D₂O)  3. MH⁺ (ESI) |
|---|---|---|---|
| 192 | 234 | 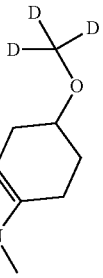<br>Free base | Analytical data as described for the corresponding preparative example |
| 193 | 233 | 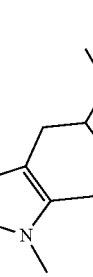<br>Free base | Analytical data as described for the corresponding preparative example |
| 194 | 301 | 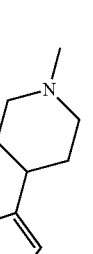<br>Free base | Analytical data as described for the corresponding preparative example |
| 195 | 327 | 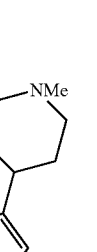 | |
| 196 | 324 | 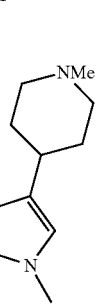 | |

TABLE 6-continued

| Example | Compound Preparative Example | Product | 1. Yield 2. ¹H-NMR (D₂O) 3. MH⁺ (ESI) |
|---|---|---|---|
| 197 | 325 | 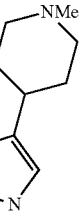 | |
| 198 | 205 | 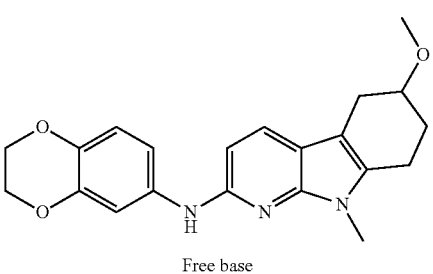
Free base | Analytical data as described for the corresponding preparative example |
| 199 | 227 | 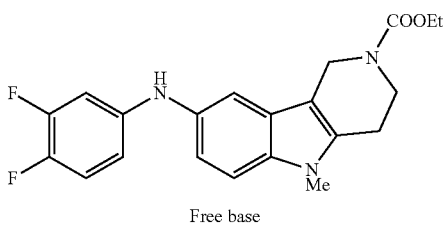
Free base | Analytical data as described for the corresponding preparative example |
| 200 | 326 | 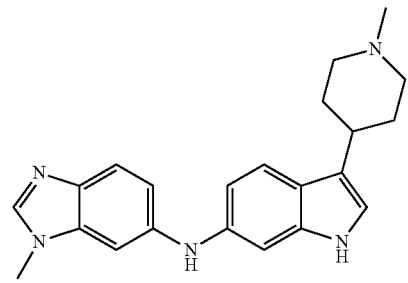 [SMILES: CN1CCC(c2c[nH]c3cc(Nc4ccc5ncn(C)c5c4)ccc23)CC1] | |
| 201 | 236 | 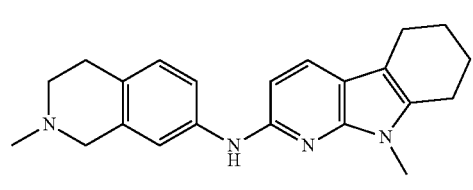
Free base | Analytical data as described for the corresponding preparative example |
| 202 | 334 | 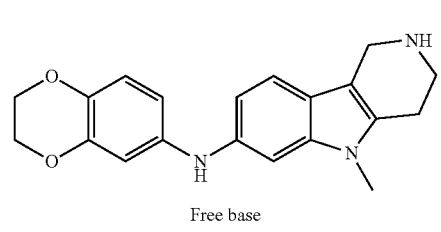
Free base | Analytical data as described for the corresponding preparative example |

TABLE 6-continued

| Example | Compound Preparative Example | Product | 1. Yield<br>2. $^1$H-NMR ($D_2O$)<br>3. $MH^+$ (ESI) |
|---|---|---|---|
| 203 | 232 | | |

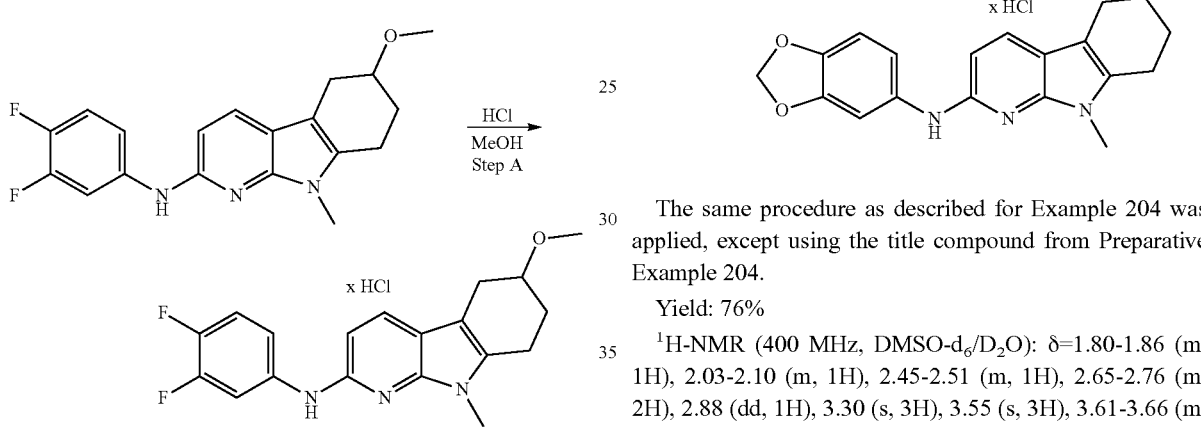

Example 204

Step A

The title compound from Preparative Example 203 (0.032 g, 0.093 mmol) was dissolved in methanol (2 mL) and concentrated aqueous hydrogen chloride solution was added. The clear solution was frozen in liquid nitrogen and the solvents were evaporated using a freeze-dryer to afford the title compound as an off-white solid (0.029 g, 81%).

$^1$H-NMR (400 MHz, DMSO-$d_6$/$D_2O$): δ=1.79-1.87 (m, 1H), 2.02-2.08 (m, 1H), 2.46-2.50 (m, 1H), 2.63-2.77 (m, 2H), 2.88 (dd, 1H), 3.26 (s, 3H), 3.55 (s, 2H), 3.60-3.65 (m, 1H), 6.50 (d, 1H), 7.22-7.40 (m, 2H), 7.62 (d, 1H), 8.10 (ddd, 1H)

MS (ESI); m/z=344.77 ($MH^+$)

Example 205

The same procedure as described for Example 204 was applied, except using the title compound from Preparative Example 204.

Yield: 76%

$^1$H-NMR (400 MHz, DMSO-$d_6$/$D_2O$): δ=1.80-1.86 (m, 1H), 2.03-2.10 (m, 1H), 2.45-2.51 (m, 1H), 2.65-2.76 (m, 2H), 2.88 (dd, 1H), 3.30 (s, 3H), 3.55 (s, 3H), 3.61-3.66 (m, 1H), 5.90 (s, 2H), 6.46 (d, 1H), 6.81 (d, 1H), 7.04 (dd, 1h), 7.57-7.61 (m, 2H)

MS (ESI); m/z=352.69 ($MH^+$)

Example 206

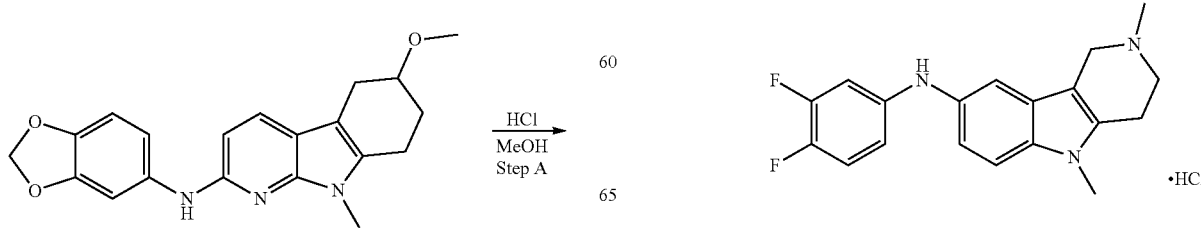

Step A

To a solution of the title compound from preparative example 332 (0.070 g, 0.223 mmol) in methanol (Volume: 4 ml) was added formaldehyde solution (0.020 ml, 0.246 mmol). The reaction mixture was stirred at room temperature for 30 min then sodium triacetoxyborohydride (0.0568 g, 0.268 mmol) was added portionwise. The resulting mixture was stirred at room temperature for 12 h. 1 ml of HCl 1.2M in water was added. After 5 min stirring at room temperature, the solution was poured into a mixture of water, saturated $Na_2CO_3$ and brine. An extraction was performed with ethyl acetate 3 times. The organic layers were collected, dried over $Na_2SO_4$, filtered and concentrated to dryness. The crude product was purified by flash chromatography in DCM/MeOH 98:2 to 90:10. The product was dissolved in DCM and HCl in ether was slowly added in order to from the corresponding HCl salt. The solvent was concentrated to dryness and the solid was dried under vacuum to afford the expected compound as a purple solid (0.028 g, 34%).

$^1$H-NMR (400 MHz, MeOD): δ=3.07 (s, 3H); 3.14-3.23 (m, 2H); 3.47-3.60 (m, 1H); 3.66 (s, 3H); 3.77-3.91 (m, 1H); 4.28 (d, J=14.0 Hz, 1H); 4.63 (d, J=14.0 Hz, 1H); 6.70 (sl, 1H); 6.79 (sl, 1H); 6.94-7.10 (m, 2H); 7.23 (sl, 1H); 7.35 (d, J=8.8 Hz, 1H)

MS (ESI); m/z=328.71 (MH$^+$)

Step A

To a mixture of the title compound from preparative example 334 (0.036 g, 0.107 mmol), the title compound from preparative example 54 (0.0281 mg, 0.107 mmol) and potassium carbonate (0.0297 mg, 0.215 mmol) was added tetrahydrofuran (Ratio: 1.000, Volume: 2 ml), then acetonitrile (Ratio: 1.000, Volume: 2.000 ml). The resulting mixture was stirred at room temperature for 2 h. The reaction mixture was concentrated to dryness. The residue was purified by flash chromatography in DCM/MeOH 0% to 10%. The product was dissolved in DCM and HCl in ether was added. The slurry was concentrated to dryness. The residue was dissolved in a few drops of MeOH and ethyl acetate was added in order to induce precipitation. The slurry was concentrated to dryness to afford the expected compound as a beige solid (0.020 g, 37%).

$^1$H-NMR (400 MHz, DMSO): δ=1.73-1.87 (m, 2H); 1.88-2.02 (m, 2H); 3.00 (s, 3H); 3.06-3.17 (m, 2H); 3.21 (t, J=7.6 Hz, 2H); 3.24-3.35 (m, 2H); 3.38-3.51 (m, 1H); 3.56 (s, 3H); 3.69-3.84 (m, 1H); 4.12-4.30 (m, 5H); 4.56 (d, J=13.6 Hz, 1H); 6.52-6.62 (m, 2H); 6.68-6.83 (m, 2H); 7.01 (sl, 1H); 7.26-7.36 (m, 1H); 10.62 (sl, NH)

MS (ESI); m/z=470.68 (MH$^+$)

Examples 208 to 210

The title compounds were prepared according to the procedure described in the Example 207 using the iodo-derivative as indicated in the Table below.

Example 207

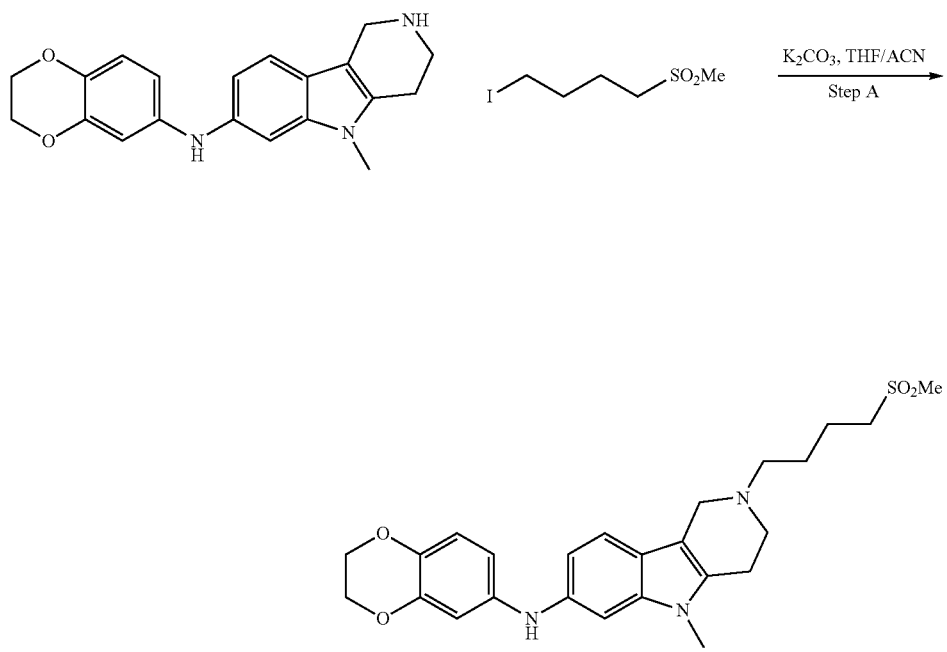

TABLE 7

| Example | Compound Preparative Example | Iodo-derivative | Product | 1. Yield  2. 1H-NMR (DMSO-d6/D2O)  3. MH+ (ESI) |
|---|---|---|---|---|
| 208 | | | | 1. 58%  2. 1.77 (quint, J = 7.6 Hz, 2H); 1.94 (quint, J = 7.6 Hz, 2H); 2.64 (t, J = 7.2 Hz, 2H); 2.78-2.85 (m, 2H); 2.85-2.92 (m, 5H); 3.06 (dd, J1 = 7.2 Hz, J2 = 7.6 Hz, 2H); 3.60 (s, 3H); 3.63 (s, 2H); 6.44-6.54 (m, 1H); 6.63 (ddd, J1 = 2.8 Hz, J2 = 6.8 Hz, J3 = 12.8 Hz, 1H); 6.86-6.99 (m, 2H); 7.13 (sl, 1H); 7.19 (d, J = 8.4 Hz, 1H)  3. 448.69 |
| 209 | | | | 1. 40%  2. 1.68-1.82 (m, 2H); 1.84-1.97 (m, 2H); 2.63 (t, J = 6.8 hz, 2H); 2.75-2.83 (m, 2H); 2.83-2.91 (m, 5H); 3.04 (t, J = 8.0 Hz, 2H); 3.55 (s, 3H); 3.62 (s, 2H); 4.10-4.25 (m, 4H); 6.42 (dd, J1 = 2.8 Hz, J2 = 8.8 Hz, 1H); 6.48 (d, J = 2.8 Hz, 1H); 6.70 (d, J = 8.4 Hz, 1H); 6.88 (dd, J1 = 1.6 Hz, J2 = 8.4 Hz, 1H); 7.07 (d, J = 1.6 hz, 1H); 7.13 (d, J = 8.4 Hz, 1H)  3. 470.72 |
| 210 | | | | 1. 42%  2. 1.79 (quint, J = 7.2 Hz, 2H); 1.94 (quint, J = 7.2 Hz, 2H); 2.66 (t, J = 7.2 Hz, 2H); 2.77-2.85 (m, 2H); 2.85-2.94 (m, 5H); 3.07 (dd, J1 = 7.2 Hz, J2 = 7.6 Hz, 2H); 3.54 (s, 3H); 3.68 (s, 2H); 6.54-6.62 (m, 1H); 6.74 (ddd, J1 = 2.8 Hz, J2 = 6.8 Hz, J3 = 12.8 Hz, 1H); 6.82 (d, J = 8.4 Hz, 1H); 6.91-7.02 (m, 2H); 7.30 (d, J = 8.0 Hz, 1H)  3. 448.66 |

Examples 211 to 218

If one were to treat the title compounds from the Preparative Examples with the iodo-derivatives as described in the Example 207, one would obtain the desired Examples as indicated in the Table below.

TABLE 8

| Example | Compound Preparative Example | Iodo-derivative | Product |
|---|---|---|---|
| 211 | | | |
| 212 | | | |
| 213 | | | |
| 214 | | | |
| 215 | | | |

TABLE 8-continued

| Example | Compound Preparative Example | Iodo-derivative | Product |
|---|---|---|---|
| 216 | 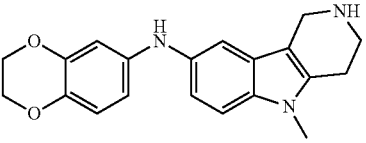 [SMILES: Cn1c2c(c3cc(Nc4ccc5c(c4)OCCO5)ccc31)CNCC2] | 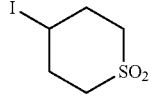 | 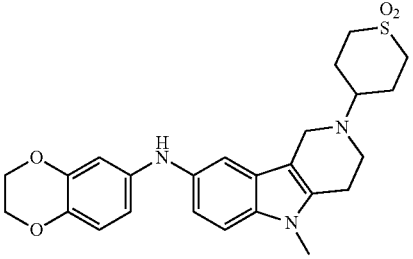 [SMILES: Cn1c2c(c3cc(Nc4ccc5c(c4)OCCO5)ccc31)CN(C1CCS(=O)(=O)CC1)CC2] |
| 217 | 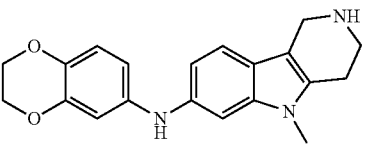 [SMILES: Cn1c2c(c3ccc(Nc4ccc5c(c4)OCCO5)cc31)CNCC2] | 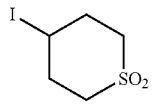 | 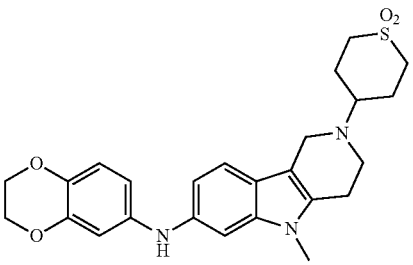 [SMILES: Cn1c2c(c3ccc(Nc4ccc5c(c4)OCCO5)cc31)CN(C1CCS(=O)(=O)CC1)CC2] |
| 218 | 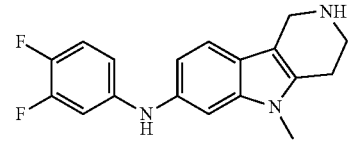 [SMILES: Cn1c2c(c3ccc(Nc4ccc(F)c(F)c4)cc31)CNCC2] | 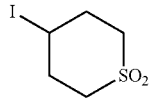 | 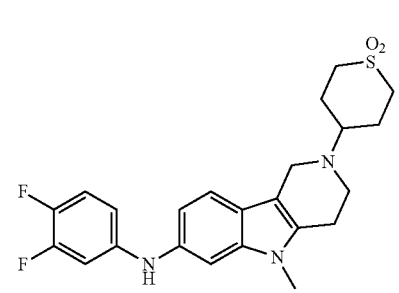 [SMILES: Cn1c2c(c3ccc(Nc4ccc(F)c(F)c4)cc31)CN(C1CCS(=O)(=O)CC1)CC2] |

Examples 219 to 222

If one were to treat the title compounds from the Preparative Examples with the vinylsulfone derivatives according to Ref. WO2008/150799, one would obtain the desired title compounds as indicated in the table below.

TABLE 9

| Example | Compound Preparative Example | vinylsulfone-derivative | Product |
|---|---|---|---|
| 219 | 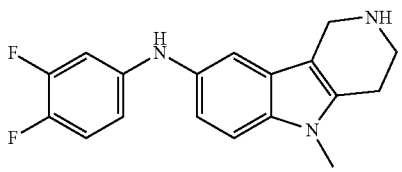 [SMILES: Cn1c2c(c3cc(Nc4ccc(F)c(F)c4)ccc31)CNCC2] | 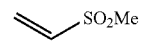 | 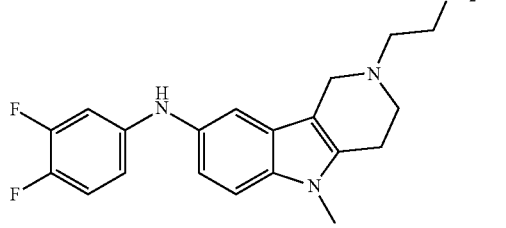 |

TABLE 9-continued

| Example | Compound Preparative Example | vinylsulfone-derivative | Product |
|---|---|---|---|
| 220 | | | |
| 221 | | | |
| 222 | | | |

Compounds of the present invention having one or more optically active carbons can exist as racemates and racemic mixtures, diasteromeric mixtures and individual diasteromers, enantiomeric mixtures and single enantiomers, tautomers, atropisomers and rotamers, with all isomeric forms being included in the present invention. Compounds described in this invention containing olefinic double bonds include both E and Z geometric isomers. Also included in this invention are all salt forms, polymorphs, hydrates and solvates. All of the above-mentioned compounds are included within the scope of the invention.

Determination of Inhibition of Aβ1-42 Aggregation

The capacity of the example compounds of the invention to inhibit the aggregation of Ab1-42 peptide was determined by using the thioflavin T spectrofluorescence assay (ThT-assay) as described below.

Preparation of Aβ Peptide Film

Aβ1-42 lyophilized powder (Bachem) was reconstituted in hexafluoroisopropanol (HFIP) to 1 mM. The peptide solution was sonicated for 15 min at room temperature, agitated overnight, and aliquots were made into non-siliconized microcentrifuge tubes. The HFIP was then evaporated under a stream of argon. The resulting peptide film was dried under vacuum for 10 min, tightly sealed and stored at −80° C. until used.

Inhibition of Aβaggregation measurement 1-42

To assay the small molecule-mediated inhibition of Aβ1-42 aggregation, the small molecules from the examples were dissolved previous to each experiment in anhydrous dimethyl sulfoxide (DMSO, Sigma-Aldrich) to reach a concentration of 7.4 mM. Aβ1-42 peptide film was dissolved in DMSO to reach 400 µM. An Assay solution in PBS was prepared in non-siliconized incubation tubes to reach the following concentrations: 330 µM small molecule, 33 µM Aβ1-42, 10 µM thioflavin T (ThT), and 12.8% DMSO. Therefore, the final molar ratio of small molecule to Aβ1-42 was 10:1. A positive control without a small molecule was prepared to measure maximum RFU. A negative control without Aβ1-42 was prepared for each small molecule. The 3-amino-pyrazole trimer (Rzepecki et. al. *Synthesis* 2003, 1815) was tested as a reference compound in all assays to ascertain reproducibility between independent experiments. The solutions were then incubated for 24 hrs at 37° C., and the spectrofluorescence (relative fluorescence units; RFU) were read in six replicates in black 384-well assay plates (Perkin-Elmer) on a Perkin-Elmer FluoroCount spectrofluorometer. The inhibition of aggregation is expressed as mean % Inhibition ± 1 standard deviation (SD) according to the following equation:

$$\% \text{ inhibition} = \frac{\left( \begin{array}{l} (RFU \text{ of positive control} - RFU \text{ of negative control}) - \\ (RFU \text{ of sample with } A\beta1-42 - RFU \text{ of sample without } A\beta1-42) \end{array} \right)}{(RFU \text{ of positive control} - RFU \text{ of negative control})} \times 100$$

The following example compounds were measured:

TABLE 10

| Example | Structure | Inhibition at 330 μM [%] |
|---|---|---|
| 1 | pyridin-2-yl-ethyl-NH-7-azaindole | 69.5 ± 4.5 |
| 2 | pyridin-2-yl-methyl-NH-7-azaindole | 47.4 ± 8.9 |
| 3 | 3,4-difluorophenyl-NH-7-azaindole | 56.6 ± 23.0 |
| 4 | 6-(trifluoromethyl)pyridin-3-yl-NH-7-azaindole | 53.5 ± 0.4 |
| 5 | 4-(N,N-dimethylcarbamoyl)phenyl-NH-7-azaindole | no inhibition |
| 6 | 3,5-difluorophenyl-NH-7-azaindole | 60.1 ± 3.5 |
| 7 | 3-(N,N-dimethylcarbamoyl)phenyl-NH-7-azaindole | no inhibition |
| 8 | bis(7-azaindol-6-yl)amine | 74.7 ± 6.8 |
| 9 | pyridin-2-yl-NH-7-azaindole | 70.8 ± 9.2 |

TABLE 10-continued

| Example | Structure | Inhibition at 330 µM [%] |
|---|---|---|
| 10 | 4-fluorophenyl-NH-7-azaindole (2-position) | 62.7 ± 4.0 |
| 11 | 7-azaindole-NH-7-azaindole | 86.2 ± 8.6 |
| 12 | 6-indole-NH-7-azaindole | 75.3 ± 14.5 |
| 13 | 4-azaindole-NH-7-azaindole | 97.8 ± 1.8 |
| 14 | 3,5-difluorophenyl-NH-4-azaindole | 52.1 ± 13.0 |
| 15 | 4-fluorophenyl-NH-(3-CN-7-azaindole) | 58.6 ± 9.5 |
| 16 | 5-indole-NH-6-indole | 93.7 ± 2.1 |
| 17 | 6-indole-NH-6-indole | 96.3 ± 0.0 |
| 18 | 5-indole-NH-6-(7-azaindole) | 97.0 ± 1.2 |
| 19 | 3,4-dimethoxyphenyl-NH-[6-(3-(1-methylpiperidin-4-yl))indole] | 92.5 ± 1.3 |

TABLE 10-continued
| Example | | Inhibition at 330 μM [%] |
|---|---|---|
| 20 | 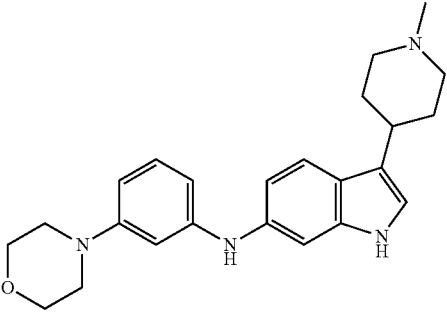 | 92.8 ± 0.1 |
| 21 | 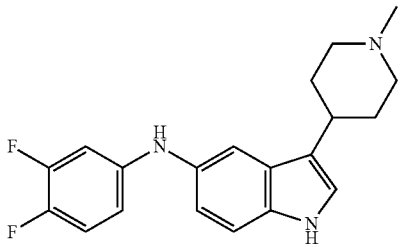 [SMILES: CN1CCC(c2c[nH]c3ccc(Nc4ccc(F)c(F)c4)cc23)CC1] | 74.0 ± 2.7 |
| 22 | 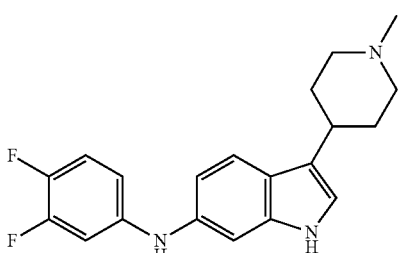 | 84.5 ± 6.8 |
| 23 | 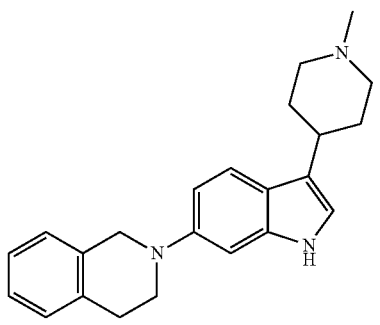 [SMILES: CN1CCC(c2c[nH]c3cc(N4CCc5ccccc5C4)ccc23)CC1] | 97.8 ± 1.5 |
| 24 | 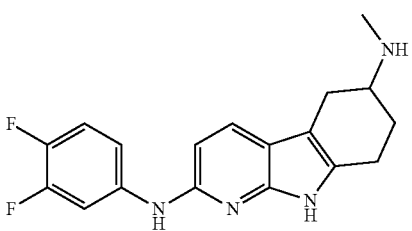 [SMILES: CNC1CCc2[nH]c3nc(Nc4ccc(F)c(F)c4)ccc3c2C1] | 77.4 ± 15.6 |

TABLE 10-continued
| Example | | Inhibition at 330 μM [%] |
|---|---|---|
| 25 | 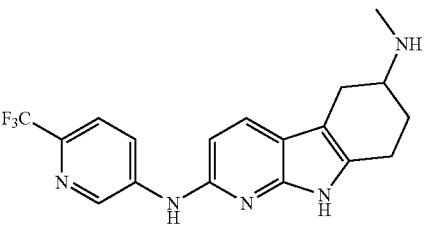 [SMILES: CNC1CCc2[nH]c3nc(Nc4ccc(C(F)(F)F)nc4)ccc3c2C1] | 63.4 ± 9.0 |
| 26 | 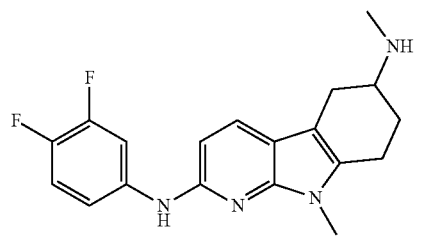 [SMILES: CNC1CCc2c(c3ccc(Nc4ccc(F)c(F)c4)nc3n2C)C1] | 93.4 ± 3.9 |
| 27 | 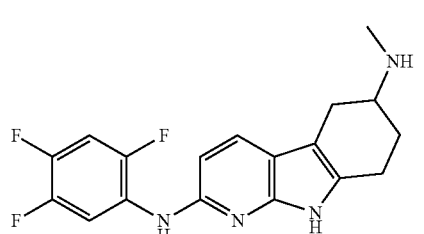 | 86.7 ± 0.8 |
| 28 | 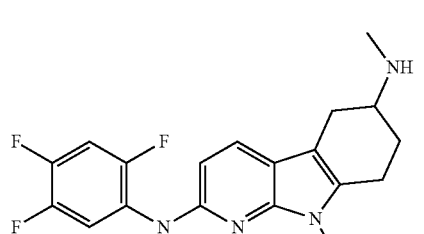 | 91.4 ± 2.9 |
| 29 | 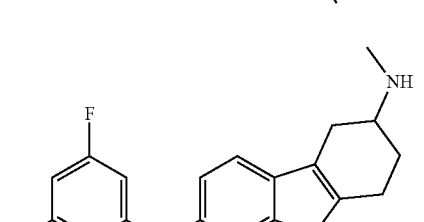 | 85.4 ± 0.4 |
| 30 | 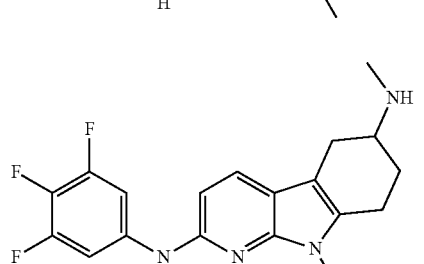 | 84.3 ± 3.1 |

TABLE 10-continued
| Example | | Inhibition at 330 µM [%] |
|---|---|---|
| 31 | 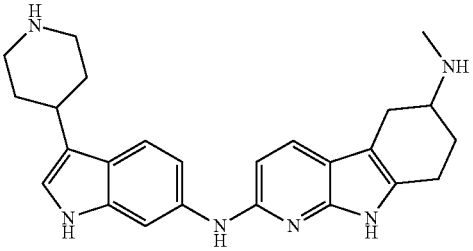 [SMILES: CNC1CCc2[nH]c3nc(Nc4ccc5c(C6CCNCC6)c[nH]c5c4)ccc3c2C1] | 96.5 ± 0.6 |
| 32 | 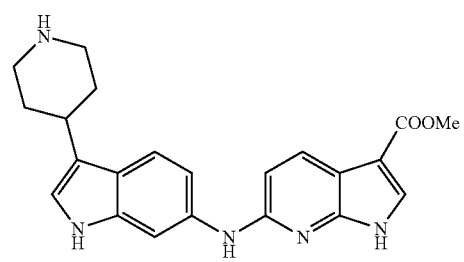 [SMILES: COC(=O)c1c[nH]c2nc(Nc3ccc4c(C5CCNCC5)c[nH]c4c3)ccc12] | 94.7 ± 1.0 |
| 33 | 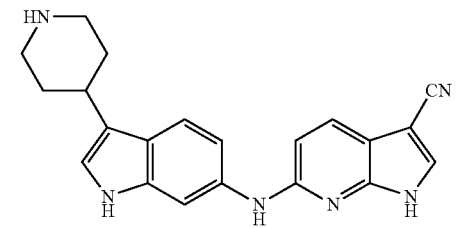 [SMILES: N#Cc1c[nH]c2nc(Nc3ccc4c(C5CCNCC5)c[nH]c4c3)ccc12] | 95.1 ± 3.9 |
| 34 | 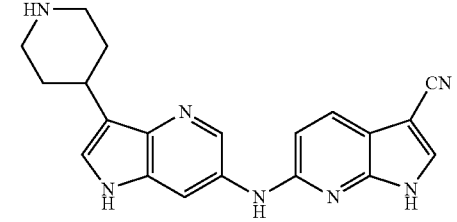 [SMILES: N#Cc1c[nH]c2nc(Nc3cnc4c(C5CCNCC5)c[nH]c4c3)ccc12] | 79.2 ± 16.2 |
| 35 | 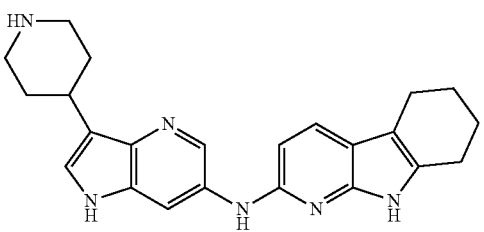 [SMILES: c1nc2c(C3CCNCC3)c[nH]c2cc1Nc1ccc2c3c([nH]c2n1)CCCC3] | 97.7 ± 0.3 |

TABLE 10-continued

| Example | | Inhibition at 330 µM [%] |
|---|---|---|
| 36 | | 98.2 ± 0.3 |
| 37 | | 47.4 ± 5.2 |
| 38 | | 90.9 ± 2.7 |
| 39 | | 81.3 ± 5.1 |
| 40 | | 94.8 ± 1.0 |

TABLE 10-continued

| Example | | Inhibition at 330 μM [%] |
|---|---|---|
| 41 | [structure] | 98.0 ± 0.5 |
| 42 | [structure] | 96.2 ± 2.8 |
| 43 | [structure] | 48.4 ± 20.3 |
| 44 | [structure] | 98.1 ± 0.3 |
| 45 | [structure] | 96.5 ± 3.7 |
| 46 | [structure] | 99.4 ± 0.0 |

TABLE 10-continued
| Example | | Inhibition at 330 μM [%] |
|---|---|---|
| 47 | 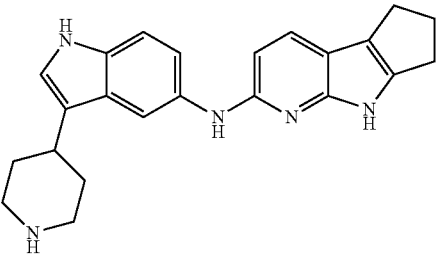 | 99.1 ± 0.5 |
| 48 | 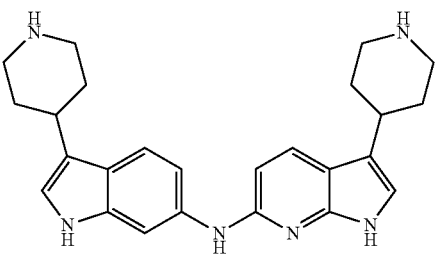 [SMILES: c1cc2c(C3CCNCC3)c[nH]c2cc1Nc1ccc2c(C3CCNCC3)c[nH]c2n1] | 92.0 ± 0.8 |
| 49 | 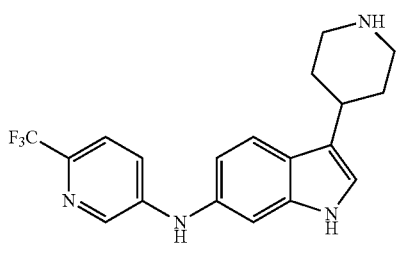 [SMILES: FC(F)(F)c1ccc(Nc2ccc3c(C4CCNCC4)c[nH]c3c2)cn1] | 81.9 ± 0.6 |
| 50 | 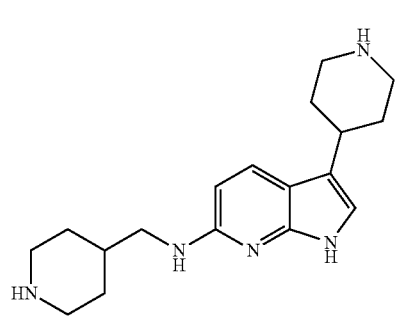 [SMILES: c1cc2c(C3CCNCC3)c[nH]c2nc1NCC1CCNCC1] | 67.5 ± 0.1 |
| 51 | 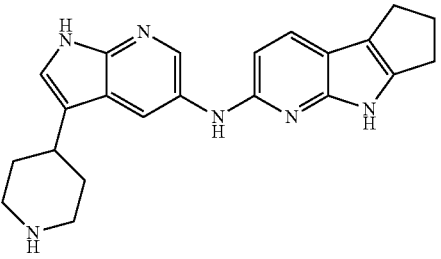 [SMILES: c1nc2[nH]cc(C3CCNCC3)c2cc1Nc1ccc2c3c([nH]c2n1)CCC3] | 95.5 ± 1.0 |

TABLE 10-continued

| Example | Inhibition at 330 μM [%] |
|---|---|
| 52 | 83.6 ± 2.8 |
| 53 | 96.0 ± 2.1 |
| 54 | 96.0 ± 2.7 |
| 55 | 75.8 ± 0.8 |
| 56 | 58.5 ± 2.7 |

TABLE 10-continued
| Example | | Inhibition at 330 μM [%] |
|---|---|---|
| 57 | 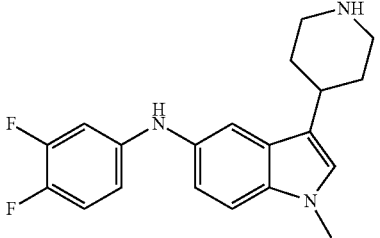 [SMILES: Cn1cc(C2CCNCC2)c2cc(Nc3ccc(F)c(F)c3)ccc21] | 85.1 ± 3.2 |
| 58 | 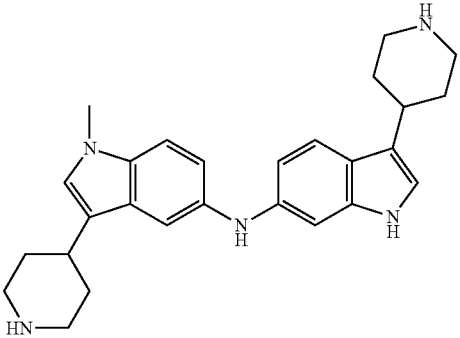 [SMILES: Cn1cc(C2CCNCC2)c2cc(Nc3ccc4c(C5CCNCC5)c[nH]c4c3)ccc21] | 97.2 ± 1.2 |
| 59 | 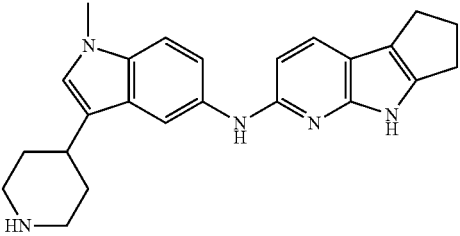 [SMILES: Cn1cc(C2CCNCC2)c2cc(Nc3ccc4c5c([nH]c4n3)CCC5)ccc21] | 99.0 ± 0.3 |
| 60 | 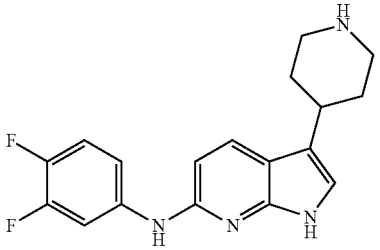 [SMILES: Fc1ccc(Nc2ccc3c(C4CCNCC4)c[nH]c3n2)cc1F] | 83.1 ± 3.4 |
| 61 | 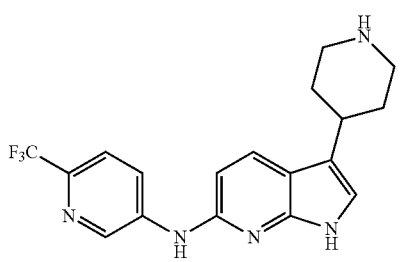 [SMILES: FC(F)(F)c1ccc(Nc2ccc3c(C4CCNCC4)c[nH]c3n2)cn1] | 83.0 ± 2.1 |

TABLE 10-continued

| Example | | Inhibition at 330 μM [%] |
|---|---|---|
| 62 | (structure) | 99.7 ± 0.3 |
| 63 | (structure) | 91.5 ± 2.5 |
| 64 | (structure) | 95.4 ± 0.3 |
| 65 | (structure) | 95.9 ± 1.3 |
| 66 | (structure) | 85.1 ± 0.8 |

TABLE 10-continued

| Example | Structure | Inhibition at 330 μM [%] |
|---|---|---|
| 67 | | 87.8 ± 4.2 |
| 68 | | 90.4 ± 5.3 |
| 69 | | 86.5 ± 7.2 |
| 70 | | 91.0 ± 1.2 |
| 71 | | 90.7 ± 3.0 |

TABLE 10-continued

| Example | | Inhibition at 330 μM [%] |
|---|---|---|
| 72 | (structure) | 97.9 ± 0.5 |
| 73 | (structure) | 99.2 ± 0.3 |
| 74 | (structure) | 99.6 ± 0.5 |
| 75 | (structure) | 97.1 ± 2.0 |
| 76 | (structure) | 96.9 ± 2.3 |

TABLE 10-continued

| Example | Inhibition at 330 µM [%] |
|---|---|
| 77 | 98.0 ± 0.6 |
| 78 | 75.0 ± 1.4 |
| 79 | 91.0 ± 4.2 |
| 80 | 83.3 ± 0.1 |
| 81 | 90.5 ± 0.5 |

TABLE 10-continued
| Example | | Inhibition at 330 μM [%] |
|---|---|---|
| 82 | 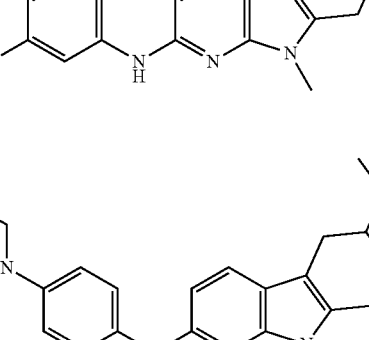 | 96.6 ± 2.0 |
| 83 | 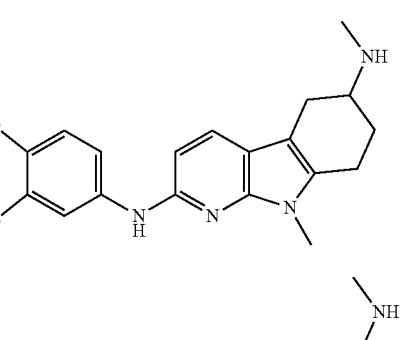 | 82.7 ± 0.7 |
| 84 | 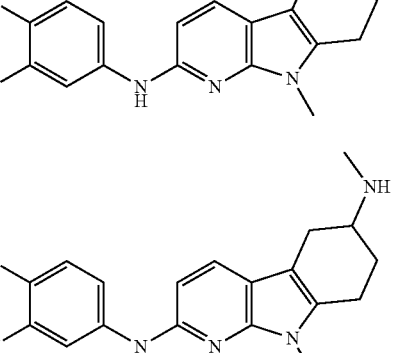 | 91.7 ± 0.2 |
| 85 | 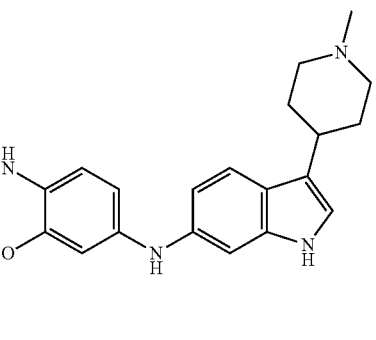 | 95.1 ± 0.9 |
| 86 | 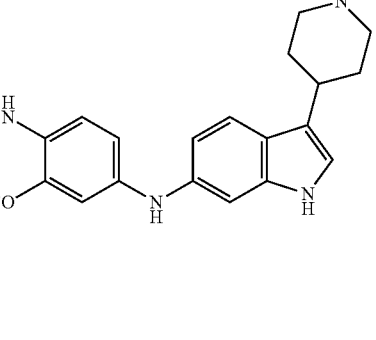 | 96.6 ± 0.7 |
| 87 | 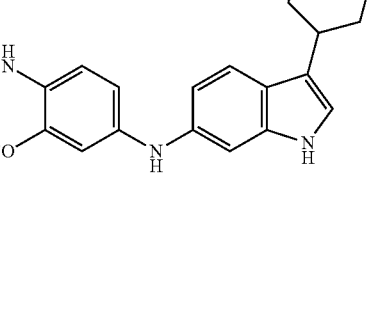 | 80.8 ± 0.5 |

TABLE 10-continued
| Example | | Inhibition at 330 μM [%] |
|---|---|---|
| 88 | 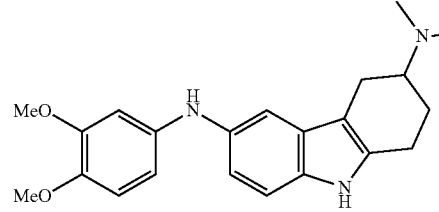 | 96.9 ± 2.6 |
| 89 | 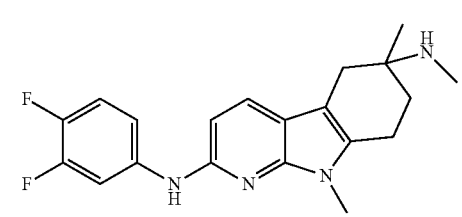 [SMILES: CNC1(C)CCc2c(c3ccc(Nc4ccc(F)c(F)c4)nc3n2C)C1] | 89.6 ± 5.0 |
| 90 | 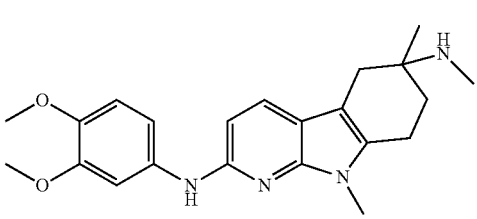 | 75.1 ± 0.3 |
| 91 | 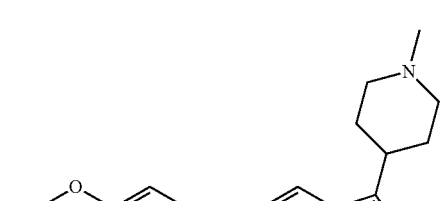 | 92.5 ± 1.3 |
| 92 | 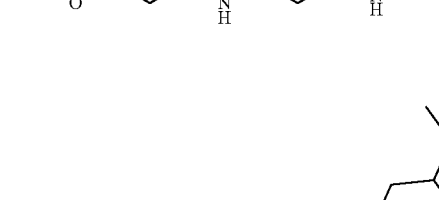 | 99.6 ± 0.6 |

TABLE 10-continued

| Example | | Inhibition at 330 μM [%] |
|---|---|---|
| 93 | | 90.4 ± 5.3 |
| 94 | | 94.4 ± 3.6 |
| 95 | | 89.9 ± 6.1 |
| 96 | | 94.6 ± 1.6 |
| 97 | | 83.8 ± 3.7 |

TABLE 10-continued

| Example | | Inhibition at 330 μM [%] |
|---|---|---|
| 98 | | 95.3 ± 0.1 |
| 99 | | 94.4 ± 0.1 |
| 100 | | 66.6 ± 1.3 |
| 101 | | 70.2 ± 9.8 |
| 102 | | 84.1 ± 1.5 |

TABLE 10-continued
| Example | | Inhibition at 330 μM [%] |
|---|---|---|
| 103 | 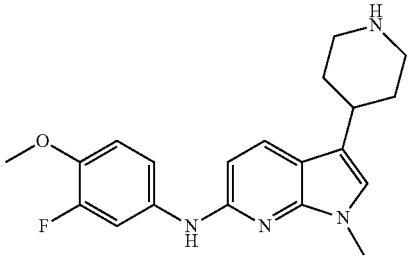 [SMILES: COc1ccc(Nc2ccc3c(C4CCNCC4)cn(C)c3n2)cc1F] | 93.2 ± 3.7 |
| 104 | 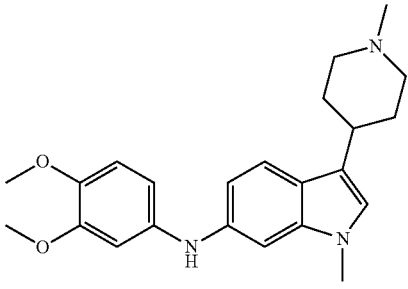 [SMILES: COc1ccc(Nc2ccc3c(C4CCN(C)CC4)cn(C)c3c2)cc1OC] | 89.3 ± 10.6 |
| 105 | 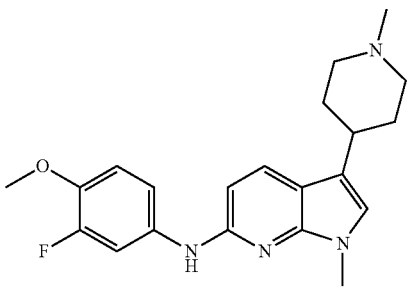 [SMILES: COc1ccc(Nc2ccc3c(C4CCN(C)CC4)cn(C)c3n2)cc1F] | 96.7 ± 0.7 |
| 106 | 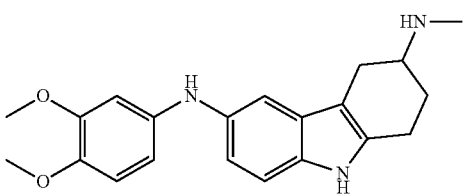 | 86.4 ± 3.8 |
| 107 | 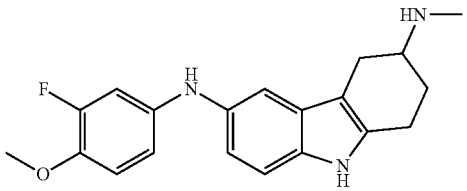 | 86.8 ± 1.9 |

TABLE 10-continued
| Example | | Inhibition at 330 μM [%] |
|---|---|---|
| 108 | 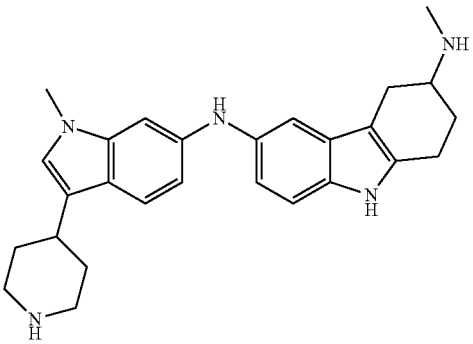 [SMILES: CNC1CCc2[nH]c3ccc(Nc4ccc5c(C6CCNCC6)cn(C)c5c4)cc3c2C1] | 98.9 ± 0.5 |
| 109 | 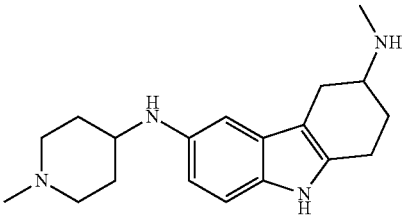 [SMILES: CNC1CCc2[nH]c3ccc(NC4CCN(C)CC4)cc3c2C1] | 63.6 ± 2.0 |
| 111 | 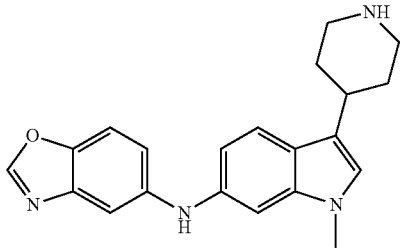 [SMILES: Cn1cc(C2CCNCC2)c2ccc(Nc3ccc4ocnc4c3)cc21] | 99.5 ± 0.1 |
| 112 | 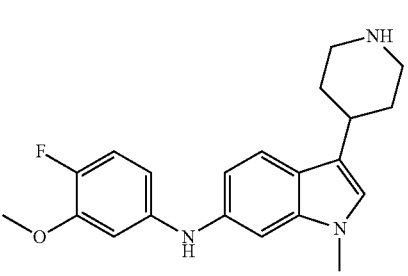 [SMILES: COc1cc(Nc2ccc3c(C4CCNCC4)cn(C)c3c2)ccc1F] | 91.3 ± 1.3 |
| 113 | 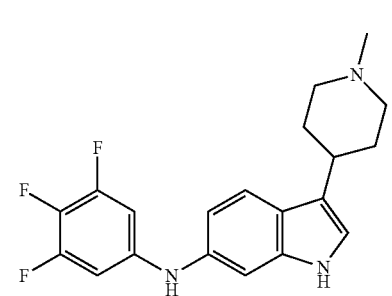 [SMILES: CN1CCC(c2c[nH]c3cc(Nc4cc(F)c(F)c(F)c4)ccc23)CC1] | 90.5 ± 0.5 |

TABLE 10-continued

| Example | | Inhibition at 330 μM [%] |
|---|---|---|
| 114 | | 82.2 ± 1.6 |
| 115 | | 94.0 ± 0.8 |
| 116 | | 89.0 ± 3.6 |
| 117 | | 90.7 ± 7.9 |
| 118 | | 96.8 ± 0.9 |

TABLE 10-continued
| Example | | Inhibition at 330 μM [%] |
|---|---|---|
| 119 | 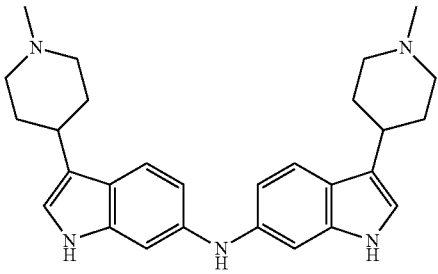 [SMILES: CN1CCC(c2c[nH]c3cc(Nc4ccc5c(C6CCN(C)CC6)c[nH]c5c4)ccc23)CC1] | 99.2 ± 0.3 |
| 120 | 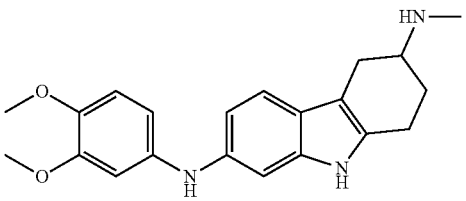 | 100.0 ± 0.0 |
| 121 | 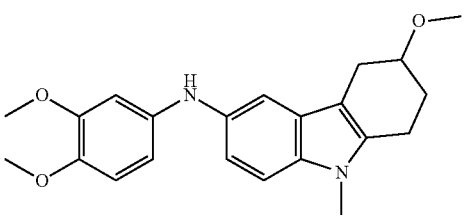 | 91.0 ± 2.5 |
| 122 | 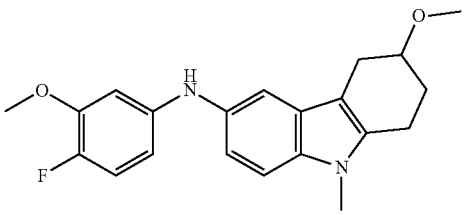 | 80.8 ± 2.9 |
| 123 | 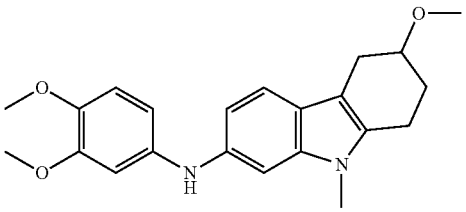 | 93.0 ± 2.2 |
| 124 | 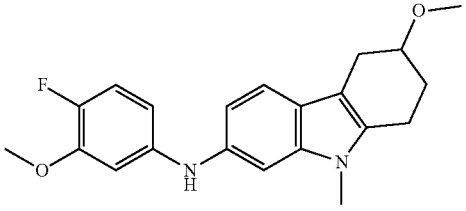 | 79.1 ± 3.8 |

TABLE 10-continued
| Example | | Inhibition at 330 µM [%] |
|---|---|---|
| 125 | 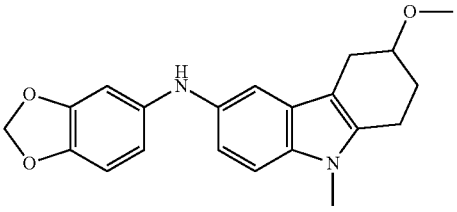 [SMILES: COC1CCc2c(c3cc(Nc4ccc5c(c4)OCO5)ccc3n2C)C1] | 84.2 ± 5.8 |
| 126 | 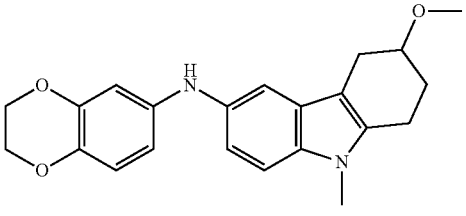 [SMILES: COC1CCc2c(c3cc(Nc4ccc5c(c4)OCCO5)ccc3n2C)C1] | 82.2 ± 2.2 |
| 127 | 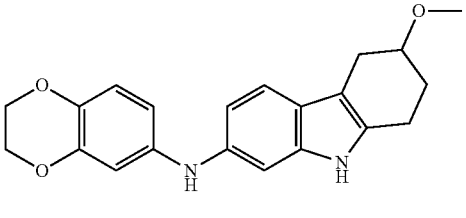 [SMILES: COC1CCc2[nH]c3cc(Nc4ccc5c(c4)OCCO5)ccc3c2C1] | 91.5 ± 2.5 |
| 128 | 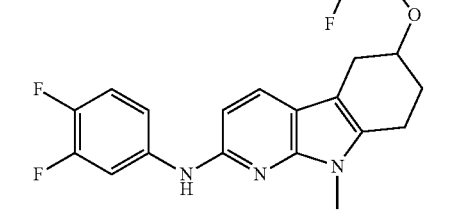 | 88.6 ± 1.2 |
| 129 | 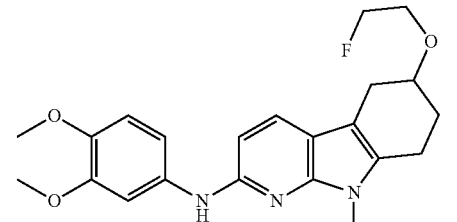 | 79.9 ± 0.6 |
| 130 | 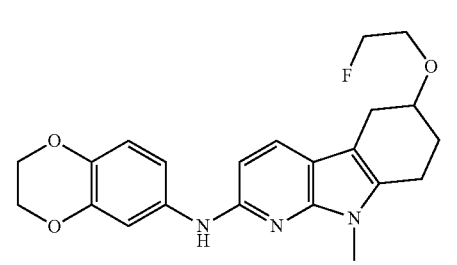 [SMILES: Cn1c2c(c3ccc(Nc4ccc5c(c4)OCCO5)nc31)CC(OCCF)CC2] | 91.6 ± 0.2 |

TABLE 10-continued
| Example | | Inhibition at 330 µM [%] |
|---|---|---|
| 131 | 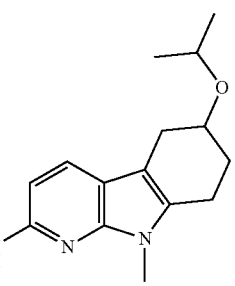 | 91.4 ± 0.2 |
| 132 | 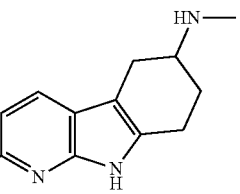 | 99.4 ± 0.8 |
| 133 | 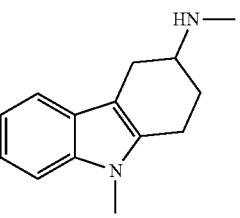 | 99.2 ± 0.3 |
| 134 | 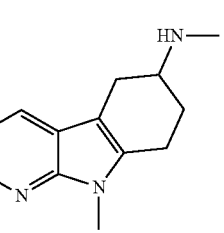 | 67.3 ± 10.4 |
| 135 | 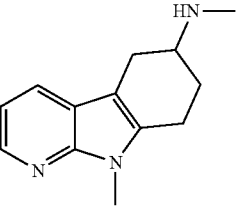 | 51.9 ± 5.5 |
| 136 | 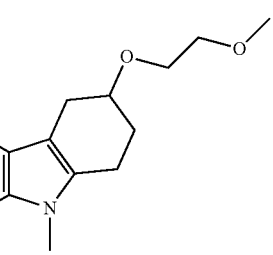 | 88.0 ± 1.4 |

TABLE 10-continued
| Example | | Inhibition at 330 µM [%] |
|---|---|---|
| 137 | 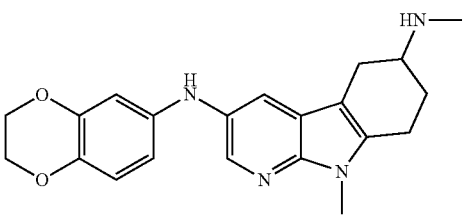 [SMILES: CNC1CCc2c(c3cc(Nc4ccc5c(c4)OCCO5)cnc3n2C)C1] | 83.3 ± 3.3 |
| 138 | 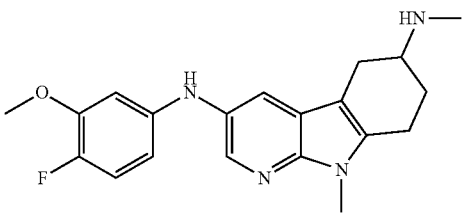 | 69.3 ± 0.7 |
| 139 | 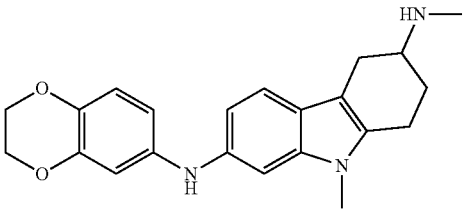 [SMILES: CNC1CCc2c(c3ccc(Nc4ccc5c(c4)OCCO5)cc3n2C)C1] | 93.8 ± 1.6 |
| 140 | 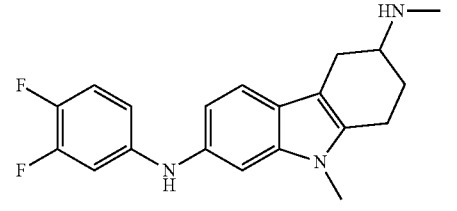 [SMILES: CNC1CCc2c(c3ccc(Nc4ccc(F)c(F)c4)cc3n2C)C1] | 93.8 ± 0.6 |
| 141 | 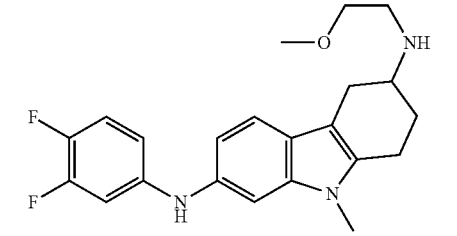 [SMILES: COCCNC1CCc2c(c3ccc(Nc4ccc(F)c(F)c4)cc3n2C)C1] | 87.5 ± 1.4 |
| 142 | 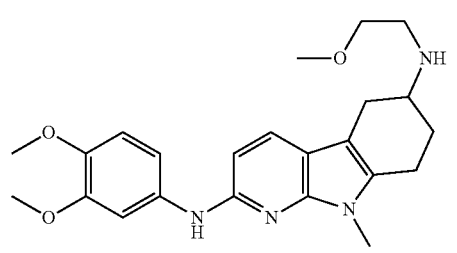 [SMILES: COCCNC1CCc2c(c3ccc(Nc4ccc(OC)c(OC)c4)nc3n2C)C1] | 73.2 ± 6.2 |

TABLE 10-continued

| Example | Structure | Inhibition at 330 μM [%] |
|---|---|---|
| 143 | | 64.8 ± 3.7 |
| 144 | | 95.9 ± 1.3 |
| 145 | | 88.3 ± 4.9 |
| 156 | | 85.1 ± 0.8 |
| 147 | | 87.8 ± 4.2 |
| 148 | | 88.7 ± 2.2 |

TABLE 10-continued
| Example | | Inhibition at 330 μM [%] |
|---|---|---|
| 149 | 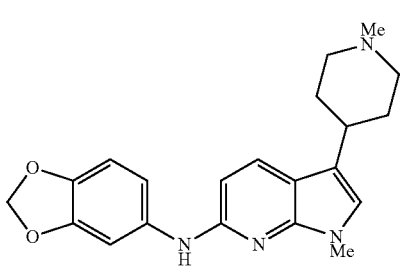 | 84.4 ± 4.1 |
| 150 | 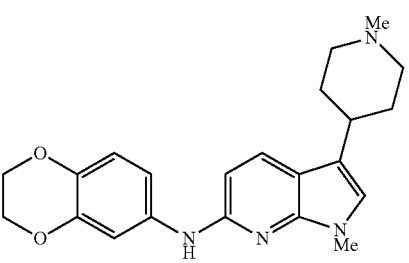 [SMILES: CN1CCC(c2cn(C)c3nc(Nc4ccc5c(c4)OCCO5)ccc23)CC1] | 83.9 ± 1.5 |
| 151 | 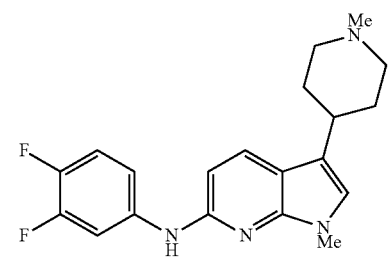 [SMILES: CN1CCC(c2cn(C)c3nc(Nc4ccc(F)c(F)c4)ccc23)CC1] | 88.5 ± 2.8 |
| 152 | 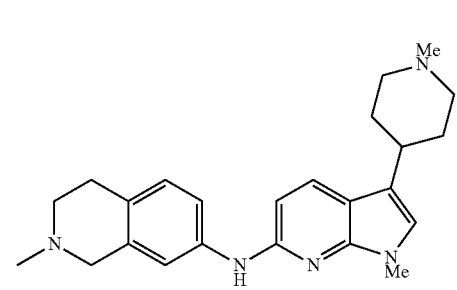 [SMILES: CN1CCC(c2cn(C)c3nc(Nc4ccc5c(c4)CN(C)CC5)ccc23)CC1] | 80.8 ± 3.6 |
| 153 | 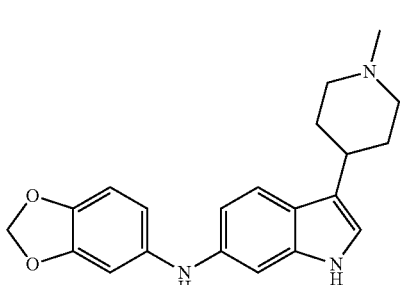 | 91.3 ± 4.2 |

TABLE 10-continued

| Example | | Inhibition at 330 μM [%] |
|---|---|---|
| 154 | | 86.3 ± 2.6 |
| 156 | | 97.4 ± 0.4 |
| 157 | | 95.0 ± 1.5 |
| 158 | | 87.8 ± 3.6 |
| 159 | | 91.9 ± 1.6 |
| 160 | | 96.3 ± 0.3 |

TABLE 10-continued

| Example | Inhibition at 330 μM [%] |
|---|---|
| 162 | 94.5 ± 3.1 |
| 163 | 32.7 ± 0.9 |
| 164 | 69.4 ± 2.7 |
| 165 | 78.1 ± 0.2 |
| 166 | 93.6 ± 2.2 |
| 167 | 88.9 ± 2.6 |
| 168 | 82.1 ± 7.0 |

TABLE 10-continued
| Example | | Inhibition at 330 µM [%] |
|---|---|---|
| 169 | 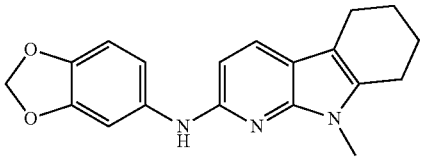 [SMILES: Cn1c2c(c3ccc(Nc4ccc5c(c4)OCO5)nc31)CCCC2] | 92.4 ± 4.0 |
| 170 | 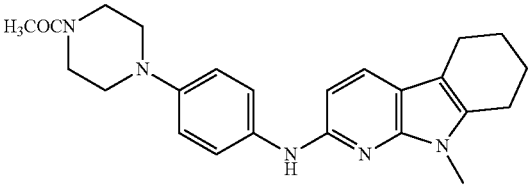 | 70.8 ± 2.3 |
| 172 | 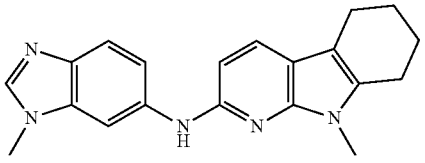 [SMILES: Cn1cnc2ccc(Nc3ccc4c5c(n(C)c4n3)CCCC5)cc21] | 68.3 ± 0.8 |
| 173 | 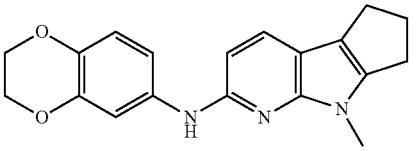 [SMILES: Cn1c2c(c3ccc(Nc4ccc5c(c4)OCCO5)nc31)CCC2] | 90.1 ± 2.3 |
| 174 | 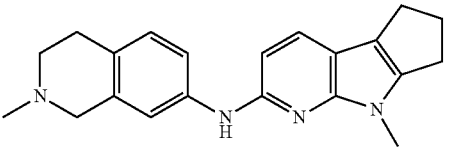 [SMILES: CN1CCc2ccc(Nc3ccc4c5c(n(C)c4n3)CCC5)cc2C1] | 87.2 ± 1.3 |
| 175 | 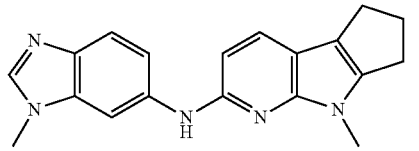 [SMILES: Cn1cnc2ccc(Nc3ccc4c5c(n(C)c4n3)CCC5)cc21] | 75.5 ± 7.8 |
| 176 | 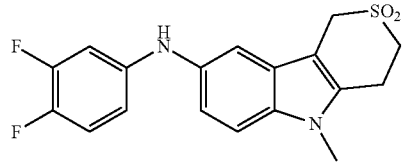 [SMILES: Cn1c2c(c3cc(Nc4ccc(F)c(F)c4)ccc31)CS(=O)(=O)CC2] | 41.5 ± 3.6 |
| 177 | 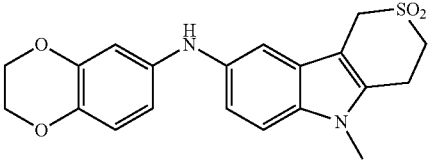 [SMILES: Cn1c2c(c3cc(Nc4ccc5c(c4)OCCO5)ccc31)CS(=O)(=O)CC2] | 29.6 ± 6.2 |
| 178 | 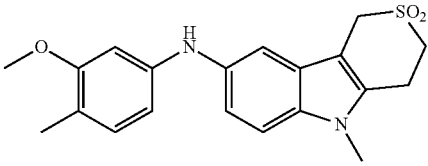 [SMILES: COc1cc(Nc2ccc3c(c2)c2c(n3C)CCS(=O)(=O)C2)ccc1C] | 35.4 ± 5.9 |

TABLE 10-continued

| Example | Structure | Inhibition at 330 μM [%] |
|---|---|---|
| 179 | | 30.2 ± 0.9 |
| 180 | | 50.2 ± 0.9 |
| 181 | | 56.6 ± 4.3 |
| 182 | | 66.1 ± 6.9 |
| 183 | | 42.3 ± 3.1 |
| 184 | | 41.3 ± 1.1 |
| 185 | | 55.2 ± 6.0<br>Not included in the claims |
| 186 | | 66.5 ± 2.4<br>Not included in the claims |
| 187 | | 82.2 ± 6.0<br>Not included in the claims |

TABLE 10-continued
| Example | | Inhibition at 330 µM [%] |
|---|---|---|
| 188 | 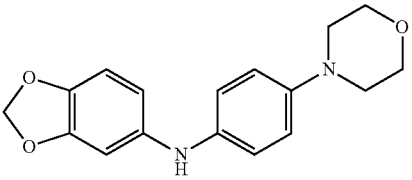 [SMILES: c1cc(N2CCOCC2)ccc1Nc1ccc2c(c1)OCO2] | 83.3 ± 6.0 Not included in the claims |
| 189 | 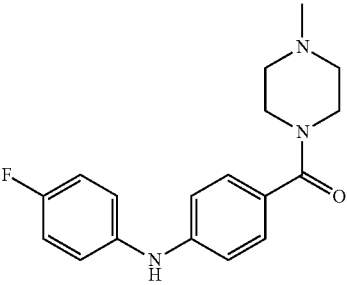 [SMILES: CN1CCN(C(=O)c2ccc(Nc3ccc(F)cc3)cc2)CC1] | 12.6 ± 5.5 Not included in the claims |
| 190 | 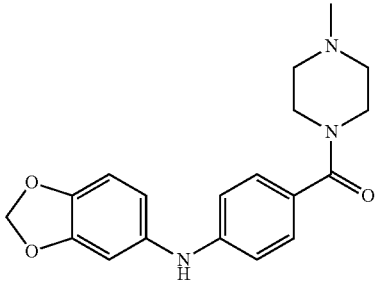 [SMILES: CN1CCN(C(=O)c2ccc(Nc3ccc4c(c3)OCO4)cc2)CC1] | 20.1 ± 4.6 Not included in the claims |
| 191 | 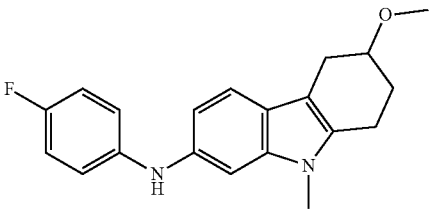 [SMILES: COC1CCc2c(c3ccc(Nc4ccc(F)cc4)cc3n2C)C1] | 89.7 ± 1.4 |
| 192 | 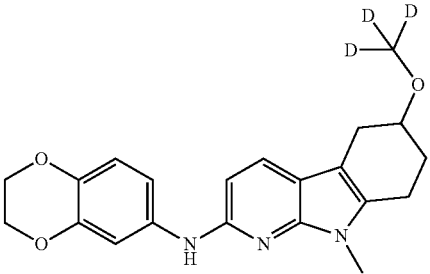 [SMILES: [2H]C([2H])([2H])OC1CCc2c(c3ccc(Nc4ccc5c(c4)OCCO5)nc3n2C)C1] | 93.8 ± 0.2 |
| 193 | 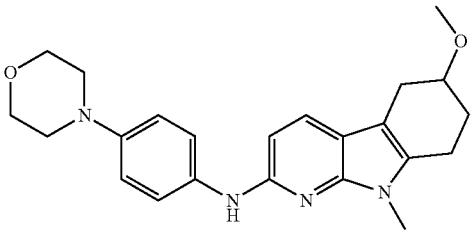 [SMILES: COC1CCc2c(c3ccc(Nc4ccc(N5CCOCC5)cc4)nc3n2C)C1] | 54.3 ± 3.4 |

TABLE 10-continued
| Example | | Inhibition at 330 µM [%] |
|---|---|---|
| 194 | 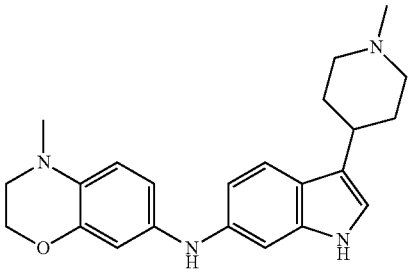 [SMILES: CN1CCC(c2c[nH]c3cc(Nc4ccc5c(c4)OCCN5C)ccc23)CC1] | 106.1 ± 0.3 |
| 195 | 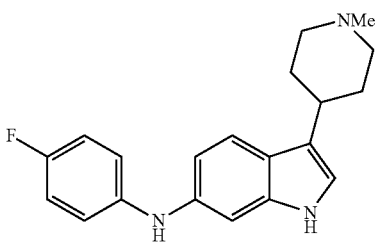 [SMILES: CN1CCC(c2c[nH]c3cc(Nc4ccc(F)cc4)ccc23)CC1] | 89.7 ± 2.4 |
| 196 | 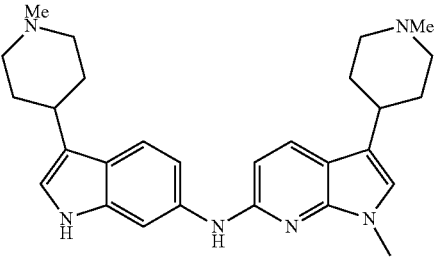 [SMILES: CN1CCC(c2c[nH]c3cc(Nc4ccc5c(C6CCN(C)CC6)cn(C)c5n4)ccc23)CC1] | 80.0 ± 4.6 |
| 197 | 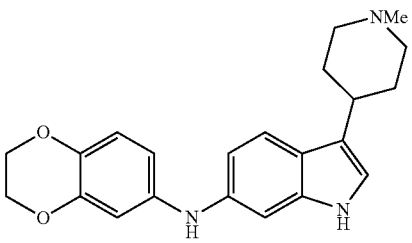 [SMILES: CN1CCC(c2c[nH]c3cc(Nc4ccc5c(c4)OCCO5)ccc23)CC1] | 87.7 ± 10.3 |
| 198 | 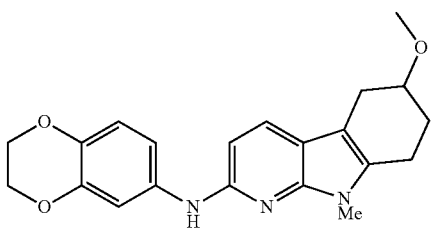 [SMILES: COC1CCc2c(c3ccc(Nc4ccc5c(c4)OCCO5)nc3n2C)C1] | 92.1 ± 0.3 |
| 199 | 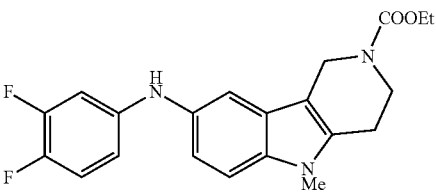 [SMILES: CCOC(=O)N1CCc2c(c3cc(Nc4ccc(F)c(F)c4)ccc3n2C)C1] | 68.6 ± 0.5 |

TABLE 10-continued

| Example | Inhibition at 330 μM [%] |
|---|---|
| 200 | 67.4 ± 3.4 |
| 201 | 93.3 ± 0.1 |
| 202 | 86.1 ± 1.6 |
| 203 | 93.4 ± 3.5 |
| 204 | 93.5 ± 0.4 |
| 205 | 91.7 ± 0.1 |
| 206 | 94.5 ± 0.7 |

TABLE 10-continued

| Example | | Inhibition at 330 µM [%] |
|---|---|---|
| 207 | [structure with 2,3-dihydrobenzo[b][1,4]dioxine-NH-linked tetrahydro-β-carboline with N-butyl-SO₂Me] | 75.6 ± 13.4 |
| 208 | [structure with 3,4-difluorophenyl-NH-linked tetrahydro-β-carboline with N-butyl-SO₂Me] | 85.0 ± 3.3 |
| 209 | [structure with 2,3-dihydrobenzo[b][1,4]dioxine-NH-linked tetrahydro-β-carboline with N-butyl-SO₂Me] | 66.2 ± 6.5 |
| 210 | [structure with 3,4-difluorophenyl-NH-linked tetrahydro-β-carboline with N-butyl-SO₂Me] | 43.2 ± 12.9 |

Table 10:

Inhibition of Aβ1-42 aggregation of preformed Aβ1-42 fibers by the molecules. Results are expressed as mean +/− standard deviation of two independent experiments.

Inhibition of Aβ1-42 aggregation of preformed Aβ1-42 fibers could not be determined for examples 5 and 7 due to very strong autofluorescence.

Example 211

Effect of ACI-636 on Plaque Formation of hAPPSL Transgenic Mice

The objective of this study was the assessment of the properties of the ACI636 regarding inhibition of plaque formation and disaggregation of existing plaques.

211.1 Methods

Transgenic (Tg) mice over-expressing human amyloid protein (hAPP) are suitable models to study the influence of drugs on amyloid production, sequestration, and deposition. For the study, mice over-expressing the 751 amino acid form of hAPP with London (V717I) and Swedish (KM670/671NL) mutations under the control of the murine Thy-1 promoter (hAPPSL mice) were used. The hAPPSL mice show an age-dependent increase of the β-amyloid peptides (Aβ) and develop plaques consisting of amyloid depositions in early age (starting at 4-6 months). Severity of the brain pathology correlates with increasing age and behavioral deficits. Starting at 13 to 14 months of age, female hAPPSL Tg mice were treated once daily by gavage with 10 mg/kg of ACI-636 as described in the following table:

| Group | Mouse strain | n | Genotype | T.I | Application route | Treatment period | Age at start | Tissue sampling |
|---|---|---|---|---|---|---|---|---|
| A | hAPPSL Tg mice | 10 | Tg | PBS | Once daily 10 mg/kg/day p.o. | 14 days | 13 to 14 months | Blood (plasma), brain |
| B | | 10 | Tg | ACI636 | | 14 days | | Blood (plasma), brain |

At the end of the treatment period, animals were sacrificed and blood (plasma) and brains were collected. The effects of ACI-636 on Aβ levels (Aβ38, Aβ40, Aβ42) in four different brain homogenate fractions (TBS, Triton X-100, SDS and FA) were measured with an Aβ-kit from Mesoscale Discovery. Furthermore, amyloid depositions were determined immunohisto-chemically in brain sampled detected by 6E10 antibody. Aβ levels were evaluated in comparison to a peptide standard as pg/mg wet brain weight.

211.2 Results

Overall, animals receiving ACI-636 for 14 days showed a tendency toward increased soluble Aβ levels (TBS and Triton X-100 fractions) but decreased insoluble Aβ levels (SDS and FA fractions) compared to the PBS treated animals. The effect of treatment of the animals with ACI-636 as compared to vehicle (PBS) is referred as "treatment induced difference". The quantification of cortical (a and b) and hippocampal (c and d) 6E10 immunofluorescence is shown in FIG. 1. The effect of treatment to female mice treated for 14 days affects number and total area of plaques (note: minimum object size>150 µm$^2$). Abbreviations: Vehicle (A); ACI-636 10 mg/kg/day (B).

Compared to vehicle, treatment with ACI636 consistently reduced plaque load in female Tg mice after 14 days of treatment.

211.3 Conclusions

Animals receiving ACI636 for 14 days showed a tendency towards increased soluble Aβ levels (TBS and Triton X-100 fractions) but decreased insoluble Aβ levels (SDS and FA fractions) compared to the vehicle treated animals. ACI636 selectively reduced amyloid burden in female hAPP751SL transgenic mice, if administered for 14 days, in both extracellular plaque load and total amyloid burden, including intracellular amyloid. The effect was more pronounced in the cortex than in the hippocampus.

Example 212

Effect of ACI-636 on the Behavior of APPV171I Transgenic Mice

The objective of this study was to determine the efficacy of ACI-636 in a mouse model of Alzheimer's disease. The influence of treatment on memory capacity was assessed by the space recognition test (SRT)

212.1 Methods 212.1.1 Space Recognition Test (SRT)

The novel object recognition test (ORT) is an in vivo test for investigation of effects of a test substance on memory in rodents (mice, rats). This test was introduced to measure non spatial memory in rodents by their ability to recognize a novel object in an otherwise familiar environment (Ennaceur, A. and Delacour, J. Behav. Brain Res. 1988, 31, 47-59). The test gives information on short-term or long term memory, a promnesic or amnesic effect of a test substance and exploratory behavior, which is related to attention. In the learning phase of the test, the animal is confronted with two identical objects, placed in an open field, in order to get familiarized with the objects. In the retention (memory) phase, the animal is exposed to two dissimilar objects placed in the open field: one familiar object, used in the learning phase, and one novel object. In the retention phase, the time spent exploring each of the objects is measured. Exploration of an object is defined as time spent with the head oriented towards and within 2 centimeters of the object. Non-amnesic animals will spend more time exploring the novel object than the familiar one. In order to increase the challenge for the animals the ORT test was modified to include a spatial memory component (space recognition test (SRT)) using two identical objects. In the SRT-setting one object remains in the retention phase at the same place as before in the learning phase while the other object is placed at a different position. A total of 24 female APPV171I transgenic mice (10 months old) were treated by gavage once daily (12 mice treated with ACI-636; 10 mg/kg)) and with PBS (12 mice treated). The SRT-test was performed after 21 days of treatment in a grey polypropylene maze (circular open field, diameter 40 cm, height 32.4 cm) using two different objects (1 cube of lego (2.9 cm×5.8 cm) and a black glass bottle (5.3 cm×5.3 cm)). The experiment was designed as followed:

Day 1:
  Habituation to the apparatus (10 minutes) for each animal without object.
Day 2:
  Learning session: two identical objects (cube of lego or black glass bottle) were presented (10 minutes) on one side of the maze.
  Retention test (3 hours post learning): one of the identical objects was moved to the opposite side of the maze and was presented (10 minutes).

212.2 Results

Figure 2:
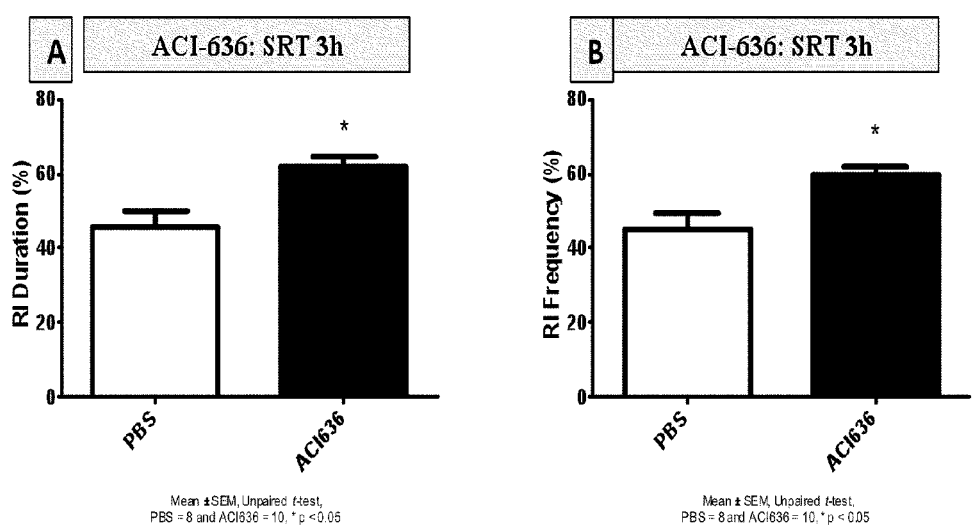
In FIGS. 2A and 2B, APPV171I transgenic mice that had been treated with PBS and ACI-636 have been analysed.

In FIGS. 2A and 2B, APPV171I transgenic mice that had been treated with PBS and ACI-636 have been analysed. The statistical analysis of Recognition Index (RI) for duration and frequency (FIGS. 2A and 2B) using a paired t-test analysis showed a significant difference between APPV171I transgenic mice that had been treated with PBS and ACI-636 (p<0.05).

212.3 Conclusions

In the space recognition test (SRT), APPV171I transgenic mice treated with ACI-636 spent more time exploring the moved object than the familiar object compared to APPV171I transgenic mice treated with vehicle (PBS) demonstrating an effect of ACI-636 on short term memory retention with the space recognition test.

Example 213

Preparation of Compound 213a and 213b (Enantiomers of Compound 26): Chiral Separation 213.1 Objective and Design of the Study The objective of this study was to separate and characterize the two enantiomers of compound 26.

213.2 Methods

Separation of the Boc-protected precursor of compound 26 (N$^2$-(3,4-difluorophenyl)-N$^{6,9}$-dimethyl-6,7,8,9-tetrahydro- 5H-pyrido[2,3-b]indole-2,6-diamine hydrogenchloride; racemate) by HPLC using a chiral phase

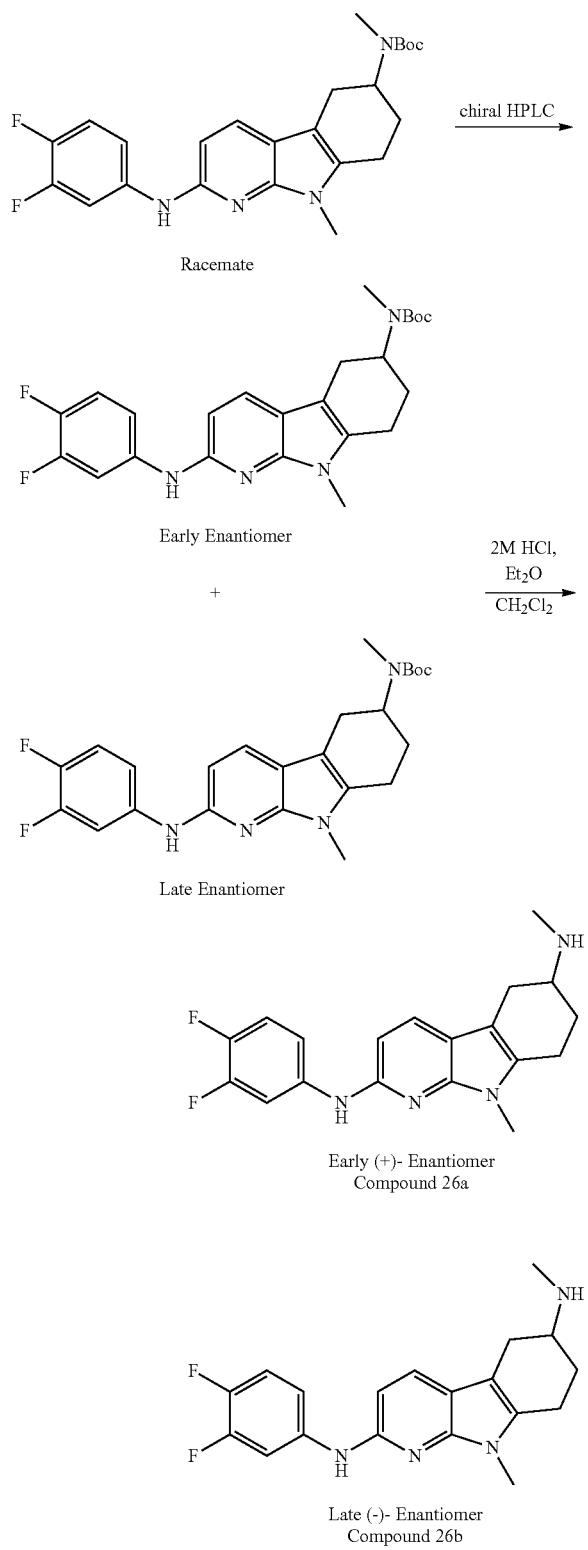

Racemate

Early Enantiomer

Late Enantiomer

Early (+)- Enantiomer
Compound 26a

Late (−)- Enantiomer
Compound 26b

The enantiomers of the Boc-protected precursor of compound 26 (0.110 g, racemate) were separated. A total of 0.040 g of the early enantiomer and 0.033 g of the late enantiomer were obtained. Each enantiomer contained <1% of the other enantiomer as judged by chiral HPLC.

Figure 3:
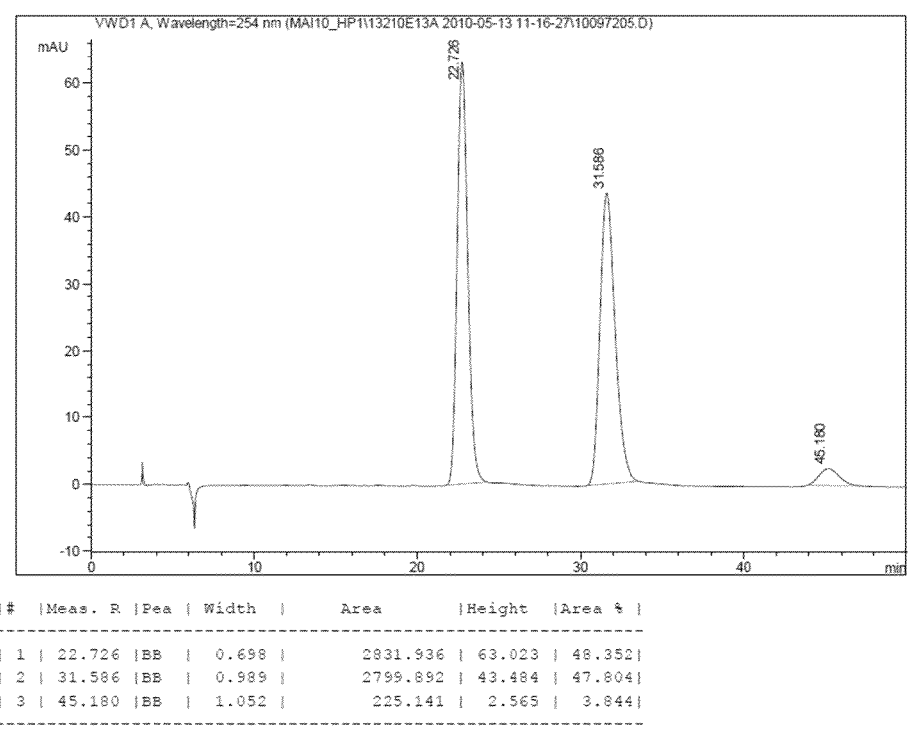
FIG. 3 shows the separation of Boc-protected precursor of compound 26 by chiral HPLC.
Figure 4:
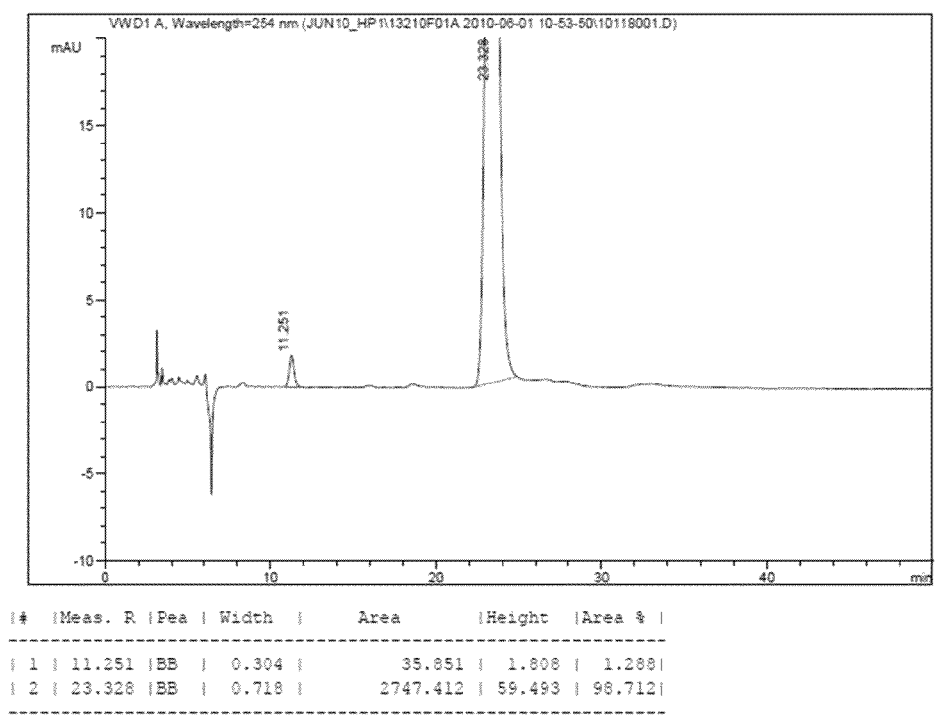
FIG. 4 shows the early enantiomer after separation.
Figure 5:
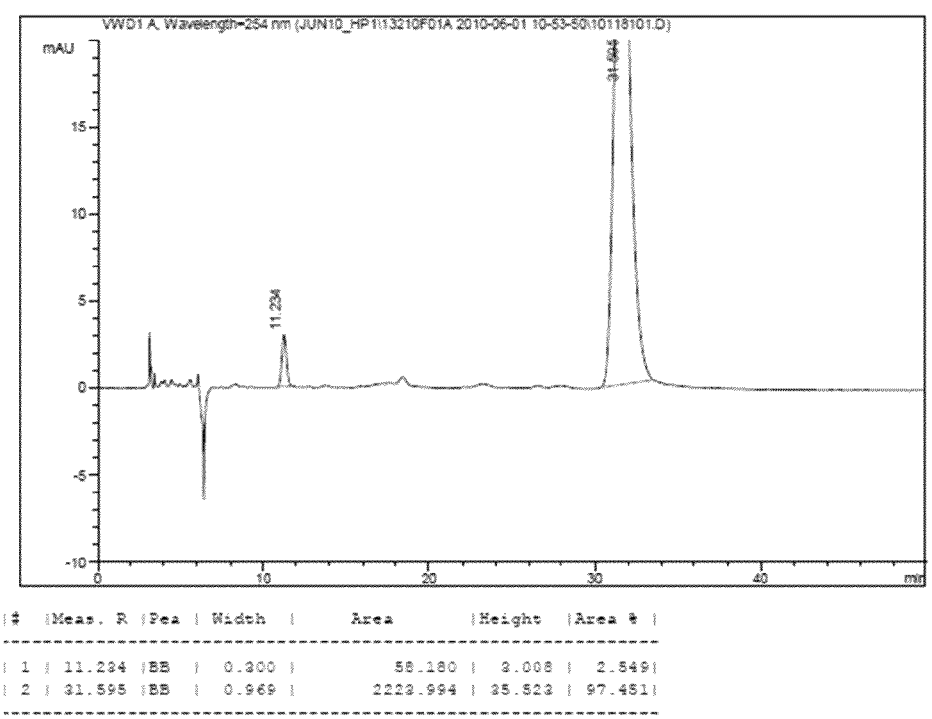
FIG. 5 shows the late enantiomer after separation.

Chiral HPLC Conditions
  Chiralpak IA, 4.6×250 mm, 5 μm
  Mobile phase: n-heptane/iso-propanol (95:5)
  Flow rate: 1 mL/min
  Wavelength: 254 nm
  FIG. 3 shows the separation of Boc-protected precursor of compound 26 by chiral HPLC
  $R_t$ (early enantiomer): 22.7 Min
  $R_t$ (late enantiomer): 31.6 Min
  FIG. 4 shows the early enantiomer after separation, while FIG. 5 shows the late enantiomer after separation.

213.3 Preparation of Final Compounds

All reagents and solvents were obtained from commercial sources and used without further purification. Proton ($^1$H) spectra were recorded on a 400 MHz NMR spectrometer in deuterated solvents. Mass spectra (MS) were recorded on a Finnigan MAT TSQ 7000 spectrometer. Optical rotation of the enantiomers was recorded in methanol on a JASCO polarimeter at 25° C. using a wavelength of 589 nm.

213.3.1 Preparation of Compound 213a

The early enantiomer after HPLC separation (0.039 g, 0.088 mmol) was dissolved in dichloromethane (1.2 mL) and treated with a 2 M solution of hydrogen chloride (1.2 mL) in diethylether. The mixture was stirred at room temperature overnight and the precipitate was collected by filtration. The solids were washed with diethylether (5 mL) and dried under reduced pressure to afford the title compound as an off white solid (0.029 g, 88%).

$^1$H-NMR (400 MHz, DMSO-$d_6$/$D_2$O): δ=1.90-2.02 (m, 1H), 2.27-2.36 (m, 1H), 2.65-2.73 (m, 4H), 2.75-2.94 (m, 2H), 3.10-3.18 (m, 1H), 3.42-3.48 (m, 1H), 3.63 (s, 3H), 6.60 (d, 1H), 7.25-7.33 (m, 1H), 7.36-7.42 (m, 1H), 7.70 (d, 1H), 8.14-8.20 (m, 1H)

MS (ESI); m/z=343.70 (MH$^+$)

$[\alpha]^{25}$=+45.4° (c 0.066, MeOH)

213.3.2 Preparation of Compound 213B

The late enantiomer after HPLC separation (0.022 g, 0.05 mmol) was dissolved in dichloromethane (1 mL) and treated with a 2 M solution of hydrogen chloride (1 mL) in diethylether. The mixture was stirred at room temperature overnight and the precipitate was collected by filtration. The solids were washed with diethylether (5 mL) and dried under reduced pressure to afford the title compound as an off white solid (0.013 g, 71%).

$^1$H-NMR (400 MHz, DMSO-$d_6$/$D_2$O): δ=1.90-1.98 (m, 1H), 2.26-2.33 (m, 1H), 2.62-2.72 (m, 4H), 2.77-2.93 (m, 2H), 3.10-3.16 (m, 1H), 3.40-3.47 (m, 1H), 3.62 (s, 3H), 6.58 (d, 1H), 7.25-7.33 (m, 1H), 7.36-7.41 (m, 1H), 7.70 (d, 1H), 8.11-8.18 (m, 1H)

MS (ESI); m/z=343.68 (MH$^+$)

$[\alpha]^{25}$=−37.5° (c 0.064, MeOH)

213.4 Conclusions

The racemic Boc-protected precursor of compound 26 was successfully separated into its two enantiomers. Cleavage of the protecting group of the early eluting enantiomers yielded (+)-enantiomer compound 213a, while the late eluting enantiomer yielded (−)-enantiomer compound 213b.

Preparative Example 336

Preparation of Single Enantiomers of tert-butyl-(2-bromo-9-methyl-6,7,8,9-tetrahydro-5H-pyrido[2,3-b]indol-6-yl)methyl)carbamate by Separation of Diastereomers 336.1 Objective and Design of the Study The aim of this study was to develop a method for preparation of single enantiomers of tert-butyl-(2-bromo-9-methyl-6,7,8,9-tetrahydro-5H-pyrido[2,3-b]indol-6-yl)methyl)carbamate via separation of diastereomers.

342.2 Methods 336.2.1 Principle of Enantiomers Separation

The racemic compound was reacted with an optically active reagent L (amino acid-derivative) to yield a mixture of diastereomers (RL and SL) which was separated by chromatography. The chiral reagent was subsequently removed by acidic treatment to generate the enantiomerically enriched building block.

Synthesis Scheme for the Preparation of Enantiomerically Enriched (tert-butyl-(2-bromo-9-methyl-6,7,8,9-tetrahydro-5H-pyrido[2,3-b]indol-6-yl)-methyl)carbamate

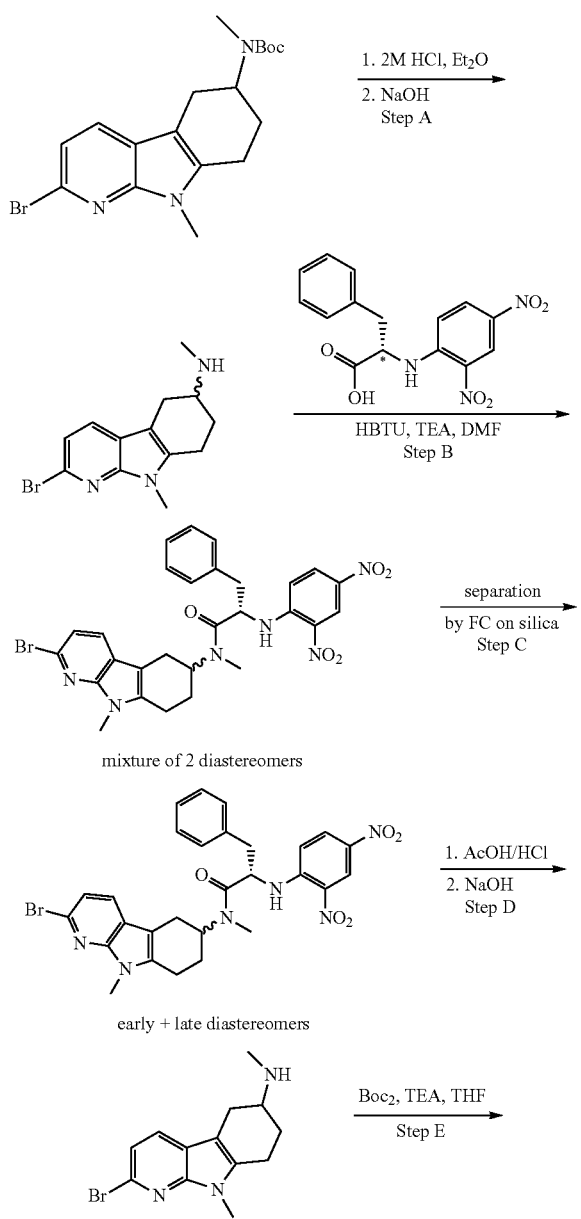

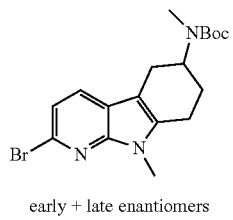

early + late enantiomers

Preparation of the Chiral Auxiliary (S)-2-((2,4-dinitrophenyl)amino)-3-phenylpropanoic acid To a mixture of L-phenylalanine (8.88 g, 53.7 mmol) and 1-fluoro-2,4-dinitrobenzene (3.24 ml, 26.9 mmol) was added triethylamine (7.86 ml, 56.4 mmol). The resulting mixture was warmed using a Biotage Initiator microwave to 100° C. for 4 min. The solid was diluted with MeOH and the slurry was dropped into distilled water. Dichloromethane was added to the slurry and the organic phase was separated. The organic phase was further extracted with 1.2 M hydrogen chloride solution and brine. The organic phase was dried over $Na_2SO_4$, filtered and the solvents were evaporated. The residue was diluted with dichlormethane and the slurry was filtered. The precipitate was then washed with a small amount of dichlormethane. The combined filtrates were evaporated and the residue was purified by flash chromatography using a dichloromethane/methanol gradient (0% to 5%) to afford the title compound.

MS ESI MeOH (Neg): 329.96 (M–H)/375.99 (M+FA-H)/661.13 (2M–H)/992.32 (3M–H)

Step A

To a solution of racemic tert-butyl-(2-bromo-9-methyl-6,7,8,9-tetrahydro-5H-pyrido[2,3-b]indol-6-yl)methyl)carbamate (0.9 g, 2.28 mmol) in 20 ml of dichloromethane, 11.34 ml (22.8 mmol) of a 2 M solution of hydrogen chloride in diethylether were added and the reaction mixture was stirred at room temperature for 12 h. After dilution with dichloromethane, the solution was basified with aqueous sodium hydroxide solution until pH 13-14. The organic phase was separated and the aqueous phase was extracted with dichloromethane (4×100 mL). The combined organic phase was dried over $Na_2SO_4$, filtered and the solvent was removed to afford the title compound as a brownish oil.

Step B

The crude title compound from Step A above (2.28 mmol) was dissolved in N,N'-dimethylformamide (14 mL). (S)-2-((2,4-Dinitrophenyl)amino)-3-phenylpropanoic acid (0.944 g, 2.85 mmol) was added, followed by HBTU (1.08 g, 2.85 mmol) and triethyl amine (0.68 mL, 5.01 mmol). The solution was stirred at room temperature for 12 h. The reaction mixture was diluted with dichloromethane (500 mL) and washed with water (100 mL). The organic phase was separated and the aqueous phase was extracted with dichloromethane (4×100 mL). The combined organic phase was dried over $Na_2SO_4$, filtered and the solvent was removed to afford the crude product as an orange solid.

Step C

Diastereomer Separation by Flash Chromatography on Silica

The mixture of diastereomers from Step B above was separated using a Biotage Isolera One flash chromatography system to yield 0.64 g of early diastereoisomer and 0.7 g of late diastereoisomer.

The following conditions were used:
Cartridge Loading: 250 mg—500 mg of mixture applied to 100 g HP-Sil SNAP cartridge
Solvent gradient: EtOAc/n-Heptane: 30-50%

The chromatographic separation of the mixture of diasteromers was conducted on silica-gel (Flow rate: 50 ml/min) using an ethylacetate/n-heptane gradient (30/70→60/40).

Figure 11:
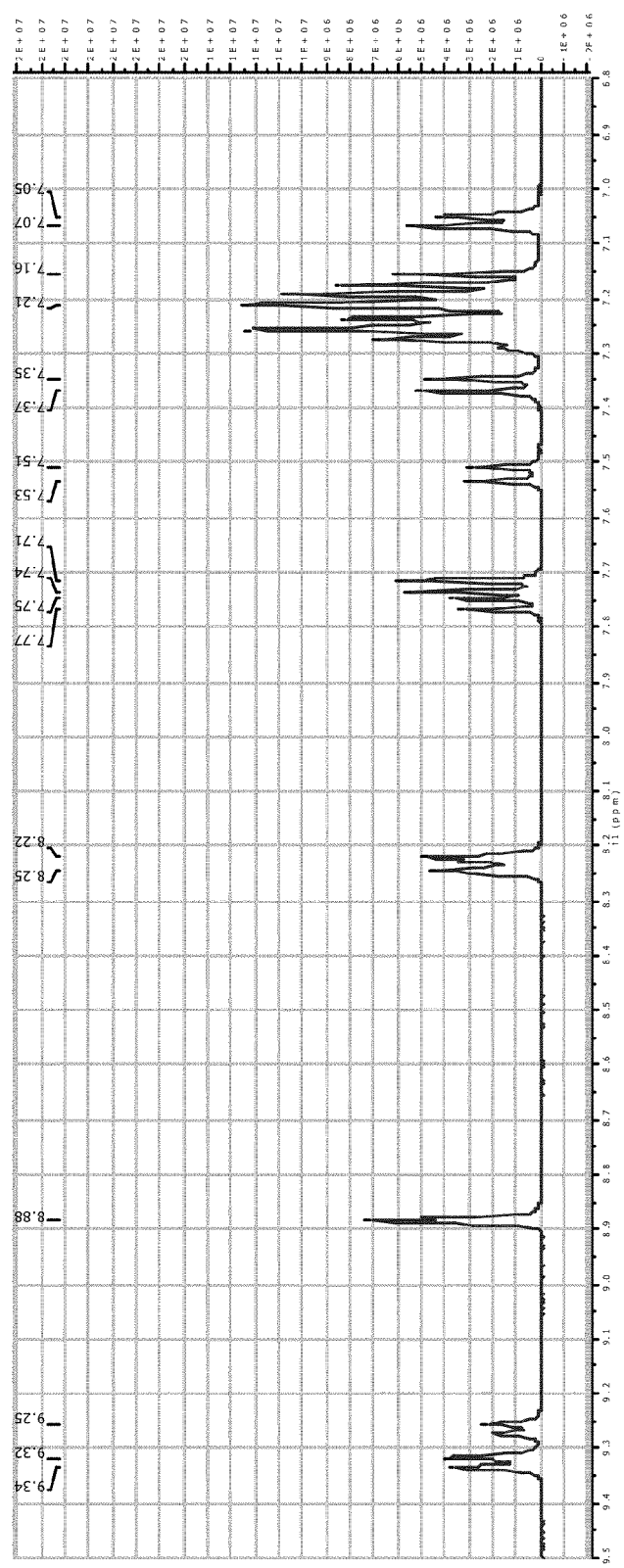
FIG. 11 shows the $^1$H-NMR data of the early diastereomer (only aromatic region, impurities present in the region 7.1-7.3 ppm).

$^1$H-NMR data of the early diastereomer (only aromatic region, impurities present in the region 7.1-7.3 ppm) is presented in FIG. 11.

$^1$H-NMR (400 MHz, DMSO-d$_6$): δ=7.07 (d, 1H), 7.35 (d, 1H), 7.51 (d, 1H), 7.71-7.76 (dd, 2H), 8.21-8.25 (m, 2H), 8.87-8.88 (m, 1H), 9.25-9.33 (dd, 2H).

Figure 12:
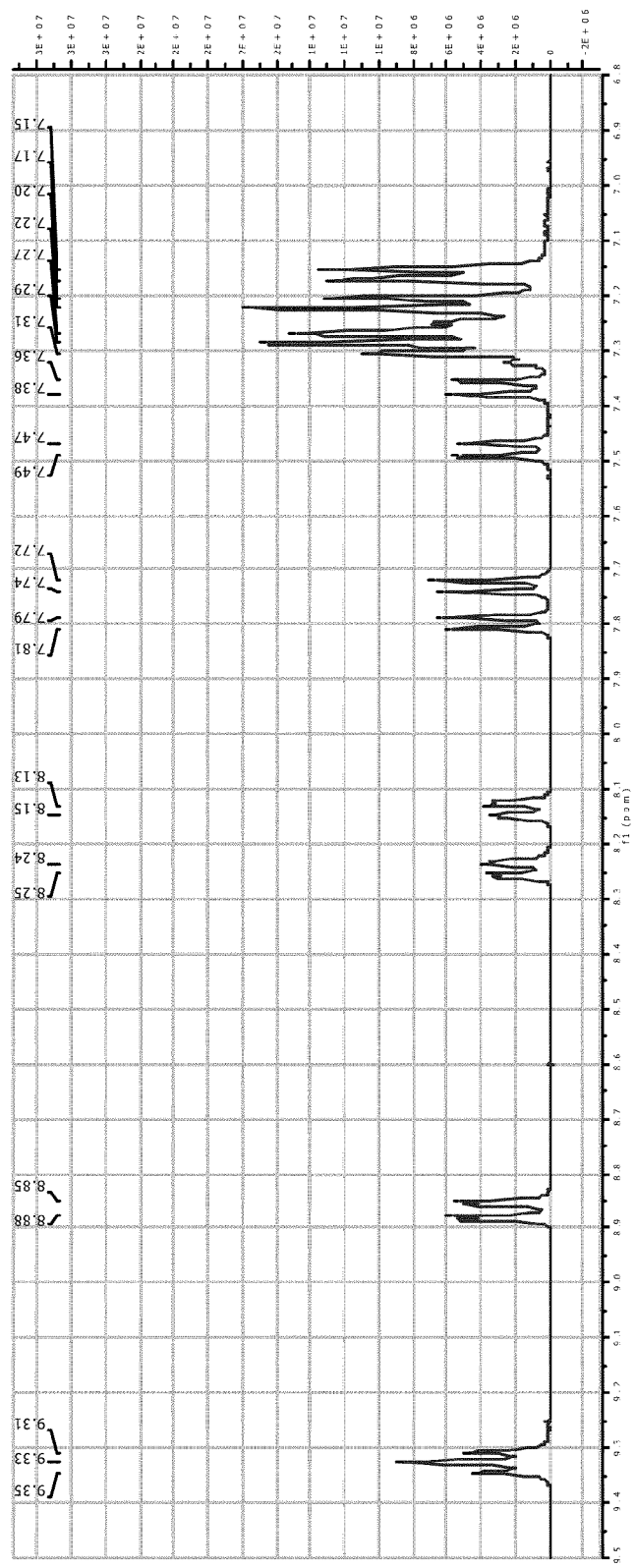
FIG. 12 shows the $^1$H-NMR data of the late diastereomer (only aromatic region, impurities present in the region 7.1-7.3 ppm).

$^1$H-NMR data of the late diastereomer (only aromatic region, impurities present in the region 7.1-7.3 ppm) is presented in FIG. 12.

$^1$H-NMR (400 MHz, DMSO-d$_6$): δ=7.17 (d, 1H), 7.36 (d, 1H), 7.48 (d, 1H), 7.43 (d, 1H), 7.80 (d, 1H), 8.14 (dd, 1H), 8.23 (dd, 1H), 8.87 (dd, 1H), 9.32 (t, 2H).

Step D

The late diastereoisomer (0.7 g, 1.15 mmol) from Step C above was dissolved in 18 mL of glacial acetic acid and then 18 mL of concentrated hydrochloric acid (36-38%) were added. The mixture was heated at 120° C. in a sand bath for 5 days. The reaction mixture was cooled at room temperature and then diluted with 400 mL dichloromethane and basified with 1 M aqueous sodium hydroxide solution until pH 13-14. The organic phase was separated and the aqueous phase was extracted with dichloromethane (4×100 mL). The combined organic phase was dried over Na$_2$SO$_4$, filtered and the solvent was removed to afford the crude product as a brownish oil.

Step E

The crude compound from Step D above (1.15 mmol) was dissolved in tetrahydrofurane (16 mL) and treated with triethylamine (0.176 mL) and di-tert-butyl dicarbonate (0.95 g, 12.4 mmol). The mixture was at room temperature overnight. The solvent was removed and the residue was purified using Biotage purification system (EtOAc/n-heptane: 10-40%) to afford the Boc-protected tricyclic building block derived from the late diastereomer as an off-white solid (0.22 g, 24% for 4 steps).

$^1$H-NMR (400 MHz, DMSO-d$_6$): δ=1.41 (s, 9H), 1.91-2.06 (m, 2H), 2.71 (m, 2H), 2.78 (s, 3H), 2.96-2.83 (m, 2H), 3.62 (s, 3H), 4.25 (br-m, 1H), 7.17 (d, 1H), 7.78 (d, 1H).

The early diastereomer was treated as described above (Step D and Step E) to yield the corresponding early enantiomer tricyclic building block.

$^1$H-NMR (400 MHz, DMSO-d$_6$): δ=1.41 (s, 9H), 1.91-2.06 (m, 2H), 2.71 (m, 2H), 2.78 (s, 3H), 2.96-2.83 (m, 2H), 3.62 (s, 3H), 4.25 (br-m, 1H), 7.17 (d, 1H), 7.78 (d, 1H).

Preparative Example 337

Preparation of Single Enantiomers of tert-butyl-(2-bromo-9-methyl-6,7,8,9-tetrahydro-5H-pyrido[2,3-b]indol-6-yl)methyl)carbamate by Separation of Diastereomeric Salts 337.1 Objective and Design of the Study The aim of this study was to develop a method for the separation of racemic tert-butyl-(2-bromo-9-methyl-6,7,8,9-tetrahydro-5H-pyrido[2,3-b]indol-6-yl)methyl)carbamate via diastereomeric salts.

337.2 Methods 337.2.1 Principle of Enantiomers Separation

The racemic compound as free base was reacted with an optically active acid to yield a mixture of diastereomeric salts ($R^+L_1^-+S^+L_1^-$). Crystallization of the diasteromeric salts with a suitable solvent and removal of the chiral auxiliary yielded the individual enantiomers.

Synthesis Scheme for the Preparation of the Individual Enantiomers of tert-butyl-(2-bromo-9-methyl-6,7,8,9-tetrahydro-5H-pyrido[2,3-b]indol-6-yl)methyl)carbamate

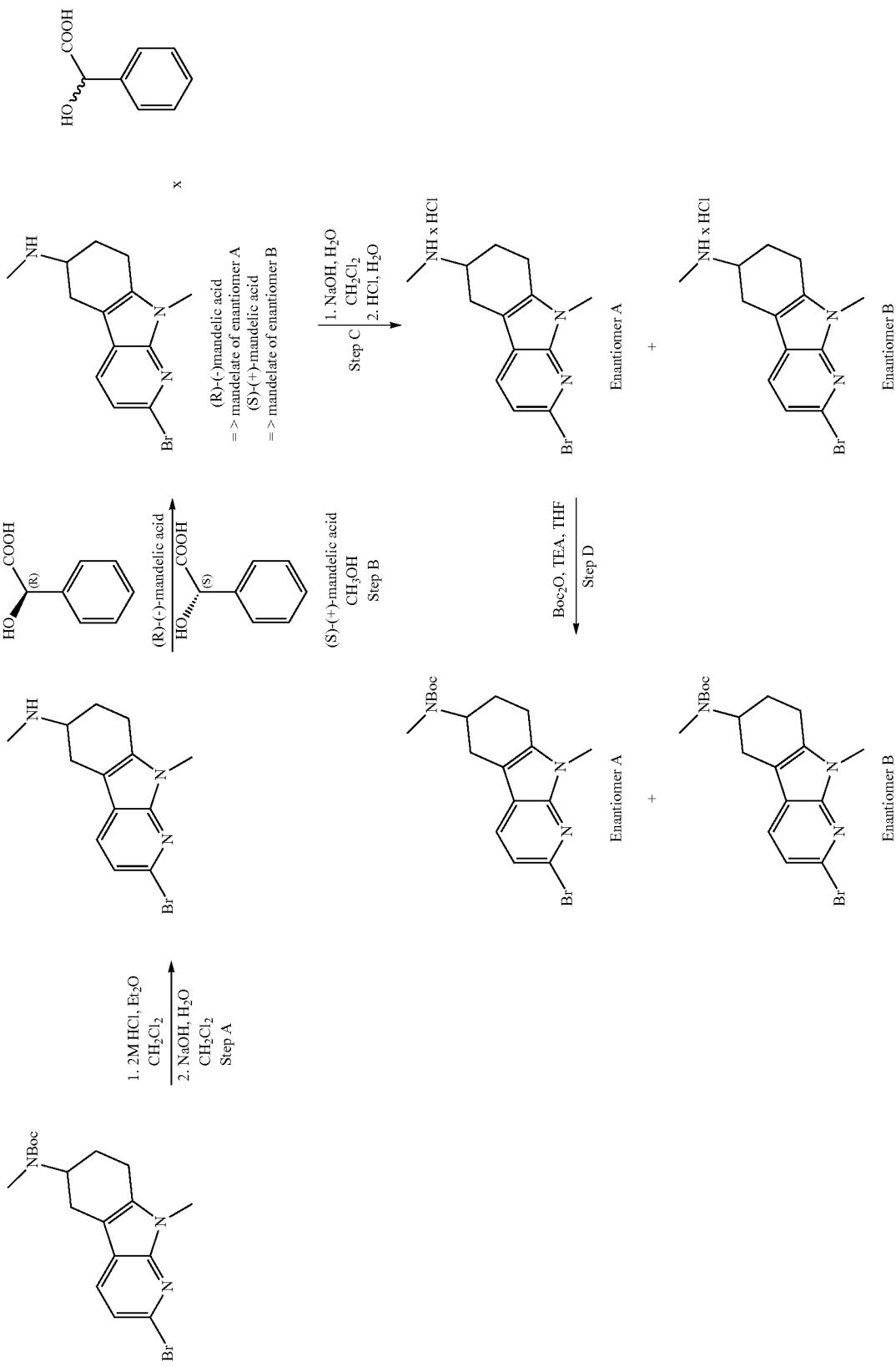

Step A

A solution of racemic tert-butyl-(2-bromo-9-methyl-6,7,8,9-tetrahydro-5H-pyrido[2,3-b]indol-6-yl)methyl)carbamate (12.48 g, 31.87 mmol) in 300 ml of dichloromethane was cooled to 0° C. Then 150 ml (300 mmol) of a solution 2 M solution of hydrogen chloride in diethylether was added at 0° C. After the addition was completed, the ice-bath was removed and the reaction mixture was stirred at room temperature for 16 h. The precipitate was collected by filtration, washed with diethylether (100 mL) and air-dried to afford the di-hydrochloride salt as an off-white solid (11.5 g, quant.). To a 250 mL flask equipped with a magnetic stirrer containing the di-hydrochloride salt (3.65 g, 10 mmol) as a suspension in water (37 mL) was added an aqueous solution of sodium hydroxide (1.27 g, 32 mmol of NaOH in 22 mL water) (addition time 1 min). Then the flask containing the sodium hydroxide solution was rinsed with additional water (2×3 mL). The resulting white suspension was stirred vigorously for 5 min before adding dichloromethane (65 mL). The resulting mixture was stirred vigorously for 5 min. Organic phase was recovered and the aqueous phase was extracted with 3×65 mL dichloromethane. The combined organic phases were dried over $MgSO_4$ and evaporated under vacuum at room temperature to dryness yielding 2.63 g (90%) of the title compound as a yellow solid.

Enantiomer Separation Via Diasteromeric Salts:
Step B (Reaction with (S)-(+)-mandelic Acid to Obtain Enantiomer B, $R_t$=26.1 Min)

To a 250 mL flask equipped with a magnetic stirrer containing the title compound from Step A above (5.46 g, 18.6 mmol) dissolved in methanol (30 mL) at 35° C., was added (S)-(+)-mandelic acid (1.35 g, 8.9 mmol) dissolved in methanol (50 mL). The resulting mixture was stirred at 35° C. (internal temperature) for 24 h and then filtered through a sintered glass funnel. Mother liquors were separated and the resulting white solid was washed with methanol at room temperature (3×20 mL). The salt was dried under vacuum to afford 2.55 g (31%) of the title compound (enantiomer B and (S)-(+)-mandelic acid, HPLC 97% ee) as a white solid. Mother liquors were evaporated to dryness before adding 0.5 M aqueous sodium hydroxide solution (20 mL). The aqueous solution was extracted with dichloromethane (3×10 mL), the combined organic phases were dried over $MgSO_4$ and evaporated under vacuum at room temperature to afford a yellow-brown paste corresponding to a 7:3 (enantiomer A: enantiomer B) mixture of the enantiomers (3.24 g, 59%). (Reaction of the mother liquors with (R)-(−)-mandelic acid to obtain enantiomer A, $R_t$=24.3 Min)

To a 100 mL flask equipped with a magnetic stirrer containing a solution of a 7:3 (enantiomer A: enantiomer B) mixture of the enantiomers (3.24 g, 11 mmol) in methanol (30 mL) at 35° C. was added (R)-(−)-mandelic acid (1.09 g, 7.2 mmol) dissolved in methanol (35 mL). The resulting mixture was stirred at an internal temperature of 35° C. for 24 h. The crystallized solid was filtered through a sintered glass funnel, washed with methanol at room temperature (3×16 mL) and dried under vacuum to afford 3.08 g (63%) of the title compound (enantiomer A and (R)-(−)-mandelic acid, HPLC 97% ee) as a white solid.

Step C
Formation of the Dihydrochloride of Enantiomer A from the Corresponding Mandelate To a 250 mL flask equipped with a magnetic stirrer containing the mandelate salt of enantiomer A (3.08 g, 6.9 mmol) was added 1 M sodium hydroxide solution (30 mL) and dichloromethane (60 mL). After 5 min of vigorous stirring, the organic phase was recovered and the aqueous phase was extracted with dichloromethane (2×60 mL). The combined organic phases were washed with brine (30 mL), dried over $MgSO_4$ and evaporated to dryness at room temperature. The resulting brown-yellow paste was dissolved in 1 M aqueous hydrogen chloride solution (50 mL) and the solvent was evaporated to dryness to afford a white solid. When this solid was dried under high vacuum at 25° C. until constant weight, it melted and re-crystallized to afford the title compound as a yellow solid (1.97 g, 78% HPLC 97.8% ee).

Formation of the Dihydrochloride of Enantiomer B from the Corresponding Mandelate To a 100 mL flask equipped with a magnetic stirrer containing the mandelate salt of enantiomer B (2.1 g, 4.7 mmol) was added 1 M sodium hydroxide solution (20 mL) and dichloromethane (40 mL). After 5 min of vigorous stirring, the organic phase was recovered and the aqueous phase was extracted with dichloromethane (2×40 mL). The combined organic phases were washed with brine (20 mL), dried over $MgSO_4$ and evaporated to dryness at room temperature. The resulting brown-yellow paste was dissolved in 1 M aqueous hydrogen chloride solution (30 mL) and the solvent was evaporated to dryness to afford a white solid. When this solid was dried under high vacuum at 25° C. until constant weight, it melted and re-crystallized afford the title compound as a yellow solid (1.57 g, 91%, HPLC 97.7% ee).

Figure 6:
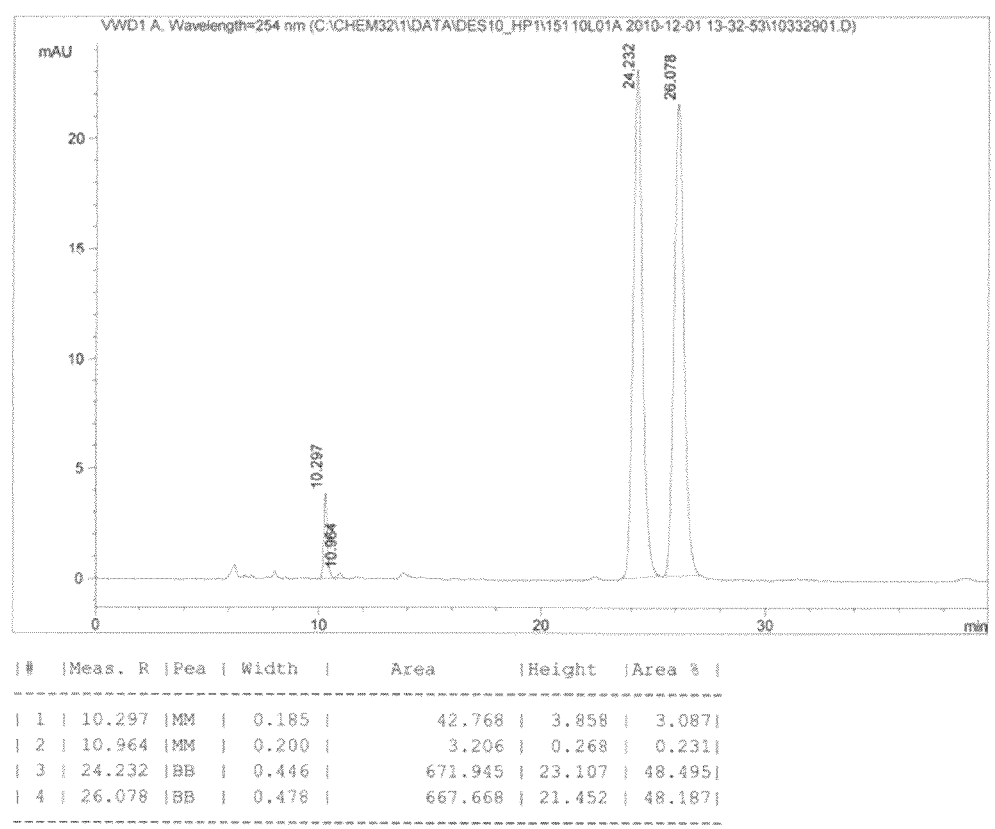
FIG. 6 shows the racemic mixture (di-hydrochloric acid salts) before crystallization.
Figure 7:
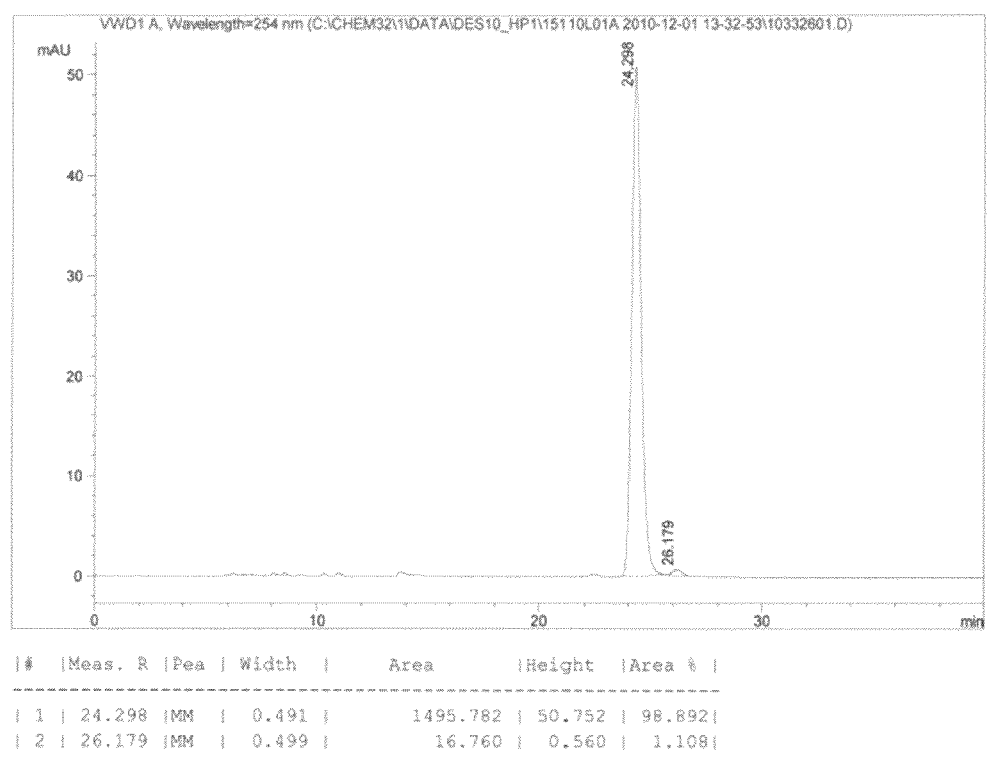
FIG. 7 shows the early eluting enantiomer A (di-hydrochloric acid salt) after crystallization.
Figure 8:
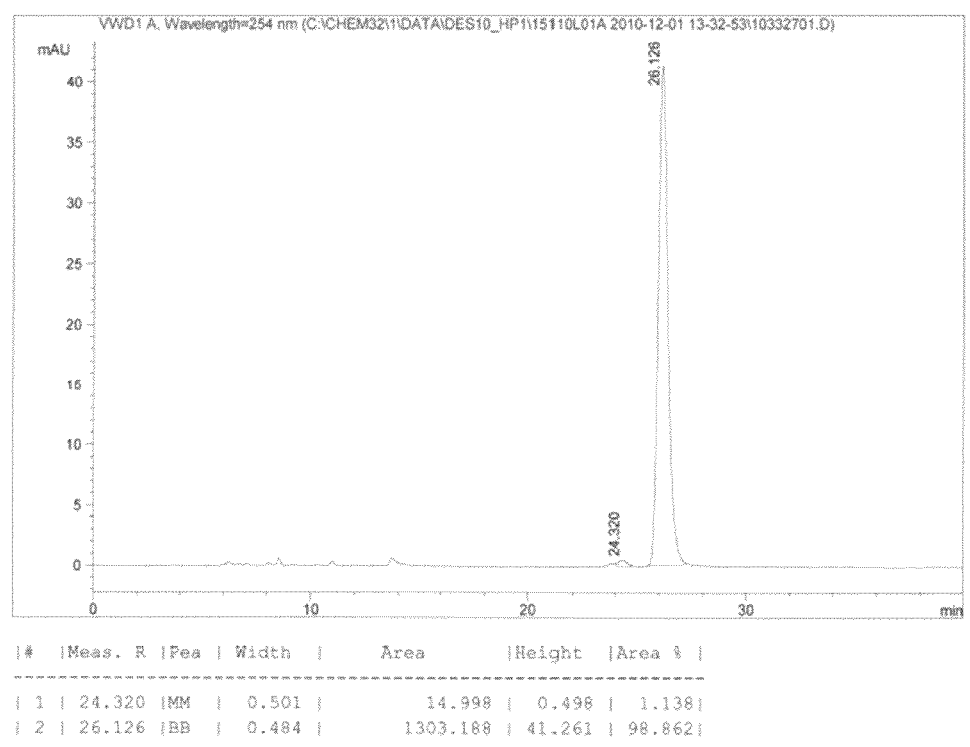
FIG. 8 shows the late eluting enantiomer B (di-hydrochloric acid salt) after crystallization.

Chiral HPLC Conditions:
Sample: 2 mg eq. base/mL in n-heptane/(ethanol-0.2% DEA) (90:10)
Column: Chiracel AD-H
Solvent: n-heptane/(ethanol-0.2% DEA) (90:10)
Injection volume: 5 µL FIG. 6 shows the racemic mixture (di-hydrochloric acid salts) before crystallization
$R_t$ (early eluting enantiomer A): 24.3 Min
$R_t$ (late eluting enantiomer B): 26.1 Min FIG. 7 shows the early eluting enantiomer A (di-hydrochloric acid salt) after crystallization FIG. 8 shows the late eluting enantiomer B (di-hydrochloric acid salt) after crystallization Step D
Boc-Protection of Early Eluting Enantiomer A 2-Bromo-$N^6$,9-dimethyl-6,7,8,9-tetrahydro-5H-pyrido[2,3-b]indol-6-amine di-hydrochloride (0.94 g 2.56 mmol; enantiomer A) was dissolved in tetrahydrofuran (50 mL) and treated with triethylamine (1.95 mL, 13.9 mmol) and di-tert-butyl dicarbonate (1.8 g, 8.55 mmol). The mixture was stirred at room temperature overnight. The solvent was removed and the residue was purified using a Biotage Isolera One purification system employing an ethyl acetate/n-heptane gradient (5/95 to 30/70) to afford the title compound (enantiomer A) as an off-white solid (0.969 g, 96%).

$^1$H-NMR (400 MHz, DMSO-$d_6$): δ=1.41 (s, 9H), 1.91-2.06 (m, 2H), 2.71 (m, 2H), 2.78 (s, 3H), 2.96-2.83 (m, 2H), 3.62 (s, 3H), 4.25 (br-m, 1H), 7.17 (d, 1H), 7.78 (d, 1H).

$^1$H-NMR (400 MHz, CDCl$_3$): δ=1.60 (s, 9H), 2.10-2.23 (m, 2H), 2.82-3.01 (m, 7H), 3.81 (s, 3H), 4.38-4.64 (br-m, 1H), 7.25 (d, 1H), 7.67 (d, 1H).

Boc-Protection of Late Eluting Enantiomer B
The late eluting enantiomer B was treated as described above (Step C and Step D) to yield the corresponding Boc-protected tricyclic building block.

$^1$H-NMR (400 MHz, DMSO-$d_6$): δ=1.41 (s, 9H), 1.91-2.06 (m, 2H), 2.71 (m, 2H), 2.78 (s, 3H), 2.96-2.83 (m, 2H), 3.62 (s, 3H), 4.25 (br-m, 1H), 7.17 (d, 1H), 7.78 (d, 1H).

337.3 Conclusions

Enantiomerically pure building blocks were prepared via separation of the racemic mixture via crystallization of diastereomeric salts. The purity of the individual enantiomeric building blocks was 97.8% ee for enantiomer A and 97.7% ee for enantiomer B.

Example 214

Preparation of Compounds 214a and 214b (Enantiomers of Compound 26) Using the Title Compounds from Preparative Example 336 (Diastereomer Separation)

214.1 Objective and Design of the Study

The aim of this study was to synthesize compounds 214a and 214b, the two enantiomers of compound 26 using enantiomerically enriched building blocks prepared via diastereomer separation.

214.2 Synthesis Scheme of Enantiomerically Enriched Compound 214b

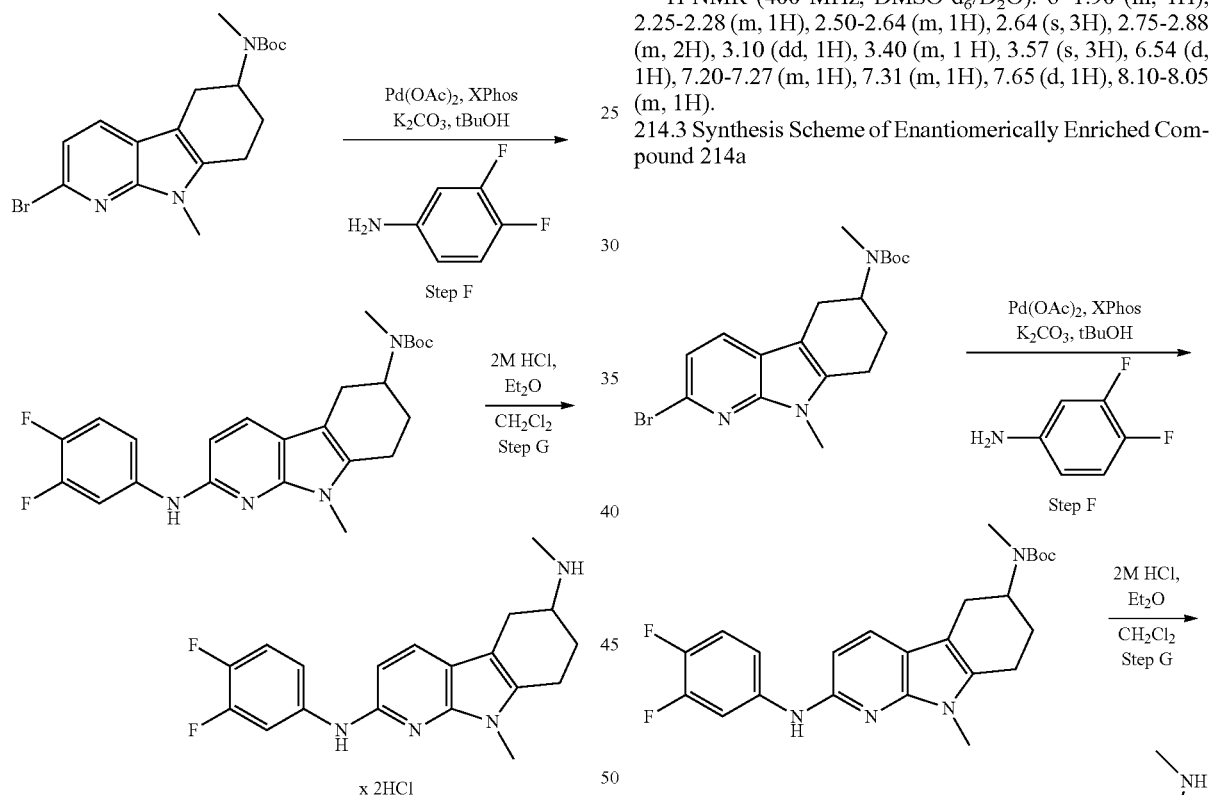

Step A

Tert-butanol (2 mL) was added to a mixture of 2-dicyclohexylphosphino-2',4',6'-triisopropylbiphenyl (XPhos, 0.036 g, 0.075 mmol) and palladium(II) acetate (0.0056 g, 0.025 mmol). The mixture was degassed by sonication for 1 min while a stream of argon was passed through the solution. This mixture was heated at ~100° C. in a sand-bath for 1 min to generate the catalyst. To the faint red catalyst solution was then added the title compound of Preparative Example 336 obtained from the late diastereomer (0.1 g, 0.25 mmol), commercially available 3,4-difluoro aniline (0.041 g, 0.31 mmol) and potassium carbonate (0.086 g, 0.625 mmol). The mixture was heated in a sand-bath at ~110° C. for 3 h. The mixture was diluted with ethyl acetate (100 mL) and water (10 mL). The organic phase was separated, dried over $Na_2SO_4$, filtered and the solvents were removed. The residue was purified twice using Biotage Isolera flash purification (MeOH/DCM: 0-1% followed by EtOAc/n-heptane: 10-30%) system to afford the title compound as an off-white solid (0.087 g, 97%).

$^1$H-NMR (400 MHz, $CDCl_3$): δ=1.49 (s, 9H), 2.04 (m, 2H), 2.69-2.85 (m, 7H), 3.70 (s, 3H), 4.29-4.50 (br-m, 1H), 6.51 (d, 1H), 7.00-7.02 (m, 1H), 7.05-7.12 (m, 1H), 7.61 (m, 2H).

MS (ESI); m/z=443.64 ($MH^+$)

FIG. 8 shows the Boc-protected precursor of compound 214b derived from late diastereomer Step B The title compound of Step A above (0.08 g, 0.045 mmol) was dissolved in dichloromethane (2.0 mL) and treated with a 2 M solution of hydrogen chloride (2 mL) in diethylether. The mixture was stirred at room temperature overnight and the precipitate was collected by filtration. The solids were washed with diethylether (5 mL) and dried under reduced pressure to afford the title compound as an off white solid (0.068 g, 97%).

$^1$H-NMR (400 MHz, $DMSO-d_6/D_2O$): δ=1.90 (m, 1H), 2.25-2.28 (m, 1H), 2.50-2.64 (m, 1H), 2.64 (s, 3H), 2.75-2.88 (m, 2H), 3.10 (dd, 1H), 3.40 (m, 1 H), 3.57 (s, 3H), 6.54 (d, 1H), 7.20-7.27 (m, 1H), 7.31 (m, 1H), 7.65 (d, 1H), 8.10-8.05 (m, 1H).

214.3 Synthesis Scheme of Enantiomerically Enriched Compound 214a

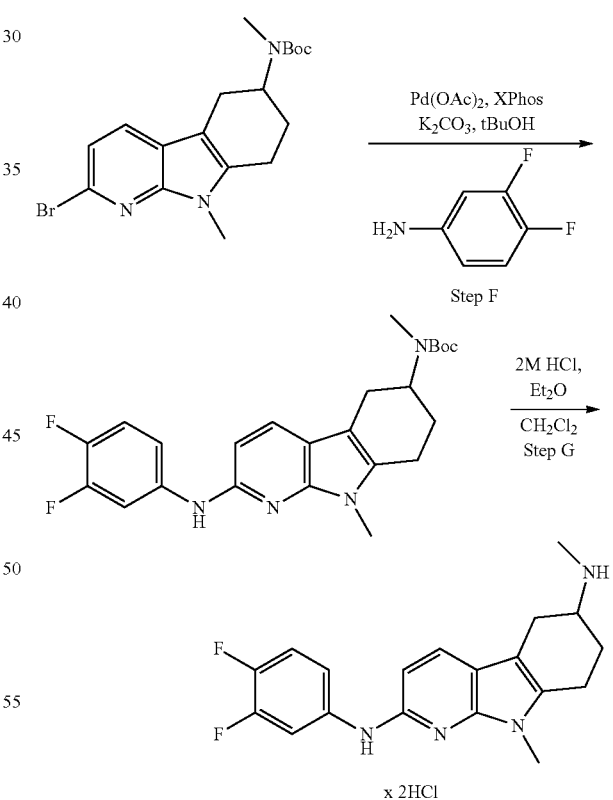

The same procedure for Step A as described for the synthesis of compound 214b was applied for the enantiomerically enriched building block derived from the early diastereomer of Preparative Example 336, yielding the Boc-protected precursor of compound 214a.

$^1$H-NMR (400 MHz, $CDCl_3$): δ=1.49 (s, 9H), 2.04 (m, 2H), 2.69-2.85 (m, 7H), 3.70 (s, 3H), 4.29-4.50 (br-m, 1H), 6.51 (d, 1H), 7.00-7.02 (m, 1H), 7.05-7.12 (m, 1H), 7.61 (m, 2H). MS (ESI); m/z=443.64 (MH+)

Figure 9:
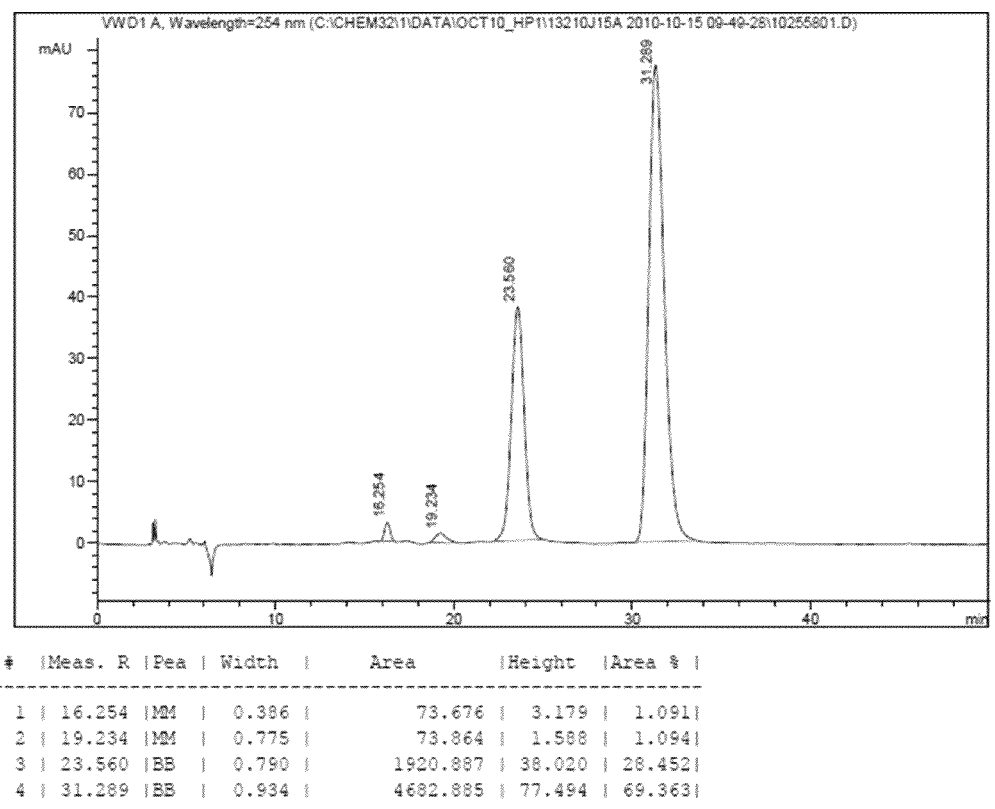
FIG. 9 shows the Boc-protected precursor of compound 214b derived from late diastereomer.
Figure 10:
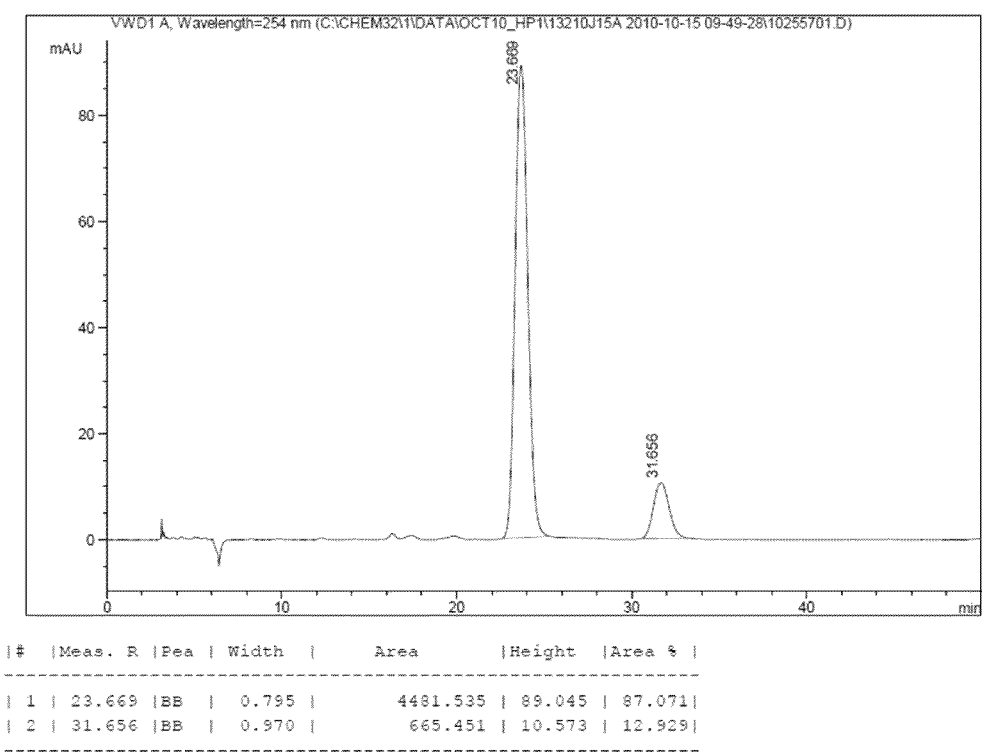
FIG. 10 shows the Boc-protected precursor of 214a derived from early diastereomer.

FIG. 9 shows the Boc-protected precursor of 214a derived from early diastereomer The same procedure for Step B as described for the synthesis of compound 214b was applied for the enantiomerically enriched building block derived from the early diastereomer, yielding compound 214a.

¹H-NMR (400 MHz, DMSO-d₆/D₂O): δ=1.90 (m, 1H), 2.25-2.28 (m, 1H), 2.50-2.64 (m, 1H), 2.64 (s, 3H), 2.75-2.88 (m, 2H), 3.10 (dd, 1H), 3.40 (m, 1H), 3.57 (s, 3H), 6.54 (d, 1H), 7.20-7.27 (m, 1H), 7.31 (m, 1H), 7.65 (d, 1H), 8.10-8.05 (m, 1H).

214.4 Conclusions

Enantiomerically enriched compounds 214a and 214b were prepared using the building blocks obtained from the separation of diastereomers. The building block derived from the early diastereomer yielded an enantiomerically enriched compound (Boc-protected compound 214a) containing 89% of the early enantiomer and 10.6% of the late enantiomer. The building block derived from the late diastereomer yielded an enantiomerically enriched compound (Boc-protected compound 214b) containing 28.5% of the early enantiomer and 69.4% of the late enantiomer.

Example 215

Preparation of Compounds 215a and 215b
(Enantiomers of Compound 26) Using the Title
Compounds from Preparative Example 337
(Separation by Crystallization)

215.1 Objective and Design of the Study

The aim of this study was to synthesize compounds 215a and 215b, the two enantiomers of compound 26 using enantiomerically pure building blocks prepared via crystallization of diastereomeric salts.

215.2 Synthesis Scheme of Enantiomerically Pure Compound 215b

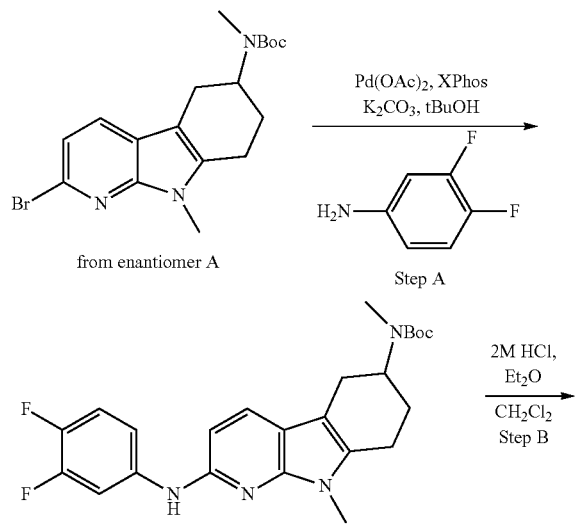

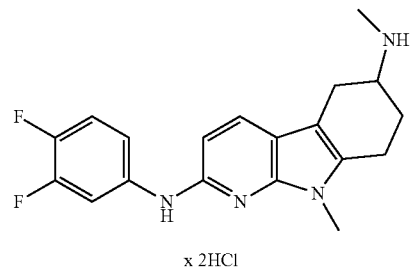

Step A

Tert-butanol (13 mL) was added to a mixture of 2-dicyclohexylphosphino-2',4',6'-triisopropylbiphenyl (XPhos, 0.119 g, 0.25 mmol) and palladium(II) acetate (0.0198 g, 0.084 mmol). The mixture was degassed by sonication for 1 min while a stream of argon was passed through the solution. This mixture was heated at ~100° C. in a sand-bath for 1 min to generate the catalyst. To the faint red catalyst solution was then added the title compound from Preparative Example 337 obtained from the early eluting enantiomer A (0.33 g, 0.84 mmol), commercially available 3,4-difluoro aniline (0.125 g, 0.99 mmol) dissolved in 1 mL of tert-butanol and potassium carbonate (0.257 g, 1.85 mmol). The mixture was heated in a sand-bath at ~110° C. for 3 h. The mixture was diluted with ethyl acetate (250 mL) and water (25 mL). The organic phase was separated, dried over Na₂SO₄, filtered and the solvents were removed. The residue was purified using a Biotage Isolera One purification system employing an ethyl acetate/n-heptane gradient (5/95 to 30/70) to afford the title compound as an off-white solid (0.35 g, 95%).

¹H-NMR (400 MHz, DMSO-d₆): δ=1.42 (s, 9H), 1.92-2.04 (m, 2H), 2.67 (m, 2H), 2.78-2.92 (m, 7H), 3.61 (s, 3H), 4.08-4.34 (br-m, 1H), 6.53 (d, 1H), 7.25-7.33 (m, 1H), 7.35-7.38 (m, 1H), 7.65 (d, 1H), 8.17 (dd, 1H), 9.16 (s, 1H).

¹H-NMR (400 MHz, CDCl₃): δ=1.58 (s, 9H), 2.10-2.18 (m, 2H), 2.82-3.00 (m, 7H), 3.77 (s, 3H), 4.34-4.63 (br-m, 1H), 6.48 (br-s, 1H), 6.60 (d, 1H), 7.09-7.12 (m, 1H), 7.13-7.22 (m, 1H), 7.67 (d, 1H), 7.85 (ddd, 1H).

MS (ESI); m/z=443.64 (MH+)

Step B

The title compound of Step A above (0.35 g, 0.79 mmol) was dissolved in dichloromethane (8 mL). The solution was cooled at 0° C. and then treated with a 2 M solution of hydrogen chloride (8 mL) in diethylether. The mixture was stirred at room temperature overnight and the precipitate was collected by filtration. The solids were washed with diethylether (15 mL) and dried to afford the title compound as an off white solid (0.32 g, 95%).

¹H-NMR (400 MHz, DMSO-d₆/D₂O): δ=1.85-1.95 (m, 1H), 2.25-2.28 (m, 1H), 2.59-2.64 (m, 1H), 2.64 (s, 3H), 2.73-2.88 (m, 2H), 3.10 (dd, 1H), 3.40 (m, 1H), 3.57 (s, 3H), 6.54 (d, 1H), 7.20-7.27 (m, 1H), 7.32-7.34 (m, 1H), 7.65 (d, 1H), 8.10-8.05 (m, 1H).

[α]²⁵_D=-54.0° (c 0.1, MeOH)

215.3 Synthesis Scheme of Enantiomerically Pure Compound 215a

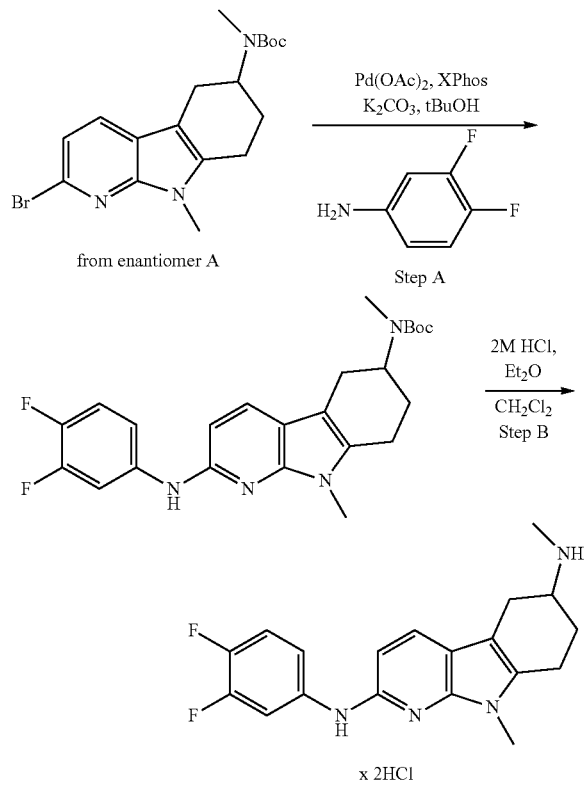

from enantiomer A

Step A

Tert-butanol (4 mL) was added to a mixture of 2-dicyclohexylphosphino-2',4',6'-triisopropylbiphenyl (XPhos, 0.031 g, 0.065 mmol) and palladium(II) acetate (0.0049 g, 0.022 mmol). The mixture was degassed by sonication for 1 Min while a stream of argon was passed through the solution. This mixture was heated at ~100° C. in a sand-bath for 1 Min to generate the catalyst. To the faint red catalyst solution was then added the title compound from Preparative Example 337 obtained from the late eluting enantiomer B (0.086 g, 0.218 mmol), commercially available 3,4-difluoro aniline (0.024 ml, 0.240 mmol) dissolved in 1 mL of tert-butanol and potassium carbonate (0.060 g, 0.436 mmol). The mixture was heated in a sand-bath at ~110° C. for 3 h. The mixture was diluted with ethyl acetate (250 mL) and water (25 mL). The organic phase was separated, dried over $Na_2SO_4$, filtered and the solvents were removed. The residue was purified using a Biotage Isolera One purification system employing an ethyl acetate/n-heptane gradient (10/90 to 30/70) to afford the title compound as an off-white solid (0.095 g, 98%).

$^1$H-NMR (400 MHz, $CDCl_3$): δ=1.49 (s, 9H), 2.04 (m, 2H), 2.69-2.85 (m, 7H), 3.70 (s, 3H), 4.29-4.50 (br-m, 1H), 6.51 (d, 1H), 7.00-7.02 (m, 1H), 7.05-7.12 (m, 1H), 7.61 (m, 2H).

MS (ESI); m/z=443.68 (MH$^+$)

Step B.

The title compound of Step A above (0.095 g, 0.21 mmol) was dissolved in dichloromethane (4 mL). The solution was cooled at 0° C. and then treated with a 2 M solution of hydrogen chloride (2 mL) in diethylether. The mixture was stirred at room temperature overnight and the precipitate was collected by filtration. The solids were washed with diethylether (10 mL) and dried to afford the title compound as an off white solid (0.078 g, 87%).

$^1$H-NMR (400 MHz, DMSO-$d_6$/$D_2O$): δ=1.82-2.00 (m, 1H); 2.21-2.35 (m, 1H); 2.57-2.70 (m, 4H); 2.72-2.93 (m, 2H); 3.10 (dd, 1H); 3.34-3.48 (m, 1H); 3.58 (s, 3H); 6.56 (d, 1H); 7.25 (q, 1H); 7.31-7.40 (m, 1H); 7.66 (d, 1H); 8.10 (dd, 1H)

MS (ESI); m/z=343.78 (M+H)

$[α]^{25}_D$=+20.0° (c 0.1, MeOH)

215.4 Conclusions

Enantiomerically pure compounds 215a and 215b were prepared using the enantiomeric building blocks obtained via crystallization of diastereomeric salts.

Example 216

Preparation of Compounds 216a and 216b (Enantiomers of Compound 42) Using the Title Compounds from Preparative Example 336 (Diastereomer Separation)

216.1 Objective and Design of the Study

The aim of this study was to synthesize compounds 216a and 216b, the two enantiomers of compound 42 using enantiomerically enriched building blocks prepared via diastereomer separation.

216.2 Synthesis Scheme of Enantiomerically Enriched Compound 216b

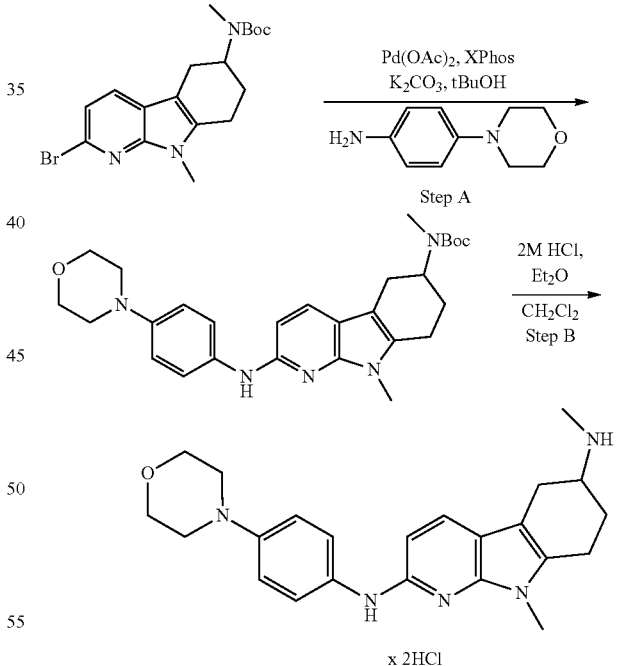

Step A

Tert-butanol (2 mL) was added to a mixture of 2-dicyclohexylphosphino-2',4',6'-triisopropylbiphenyl (XPhos, 0.0108 g, 0.022 mmol) and palladium(II) acetate (0.0017 g, 0.0076 mmol). The mixture was degassed by sonication for 1 min while a stream of argon was passed through the solution. This mixture was heated at ~100° C. in a sand-bath for 1 min to generate the catalyst. To the faint red catalyst solution was then added the title compound of Preparative Example 336 obtained from the late diastereomer (0.03 g, 0.076 mmol), commercially available 4-morpholinoaniline (0.0169 g, 0.095 mmol) and potassium carbonate (0.0262 g, 0.19 mmol). The mixture was heated in a sand bath at ~110° C. for 3 h. The mixture was diluted with ethyl acetate (100 mL) and water (10 mL). The organic phase was separated, dried over $Na_2SO_4$, filtered and the solvents were removed. The residue was purified twice using Biotage Isolera flash purification (MeOH/DCM: 0-1% followed by EtOAc/n-heptane: 10-30%) system to afford the title compound as an off-white solid (0.024 g, 64%).

$^1$H-NMR (400 MHz, $CDCl_3$): δ=1.49 (s, 9H), 2.02 (m, 2H), 2.76-2.86 (m, 6H), 3.02-3.32 (m, 2H), 3.63 (s, 3H), 3.88 (m, 4H), 4.31-4.52 (br-m, 1H), 6.93 (brs, 1H), 7.17-7.19 (m, 1H), 7.24-7.27 (m, 1H), 7.52 (brs, 1H).

MS (ESI); m/z=492.72 ($MH^+$)

Step B

The title compound Step A above (0.02 g, 0.040 mmol) was dissolved in dichloromethane (2.0 mL) and treated with a 2 M solution of hydrogen chloride (0.5 mL) in diethylether. The mixture was stirred at room temperature overnight and the precipitate was collected by filtration. The solids were washed with diethylether (5 mL) and dried under reduced pressure to afford the title compound as an white solid (0.016 g, 99%).

$^1$H-NMR (400 MHz, $D_2O$): δ=2.11 (m, 1H), 2.36 (m, 1H), 2.71-2.79 (m, 6H), 3.06-3.13 (m, 1H), 3.53 (m, 8H), 4.0 (m, 4H), 6.59 (s, 1H), 7.4 (m, 2H), 7.55 (m, 2H), 7.77 (s, 1H).

216.2 Synthesis Scheme of Enantiomerically Enriched Compound 216a

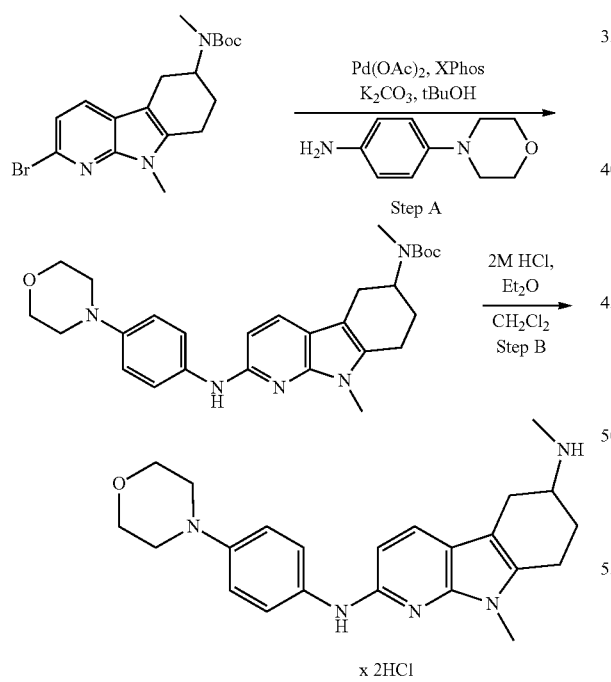

The same procedure for Step A and B as described for the synthesis of compound 216b was applied for the enantiomerically enriched building block derived from the early diastereomer of Preparative Example 336, yielding compound 216a.

MS (ESI); m/z=391.99 (M+H)

216.4 Conclusions

Enantiomerically enriched compounds 216a and 216b were prepared using the building blocks obtained from the separation of diastereomers.

Example 217

Preparation of Compounds 217a and 217b (Enantiomers of Compound 156) Using the Title Compounds from Preparative Example 336 (Diastereomer Separation)

217.1 Objective and Design of the Study

The aim of this study was to synthesize compounds 217a and 217b, the two enantiomers of compound 156 using enantiomerically enriched building blocks prepared via diastereomer separation.

217.2 Synthesis Scheme of Enantiomerically Enriched Compound 217b

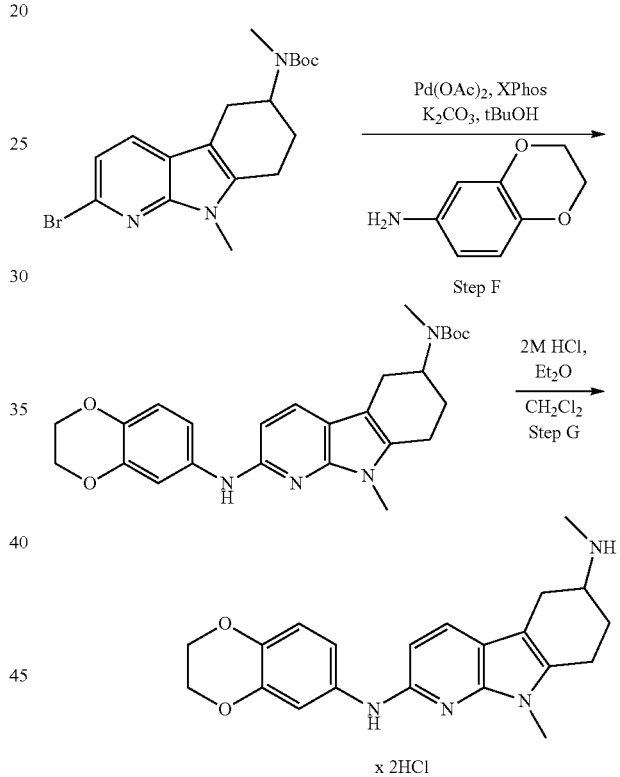

Step A

To a mixture of XPhos (0.0108 mg, 0.023 mmol) and palladium(II) acetate (0.0017 g, 0.008 mmol) was added 4 mL of degased tert-butanol (sonicated under an argon stream). The resulting solution was warmed to 80° C. for 90 s (until a deep red color could be observed). The activated catalyst was transferred into a second vial containing the title compound of Preparative Example 336 obtained from the late diastereomer above (0.030 g, 0.076 mmol), 2,3-dihydrobenzo [b][1,4]dioxin-6-amine (0.0115 g, 0.076 mmol) and potassium carbonate (0.021 g, 0.152 mmol). The resulting mixture was warmed to 110° C. for 3 h. The reaction mixture was concentrated to dryness. The residue was purified by Biotage flash chromatography in EtOAc/n-heptane 15% to 30% system to afford the title compound as a beige foam (0.036 g, 100%).

MS (ESI); m/z=465.70 (M+H)

Step B

To a solution of the title compound of Step A above (0.034 g, 0.073 mmol) in 4 ml of dichlormethane was added a 2 M solution of hydrogen chloride in diethyl ether (0.183 ml, 0.366 mmol) and 0.050 ml of methanol. The resulting mixture was stirred at room temperature for 12 h. Upon completion, the mixture was concentrated to dryness and a few drops of MeOH were added in order to dissolve the residue. Finally EtOAc was added in order to precipitate the product. The slurry was filtered and dried under vacuum for 2 h affording the title compound as a yellow solid (0.016 g, 50%).

$^1$H-NMR (400 MHz, MeOD): δ=2.03-2.17 (m, 1H); 2.36-2.48 (m, 1H); 2.70-3.03 (m, 6H); 3.18-3.30 (m, 1H); 3.51-3.63 (m, 1H); 3.74 (s, 3H); 4.27 (s, 4H); 6.64 (d, J=8.0 Hz, 1H); 6.78-7.05 (m, 3H); 8.05 (d, J=8.0 Hz, 1H)

MS (ESI); m/z=365.75 (M+H)/406.79 (M+ACN+H)

217.3 Synthesis Scheme of Enantiomerically Enriched Compound 217a

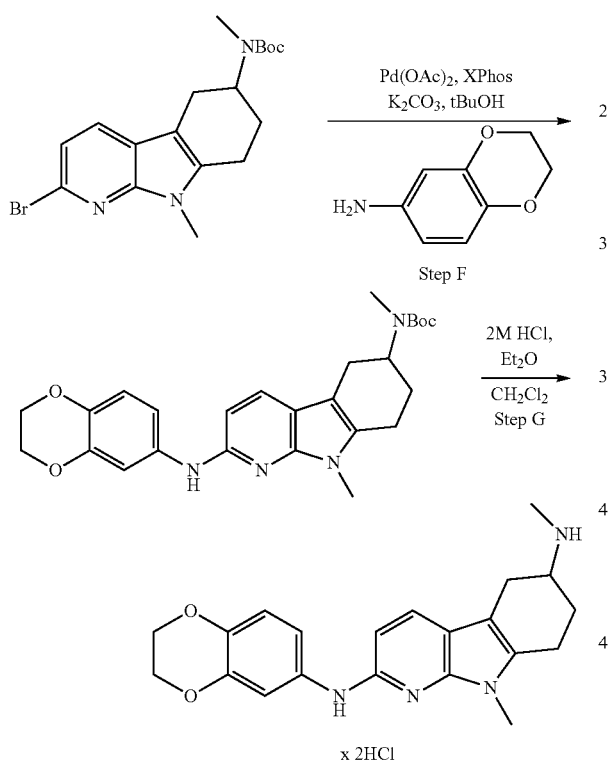

The same procedure for Step A as described for the synthesis of compound 217b was applied for the enantiomerically enriched building block derived from the early diastereomer of Preparative Example 336, yielding the Boc-protected precursor of compound 217a.

MS (ESI); m/z=465.70 (M+H)

Step B

The same procedure for Step B as described for the synthesis of compound 217b was applied for the enantiomerically enriched building block derived from the early diastereomer, yielding compound 217a (0.015 g, 42%).

$^1$H-NMR (400 MHz, MeOD): δ=2.03-2.19 (m, 1H); 2.34-2.49 (m, 1H); 2.70-3.06 (m, 6H); 3.18-3.36 (m, 1H); 3.50-3.65 (m, 1H); 3.74 (s, 3H); 4.26 (s, 4H); 6.64 (d, J=8.0 Hz, 1H); 6.77-7.05 (m, 3H); 8.05 (d, J=8.0 Hz, 1H)

MS (ESI); m/z=365.74 (M+H)/406.77 (M+ACN+H)

217.4 Conclusions

Enantiomerically enriched compounds 217a and 217b were prepared using the building blocks obtained from the separation of diastereomers.

Example 218

Preparation of Compounds 218a and 218b (Enantiomer of Compound 156) Using the Title Compound from Preparative Example 337 (Separation by Crystallization)

218.1 Objective and Design of the Study

The aim of this study was to synthesize compounds 218a and 218b, the two enantiomers of compound 156 using enantiomerically pure building blocks prepared via crystallization of diastereomeric salts 218.2 Synthesis Scheme of Enantiomerically Pure Compound 218b

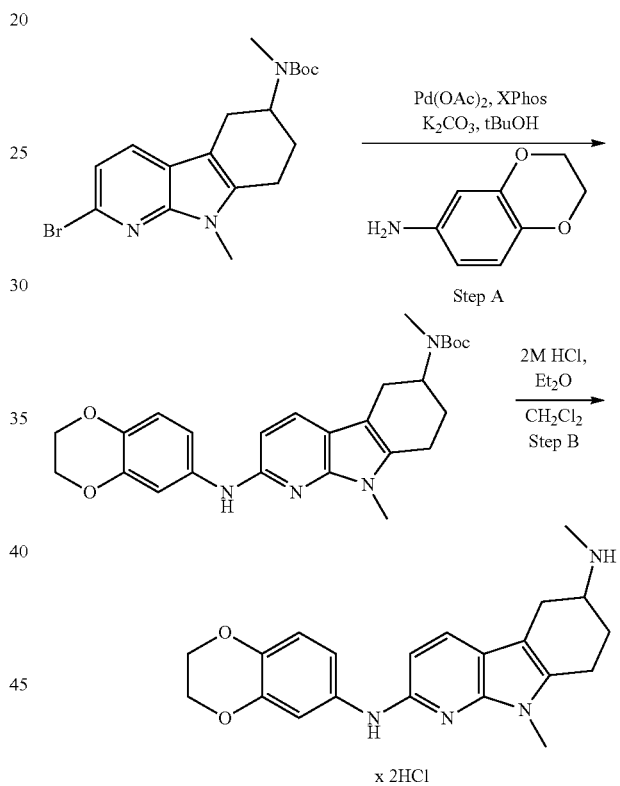

Step A

To a mixture of XPhos (0.0272 mg, 0.057 mmol) and palladium(II) acetate (0.0042 g, 0.019 mmol) was added 4 mL of degassed tert-butanol (sonicated under an argon stream). The resulting solution was warmed to 80° C. for 90 s (until a deep red color could be observed). The activated catalyst was transferred into a second vial containing the title compound of Preparative Example 337 obtained from the early eluting enantiomer A (0.075 g, 0.190 mmol), 2,3-dihydrobenzo[b][1,4]dioxin-6-amine (0.0288 mg, 0.190 mmol) and potassium carbonate (0.0526 mg, 0.380 mmol). The resulting mixture was warmed to 110° C. for 3 h. The reaction mixture was concentrated to dryness. The residue was purified by Biotage flash chromatography in EtOAc/n-heptane 15% to 35% system to afford the title compound as a white solid (0.083 g, 94%).

MS (ESI); m/z=465.70 (M+H)

Step B

To a solution of the title compound of Step A above (0.082 g, 0.177 mmol) in 4 ml of dichlormethane was added a 2 M solution of hydrogen chloride in diethyl ether (0.183 ml, 0.366 mmol) and 0.050 ml of methanol. The resulting mixture was stirred at room temperature for 12 h. Upon completion, the mixture was concentrated to dryness and a few drops of MeOH were added in order to dissolve the residue. Finally EtOAc was added in order to precipitate the product. The slurry was filtered and dried under vacuum for 2 h affording the title compound as a yellowish solid (0.074 g, 96%).

$^1$H-NMR (400 MHz, DMSO-d6): δ=1.88-2.07 (m, 1H); 2.27-2.40 (m, 1H); 2.62 (t, J=5.2 Hz, 3H); 2.67-2.95 (m, 3H); 3.10 (dd, J1=5.2 hz, J2=15.2 Hz, 1H); 3.33-3.48 (m, 1H); 3.60 (s, 3H); 4.15-4.27 (m, 4H); 6.53 (d, J=8.4 Hz, 1H); 6.75 (d, J=8.8 Hz, 1H); 7.06 (dd, J1=2.4 Hz, 8.4 Hz, 1H); 7.61 (s, 1H); 7.62 (d, J=10.0 Hz, 1H); 7.60 (d, J=2.4 Hz, 1H); 7.62 (d, J=8.4 Hz, 1H); 9.23 (sl, 2H)

MS (ESI); m/z=365.75 (M+H)/406.79 (M+ACN+H)

218.3 Synthesis Scheme of Enantiomerically Enriched Compound 218a

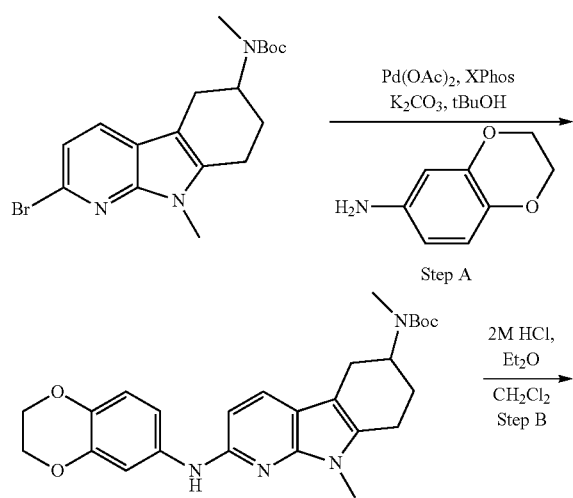

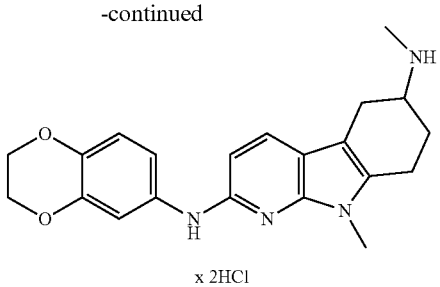

x 2HCl

The same procedure for Step A as described for the synthesis of compound 218b was applied for the enantiomerically pure building block derived from the late eluting Enantiomer B of Preparative Example 337, yielding the Boc-protected precursor of compound 218a.

MS (ESI); m/z=465.70 (M+H)

Step B

The same procedure for Step B as described for the synthesis of compound 218b was applied for the enantiomerically pure building block derived from the late eluting enantiomer B, yielding compound 218a (0.069 g, 85%) as a light yellow solid.

$^1$H-NMR (400 MHz, DMSO-d6): δ=1.89-2.05 (m, 1H); 2.26-2.40 (m, 1H); 2.64 (t, J=5.2 Hz, 3H); 2.67-2.95 (m, 3H); 3.10 (dd, J1=4.4 Hz, J2=14.4 Hz, 1H); 3.33-3.48 (m, 1H); 3.60 (s, 3H); 4.13-4.27 (m, 4H, under water peak); 6.53 (d, J=8.4 Hz, 1H); 6.76 (d, J=8.8 Hz, 1H); 7.05 (dd, J1=2.4 Hz, 8.4 Hz, 1H); 7.61 (s, 1H); 7.62 (d, J=10.0 Hz, 1H); 9.18 (sl, 2H)

MS (ESI); m/z=365.74 (M+H)/406.77 (M+ACN+H)

Example 219

Inhibition of Amyloid Beta (Aβ)$_{1-42}$ Peptide Aggregation (ThT Assay)

Racemic compounds and their enantiomers were tested for their ability to inhibit amyloid peptide aggregation using the ThT assay. To determine the IC$_{50}$, the following dilutions of the compounds were used in the ThT assay described above: 330 μM, 82.50 μM, 20.63 μM, 5.16 μM, 1.29 μM, 0.32 μM and 0.08 μM

| Example | | IC$_{50}$ μM 1$^{st}$ assay | IC$_{50}$ μM 2$^{nd}$ assay |
|---|---|---|---|
| 26 | | 12.2 | 16.8 |

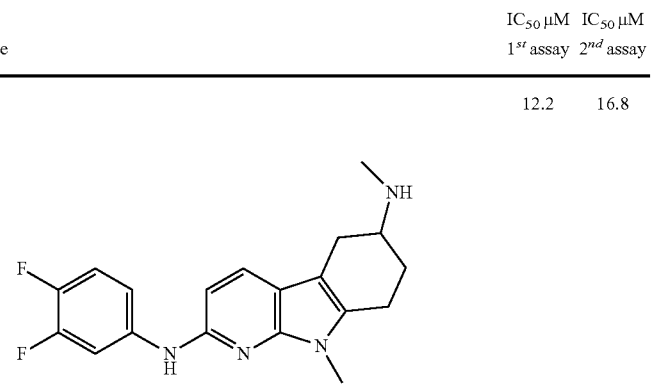

| 214a | Prepared using the early eluting diastereomeric building block of the diastereomer separation | 35.4 | 33.5 |
| 214b | Prepared using the late eluting diastereomeric building block of the diastereomer separation | 13.4 | 7.7 |

-continued

| Example | | IC$_{50}$ μM 1$^{st}$ assay | IC$_{50}$ μM 2$^{nd}$ assay |
|---|---|---|---|
| 42 | 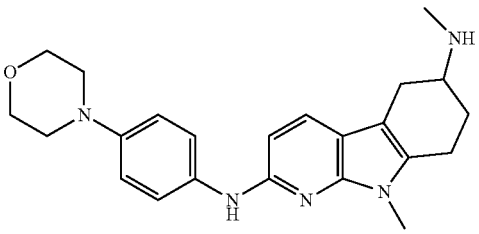 [SMILES: CNC1CCc2c(c3ccc(Nc4ccc(N5CCOCC5)cc4)nc3n2C)C1] | 63.0 | 111.6 |
| 216a | Prepared using the early eluting diastereomeric building block of the diastereomer separation | 99.3 | 54.9 |
| 216b | Prepared using the late eluting diastereomeric building block of the diastereomer separation | 45.0 | 34.5 |
| 156 | 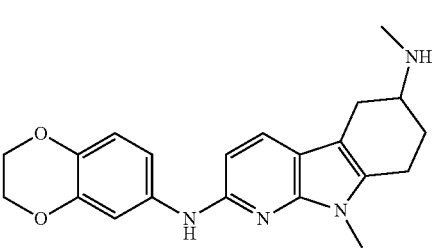 [SMILES: CNC1CCc2c(c3ccc(Nc4ccc5c(c4)OCCO5)nc3n2C)C1] | 39.7 | 26.7 |
| 217a | Prepared using the early eluting diastereomeric building block of the diastereomer separation | 28 | 23.6 |
| 217b | Prepared using the late eluting diastereomeric building block of the diastereomer separation | 6.6 | 5.9 |

Items of the invention are summarized in the following:

1. A compound of formula (I):

A-L$_1$-B    (I)

and all stereoisomers, racemic mixtures, pharmaceutically acceptable salts, hydrates, solvates and polymorphs thereof;

wherein

A is selected from the group consisting of

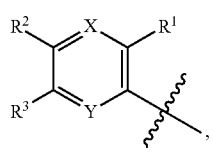

(i)

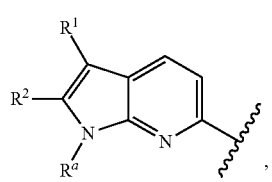

(ii)

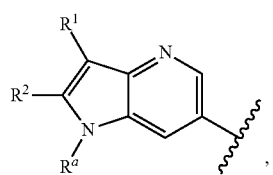

(iii)

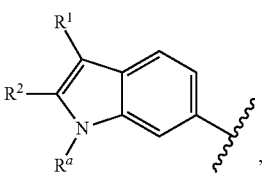

(iv)

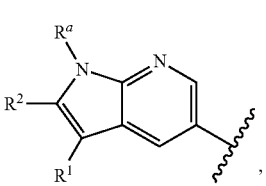

(v)

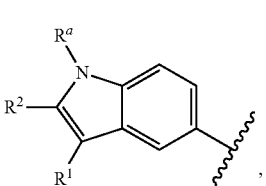

(vi)

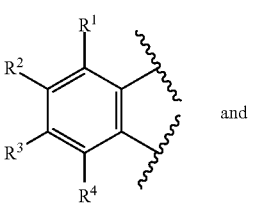

(vii)

and

-continued

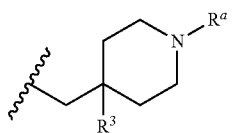
(viii)

L₁ is directionally selected from the group consisting of:

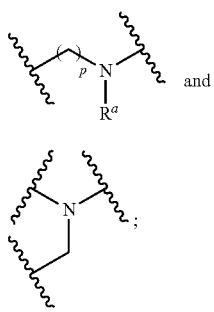
(a)

(b)

B is selected from the group consisting of:

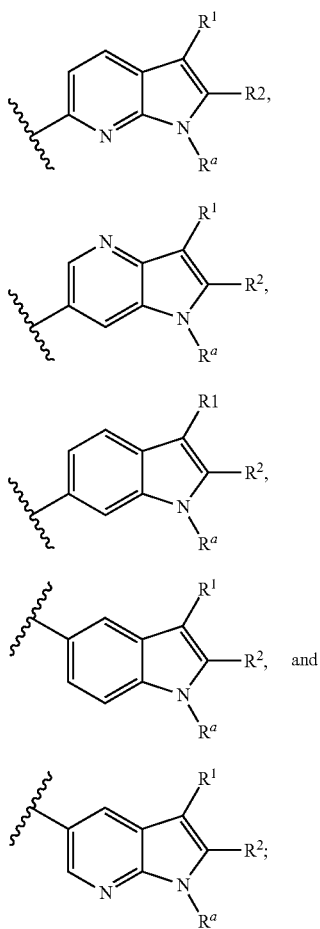
(ix)

(x)

(xi)

(xii)

(xiii)

wherein
$R^1$, $R^2$, $R^3$ and $R^4$ are each independently selected from the group consisting of hydrogen, halogen, CN, $CF_3$, $CONR^{30}R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if any of the groups $R^1/R^2/R^3/R^4$ are adjacent, they can optionally be taken together and can form a 5- to 8-membered ring containing carbon atoms and optionally one or more heteroatoms selected from O, S, or N or optionally one or more heteroatom (e.g., N, O and/or S)-containing moieties and wherein the 5- to 8-membered ring may be substituted by $NR^{20}R^{21}$;

for each occurrence, $R^a$ is independently selected from the group consisting of hydrogen, alkyl, haloalkyl, $S(O)_tNR^{30}R^{31}$, $S(O)_tR^{30}$, $C(O)OR^{30}$, $C(O)R^{30}$, and $C(O)NR^{30}R^{31}$;

for each occurrence, $R^b$ is independently selected from the group consisting of: hydrogen, halogen, CN, $CF_3$, $CONR^{30}R^{31}$, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence, $R^{30}$, $R^{31}$, $R^{20}$ and $R^{21}$ are each independently selected from the group consisting of: hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted, or wherein $R^{20}$ and $R^{21}$, when taken together with the nitrogen to which they are attached, can form a 3- to 8-membered ring containing carbon atoms and optionally one or more further heteroatoms selected from O, S, or N or optionally one or more heteroatom (e.g., N, O and/or S)-containing moieties and wherein the 3- to 8-membered ring may be optionally substituted;

X and Y are each independently selected from the group consisting of $CR^b$ and N;

t is 1 or 2; and p is 0, 1 or 2 with the proviso that the following compounds are excluded:

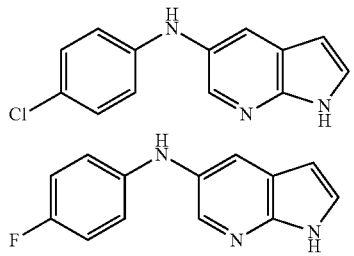

523
-continued
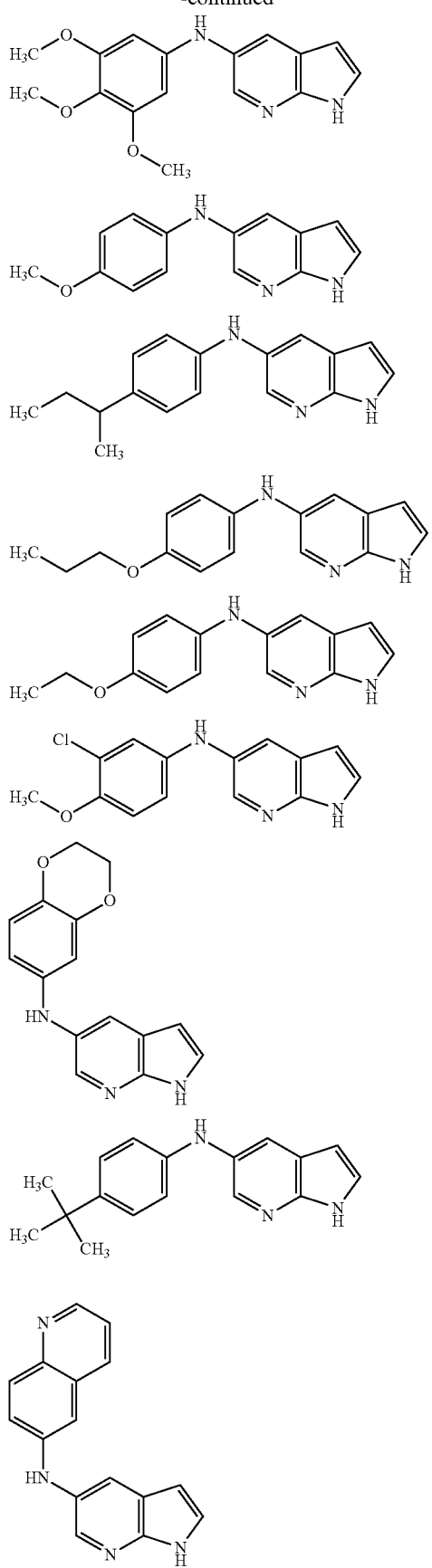
524
-continued
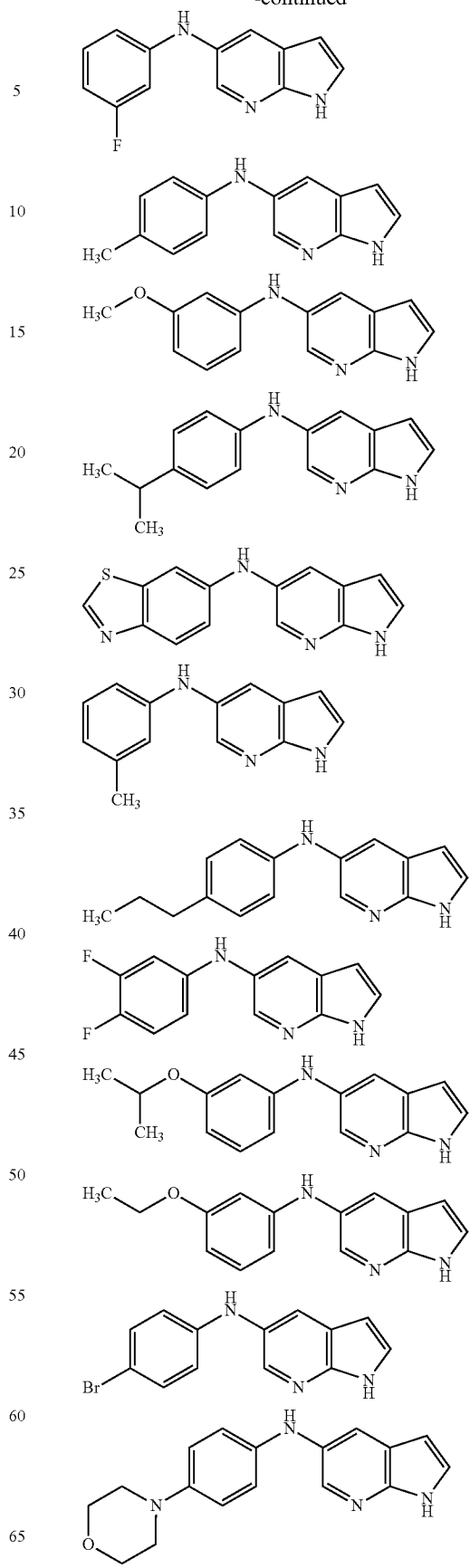

525
-continued
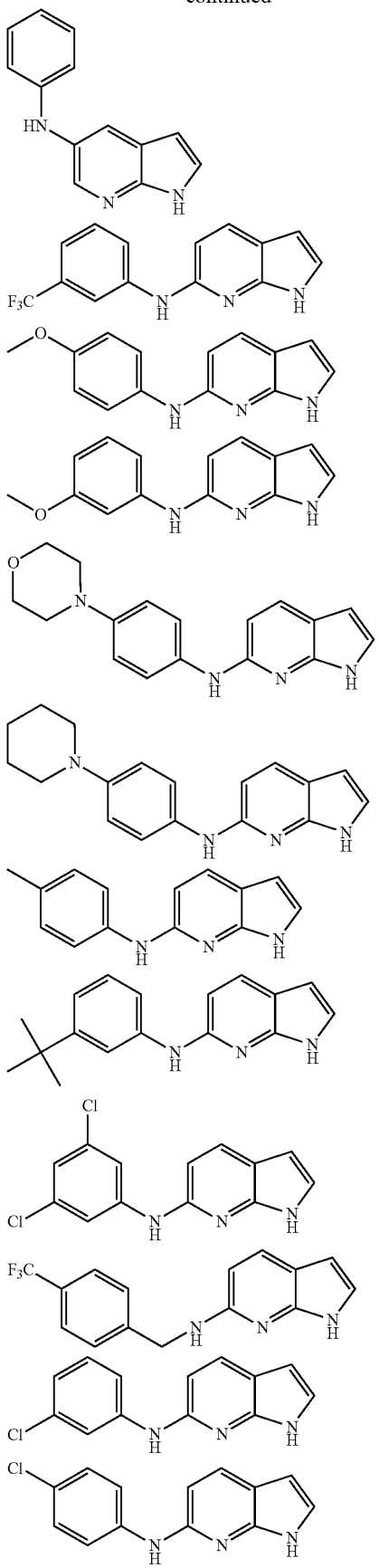
526
-continued
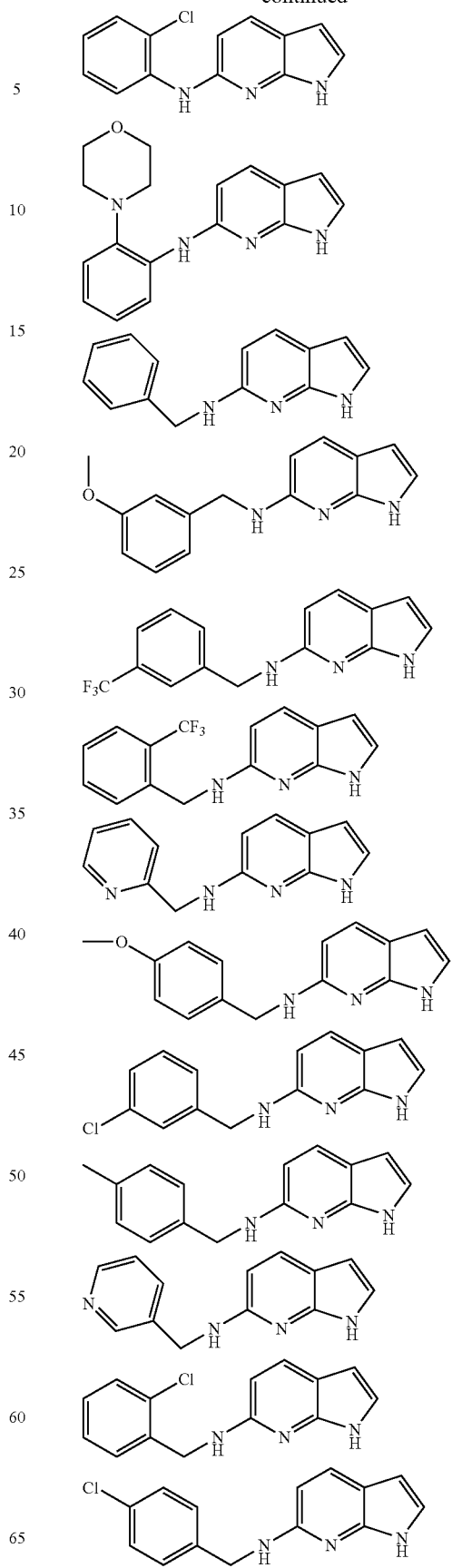

-continued
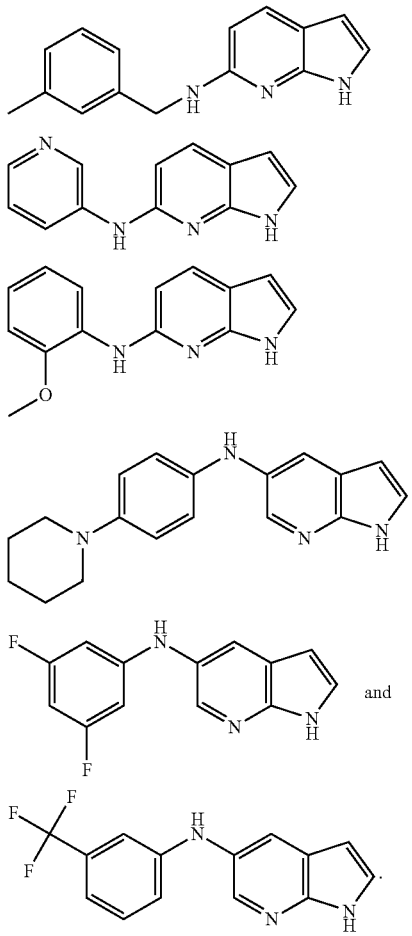
2. The compound of item 1, wherein
A is selected from the group consisting of:
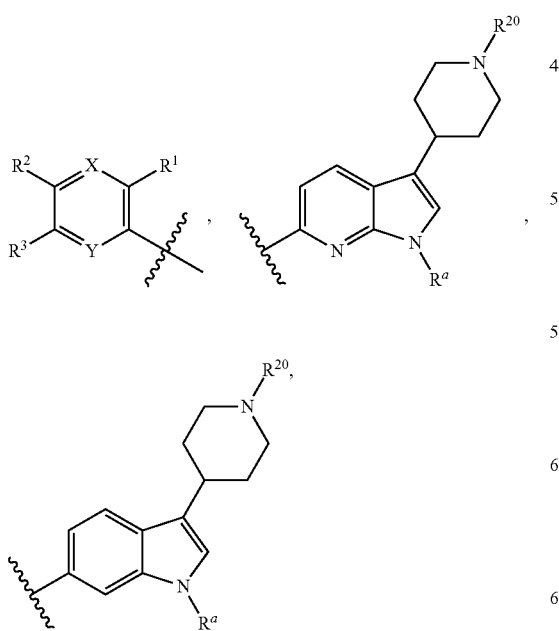
-continued
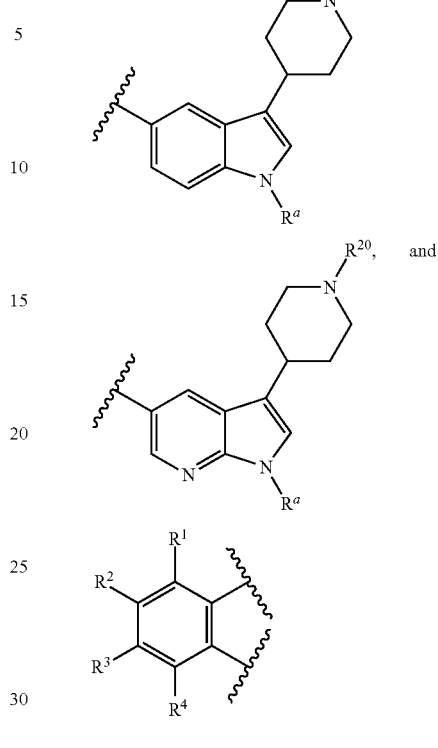
$L_1$ is
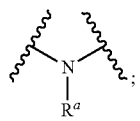
B is selected from the group consisting of:
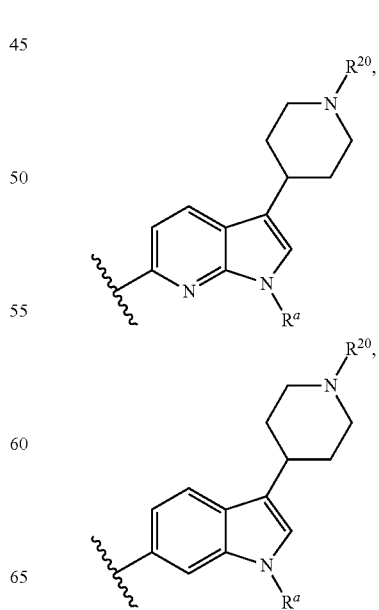

-continued wherein:
R¹, R², R³, R⁴, Rᵃ, R²⁰, X and Y have the same meanings as in item 1;
V is absent or NR²⁰R²¹ and
z is 1 or 2.

3. The compound of item 1 or 2, wherein A has the formula (i).
4. The compound of any of the preceding items, wherein $L_1$ has the formula (a) and preferably p is 0.
5. The compound of any of the preceding items, wherein R¹, R², R³ and R⁴ are each independently selected from hydrogen, halogen (such as F), CN, CF₃, CONR³⁰R³¹, —O—alkyl, heterocycloalkyl (such as 6. The compound of item 1, wherein formula (vii) in A is selected from 7. The compound of any of the preceding items, wherein Rᵃ is hydrogen or $C_{1-4}$ alkyl.

8. The compound of item 1, wherein A has the formula (i)

9. The compound of item 1, wherein A has the formula (ii)

10. The compound of item 1, wherein A has the formula (iii)

11. The compound of item 1, wherein A has the formula (iv)

12. The compound of item 1, wherein A has the formula (v)

13. The compound of item 1, wherein A has the formula (vi)

14. The compound of item 1, wherein A has the formula (vii)

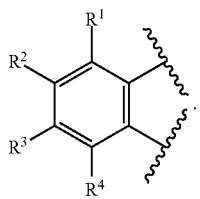

15. The compound of item 1, wherein $L_1$ has the formula (a)

(a)

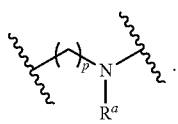

16. The compound of item 1, wherein B has the formula (ix)

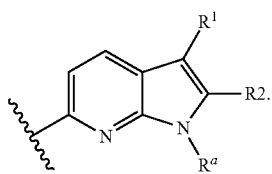

17. The compound of item 1, wherein B has the formula (x)

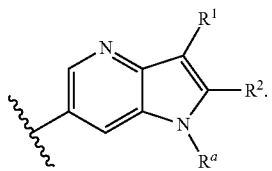

18. The compound of item 1, wherein B has the formula (xi)

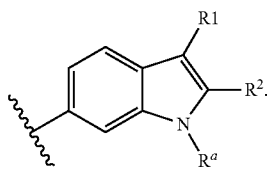

19. The compound of item 1, wherein B has the formula (xii)

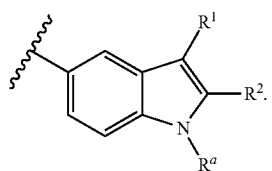

20. The compound of item 1, wherein B has the formula (xiii)

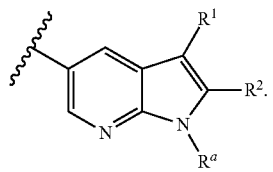

21. The compound of item 1 having the formula (I):

A-L$_1$-B   (I)

and all stereoisomers, racemic mixtures, pharmaceutically acceptable salts, hydrates, solvates and polymorphs thereof;

wherein A is:

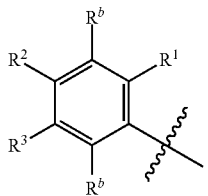

$L_1$ is:

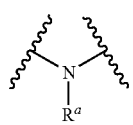

B is:

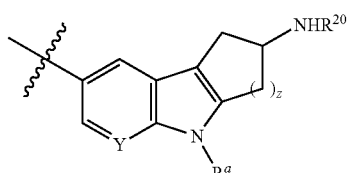

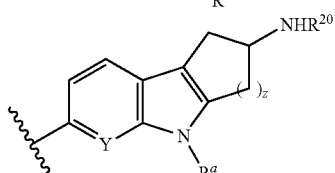

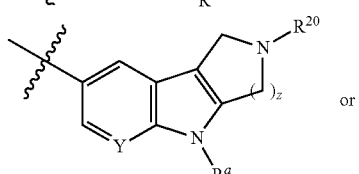 or

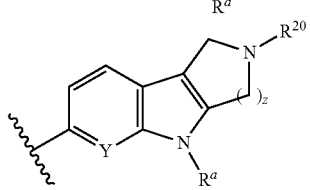

wherein
R¹ and R² are each independently selected from the group consisting of hydrogen, halogen, CN, CF₃, CONR³⁰R³¹, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if R¹ and R² are adjacent, they can optionally be taken together and can form a 5- or 6-membered ring containing carbon atoms and optionally one or two heteroatoms selected from O, S, or N or the heteroatom-containing moiety NR⁵⁰:

R³ is hydrogen or halogen;

Rᵃ is hydrogen or alkyl;

for each occurrence, Rᵇ is independently selected from the group consisting of: hydrogen, halogen, CN, CF₃, CONR³⁰R³¹, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence, R³⁰, R³¹, R²⁰ and R²¹ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

R⁵⁰ is for each occurrence R²⁰, S(O)ₜNR²⁰R²¹, S(O)ₜR²⁰, C(O)OR²⁰, C(O)R²⁰C(=NRᵃ)NR²⁰R²¹, C(=NR²⁰)NR²¹Rᵃ, C(=NOR²⁰)R²¹ or C(O)NR²⁰R²¹;

Y is each independently CH or N t is 1 or 2; and z is 1 or 2.

22. A compound of item 1 having the formula (I):

A-L₁-B    (I)

and all stereoisomers, racemic mixtures, pharmaceutically acceptable salts, hydrates, solvates and polymorphs thereof;

wherein A is:

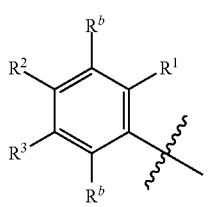

L₁ is:

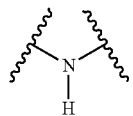

B is:

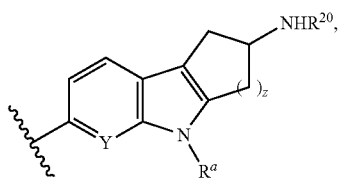

wherein
R¹ and R² are each independently selected from the group consisting of hydrogen, halogen, CN, CF₃, CONR³⁰R³¹, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if R¹ and R² are adjacent, they can optionally be taken together and can form a 5- or 6-membered ring containing carbon atoms and optionally one or two heteroatoms selected from O, S, or N or the heteroatom-containing moiety NR⁵⁰;

R³ is hydrogen or halogen;

Rᵃ is hydrogen or alkyl;

for each occurrence, Rᵇ is independently selected from the group consisting of: hydrogen, halogen, CN, CF₃, CONR³⁰R³¹, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence, R³⁰, R³¹, R²⁰ and R²¹ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

R⁵⁰ is, for each occurrence, R²⁰, S(O)ₜNR²⁰R²¹, S(O)ₜR²⁰C(O)OR²⁰, C(O)R²⁰C(=NRᵃ)NR²⁰R²¹, C(=NR²⁰)NR²¹Rᵃ, C(=NOR²⁰)R²¹ or C(O)NR²⁰R²¹;

Y is each independently CH or N;

t is 1 or 2; and z is 1 or 2.

23. A compound of item 1 having the formula (I):

A-L₁-B    (I)

and all stereoisomers, racemic mixtures, pharmaceutically acceptable salts, hydrates, solvates and polymorphs thereof;

wherein A is:

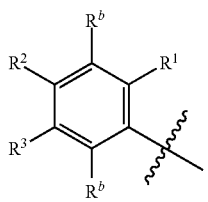

L₁ is:

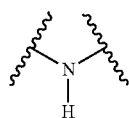

B is:

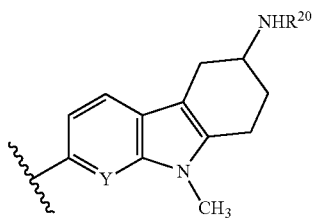

wherein
R¹ and R² are each independently selected from the group consisting of hydrogen, halogen, CN, CF₃, CONR³⁰R³¹, alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl can be optionally substituted, or if R¹ and R² are adjacent, they can optionally be taken together and can form a 5- or 6-membered ring containing carbon atoms and optionally one or two heteroatoms selected from O, S, or N or the heteroatom-containing moiety NR⁵⁰;

R³ is hydrogen or halogen;

Rᵃ is hydrogen or alkyl;

for each occurrence, Rᵇ is independently selected from the group consisting of: hydrogen, halogen, CN, CF₃, CONR³⁰R³¹, alkyl, —O-alkyl, —C(O)O-alkyl, cycloalkyl, cycloalkylalkyl, heterocycloalkyl, fluoroalkyl, heterocycloalkylalkyl, alkenyl, alkynyl, aryl, heteroaryl, arylalkyl and heteroarylalkyl, wherein alkyl, cycloalkyl, cycloalkylalkyl, heterocycloalkyl, fluoroalkyl, heterocycloalkylalkyl, alkenyl, alkenyl, alkynyl, aryl, heteroaryl, arylalkyl, heteroarylalkyl and aminoalkyl can be optionally substituted;

for each occurrence R³⁰, R³¹, R²⁰ and R²¹ are each independently selected from the group consisting of hydrogen, alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl can be optionally substituted;

R⁵⁰ is, for each occurrence, R²⁰, S(O)ₜNR²⁰R²¹, S(O)ₜR²⁰, C(O)OR²⁰, C(O)R²⁰C(=NRᵃ)NR²⁰R²¹, C(=NR²⁰)NR²¹Rᵃ, C(=NOR²⁰)R²¹ or C(O)NR²⁰R²¹;

Y is each independently CH or N; and t is 1 or 2.

24. A compound of item 1 having the formula (I):

A-L₁-B     (I)

and all stereoisomers, racemic mixtures, pharmaceutically acceptable salts, hydrates, solvates and polymorphs thereof;

wherein A is:

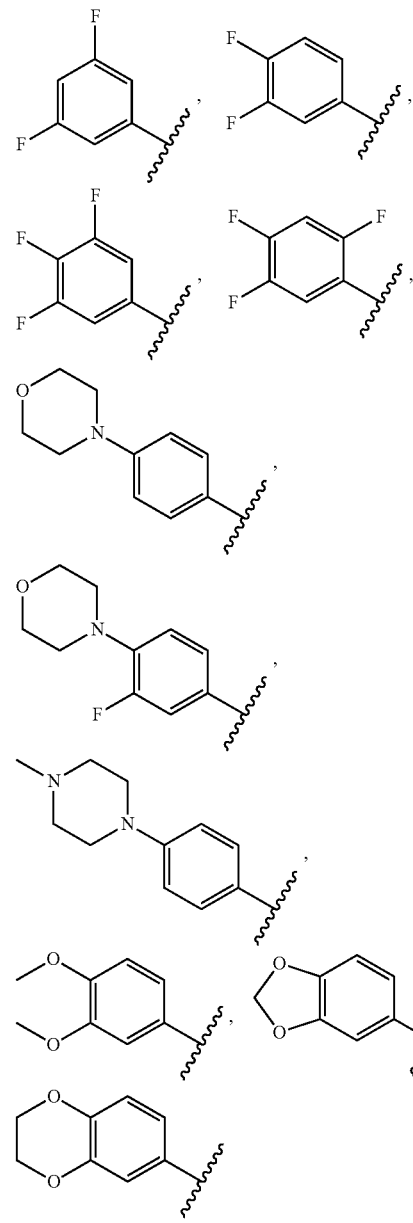

$L_1$ is:
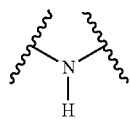
and
B is:
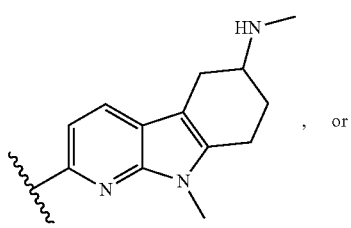, or
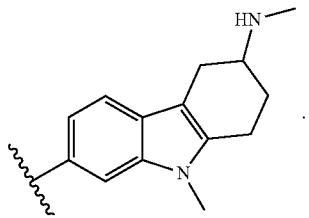.
25. The compound of any of the preceding items, wherein the compound is selected from the group consisting of
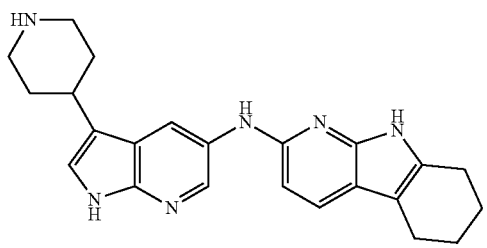
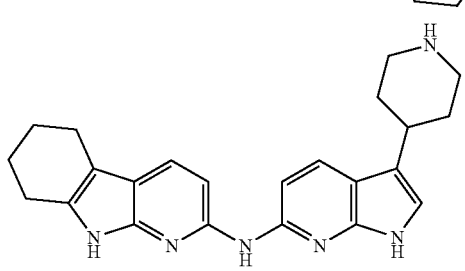
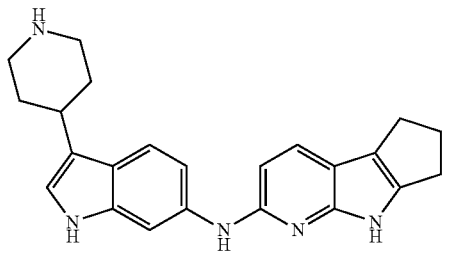
-continued
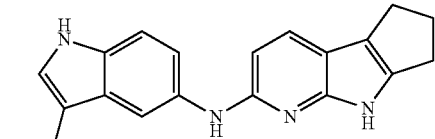
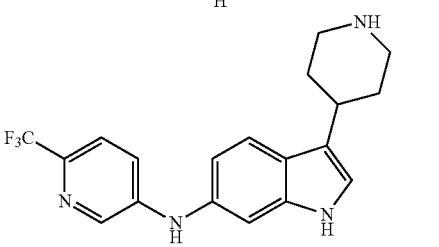
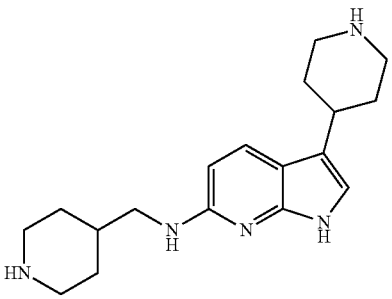
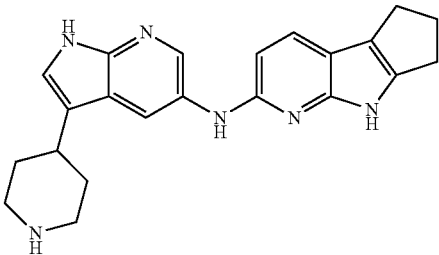
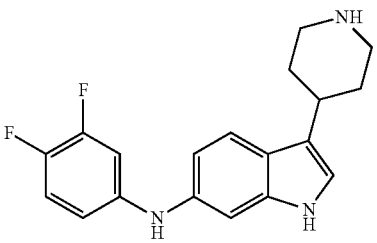

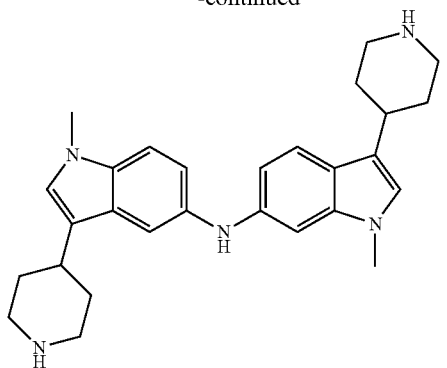
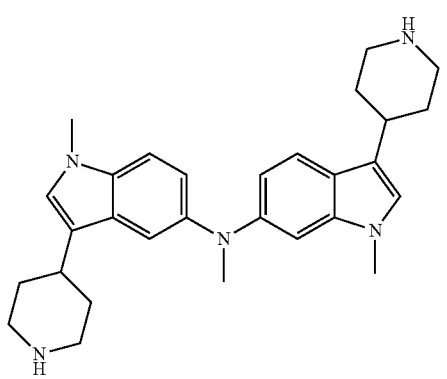
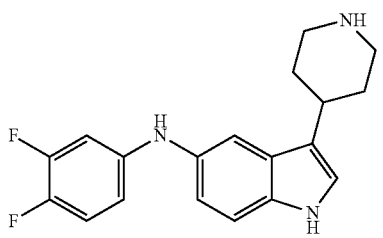
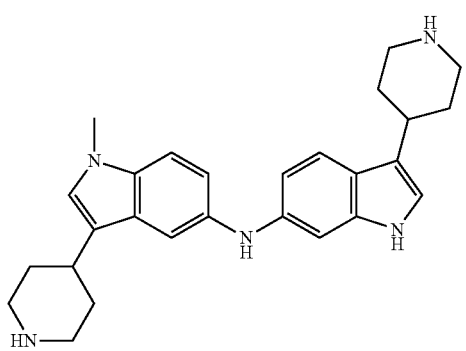
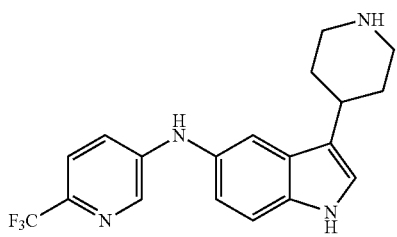
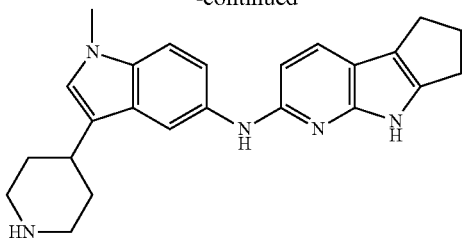
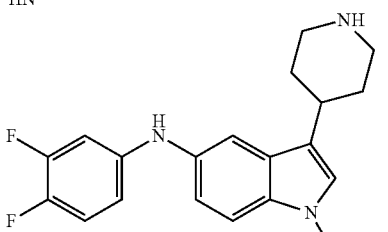
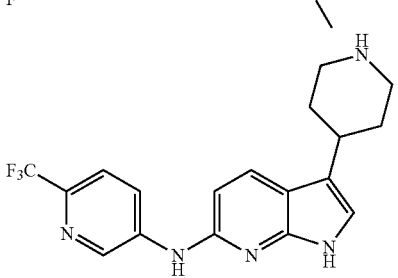
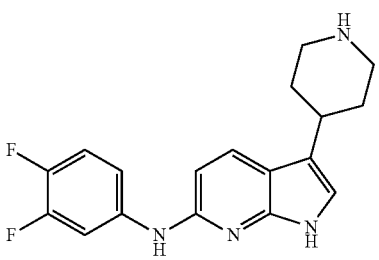
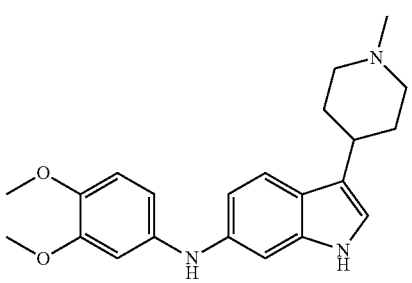
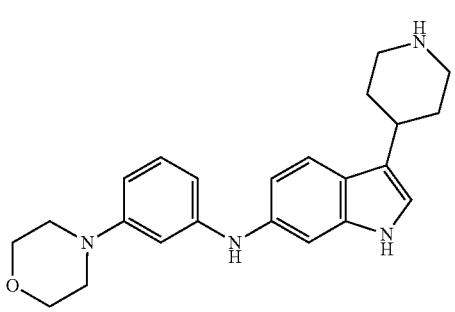

541
-continued
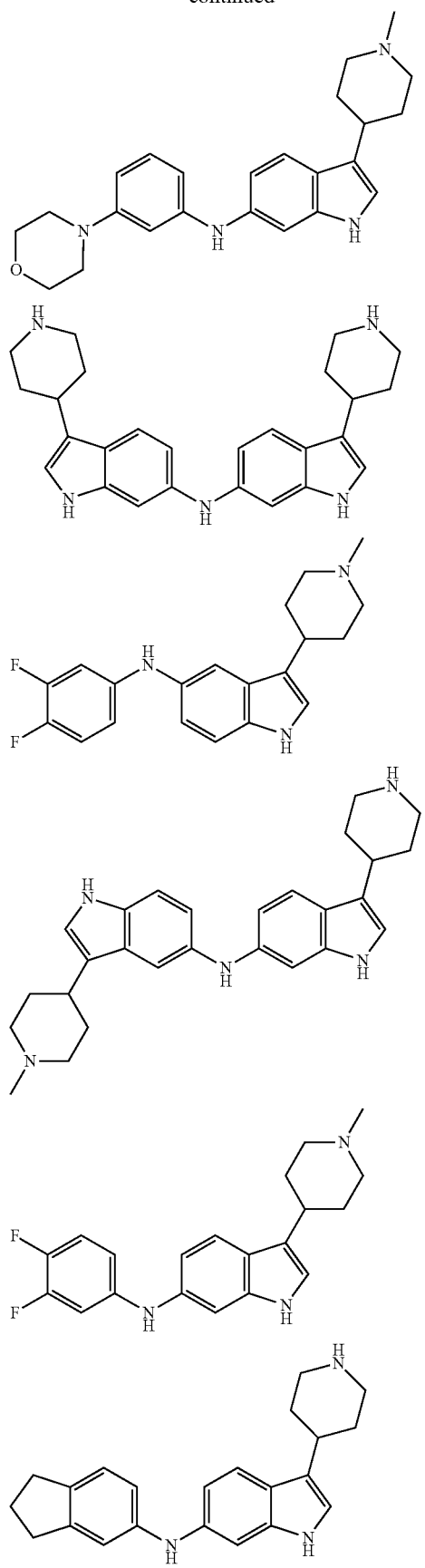
542
-continued
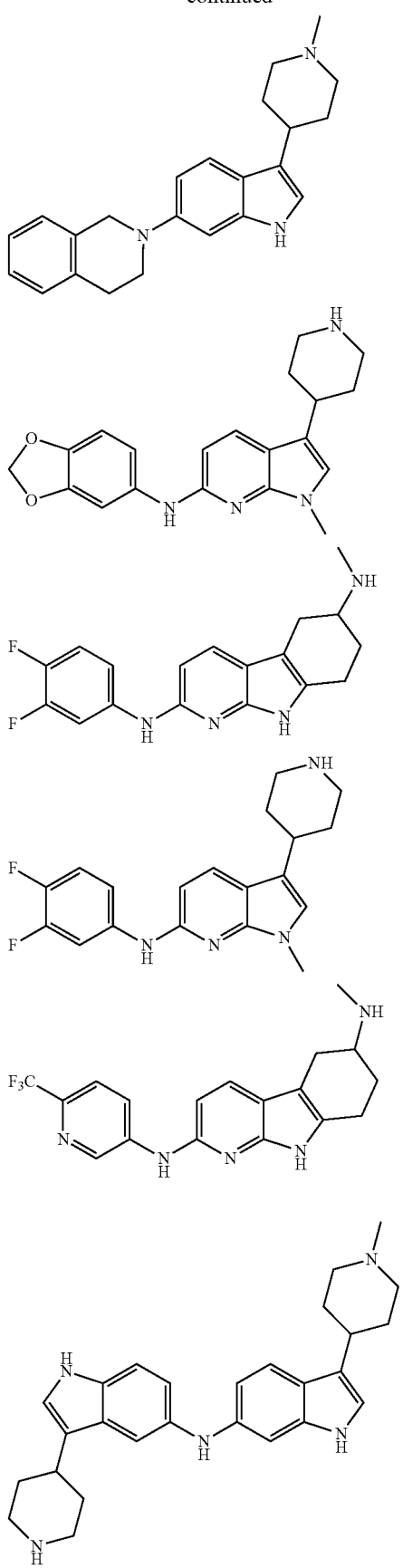

543
-continued
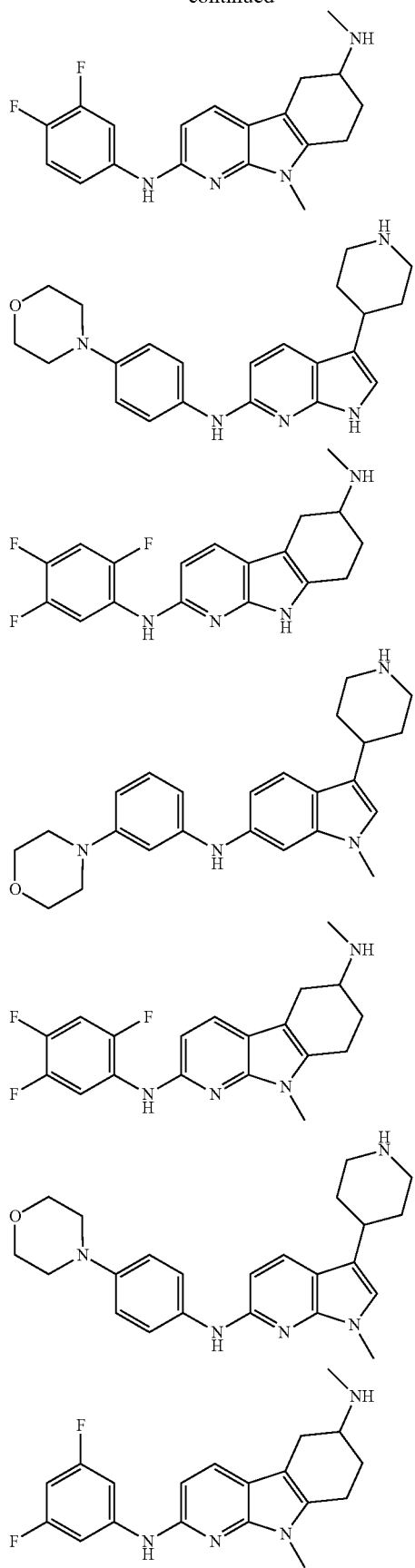
544
-continued
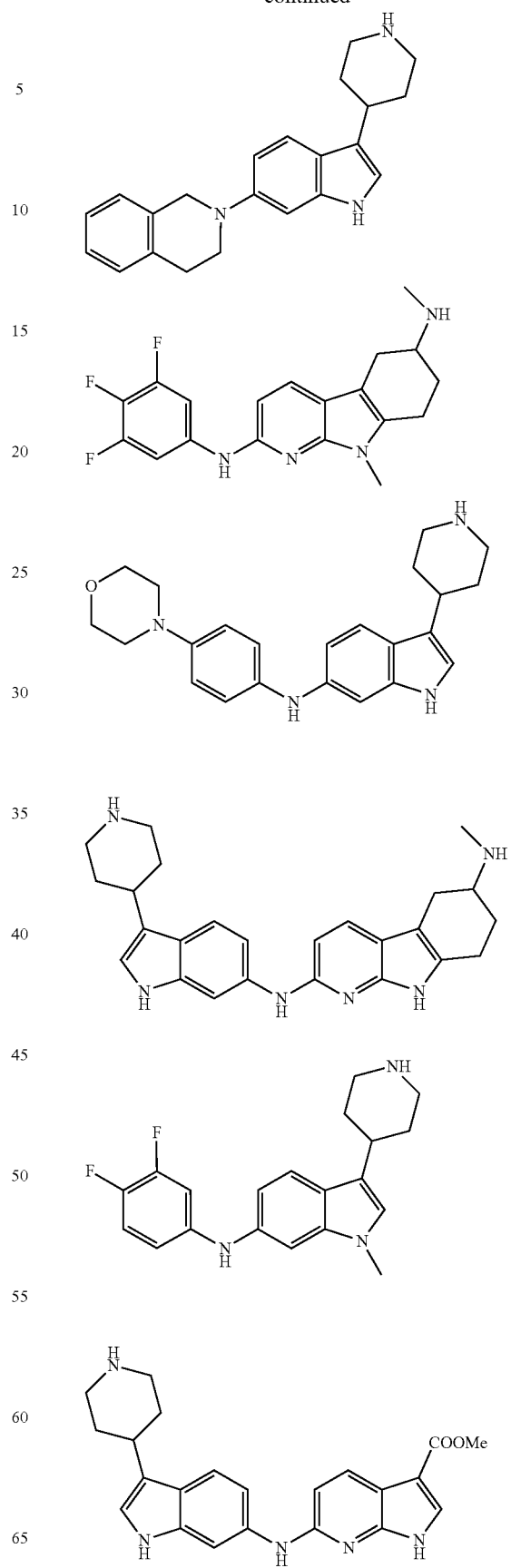

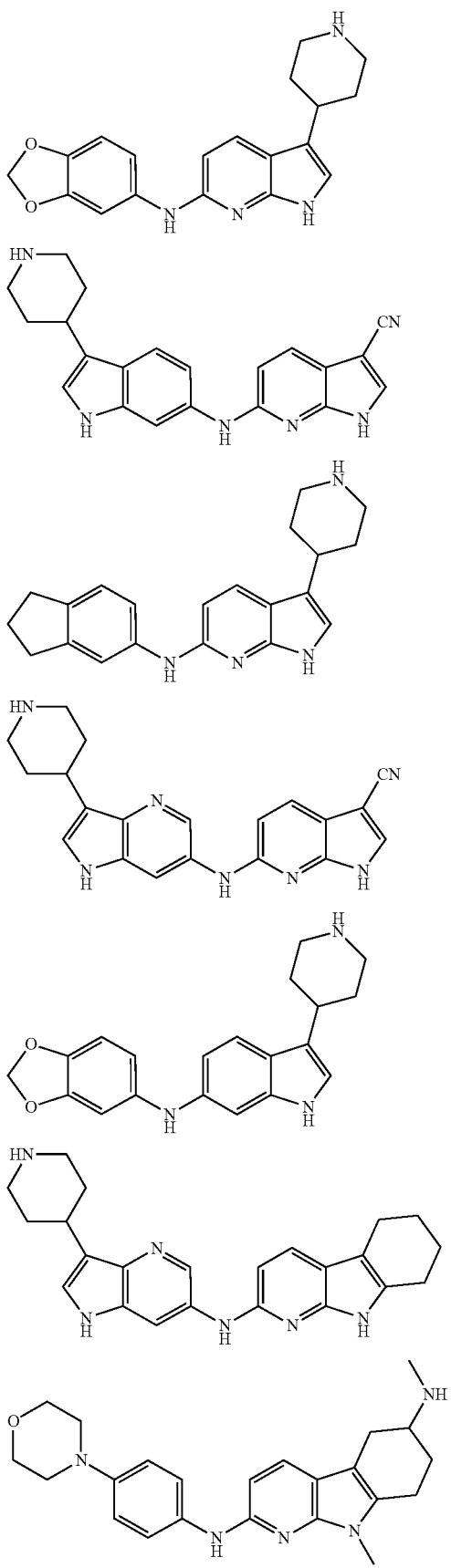

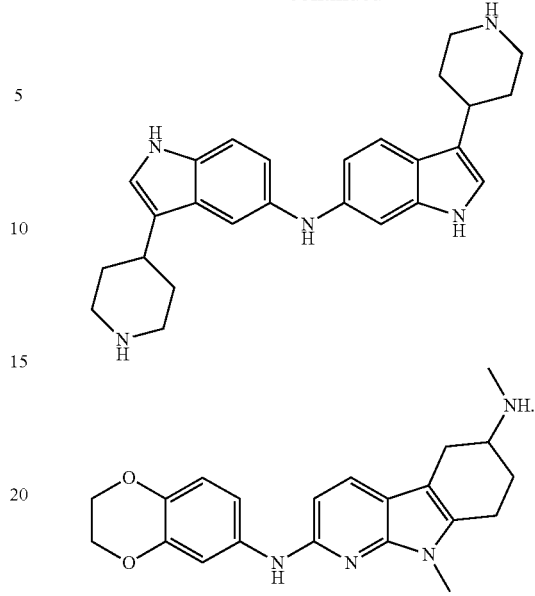

26. A compound as defined in any one of items 1 to 25 comprising a radionuclide wherein the compounds disclaimed in item 1 are disclaimed.

27. A radiopharmaceutical formulation comprising a compound as defined in any one of items 1 to 25 comprising a radionuclide wherein the compounds disclaimed in item 1 are disclaimed or are not disclaimed.

28. A pharmaceutical composition comprising a compound as defined in any one of items 1 to 25 wherein the compounds disclaimed in item 1 are disclaimed.

29. The pharmaceutical composition of item 28 further comprising a pharmaceutically acceptable carrier or excipient.

30. Use of the compound as defined in any one of items 1 to 25 wherein the compounds disclaimed in item 1 are disclaimed or are not disclaimed for the preparation of a medicament for treating or preventing a disease or condition associated with an amyloid and/or amyloid-like protein.

31. The use of item 30, wherein the disease is a neurological disorder.

32. The use of item 31, wherein the neurological disorder is Alzheimer's disease (AD), Lewy body dementia (LBD), Down's syndrome, hereditary cerebral hemorrhage with amyloidosis (Dutch type), the Guam Parkinson-Dementia complex or mild cognitive impairment (MCI).

33. The use of item 32, wherein the neurological disorder is Alzheimer's disease.

34. The use of item 30, wherein the disease is progressive supranuclear palsy, multiple sclerosis, inclusion-body myositis (IBM), Creutzfeld Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, or lattice dystrophy.

35. A method of treating or preventing a disease or condition associated with an amyloid and/or amyloid-like protein comprising administering to a subject in need of such treatment an effective amount of a compound as defined in any one of items 1 to 25 wherein the compounds disclaimed in item 1 are disclaimed or are not disclaimed.
36. The method of item 35, wherein the disease is a neurological disorder.
37. The method of item 36, wherein the neurological disorder is Alzheimer's disease (AD), Lewy body dementia (LBD), Down's syndrome, hereditary cerebral hemorrhage with amyloidosis (Dutch type), the Guam Parkinson-Dementia complex or mild cognitive impairment (MCI).
38. The method of item 37, wherein the neurological disorder is Alzheimer's disease.
39. The method of item 35, wherein the disease is progressive supranuclear palsy, multiple sclerosis, inclusion-body myositis (IBM), Creutzfeld Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, or lattice dystrophy).
40. The compound as defined in any one of items 1 to 25 wherein the compounds disclaimed in item 1 are disclaimed or are not disclaimed for use in the treatment or prevention a disease or condition associated with an amyloid and/or amyloid-like protein.
41. The compound of item 40, wherein the disease is a neurological disorder.
42. The compound of item 41, wherein the neurological disorder is Alzheimer's disease (AD), Lewy body dementia (LBD), Down's syndrome, hereditary cerebral hemorrhage with amyloidosis (Dutch type), the Guam Parkinson-Dementia complex or mild cognitive impairment (MCI).
43. The compound of item 42, wherein the neurological disorder is Alzheimer's disease.
44. The compound of item 40, wherein the disease is progressive supranuclear palsy, multiple sclerosis, inclusion-body myositis (IBM), Creutzfeld Jacob disease, Parkinson's disease, HIV-related dementia, amyotropic lateral sclerosis (ALS), inclusion-body myositis (IBM), adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, or lattice dystrophy.
45. A mixture comprising a compound as defined in any one of items 1 to 25 wherein the compounds disclaimed in item 1 are disclaimed or are not disclaimed and optionally at least one further biologically active compound and/or a pharmaceutically acceptable carrier and/or a diluent and/or an excipient.
46. The mixture according to item 45, wherein the further biologically active compound is a compound used in the treatment of amyloidosis.
47. The mixture according to item 45 or 46, wherein the further biologically active compound is selected from the group consisting of antibodies, vaccines, compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), α-secretase activators, β- and γ-secretase inhibitors, tau proteins, neurotransmitters, (β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements.
48. The mixture according to item 47, wherein the further biologically active compound is a cholinesterase inhibitor (ChEI).
49. The mixture according to item 47, wherein the further biologically active compound is selected from the group consisting of tacrine, rivastigmine, donepezil, galantamine, niacin and memantine.
50. The mixture according to item 45, wherein the further biologically active compound is an antibody, particularly a monoclonal antibody, including any functionally equivalent antibody or functional parts thereof.
51. The mixture according to item 50, wherein the antibody, particularly the monoclonal antibody, including any functionally equivalent antibody or functional parts thereof, is an antibody which binds amyloid β.
52. The mixture according to item 50 or 51, wherein the antibody, particularly the monoclonal antibody, including any functionally equivalent antibody or functional parts thereof, is an antibody which antibody, upon co-incubation with amyloid monomeric and/or polymeric soluble amyloid peptides, particularly with β-amyloid monomeric peptides such as, for example, Aβ monomeric peptides 1-39; 1-40, 1-41, or 1-42, and/or a polymeric soluble β-amyloid peptide comprising a plurality of the Aβ monomeric units, but especially with an $A\beta_{1-42}$ monomeric and/or an Aβ polymeric soluble amyloid peptide comprising a plurality of the $A\beta_{1-42}$ monomeric units, inhibits the aggregation of the Aβ monomers into high molecular polymeric fibrils or filaments and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, or 1-42, but especially $A\beta_{1-42}$ monomeric peptides, is capable of disaggregating preformed polymeric fibrils or filaments.
53. The mixture according to item 50, wherein the antibody is a chimeric antibody or a functional part thereof, or a humanized antibody or a functional part thereof.
54. The mixture according to item 50, wherein the antibody is a monoclonal antibody selected from the group of antibodies having the characteristic properties of an antibody produced by the hybridoma cell line:
  a) FP 12H3, deposited on Dec. 1, 2005 and Dec. 9, 2005, respectively, as DSM ACC2752;
  b) FP 12H3-C2, deposited on Dec. 1, 2005 and Dec. 9, 2005, respectively, as DSM ACC2750;
  c) FP 12H3-G2, deposited on Dec. 1, 2005 and Dec. 9, 2005, respectively, as DSM ACC2751;
  d) ET 7E3, deposited on Dec. 8, 2005 as DSM ACC2755; and
  e) EJ 7H3, deposited on Dec. 8, 2005 as DSM ACC2756.
55. The mixture according to item 50, wherein the antibody is a monoclonal antibody selected from the group of antibodies produced by the hybridoma cell line:
  a) FP 12H3, deposited on Dec. 1, 2005 and Dec. 9, 2005, respectively, as DSM ACC2752;
  b) FP 12H3-C2, deposited on Dec. 1, 2005 and Dec. 9, 2005, respectively, as DSM ACC2750;
  c) FP 12H3-G2, deposited on Dec. 1, 2005 and Dec. 9, 2005, respectively, as DSM ACC2751;
  d) ET 7E3, deposited on Dec. 8, 2005 as DSM ACC2755; and
  e) EJ 7H3, deposited on Dec. 8, 2005 as DSM ACC2756.

56. The mixture according to item 50, wherein the antibody is a humanized antibody exhibiting a light chain and a heavy chain as depicted in SEQ ID No. 2 and SEQ ID No. 4.
57. The mixture according to item 50, wherein the antibody is a humanized antibody exhibiting a light chain variable region and a heavy chain variable region as depicted in SEQ ID No. 1 and SEQ ID No. 3.
58. The mixture according to item 45, wherein the further biologically active compound is an Aβ antigenic peptide fragment consisting of a single or repetitive stretch of a plurality of contiguous amino acid residues from the N-terminal part of the Aβ peptide, particularly a stretch of between 13 and 15 contiguous amino acid residues.
59. The mixture according to item 58, wherein the Aβ antigenic peptide fragment is an $Aβ_{1-15}$ peptide antigen.
60. The mixture according to item 58, wherein the $Aβ_{1-15}$ peptide antigen is a palmitoylated $Aβ_{1-15}$ peptide antigen modified by covalently attached palmitoyl residues, particularly between 2 and 4, more particularly 4 residues, at each end of the peptide reconstituted in a liposome.
61. The mixture according to any one of items 45 to 60, wherein the compound and/or the further biologically active compound are present in a therapeutically effective amount.
62. A method of collecting data for the diagnosis of an amyloid-associated disease or condition in a sample or a patient comprising:
    (a) bringing a sample or a specific body part or body area suspected to contain, an amyloid protein into contact with a compound as defined in any one of claims 1 to 25 wherein the compounds disclaimed in claim 1 are disclaimed or are not disclaimed;
    (b) allowing the compound to bind to the amyloid protein;
    (c) detecting the compound bound to the protein; and
    (d) optionally correlating the presence or absence of compound binding with the amyloid protein with the presence or absence of amyloid protein in the sample or specific body part or body area.
63. A method of determining the extent of amyloidogenic plaque burden in a tissue and/or a body fluid comprising:
    (a) providing a sample representative of the tissue and/or body fluid under investigation;
    (b) testing the sample for the presence of amyloid protein with a compound as defined in any one of items 1 to 25 wherein the compounds disclaimed in item 1 are disclaimed or are not disclaimed;
    (c) determining the amount of compound bound to the amyloid protein; and
    (d) calculating the plaque burden in the tissue and/or body fluid.
64. The method according to item 63, wherein the determination in step (c) is conducted such that presence or absence of the compound binding with the amyloid protein correlates with presence or absence of amyloid protein.
65. A method of collecting data for determining a predisposition to an amyloid-associated disease or condition in a patient comprising detecting the specific binding of a compound as defined in any one of claims 1 to 25 wherein the compounds disclaimed in claim 1 are disclaimed or are not disclaimed to an amyloid protein in a sample or in situ which comprises the steps of:
    (a) bringing the sample or a specific body part or body area suspected to contain the amyloid protein into contact with a compound as defined in any one of items 1 to 25 wherein the compounds disclaimed in item 1 are disclaimed or are not disclaimed, which compound specifically binds to the amyloid protein;
    (b) allowing the compound to bind to the amyloid protein to form a compound/protein complex;
    (c) detecting the formation of the compound/protein complex;
    (d) optionally correlating the presence or absence of the compound/protein complex with the presence or absence of amyloid protein in the sample or specific body part or body area; and
    (e) optionally comparing the amount of the compound/protein complex to a normal control value.
66. A method of collecting data for monitoring minimal residual disease in a patient following treatment with an antibody or a vaccine composition, wherein the method comprises:
    (a) bringing a sample or a specific body part or body area suspected to contain an amyloid protein into contact with a compound as defined in any one of items 1 to 25 wherein the compounds disclaimed in item 1 are disclaimed or are not disclaimed, which compound specifically binds to the amyloid protein;
    (b) allowing the compound to bind to the amyloid protein to form a compound/protein complex;
    (c) detecting the formation of the compound/protein complex;
    (d) optionally correlating the presence or absence of the compound/protein complex with the presence or absence of amyloid protein in the sample or specific body part or body area; and
    (e) optionally comparing the amount of the compound/protein complex to a normal control value.
67. A method of collecting data for predicting responsiveness of a patient being treated with an antibody or a vaccine composition comprising:
    (a) bringing a sample or a specific body part or body area suspected to contain an amyloid protein into contact with a compound as defined in any one of items 1 to 25 wherein the compounds disclaimed in item 1 are disclaimed or are not disclaimed, which compound specifically binds to the amyloid protein;
    (b) allowing the compound to bind to the amyloid protein to form a compound/protein complex;
    (c) detecting the formation of the compound/protein complex;
    (d) optionally correlating the presence or absence of the compound/protein complex with the presence or absence of amyloid protein in the sample or specific body part or body area; and
    (e) optionally comparing the amount of the compound/protein complex to a normal control value.
68. A test kit for detection and/or diagnosis of an amyloid-associated disease or condition comprising a compound as defined in any one of items 1 to 25 wherein the compounds disclaimed in item 1 are disclaimed or are not disclaimed.
69. The test kit according to item 68 comprising a container holding one or more compounds as defined in any one of items 1 to 25 wherein the compounds disclaimed in item 1 are disclaimed or are not disclaimed and instructions for using the compound for the purpose of binding to an amyloid protein to form a compound/protein complex and detecting the formation of the compound/protein complex such that presence or absence of the compound/protein complex correlates with the presence or absence of the amyloid protein.
70. Use of the compound as defined in any one of items 1 to 25 wherein the compounds disclaimed in item 1 are disclaimed or are not disclaimed for the preparation of a medicament for treating or preventing an ocular disease or condition associated with a pathological abnormality/change in the tissue of the visual system, particularly associated with an amyloid-beta-related pathological abnormality/change in the tissue of the visual system.

71. The use of item 70, wherein the ocular disease or condition is selected from the group consisting of neuronal degradation, cortical visual deficits, glaucoma, cataract due to beta-amyloid deposition, ocular amyloidosis, primary retinal degeneration, macular degeneration, for example age-related macular degeneration, optic nerve drusen, optic neuropathy, optic neuritis, and lattice dystrophy.

72. A method of treating or preventing an ocular disease or condition associated with a pathological abnormality/change in the tissue of the visual system, particularly associated with an amyloid-beta-related pathological abnormality/change in the tissue of the visual system comprising administering to a subject in need of such treatment an effective amount of a compound as defined in any one of items 1 to 25 wherein the compounds disclaimed in item 1 are disclaimed or are not disclaimed.

73. The method of item 72, wherein the ocular disease or condition is selected from the group consisting of neuronal degradation, cortical visual deficits, glaucoma, cataract due to beta-amyloid deposition, ocular amyloidosis, primary retinal degeneration, macular degeneration, for example age-related macular degeneration, optic nerve drusen, optic neuropathy, optic neuritis, and lattice dystrophy.

74. A compound as defined in any one of items 1 to 25 wherein the compounds disclaimed in item 1 are disclaimed or are not disclaimed for use in the treatment or prevention of an ocular disease or condition associated with a pathological abnormality/change in the tissue of the visual system, particularly associated with an amyloid-beta-related pathological abnormality/change in the tissue of the visual system.

75. The compound of item 74, wherein the ocular disease or condition is selected from the group consisting of neuronal degradation, cortical visual deficits, glaucoma, cataract due to beta-amyloid deposition, ocular amyloidosis, primary retinal degeneration, macular degeneration, for example age-related macular degeneration, optic nerve drusen, optic neuropathy, optic neuritis, and lattice dystrophy.

76. A compound as defined in any one of items 1 to 25 wherein the compounds disclaimed in item 1 are disclaimed or are not disclaimed for use in inhibiting protein aggregation, in particular for use in inhibiting Aβ1-42 aggregation, Tau aggregation or alpha-synuclein aggregation.

77. Use of the compound as defined in any one of items 1 to 25 wherein the compounds disclaimed in item 1 are disclaimed or are not disclaimed for the preparation of a medicament for (a) reducing the β-amyloid plaque load, and/or (b) inhibiting the formation of β-amyloid plaques and/or (c) retarding the increase of amyloid load in the brain of a patient.

78. A method of (a) reducing the β-amyloid plaque load, and/or (b) inhibiting the formation of β-amyloid plaques and/or (c) retarding the increase of amyloid load in the brain of a subject comprising administering to a subject in need of such treatment an effective amount of a compound as defined in any one of items 1 to 25 wherein the compounds disclaimed in item 1 are disclaimed or are not disclaimed.

79. A compound as defined in any one of items 1 to 25 wherein the compounds disclaimed in item 1 are disclaimed or are not disclaimed for use in (a) the reduction of the β-amyloid plaque load, and/or (b) the inhibition of the formation of β-amyloid plaques and/or (c) the retardation of the increase of amyloid load in the brain of a patient.

80. The use of item 77, the method of item 78 or the compound of item 79, wherein reducing the β-amyloid plaque load, inhibiting the formation of β-amyloid plaques and/or retarding the increase of amyloid load lead to a reduction and/or amelioration of the effects of a disease or condition caused by or associated with the formation and deposition of β-amyloid plaques in the brain.

81. Use of the compound as defined in any one of items 1 to 25 wherein the compounds disclaimed in item 1 are disclaimed or are not disclaimed for the preparation of a medicament for retaining or increasing cognitive memory capacity in a subject suffering from memory impairment.

82. A method of retaining or increasing cognitive memory capacity in a subject suffering from memory impairment comprising administering to a subject in need of such treatment an effective amount of a compound as defined in any one of items 1 to 25 wherein the compounds disclaimed in item 1 are disclaimed or are not disclaimed.

83. A compound as defined in any one of items 1 to 25 wherein the compounds disclaimed in item 1 are disclaimed or are not disclaimed for use in the retention or increase of cognitive memory capacity in a subject suffering from memory impairment.

84. The use of item 30, the method of item 35 or the compound of item 40, wherein the amyloid-associated condition is characterized by a loss of cognitive memory capacity.

85. The use, method or compound of item 84, wherein the treatment of the amyloid-associated condition characterized by a loss of cognitive memory capacity leads to an increase in the retention of cognitive memory capacity.

86. The use, method or compound of item 84, wherein the treatment of the amyloid-associated condition characterized by a loss of cognitive memory capacity leads to a complete restoration of cognitive memory capacity.

We claim:

1. A compound having the formula (I):

A-L$_1$-B  (I)

and all stereoisomers, racemic mixtures, and pharmaceutically acceptable salts thereof;

wherein A is:

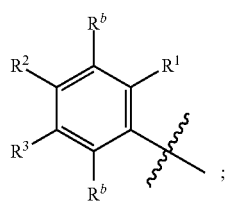

L$_1$ is:

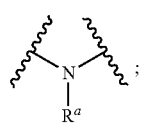

B is:

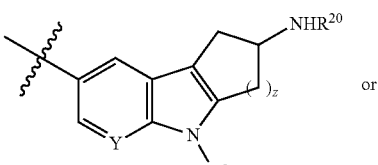 or

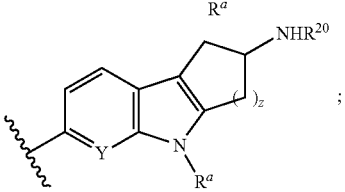;

wherein

R$^2$ and R$^3$ are each independently selected from the group consisting of hydrogen, halogen, —CN, —CF$_3$, —CONR$^{30}$R$^{31}$, —N(R$^{30}$)—C(O)—R$^{31}$, a —O—C$_1$-C$_6$ alkyl, and C$_5$-C$_{10}$ heterocycloalkyl, or wherein R$^2$ and R$^3$ taken together form a 5- or 6-membered ring containing carbon atoms and optionally one or two heteroatoms selected from O, S, or N;

R$^1$ is hydrogen or halogen;

R$^a$ is hydrogen or C$_1$-C$_6$ alkyl;

for each occurrence, R$^b$ is independently selected from the group consisting of: hydrogen, halogen, CN, CONR$^{30}$R$^{31}$, or C$_1$-C$_6$ alkyl;

for each occurrence, $R^{30}$, $R^{31}$, and $R^{20}$ are each independently selected from the group consisting of hydrogen, or $C_1$-$C_6$ alkyl;

Y is CH or N; and z is 1 or 2.

2. The compound of claim 1, wherein Y is N.
3. The compound of claim 1, wherein Y is CH.
4. The compound of claim 1, wherein z is 1.
5. The compound of claim 1, wherein z is 2.
6. The compound of claim 1, wherein Y is N and z is 2.
7. The compound of claim 1
wherein
B is:

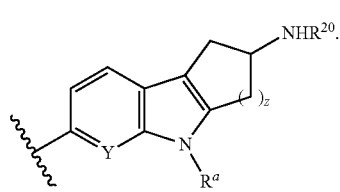

8. The compound of claim 7
wherein
B is:

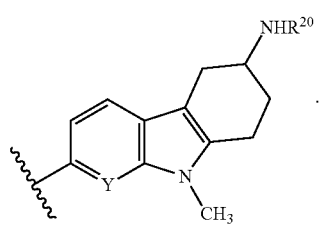

9. The compound of claim 8
wherein A is:

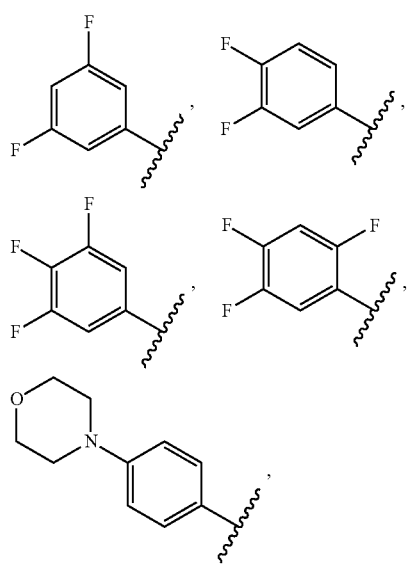

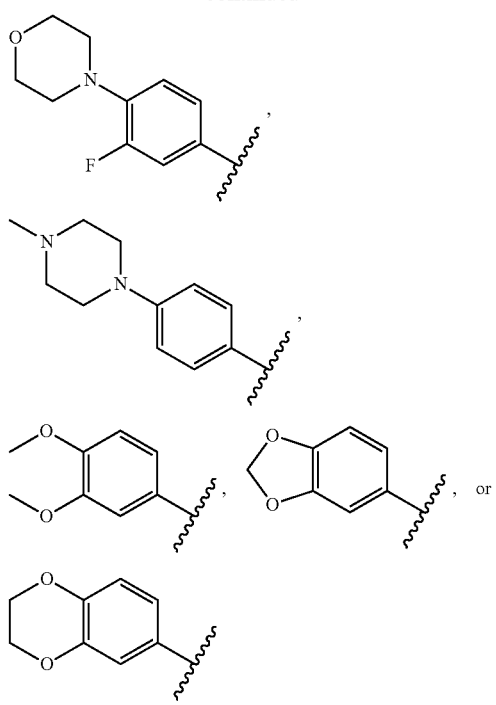

$L_1$ is:

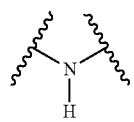 [SMILES: *N*]

and

B is:

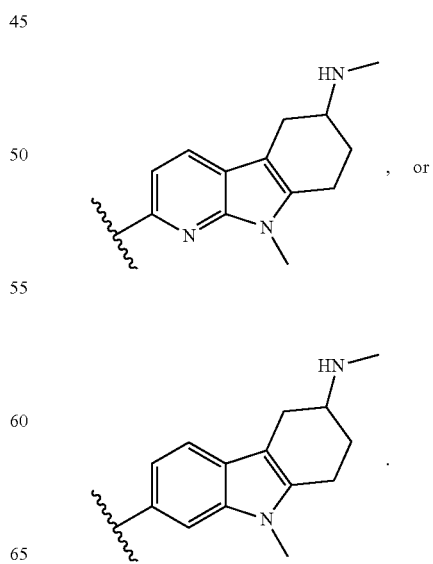

10. The compound of claim 9, comprising:
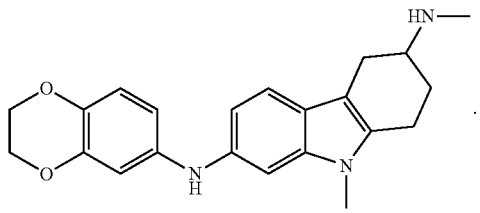 [SMILES: CNC1CCc2c(c3ccc(Nc4ccc5c(c4)OCCO5)cc3n2C)C1]
11. The compound of claim 9, comprising:
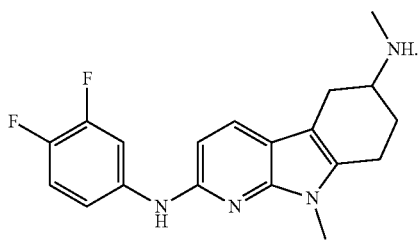 [SMILES: CNC1CCc2c(c3ccc(Nc4ccc(F)c(F)c4)nc3n2C)C1]
12. The compound of claim 1 wherein B is:
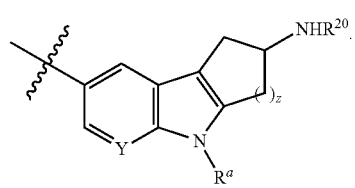
13. The compound of claim 1, wherein the compound is selected from:
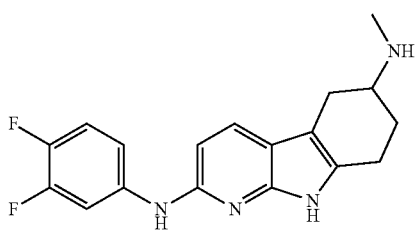 [SMILES: CNC1CCc2[nH]c3nc(Nc4ccc(F)c(F)c4)ccc3c2C1]
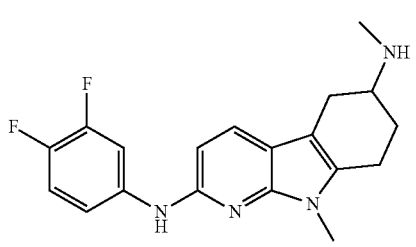
-continued
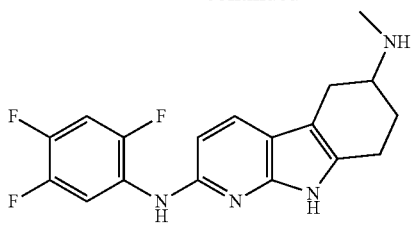
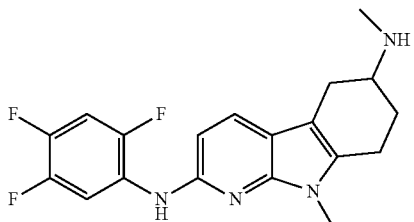
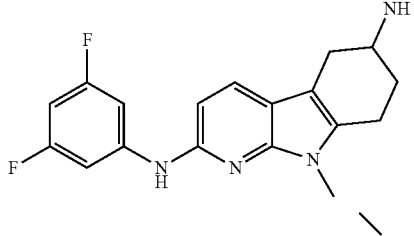
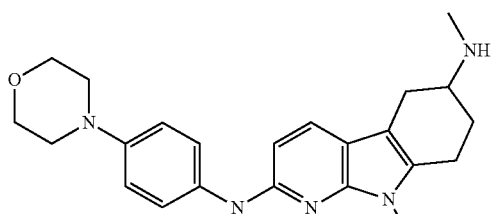
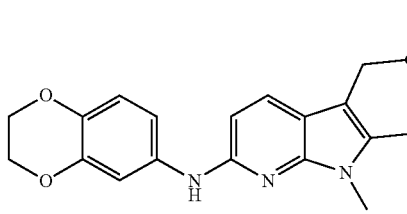
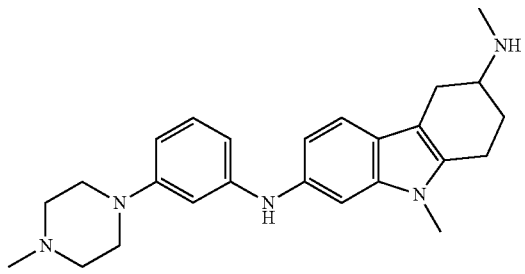

563
-continued
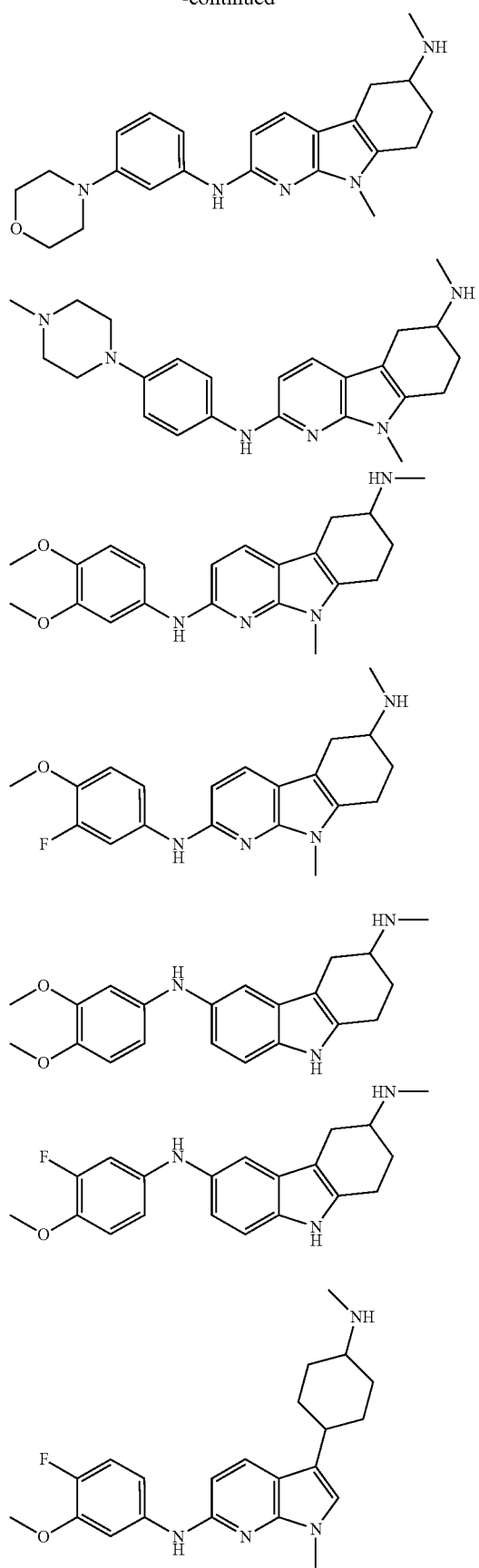
564
-continued
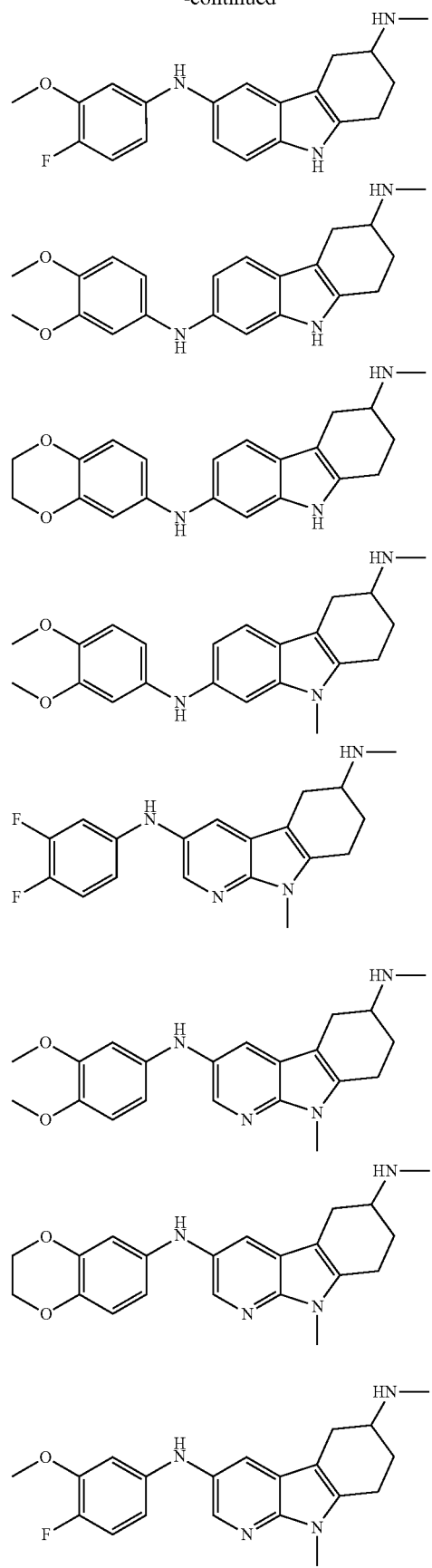

-continued

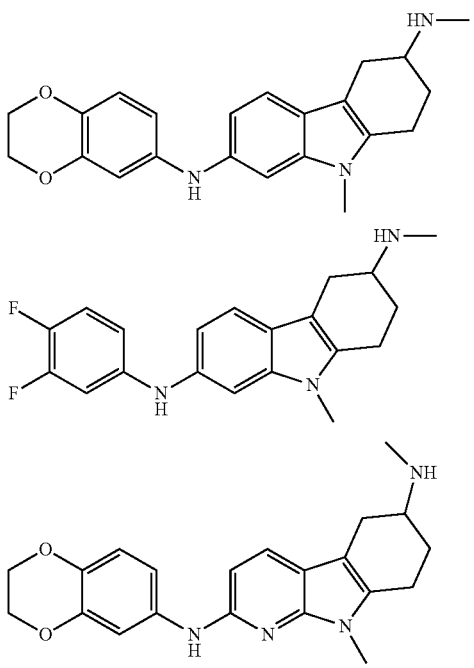

-continued

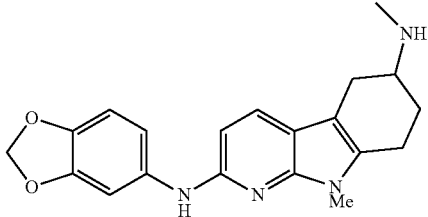

14. A pharmaceutical composition comprising the compound of claim 1.

15. The pharmaceutical composition of claim 14, further comprising a pharmaceutically acceptable carrier or excipient.

16. The composition of claim 15 further comprising a cholinesterase inhibitor (ChEI).

17. The composition of claim 15 further comprising: pirenzepin, 3-amino-1-propanesulfonic acid (3APS), 1,3-propanedisulfonate (1,3PDS), α-secretase activator, βsecretase, γ-secretase inhibitor, tau protein, pyroglutamated amyloid beta 3-42, M1 agonists, neurotransmitters, β-sheet breakers, tacrine, rivastigmine, donepezil, galantamine, niacin and memantine.

18. The compound of claim 1 wherein the compound comprises a radionuclide.

* * * * *

SEQUENCE LISTING

```
<160> NUMBER OF SEQ ID NOS: 4

<210> SEQ ID NO 1
<211> LENGTH: 112
<212> TYPE: PRT
<213> ORGANISM: Artificial Sequence
<220> FEATURE:
<223> OTHER INFORMATION: Artificial humanized c2 HuVK 1 variable light
      chain

<400> SEQUENCE: 1
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 2
<211> LENGTH: 219
<212> TYPE: PRT
<213> ORGANISM: Artificial Sequence
<220> FEATURE:
<223> OTHER INFORMATION: Artificial humanized c2 light chain

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 3
<211> LENGTH: 112
<212> TYPE: PRT
<213> ORGANISM: Artificial Sequence
```

```
<220> FEATURE:
<223> OTHER INFORMATION: Artificial humanized c2 HuVH AF 4 variable
      heavy chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 4
<211> LENGTH: 439
<212> TYPE: PRT
<213> ORGANISM: Artificial Sequence
<220> FEATURE:
<223> OTHER INFORMATION: Artificial humanized c2 heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220
```

-continued

```
Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly Lys
            435
```